US012583866B2

(12) United States Patent
Li et al.

(10) Patent No.: US 12,583,866 B2
(45) Date of Patent: Mar. 24, 2026

(54) PYRIDO[2,3-B][1,4]OXAZINES OR TETRAHYDROPYRIDO[2,3-B][1,4] OXAZEPINES AS IAP ANTAGONISTS

(71) Applicant: BEIGENE, LTD., Camana Bay (KY)

(72) Inventors: Jing Li, Beijing (CN); Fengtao Song, Beijing (CN); Zhiwei Wang, Beijing (CN)

(73) Assignee: BeOne Medicines I GmbH, Basel (CH)

( * ) Notice: Subject to any disclaimer, the term of this patent is extended or adjusted under 35 U.S.C. 154(b) by 753 days.

(21) Appl. No.: 17/928,949

(22) PCT Filed: Jun. 3, 2021

(86) PCT No.: PCT/CN2021/098123
§ 371 (c)(1),
(2) Date: Jun. 6, 2023

(87) PCT Pub. No.: WO2021/244608
PCT Pub. Date: Dec. 9, 2021

(65) Prior Publication Data
US 2023/0219975 A1 Jul. 13, 2023

(30) Foreign Application Priority Data

Jun. 4, 2020 (WO) ................ PCT/CN2020/094309
Oct. 9, 2020 (WO) ................ PCT/CN2020/119974
Dec. 8, 2020 (WO) ................ PCT/CN2020/134610

(51) Int. Cl.
*C07D 498/04* (2006.01)
*C07D 519/00* (2006.01)

(52) U.S. Cl.
CPC ......... *C07D 498/04* (2013.01); *C07D 519/00* (2013.01)

(58) Field of Classification Search
CPC ............................ C07D 498/04; C07D 519/00
USPC .................................................... 514/210.18
See application file for complete search history.

(56) References Cited

U.S. PATENT DOCUMENTS

2016/0108039 A1 4/2016 Allerheiligen et al.

FOREIGN PATENT DOCUMENTS

| | | |
|---|---|---|
| CN | 101801962 | 8/2010 |
| CN | 104945345 | 9/2015 |
| CN | 105408331 | 3/2016 |
| EP | 2266989 | 12/2010 |
| WO | 2009/007748 | 1/2009 |
| WO | 2012143726 | 10/2012 |
| WO | 2014060767 | 4/2014 |
| WO | 2014060770 | 4/2014 |
| WO | 2015092420 | 6/2015 |
| WO | 2018237370 | 12/2018 |

OTHER PUBLICATIONS

Johnson, Christopher N., et al. "A Fragment-Derived Clinical Candidate for Antagonism of X-Linked and Cellular Inhibitor of Apoptosis Proteins: 1-(6-[(4-Fluorophenyl) methyl]-5-(hydroxymethyl)-3, 3-dimethyl-1 H, 2 H, 3 H-pyrrolo [3,2-b] pyridin-1-yl)-2-[(2 R, 5 R)-5-methyl-2-([(3R)-3-methylmorpholin-4-yl] methyl) piperazin-1-yl] ethan-1-one (ASTX660)." Journal of Medicinal Chemistry 61.16 (2018): 7314-7329.
Fontanella, L., "New synthesis of 1-phenyl-2,6-dimethylpiperazine", Il Farmaco, Elsevier France * Editions Scientifiques et Medicales, FR, FR , (Dec. 31, 1982), vol. 37, No. fasc. 6, ISSN 0014-827X, 1 page, XP009546736.
Cohen, "Protein kinases—the major drug targets of the twenty-first century?", Nature, 1: 309-315 (2002).
Gaestel et al., "Protein Kinases as Small Molecule Inhibitor Targets in Inflammation", Curr. Med. Chem. 14: 2214-223 (2007).
Grimminger et al. "Targeting non-malignant disorders with tyrosine kinase inhibitors", Nat. Rev. Drug Disc. 9 (12) : 956-970 (2010).
Cohen, "The role of protein phosphorylation in human health and disease," Eur. J. Biochem., 268: 5001-5010 (2001).
Cohen, 2005, Protein Kinase Inhibitors for the Treatment of Disease: The Promise and the Problems, Handbook of Experimental Pharmacology, Springer Berlin Heidelberg, 167:1-7.
Kerr, J.F., et al., "Apoptosis: a Basic Biological Phenomenon With Wide-Ranging Implications in Tissue Kinetics," Br J Cancer, 1972, 26, 239-257.
Nicholson, D.W., et al., "From bench to clinic with apoptosis-based therapeutic agents", Nature, 2000, 407, 810-816.
Hanahan, D., et al., "The Hallmarks of Cancer," cell 2000, 100, 57-70.
Hanahan, Douglas, and Robert A. Weinberg. "Hallmarks of cancer: the next generation." cell 144.5 (2011): 646-674.
(Continued)

*Primary Examiner* — Kahsay Habte
(74) *Attorney, Agent, or Firm* — McNeill PLLC

(57) ABSTRACT

Disclosed herein are novel 2,3-dihydro-1H-pyrido[2,3-b][1,4]oxazine or 1,2,3,4-tetrahydropyrido[2,3-b][1,4]oxazepine derivatives used as antagonists of IAPs (Inhibitors Apoptosis Proteins), also known as Smac mimetics. Disclosed herein is the use of these antagonists for inducing or sensitizing cells to the induction of apoptotic cell death, and the use of such compounds for treating proliferative disease such as cancer.

(I)

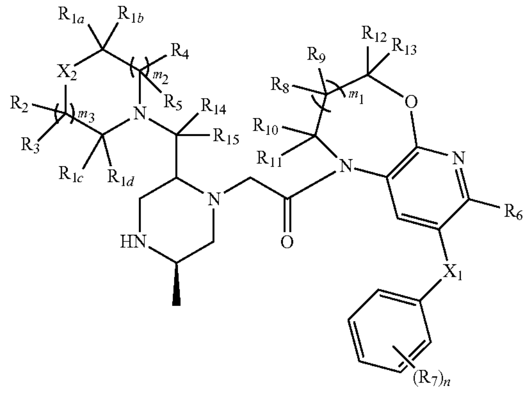

19 Claims, No Drawings

(56) References Cited

OTHER PUBLICATIONS

Elmore, S., "Aptosis: A Review of Programmed Cell Death," Toxicol Pathol, 2007, 35, 495-516.
Birnbaum, M.J., et al., "An Apoptosis-Inhibiting Gene from a Nuclear Polyhedrosis Virus Encoding a Polypeptide with Cys/His Sequence Motifs," J Virol, 1994, 68, 2521-2528.
Yang, Y.L., "The IAP family: endogenous caspase inhibitors with multiple biological activities," Cell Res, 2000, 10, 169-177.
Salvesen, G.S., et al., "IAP Proteins: Blocking the Road to Death's Door", Nat Rev Mol Cell Bio, 2002, 3, 401-410.
Derakhshan, A., et al., "Therapeutic Small Molecules Target Inhibitor of Apoptosis Proteins in Cancers with Deregulation of Extrinsic and Intrinsic Cell Death Pathways," Clin Cancer Res, 2017, 23, 1379-1387.
Samuel T., et al., "Distinct BIR Domains of cIAP1 Mediate Binding to and Ubiquitination of Tumor Necrosis Factor Receptor-associated Factor 2 and Second Mitochondrial Activator of Caspases," J Biol Chem, 2006, 281, 1080-1090.
Vince J.E., et al., "TRAF2 Must Bind to Cellular Inhibitors of Apoptosis for Tumor Necrosis Factor (TNF) to Efficiently Activate NF-kB and to Prevent TNF-induced Apoptosis," J Biol Chem, 2009, 284, 35906-35915.
Wang C., et al., "TAK1 is a ubiquitin-dependent kinase of MKK and IKK", Nature, 2001, 412, 346-351.
Deveraux Q. L., et al., "X-linked IAP is a direct inhibitor of cell-death proteases", Nature, 1997, 388, 300-304.
Chai J., et al., "Structural Basis of Caspase-7 Inhibition by XIAP," Cell, 2001, 104, 769-780.
Riedl S.J., et al., "Structural Basis for the Inhibition of Caspase-3 by XIAP," Cell, 2001, 104, 791-800.
Shiozaki E.N., et al., "Mechanism of XIAP-Mediated Inhibition of Caspase-9," Mol Cell, 2003, 11, 519-527.
Che, Xiangyu, et al. "Nuclear cIAP1 overexpression is a tumor stage-and grade-independent predictor of poor prognosis in human bladder cancer patients." Urologic Oncology: Seminars and Original Investigations. vol. 30. No. 4. Elsevier, 2012; pp. 450-456.
Yang C., et al., "LCL161 increases paclitaxel-induced apoptosis by degrading cIAP1 and cIAP2 in NSCLC," J Exp Clin Cancer Res, 2016, 17 pages.
Gu H., et al., "Aging exacerbates mortality of Acinetobacter baumannii pneumonia and reduces the efficacies of antibiotics and vaccine," Aging (Albany NY) , 2018, 10, 1597-1608.
Du C., et al., "Smac, a Mitochondrial Protein that Promotes Cytochrome c-Dependent Caspase Activation by Eliminating IAP Inhibition," Cell, 2000, 102, 33-42.
Verhagen A.M., et al., "Identification of Diablo, a Mammalian Protein that Promotes Apoptosis by Binding to and Antagonizing IAP Proteins" Cell, 2000, 102, 43-53.
Chai J., et al., "Structural and biochemical basis of apoptotic activation by Smac/Diablo," Nature, 2000, 406, 855-862.
Dueber E.C., et al., "Antagonists Induce a Conformational Change in cIAP1 That Promotes Autoubiquitination", Science, 2011, 334, 376-380.
Micheau, O., et al., "Induction of TNF Receptor I-Mediated Apoptosis vai Two Sequential Signaling Complexes," Cell, 2003, 114, 181-190.
Liu Z., et al., Nature, "Sturctural basis for binding of Smac/Diablo to the XIAP BIR3 domain", 2000, 408, 1004-1008.
Dieter Enders, et al., "(S,S)-3,5-Dimethylmorpholine, a Novel C2-Symmetric Auxiliary. First Application in [4+2]-Cycloadditions Leading to 4-Oxohexahydropyridazine Derivatives", Synthesis, 1994 (01) , 66-72.
G. Cignarella et al., "Antiadrenergic substances", Gazz. Chim. Ital., 1962, 92, 1 page.

PYRIDO[2,3-B][1,4]OXAZINES OR TETRAHYDROPYRIDO[2,3-B][1,4]OXAZEPINES AS IAP ANTAGONISTS

CROSS-REFERENCE TO RELATED APPLICATIONS

This application is a U.S. National Stage Application under 35 U.S.C. § 371 of International Application No. PCT/CN2021/098123, filed Jun. 3, 2021, which claims priority to Patent Application Nos. PCT/CN2020/134610, filed on Dec. 8, 2020, PCT/CN2020/119974, filed on Oct. 9, 2020, and PCT/CN2020/094309, filed on Jun. 4, 2020.

FIELD OF THE INVENTION

Disclosed herein are novel 2,3-dihydro-1H-pyrido[2,3-b][1,4]oxazine or 1,2,3,4-tetrahydropyrido[2,3-b][1,4]oxazepine derivatives used as antagonists of IAPB (Inhibitors Apoptosis Proteins), also known as Smac mimetics. Disclosed herein is the use of these antagonists for inducing or sensitizing cells to the induction of apoptotic cell death, and the use of such compounds for treating proliferative diseases such as cancer.

BACKGROUND OF THE INVENTION

Apoptosis plays a critical role in the development and homeostasis of cells in higher organisms and is a tightly regulated process to eliminate damaged or unwanted cells (Kerr, J. F., et al., Br *J Cancer,* 1972, 26, 239-257). Aberrations in the apoptotic process are implicated in many human diseases, including cancer, autoimmune diseases and inflammation (Nicholson, D. W., et al., *Nature,* 2000, 407, 810-816). Indeed, resistance to apoptosis is a hallmark of cancer (Hanahan, D., et al., cell 2000, 100, 57-70; Hanahan, D., et al., cell, 2011, 144, 646-674). Apoptosis can be triggered through either the extrinsic stimulation of death receptors or the intrinsic stimuli released by mitochondria within the cell (Elmore, S., *Toxicol Pathol,* 2007, 35, 495-516). Inhibitors of apoptosis proteins (IAPB) are a class of pivotal negative regulators of both extrinsic and intrinsic apoptotic pathways. IAP was initially identified in baculovirus and able to inhibit apoptosis in the infected cells (Birnbaum, M J, et al., *J Virol,* 1994, 68, 2521-2528). The IAPB are characterized by the presence of baculoviral IAP repeat (BIR) domains. BIR domain is approximately 70-80 amino acids in length and contains a Zn-binding motif which can facilitate protein-protein interactions involved in IAP function (Yang, Y. L., *Cell Res,* 2000, 10, 169-177). The human IAP family contains eight proteins: neuronal IAP (BIRC1), cellular IAP1 (cIAP1, BIRC2), cellular IAP2 (cIAP2, BIRC3), X chromosome-linked IAP (XIAP, BIRC4), survivin (BIRC5), ubiquitin-conjugating BIR domain enzyme apollon (BIRC6), melanoma IAP (ML-IAP, BIRC7), and IAP-like protein 2 (BIRC8). Among these, cIAP1, cIAP2 and XIAP play a direct role in apoptosis regulation (Salvesen, G. S., et al., *Nat Rev Mol Cell Bio,* 2002, 3, 401-410).

cIAP1 and cIAP2 (cIAPs) inhibit caspase-8 dependent extrinsic apoptotic pathway such as that induced by TNF-α through their ubiquitin ligase activity (Derakhshan, A., et al., *Clin Cancer Res,* 2017, 23, 1379-1387). Upon ligation of TNF-α to its receptor TNFR1, cIAPs, as well as tumor necrosis factor receptor type 1-associated death domain (TRADD), receptor-interacting serine/threonine kinase 1 (RIPK1) and TNF receptor-associated factors (TRAFs) are recruited to form complex I leading to activation of canonical nuclear factor-κB (NF-κB) pathway, well known to promote inflammation, proliferation and cell survival (Samuel T, et al., *J Biol Chem,* 2006, 281, 1080-1090; Vince J. E., et al., *J Biol Chem,* 2009, 284, 35906-35915; Wang C., et al., *Nature,* 2001, 412, 346-351).

XIAP is the only IAP protein that inhibits both extrinsic and intrinsic apoptotic pathways by directly counteracting caspase activation through their BIR domains (Deveraux Q. L., et al., *Nature,* 1997, 388, 300-304). The $BIR_2$ domain and the preceding linker region of XIAP associates to the IAP-binding motif (IBM) and active site of caspase-3 and -7, the executioner caspases shared by extrinsic and intrinsic apoptosis, and inhibits their function (Chai J., et al., *Cell,* 2001, 104, 769-780; Riedl S. J., et al., *Cell,* 2001, 104, 791-800). XIAP binds to pro-caspase-9 via its $BIR_3$ domain and prevents the dimerization and subsequent activation of caspase-9, the critical initiator caspase in the intrinsic pathway (Shiozaki E. N., et al., *Mol Cell,* 2003, 11, 519-527).

cIAP1, cIAP2 and XIAP proteins are broadly expressed in various tumor types. And positive expression of cIAPs and XIAP is associated with high-grade cancer and poor prognosis (Che X, et al., *Urol Oncol,* 2012, 30, 450-456; Yang C., et al., *J Exp Clin Cancer Res,* 2016, 35, 158). Moreover, downregulation or depletion of these IAPs has shown to restore sensitivity to extrinsic or intrinsic apoptotic stimuli (Gu H., et al., *Aging* (Albany NY), 2018, 10, 1597-1608). Taken together, targeting IAP proteins provides a potential anti-tumor strategy.

The second mitochondrial-derived activator of caspases (Smac), also known as direct IAP binding protein with low pI (DIABLO), is an endogenous antagonist of cIAP1, cIAP2 and XIAP to promote apoptosis (Du C., et al., *Cell,* 2000, 102, 33-42; Verhagen A. M, et al., *Cell,* 2000, 102, 43-53). Smac is normally sequestered in the mitochondria and released into cytosol when cells undergo apoptosis. In cytosol, the N-terminal mitochondria-targeting sequence of Smac is cleaved to expose the tetrapeptide (Ala-Val-Pro-Ile) that allows Smac to interact with the BIR domains of IAPs (Chai J., et al., *Nature,* 2000, 406, 855-862). Binding of Smac to $BIR_3$ domain of cIAP1 and cIAP2 stimulates their E3 ubiquitin ligase activity and induces their proteasomal degradation. Loss of cIAP proteins promotes the formation of RIPK1, caspase-8 and Fas-associated protein with death domain (FADD) containing complex II and triggers TNF-α mediated apoptosis (Dueber E. C., et al., *Science,* 2011, 334, 376-380).

Dimerized Smac binds to the $BIR_2$ and $BIR_3$ domains of XIAP and disrupts its interaction with caspase-3, -7 and -9, leading to caspase-dependent apoptosis (Micheau, O., et al., *Cell,* 2003, 114, 181-190; Chai J., et al., *Cell,* 2001, 104, 769-780; Liu Z., et al., *Nature,* 2000, 408, 1004-1008).

Smac mimetics are small molecules that contain 4 amino acids that mimic the N-terminal (Ala-Val-Pro-Ile) of Smac. Similar to Smac, Smac mimetics bind to BIR domains of IAPs and antagonize their function to promote apoptosis in cancer cells (Chai J., et al., *Cell,* 2001, 104, 769-780; Dueber E. C., et al., *Science,* 2011, 334, 376-380; Liu Z., et al., *Nature,* 2000, 408, 1004-1008; Verhagen A. M, et al., *Cell,* 2000, 102, 43-53). Taken together, Smac mimetics become a new class of cancer therapeutic candidates.

SUMMARY OF THE INVENTION

In one embodiment, disclosed herein is 2,3-dihydro-1H-pyrido[2,3-b][1, 4]oxazine or 1, 2, 3, 4-tetrahydropyrido[2, 3-b][1, 4]oxazepine derivatives of Formula (I). The embodiment comprises the following aspects:

Aspect 1: A compound of Formula (I):

(I)

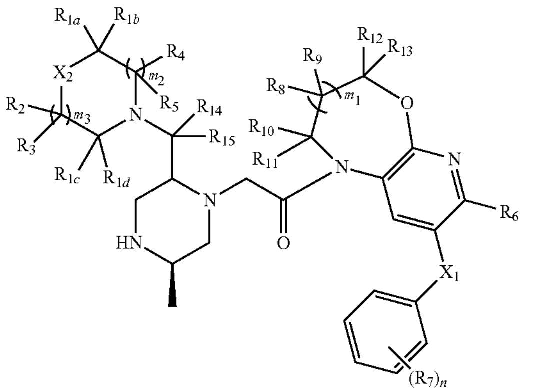

or a pharmaceutically acceptable salt thereof, or a stereoisomer, a tautomer or a prodrug thereof, wherein $X_1$ and $X_2$ are each independently —O—, —S—, —$NR^a$—, or —$CR^aR^b$—;

$m_1$, $m_2$, and $m_3$ are each independently 0, 1 or 2;

$R_{1a}$, $R_{1b}$, $R_{1c}$, $R_{1d}$, and $R_7$, which may be the same or different, are each independently hydrogen, halogen, —$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR^a$, —$SR^a$, —$SO_2R^a$, —$COR^a$, —$CO_2R^a$, —$CONR^aR^b$, —$C(=NR^a)NR^bR^c$, —$NR^aR^b$, —$NR^aCOR^b$, —$NR^aCONR^bR^c$, —$NR^aCO_2R^b$, —$NR^aSONR^bR^c$, —$NR^aSO_2NR^bR^c$, —$SO_2NR^aR^b$, or —$NR^aSO_2R^b$, each of said —$C_{1-8}$alkyl, —$C_{2-8}$alkenyl, —$C_{2-8}$-alkynyl, —$C_{3-8}$-cycloalkyl, heterocyclyl, aryl, or heteroaryl is optionally substituted with 1-3 $R^d$;

n is 0, 1, 2, 3 or 4;

$R_3$ and $R_5$ are each independently hydrogen, halogen, —$C_{3-8}$cycloalkyl, or —$C_{1-8}$alkyl, said —$C_{1-8}$alkyl or —$C_{3-8}$cycloalkyl is optionally substituted with at least one halogen or —$OR^a$;

$R_2$ and $R_4$ are each independently hydrogen or —$C_{1-8}$alkyl; or $R_4$ and $R_5$ together with the same carbon atom to which they are attached form a spiro 3- to 5-membered carbon ring; or $R_2$ at one of its occurrences and $R_4$ at one of its occurrences together form a bridge comprising zero, one or two —$CH_2$— moieties in the bridge; or or $R_{1b}$ and $R_4$ at one of its occurrences together form a 3- to 6-membered carbon ring;

or $R_{1d}$ and $R_4$ at one of its occurrences together form a bridge comprising one or two —$CH_2$— moieties in the bridge;

$R_6$ is hydrogen, halogen, —$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR^a$, —$SR^a$, —$SO_2R^a$, —$COR^a$, —$CO_2R^a$, —$CONR^aR^b$, —$C(=NR^a)NR^bR^c$, —$NR^aR^b$, —$NR^aCOR^b$, —$NR^aCONR^bR^c$, —$NR^aCO_2R^b$, —$NR^aSONR^bR^c$, —$NR^aSO_2NR^bR^c$, —$SO_2NR^aR^b$, or —$NR^aSO_2R^b$, each of said —$C_{1-8}$alkyl, —$C_{2-8}$alkenyl, —$C_{2-8}$alkynyl, —$C_{3-8}$cycloalkyl, heterocyclyl, aryl, or heteroaryl is optionally substituted with 1-3 $R^d$; $R_8$ and $R_9$ are each independently hydrogen, —$C_{1-8}$alkyl, $C_{1-8}$alkoxy-$C_{1-8}$alkyl-, —$C_{2-8}$alkenyl, —$C_{2-8}$alkynyl or $C_{3-8}$cycloalkyl;

$R_{10}$ and $R_{11}$ are each independently hydrogen, —$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR^a$, —$SR^a$, —$SO_2R^a$, —$COR^a$, —$COR^a$, —$CO_2R^a$, —$CONR^aR^b$, —$C(=NR^a)NR^bR^c$, —$NR^aR^b$, —$NR^aCOR^b$, —$NR^aCONR^bR^c$, —$NR^aCO_2R^b$, —$NR^aSONR^bR^c$, —$NR^aSO_2NR^bR^c$, —$SO_2NR^aR^b$, or —$NR^aSO_2R^b$, each of said —$C_{1-8}$alkyl, —$C_{2-8}$alkenyl, —$C_{2-8}$alkynyl, —$C_{3-8}$cycloalkyl, heterocyclyl, aryl, or heteroaryl is optionally substituted with 1-3 $R^d$; or $R_{10}$ and $R_{11}$ together form a Spiro 3- to 5-membered carbon ring optionally substituted with 1-3 $R^d$;

$R_{12}$ and $R_{13}$ are each independently hydrogen, —$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR^a$, —$SR^a$, —$SO_2R^a$, —$COR^a$, —$CO_2R_a$, —$CONR^aR^b$, —$C(=NR^a)NR^bR^c$, —$NR^aR^b$, —$NR^aCOR^b$, —$NR^aCONR^bR^c$, —$NR^aCO_2R^b$, —$NR^aSONR^bR^c$, —$NR^aSO_2NR^bR^c$, —$SO_2NR^aR^b$, or —$NR^aSO_2R^b$, each of said —$C_{1-8}$alkyl, —$C_{2-8}$alkenyl, —$C_{2-8}$alkynyl, cycloalkyl, heterocyclyl, aryl, or heteroaryl is optionally substituted with 1-3 $R^d$; or $R_{12}$ and $R_{13}$ together form a spiro 3- to 5-membered carbon ring optionally substituted with 1-3 $R^d$;

$R_{14}$ and $R_{15}$ are each independently selected from hydrogen or —$C_{1-8}$alkyl;

each $R^a$, $R^b$, and $R^c$ are independently hydrogen, —$C_{1-8}$alkyl, —$C_{2-8}$alkenyl, —$C_{2-8}$alkynyl, cycloalkyl, heterocyclyl, aryl, or heteroaryl; each of said —$C_{1-8}$alkyl, —$C_{2-8}$alkenyl, —$C_{2-8}$alkynyl, cycloalkyl, heterocyclyl, aryl, or heteroaryl is optionally substituted with 1-3 $R^d$; or ($R^a$ and $R^b$), ($R^a$ and $R^c$) or ($R^b$ and $R^c$), together with the atom(s) to which they are attached, form a 3- to 8-member ring, said ring comprising 0, 1 or 2 additional heteroatoms independently selected from nitrogen, oxygen or optionally oxidized sulfur as ring member(s), said ring is optionally substituted with 1-3 $R^d$;

$R^d$, at each of its occurrences, is independently hydrogen, halogen, —$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR^e$, —$SR_a$, —$SO_2R^e$, —$SO_2NR^eR^f$, —$COR^e$, —$CO_2R^e$, —$CONR^eR^f$, —$C(=NR^e)NR^fR^g$, —$NR^eR^f$, —$NR^eCOR^f$, —$NR^eCONR^fR^g$, —$NR^eCO_2R^f$, —$NR^eSONR^fR^g$, —$NR^eSO_2NR^fR^g$, or —$NR^eSO_2R^f$, each of said —$C_{1-8}$alkyl, —$C_{2-8}$alkenyl, —$C_{2-8}$alkynyl, —$C_{3-8}$cycloalkyl, heterocyclyl, aryl, or heteroaryl is optionally substituted with at least one substituent selected from halogen, —$C_{1-8}$alkyl, —$OR^h$, —$NR^hR^i$, cycloalkyl, heterocyclyl, aryl, or heteroaryl; and $R^e$, $R^f$, $R^g$, $R^h$, and $R^i$ are each independently hydrogen, —$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl, aryl-$C_{1-8}$alkyl- or heteroaryl.

In some embodiments, $m_2$ is 1 and $m_3$ is 1, and $R_2$ and $R_4$ together form a bridge comprising zero, one or two —$CH_2$— moieties in the bridge; or, $m_2$ is 1 and $m_3$ is 2, and $R_2$ and one of the two $R_4$ together form a bridge comprising zero, one or two —$CH_2$— moieties in the bridge; or, $m_2$ is 2 and $m_3$ is 1, and one of the two $R_2$ and $R_4$ together form a bridge comprising zero, one or two —$CH_2$— moieties in the bridge; or, $m_2$ is 2 and $m_3$ is 2, and one of the two $R_2$ and one of the two $R_4$ together form a bridge comprising zero, one or two —$CH_2$— moieties in the bridge.

In some embodiments, $m_2$ is 1, and $R_{1b}$ and $R_4$ together form a 3- to 6-membered carbon ring; or $m_2$ is 2, and $R_{1b}$ and one of the two $R_4$ together form a 3- to 6-membered carbon ring.

In some embodiments, $m_2$ is 1, and $R_{1d}$ and $R_4$ together form a bridge comprising one or two —$CH_2$— moieties in the bridge; or $m_2$ is 2, and $R_{1d}$ and one of the two $R_4$ together form a bridge comprising one or two —$CH_2$— moieties in the bridge.

Aspect 2: A compound of Formula (Ill:

(II)

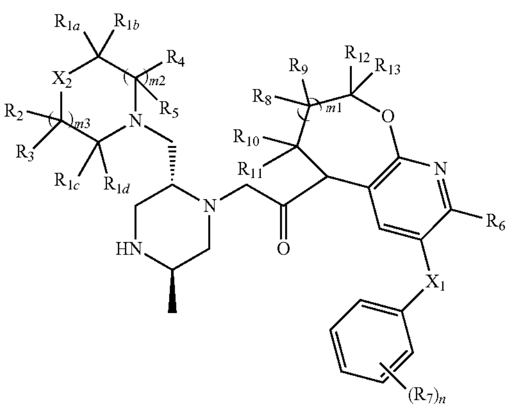

or a pharmaceutically acceptable salt thereof, or a stereoisomer, a tautomer or a prodrug thereof, wherein $X_1$ and $X_2$ are each independently —O—, —S—, —$NR^a$—, or —$CR^aR^b$—;

$m_{1a}$, $m_2$, and $m_3$ are each independently 0, 1 or 2;

$R_{1a}$, $R_{1b}$, $R_{1c}$, $R_{1d}$, and $R_7$, which may be the same or different, are each independently hydrogen, halogen, —$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR_a$, —$SR_a$, —$SO_2R_a$, —$COR_a$, —$CO_2R_a$, —$CONR^aR^b$, —$C(=NR^a)NR^bR^c$, —$NR^aR^b$, —$NR^a$-$COR^b$, —$NR^aCONR^bR^c$, —$NR^aCO_2R^b$, —$NR^a$-$SONR^bR^c$, —$NR^aSO_2NR^bR^c$, —$SO_2NR^aR^b$, or —$NR^aSO_2R^b$, each of said —$C_{1-8}$alkyl, —$C_{2-8}$alkenyl, —$C_{2-8}$alkynyl, —$C_{3-8}$cycloalkyl, heterocyclyl, aryl, or heteroaryl is optionally substituted with 1-3 $R^d$; n is 0, 1, 2, 3 or 4;

$R_3$ and $R_5$ are each independently hydrogen, halogen, —$C_{3-8}$cycloalkyl, or —$C_{1-8}$alkyl, said —$C_{1-8}$alkyl or —$C_{3-8}$cycloalkyl is optionally substituted with at least one halogen or —$OR^a$;

$R_2$ and $R_4$ are each independently hydrogen or —$C_{1-8}$alkyl; or $R_4$ and $R_5$ together with the same carbon atom to which they are attached form a Spiro 3- to 5-membered carbon ring; or $R_2$ at one of its occurrences and $R_4$ at one of its occurrences together form a bridge comprising zero, one or two —$CH_2$— moieties in the bridge; or or $R_{1b}$ and $R_4$ at one of its occurrences together form a 3- to 6-membered carbon ring; or $R_{1d}$ and $R_4$ at one of its occurrences together form a bridge comprising one or two —$CH_2$— moieties in the bridge;

$R_6$ is hydrogen, halogen, —$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$NO_2$, —$SR_a$, —$SO_2R_a$, —$COR^a$, —$CO_2R_a$, —$CONR^aR^b$, —$C(=NR^a)NR^bR^c$, —$NR^aR^b$, —$NR^aCOR^b$, —$NR^a$-$CONR^b$W, —$NR^aCO_2R^b$, —$NR^aSONR^bR^c$, —$NR^aSO_2NR^bR^c$, —$SO_2NR^aR^b$, or —$NR^aSO_2R^b$, each of said —$C_{1-8}$alkyl, —$C_{2-8}$alkenyl, —$C_{2-8}$alkynyl, —$C_{3-8}$cycloalkyl, heterocyclyl, aryl, or heteroaryl is optionally substituted with 1-3 $R^d$;

$R_8$ and $R_9$ are each independently hydrogen, —$C_{1-8}$alkyl, $C_{1-8}$alkoxy-$C_{1-8}$alkyl-, —$C_{2-8}$alkenyl, —$C_{2-8}$alkynyl or $C_{3-8}$cycloalkyl;

$R_{10}$ and $R_{11}$ are each independently hydrogen, —$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR_a$, —$SR^a$, —$SO_2R_a$, —$COR_a$, —$CO_2R_a$, —$CONR^aR^b$, —$C(=NR^a)NR^bR^c$, —$NR^aR^b$, —$NR^a$-$COR^b$, —$NR^aCONR^bR^c$, —$NR^aCO_2R^b$, —$NR^a$-$SONR^bR^c$, —$NR^aSO_2NR^bR^c$, —$SO_2NR^aR^b$, or —$NR^aSO_2R^b$, each of said —$C_{1-8}$alkyl, —$C_{2-8}$alkenyl, —$C_{2-8}$alkynyl, —$C_{3-8}$cycloalkyl, heterocyclyl, aryl, or heteroaryl is optionally substituted with 1-3 $R^d$; or $R_{10}$ and $R_{11}$ together form a spiro 3- to 5-membered carbon ring optionally substituted with 1-3 $R^d$;

$R_{12}$ and $R_{13}$ are each independently hydrogen, —$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR_a$, —$SR_a$, —$SO_2R_a$, —$COR_a$, —$CO_2R_a$, —$CONR^aR^b$, —$C(=NR^a)NR^bR^c$, —$NR^aR^b$, —$NR^a$-$COR^b$, —$NR^aCONR^bR^c$, —$NR^aCO_2R^b$, —$NR^a$-$SONR^bR^c$, —$NR^aSO_2NR^bR^c$, —$SO_2NR^aR^b$, or —$NR^aSO_2R^b$, each of said —$C_{1-8}$alkyl, —$C_{2-8}$alkenyl, —$C_{2-8}$alkynyl, cycloalkyl, heterocyclyl, aryl, or heteroaryl is optionally substituted with 1-3 $R^d$; or $R_{12}$ and $R_{13}$ together form a Spiro 3- to 5-membered carbon ring optionally substituted with 1-3 $R^d$;

each $R^a$, $R^b$, and $R^c$ are independently hydrogen, —$C_{1-8}$alkyl, —$C_{2-8}$alkenyl, —$C_{2-8}$alkynyl, cycloalkyl, heterocyclyl, aryl, or heteroaryl; each of said —$C_{1-8}$alkyl, —$C_{2-8}$alkenyl, —$C_{2-8}$alkynyl, cycloalkyl, heterocyclyl, aryl, or heteroaryl is optionally substituted with 1-3 $R^d$; or ($R^a$ and $R^b$), ($R^a$ and $R^c$) or ($R^b$ and $R^c$), together with the atom(s) to which they are attached, form a 3- to 8-member ring, said ring comprising 0, 1 or 2 additional heteroatoms independently selected from nitrogen, oxygen or optionally oxidized sulfur as ring member(s), said ring is optionally substituted with 1-3 $R^d$;

$R^d$, at each of its occurrences, is independently hydrogen, halogen, —$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR^e$, —$SR_a$, —$SO_2R^e$, —$SO_2NR^eR^f$, —$COR^e$, —$CO_2R^e$, —$CONR^eR^f$, —$C(=NR^e)NR^fR^g$, —$NR^eR^f$, —$NR^eCOR^f$, —$NR^e$-$CONR^fR^g$, —$NR^eCO_2R^f$, —$NR^eSONR^fR^g$, —$NR^eSO_2NR^fR^g$, or —$NR^eSO_2R^f$, each of said —$C_{1-8}$alkyl, —$C_{2-8}$alkenyl, —$C_{2-8}$alkynyl, —$C_{3-8}$cycloalkyl, heterocyclyl, aryl, or heteroaryl is optionally substituted with at least one substituent selected from halogen, —$C_{1-8}$alkyl, —$OR^h$, —$NR^hR^i$, cycloalkyl, heterocyclyl, aryl, or heteroaryl; and $R^e$, $R^f$, $R^g$, $R^h$, and $R^i$ are each independently hydrogen, —$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl, aryl-$C_{1-8}$alkyl- or heteroaryl.

In some embodiments, $m_2$ is 1 and $m_3$ is 1, and $R_2$ and $R_4$ together form a bridge comprising zero, one or two $—CH_2—$ moieties in the bridge; or, $m_2$ is 1 and $m_3$ is 2, and $R_2$ and one of the two $R_4$ together form a bridge comprising zero, one or two $—CH_2—$ moieties in the bridge; or, $m_2$ is 2 and $m_3$ is 1, and one of the two $R_2$ and $R_4$ together form a bridge comprising zero, one or two $—CH_2—$ moieties in the bridge; or, $m_2$ is 2 and $m_3$ is 2, and one of the two $R_2$ and one of the two $R_4$ together form a bridge comprising zero, one or two $—CH_2—$ moieties in the bridge.

In some embodiments, $m_2$ is 1, and $R_{1b}$ and $R_4$ together form a 3- to 6-membered carbon ring; or $m_2$ is 2, and $R_{1b}$ and one of the two $R_4$ together form a 3- to 6-membered carbon ring.

In some embodiments, $m_2$ is 1, and $R_{1d}$ and $R_4$ together form a bridge comprising one or two $—CH_2—$ moieties in the bridge; or $m_2$ is 2, and $R_{1d}$ and one of the two $R_4$ together form a bridge comprising one or two $—CH_2—$ moieties in the bridge.

Aspect 3: The compound according to Aspects 1 or 2, wherein $X_1$ is —O—, —S—, —NH—, or $—CH_2—$.

Aspect 4: The compound according to Aspect 3, wherein $X_1$ is $—CH_2—$.

Aspect 5: The compound according to Aspects 1 or 2, wherein $X_2$ is —O—, —S—, $—CH_2—$ or $—NR^a$; $R^a$ is H or $—C_{1-8}$alkyl (methyl or ethyl).

Aspect 6: The compound according to Aspect 5, wherein $X_2$ is —O—, or $—NR^a—$; $R^a$ is hydrogen or $—C_{1-8}$alkyl (methyl or ethyl).

Aspect 7: The compound according to Aspects 1 or 2, wherein $m_1$ is 0.

Aspect 8: The compound according to Aspects 1 or 2, wherein $m_2$ is 1; and $m_3$ is 0 or 1.

Aspect 9: The compound according to Aspects 1 or 2, wherein $R_2$, $R_3$, $R_4$, and $R_5$ are each hydrogen, methyl or ethyl, $—CH_2OH$, $—CH_2OCH_3$, $—CH_2OC_2H_5$, $—CHF_2$, $—CH_2OCH(CH_3)_2$, cyclopropyl, or $CF_3$.

Aspect 10: The compound according to Aspects 1 or 2, wherein $R_4$ and $R_5$ together with the same carbon atom to which they are attached form a spiro 3- to 5-membered carbon ring.

Aspect 11: The compound according to Aspect 1 or 2, wherein

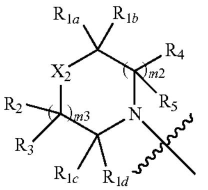

is

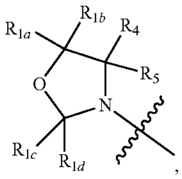

,

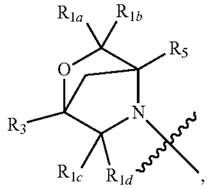

,

-continued

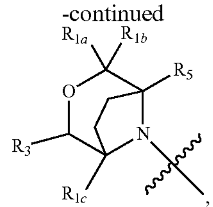

,

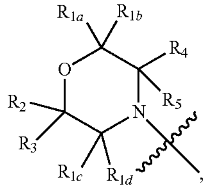

, or

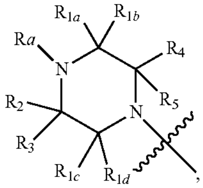

,

Wherein $R_{1a}$, $R_{1b}$, $R_{1d}$, $R_{1d}$, $R_2$, $R_3$, $R_4$, $R_5$ and $R_a$ are defined as for Formula (I).

Aspect 12: The compound according to Aspect 11, wherein

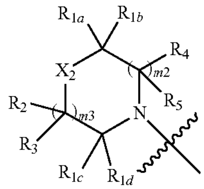

is

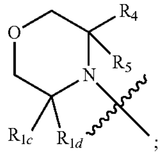

;

wherein $R_{1c}$, $R_{1d}$, $R_4$ and $R_5$ are independently hydrogen or $—C_{1-8}$alkyl.

Aspect 13: The compound according to Aspect 12, wherein $R_{1c}$ and $R_4$ are hydrogen, $R_{1d}$ and $R_5$ are independently hydrogen or $—C_{1-8}$alkyl; preferably, $R_{1c}$ and $R_4$ are hydrogen, $R_{1d}$ and $R_5$ are methyl.

Aspect 14: The compound according to Aspect 11, wherein $R_{1a}$, $R_{1b}$, $R_{1c}$, $R_{1d}$, $R_2$, $R_3$, $R_4$, $R_5$ and $R_a$ are each independently hydrogen, halogen, $—C_{1-8}$alkyl (such as $—CH_3$ or $—C_2H_5$), or oxo, wherein said $—C_{1-8}$alkyl is optionally substituted with at least one halogen (for example 1-3 halogen).

Aspect 15: The compound according to Aspect 14, wherein $R_5$ is halogen, $—C_2H_5$, $—CH_3$, oxo, cyclopropyl, $CHF_2$, $—CH_2F$, $—CF_3$, $—CH_2OH$, $—CH_2OCH_3$, $—CH_2OC_2H_5$, $—CH_2OCH(CH_3)_2$; and $R_4$ is hydrogen or $—CH_3$; or $R_5$ and $R_4$ together with the carbon atom attached form a 3- to 5-membered carbon ring; or $R_2$ and $R_4$ together form a bridge comprising one $—CH_2—$ moiety in the bridge, and $R_3$ and $R_5$ are each hydrogen; or $R_{1b}$ and $R_4$ together form a 3-membered carbon ring, and $R_{1a}$ and $R_5$ are each hydrogen; or $R_{1d}$ and $R_4$ together form a bridge comprising two $—CH_2—$ moieties in the bridge, and $R_{1c}$ and $R_5$ are each hydrogen.

Aspect 16: The compound according to Aspect 11 or 12, wherein
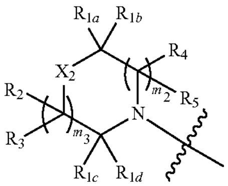
is
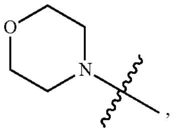
,
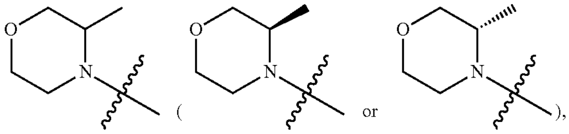
( or ),
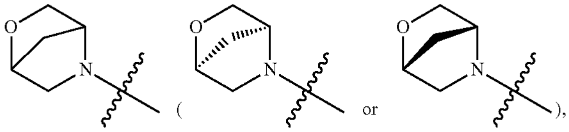
( or ),
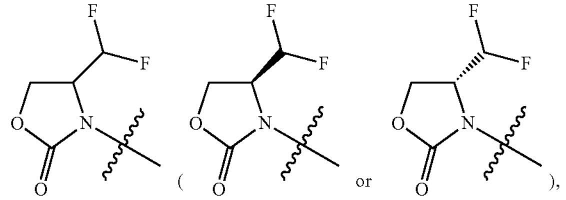
( or ),
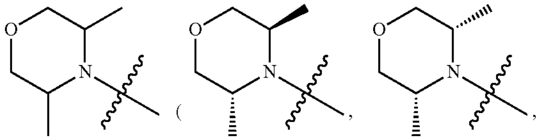
( , ,
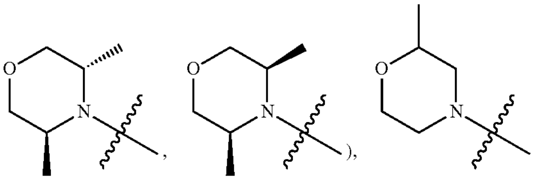
, ),
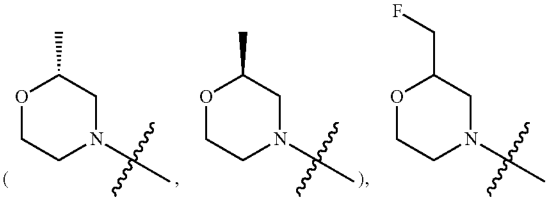
( , ),
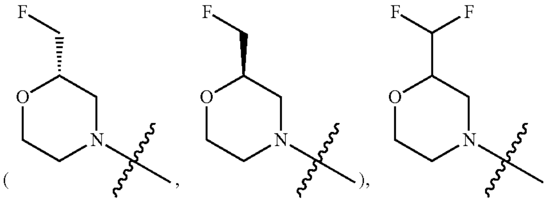
( , ),
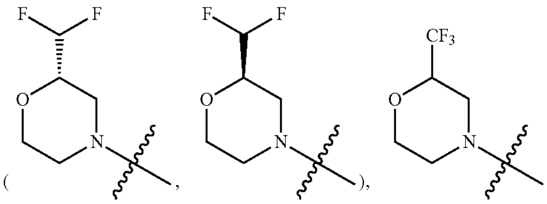
( , ),
-continued
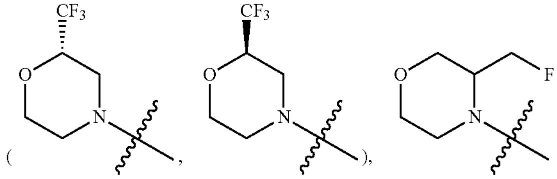
( , ),
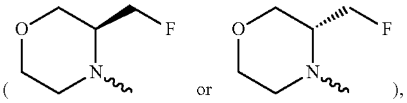
( or ),
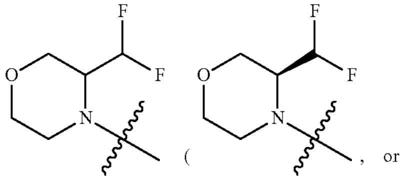
( , or
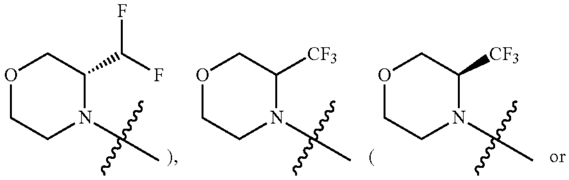
), ( or
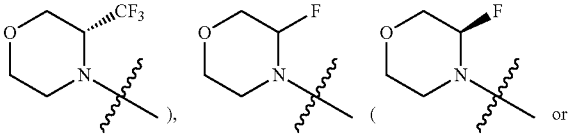
), ( or
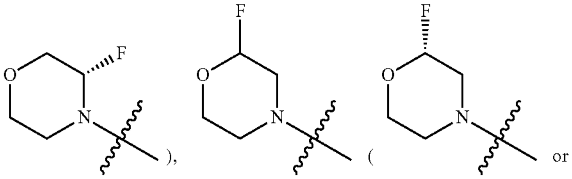
), ( or
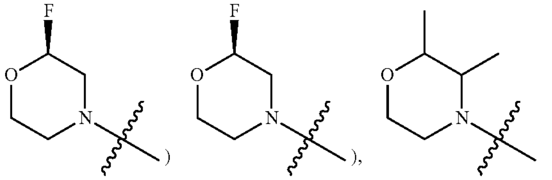
) ),
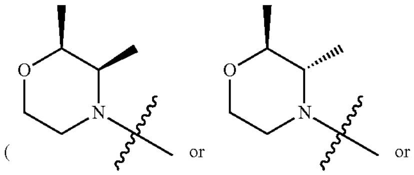
( or or
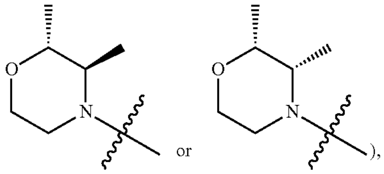
or ),
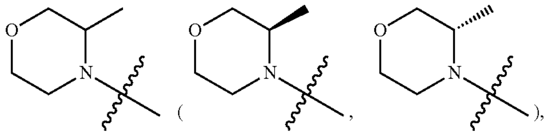
( , ), -continued
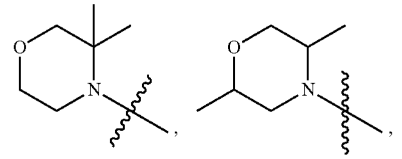
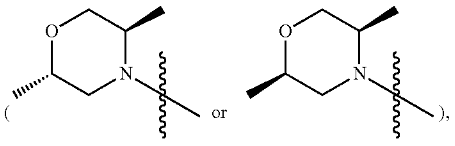
or
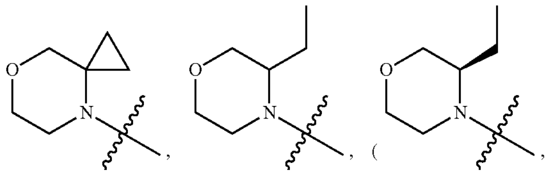
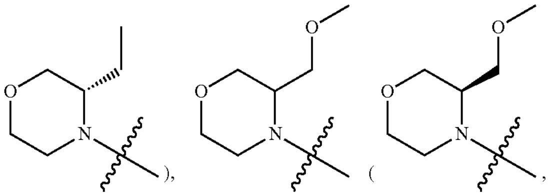
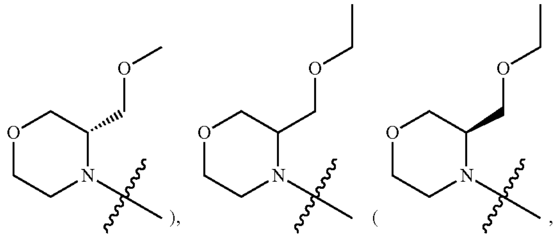
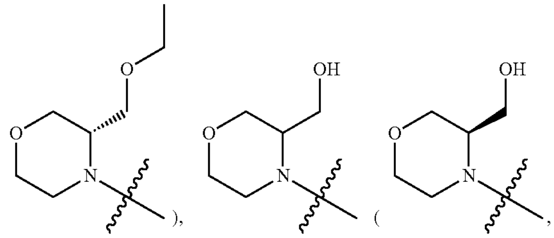
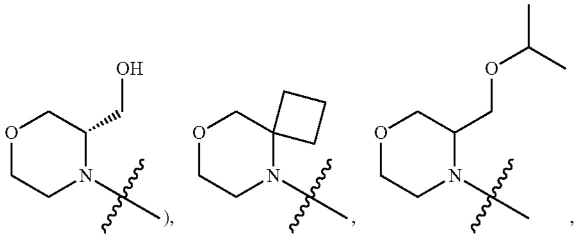
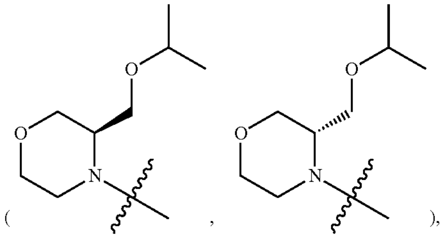
-continued
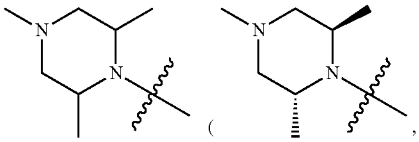
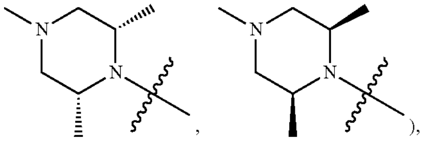
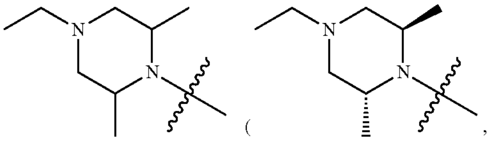
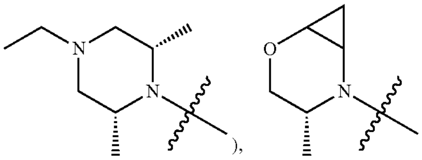
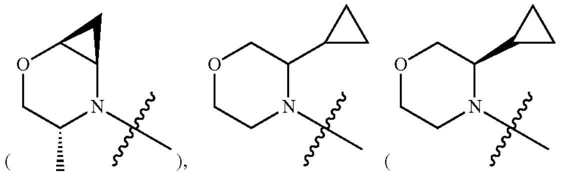
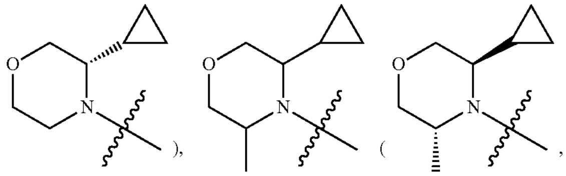
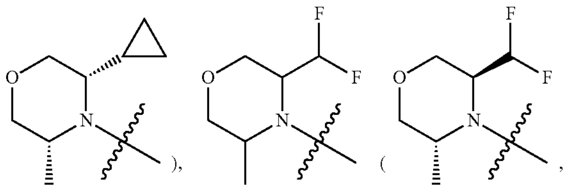
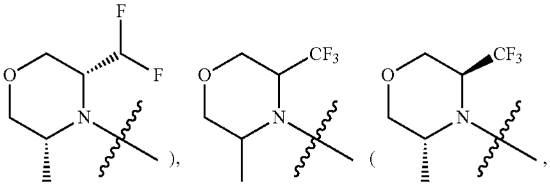
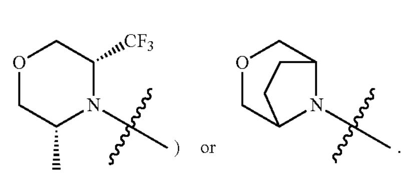
or
Aspect 17: The compound according to Aspects 1 or 2, wherein

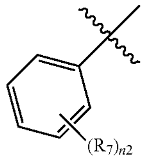

is

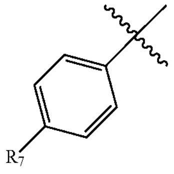

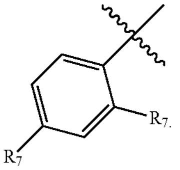

Aspect 18: The compound according to Aspect 17, wherein $R_7$ is halogen.

Aspect 19: The compound according to Aspect 18, wherein $R_7$ is F.

Aspect 20: The compound according to Aspects 1 or 2, wherein $R_6$ is hydrogen, —CN, halogen, morpholino, —$CONR^aR^b$, —$OR^a$, —$NR^aR^b$, —$C_{3-5}$cycloalkyl, phenyl or —$C_{1-8}$alkyl, said —$C_{1-8}$alkyl or —$C_{3-5}$cycloalkyl or phenyl is optionally substituted with at least one $R^d$; $R^a$ and $R^b$ are each hydrogen, —$C_{3-6}$cycloalkyl or —$C_{1-8}$alkyl; $R^d$, at each of its occurrences, is independently —$CH_2F$, —$CHF_2$, —$CF_3$, —F, —Cl, —Br, —OH, —$NH_2$, —SH, —CN, —$CONH_2$, —H, —$CH_3$, —$C_2H_5$, —$C_3H_7$, —$CH_2OH$, —$OCH_3$, —$OC_2H_5$, morpholino,

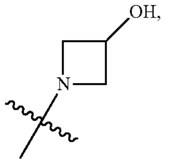

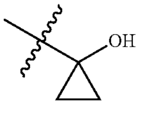

or cyclopropyl.

Aspect 21: The compound according to Aspects 1 or 2, wherein $R_6$ is —$CONR^aR^b$, —$NR^aR^b$, —$NR^aCO$—$R^b$, —$NR^a$—$SO_2$—$R^b$, or —$OR^a$; $R^a$ and $R^b$ are each hydrogen, —$C_{3-6}$ cycloalkyl, —$C_{1-8}$alkyl, 5- or 6-membered heterocyclyl, aryl or heteroaryl; each of said —$C_{1-8}$alkyl, —$C_{3-6}$ cycloalkyl, 5- or 6-membered heterocyclyl, aryl, or heteroaryl is optionally substituted with 1-3 $R^d$; or $R^a$ and $R^b$ together with the atom(s) to which they are attached, form a 3- to 8-member ring, said ring comprising 0, 1 or 2 additional heteroatoms independently selected from nitrogen, oxygen or optionally oxidized sulfur as ring member(s), said ring is optionally substituted with 1-3 $R^d$;

$R^d$, at each of its occurrences, is independently hydrogen, halogen, —$C_{1-8}$alkyl, —$C_{2-8}$alkenyl, —$C_{2-8}$alkynyl, —$C_{3-8}$cycloalkyl, heterocyclyl, aryl, heteroaryl, oxo, —CN, —$NO_2$, —$OR^e$, —$SR_a$, —$SO_2R^e$, —$SO_2NR^eR^f$, —$COR^e$, —$CO_2R^e$, —$CONR^eR^f$, —C(=$NR^e$)$NR^fR^g$, —$NR^eR^f$, —$NR^eCOR^f$, —$NR^e$-$CONR^fR^g$, —$NR^eCO_2R^f$, —$NR^eSONR^fR^g$, —$NR^eSO_2NR^fR^g$, or —$NR^eSO_2R^f$, each of said —$C_{1-8}$alkyl, —$C_{2-8}$alkenyl, —$C_{2-8}$alkynyl, —$C_{3-8}$cycloalkyl, heterocyclyl, aryl, or heteroaryl is optionally substituted with at least one substituent selected from halogen, —$C_{1-8}$alkyl, —$OR^h$, —$NR^hR^i$, cycloalkyl, heterocyclyl, aryl, or heteroaryl; and $R^e$, $R^f$, $R^g$, $R^h$, and $R^i$ are each independently hydrogen, —$C_{1-8}$alkyl, $C_{1-8}$alkoxy-$C_{1-8}$alkyl-, —$C_{2-8}$alkenyl, —$C_{2-8}$alkynyl, cycloalkyl, heterocyclyl, aryl, aryl-$C_{1-8}$alkyl- or heteroaryl.

Aspect 22: The compound according to Aspect 21, wherein $R_6$ is —$CONR^aR^b$ or —$NR^aCO$—$R^b$, $R^a$ and $R^b$) are each hydrogen, —$C_{1-3}$alkyl, —$C_{3-6}$ cycloalkyl, phenyl, 5- or 6-membered heterocyclyl (such as azetidine, pyrrolidine, piperidine, oxazolidine, isoxazolidine, oxazinane, morpholine, piperazine, tetrahydropyran or tetrahydrofuran); said —$C_{1-3}$alkyl, —$C_{3-6}$ cycloalkyl, phenyl, 5- or 6-membered heterocyclyl(such as azetidine, pyrrolidine, piperidine, oxazolidine, isoxazolidine, oxazinane, morpholine, piperazine, tetrahydropyran or tetrahydrofuran) optionally substituted with at least one substituent selected from halogen, —$C_{1-3}$alkyl, morpholine, $OR^e$ or —$NR^eR^f$; $R^e$ and $R^f$ are independently hydrogen, halogen, —$C_{1-8}$alkyl or $C_{1-8}$alkoxy-$C_{1-8}$alkyl-.

Aspect 23: The compound according to Aspect 21, wherein $R_6$ is —$CONR^aR^b$, $R^a$ and $R^b$ together with the nitrogen atom to which they are attached, form a 4- to 6-member ring, said ring comprising 0, 1 or 2 additional heteroatoms independently selected from nitrogen, oxygen or optionally oxidized sulfur as ring member(s), said ring is optionally substituted with 1-3 $R^d$; $R^d$, at each of its occurrences, is independently halogen, —$C_{1-3}$alkyl, or $OR^e$; $R^e$ is independently hydrogen, halogen or —$C_{1-8}$alkyl.

Aspect 24: The compound according to Aspect 21, wherein $R_6$ is —$NH_2$, —$CONH_2$, —$CONHCH_3$, —$CONHC_2H_5$, —$CON(CH_3)_2$, —$CONHCH_2CF_3$, —$CONHC_2H_4OCH_3$, —$CONHC_2H_4OC_2H_4OCH_3$, —$CONHCH(CH_3)_2$, —$CONHC_2H_4OH$, —$CONHC_2H_4N(CH_3)_2$,

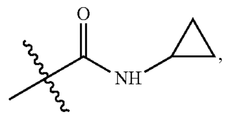

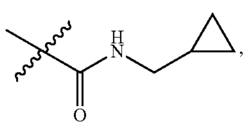

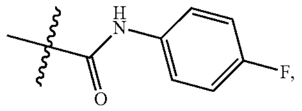

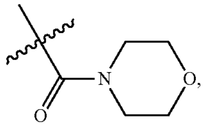

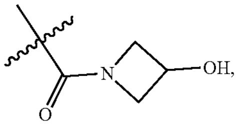

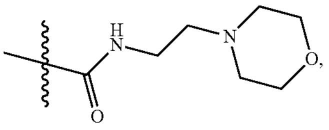

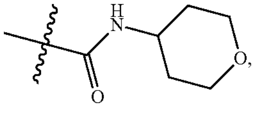

-continued
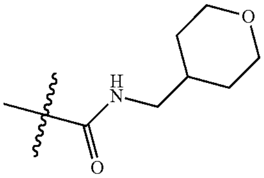,
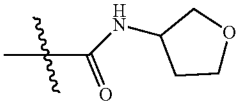
(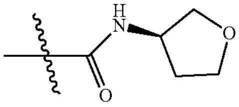, 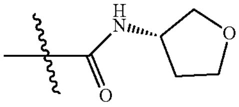),
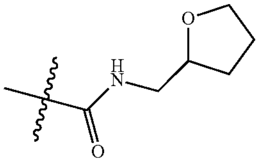
(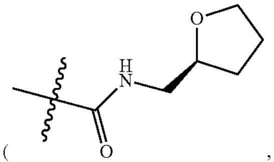,
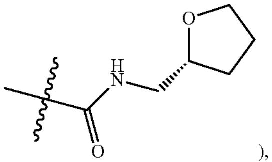),
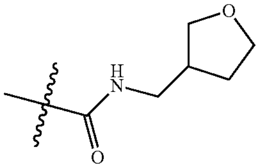
(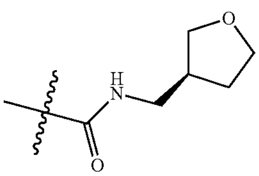,
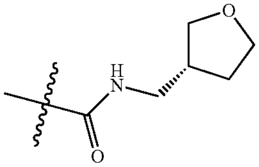),
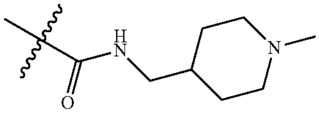,
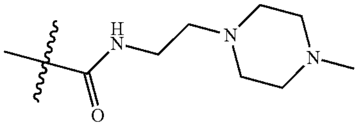,
-continued
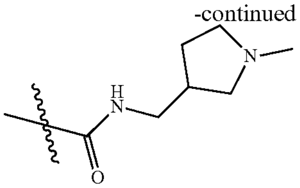
(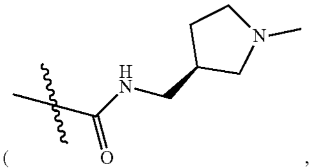,
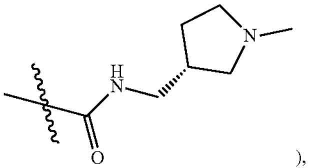),
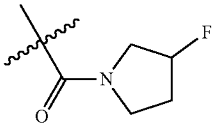 (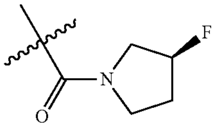,
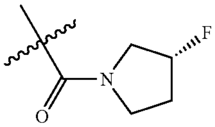), 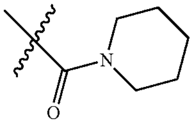,
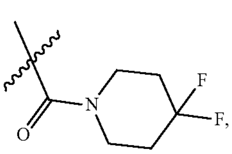, 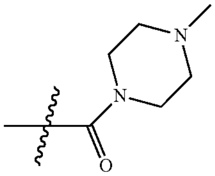,
$-O-(CH_2)_2-OCH_3$, $-O-(CH_2)_2-OH$,
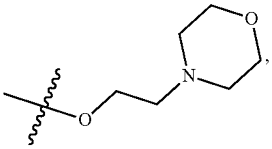 [SMILES: *OCCN1CCOCC1],
$-NH-(CH_2)_2-OCH_3$, $-NH-(CH_2)_2-OH$,
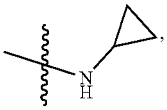 [SMILES: *NC1CC1],
$-NH-CO-CH_3$, $-NH-CO-C_2H_5$, $-NH-CO-CH(CH_3)_2$,
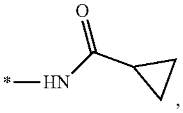, -continued

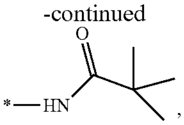

,

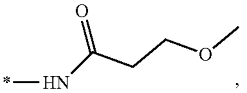

,

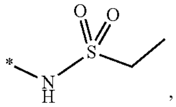

,

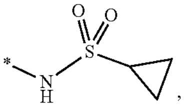

,

—$NHC_2H_5$, —NH—$CH_2$—$CF_3$, $CH_3CH_2SO_2NH$—, or Cyclopropyl$SO_2NH$—.

Aspect 25: The compound according to Aspect 20, wherein $R_6$ is hydrogen, halogen, —CN, —$CONH_2$,

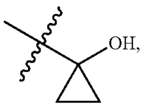 [SMILES: *C1(O)CC1]

cyclopropyl, —$CH_2OH$, —$CF_3$, —OH, —$CH_3$ or —$OC_2H_5$.

Aspect 26: The compound according to Aspects 1 or 2, wherein $R_{12}$ and $R_{13}$ are each independently hydrogen or —$C_{1-8}$alkyl.

Aspect 27: The compound according to Aspect 26, wherein $R_{12}$ is hydrogen or —$CH_3$; $R_{13}$ is hydrogen or —$CH_3$.

Aspect 28: The compound according to Aspects 1 or 2, wherein $R_{10}$ and $R_{11}$ are each independently hydrogen, —$C_{1-8}$alkyl, —$C_{3-8}$cycloalkyl, —$C_{5-6}$aryl, 5- to 6-membered heteroaryl, or —$CONR^aR^b$, wherein each of said —$C_{1-8}$alkyl, —$C_{3-8}$cycloalkyl, —$C_{5-6}$aryl, or 5- to 6-membered heteroaryl is optionally substituted with 1-3 $R^d$;

$R^a$ and $R^b$ are each independently hydrogen or —$C_{1-8}$alkyl; or ($R^a$ and $R^b$), together with the nitrogen atom to which they are attached, form a 3- to 6-member ring, said ring comprising 0 or 1 additional oxygen atom; said ring is optionally substituted with one $R^d$;

$R^d$, at each of its occurrences, is independently —$C_{1-8}$alkyl, halogen, aryl or —$OR^e$, wherein $R^e$ are each independently hydrogen or —$C_{1-8}$alkyl, phenylethyl, benzyl, or phenyl.

Aspect 29: The compound according to Aspect 28, wherein $R_{10}$ is hydrogen; $R_{11}$ is —$CONR^aR^b$, phenyl, benzyl, pyridinyl, or furyl, wherein each of said phenyl, benzyl, pyridinyl or furyl is optionally substituted with 1-3 $R^d$ selected from methyl, methoxy, or halogen; $R^a$ and $R^b$ each are independently hydrogen or methyl, or ($R^a$ and $R^b$), together with the nitrogen atom to which they are attached, form a 5- to 6-member ring, said ring comprising 0 or 1 additional oxygen atom.

Aspect 30: The compound according to Aspect 29, wherein $R_{10}$ is hydrogen; and $R_{11}$ is hydrogen, methyl, ethyl, 1-propyl, 2-propyl, 1-butyl, tert-butyl, 1-methylpropyl, 1,1-dimethylethyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2, 3-dimethyl-2-butyl, 3, 3-dimethyl-2-butyl, cyclopropyl, cyclobutyl, cyclopentyl, cyclohexyl, vinyl, —$CH_2OH$, —$CH_2CH_2OH$, —$CH_2CH_2OCH_3$, —$CH_2OCH_3$, —$CH_2OCH(CH_3)_2$, —$CH_2OC_2H_5$, —$CH_2F$, —$CF_3$, —H, —F, —Cl, —Br, —I, —OH, —$NH_2$, —SH, —$CONH_2$, —$CONHCH_3$, —$CON(CH_3)_2$,

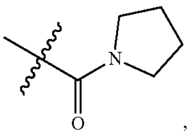

,

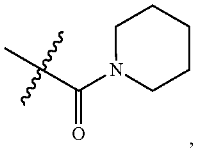

,

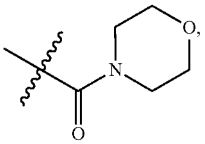

—$CH_2O$-Ph, —$CH_2$-Ph, —$CH_2O$—$CH_2$-Ph, phenyl, 4-methyl-phenyl, 4-methoxy-phenyl, 4-F-phenyl, benzyl, pyridinyl (4-pyridinyl, 3-pyridinyl or 2-pyridinyl), or furyl (2-furyl or 3-furyl). Aspect 31: The compound according to Aspect 30, wherein $R_{10}$ is hydrogen; and $R_{11}$ is hydrogen, methyl, ethyl, 2-propyl, —$CF_3$, —$CHF_2$, —$CH_2CH_2OCH_3$, —$CH_2OH$, —$CH_2OCH_3$, —$CH_2OCH(CH_3)_2$, —$CH_2OC_2H_5$, cyclopropyl, cyclobutyl, cyclopentyl, cyclohexyl, —$CONH_2$, —$CONHCH_3$, —$CON(CH_3)_2$,

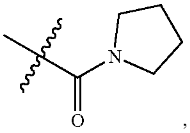

,

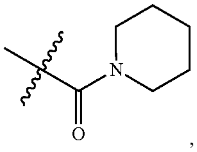

,

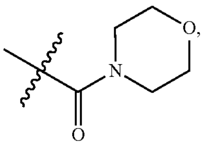

—$CH_2O$-Ph, —$CH_2O$—$CH_2$-Ph, phenyl, 4-methyl-phenyl, 4-methoxy-phenyl, 4-F-phenyl, benzyl, 4-pyridinyl, 3-pyridinyl, 2-pyridinyl, 2-furyl or 3-furyl.

Aspect 32: The compound according to any one of Aspects 1-31, wherein the carbon atom to which $R_{10}$ and $R_{11}$ are attached is in (S)-configuration in the case that $R_{10}$ and $R_{n}$ are different.

Aspect 33: The compound according to Aspects 1 or 2, wherein $R_{10}$ and $R_{11}$ together form a 3-membered carbon ring.

Aspect 34: The compound according to Aspects 1 or 2, which is
(III)
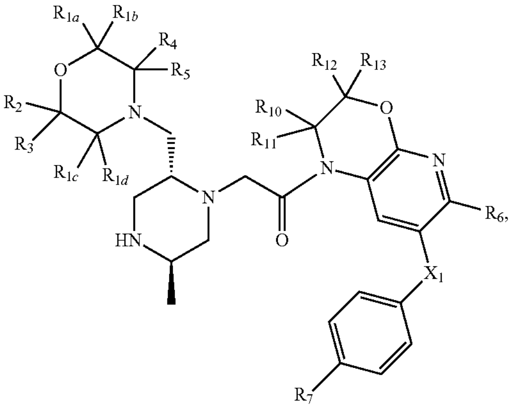
wherein $R_{1a}$, $R_{1b}$, $R_{1c}$, $R_{1d}$, $R_2$, $R_3$, $R_4$, $R_5$, $R_6$, $R_7$, $R_{1c}$, $R_n$, $R_{1a}$, $R_{13}$ and $X_1$ are defined as for Formula (II).
Aspect 35: The compound according to Aspects 1 or 2, wherein $R_{14}$ and $R_{15}$ are each independently selected from hydrogen, or —$C_{1-8}$alkyl (methyl or ethyl).
Aspect 36: The compound according to Aspect 1, which is
1
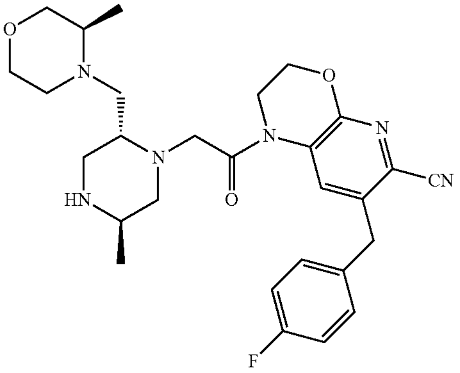
2
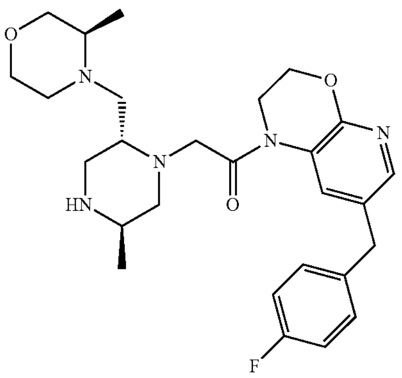
-continued
3
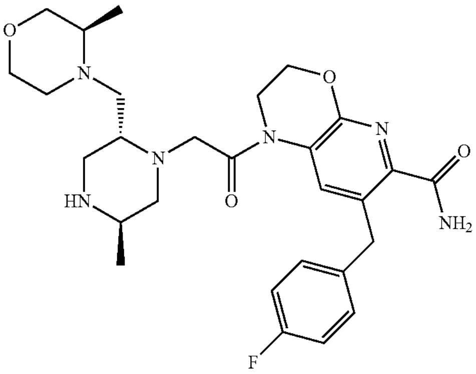
4
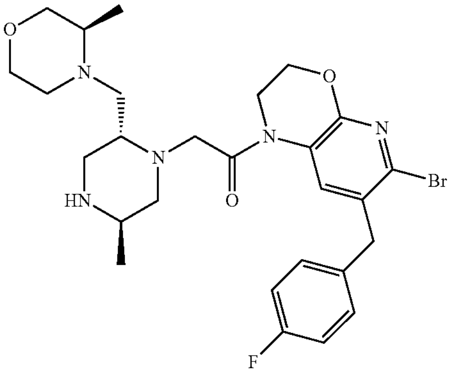
5
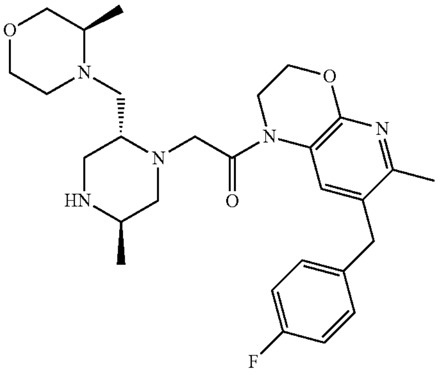
6
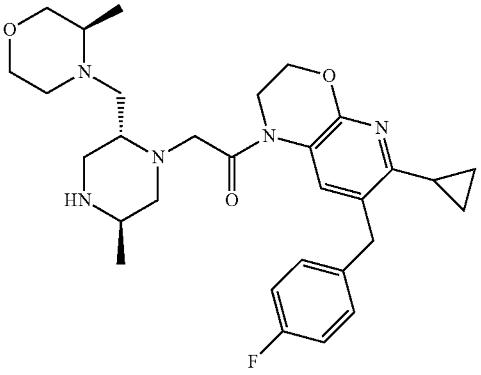

-continued
7
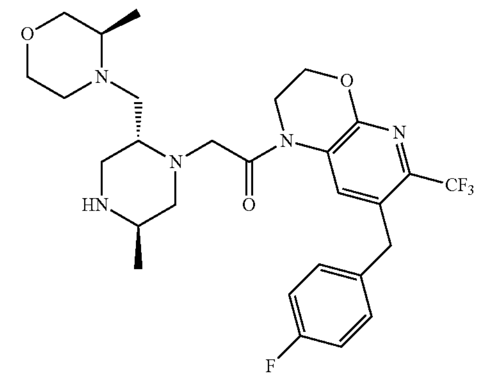
8
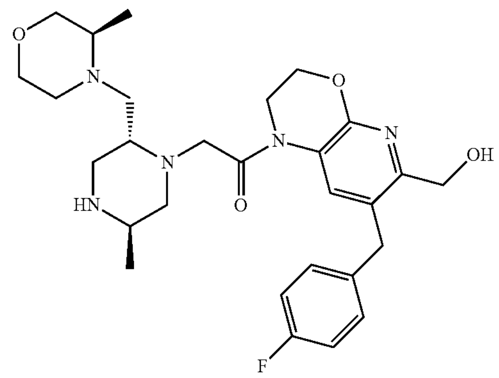
9
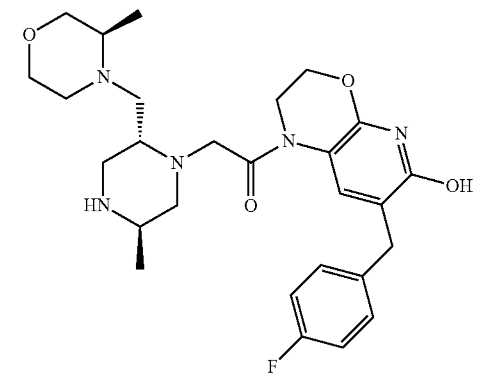
10
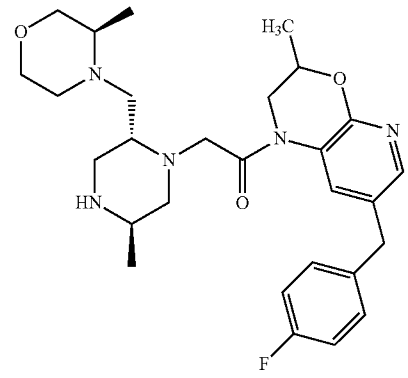
-continued
11
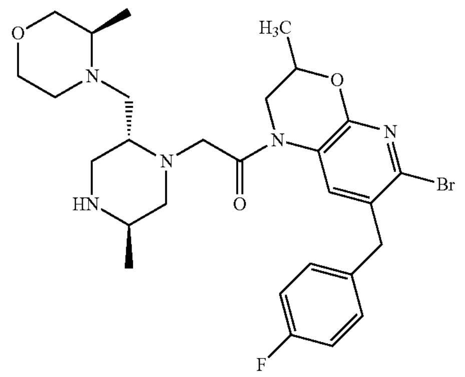
12
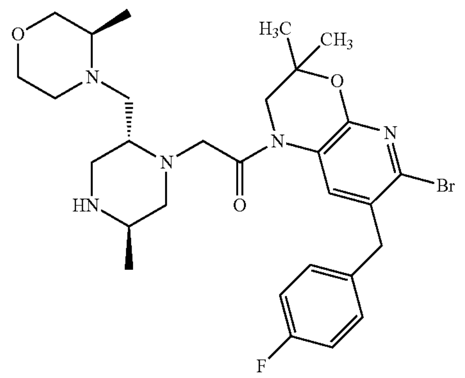
13
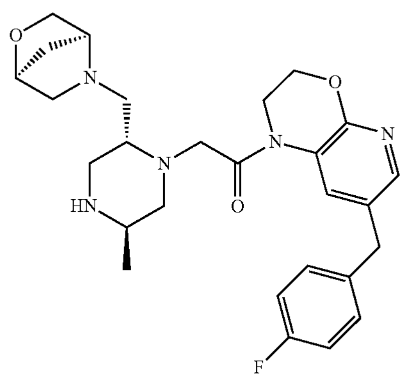
14
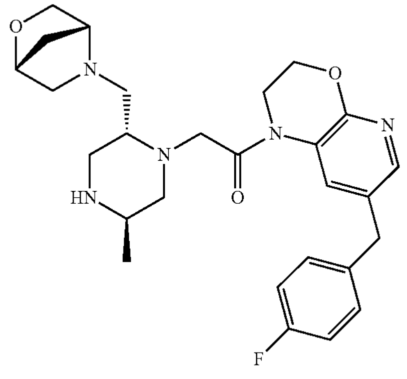

-continued
15
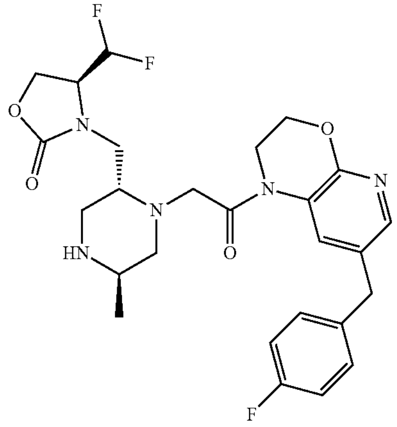
16
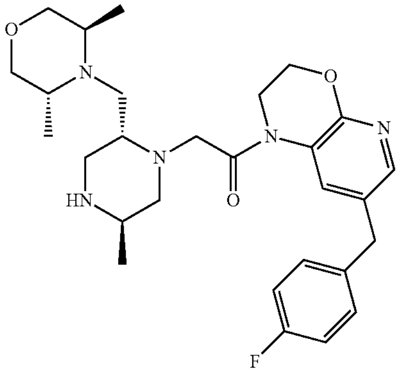
17
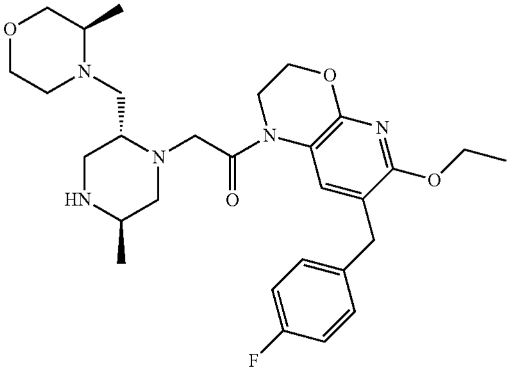
18
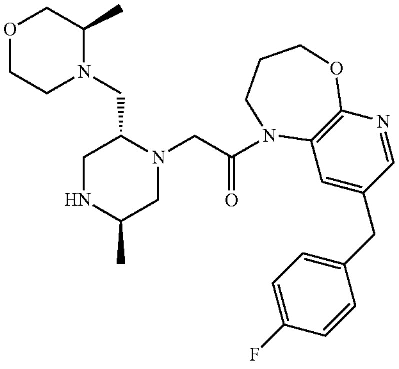
-continued
19
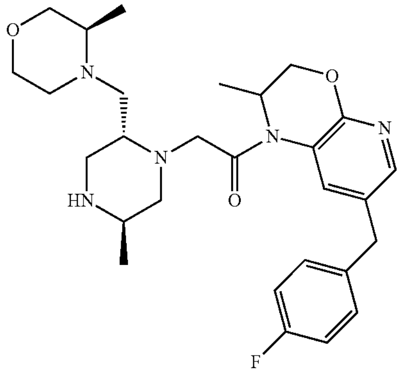
19A/19B
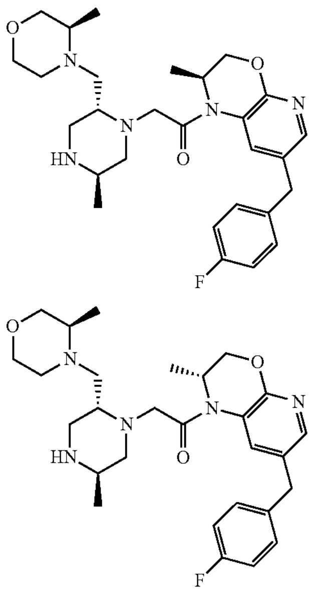
20
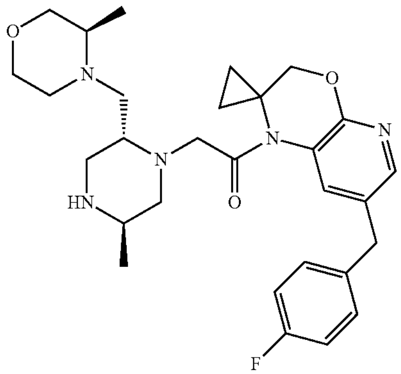

-continued
21
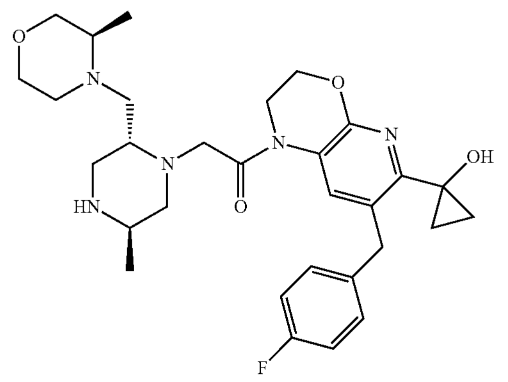
22
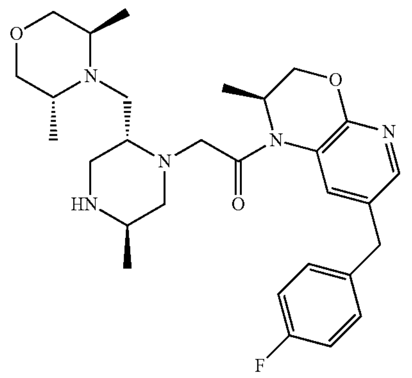
23
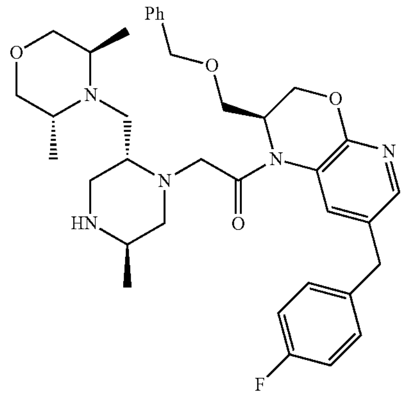
24
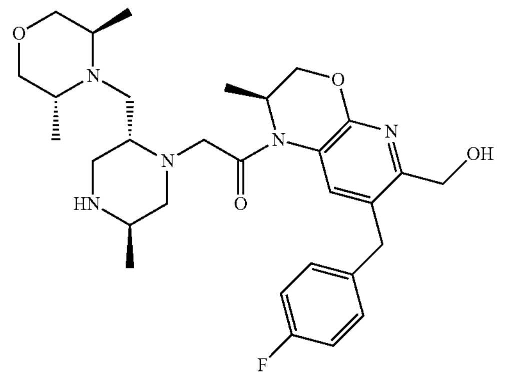
-continued
25
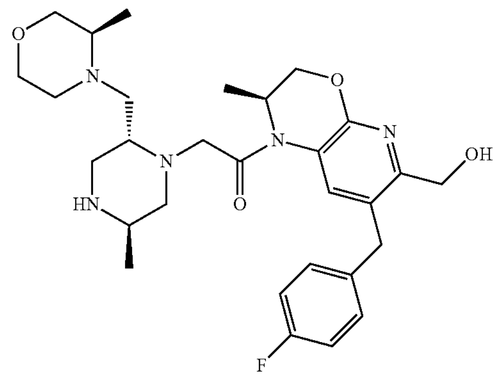
26
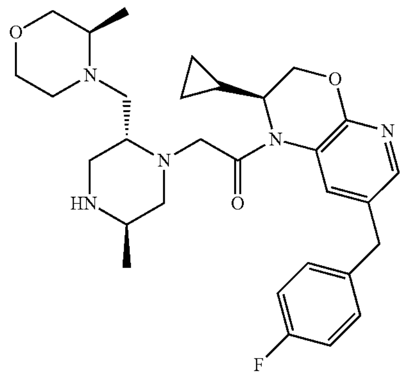
27
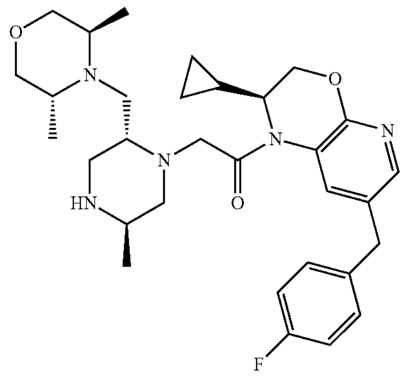
28
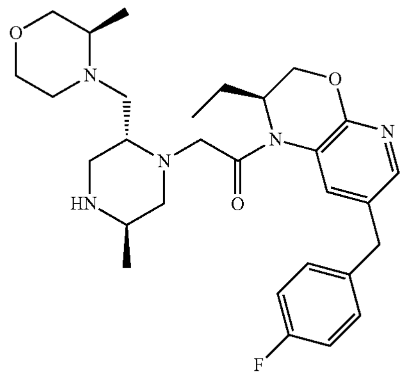

-continued
29
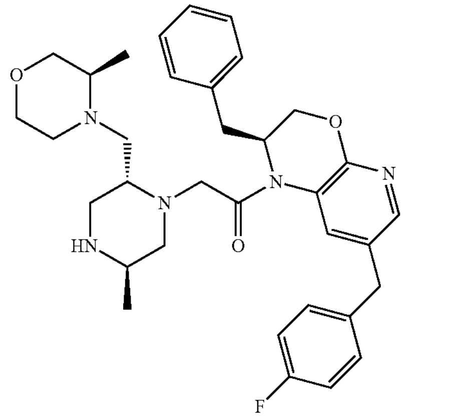
30
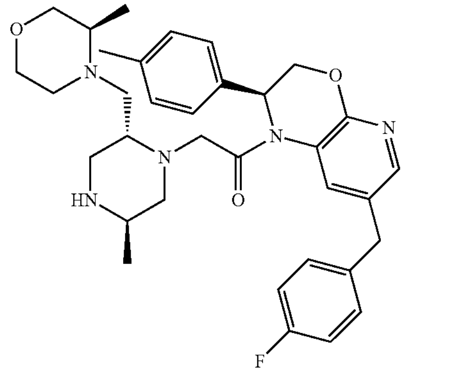
31
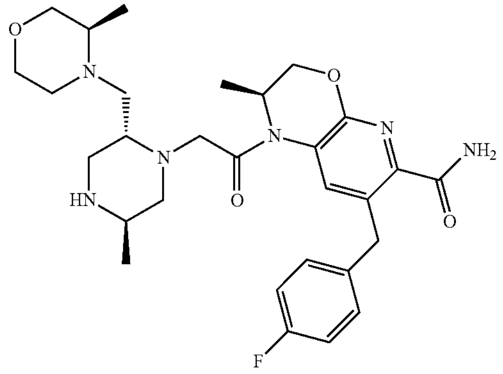
32
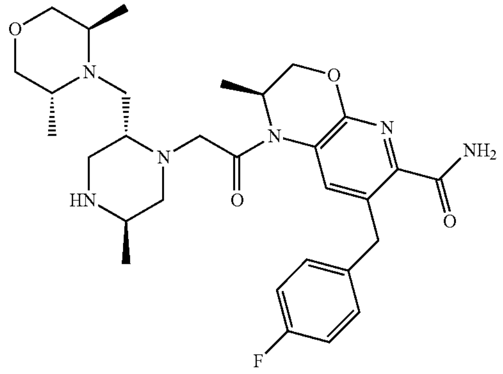
-continued
33
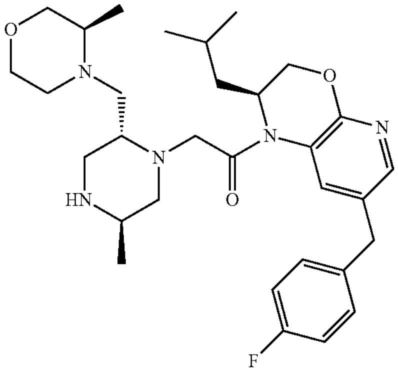
34
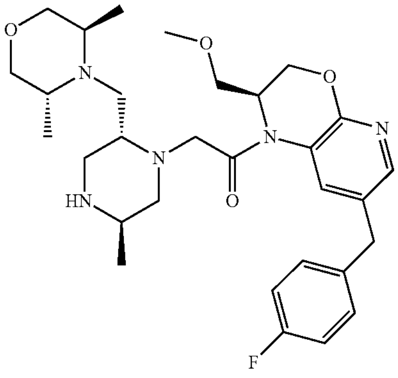
35
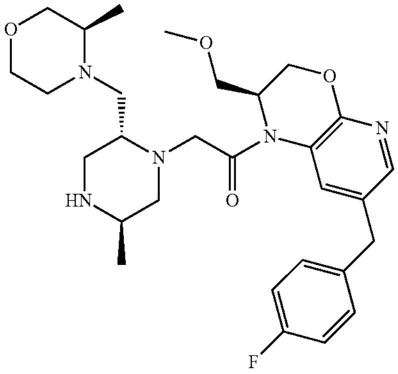
36
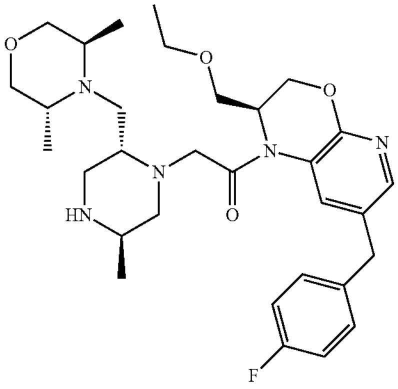

-continued
37
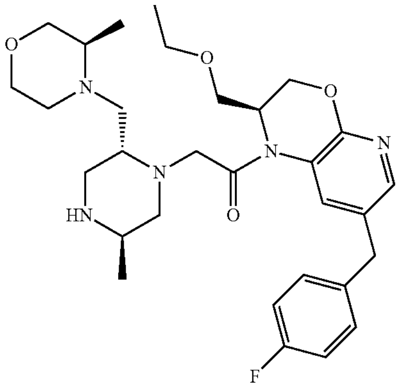
38
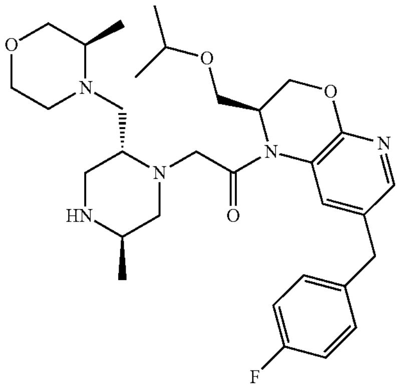
39
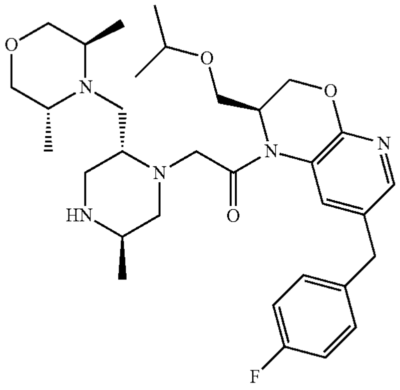
40
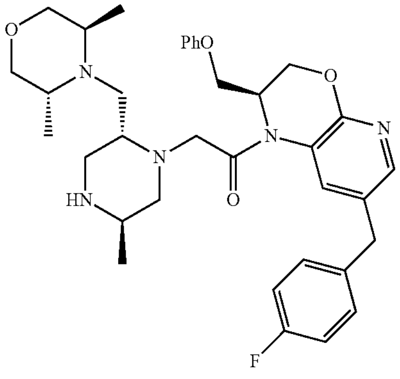
-continued
41
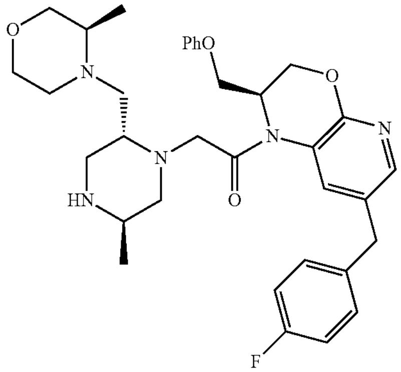
42
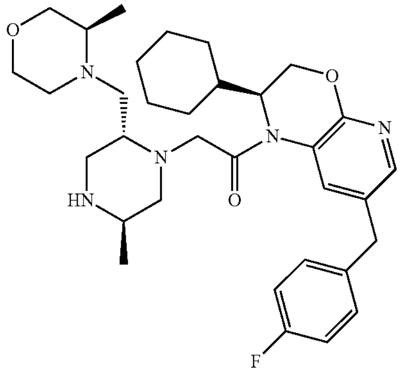
43
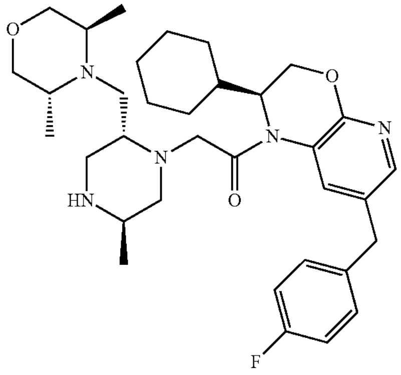
44
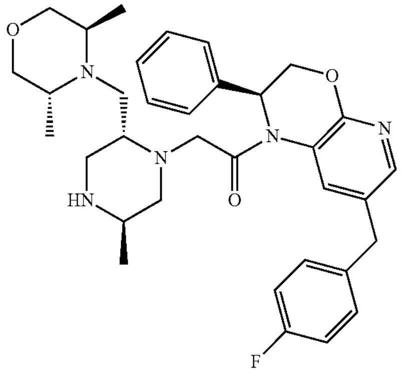

45
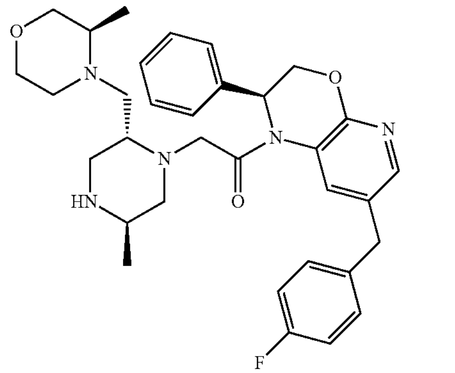
46
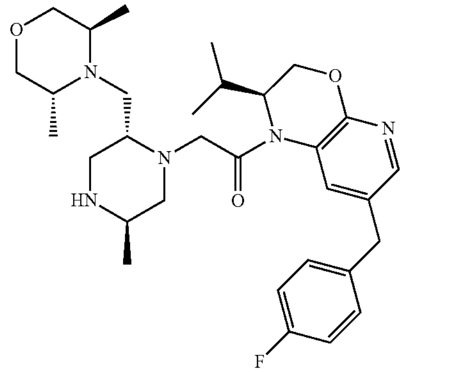
47
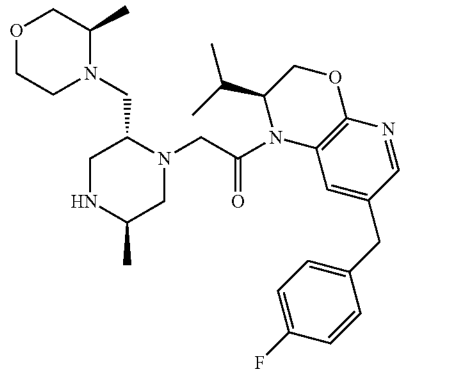
48
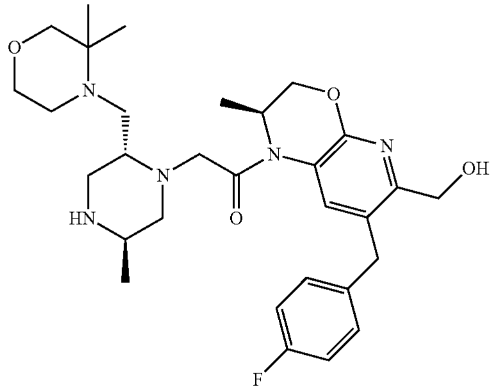
49
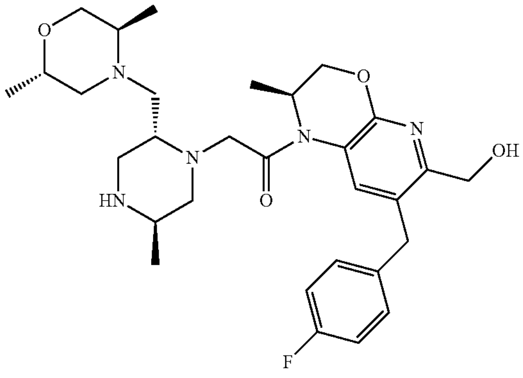
50
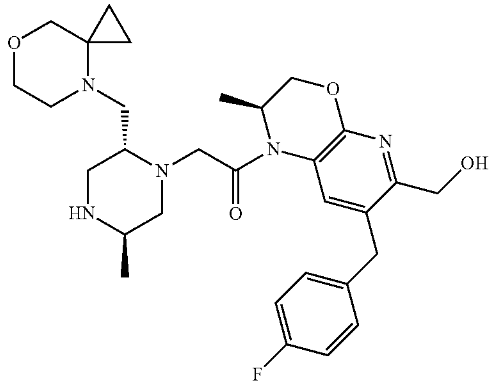
51
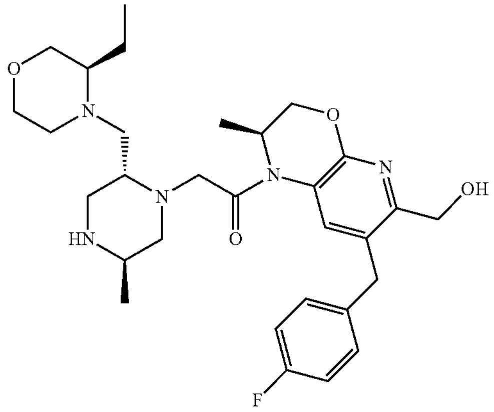
52
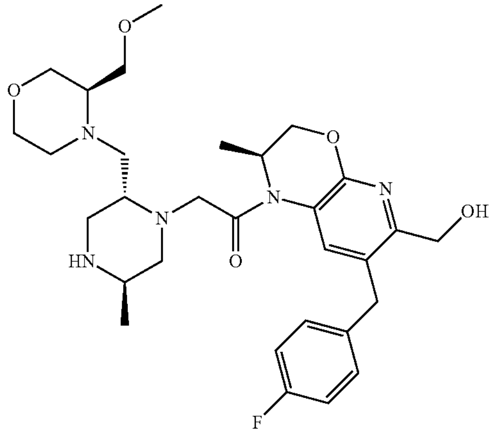

-continued
53
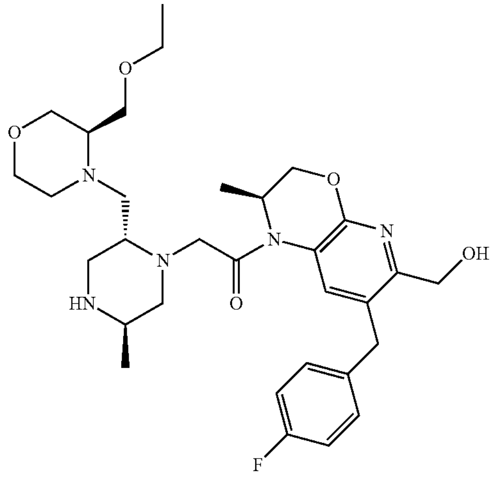
54
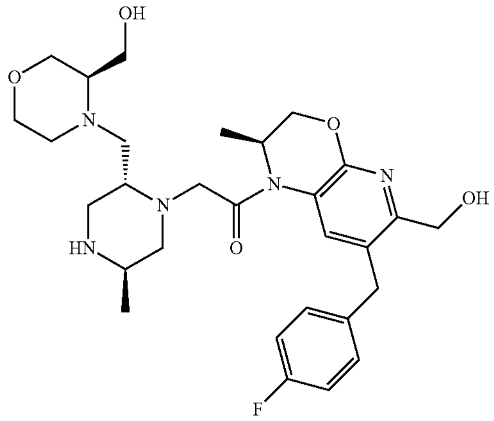
55
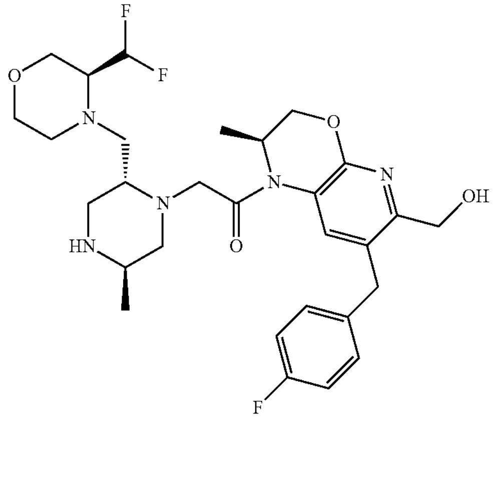
-continued
56
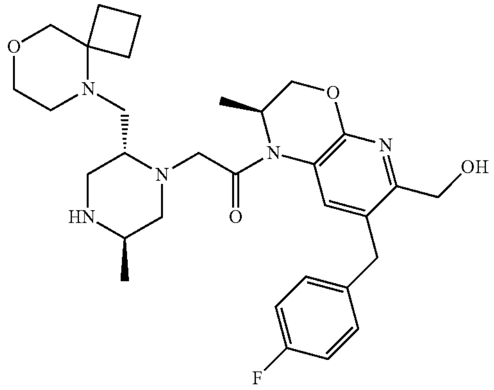
57
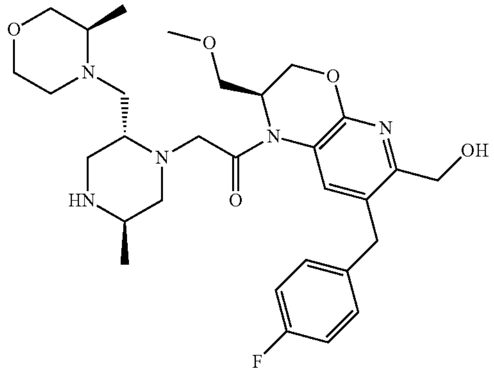
58
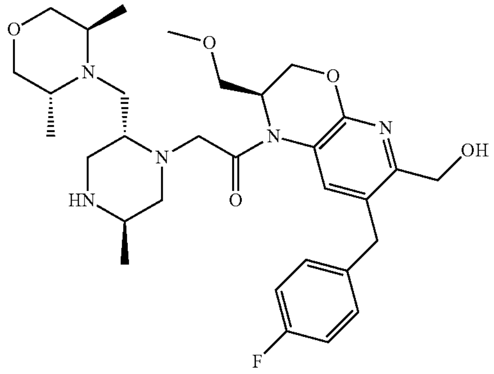
59
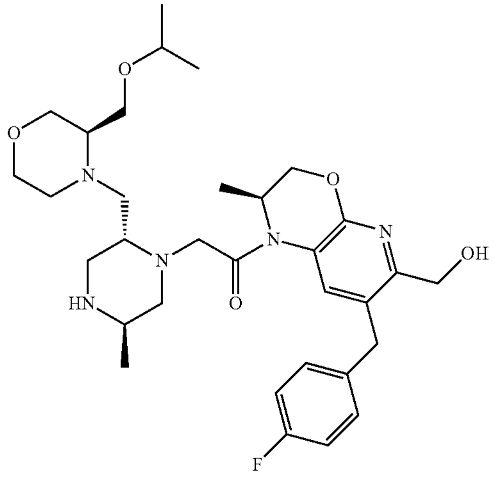

-continued
60
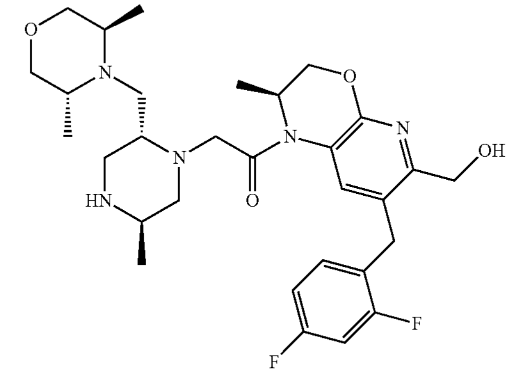
61
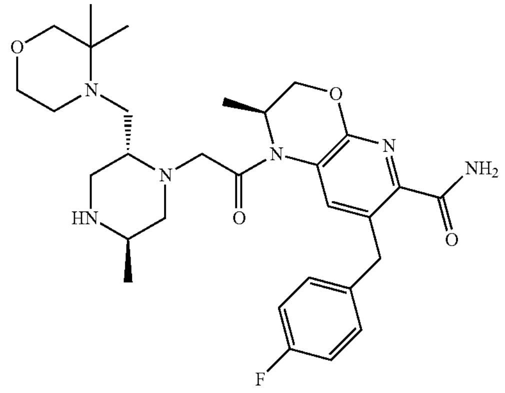
62
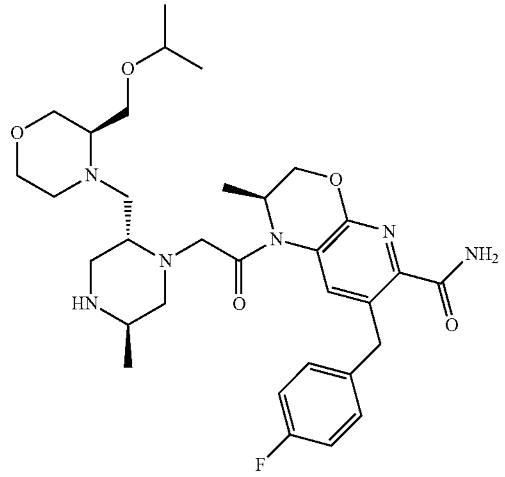
63
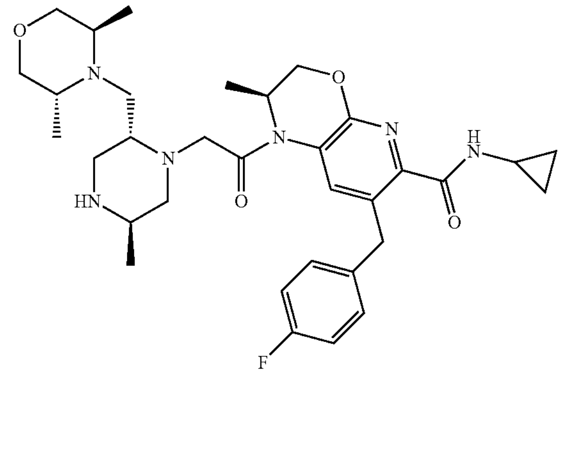
-continued
64
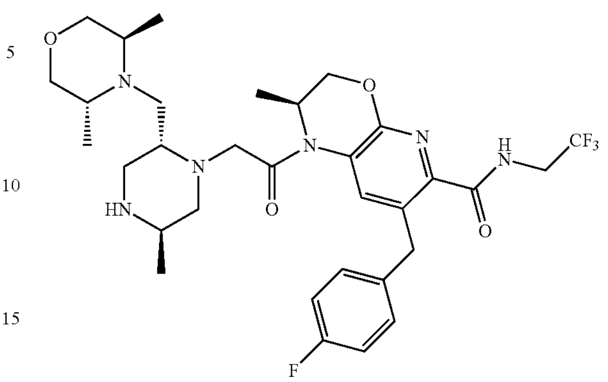
65
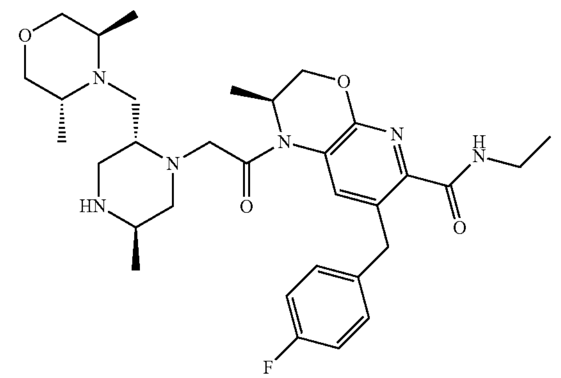
66
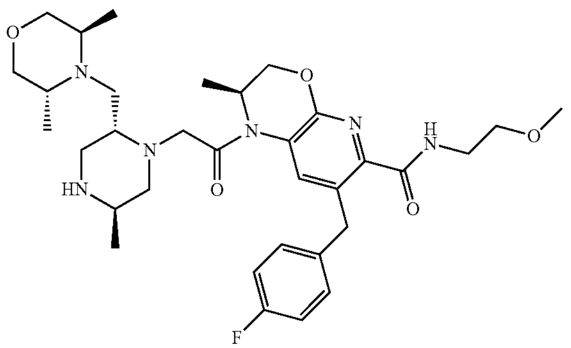
67
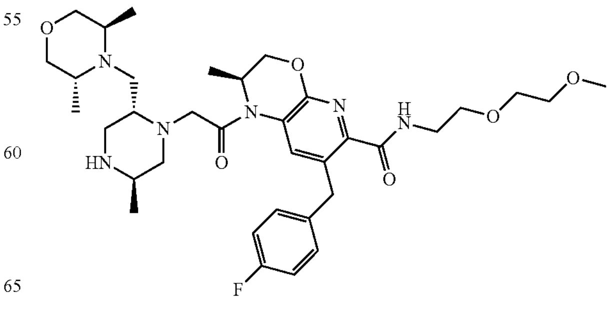

-continued
68
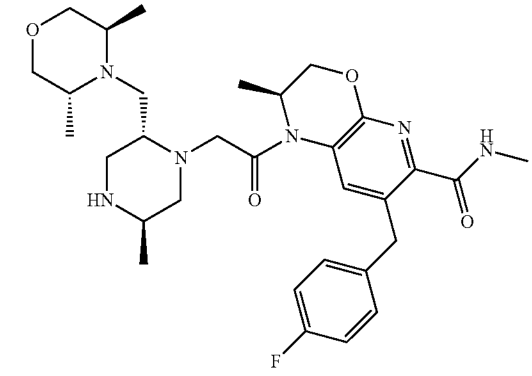
69
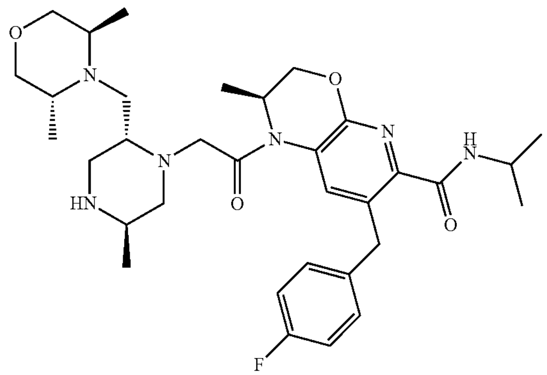
70
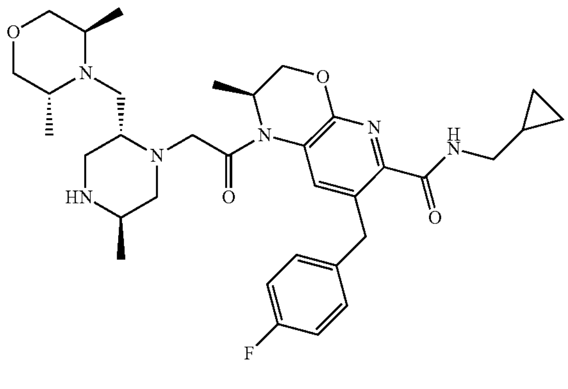
71
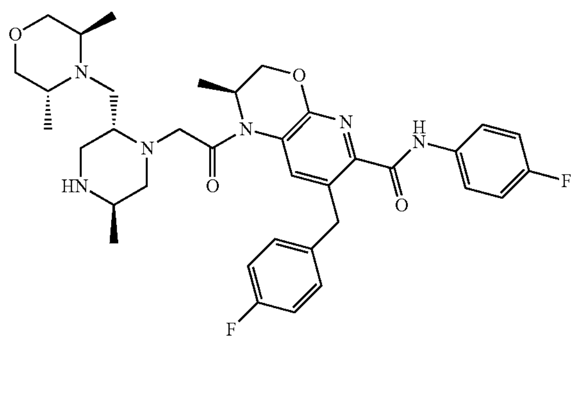
-continued
72
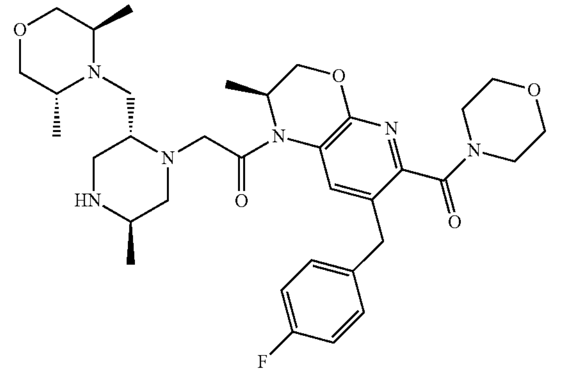
73
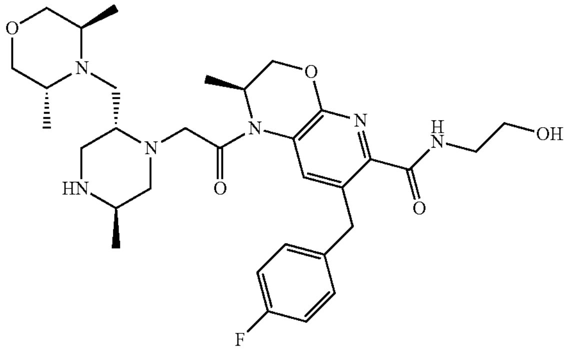
74
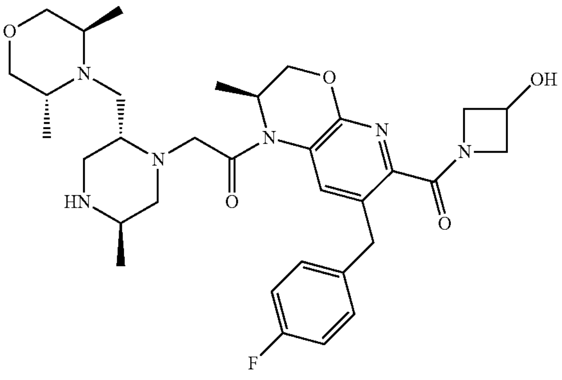
75
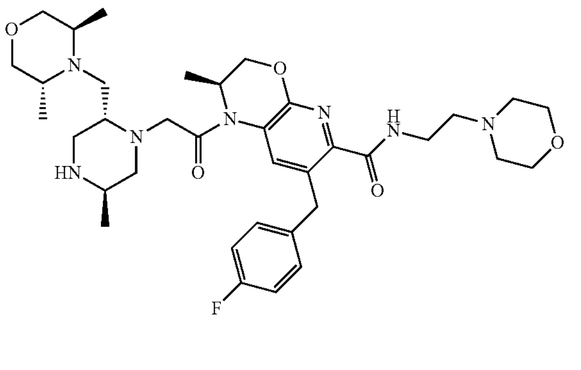

-continued
76
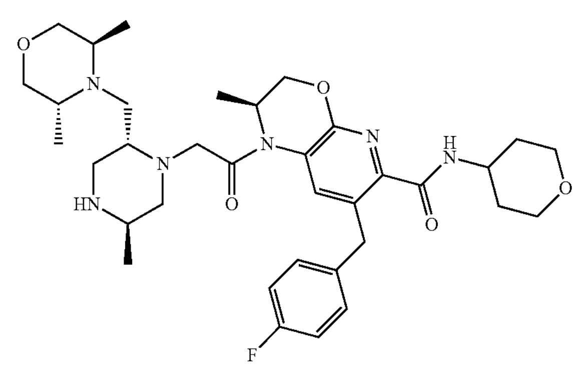
77
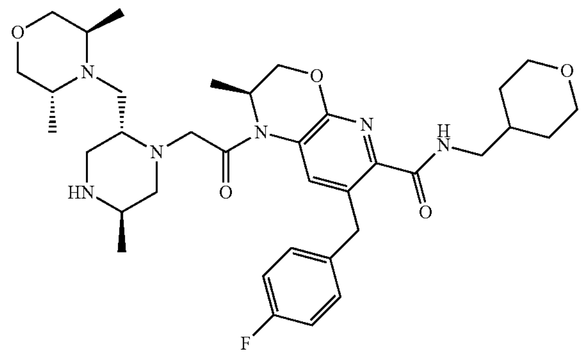
78
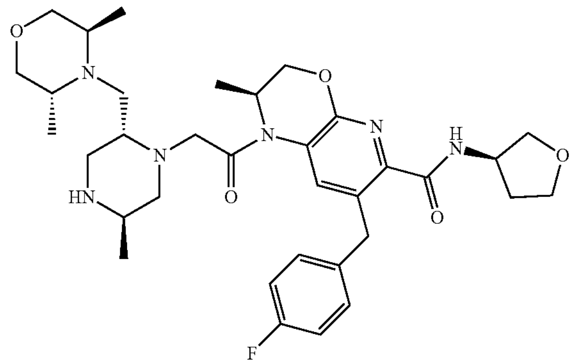
79
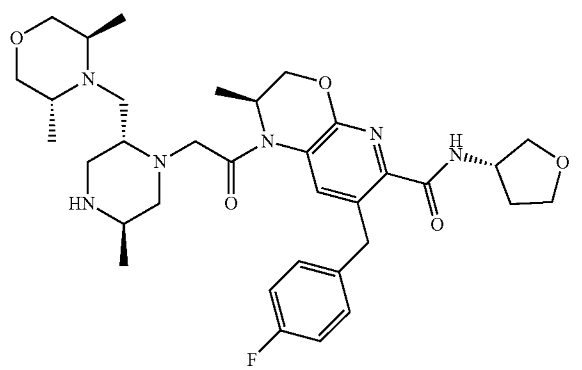
-continued
80
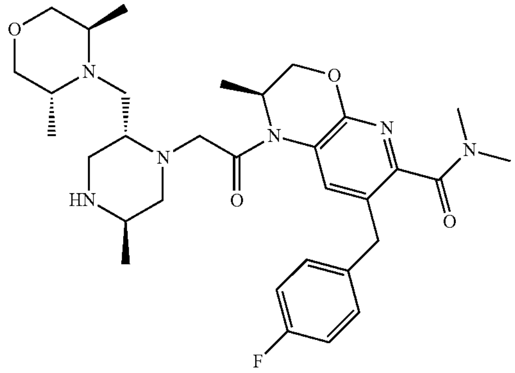
81
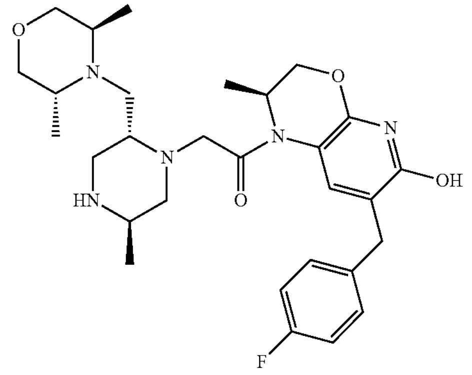
82
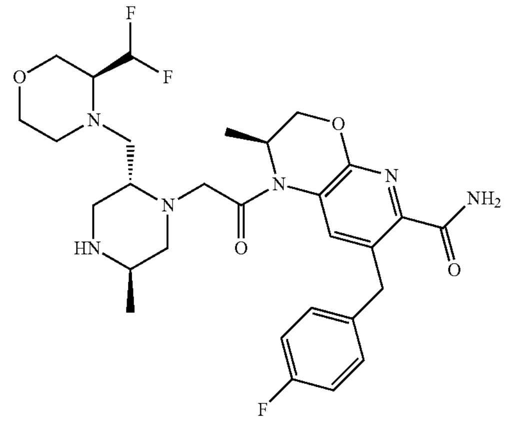
83
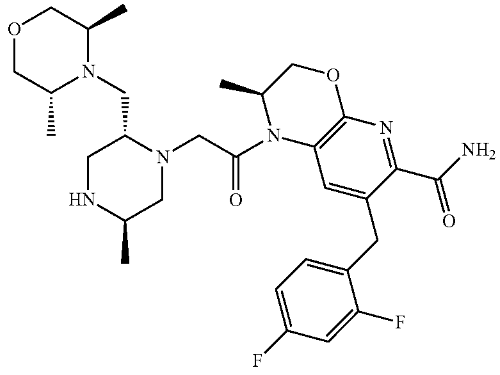

84A/84B
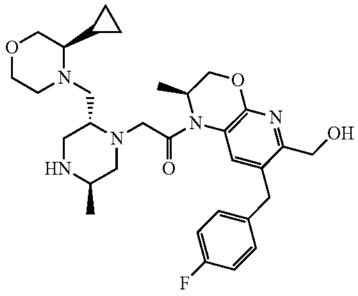
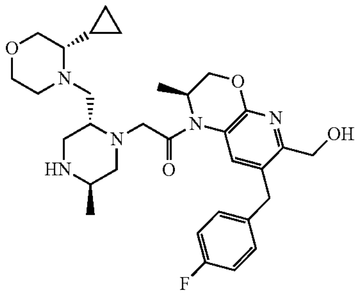
85
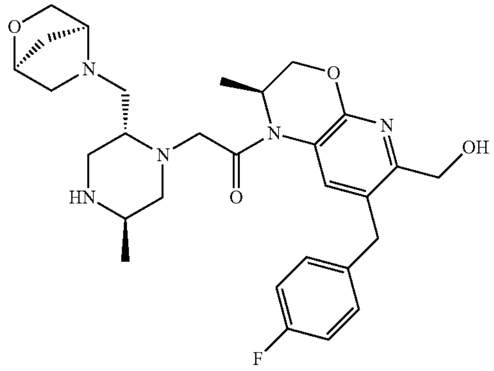
86
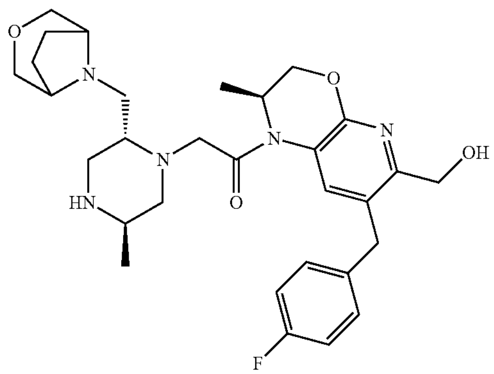
87
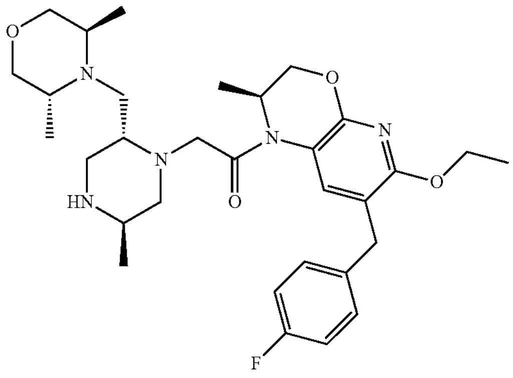
88
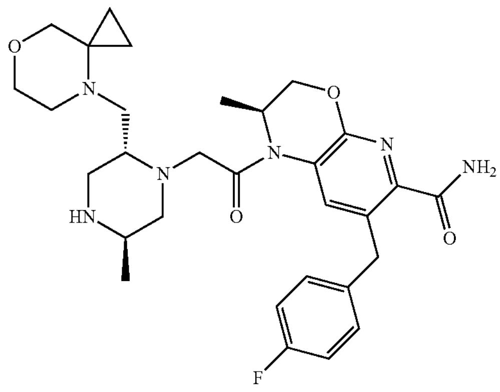
89
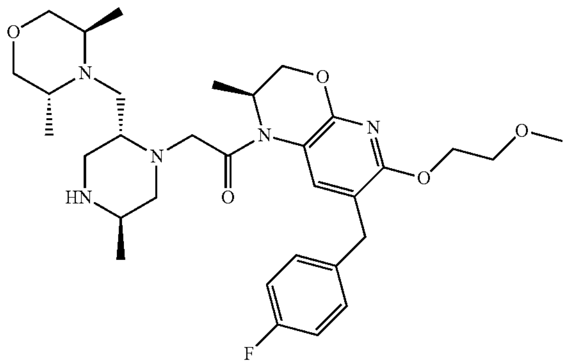
90
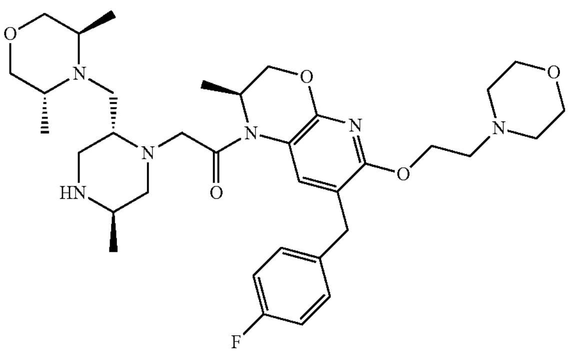

91A/91B
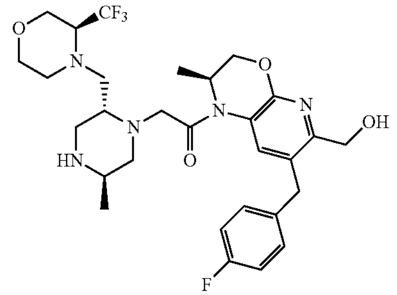
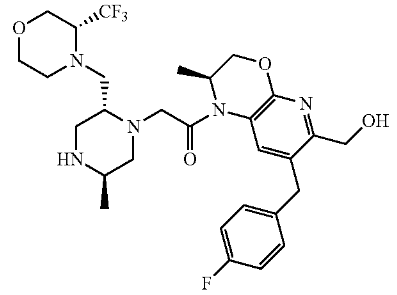
92
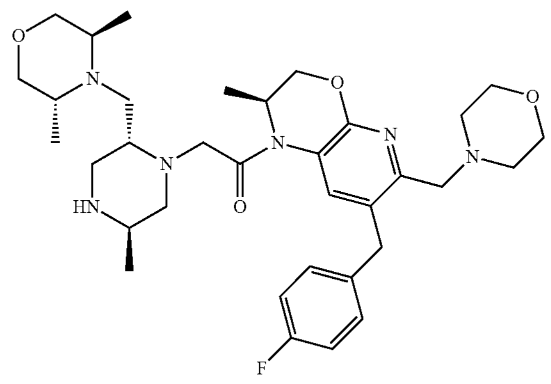
93
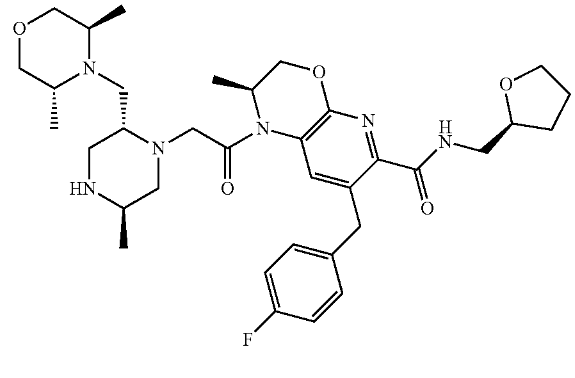
94
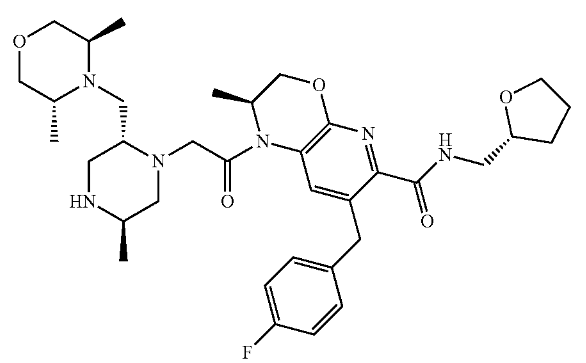
95
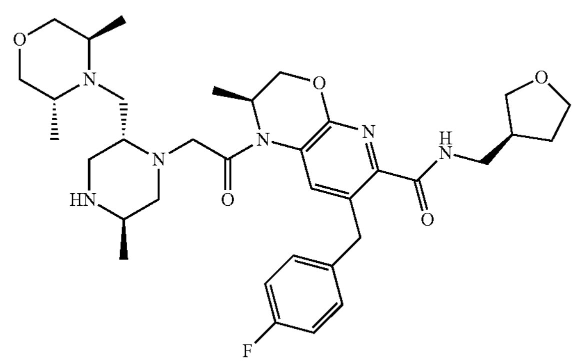
96
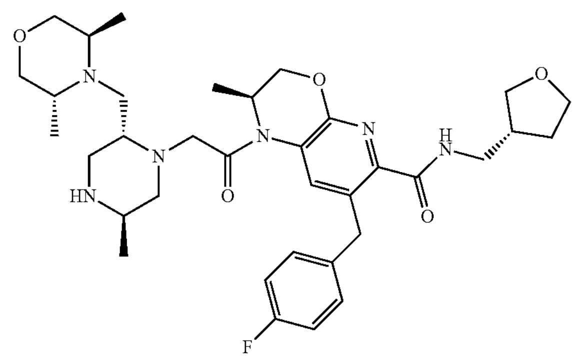
97
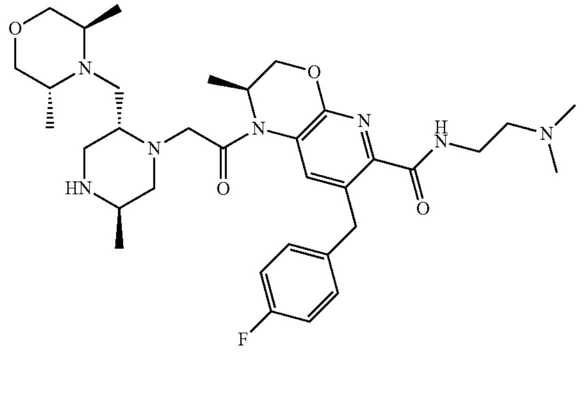

-continued
98
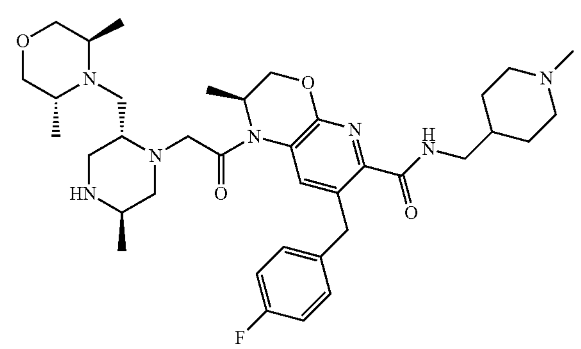
99
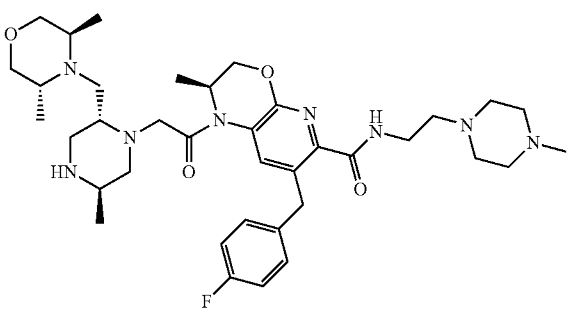
100
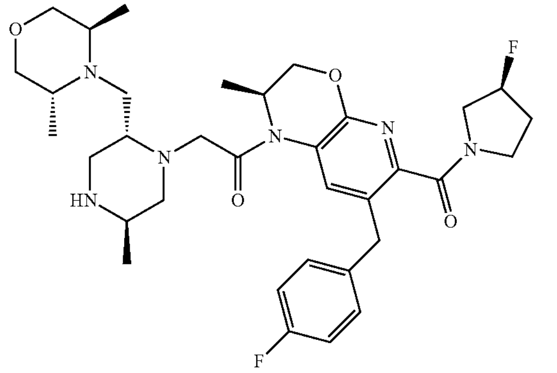
101
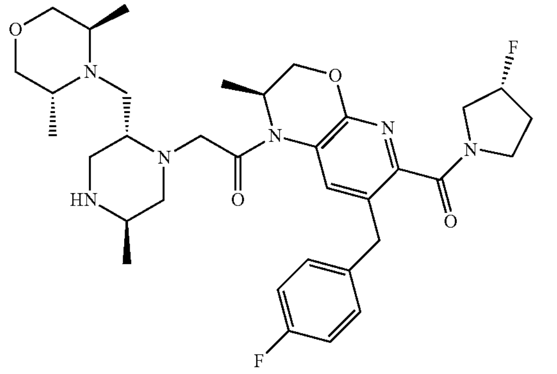
-continued
102
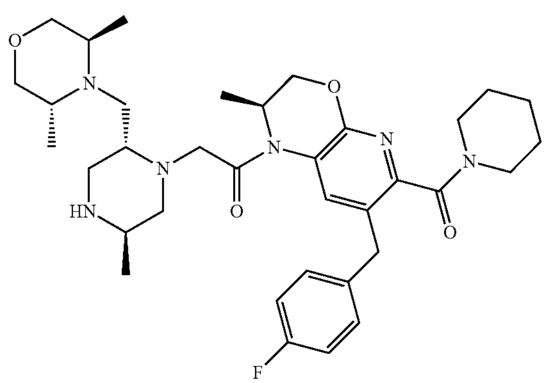
103
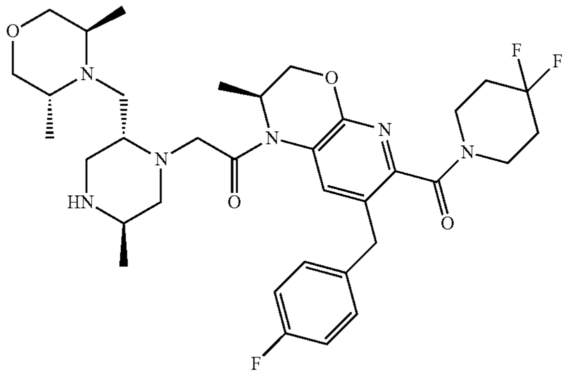
104
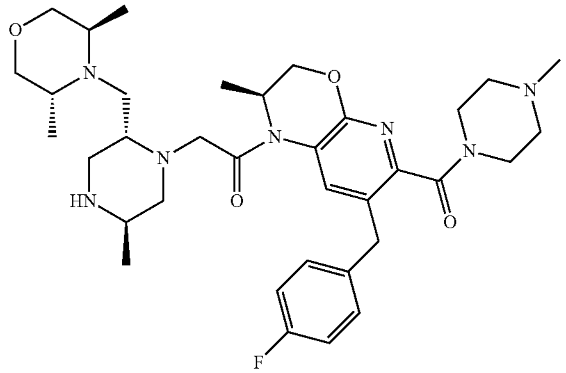
105
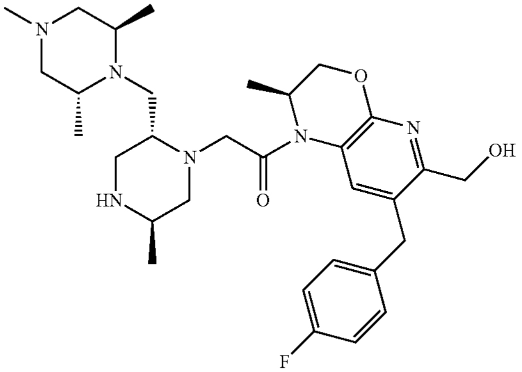

-continued
106
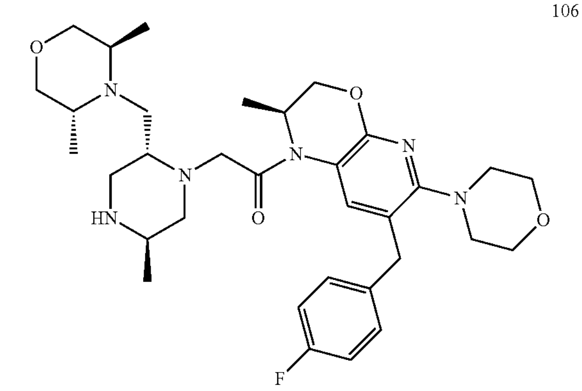
107
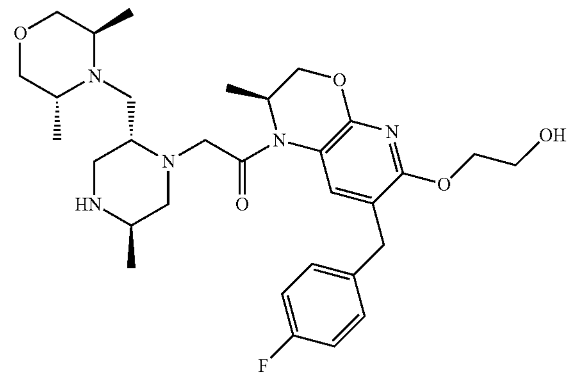
108
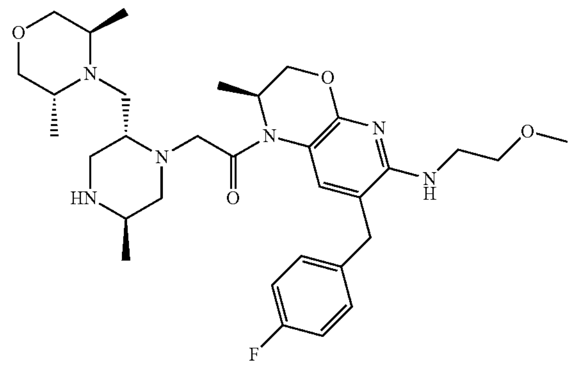
109
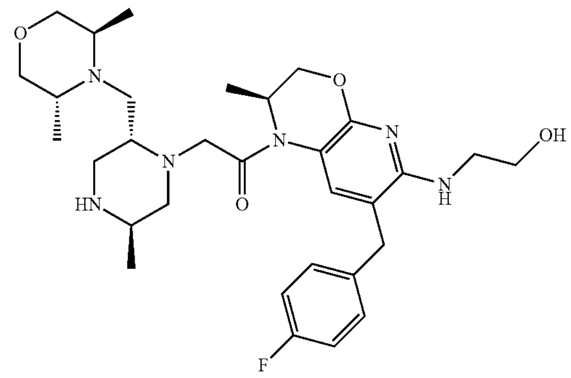
-continued
110
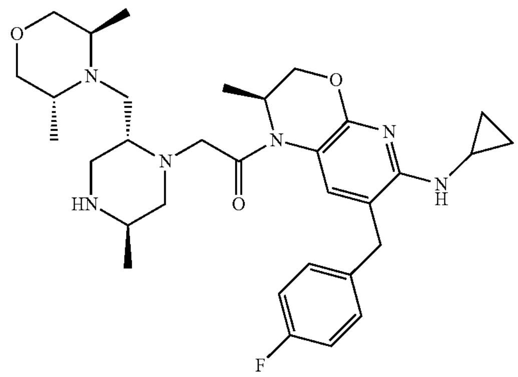
111
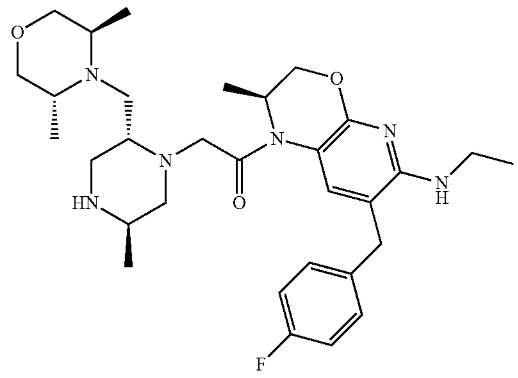
112
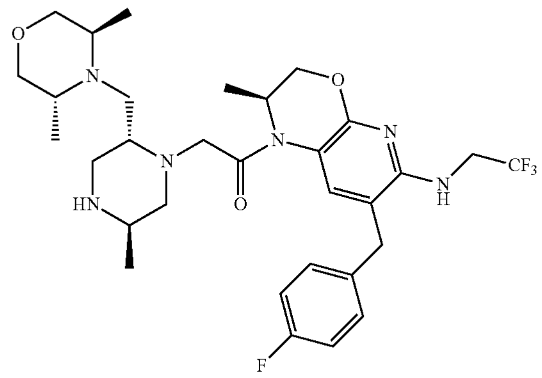
113
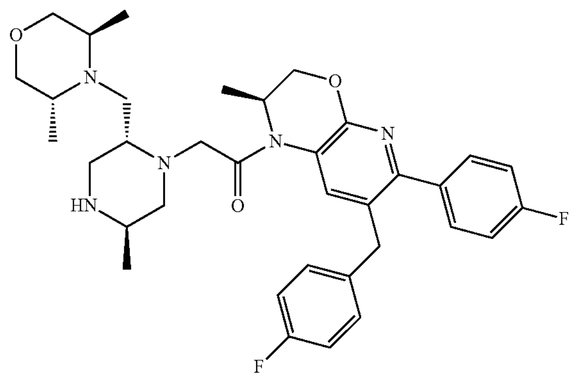

-continued
114
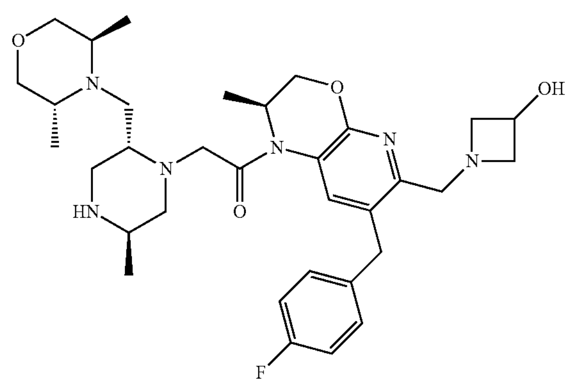
115
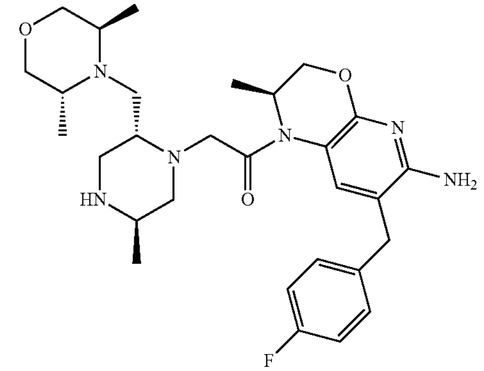
116
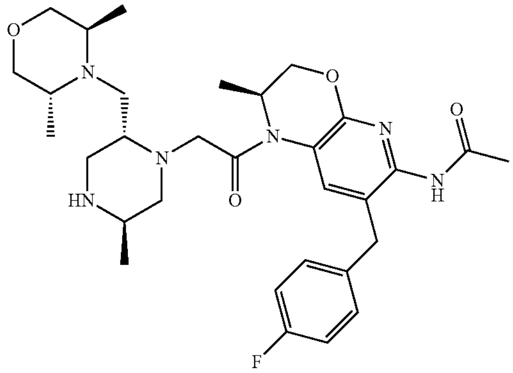
117
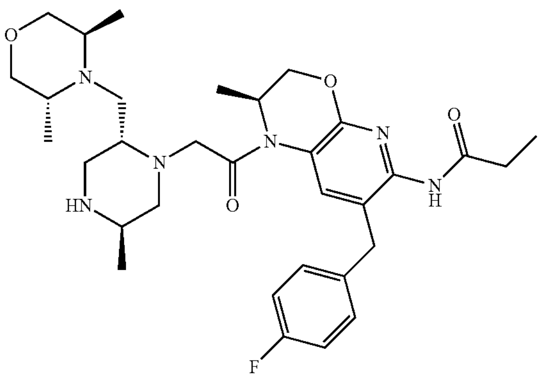
-continued
118
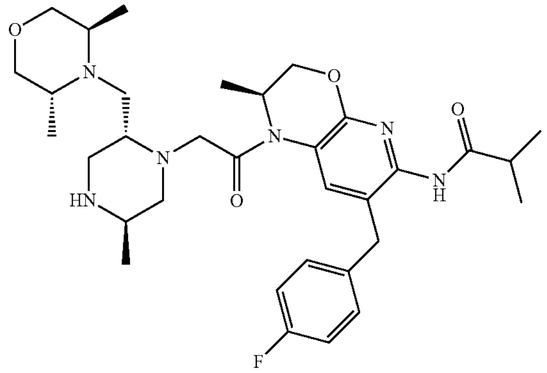
119
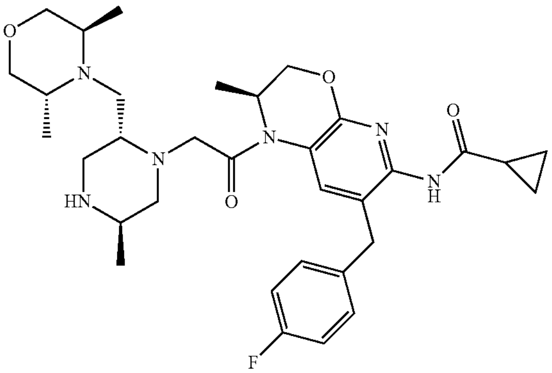
120
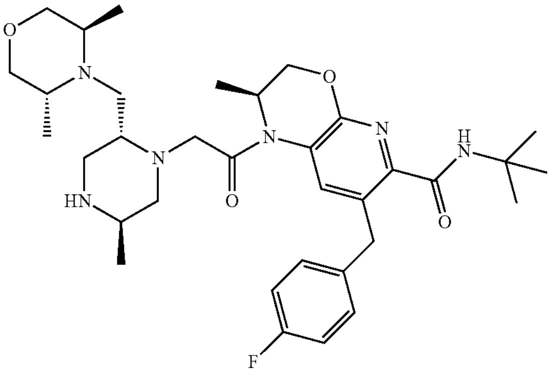
121
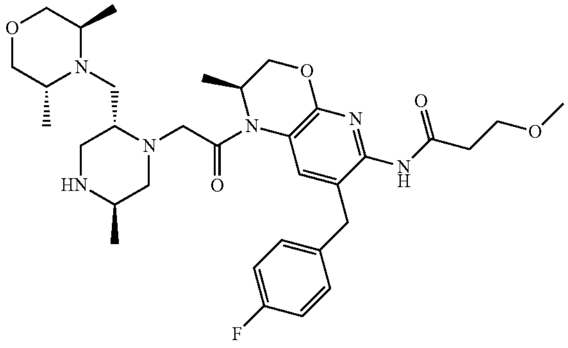

-continued
122
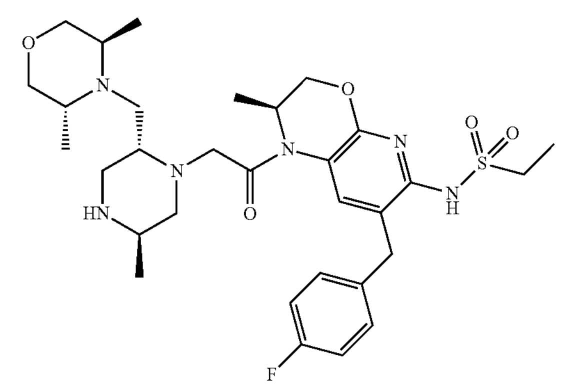
123
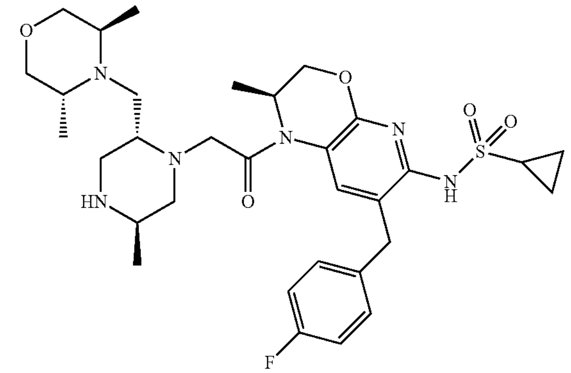
124
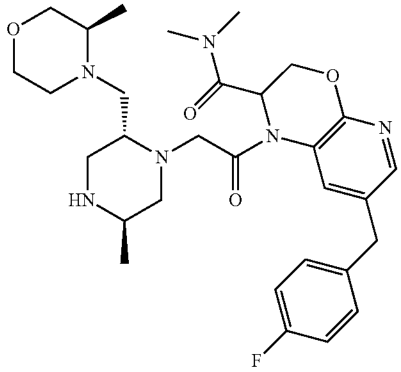
125
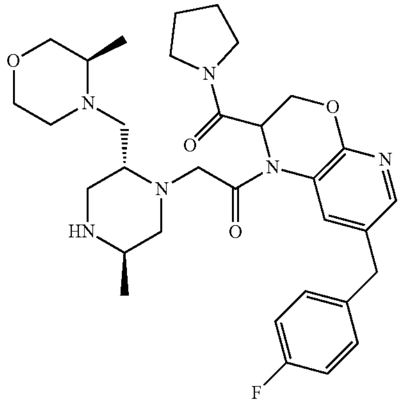
-continued
126
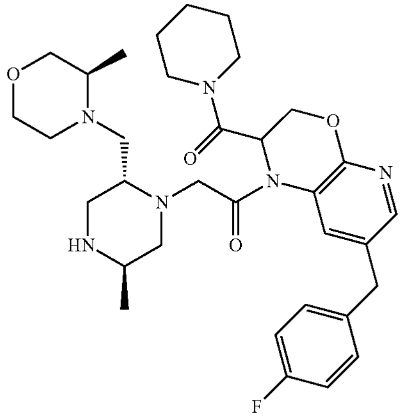
127
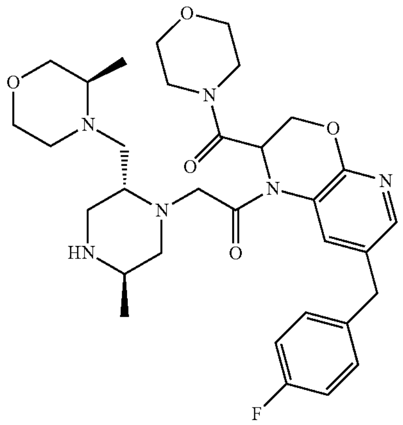
128
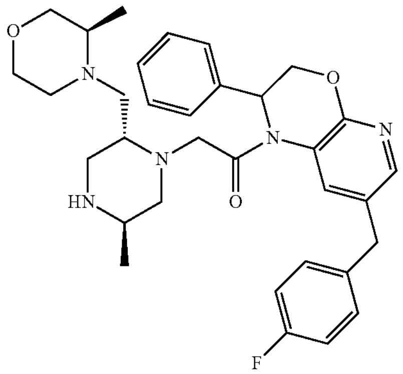
129
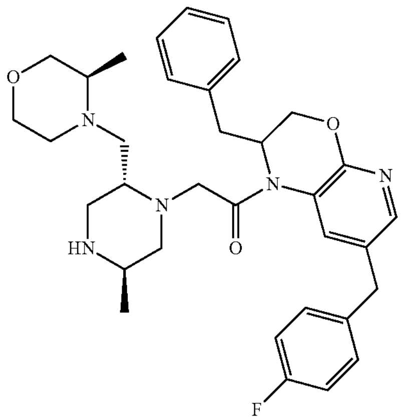

130
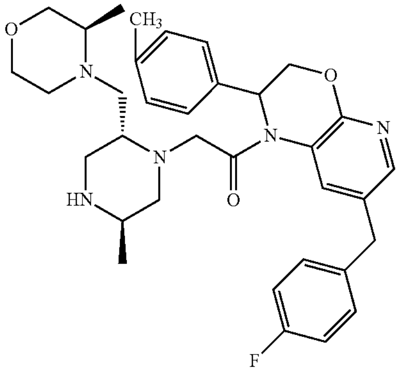
131
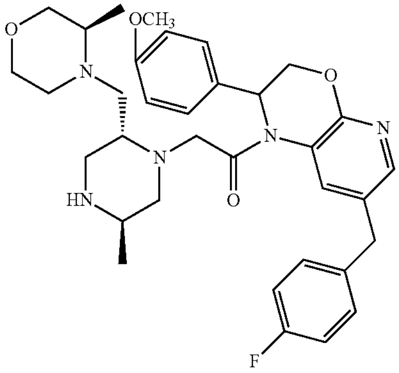
132
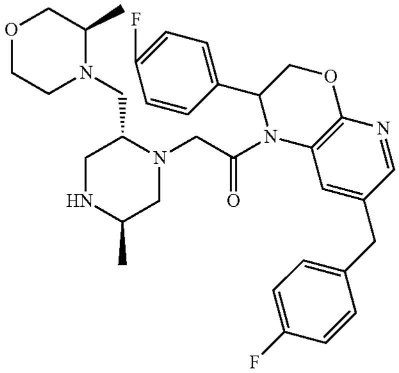
133
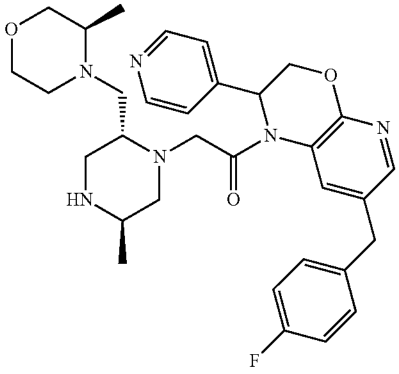
134
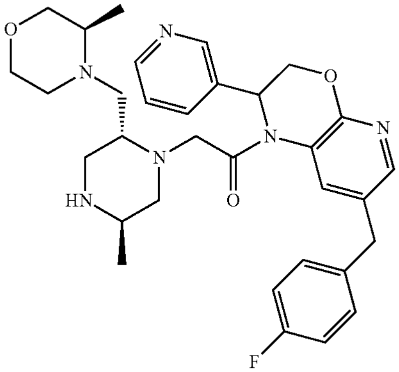
135
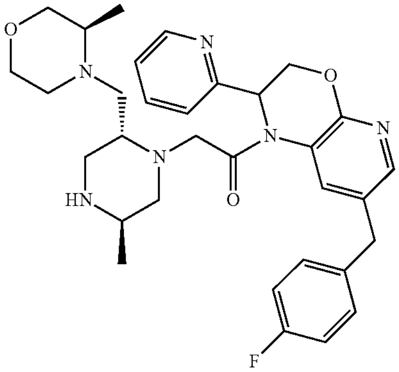
136
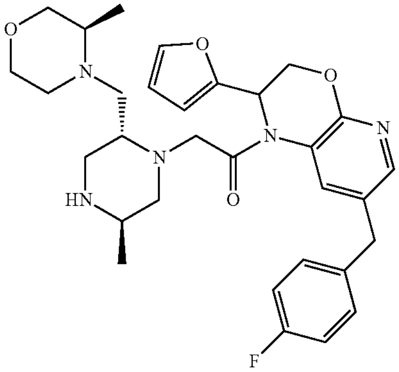
137
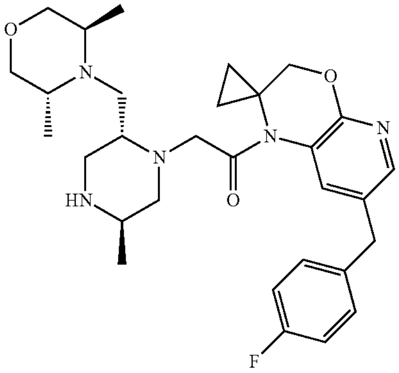

-continued
138
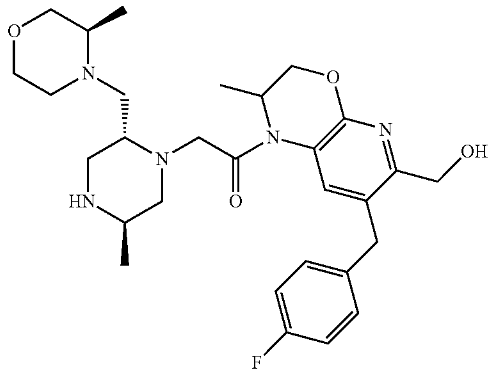
139
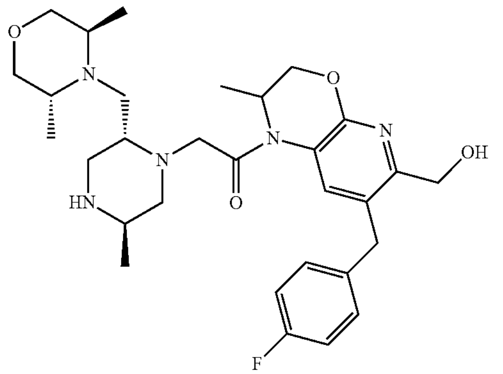
140
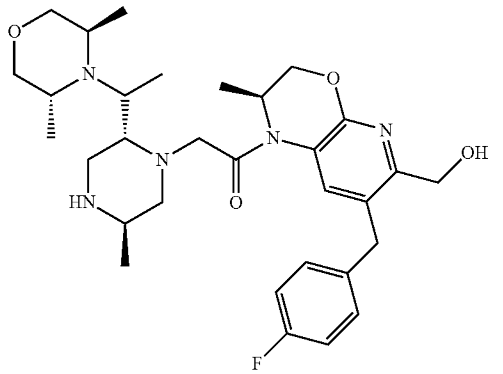
141
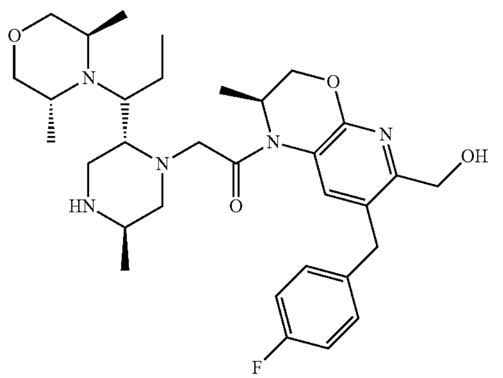
-continued
142
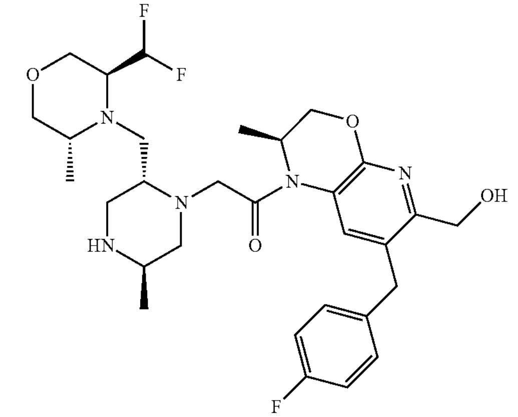
143
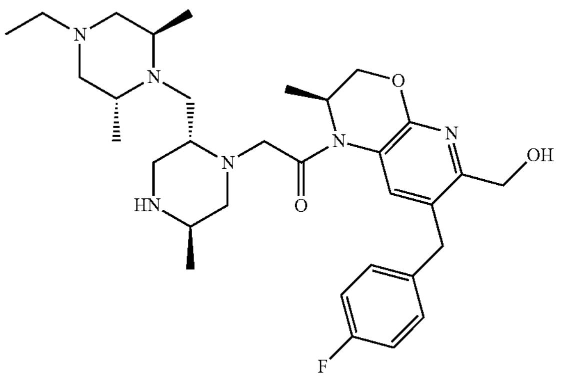
144
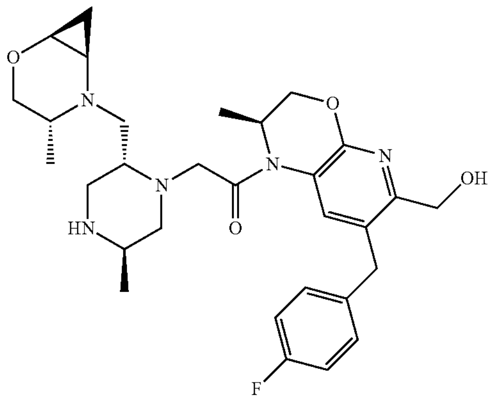
145
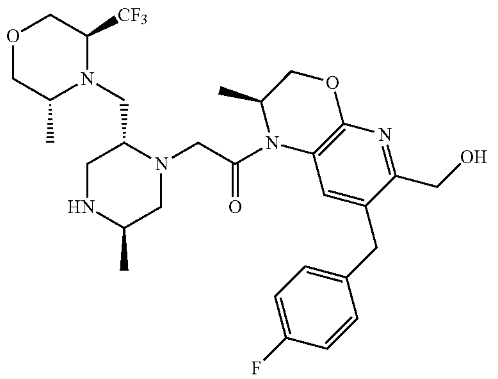

-continued
146
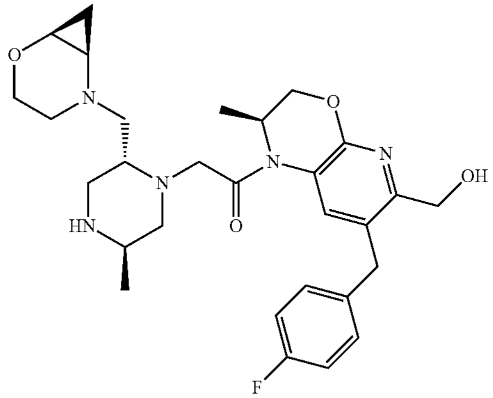
147
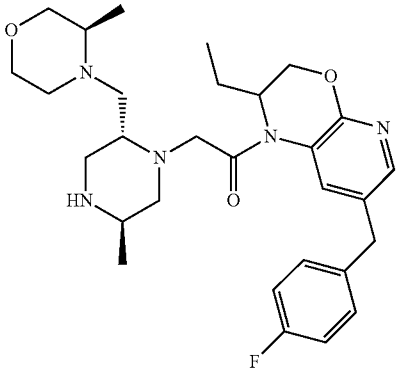
148
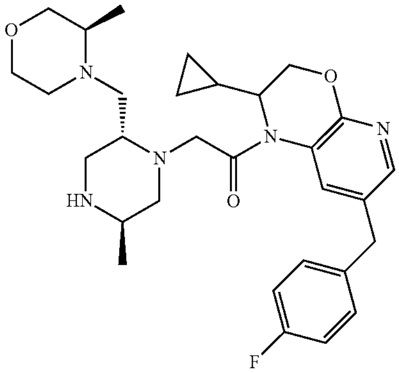
149
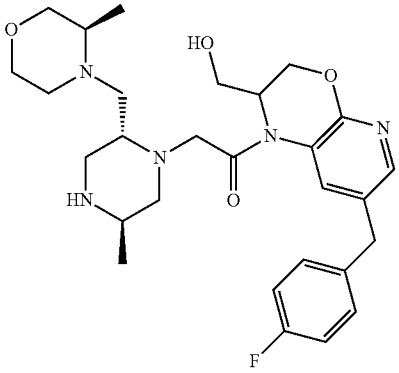
-continued
150
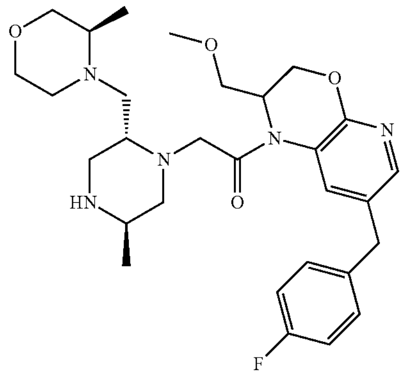
151
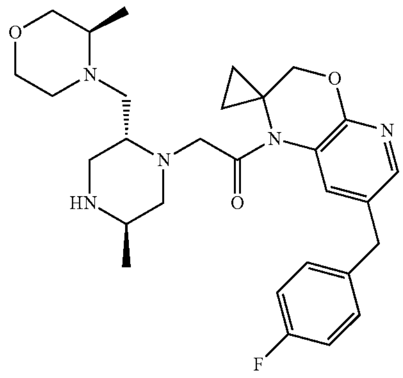
152
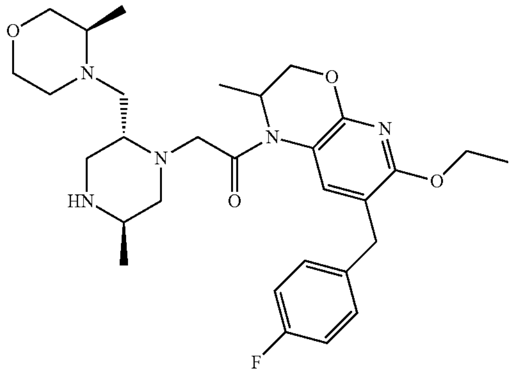
153
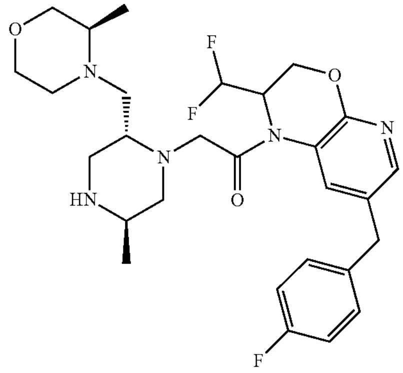

-continued
154
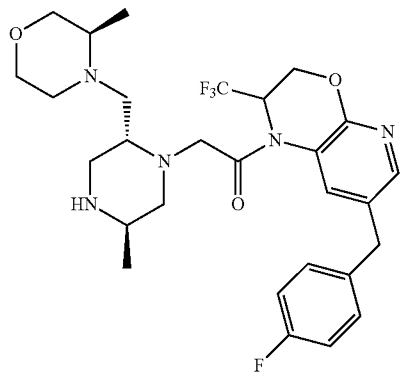
155
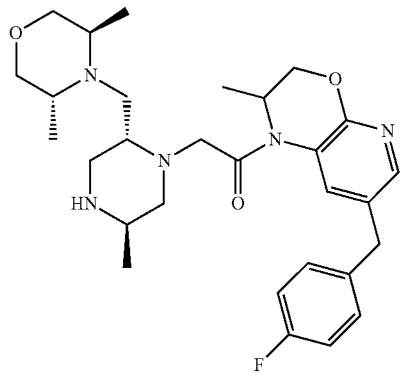
156
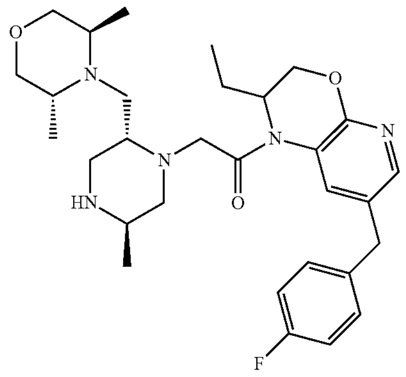
157
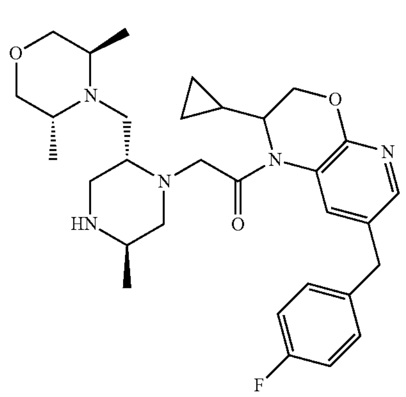
-continued
158
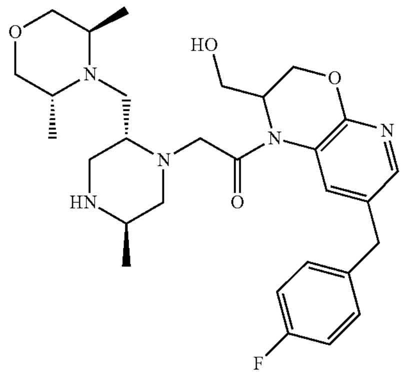
159
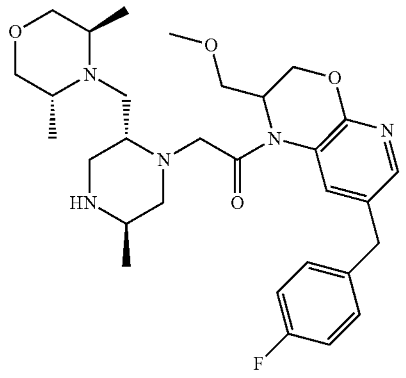
160
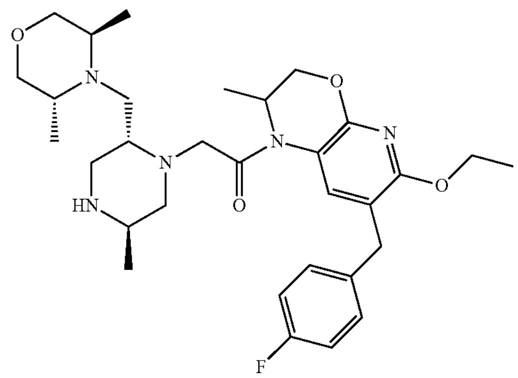
161
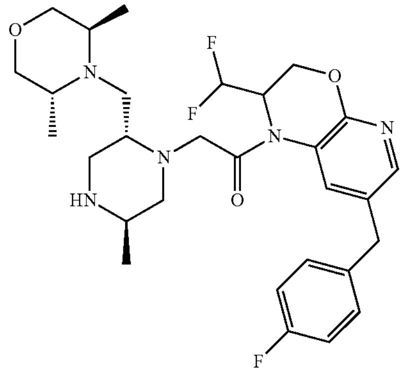

-continued
162
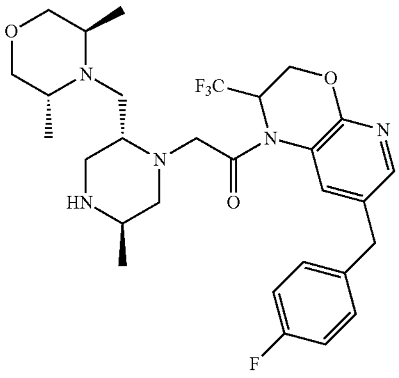
163
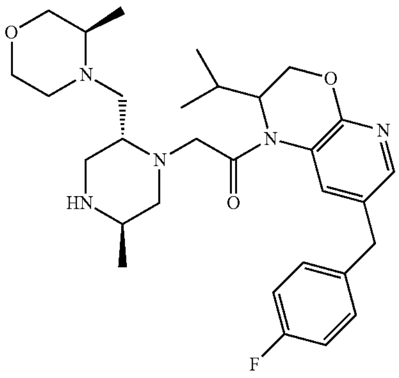
164
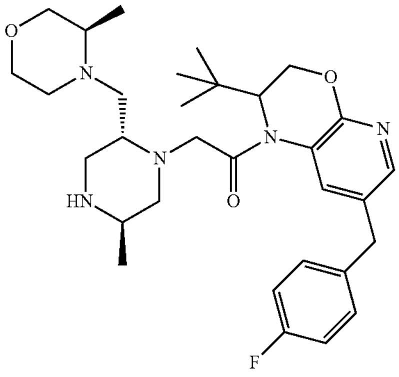
165
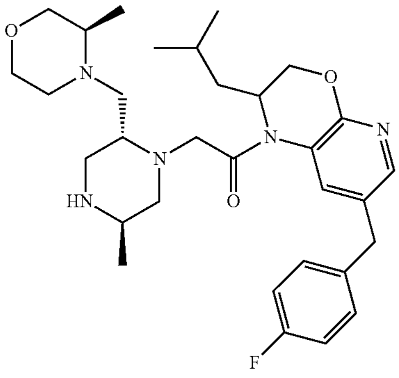
-continued
166
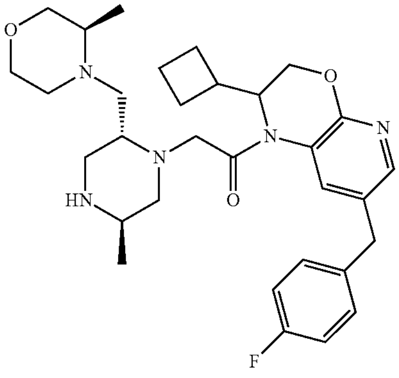
167
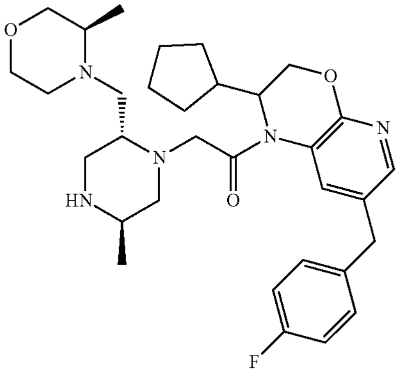
168
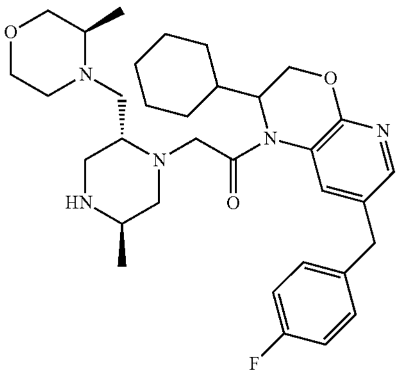
169
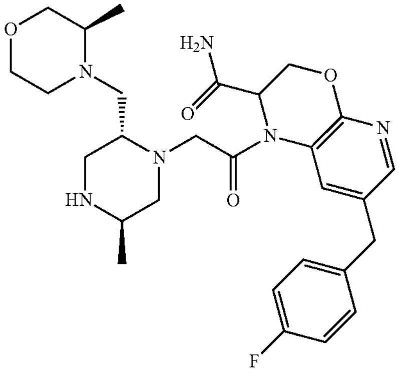

-continued

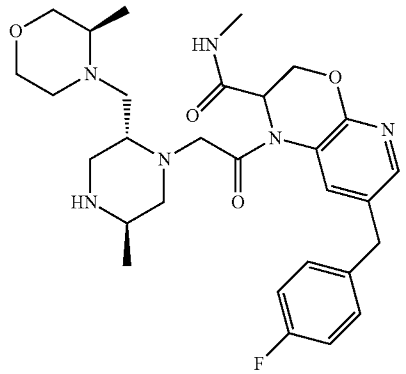

170 or a pharmaceutically acceptable salt thereof, or a stereoisomer, a tautomer or a prodrug thereof.

In one embodiment, disclosed herein is a pharmaceutical composition comprising a compound disclosed herein, or a pharmaceutically acceptable salt thereof, or a stereoisomer, a tautomer or a prodrug thereof, and at least one pharmaceutically acceptable carrier or excipient.

In one embodiment, disclosed herein is a method of treating a disease responsive to inhibition of cIAPs, comprising administering to a subject in need thereof a compound disclosed herein, or a pharmaceutically acceptable salt, or a stereoisomer, a tautomer or a prodrug thereof.

In one embodiment, disclosed herein is a method of treating cancer modulated by cIAPs, comprising administering to a subject in need thereof a compound disclosed herein, or a pharmaceutically acceptable salt, or a stereoisomer, a tautomer or a prodrug thereof.

DETAILED DESCRIPTION OF THE INVENTION

The following terms have the indicated meanings throughout the specification: As used herein, including the appended Aspects, the singular forms of words such as "a", "an", and "the", include their corresponding plural references unless the context clearly dictates otherwise.

The term "or" is used to mean, and is used interchangeably with, the term "and/or" unless the context clearly dictates otherwise.

The term "alkyl" refers to a hydrocarbon group selected from linear and branched saturated hydrocarbon groups comprising from 1 to 18, such as from 1 to 12, further such as from 1 to 10, more further such as from 1 to 8, or from 1 to 6, or from 1 to 4, carbon atoms. Examples of alkyl groups comprising from 1 to 6 carbon atoms (i.e., $C_{1-6}$ alkyl) include, but not limited to, methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), 1,1-dimethylethyl or t-butyl ("t-Bu"), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl butyl and 3,3-dimethyl-2-butyl groups.

The term "cycloalkyl" refers to a hydrocarbon group selected from saturated cyclic hydrocarbon groups, comprising monocyclic and polycyclic (e.g., bicyclic and tricyclic) groups including fused, bridged or Spiro cycloalkyl.

The term "aryl" used alone or in combination with other terms refers to a group selected from:

5- and 6-membered carbocyclic aromatic rings, e.g., phenyl;

bicyclic ring systems such as 7- to 12-membered bicyclic ring systems, wherein at least one ring is carbocyclic and aromatic, e.g., naphthyl and indanyl; and, tricyclic ring systems such as 10- to 15-membered tricyclic ring systems wherein at least one ring is carbocyclic and aromatic, e.g., fluorenyl.

The terms "aromatic hydrocarbon ring" and "aryl" are used interchangeable throughout the disclosure herein. In some embodiments, a monocyclic or bicyclic aromatic hydrocarbon ring has 5 to 10 ring-forming carbon atoms (i.e., $C_{5-10}$ aryl). Examples of a monocyclic or bicyclic aromatic hydrocarbon ring include, but not limited to, phenyl, naphth-1-yl, naphth-2-yl, anthracenyl, phenanthrenyl, and the like. In some embodiments, the aromatic hydrocarbon ring is a naphthalene ring (naphth-1-yl or naphth-2-yl) or phenyl ring. In some embodiments, the aromatic hydrocarbon ring is a phenyl ring.

The term "aryl-alkyl-" refers to an alkyl group as defined above which is further substituted by an aryl group. Examples of an aryl-alkyl group include aryl-$C_{1-8}$alkyl, such as phenylethyl, or phenylmethyl (benzyl).

The term "heteroaryl" refers to a group selected from:

5-, 6- or 7-membered aromatic, monocyclic rings comprising at least one heteroatom, for example, from 1 to 4, or, in some embodiments, from 1 to 3, in some embodiments, from 1 to 2, heteroatoms, selected from nitrogen (N), sulfur (S) and oxygen (O), with the remaining ring atoms being carbon;

7- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. When the heteroaryl group contains more than one heteroatom ring member, the heteroatoms may be the same or different. The nitrogen atoms in the ring(s) of the heteroaryl group can be oxidized to form N-oxides. The term "C-linked heteroaryl" as used herein means that the heteroaryl group is connected to the core molecule by a bond from a C-atom of the heteroaryl ring The terms "aromatic heterocyclic ring" and "heteroaryl" are used interchangeable throughout the disclosure herein. In some embodiments, a monocyclic or bicyclic aromatic heterocyclic ring has 5-, 6-, 7-, 8-, 9- or 10-ring forming members with 1, 2, 3, or 4 heteroatom ring members independently selected from nitrogen (N), sulfur (S) and oxygen (O) and the remaining ring members being carbon. In some embodiments, the monocyclic or bicyclic aromatic heterocyclic ring is a monocyclic or bicyclic ring comprising 1 or 2 heteroatom ring members independently selected from nitrogen (N), sulfur (S) and oxygen (O). In some embodiments, the monocyclic or bicyclic aromatic heterocyclic ring is a 5- to 6-membered heteroaryl ring, which is monocyclic and which has 1 or 2 heteroatom ring members independently selected from nitrogen (N), sulfur (S) and oxygen (O). In some embodiments, the monocyclic or bicyclic aromatic heterocyclic ring is an 8- to 10-membered heteroaryl ring, which is bicyclic and which has 1 or 2 heteroatom ring members independently selected from nitrogen, sulfur and oxygen.

"Heterocyclyl", "heterocycle" or "heterocyclic" are interchangeable and refer to a non-aromatic heterocyclyl group comprising one or more heteroatoms selected from nitrogen, oxygen or optionally oxidized sulfur as ring members, with the remaining ring members being carbon, including monocyclic, fused, bridged, and Spiro ring, i.e., containing monocyclic heterocyclyl, bridged heterocyclyl, spiro heterocyclyl, and fused heterocyclic groups. The term "optionally oxidized sulfur" used herein refers to S, SO or $SO_2$.

Compounds disclosed herein may contain an asymmetric center and may thus exist as enantiomers. "Enantiomers" refer to two stereoisomers of a compound which are non-superimposable mirror images of one another. Where the compounds disclosed herein possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds disclosed herein and/or pharmaceutically acceptable salts thereof are intended to be included. Unless specifically mentioned otherwise, the reference to one isomer applies to any of the possible isomers. Whenever the isomeric composition is unspecified, all possible isomers are included.

The term "substantially pure" as used herein means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s). When compounds disclosed herein contain olefinic double bonds, unless specified otherwise, such double bonds are meant to include both E and Z geometric isomers.

When compounds disclosed herein contain a di-substituted cyclohexyl or cyclobutyl group, substituents found on cyclohexyl or cyclobutyl ring may adopt cis and trans formations. Cis formation means that both substituents are found on the upper side of the 2 substituent placements on the carbon, while trans would mean that they were on opposing sides.

It may be advantageous to separate reaction products from one another and/or from starting materials. The desired product of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

"Diastereomers" refers to stereoisomers of a compound with two or more chiral centers but which are not mirror images of one another. Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

"Pharmaceutically acceptable salts" refers to those salts which are, within the scope of sound medical judgment, suitable for use in contact with the tissues of humans and lower animals without undue toxicity, irritation, allergic response and the like, and are commensurate with a reasonable benefit/risk ratio. A pharmaceutically acceptable salt may be prepared in situ during the final isolation and purification of the compounds disclosed herein, or separately by reacting the free base function with a suitable organic acid or by reacting the acidic group with a suitable base.

In addition, if a compound disclosed herein is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and/or water and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

As defined herein, "a pharmaceutically acceptable salt thereof" includes salts of at least one compound of Formula (I), and salts of the stereoisomers of the compound of Formula (I), such as salts of enantiomers, and/or salts of diastereomers.

The terms "administration", "administering", "treating" and "treatment" herein, when applied to an animal, human, experimental subject, cell, tissue, organ, or biological fluid, mean contact of an exogenous pharmaceutical, therapeutic, diagnostic agent, or composition to the animal, human, subject, cell, tissue, organ, or biological fluid. Treatment of a cell encompasses contact of a reagent to the cell, as well as the contact of a reagent to a fluid, where the fluid is in contact with the cell. The term "administration" and "treatment" also means in vitro and ex vivo treatments, e.g., of a cell, by a reagent, diagnostic, binding compound, or by another cell. The term "subject" herein includes any organism, preferably an animal, more preferably a mammal (e.g., rat, mouse, dog, cat, and rabbit) and most preferably a human.

The term "effective amount" or "therapeutically effective amount" refers to an amount of the active ingredient, such as a compound that, when administered to a subject for treating a disease, or at least one of the clinical symptoms of a disease or disorder, is sufficient to affect such treatment for the disease, disorder, or symptom. The "therapeutically effective amount" can vary with the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In some embodiments, "therapeutically effective amount" is an amount of at least one compound and/or at least one stereoisomer thereof, and/or at least one pharmaceutically acceptable salt thereof disclosed herein effective to "treat" as defined above, a disease or disorder in a subject. In the case of combination therapy, the "therapeutically effective amount" refers to the total amount of the combination objects for the effective treatment of a disease, a disorder or a condition.

The pharmaceutical composition comprising the compound disclosed herein can be administrated via oral, inhalation, rectal, parenteral or topical administration to a subject in need thereof. For oral administration, the pharmaceutical composition may be a regular solid formulation such as tablets, powder, granule, capsules and the like, a liquid formulation such as water or oil suspension or other liquid formulation such as syrup, solution, suspension or the like; for parenteral administration, the pharmaceutical composition may be a solution, water solution, oil suspension concentrate, lyophilized powder or the like. Preferably, the formulation of the pharmaceutical composition is selected from a tablet, coated tablet, capsule, suppository, nasal spray or injection, more preferably tablet or capsule. The pharmaceutical composition can be a single unit administration with an accurate dosage. In addition, the pharmaceutical composition may further comprise additional active ingredients.

All formulations of the pharmaceutical composition disclosed herein can be produced by the conventional methods in the pharmaceutical field. For example, the active ingredient can be mixed with one or more excipients, then to make the desired formulation. The "pharmaceutically acceptable excipient" refers to conventional pharmaceutical carriers suitable for the desired pharmaceutical formulation, for example: a diluent, a vehicle such as water, various organic solvents, etc., a filler such as starch, sucrose, etc. a binder such as cellulose derivatives, alginates, gelatin and polyvinylpyrrolidone (PVP); a wetting agent such as glycerol; a disintegrating agent such as agar, calcium carbonate and sodium bicarbonate; an absorption enhancer such as quaternary ammonium compound; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises other pharmaceutically acceptable excipients such as a decentralized agent, a stabilizer, a thickener, a complexing agent, a buffering agent, a permeation enhancer, a polymer, aromatics, a sweetener, and a dye.

The term "disease" refers to any disease, discomfort, illness, symptoms or indications, and can be interchangeable with the term "disorder" or "condition".

Throughout this specification and the Aspects which follow, unless the context requires otherwise, the term "comprise", and variations such as "comprises" and "comprising" are intended to specify the presence of the features thereafter, but do not exclude the presence or addition of one or more other features. When used herein the term "comprising" can be substituted with the term "containing", "including" or sometimes "having".

Throughout this specification and the Aspects which follow, the term "$C_{n-m}$" indicates a range which includes the endpoints, wherein n and m are integers and indicate the number of carbons. Examples include $C_{1-8}$, $C_{1-6}$, and the like. Unless specifically defined elsewhere in this document, all other technical and scientific terms used herein have the meaning commonly understood by one of ordinary skill in the art to which this invention belongs.

General Synthesis

Compounds disclosed herein, including salts thereof, can be prepared using known organic synthesis techniques and can be synthesized according to any of numerous possible synthetic routes.

The reaction for preparing compounds disclosed herein can be carried out in suitable solvents which can be readily selected by one of skill in the art of organic synthesis. Suitable solvents can be substantially non-reactive with the starting materials, the intermediates, or products at the temperatures at which the reactions are carried out, e.g., temperatures which can range from the solvent's boiling temperature. A given reaction can be carried out in one solvent or mixture of solvents.

The selection of an appropriate protecting group can be readily determined by one skilled in the art.

Reactions can be monitored according to any suitable method known in the art, such as NMR, UV, HPLC, LC-MS and TLC. Compounds can be purified by a variety of methods, including HPLC and normal phase silica chromatography.

Scheme I

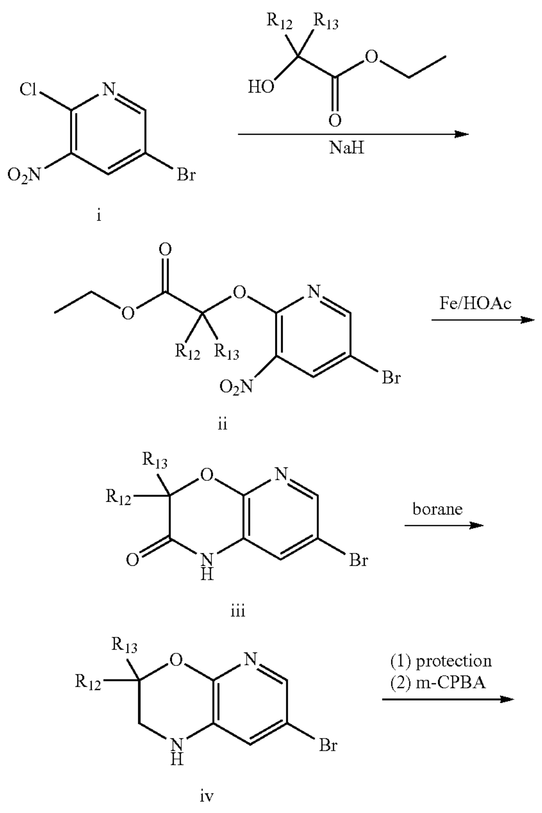

i, ii, iii, iv

-continued

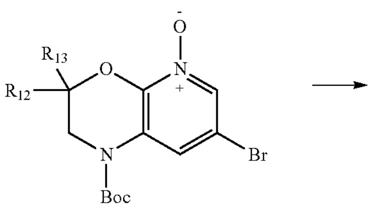

v

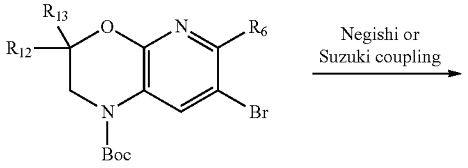

vi

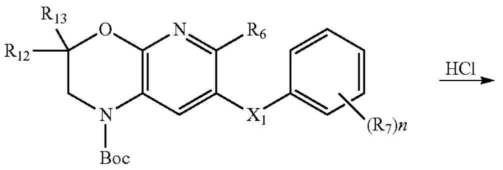

vii

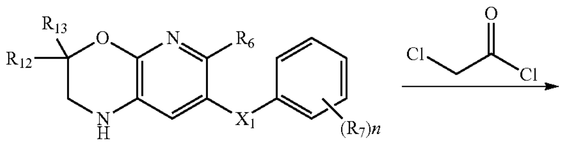

viii

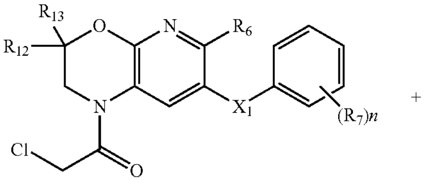

ix

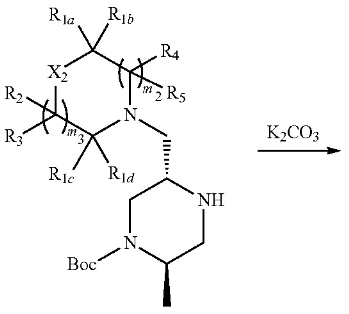

x

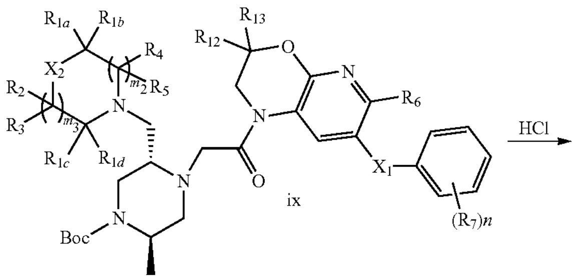

xi

-continued

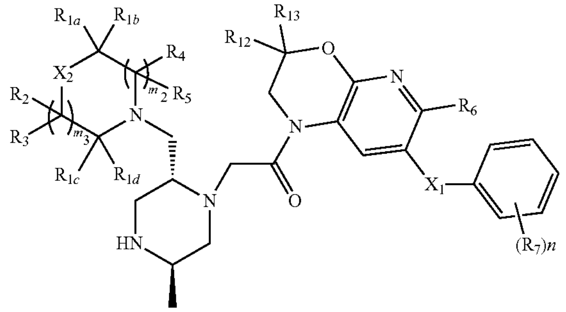

xii
Formular (I)

Compounds of Formula (I) can be prepared as shown in Scheme I. Nucleophilic substitution between the alcohol and compound (i) afforded compound (ii) which is followed by iron-mediated reductive cyclization to afford compound (iii). Compound (iii) was converted to compound (iv) via borane-mediated reduction. The three-step procedure gave compound (vi).

Subsequent Negishi or Suzuki coupling afforded compound (vii). Deprotection and the following acylation afforded compound (ix). Compound (ix) reacted with key intermediate (x) to afford compound (xi). Final deprotection furnished compound (xii) described in Formula (I).

Scheme II

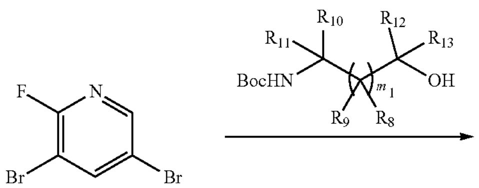

i

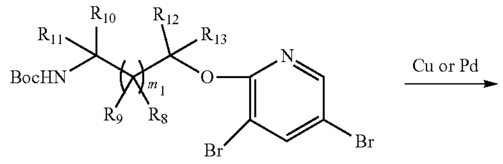

ii

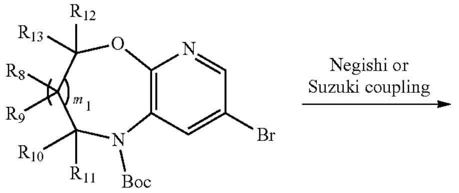

iii

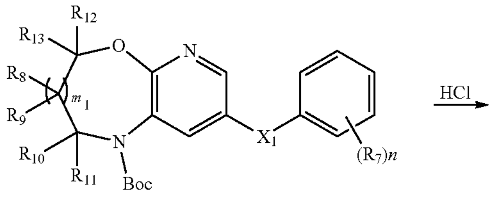

iv

-continued

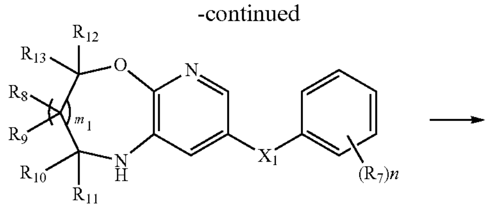

v

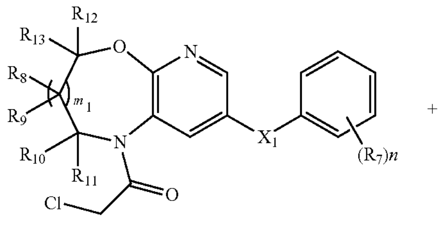

vi

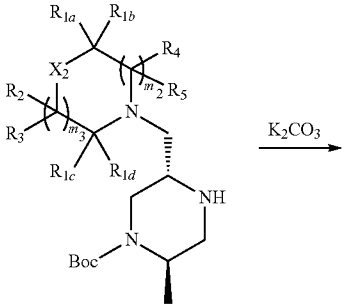

vii

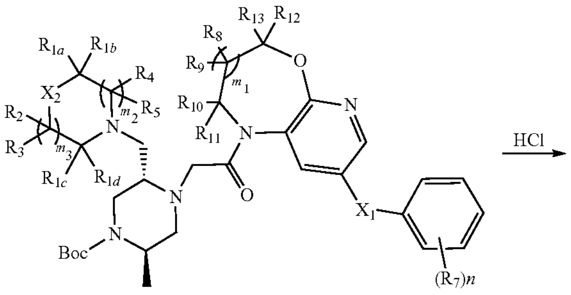

viii

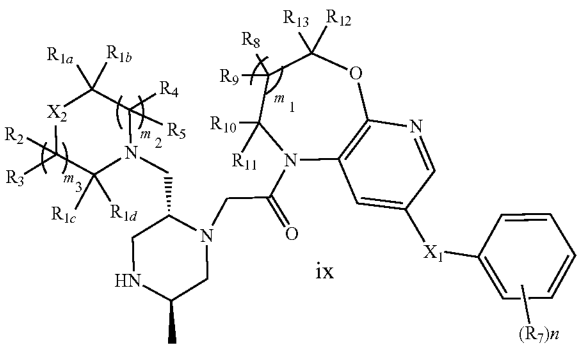

ix
Formular (I)

Compounds of Formula (I) can also be synthesized as shown in Scheme II. Nucleophilic substitution between compound (i) and Boc-protected amino alcohol afforded compound (ii). Subsequent Cu or Pd mediated C—N coupling afforded compound (iii) which is followed by Negishi or Suzuki coupling to give compound (iv). Deprotection afforded compound (v). Compound (v) reacted with 2-chloroacetyl chloride to afford compound (vi). Compound (vi) reacted with key intermediate (vii) to afford compound (viii). Final deprotection furnished compound (ix) described in Formula (I).

ABBREVIATIONS $(Boc)_2O$ di-tert-butyl dicarbonate
$Ac_2O$ Acetic anhydride
AcOH Acetic Acid
DCM dichloromethane
DIEA diisopropylethylamine
DMAP 4-dimethylaminopyridine
DMF Dimethylformamide
DMSO Dimethyl sulfoxide
EA Ethyl acetate
EA, EtOAc Ethyl acetate
EDC 1-(3-Dimethylaminopropyl)-3-ethylcarbodiimide hydrochloride
EDCI N-Ethyl-N'-(3-dimethylaminopropyl)carbodiimide hydrochloride
Eq. equivalent
$Et_3N$, TEA triethyl amine
EtOH ethanol
Fe iron
HATU 1-[bis(dimethylamino)methylene]-1H-1,2,3-triazolo[4,5-b]
pyridinium 3-oxid hexafluorophosphate
HCl Hydrochloric Acid
HOBT 1-Hydroxybenzotriazole
MeCN acetonitrile
MeOH Methanol
NaB $H_4$ Sodium borohydride
NBS N-Bromosuccinimide
$Pd(dppf)Cl_2$ [1,1'-Bis(diphenylphosphino)ferrocene]dichloropalladium(II)
Pd(OAc)2 Palladium(II)acetate
PE petroleum ether
PreP-HPLC Preparative High-Performance Liquid Chromatography
Prep-TCL Preparative thin-layer chromatography
rt room temperature
t-BuONO tert-Butyl nitrite
TFA trifluoroacetic acid
THF tetrahydrofuran
TLC thin-layer chromatography
TMSCN Trimethylsilyl cyanide
Tol toluene

REPRESENTATIVE EXAMPLES

Example 1: 7-(4-fluorobenzyl)-1-(2-((2R,5R)-5-methyl-2-(((R)-3-methylmorpholino)methyl)piperazin-1-yl)acetyl)-2,3-dihydro-1H-pyrido[2,3-b][1,4]oxazine-6-carbonitrile formate (Compound 1)

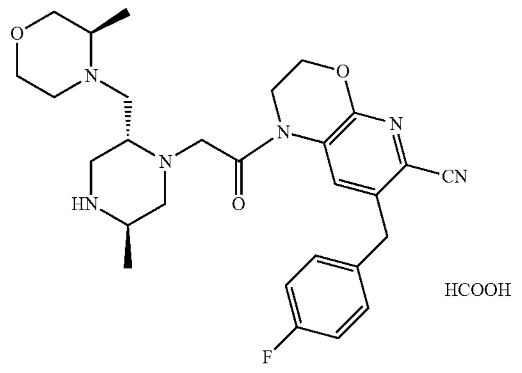 [SMILES: C[C@@H]1CN(CC(=O)N2CCOc3nc(C#N)c(Cc4ccc(F)cc4)cc32)[C@@H](CN2CCOC[C@H]2C)CN1 ; "HCOOH"]

Step 1: ethyl 2-((5-bromo-3-nitropyridin-2-yl)oxy)acetate

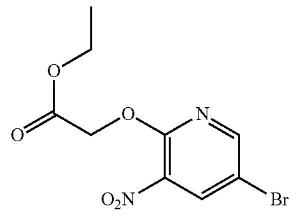 [SMILES: CCOC(=O)COc1ncc(Br)cc1[N+](=O)[O-]]

To 5-bromo-2-chloro-3-nitropyridine (20 g, 84.2 mmol) and ethyl 2-hydroxyacetate (9.6 g, 92.6 mmol) in anhydrous THF (100 mL) was added NaH (4.4 g, 60% dispersion in mineral oil, 109.5 mmol) slowly at 0° C. The resulting solution was stirred at room temperature for 1 h. The reaction was quenched by water (20 mL) and extracted with EtOAc (100 mL*3). The combined organic layers were dried over $Na_2SO_4$, filtered and evaporated in vacuo. The residue was purified by silica gel chromatography (PE: EtOAc=10:1) to give the product (13 g, 51% yield). LC-MS $(M+H)^+$305.0, 307.0.

Step 2: 7-bromo-1H-pyrido[2,3-b][1,4]oxazin-2(3H)-one

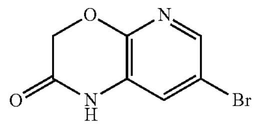 [SMILES: O=C1COc2ncc(Br)cc2N1]

Ethyl 2-((5-bromo-3-nitropyridin-2-yl)oxy)acetate (13 g, 42.6 mmol) in AcOH (300 mL) was added Fe powder (13 g, 232 mmol) slowly at 70° C., the resulting mixture was stirred at 70° C. for 1 h. AcOH was removed in vacuo. The resulting solid was washed with MeOH (200 mL) and filtered. Repeat this manipulation for 5 times. MeOH phase was concentrated in vacuo to give the crude product (9.6 g, 98% yield), which was used directly in the next step. LC-MS $(M+H)^+$=228.9, 230.9.

Step 3: 7-bromo-2,3-dihydro-1H-pyrido[2,3-b][1,4]oxazine

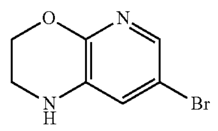 [SMILES: Brc1cnc2c(c1)NCCO2]

7-bromo-1H-pyrido[2,3-b][1,4]oxazin-2(3H)-one (9 g, 39.3 mmol) in anhydrous THF (150 mL) was added $BH_3$ (98.3 mL, 1 N in THF) dropwise at room temperature, the resulting solution was stirred at 60° C. for 1 h. The reaction was cooled to room temperature, quenched by MeOH (10 mL), adjusted pH to 1~2 by addition of 1 N HCl, and stirred at 60° C. for 1 h. The reaction mixture was cooled to room temperature, Water (100 mL) was added and adjusted pH to 8-9. The mixture was extracted with EtOAc (100 mL*3), the combined organic layers were dried over $Na_2SO_4$, filtered and evaporated in vacuo to give the crude product (7.46 g, 88% yield), which was used in the next step directly. LC-MS $(M+H)^+$=215.1, 217.1.

Step 4: tert-butyl 7-bromo-2,3-dihydro-1H-pyrido[2,3-b][1,4]oxazine-1-carboxylate

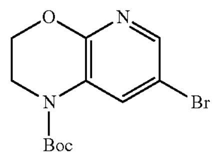 [SMILES: CC(C)(C)OC(=O)N1CCOc2ncc(Br)cc21]

7-bromo-2,3-dihydro-1H-pyrido[2,3-b][1,4]oxazine (6.9 g, 32 mmol), $(Boc)_2O$ (10.5 g, 48 mmol), DMAP (3.9 g, 32 mmol) and $Et_3N$ (6.46 g, 64 mmol) in THF (200 mL) was stirred at room temperature for 12 hours. The reaction was washed with water (100 mL), extracted with EtOAc (100 mL*3), the combined organic layers were dried over $Na_2SO_4$, filtered and evaporated in vacuo. The residue was purified by silica gel chromatography (PE:EtOAc=5:1) to give the product (9 g, 90% yield). LC-MS $(M+H)^+$=315.2, 317.2.

Step 5: 7-bromo-1-(tert-butoxycarbonyl)-2,3-dihydro-1H-pyrido[2,3-b][1,4]oxazine 5-oxide

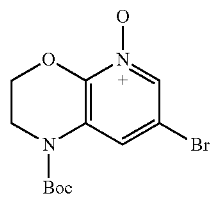

To tert-butyl 7-bromo-2,3-dihydro-1H-pyrido[2,3-b][1,4]oxazine-1-carboxylate (7 g, 22.2 mmol) in DCM (200 mL) was added 3-chlorobenzoperoxoic acid (11.5 g, 66.67 mmol) at room temperature, the resulting mixture was stirred at 50° C. for 18 h. The reaction mixture was cooled to room temperature and filtered to remove the solid, washed with saturated a.q $NaHCO_3$ solution (100 mL), extracted with DCM (100 mL*3), the combined organic layers were dried, filtered and concentrated. The residue was purified by silica gel chromatography (DCM:MeOH=20:1) to give the product (5.8 g, 78.8% yield). LC-MS $(M+H)^+$=331.1, 333.1.

Step 6: tert-butyl 7-bromo-6-cyano-2,3-dihydro-1H-pyrido[2,3-b][1,4]oxazine-1-carboxylate

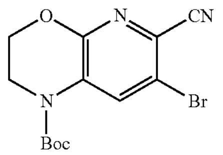 [SMILES: CC(C)(C)OC(=O)N1CCOc2nc(C#N)c(Br)cc21]

To a solution of 7-bromo-1-(tert-butoxycarbonyl)-2,3-dihydro-1H-pyrido[2,3-b][1,4]oxazine 5-oxide (2.9 g, 8.8 mmol) in MeCN (100 mL) was added TMSCN (13.04 g, 131.4 mmol) at room temperature under $N_2$, the resulting solution was stirred at 80° C. for 12 h. The reaction was concentrated in vacuo, the residue was purified by silica gel chromatography (DCM:MeOH=50:1) to give the product (715 mg, 24% yield). LC-MS $(M+H)^+$=340.2, 342.2.

Step 7: tert-butyl 6-cyano-7-(4-fluorobenzyl)-2,3-dihydro-1H-pyrido[2,3-b][1,4]oxazine-1-carboxylate

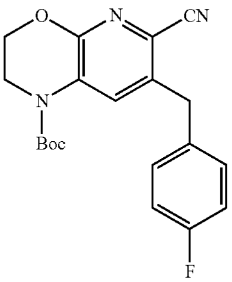

To a solution of tert-butyl 7-bromo-6-cyano-2,3-dihydro-1H-pyrido[2,3-b][1,4]oxazine-1-carboxylate (715 mg, 2.1 mmol) and bis(tri-tert-butylphosphine)palladium (54 mg, 0.11 mmol) in anhydrous THF (100 mL) was added (4-fluorobenzyl)zinc(II) chloride (8.4 mL, 4.2 mmol, 0.5 M solution in THF) dropwise, the resulting solution was stirred at 60° C. for 2 h. The reaction was quenched by MeOH (5 mL) and concentrated in vacuo, the residue was purified by silica gel chromatography (PE:EtOAc=5:1) to give the product (470 mg, 61% yield). LC-MS $(M+H)^+$=370.4.

Step 8: 7-(4-fluorobenzyl)-2,3-dihydro-1H-pyrido[2,3-b][1,4]oxazine-6-carbonitrile

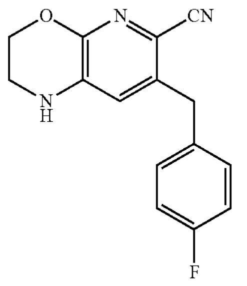

To a solution of tert-butyl 6-cyano-7-(4-fluorobenzyl)-2,3-dihydro-1H-pyrido[2,3-b][1,4]oxazine-1-carboxylate (360 mg, 0.98 mmol) in DCM (10 mL) was added HCl in 1,4-dioxane solution (4 N, 2.5 mL, 10 mmol), the resulting solution was stirred at room temperature for 12 h. The solution was concentrated in vacuo. The mixture was neutralized with aq. $NaHCO_3$ solution and extracted with EtOAc. The combined organic layers were dried, filtered and concentrated to afford the title compound (260 mg, 99% yield). LC-MS $(M+H)^+$=270.4.

Step 9: 1-(2-chloroacetyl)-7-(4-fluorobenzyl)-2,3-dihydro-1H-pyrido[2,3-b][1,4]oxazine-6-carbonitrile

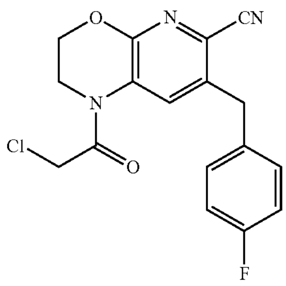 [SMILES: N#Cc1nc2c(cc1Cc1ccc(F)cc1)N(C(=O)CCl)CCO2]

2-chloroacetyl chloride (111 mg, 0.98 mmol) was added to a solution of 7-(4-fluorobenzyl)-2,3-dihydro-1H-pyrido[2,3-b][1,4]oxazine-6-carbonitrile (100 mg, 0.37 mmol) and $Et_3N$ (99 mg, 0.98 mmol) in MeCN (10 mL) at room temperature, the resulting solution was stirred at room temperature for 12 h. The solution was concentrated in vacuo and the residue was purified by Prep-TLC (DCM:MeOH=20:1) to afford the title product (68 mg, 53% yield). LC-MS $(M+H)^+$=346.3.

Step 10: methyl ((benzyloxy)carbonyl)-L-seryl-D-alaninate

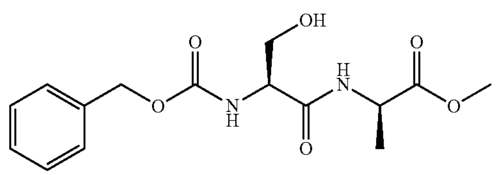 [SMILES: COC(=O)[C@@H](C)NC(=O)[C@H](CO)NC(=O)OCc1ccccc1]

DIEA (36.9 g, 286.4 mmol) was added dropwise to a cooled mixture of (R)-2-amino-propionic acid methyl ester hydrochloride (20 g, 143.2 mmol), EDC (33 g, 171.8 mmol), ((benzyloxy)carbonyl)-L-serine (34.3 g, 143.2 mmol) and DCM (700 mL). The resultant mixture was stirred at ambient temperature for 16 h under nitrogen atmosphere. The mixture was concentrated, the residue was diluted with saturated sodium carbonate solution, water and extracted with EtOAc. The combined organic layers were washed with 2M HCl solution, saturated brine solution, dried over $Na_2SO_4$ and concentrated to afford the product (20 g, 43% yield). LC-MS $(M+H)^+$=325.1.

Step 11: (3 S,6R)-3-(hydroxymethyl)-6-methylpiperazine-2,5-dione

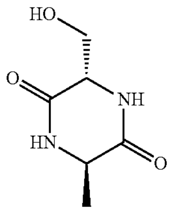

To methyl ((benzyloxy)carbonyl)-L-seryl-D-alaninate (10 g, 30.8 mmol) was added 10% Pd/C (500 mg), MeOH (100 mL) and cyclohexene (65 mL) under nitrogen. The mixture was heated to reflux and stirred at this temperature for overnight. The hot reaction mixture was filtered through celite with the cake being washed with hot MeOH. The combined filtrates were concentrated. The resulting solid was slurried in 2-butanone and petroleum ether was added gradually over 10 min. After stirring for 30 min, the solid was filtered, further washed with PE/2-butanone (v/v=2/1) mixture. The cake was thoroughly dried to afford the product (2.5 g, 51% yield). LC-MS $(M+H)^+$=159.1.

Step 12: ((2R,5R)-5-methylpiperazin-2-yl)methanol hydrochloride salt

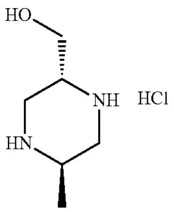

To (3S,6R)-3-(hydroxymethyl)-6-methylpiperazine-2,5-dione (2.5 g, 15.8 mmol) was added a solution of borane in THF (1M, 126 mL, 126.4 mmol) and the mixture was heated to 70° C. for 18 h. The solution was cooled in ice, then MeOH (30 mL) was gradually added, followed by 5N HCl (8 mL). The mixture was warmed to 70° C. for 2 h and then cooled to room temperature. The resulting solid was filtered, washed with THF and dried to afford the product (2.0 g, 77% yield). LC-MS $(M+H)^+$=131.1.

Step 13: tert-butyl (2R,5R)-5-(hydroxymethyl)-2-methylpiperazine-1-carboxylate

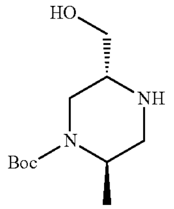

To ((2R,5R)-5-methylpiperazin-2-yl)methanol hydrochloride salt (2 g, 12.0 mmol) in MeOH (20 mL) at 0° C. was added TEA (3.6 g, 36.0 mmol). Then $(Boc)_2O$ (6.3 g, 28.8 mmol) was added dropwise. The resulting mixture was slowly warmed to room temperature and heated to 50° C. for overnight. The resulting mixture was concentrated and the residue was dissolved in ethanol (40 mL). A solution of NaOH (2.4 g, 60 mmol) in water (40 mL) was added and the reaction was heated to 100° C. for 18 h, then cooled to ambient temperature. The mixture was neutralized with 1N HCl to pH~9, then extracted with DCM. The combined organic layers were dried, filtered and concentrated to afford the title product (1.6 g, 58% yield). LC-MS $(M+H)^+$=231.1.

Step 14: tert-butyl (2R,5R)-4-benzyl-5-(hydroxymethyl)-2-methylpiperazine-1-carboxylate

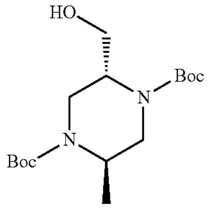 [SMILES: C[C@@H]1CN(C(=O)OC(C)(C)C)[C@@H](CO)CN1C(=O)OC(C)(C)C]

A mixture of tert-butyl (2R,5R)-5-(hydroxymethyl)-2-methylpiperazine-1-carboxylate (1.6 g, 6.9 mmol), benzaldehyde (805 mg, 7.6 mmol), sodium triacetoxyborohydride (1.8 g, 8.5 mmol) and DCM (30 mL) was stirred at room temperature for overnight. Then the mixture was partitioned between saturated $NaHCO_3$ solution and DCM. The combined organic layers were dried, filtered and concentrated. The residue was purified by silica gel column chromatography (DCM:MeOH=20:1) to afford the title product (2.0 g, 90% yield). LC-MS $(M+H)^+$=321.2.

Step 15: tert-butyl (2R,5R)-4-benzyl-5-(chloromethyl)-2-methylpiperazine-1-carboxylate

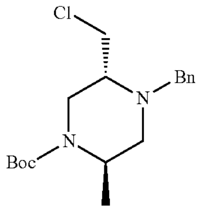 [SMILES: C[C@@H]1CN(Cc2ccccc2)[C@@H](CCl)CN1C(=O)OC(C)(C)C]

Methanesulfonyl chloride (0.6 mL, 7.4 mmol) was added to a solution of tert-butyl (2R,5R)-4-benzyl-5-(hydroxymethyl)-2-methylpiperazine-1-carboxylate (2.0 g, 6.2 mmol) containing TEA (2.6 mL, 18.4 mmol) in DCM (30 mL) at 0° C. The mixture was stirred at room temperature for overnight. The reaction was partitioned between $NH_4Cl$ solution and DCM. The combined organic layers were dried, filtered and concentrated. The crude material was purified by silica gel column chromatography (PE:EtOAc=3:1) to afford the title product (1.4 g, 67% yield). LC-MS $(M+H)^+$=339.2.

Step 16: tert-butyl (2R,5S)-4-benzyl-2-methyl-5-(((R)-3-methylmorpholino)methyl)piperazine-1-carboxylate

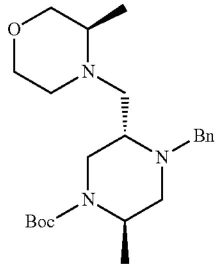 [SMILES: C[C@@H]1COCCN1C[C@H]1CN(C(=O)OC(C)(C)C)[C@H](C)CN1Cc1ccccc1]

To tert-butyl (2R,5R)-4-benzyl-5-(chloromethyl)-2-methylpiperazine-1-carboxylate (1.4 g, 4.1 mmol) in MeCN (20 mL) was added $K_2CO_3$ (1.7 g, 12.3 mmol), KI (1.4 g, 8.4 mmol) and (R)-3-methylmorpholine (630 mg, 6.2 mmol). The mixture was stirred at 70° C. for overnight. The solid was filtered off and the solvent was concentrated. The residue was partitioned between water and DCM. The combined organic layers were dried, filtered and evaporated. The crude residue was purified by silica gel column chromatography (DCM:MeOH=40:1) to afford the product (1.3 g, 78% yield). LC-MS $(M+H)^+$=404.3.

Step 17: tert-butyl (2R,5S)-2-methyl-5-(((R)-3-methylmorpholino)methyl)piperazine-1-carboxylate

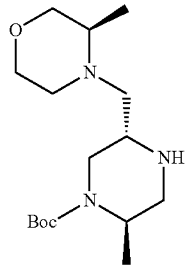 [SMILES: C[C@@H]1COCCN1C[C@H]1CN(C(=O)OC(C)(C)C)[C@H](C)CN1]

To tert-butyl (2R,5S)-4-benzyl-2-methyl-5-(((R)-3-methylmorpholino)methyl)piperazine-1-carboxylate (1.3 g, 3.2 mmol) in EtOH (20 mL) was cautiously added Pd/C (130 mg) and several drops of AcOH. The mixture was stirred under $H_2$ atmosphere at ambient temperature for 3 h. The mixture was concentrated and extracted with DCM. The combined organic layers were washed with saturated $NaHCO_3$ solution, dried, filtered and concentrated. The obtained title compound (1.0 g) was used in next step without purification. LC-MS $(M+H)^+$=314.2.

Step 18: tert-butyl (2R,5S)-4-(2-(6-cyano-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

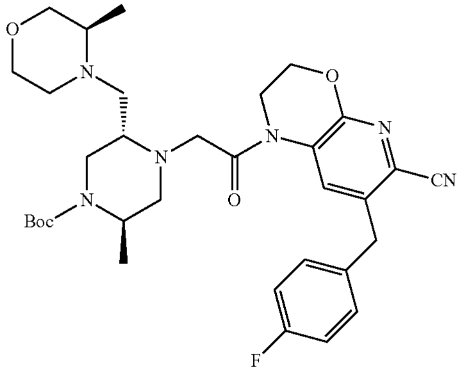 [SMILES: C[C@@H]1COCCN1C[C@H]1CN(C(=O)OC(C)(C)C)[C@H](C)CN1CC(=O)N1CCOc2nc(C#N)c(Cc3ccc(F)cc3)cc21]

A solution of 1-(2-chloroacetyl)-7-(4-fluorobenzyl)-2,3-dihydro-1H-pyrido[2,3-b][1,4]oxazine-6-carbonitrile (68 mg, 0.196 mmol), tert-butyl (2R,5S)-2-methyl-5-(((R)-3-methylmorpholino)methyl)piperazine-1-carboxylate (62 mg, 0.196 mmol), KI (65 mg, 0.392 mmol) and $K_2CO_3$ (81 mg, 0.588 mmol) in MeCN (10 mL) was stirred at room temperature for 2 h. The reaction solution was concentrated in vacuo to remove solvent, the residue was washed with $H_2O$ (10 mL), extracted with EtOAc (10 mL*3). The combined organic layers were concentrated and purified by Prep-TLC (DCM:MeOH=20:1) to afford the title compound (80 mg, 65.5% yield). LC-MS $(M+H)^+$=623.7.

Step 19: 7-(4-fluorobenzyl)-1-(2-((2R,5R)-5-methyl-2-(((R)-3-methylmorpholino)methyl)piperazin-1-yl)acetyl)-2,3-dihydro-1H-pyrido[2,3-b][1,4]oxazine-6-carbonitrile formate (Compound 1)

To tert-butyl (2R,5S)-4-(2-(6-cyano-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate (80 mg, 0.128 mmol) in DCM (10 mL) was added hydrochloric acid in 1,4-dioxane solution (4 N, 2.5 mL), the resulting solution was stirred at room temperature for 4 h. The solution was concentrated in vacuo, dissolved in MeOH (10 mL), adjusted pH to 8~9 by addition of aq $NaHCO_3$ solution, then concentrated in vacuo to removed solvents and the residue was purified by Prep-HPLC (gradient eluent: $CH_3CN/H_2O$ from 10% to 25%, containing 0.1% FA respectively) to afford compound 1 as formic acid salt (30 mg, 41% yield). $^1H$ NMR (400 MHz, DMSO-d6) δ 11.31-9.78 (m, 1H), 8.63 (s, 1H), 8.26 (s, 2H), 7.31-7.22 (m, 2H), 7.22-7.11 (m, 2H), 4.53-4.34 (m, 2H), 4.17-3.79 (m, 6H), 3.52-3.31 (m, 2H), 3.26-2.53 (m, 10H), 2.23-2.09 (m, 1H), 2.04-1.92 (s, 1H), 1.91-1.78 (m, 1H), 1.08-1.01 (m, 3H), 0.90-0.82 (m, 3H). LC-MS $(M+H)^+$=523.5.

Example 2: 1-(7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl) ethan-1-one formate (Compound 2)

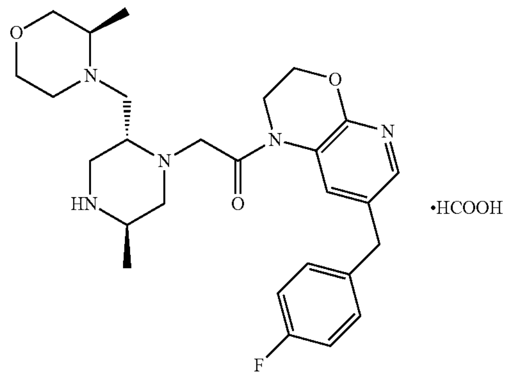 [SMILES: C[C@@H]1CN(CC(=O)N2CCOc3ncc(Cc4ccc(F)cc4)cc32)[C@@H](CN2CCOC[C@H]2C)CN1 ; "·HCOOH"]

Step 1: tert-butyl 7-(4-fluorobenzyl)-2,3-dihydro-1H-pyrido[2,3-b][1,4]oxazine-1-carboxylate

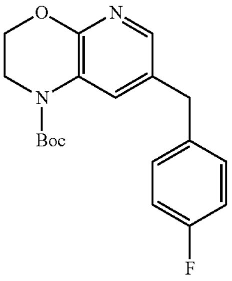 [SMILES: CC(C)(C)OC(=O)N1CCOc2ncc(Cc3ccc(F)cc3)cc21]

The title compound of Step 1 (1.56 g) was prepared in a manner similar to that described in Example 1 step 7 from tert-butyl 7-bromo-2,3-dihydro-1H-pyrido[2,3-b][1,4] oxazine-1-carboxylate and (4-fluorobenzyl)zinc(II) chloride. LCMS $(M+H)^+$=345.2.

Step 2: 7-(4-fluorobenzyl)-2,3-dihydro-1H-pyrido[2,3-b][1,4]oxazine

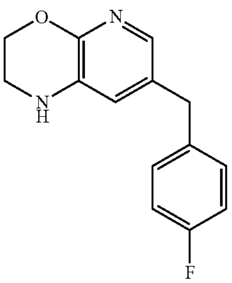 [SMILES: Fc1ccc(Cc2cnc3c(c2)NCCO3)cc1]

The title compound of Step 2 (100 mg) was prepared in a manner similar to that described in Example 1 step 8 from tert-butyl 7-(4-fluorobenzyl)-2,3-dihydro-1H-pyrido[2,3-b][1,4]oxazine-1-carboxylate. LC-MS $(M+H)^+$=245.2.

Step 3: 2-chloro-1-(7-(4-fluorobenzyl)-2,3-dihydro-1H-pyrido[2,3-b][1,4]oxazin-1-yl)ethan-1-one

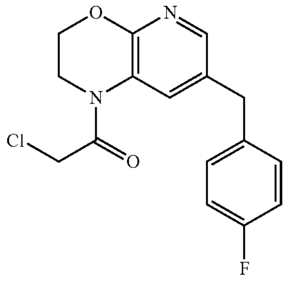 [SMILES: O=C(CCl)N1CCOc2ncc(Cc3ccc(F)cc3)cc21]

The title compound of Step 3 (80 mg) was prepared in a manner similar to that described in Example 1 step 9 from 7-(4-fluorobenzyl)-2,3-dihydro-1H-pyrido[2,3-b][1,4] oxazine and 2-chloroacetyl chloride. LC-MS $(M+H)^+$=321.1.

Step 4: tert-butyl (2R,5S)-4-(2-(7-(4-fluorobenzyl)-2,3-dihydro-1H-pyrido[2,3-b][1,4]oxazin-1-yl)-2-oxoethyl)-2-methyl-5-(((R)-3-methylmorpholino) methyl)piperazine-1-carboxylate

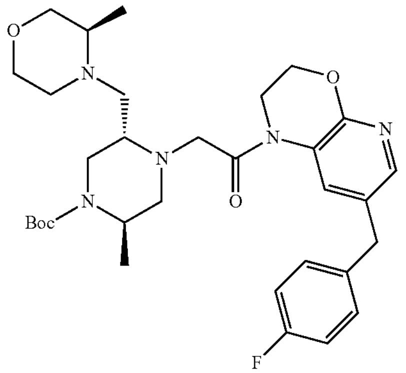 [SMILES: C[C@@H]1COCCN1C[C@H]1CN(C(=O)OC(C)(C)C)[C@H](C)CN1CC(=O)N1CCOc2ncc(Cc3ccc(F)cc3)cc21]

The title compound of Step 4 (80 mg) was prepared in a manner similar to that described in Example 1 step 18 from 2-chloro-1-(7-(4-fluorobenzyl)-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=598.6.

Step 5: 1-(7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl) ethan-1-one formate (Compound 2)

Compound 2 (20 mg) as its formic acid salt was prepared in a manner similar to that described in Example 1 step 19 from tert-butyl (2R,5S)-4-(2-(7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate. $^1$H NMR (400 MHz, DMSO-d6) δ 8.64-8.11 (s, 3H), 7.85 (s, 1H), 7.30-7.19 (m, 2H), 7.18-7.04 (m, 2H), 4.45-4.26 (m, 2H), 4.07-3.71 (m, 6H), 3.52-3.33 (m, 2H), 3.22-3.04 (m, 2H), 3.03-2.59 (m, 7H), 2.47-2.37 (m, 1H), 2.21-2.07 (m, 1H), 2.04-1.91 (m, 1H), 1.89-1.74 (m, 1H), 1.02 (d, J=5.8 Hz, 3H), 0.91-0.74 (m, 3H). LC-MS $(M+H)^+$ =498.6.

Example 3: 7-(4-fluorobenzyl)-1-(2-((2R,5R)-5-methyl-2-(((R)-3-methylmorpholino)methyl)piperazin-1-yl)acetyl)-2,3-dihydro-1H-pyrido[2,3-b][1,4]oxazine-6-carboxamide formate (Compound 3)

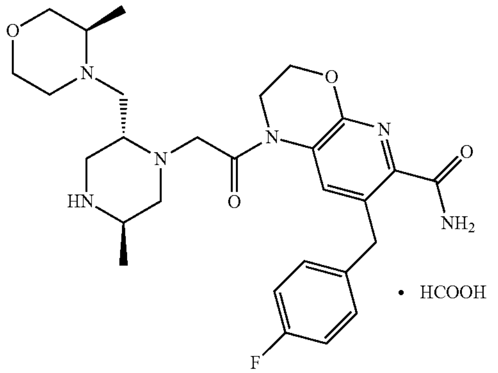 [SMILES: C[C@@H]1CN(CC(=O)N2CCOc3nc(C(N)=O)c(Cc4ccc(F)cc4)cc32)[C@@H](CN2CCOC[C@H]2C)CN1 ; "HCOOH"]

Step 1: 7-(4-fluorobenzyl)-2,3-dihydro-1H-pyrido[2,3-b][1,4]oxazine-6-carboxamide

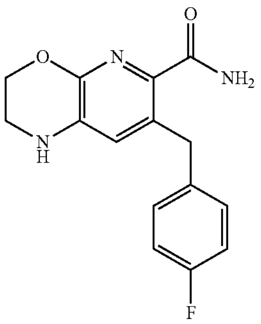 [SMILES: NC(=O)c1nc2c(cc1Cc1ccc(F)cc1)NCCO2]

To tert-butyl 6-cyano-7-(4-fluorobenzyl)-2,3-dihydro-1H-pyrido[2,3-b][1,4]oxazine-1-carboxylate (680 mg, 1.84 mmol) in DMSO (6 mL) and $H_2O$ (10 mL) was added KOH (1.55 g, 27.6 mmol), the resulting solution was stirred at 120° C. for 12 h. Solvents was removed in vacuo, the residue was purified by Prep-TLC (DCM:MeOH=30:1) to afford the title product (40 mg, 7.5% yield). LC-MS $(M+H)^+$=288.1.

Step 2: 7-(4-fluorobenzyl)-1-(2-((2R,5R)-5-methyl-2-(((R)-3-methylmorpholino)methyl)piperazin-1-yl)acetyl)-2,3-dihydro-1H-pyrido[2,3-b][1,4]oxazine-6-carboxamide formate (Compound 3)

Compound 3 (30 mg) as its formic acid salt was prepared in a manner similar to that described in Example 1 step 9 and step 18~19 from 7-(4-fluorobenzyl)-2,3-dihydro-1H-pyrido[2,3-b][1,4]oxazine-6-carboxamide and tert-butyl (2R,5S)-2-methyl-5-(((R)-3-methylmorpholino)methyl)piperazine-1-carboxylate. $^1H$ NMR (400 MHz, DMSO-d6) δ 10.26-8.03 (m, 4H), 7.79 (s, 1H), 7.44 (s, 1H), 7.30-7.17 (m, 2H), 7.14-6.99 (m, 2H), 4.52-4.17 (m, 4H), 4.13-3.72 (m, 4H), 3.54-3.29 (m, 2H), 3.17-3.02 (m, 2H), 3.01-2.76 (m, 4H), 2.73-2.57 (m, 3H), 2.48-2.35 (m, 1H), 2.21-2.08 (m, 1H), 2.04-1.90 (m, 1H), 1.88-1.71 (m, 1H), 1.05-0.95 (m, 3H), 0.92-0.80 (m, 3H). LC-MS $(M+H)^+$=541.6.

Example 4: 1-(6-bromo-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 4)

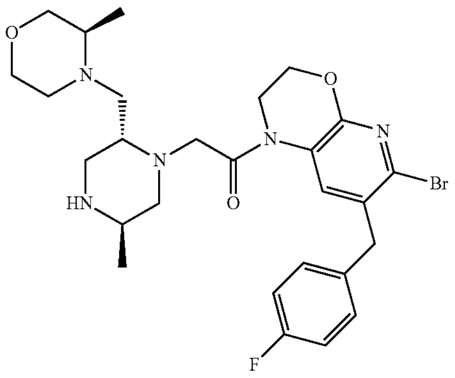 [SMILES: C[C@@H]1CN(CC(=O)N2CCOc3nc(Br)c(Cc4ccc(F)cc4)cc32)[C@@H](CN2CCOC[C@H]2C)CN1]

Step 1: 6-bromo-7-(4-fluorobenzyl)-2,3-dihydro-1H-pyrido[2,3-b][1,4]oxazine

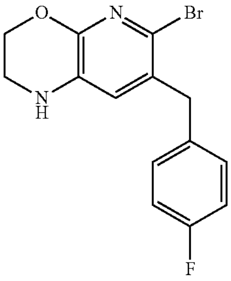 [SMILES: Fc1ccc(Cc2cc3c(nc2Br)OCCN3)cc1]

To 7-(4-fluorobenzyl)-2,3-dihydro-1H-pyrido[2,3-b][1,4]oxazine (612 mg, 2.51 mmol) in DMF (15 mL) was added NBS (446 mg, 2.51 mmol) in portions at 0° C., the resulting solution was stirred at room temperature for 2 h. Water (30 mL) was added and the mixture was extracted with EtOAc (15 mL*3). The combined organic layers were dried, filter and concentrated. The residue was purified by silica gel chromatography (DCM:MeOH=50:1) to give the title product (350 mg, 43.2% yield). LC-MS $(M+H)^+$=323.0, 325.0.

Step 2: tert-butyl 6-bromo-7-(4-fluorobenzyl)-2,3-dihydro-1H-pyrido[2,3-b][1,4]oxazine-1-carboxylate

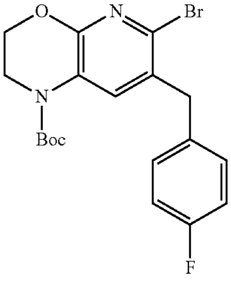 [SMILES: CC(C)(C)OC(=O)N1CCOc2nc(Br)c(Cc3ccc(F)cc3)cc21]

To 6-bromo-7-(4-fluorobenzyl)-2,3-dihydro-1H-pyrido[2,3-b][1,4]oxazine (350 mg, 1.1 mmol) in THF (10 mL) was added TEA (330 mg, 3.3 mmol). The mixture was cooled to 0° C. Then $(Boc)_2O$ (480 mg, 2.2 mmol) was added dropwise. The mixture was stirred at room temperature for overnight. The mixture was concentrated and the resulting residue was purified by silica gel column chromatography (PE:EtOAc=3:1) to afford the title product (300 mg, 64% yield). LC-MS $(M+H)^+$=423.1, 425.1.

Step 3: 1-(6-bromo-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 4)

Compound 4 as formic acid salt was prepared in a manner similar to that described in Example 1 step 8-9 and step 18-19 from tert-butyl 6-bromo-7-(4-fluorobenzyl)-2,3-dihydro-1H-pyrido[2,3-b][1,4]oxazine-1-carboxylate and tert-butyl (2R,5S)-2-methyl-5-(((R)-3-methylmorpholino)methyl)piperazine-1-carboxylate. The salt was neutralized with aq. $NaHCO_3$ and extracted with EtOAc. The combined EtOAc layers were dried, filtered and concentrated. The residue was further lyophilized to afford compound 4 (27 mg) as free base. $^1$H NMR (400 MHz, DMSO-d6) δ 8.46 (s, 1H), 8.25 (s, 1H), 7.28-7.18 (m, 2H), 7.17-7.09 (m, 2H), 4.52-4.29 (m, 2H), 4.12-3.89 (m, 3H), 3.88-3.60 (m, 2H), 3.55-3.09 (m, 4H), 3.08-2.58 (m, 7H), 2.45-2.26 (m, 2H), 2.16 (s, 1H), 2.03-1.92 (m, 1H), 1.85-1.73 (m, 1H), 1.01-0.91 (m, 3H), 0.91-0.74 (m, 3H). LC-MS $(M+H)^+$=576.5.

Example 5: 1-(7-(4-fluorobenzyl)-6-methyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 5)

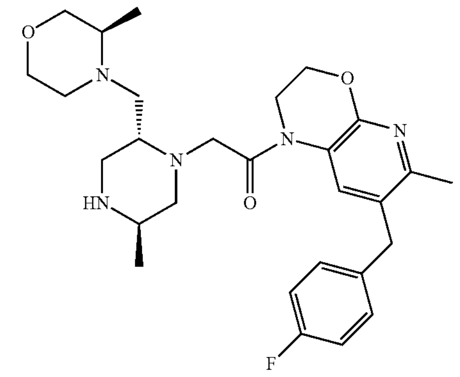 [SMILES: Cc1nc2c(cc1Cc1ccc(F)cc1)N(C(=O)CN1C[C@@H](C)NC[C@@H]1CN1CCOC[C@H]1C)CCO2]

Step 1: tert-butyl 7-(4-fluorobenzyl)-6-methyl-2,3-dihydro-1H-pyrido[2,3-b][1,4]oxazine-1-carboxylate

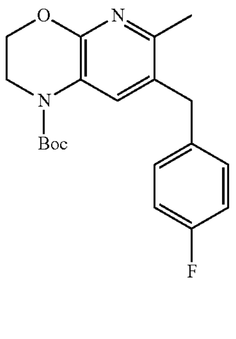 [SMILES: Cc1nc2c(cc1Cc1ccc(F)cc1)N(C(=O)OC(C)(C)C)CCO2]

To a solution of tert-butyl 6-bromo-7-(4-fluorobenzyl)-2,3-dihydro-1H-pyrido[2,3-b][1,4]oxazine-1-carboxylate (300 mg, 0.709 mmol) and methylboronic acid (128 mg, 2.13 mmol) in 1,4-dioxane (20 mL) and $H_2O$ (5 mL) was added $Pd(PPh_3)_4$ (82 mg, 0.071 mmol) and $Cs_2CO_3$ (699 mg, 2.15 mmol), the resulting solution was stirred at 100° C. for 12 h. The reaction solution was cooled to room temperature and washed by $H_2O$ (25 mL) and extracted with EtOAc (20 mL*3). The combined organic layers were dried over $Na_2SO_4$, concentrated in vacuo and purified by silica gel chromatography (PE:EtOAc=5:1) to give the title product (250 mg, 98% yield). LC-MS $(M+H)^+$=359.2.

Step 2: 1-(7-(4-fluorobenzyl)-6-methyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 5)

Compound 5 as formic acid salt was prepared in a manner similar to that described in Example 1 step 8-9 and step 1819 from tert-butyl 7-(4-fluorobenzyl)-6-methyl-2,3-dihydro-1H-pyrido[2,3-b][1,4]oxazine-1-carboxylate and tert-butyl (2R,5S)-2-methyl-5-(((R)-3-methylmorpholino)methyl)piperazine-1-carboxylate. The salt was neutralized with aq. $NaHCO_3$ and extracted with EtOAc. The combined EtOAc layers were dried, filtered and concentrated. The residue was further lyophilized to afford compound 5 (12.6 mg) as free base. $^1$H NMR (400 MHz, DMSO-d6) δ 8.49-8.06 (m, 1H), 7.21-7.03 (m, 4H), 4.45-4.24 (m, 2H), 4.10-3.96 (m, 2H), 3.92-3.84 (m, 2H), 3.85-3.70 (m, 1H), 3.59-3.41 (m, 3H), 3.29-3.15 (m, 1H), 3.07-2.65 (m, 5H), 2.63-2.53 (m, 2H), 2.31-2.18 (m, 4H), 2.18-2.06 (m, 1H), 2.01-1.84 (m, 2H), 1.78-1.65 (m, 1H), 1.00-0.66 (m, 6H). LC-MS $(M+H)^+$=512.3.

Example 6: 1-(6-cyclopropyl-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 6)

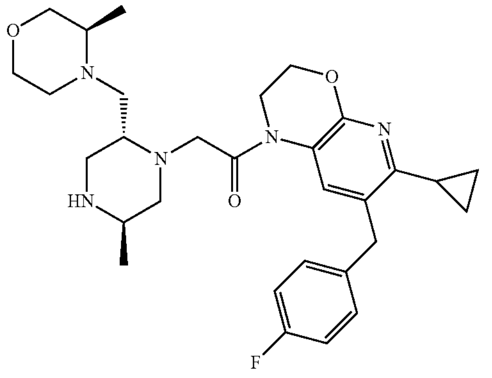 [SMILES: C[C@@H]1CN(CC(=O)N2CCOc3nc(C4CC4)c(Cc4ccc(F)cc4)cc32)[C@@H](CN2CCOC[C@H]2C)CN1]

Step 1: tert-butyl 6-cyclopropyl-7-(4-fluorobenzyl)-2,3-dihydro-1H-pyrido[2,3-b][1,4]oxazine-1-carboxylate

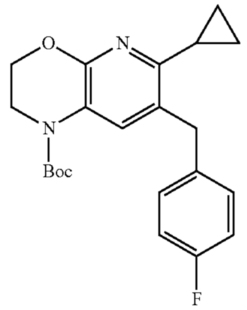 [SMILES: CC(C)(C)OC(=O)N1CCOc2nc(C3CC3)c(Cc3ccc(F)cc3)cc21]

To a solution of tert-butyl 6-bromo-7-(4-fluorobenzyl)-2,3-dihydro-1H-pyrido[2,3-b][1,4]oxazine-1-carboxylate (73 mg, 0.173 mmol) and cyclopropyl boronic acid (22 mg, 0.258 mmol) in toluene (10 mL) and $H_2O$ (5 mL) was added $Pd(OAc)_2$ (2 mg, 0.009 mmol) and tricyclohexylphospine (5 mg, 0.018 mmol) and $K_3PO_4$ (109 mg, 0.518 mmol), the resulting solution was stirred at 80° C. under $N_2$ for 12 h. The reaction solution was concentrated in vacuo to remove toluene, washed with water (10 mL) and extracted with EtOAc (10 mL*3). The combined organic layers were dried over $Na_2SO_4$, filtered and concentrated to afford crude product (78 mg), which was used in the next step without further purification. LC-MS $(M+H)^+$=385.3.

Step 2: 1-(6-cyclopropyl-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 6)

Compound 6 as formic acid salt was prepared in a manner similar to that described in Example 1 step 8~9 and step 18~19 from tert-butyl 6-cyclopropyl-7-(4-fluorobenzyl)-2,3-dihydro-1H-pyrido[2,3-b][1,4]oxazine-1-carboxylate and tert-butyl (2R,5S)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 6 (10 mg) as free base. $^1H$ NMR (400 MHz, DMSO-d6) δ 8.54 (s, 1H), 8.29 (s, 1H), 7.26-7.16 (m, 2H), 7.16-7.06 (m, 2H), 4.43-4.19 (m, 2H), 4.12-3.92 (m, 4H), 3.82-3.72 (m, 1H), 3.53-3.43 (m, 3H), 3.29-3.17 (m, 1H), 3.05-2.78 (m, 2H), 2.77-2.63 (m, 3H), 2.61-2.55 (m, 1H), 2.31-2.05 (m, 4H), 2.01-1.86 (m, 2H), 1.80-1.66 (m, 1H), 0.95-0.66 (m, 10H). LC-MS $(M+H)^+$=538.4.

Example 7: 1-(7-(4-fluorobenzyl)-6-(trifluoromethyl)-2,3-dihydro-1H-pyrido[2,3-b][1,4]oxazin-1-yl)-2-42R,5R)-5-methyl-2-(((R)-3-methylmorpholino)methyl)piperazin-1-yl)ethan-1-one (Compound 7)

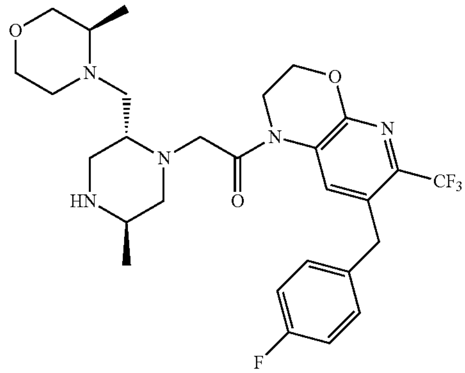 [SMILES: C[C@@H]1CN(CC(=O)N2CCOc3nc(C(F)(F)F)c(Cc4ccc(F)cc4)cc32)[C@@H](CN2CCOC[C@H]2C)CN1]

Step 1: tert-butyl 7-(4-fluorobenzyl)-6-(trifluoromethyl)-2,3-dihydro-1H-pyrido[2,3-b][1,4]oxazine-1-carboxylate

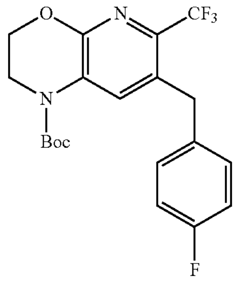 [SMILES: CC(C)(C)OC(=O)N1CCOc2nc(C(F)(F)F)c(Cc3ccc(F)cc3)cc21]

To a solution of tert-butyl 6-bromo-7-(4-fluorobenzyl)-2,3-dihydro-1H-pyrido[2,3-b][1,4]oxazine-1-carboxylate (110 mg, 0.26 mmol) and methyl 2,2-difluoro-2-(fluorosulfonyl)acetate (200 mg, 1.04 mmol) in DMF (5 mL) was added CuI (99 mg, 0.52 mmol), the resulting solution was stirred at 120° C. for 1 hour. The reaction solution was cooled to room temperature, washed by $H_2O$ (10 mL) and extracted with EtOAc (10 mL*3). The combined organic layers were dried over $Na_2SO_4$, filtered and concentrated in vacuo, the residue was purified by silica gel column chromatography (PE:EtOAc=5:1) to give the title product (73 mg, 68% yield). LC-MS $(M+H)^+$=413.2.

Step 2: 1-(7-(4-fluorobenzyl)-6-(trifluoromethyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 7)

Compound 7 as formic acid salt was prepared in a manner similar to that described in Example 1 step 8~9 and step 18~19 from tert-butyl 7-(4-fluorobenzyl)-6-(trifluoromethyl)-2,3-dihydro-1H-pyrido[2,3-b][1,4]oxazine-1-carboxylate and tert-butyl (2R,5S)-2-methyl-5-(((R)-3-methylmorpholino)methyl)piperazine-1-carboxylate. The salt was neutralized with aq. $NaHCO_3$ and extracted with EtOAc.

The combined organic layers were dried, filtered and concentrated. The residue was further lyophilized to afford compound 7 (26.4 mg) as free base. $^1H$ NMR (400 MHz, DMSO-d6) δ 8.58 (s, 1H), 7.27-7.05 (m, 4H), 4.53-4.35 (m, 2H), 4.16-3.95 (m, 4H), 3.92-3.81 (m, 1H), 3.78-3.65 (m, 1H), 3.53-3.37 (m, 2H), 3.19-3.07 (m, 1H), 2.97-2.77 (m, 4H), 2.76-2.57 (m, 3H), 2.47-2.29 (m, 2H), 2.20-2.09 (m, 1H), 2.01-1.89 (m, 1H), 1.83-1.73 (m, 1H), 0.97-0.89 (m, 3H), 0.89-0.80 (m, 3H). LCMS $(M+H)^+$=566.3.

Example 8: 1-(7-(4-fluorobenzyl)-6-(hydroxymethyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 8)

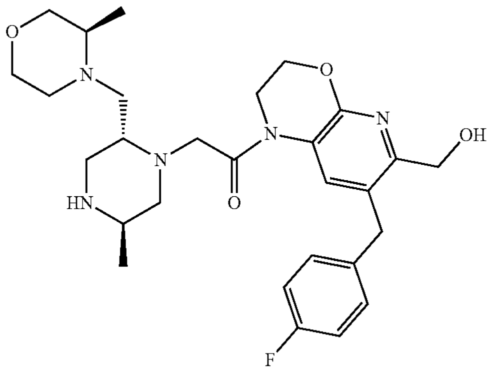 [SMILES: C[C@@H]1CN(CC(=O)N2CCOc3nc(CO)c(Cc4ccc(F)cc4)cc32)[C@@H](CN2CCOC[C@H]2C)CN1]

Step 1: 1-(tert-butoxycarbonyl)-7-(4-fluorobenzyl)-6-methyl-2,3-dihydro-1H-pyrido[2,3-b][1,4]oxazine 5-oxide

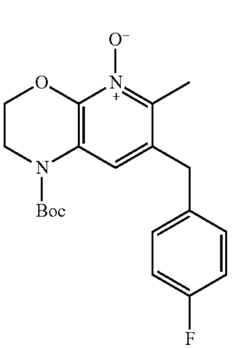

The title compound of Step 1 (1.2 g) was prepared in a manner similar to that described in Example 1 step 5 from tert-butyl 7-(4-fluorobenzyl)-6-methyl-2,3-dihydro-1H-pyrido[2,3-b][1,4]oxazine-1-carboxylate. LC-MS $(M+H)^+$=375.2.

Step 2: tert-butyl 6-(acetoxymethyl)-7-(4-fluorobenzyl)-2,3-dihydro-1H-pyrido[2,3-b][1,4]oxazine-1-carboxylate

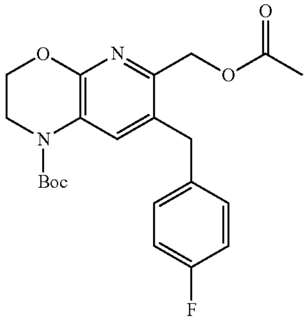 [SMILES: CC(=O)OCc1nc2c(cc1Cc1ccc(F)cc1)N(C(=O)OC(C)(C)C)CCO2]

A solution of 1-(tert-butoxycarbonyl)-7-(4-fluorobenzyl)-6-methyl-2,3-dihydro-1H-pyrido[2,3-b][1,4]oxazine 5-oxide (1.2 g, 3.2 mmol) in $Ac_2O$ (20 mL) was stirred at 130° C. for 3 hours. The reaction solution was cooled to room temperature, water (50 mL) was added and the mixture was extracted with EtOAc (5 mL*3). The combined organic layers were dried over $Na_2SO_4$, filtered and concentrated in vacuo to afford crude product (1.0 g) which was used in the next step directly without purification. LC-MS $(M+H)^+$=417.2.

Step 3: tert-butyl (2R,5S)-4-(2-(6-(acetoxymethyl)-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

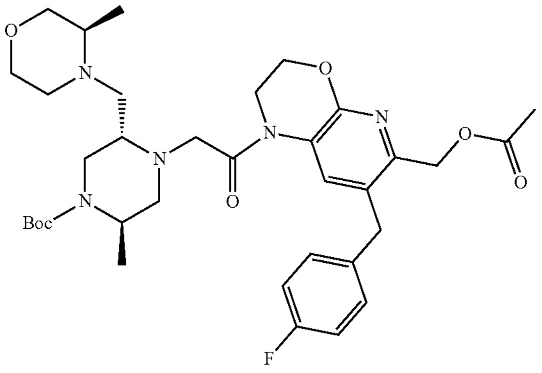 [SMILES: CC(=O)OCc1nc2c(cc1Cc1ccc(F)cc1)N(C(=O)CN1C[C@@H](C)N(C(=O)OC(C)(C)C)C[C@@H]1CN1CCOC[C@H]1C)CCO2]

The title compound of Step 3 (40 mg) was prepared in a manner similar to that described in Example 1 step 8-9 and step 18 from tert-butyl 6-(acetoxymethyl)-7-(4-fluorobenzyl)-2,3-dihydro-1H-pyrido[2,3-b][1,4]oxazine-1-carboxylate and tert-butyl (2R,5S)-2-methyl-5-(((R)-3-methylmorpholino)methyl)piperazine-1-carboxylate. LC-MS $(M+H)^+$=670.4.

Step 4: tert-butyl (2R,5S)-4-(2-(7-(4-fluorobenzyl)-6-(hydroxymethyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

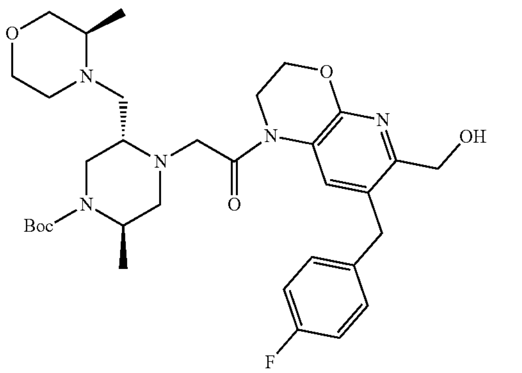 [SMILES: C[C@@H]1COCCN1C[C@H]1CN(C(=O)OC(C)(C)C)[C@H](C)CN1CC(=O)N1CCOc2nc(CO)c(Cc3ccc(F)cc3)cc21]

A solution of tert-butyl (2R,5S)-4-(2-(6-(acetoxymethyl)-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate (40 mg, 0.06 mmol) in MeOH (5 mL) and $H_2O$ (5 mL) was added NaOH (12 mg, 0.3 mmol), the resulting solution was stirred at room temperature for 3 hours. The reaction solution was extracted with EtOAc (10 mL*3). The combined organic layers were dried, filtered and concentrated. The residue was purified by Prep-TLC (DCM:MeOH+=20:1) to afford the title product (20 mg, 53% yield). LC-MS $(M+H)^+$=628.3.

Step 5: 1-(7-(4-fluorobenzyl)-6-(hydroxymethyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 8)

Compound 8 as formic acid salt was prepared in a manner similar to that described in Example 1 step 19 from tert-butyl (2R,5S)-4-(2-(7-(4-fluorobenzyl)-6-(hydroxymethyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 8 (5.7 mg) as free base. $^1H$ NMR (400 MHz, DMSO-d6) δ 8.34 (s, 1H), 7.26-7.16 (m, 2H), 7.16-7.06 (m, 2H), 5.11 (s, 1H), 4.49-4.26 (m, 4H), 4.06-3.68 (m, 6H), 3.53-3.37 (m, 2H), 3.26-2.60 (m, 10H), 2.23-2.11 (m, 1H), 2.05-1.94 (m, 1H), 1.91-1.80 (m, 1H), 1.10-1.01 (m, 3H), 0.95-0.76 (m, 3H). LC-MS $(M+H)^+$=528.3.

Example 9: 1-(7-(4-fluorobenzyl)-6-hydroxy-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 9)

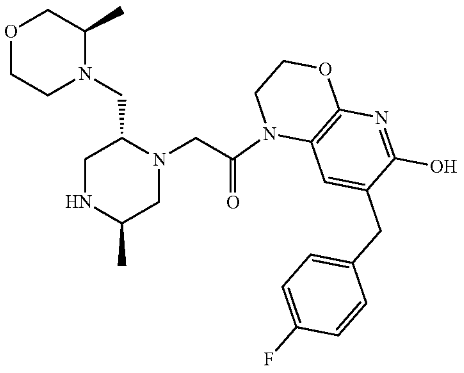 [SMILES: C[C@@H]1CN(CC(=O)N2CCOc3nc(O)c(Cc4ccc(F)cc4)cc32)[C@@H](CN2CCOC[C@H]2C)CN1]

Step 1: 1-(tert-butoxycarbonyl)-7-(4-fluorobenzyl)-2,3-dihydro-1H-pyrido[2,3-b][1,4]oxazine 5-oxide

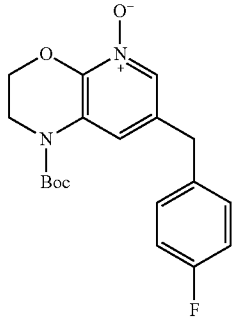

The title compound of Step 1 (166 mg) was prepared in a manner similar to that described in Example 1 step 5 from tert-butyl 7-(4-fluorobenzyl)-2,3-dihydro-1H-pyrido[2,3-b][1,4]oxazine-1-carboxylate. LC-MS $(M+H)^+$=361.3.

Step 2: tert-butyl 6-acetoxy-7-(4-fluorobenzyl)-2,3-dihydro-1H-pyrido[2,3-b][1,4]oxazine-1-carboxylate

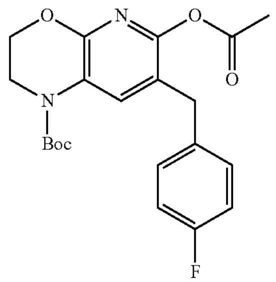 [SMILES: CC(=O)Oc1nc2c(cc1Cc1ccc(F)cc1)N(C(=O)OC(C)(C)C)CCO2]

A solution of 1-(tert-butoxycarbonyl)-7-(4-fluorobenzyl)-2,3-dihydro-1H-pyrido[2,3-b][1,4]oxazine 5-oxide (166 mg, 0.461 mmol) in $Ac_2O$ (2 mL) was stirred at 130° C. for 3 hours. The reaction solution was cooled to room temperature, water (5 mL) was added and the mixture was extracted with EtOAc (5 mL*3). The combined organic layers were dried over $Na_2SO_4$, filtered and concentrated in vacuo to afford the title product (160 mg) which was used in the next step directly without purification. LC-MS $(M+H)^+$=403.2.

Step 3: 7-(4-fluorobenzyl)-2,3-dihydro-1H-pyrido[2,3-b][1,4]oxazin-6-ol

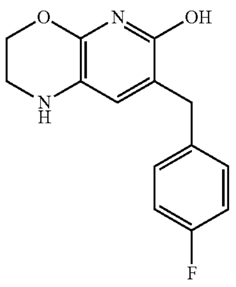 [SMILES: Oc1nc2c(cc1Cc1ccc(F)cc1)NCCO2]

To a solution of tert-butyl 6-acetoxy-7-(4-fluorobenzyl)-2,3-dihydro-1H-pyrido[2,3-b][1,4]oxazine-1-carboxylate (160 mg, 0.398 mmol) in DCM (5 mL) was added TFA (1 mL), the resulting solution was stirred at room temperature for 2 h. The reaction solution was concentrated in vacuo, the resultant residue was purified by Prep-TLC (DCM: MeOH=15:1) to afford the title product (38 mg, 37% yield). LC-MS $(M+H)^+$=261.2.

Step 4: 2-chloro-1-(7-(4-fluorobenzyl)-6-hydroxy-2,3-dihydro-1H-pyrido[2,3-b][1,4]oxazin-1-yl)ethan-1-one

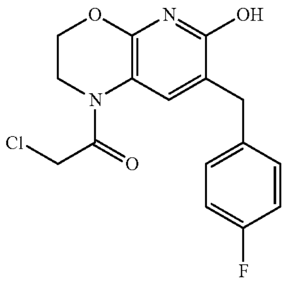

The title compound of Step 4 (60 mg) was prepared in a manner similar to that described in Example 1 step 9 from 7-(4-fluorobenzyl)-2,3-dihydro-1H-pyrido[2,3-b][1,4]oxazin-6-ol and 2-chloroacetyl chloride. LC-MS $(M+H)^+$=337.2.

Step 5: tert-butyl (2R,5S)-4-(2-(7-(4-fluorobenzyl)-6-hydroxy-2,3-dihydro-1H-pyrido[2,3-b][1,4]oxazin-1-yl)-2-oxoethyl)-2-methyl-5-(((R)-3-methylmorpholino)methyl)piperazine-1-carboxylate

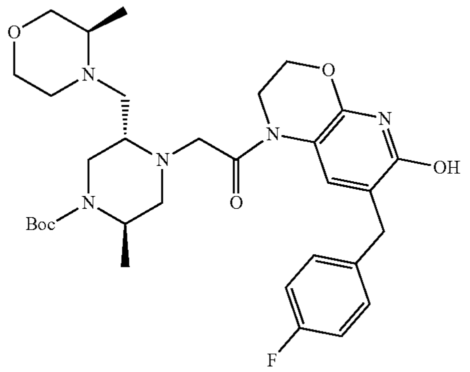 [SMILES: C[C@@H]1COCCN1C[C@H]1CN(C(=O)OC(C)(C)C)[C@H](C)CN1CC(=O)N1CCOc2nc(O)c(Cc3ccc(F)cc3)cc21]

The title compound of Step 5 (20 mg) was prepared in a manner similar to that described in Example 1 step 18 from 2-chloro-1-(7-(4-fluorobenzyl)-6-hydroxy-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=614.5.

Step 6: 1-(7-(4-fluorobenzyl)-6-hydroxy-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 9)

Compound 9 as formic acid salt was prepared in a manner similar to that described in Example 1 step 19 from tert-butyl (2R,5S)-4-(2-(7-(4-fluorobenzyl)-6-hydroxy-2,3-dihydro-1H-pyrido[2,3-b][1,4]oxazin-1-yl)-2-oxoethyl)-2-methyl-5-(((R)-3-methylmorpholino)methy)piperazine-1-carboxylate. The salt was neutralized with aq. $NaHCO_3$ and extracted with EtOAc. The combined organic layers were dried, filtered and concentrated. The residue was further lyophilized to afford compound 9 (5.2 mg) as free base. $^1H$ NMR (400 MHz, DMSO-d6) δ 9.39 (s, 1H), 8.71 (s, 1H), 8.17 (s, 1H), 7.34-7.15 (m, 2H), 7.15-7.02 (m, 2H), 4.45-4.25 (m, 2H), 4.03-3.65 (m, 6H), 3.57-3.39 (m, 3H), 3.30-3.05 (m, 3H), 3.03-2.78 (m, 4H), 2.75-2.56 (m, 2H), 2.28-2.15 (m, 1H), 2.11-2.01 (m, 1H), 1.99-1.83 (m, 1H), 1.20-1.09 (m, 3H), 0.96-0.79 (m, 3H). LC-MS $(M+H)^+$=514.5.

Example 10: 1-(7-(4-fluorobenzyl)-3-methyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 10)

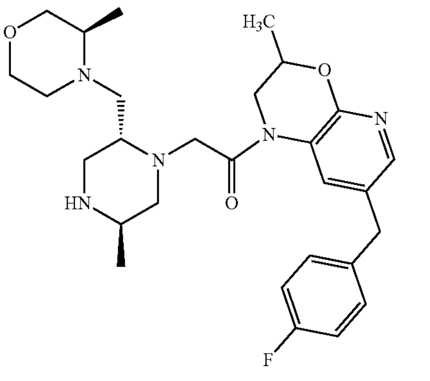 [SMILES: CC1CN(C(=O)CN2C[C@@H](C)NC[C@@H]2CN2CCOC[C@H]2C)c2cc(Cc3ccc(F)cc3)cnc2O1]

Step 1: ethyl 2-((5-bromo-3-nitropyridin-2-yl)oxy)propanoate

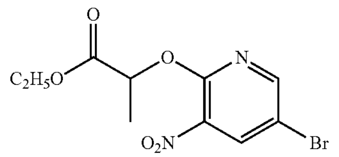

To 5-bromo-2-chloro-3-nitropyridine (11.87 g, 50 mmol) and ethyl 2-hydroxypropanoate (8.85 g, 75 mmol) in anhydrous THF (100 mL) was added NaH (4 g, 60% dispersion in mineral oil, 100 mmol) slowly at 0° C. The resulting solution was stirred at room temperature for 1 h. The reaction was quenched by water (20 mL) and extracted with EtOAc (100 mL*3), combined EtOAc phase was dried over $Na_2SO_4$, filtered and evaporated in vacuo. The residue was purified by silica gel chromatography (PE:EtOAc=10:1) to give the title product (8.5 g, 53% yield). LC-MS $(M+H)^+$=319.0, 321.0.

Step 2: 7-bromo-3-methyl-1H-pyrido[2,3-b][1,4]oxazin-2(3H)-one

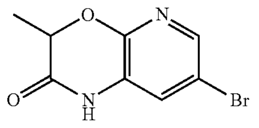

To ethyl 2-((5-bromo-3-nitropyridin-2-yl)oxy)propanoate (8.5 g, 26.7 mmol) in AcOH (100 mL) was added Fe powder (17.3 g, 310 mmol) slowly at 70° C., the resulting mixture was stirred at 70° C. for 1 h. AcOH was removed in vacuo, The resulting solid was washed with MeOH (200 mL), filtered. Repeat this procedure for 5 times. MeOH phase was concentrated in vacuo to give crude product (2.2 g), which was used directly in next step without purification. LC-MS $(M+H)^+$=243.0 245.0.

Step 3: 7-bromo-3-methyl-2,3-dihydro-1H-pyrido[2,3-b][1,4]oxazine

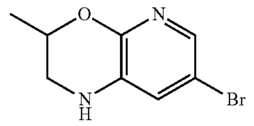

To 7-bromo-3-methyl-1H-pyrido[2,3-b][1,4]oxazin-2(3H)-one (2.2 g, 9.05 mmol) in anhydrous THF (50 mL) was added borane in THF (1N, 23 mL) dropwise at room temperature, the resulting solution was stirred at 60° C. for 1 h. The reaction was cooled to room temperature, quenched by MeOH (10 mL), adjusted pH to 1-2 by addition of 1N HCl, and stirred at 60° C. for 1 h. The reaction mixture was cooled to room temperature, Water (100 mL) was added and adjusted pH to 8-9, extracted with EtOAc (100 mL*3). The combined EtOAc layers were dried over $Na_2SO_4$, filtered and evaporated in vacuo to give the title product (1.2 g) which was used in the next step without purification. LC-MS $(M+H)^+$=229.0, 231.0.

Step 4: tert-butyl 7-bromo-3-methyl-2,3-dihydro-1H-pyrido[2,3-b][1,4]oxazine-1-carboxylate

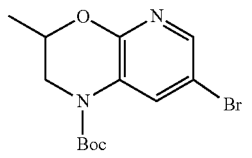 [SMILES: CC1CN(C(=O)OC(C)(C)C)c2cc(Br)cnc2O1]

To 7-bromo-3-methyl-2,3-dihydro-1H-pyrido[2,3-b][1,4]oxazine (1 g, 4.37 mmol), DMAP (0.8 g, 6.55 mmol) and $Et_3N$ (0.882 g, 8.72 mmol) in THF (30 mL) was added $(Boc)_2O$ (1.42 g, 6.55 mmol) dropwise at 0° C. The mixture was stirred at room temperature for 12 hours. The reaction was washed with water (50 mL), extracted with EtOAc (50 mL*3). The combined EtOAc layers were dried over $Na_2SO_4$, filtered and evaporated in vacuo. The residue was purified by silica gel chromatography (PE:EtOAc=5:1) to give the title product (0.99 g, 69% yield). LC-MS $(M+H)^+$=329.2, 331.2.

Step 5: tert-butyl 7-(4-fluorobenzyl)-3-methyl-2,3-dihydro-1H-pyrido[2,3-b][1,4]oxazine-1-carboxylate

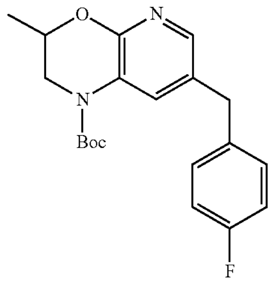 [SMILES: CC1CN(C(=O)OC(C)(C)C)c2cc(Cc3ccc(F)cc3)cnc2O1]

To a solution of tert-butyl 7-bromo-3-methyl-2,3-dihydro-1H-pyrido[2,3-b][1,4]oxazine-1-carboxylate (990 mg, 3 mmol) and bis(tri-tert-butylphosphine)palladium (77 mg, 0.15 mmol) in anhydrous THF (20 mL) was added (4-fluorobenzyl)zinc(II) chloride solution (0.5N, 12 mL, 6 mmol) dropwise, the resulting solution was stirred at 60° C. for 2 h. The reaction was quenched by MeOH (5 mL) and concentrated in vacuo, the residue was purified by silica gel chromatography (PE:EtOAc=5:1) to give the title product (850 mg, 79% yield). LC-MS $(M+H)^+$=359.4.

Step 6: 7-(4-fluorobenzyl)-3-methyl-2,3-dihydro-1H-pyrido[2,3-b][1,4]oxazine

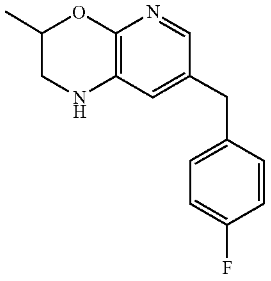 [SMILES: CC1CNc2cc(Cc3ccc(F)cc3)cnc2O1]

To a solution of tert-butyl 7-(4-fluorobenzyl)-3-methyl-2,3-dihydro-1H-pyrido[2,3-b][1,4]oxazine-1-carboxylate (850 mg, 2.37 mmol) in DCM (10 mL) was added hydrochloric acid in 1,4-dioxane solution (4 N, 2.5 mL, 10 mmol), the resulting solution was stirred at room temperature for 12 h. The solution was concentrated in vacuo. $NaHCO_3$ solution (sat, 20 mL) was added, extracted with DCM (20 mL). The combined organic layers were washed with brine (20 mL), dried with $Na_2SO_4$, concentrated to afford the title product (550 mg, 90% yield). LC-MS $(M+H)^+$=259.1.

Step 7: 2-chloro-1-(7-(4-fluorobenzyl)-3-methyl-2,3-dihydro-1H-pyrido[2,3-b][1,4]oxazin-1-yl)ethan-1-one

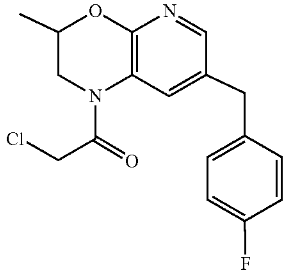 [SMILES: CC1CN(C(=O)CCl)c2cc(Cc3ccc(F)cc3)cnc2O1]

The title compound of Step 7 (110 mg) was prepared in a manner similar to that described in Example 1 step 9 from 7-(4-fluorobenzyl)-3-methyl-2,3-dihydro-1H-pyrido[2,3-b][1,4]oxazine and 2-chloroacetyl chloride. LC-MS $(M+H)^+$=334.9.

Step 8: tert-butyl (2R,5S)-4-(2-(7-(4-fluorobenzyl)-3-methyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate

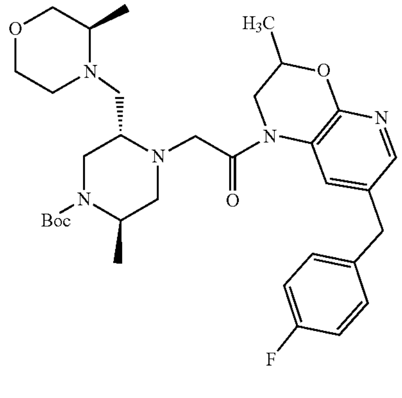 [SMILES: CC1CN(C(=O)CN2C[C@@H](C)N(C(=O)OC(C)(C)C)C[C@@H]2CN2CCOC[C@H]2C)c2cc(Cc3ccc(F)cc3)cnc2O1]

The title compound of Step 8 (45 mg) was prepared in a manner similar to that described in Example 1 step 18 from 2-chloro-1-(7-(4-fluorobenzyl)-3-methyl-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=612.3.

Step 9: 1-(7-(4-fluorobenzyl)-3-methyl-2,3-dihydro-1H-pyrido[2,3-b][1,4]oxazin-1-yl) ((2R,5R)-5-methyl-2-(((R)-3-methylmorpholino)methyl)piperazin-1-yl)ethan-1-one (Compound 10)

Compound 10 as formic acid salt was prepared in a manner similar to that described in Example 1 step 19 from tert-butyl (2R,5S)-4-(2-(7-(4-fluorobenzyl)-3-methyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 10 (8 mg) as free base. $^1H$ NMR (400 MHz, DMSO-d6) δ 8.28 (s, 1H), 7.85 (s, 1H), 7.26 (s, 2H), 7.14-7.12 (m, 2H), 4.48 (s, 1H), 4.09-4.05 (m, 2H), 3.88 (s, 2H), 3.55 (s, 1H), 3.49-3.47 (m, 3H), 3.26-3.20 (m, 1H), 2.93 (s, 1H), 2.79-2.76 (m, 3H), 2.70-2.59 (m, 4H), 2.32-2.26 (m, 1H), 2.16 (brs, 2H), 2.01-1.94 (m, 1H), 1.77-1.72 (m, 1H), 1.34-1.28 (m, 3H), 0.91-0.82 (m, 6H). LC-MS $(M+H)^+$=512.0.

Example 11: 1-(6-bromo-7-(4-fluorobenzyl)-3-methyl-2,3-dihydro-1H-pyrido[2,3-b][1,4]oxazin-1-yl)-2-42R,5R)-5-methyl-2-(((R)-3-methylmorpholino)methyl)piperazin-1-yl)ethan-1-one (Compound 11)

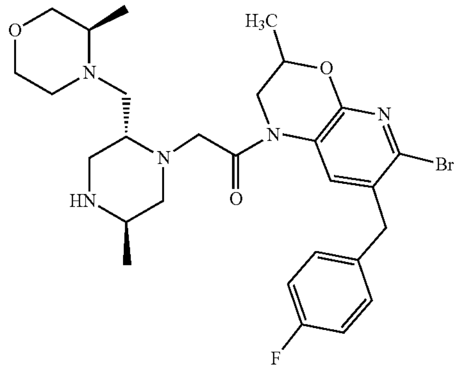 [SMILES: CC1CN(C(=O)CN2C[C@@H](C)NC[C@@H]2CN2CCOC[C@H]2C)c2cc(Cc3ccc(F)cc3)c(Br)nc2O1]

Step 1: 6-bromo-7-(4-fluorobenzyl)-3-methyl-2,3-dihydro-1H-pyrido[2,3-b][1,4]oxazine

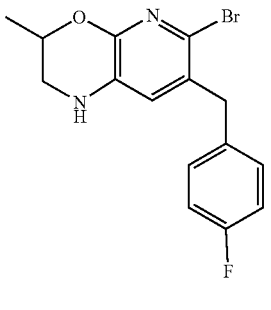 [SMILES: CC1CNc2cc(Cc3ccc(F)cc3)c(Br)nc2O1]

To 7-(4-fluorobenzyl)-3-methyl-2,3-dihydro-1H-pyrido[2,3-b][1,4]oxazine (620 mg, 2.4 mmol) in DMF (15 mL) was added NBS (428 mg, 2.4 mmol) at 0° C., the resulting solution was stirred at room temperature for 2 h. Water (30 mL) was added and extracted with EtOAc (15 mL*3). The combined organic layers were concentrated and purified by silica gel chromatography (PE:EtOAc=3:1) to afford the title product (350 mg, 43% yield). LC-MS $(M+H)^+$=337.0, 339.0

Step 2: 1-(6-bromo-7-(4-fluorobenzyl)-3-methyl-2,3-dihydro-1H-pyrido[2,3-b][1,4]oxazin-1-yl)-2-chloroethan-1-one

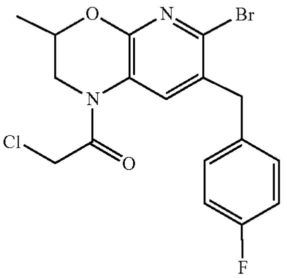 [SMILES: CC1CN(C(=O)CCl)c2cc(Cc3ccc(F)cc3)c(Br)nc2O1]

The title compound of Step 2 (140 mg) was prepared in a manner similar to that described in Example 1 step 9 from 6-bromo-7-(4-fluorobenzyl)-3-methyl-2,3-dihydro-1H-pyrido[2,3-b][1,4]oxazine and 2-chloroacetyl chloride. LC-MS $(M+H)^+$=413.3, 415.3.

Step 3: tert-butyl (2R,5S)-4-(2-(6-bromo-7-(4-fluorobenzyl)-3-methyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate

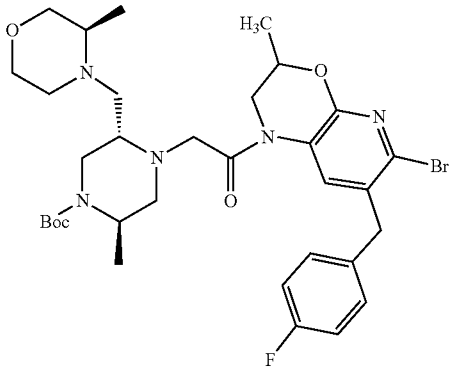 [SMILES: CC1CN(C(=O)CN2C[C@@H](C)N(C(=O)OC(C)(C)C)C[C@@H]2CN2CCOC[C@H]2C)c2cc(Cc3ccc(F)cc3)c(Br)nc2O1]

The title compound of Step 3 (80 mg) was prepared in a manner similar to that described in Example 1 step 18 from 1-(6-bromo-7-(4-fluorobenzyl)-3-methyl-2,3-dihydro-1H-pyrido[2,3-b][1,4]oxazin-1-yl)-2-chloroethan-1-one and tert-butyl (2R,5S)-2-methyl-5-(((R)-3-methylmorpholino)methyl)piperazine-1-carboxylate. LC-MS $(M+H)^+$=690.3, 692.3.

Step 4: 1-(6-bromo-7-(4-fluorobenzyl)-3-methyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 11)

Compound 11 as formic acid salt was prepared in a manner similar to that described in Example 1 step 19 from tert-butyl (2R,5S)-4-(2-(6-bromo-7-(4-fluorobenzyl)-3-methyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 11 (10 mg) as free base. $^1H$ NMR (400 MHz, DMSO-d6) δ 8.42 (s, 1H), 7.23 (s, 2H), 7.23-7.14 (m, 2H), 4.55 (s, 1H), 4.13-4.09 (m, 2H), 3.97 (s, 2H), 3.59 (brs, 1H), 3.55-3.42 (m, 3H), 3.27-3.21 (m, 1H), 2.95 (brs, 1H), 2.77-2.74 (m, 3H), 2.65-2.59 (m, 3H), 2.30-2.23 (m, 1H), 2.16 (brs, 2H), 2.00-1.95 (m, 2H), 1.76-1.73 (m, 1H), 1.33 (d, J=4.0 Hz, 3H), 0.86 (d, J=8.0 Hz, 6H). LC-MS $(M+H)^+$=590.0, 592.0.

Example 12: 1-(6-bromo-7-(4-fluorobenzyl)-3,3-dimethyl-2,3-dihydro-1H-pyrido[2,3-b][1,4]oxazin-1-yl)-2-42R,5R)-5-methyl-2-(((R)-3-methylmorpholino)methyl)piperazin-1-yl)ethan-1-one (Compound 12)

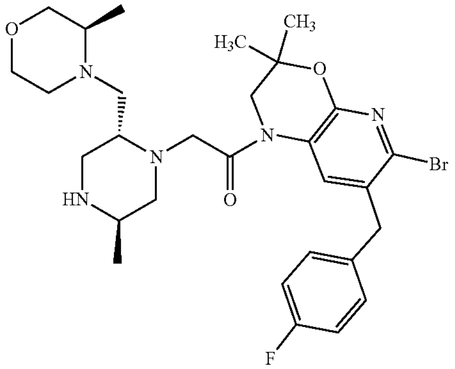 [SMILES: C[C@@H]1CN(CC(=O)N2CC(C)(C)Oc3nc(Br)c(Cc4ccc(F)cc4)cc32)[C@@H](CN2CCOC[C@H]2C)CN1]

Step 1: 2-bromo-N-(5-bromo-2-hydroxypyridin-3-yl)-2-methylpropanamide

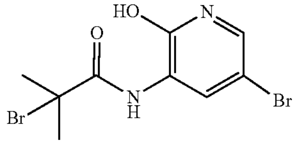

To a solution of 3-amino-5-bromopyridin-2-ol (4 g, 21.2 mmol) in THF (40 mL) was added TEA (6.4 g, 63.5 mmol). The mixture was cooled to 0° C. 2-bromo-2-methyl-propanoyl bromide (5.3 g, 23.3 mmol) was added dropwise. The mixture was slowly warmed to room temperature and stirred for 2 h. The mixture was concentrated, diluted with water and extracted with EtOAc. The combined organic layers were dried, filtered and concentrated. The residue was purified by silica gel column chromatography (PE: EtOAc=1:1) to afford the title product (4.2 g, 60% yield). LC-MS $(M+H)^+$=336.9.

Step 2: 7-bromo-3,3-dimethyl-1H-pyrido[2,3-b][1,4]oxazin-2(3H)-one

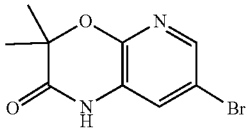

To a solution of 2-bromo-N-(5-bromo-2-hydroxypyridin-3-yl)-2-methylpropanamide (4.2 g, 12.5 mmol) in DMF (100 mL) was added $K_2CO_3$ (5.2 g, 37.5 mmol). The mixture was warmed to 70° C. and stirred for 8 h. After cooling, the mixture was concentrated, diluted with $H_2O$ and extracted with EtOAc. The combined organic layers were dried, filtered and evaporated. The residue was purified by silica gel column chromatography (DCM:MeOH=30:1) to afford the title product (1.6 g, 50% yield). LC-MS $(M+H)^+$=257.0, 259.0.

Step 3: 7-bromo-3,3-dimethyl-2,3-dihydro-1H-pyrido[2,3-b][1,4]oxazine

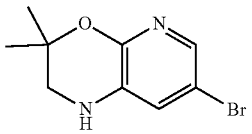

The title compound of Step 3 (830 mg) was prepared in a manner similar to that described in Example 1 step 3 from 7-bromo-3,3-dimethyl-1H-pyrido[2,3-b][1,4]oxazin-2(3H)-one. LC-MS $(M+H)^+$=243.0, 245.0.

Step 4: tert-butyl 7-bromo-3,3-dimethyl-2,3-dihydro-1H-pyrido[2,3-b][1,4]oxazine

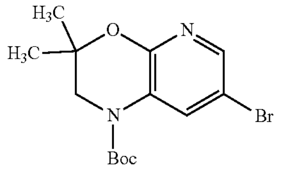 [SMILES: CC(C)(C)OC(=O)N1CC(C)(C)Oc2ncc(Br)cc21]

The title compound of Step 4 (830 mg) was prepared in a manner similar to that described in Example 10 step 4 from 7-bromo-3,3-dimethyl-2,3-dihydro-1H-pyrido[2,3-b][1,4]oxazine. LC-MS $(M+H)^+$=342.9, 344.9.

Step 5: tert-butyl 7-(4-fluorobenzyl)-3,3-dimethyl-2,3-dihydro-1H-pyrido[2,3-b][1,4]oxazine-1-carboxylate

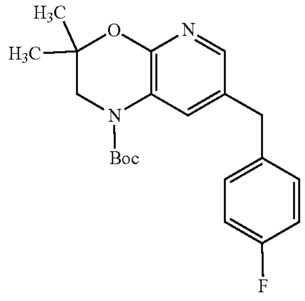 [SMILES: CC(C)(C)OC(=O)N1CC(C)(C)Oc2ncc(Cc3ccc(F)cc3)cc21]

The title compound of Step 5 (500 mg) was prepared in a manner similar to that described in Example 10 step 5 from tert-butyl 7-bromo-3,3-dimethyl-2,3-dihydro-1H-pyrido[2,3-b][1,4]oxazine-1-carboxylate. LC-MS $(M+H)^+$=373.0.

Step 6: 7-(4-fluorobenzyl)-3,3-dimethyl-2,3-dihydro-1H-pyrido[2,3-b][1,4]oxazine

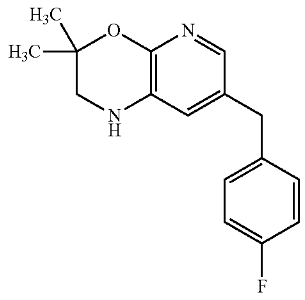 [SMILES: CC1(C)CNc2cc(Cc3ccc(F)cc3)cnc2O1]

The title compound of Step 6 (280 mg) was prepared in a manner similar to that described in Example 10 step 6 from tert-butyl 7-(4-fluorobenzyl)-3,3-dimethyl-2,3-dihydro-1H-pyrido[2,3-b][1,4]oxazine-1-carboxylate. LC-MS $(M+H)^+$=273.0.

Step 7: 6-bromo-7-(4-fluorobenzyl)-3,3-dimethyl-2,3-dihydro-1H-pyrido[2,3-b][1,4]oxazine

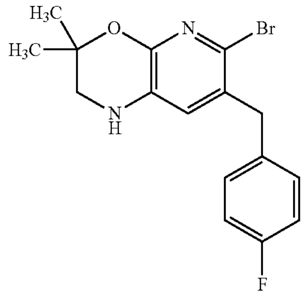 [SMILES: CC1(C)CNc2cc(Cc3ccc(F)cc3)c(Br)nc2O1]

The title compound of Step 7 (230 mg) was prepared in a manner similar to that described in Example 11 step 1 from 7-(4-fluorobenzyl)-3,3-dimethyl-2,3-dihydro-1H-pyrido[2,3-b][1,4]oxazine. LC-MS $(M+H)^+$=351.0, 353.0.

Step 8: 1-(6-bromo-7-(4-fluorobenzyl)-3,3-dimethyl-2,3-dihydro-1H-pyrido[2,3-b][1,4]oxazin-1-yl)-2-chloroethan-1-one

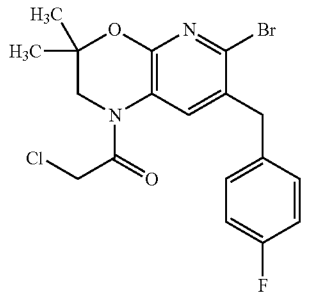 [SMILES: CC1(C)CN(C(=O)CCl)c2cc(Cc3ccc(F)cc3)c(Br)nc2O1]

The title compound of Step 8 (100 mg) was prepared in a manner similar to that described in Example 1 step 9 from 6-bromo-7-(4-fluorobenzyl)-3,3-dimethyl-2,3-dihydro-1H-pyrido[2,3-b][1,4]oxazine and 2-chloroacetyl chloride. LC-MS $(M+H)^+$=427.0, 429.0.

Step 9: tert-butyl (2R,5S)-4-(2-(6-bromo-7-(4-fluorobenzyl)-3,3-dimethyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate

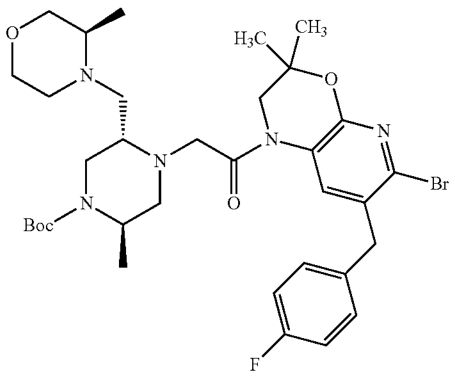 [SMILES: C[C@@H]1COCCN1C[C@H]1CN(C(=O)OC(C)(C)C)[C@H](C)CN1CC(=O)N1CC(C)(C)Oc2nc(Br)c(Cc3ccc(F)cc3)cc21]

The title compound of Step 9 (85 mg) was prepared in a manner similar to that described in Example 1 step 18 from 1-(6-bromo-7-(4-fluorobenzyl)-3,3-dimethyl-2,3-dihydro-1H-pyrido[2,3-b][1,4]oxazin-1-yl)-2-chloroethan-1-one and tert-butyl (2R,5S)-2-methyl-5-(((R)-3-methylmorpholino)methyl)piperazine-1-carboxylate. LC-MS $(M+H)^+$=704.0, 706.0.

Step 10: 1-(6-bromo-7-(4-fluorobenzyl)-3,3-dimethyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 12)

Compound 12 as formic acid salt was prepared in a manner similar to that described in Example 1 step 19 from tert-butyl (2R,5S)-4-(2-(6-bromo-7-(4-fluorobenzyl)-3,3-dimethyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 12 (15 mg) as free base. $^1H$ NMR (400 MHz, DMSO-d6) δ 8.38 (s, 1H), 7.24 (s, 2H), 7.17-7.13 (m, 2H), 4.14 (d, J=15.6 Hz, 1H), 3.97 (s, 3H), 3.57-3.47 (m, 4H), 3.26 (t, J=9.7 Hz, 1H), 2.96 (brs, 1H), 2.78-2.75 (m, 4H), 2.57-2.55 (m, 2H), 2.30-2.27 (m, 1H), 2.15 (s, 2H), 2.02-1.88 (m, 2H), 1.77 (d, J=12.4 Hz, 1H), 1.36 (s, 3H), 1.30 (s, 3H), 0.91-0.81 (m, 6H). LC-MS $(M+H)^+$=604.0, 606.0.

Example 13: 2-((2R,5R)-2-(((1 S,4S)-2-oxa-5-azabicyclo[2.2.1]heptan-5-yl)methyl) methylpiperazin-1-yl)-1-(7-(4-fluorobenzyl)-2,3-dihydro-1H-pyrido[2,3-b][1,4]oxazin yl)ethan-1-one (Compound 13)

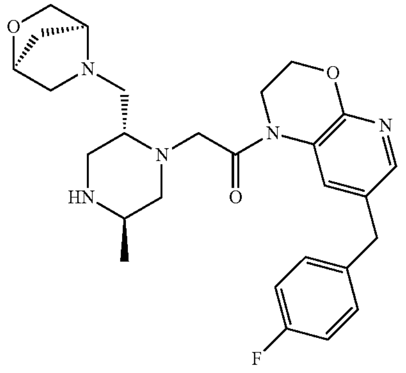 [SMILES: C[C@@H]1CN(CC(=O)N2CCOc3ncc(Cc4ccc(F)cc4)cc32)[C@@H](CN2C[C@@H]3C[C@H]2CO3)CN1]

Step 1: tert-butyl (2R,5S)-5-(((1S,4S)-2-oxa-5-azabicyclo[2.2.1]heptan-5-yl)methyl)-4-benzyl-2-methylpiperazine-1-carboxylate

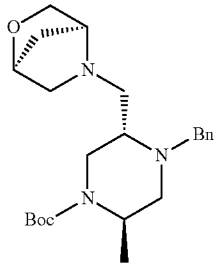 [SMILES: C[C@@H]1CN(Cc2ccccc2)[C@@H](CN2C[C@@H]3C[C@H]2CO3)CN1C(=O)OC(C)(C)C]

The title compound of Step 1 (110 mg) was prepared in a manner similar to that described in Example 1 step 16 from (1S,45)-2-oxa-5-azabicyclo[2.2.1]heptane hydrochloride and tert-butyl (2R,5R)-4-benzyl-5-(chloromethyl)-2-methylpiperazine-1-carboxylate. LC-MS $(M+H)^+$=402.0.

Step 2: tert-butyl (2R,5S)-5-(((1S,4S)-2-oxa-5-azabicyclo[2.2.1]heptan-5-yl)methyl)-2-methylpiperazine-1-carboxylate

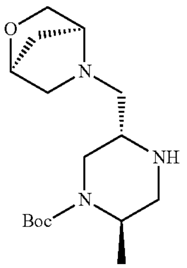

The title compound of Step 2 (60 mg) was prepared in a manner similar to that described in Example 1 step 17 from tert-butyl (2R,5S)-5-(((1S,4S)-2-oxa-5-azabicyclo[2.2.1]heptan-5-yl)methyl)-4-benzyl-2-methylpiperazine-1-carboxylate. LC-MS $(M+H)^+$=312.0.

Step 3: tert-butyl (2R,5S)-5-(((1S,45)-2-oxa-5-azabicyclo[2.2.1]heptan-5-yl)methyl)-4-(2-(7-(4-fluorobenzyl)-2,3-dihydro-1H-pyrido[2,3-b][1,4]oxazin-1-yl)-2-oxoethyl)-2-methylpiperazine-1-carboxylate

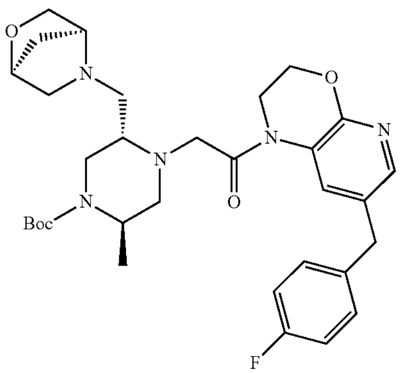 [SMILES: C[C@@H]1CN(CC(=O)N2CCOc3ncc(Cc4ccc(F)cc4)cc32)[C@@H](CN2C[C@@H]3C[C@H]2CO3)CN1C(=O)OC(C)(C)C]

The title compound of Step 3 (30 mg) was prepared in a manner similar to that described in Example 1 step 18 from tert-butyl (2R,5S)-5-(((1S,4S)-2-oxa-5-azabicyclo[2.2.1]heptan yl)methyl)-2-methylpiperazine-1-carboxylate and 2-chloro-1-(7-(4-fluorobenzyl)-2,3-dihydro-1H-pyrido[2,3-b][1,4]oxazin-1-yl)ethan-1-one. LC-MS $(M+H)^+$=596.0.

Step 4: 2-((2R,5R)-2-(((1S,45)-2-oxa-5-azabicyclo[2.2.1]heptan-5-yl)methyl)-5-methylpiperazin-1-yl)-1-(7-(4-fluorobenzyl)-2,3-dihydro-1H-pyrido[2,3-b][1,4]oxazin-1-yl)ethan-1-one (Compound 13)

Compound 13 as formic acid salt was prepared in a manner similar to that described in Example 1 step 19 from tert-butyl (2R,5S)-5-(((1S,4S)-2-oxa-5-azabicyclo[2.2.1]heptan-5-yl)methyl)-4-(2-(7-(4-fluorobenzyl)-2,3-dihydro-1H-pyrido[2,3-b][1,4]oxazin-1-yl)-2-oxoethyl)-2-methylpiperazine-1-carboxylate. The salt was neutralized with aq. $NaHCO_3$ and extracted with EtOAc. The combined organic layers were dried, filtered and concentrated. The residue was further lyophilized to afford compound 13 (8 mg) as free base. $^1H$ NMR (400 MHz, $CD_3OD$) δ 8.44 (s, 1H), 7.79 (s, 1H), 7.23 (s, 2H), 7.04-7.01 (m, 2H), 4.44-4.41 (m, 2H), 4.31 (s, 1H), 4.10-4.07 (m, 2H), 3.93 (brs, 3H), 3.79 (brs, 1H), 3.56-3.53 (m, 1H), 3.47 (d, J=7.2 Hz, 1H), 3.37 (s, 1H), 2.99 (d, J=12.0 Hz, 1H), 2.80-2.77 (m, 4H), 2.64 (s, 1H), 2.55-2.26 (m, 4H), 1.66 (d, J=9.2 Hz, 1H), 1.54 (d, J=9.3 Hz, 1H), 1.03 (s, 3H). LC-MS $(M+H)^+$=496.3.

Example 14: 2-42R,5R)-2-(41R,4R)-2-oxa-5-azabicyclo[2.2.1]heptan-5-yl)methyl)-5-methylpiperazin-1-yl)-1-(7-(4-fluorobenzyl)-2,3-dihydro-1H-pyrido[2,3-b][1,4]oxazin-1-yl)ethan-1-one (Compound 14)

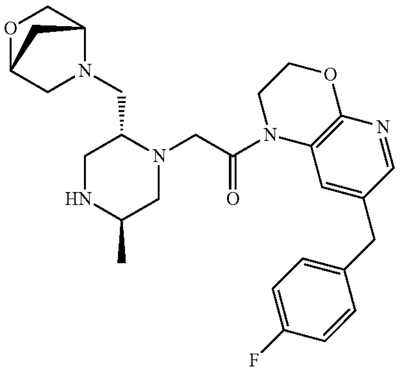 [SMILES: C[C@@H]1CN(CC(=O)N2CCOc3ncc(Cc4ccc(F)cc4)cc32)[C@@H](CN2C[C@H]3C[C@@H]2CO3)CN1]

Step 1: tert-butyl (2R,5S)-5-(((1R,4R)-2-oxa-5-azabicyclo[2.2.1]heptan-5-yl)methyl)-4-benzyl-2-methylpiperazine-1-carboxylate

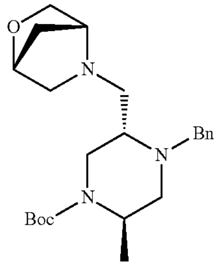 [SMILES: C[C@@H]1CN(Cc2ccccc2)[C@@H](CN2C[C@H]3C[C@@H]2CO3)CN1C(=O)OC(C)(C)C]

The title compound of Step 1 (100 mg) was prepared in a manner similar to that described in Example 1 step 16 from (1R,4R)-2-oxa-5-azabicyclo[2.2.1]heptane hydrochloride and tert-butyl (2R,5R)-4-benzyl-5-(chloromethyl)-2-methylpiperazine-1-carboxylate. LC-MS $(M+H)^+$=402.0.

Step 2: tert-butyl (2R,5S)-5-(((1R,4R)-2-oxa-5-azabicyclo[2.2.1]heptan-5-yl)methyl)-2-methylpiperazine-1-carboxylate

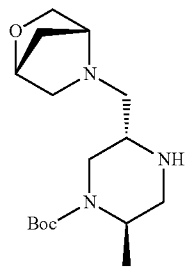 [SMILES: C[C@@H]1CN[C@@H](CN2C[C@H]3C[C@@H]2CO3)CN1C(=O)OC(C)(C)C]

The title compound of Step 2 (60 mg) was prepared in a manner similar to that described in Example 1 step 17 from tert-butyl (2R,5S)-5-(41R,4R)-2-oxa-5-azabicyclo[2.2.1]heptan-5-yl)methyl)-4-benzyl-2-methylpiperazine-1-carboxylate. LC-MS $(M+H)^+=312.0$.

Step 3: tert-butyl (2R,5S)-5-(((1R,4R)-2-oxa-5-azabicyclo[2.2.1]heptan-5-yl)methyl)-4-(2-(7-(4-fluorobenzyl)-2,3-dihydro-1H-pyrido[2,3-b][1,4]oxazin-1-yl)-2-oxoethyl)-2-methylpiperazine-1-carboxylate

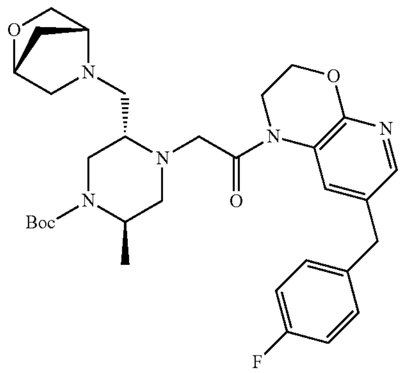 [SMILES: C[C@@H]1CN(CC(=O)N2CCOc3ncc(Cc4ccc(F)cc4)cc32)[C@@H](CN2C[C@H]3C[C@@H]2CO3)CN1C(=O)OC(C)(C)C]

The title compound of Step 3 (30 mg) was prepared in a manner similar to that described in Example 1 step 18 from tert-butyl (2R,5S)-5-(((1R,4R)-2-oxa-5-azabicyclo[2.2.1]heptan-5-yl)methyl)-2-methylpiperazine-1-carboxylate and 2-chloro-1-(7-(4-fluorobenzyl)-2,3-dihydro-1H-pyrido[2,3-b][1,4]oxazin-1-yl)ethan-1-one. LC-MS $(M+H)^+=596.0$.

Step 4: 24 (2R,5R)-2-(41R,4R)-2-oxa-5-azabicyclo[2.2.1]heptan-5-yl)methyl)-5-methylpiperazin-1-yl)-1-(7-(4-fluorobenzyl)-2,3-dihydro-1H-pyrido[2,3-b][1,4]oxazin-1-yl)ethan-1-one (Compound 14)

Compound 14 as formic acid salt was prepared in a manner similar to that described in Example 1 step 19 from tert-butyl (2R,5S)-5-(((1R,4R)-2-oxa-5-azabicyclo[2.2.1]heptan-5-yl)methyl)-4-(2-(7-(4-fluorobenzyl)-2,3-dihydro-1H-pyrido[2,3-b][1,4]oxazin-1-yl)-2-oxoethyl)-2-methylpiperazine-1-carboxylate. The salt was neutralized with aq. $NaHCO_3$ and extracted with EtOAc. The combined organic layers were dried, filtered and concentrated. The residue was further lyophilized to afford compound 14 (5 mg) as free base. $^1H$ NMR (400 MHz, $CD_3OD$) δ 8.54 (s, 1H), 7.80 (s, 1H), 7.22 (s, 2H), 7.04-7.02 (m, 2H), 4.42 (brs, 2H), 4.19 (s, 1H), 4.01-3.97 (m, 2H), 3.92 (s, 2H), 3.88-3.87 (m, 2H), 3.70 (d, J=16.6 Hz, 1H), 3.46 (d, J=7.6 Hz, 1H), 2.97 (d, J=12.2 Hz, 1H), 2.90-2.86 (m, 1H), 2.80-2.72 (m, 4H), 2.68 (s, 1H), 2.54-2.51 (m, 2H), 2.45 (d, J=12.3 Hz, 1H), 2.31 (d, J=9.4 Hz, 1H), 1.51 (s, 2H), 1.10-1.05 (m, 3H). LC-MS $(M+H)^+=496.3$.

Example 15: (S)-4-(di fluoromethyl)-3-(((2R,5R)-1-(2-(7-(4-fluorobenzyl)-2,3-dihydro-1H-pyrido[2,3-b][1,4]oxazin-1-yl)-2-oxoethyl)-5-methylpiperazin-2-yl)methyl)oxazolidin-2-one (Compound 15)

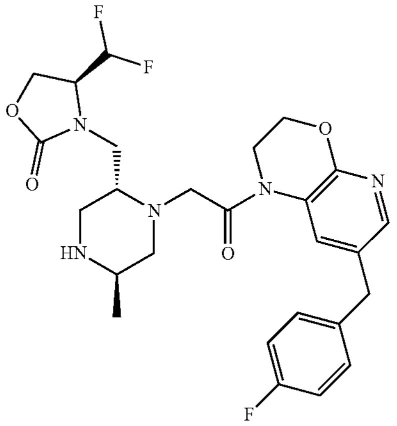 [SMILES: C[C@@H]1CN(CC(=O)N2CCOc3ncc(Cc4ccc(F)cc4)cc32)[C@@H](CN2C(=O)OC[C@H]2C(F)F)CN1]

Step 1: tert-butyl (2R,5R)-4-benzyl-5-(((S)-4-(difluoromethyl)-2-oxooxazolidin-3-yl)methyl)-2-methylpiperazine-1-carboxylate

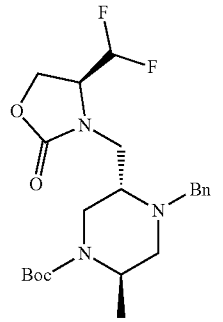 [SMILES: C[C@@H]1CN(Cc2ccccc2)[C@@H](CN2C(=O)OC[C@H]2C(F)F)CN1C(=O)OC(C)(C)C]

The title compound of Step 1 (120 mg) was prepared in a manner similar to that described in Example 1 step 16 from (S)-4-(difluoromethyl)oxazolidin-2-one and tert-butyl (2R,5R)-4-benzyl-5-(chloromethyl)-2-methylpiperazine-1-carboxylate. LC-MS $(M+H)^+=440.0$.

Step 2: tert-butyl (2R,5R)-5-(((S)-4-(difluoromethyl)-2-oxooxazolidin-3-yl)methyl)-2-methylpiperazine-1-carboxylate

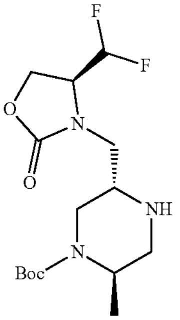 [SMILES: C[C@@H]1CN[C@@H](CN2C(=O)OC[C@H]2C(F)F)CN1C(=O)OC(C)(C)C]

The title compound of Step 2 (45 mg) was prepared in a manner similar to that described in Example 1 step 17 from tert-butyl (2R,5R)-4-benzyl-5-(((S)-4-(difluoromethyl)-2-oxooxazolidin-3-yl)methyl)-2-methylpiperazine-1-carboxylate. LC-MS $(M+H)^+=350.0$ Step 3: tert-butyl (2R,5R)-5-(((S)-4-(difluoromethyl)-2-oxooxazolidin-3-yl)methyl)-4-(2-(7-(4-fluorobenzyl)-2,3-dihydro-1H-pyrido[2,3-b][1,4]oxazin-1-yl)-2-oxoethyl)-2-methylpiperazine-1-carboxylate

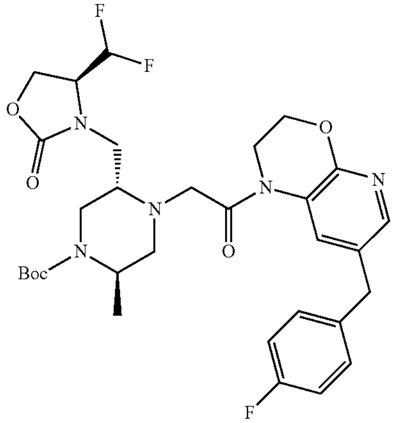 [SMILES: C[C@@H]1CN(CC(=O)N2CCOc3ncc(Cc4ccc(F)cc4)cc32)[C@@H](CN2C(=O)OC[C@H]2C(F)F)CN1C(=O)OC(C)(C)C]

The title compound of Step 3 (15 mg) was prepared in a manner similar to that described in Example 1 step 18 from tert-butyl (2R,5R)-5-(((S)-4-(difluoromethyl)-2-oxooxazolidin-3-yl)methyl)-2-methylpiperazine-1-carboxylate and 2-chloro-1-(7-(4-fluorobenzyl)-2,3-dihydro-1H-pyrido[2,3-b][1,4]oxazin-1-yl)ethan-1-one. LC-MS $(M+H)^+=634.3$.

Step 4: (S)-4-(difluoromethyl)-3-(((2R,5R)-1-(2-(7-(4-fluorobenzyl)-2,3-dihydro-1H-pyrido[2,3-b][1,4]oxazin-1-yl)-2-oxoethyl)-5-methylpiperazin-2-yl)methyl)oxazolidin-2-one (Compound 15)

Compound 15 as formic acid salt was prepared in a manner similar to that described in Example 1 step 19 from tert-butyl (2R,5R)-5-(((S)-4-(difluoromethyl)-2-oxooxazolidin-3-yl)methyl)-4-(2-(7-(4-fluorobenzyl)-2,3-dihydro-1H-pyrido[2,3-b][1,4]oxazin-1-yl)-2-oxoethyl)-2-methylpiperazine-1-carboxylate. The salt was neutralized with aq. $NaHCO_3$ and extracted with EtOAc. The combined organic layers were dried, filtered and concentrated. The residue was further lyophilized to afford compound 15 (5 mg) as free base. $^1H$ NMR (400 MHz, $CD_3OD$) δ 8.54 (s, 1H), 7.80 (s, 1H), 7.23 (s, 2H), 7.03-7.01 (m, 2H), 6.09 (t, J=54.8 Hz, 1H), 4.43 (s, 3H), 4.29-4.21 (m, 2H), 4.08 (s, 1H), 3.92 (s, 2H), 3.88-3.84 (m, 3H), 3.70-3.66 (m, 2H), 3.21-3.17 (m, 2H), 2.96-2.82 (m, 3H), 2.59 (t, J=11.3 Hz, 1H), 2.47 (s, 1H), 1.05 (d, J=4.0 Hz, 3H). LC-MS $(M+H)^+=534.3$.

Example 16: 2-((2R,5R)-2-(((3R,5R)-3,5-dimethylmorpholino)methyl)-5-methylpiperazin-1-yl)-1-(7-(4-fluorobenzyl)-2,3-dihydro-1H-pyrido[2,3-b][1,4]oxazin-1-yl)ethan-1-one (Compound 16)

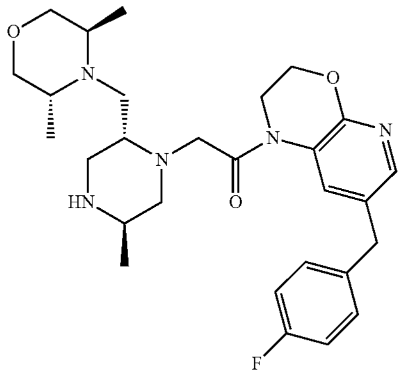 [SMILES: C[C@@H]1CN(CC(=O)N2CCOc3ncc(Cc4ccc(F)cc4)cc32)[C@@H](CN2[C@H](C)COC[C@H]2C)CN1]

Step 1: tert-butyl (2R,5S)-4-benzyl-5-(((3R,5R)-3,5-dimethylmorpholino)methyl)-2-methylpiperazine-1-carboxylate

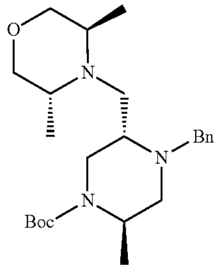 [SMILES: C[C@@H]1CN(Cc2ccccc2)[C@@H](CN2[C@H](C)COC[C@H]2C)CN1C(=O)OC(C)(C)C]

The title compound of Step 1 (80 mg) was prepared in a manner similar to that described in Example 1 step 16 from (3R,5R)-3,5-dimethylmorpholine hydrochloride and tert-butyl (2R,5R)-4-benzyl-5-(chloromethyl)-2-methylpiperazine-1-carboxylate. LC-MS $(M+H)^+=418.3$.

Step 2: tert-butyl (2R,5S)-5-(((3R,5R)-3,5-dimethylmorpholino)methyl)-2-methylpiperazine-1-carboxylate

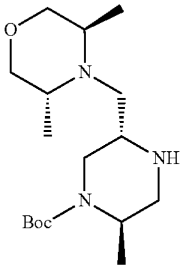 [SMILES: C[C@@H]1CN[C@@H](CN2[C@H](C)COC[C@H]2C)CN1C(=O)OC(C)(C)C]

The title compound of Step 2 (40 mg) was prepared in a manner similar to that described in Example 1 step 17 from tert-butyl (2R,5S)-4-benzyl-5-(((3R,5R)-3,5-dimethylmorpholino)methyl)-2-methylpiperazine-1-carboxylate. LC-MS $(M+H)^+=328.5$.

Step 3: tert-butyl (2R,5S)-5-(((3R,5R)-3,5-dimethylmorpholino)methyl)-4-(2-(7-(4-fluorobenzyl)-2,3-dihydro-1H-pyrido[2,3-b][1,4]oxazin-1-yl)-2-oxoethyl)-2-methylpiperazine-1-carboxylate

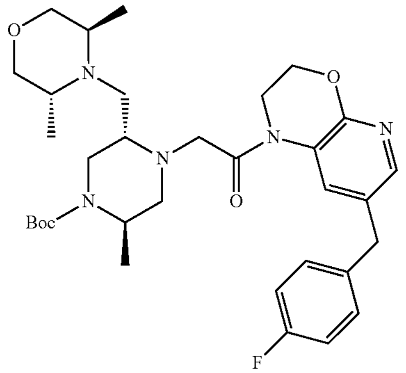 [SMILES: C[C@@H]1CN(CC(=O)N2CCOc3ncc(Cc4ccc(F)cc4)cc32)[C@@H](CN2[C@H](C)COC[C@H]2C)CN1C(=O)OC(C)(C)C]

The title compound of Step 3 (20 mg) was prepared in a manner similar to that described in Example 1 step 18 from tert-butyl (2R,5S)-5-(((3R,5R)-3,5-dimethylmorpholino)methyl)-2-methylpiperazine-1-carboxylate and 2-chloro-1-(7-(4-fluorobenzyl)-2,3-dihydro-1H-pyrido[2,3-b][1,4]oxazin-1-yl)ethan-1-one. LC-MS $(M+H)^+=612.3$.

Step 4: 24 (2R,5R)-2-(((3R,5R)-3,5-dimethylmorpholino)methyl)-5-methylpiperazin-1-yl)-1-(7-(4-fluorobenzyl)-2,3-dihydro-1H-pyrido[2,3-b][1,4]oxazin-1-yl)ethan-1-one (Compound 16)

Compound 16 as formic acid salt was prepared in a manner similar to that described in Example 1 step 19 from tert-butyl (2R,5S)-5-(((3R,5R)-3,5-dimethylmorpholino)methyl)-4-(2-(7-(4-fluorobenzyl)-2,3-dihydro-1H-pyrido[2,3-b][1,4]oxazin-1-yl)-2-oxoethyl) methylpiperazine-1-carboxylate. The salt was neutralized with $NaHCO_3$ and extracted with EtOAc. The combined organic layers were dried, filtered and concentrated. The residue was further lyophilized to afford compound 16 (4 mg) as free base. $^1H$ NMR (400 MHz, $CD_3OD$) δ 8.28 (s, 1H), 7.82 (s, 1H), 7.27-7.19 (m, 2H), 7.13-7.05 (m, 2H), 4.36 (brs, 1H), 4.30 (brs, 1H), 4.04-3.96 (m, 2H), 3.85 (brs, 2H), 3.83-3.73 (m, 1H), 3.50-3.41 (m, 1H), 3.41-3.34 (m, 2H), 3.04 (brs, 2H), 2.90-2.82 (m, 1H), 2.73 (brs, 1H), 2.65 (brs, 2H), 2.59-2.51 (m, 2H), 2.28-2.18 (m, 1H), 2.18-2.08 (m, 1H), 2.00-1.88 (m, 2H), 1.21 (brs, 1H), 0.89-0.75 (m, 9H). LC-MS $(M+H)^+=512.3$.

Example 17: 1-(6-ethoxy-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 17)

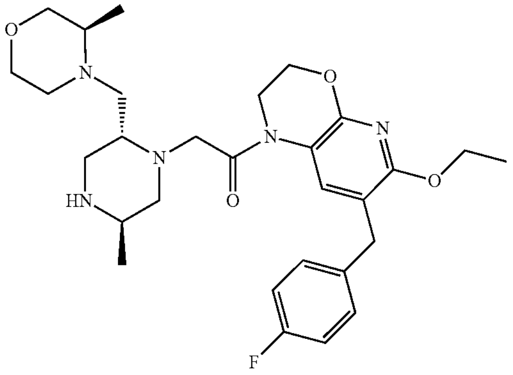 [SMILES: CCOc1nc2c(cc1Cc1ccc(F)cc1)N(C(=O)CN1C[C@@H](C)NC[C@@H]1CN1CCOC[C@H]1C)CCO2]

Step 1: 6-ethoxy-3-nitropyridin-2-amine

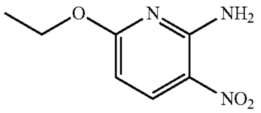

NaH (1.2 g, 60% dispersion in mineral oil, 30 mmol) was slowly added to 100 mL of ethanol and stirred for 10 min at room temperature. 2-amino-6-chloro-3-nitropyridine (5 g, 28.9 mmol) was added portionwise and the mixture was stirred for 30 min at ambient temperature. After concentration, water was added and the mixture was extracted with ethyl acetate. The combined organic layers were dried, filtered and concentrated. The residue was purified by silica gel column chromatography (PE:EtOAc=3:1) to afford the title product (3.0 g, 56% yield). LC-MS $(M+H)^+=184.1$.

Step 2: 5-bromo-6-ethoxy-3-nitropyridin-2-amine

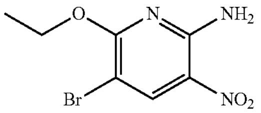

To 6-ethoxy-3-nitropyridin-2-amine (3.0 g, 16.4 mmol) was added 30 mL of DMF. The mixture was cooled to 0° C. NBS (3.2 g, 18.04 mmol) was added to the above cooled mixture in portions. The new mixture was slowly warmed to room temperature and stirred for 2 h. The mixture was diluted with water and extracted with EtOAc. The combined organic layers were washed with aq. $Na_2S_2O_3$ solution, dried, filtered and concentrated. The residue was purified by silica gel column chromatography (PE:EtOAc=3:1) to afford the title product (3.4 g, 80% yield). LC-MS $(M+H)^+$=262.0, 264.0.

Step 3: 3-bromo-6-chloro-2-ethoxy-5-nitropyridine

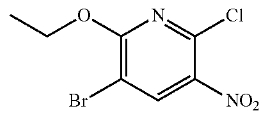

To a solution of 5-bromo-6-ethoxy-3-nitropyridin-2-amine (3.4 g, 13.02 mmol) in $CH_3CN$ (60 mL) was added CuCl (2.57 g, 26.0 mmol) and t-BuONO (2.68 g, 26.0 mmol). The mixture was warmed to 65° C. and stirred for 1.5 h. The mixture was diluted with water and extracted with EtOAc. The combined organic layers were dried, filtered and concentrated. The resultant residue was purified by silica gel column chromatography (PE:EtOAc=5:1) to afford the title product (2 g, 55% yield). LC-MS $(M+H)^+$=280.9.

Step 4: ethyl 2-((5-bromo-6-ethoxy-3-nitropyridin-2-yl)oxy)acetate

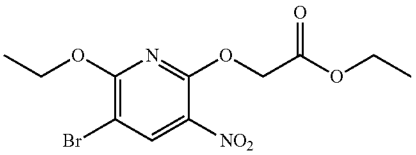 [SMILES: CCOC(=O)COc1nc(OCC)c(Br)cc1[N+](=O)[O-]]

To a solution of 3-bromo-6-chloro-2-ethoxy-5-nitropyridine (2 g, 7.14 mmol) and ethyl 2-hydroxyacetate (880 mg, 8.5 mmol) was added 60% NaH (340 mg, 8.5 mmol) in portions at 0° C. The resulting mixture was slowly warmed to room temperature and stirred for overnight. The mixture was carefully quenched, diluted and extracted with EtOAc. The combined organic layers were dried, filtered and concentrated. The residue was purified by silica gel column chromatography (PE:EtOAc=5:1) to afford the title product (2 g, 80% yield). LC-MS $(M+H)^+$=349.0.

Step 5: 7-bromo-6-ethoxy-1H-pyrido[2,3-b][1,4]oxazin-2(3H)-one

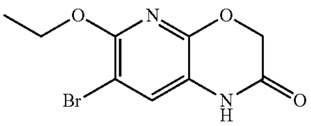

The title compound of Step 5 (1 g, crude) was prepared in a manner similar to that described in Example 1 step 2 from methyl 2-((5-bromo-6-ethoxy-3-nitropyridin-2-yl)oxy)acetate. The crude material was used in next step without purification. LC-MS $(M+H)^+$=273.0, 275.0.

Step 6: 7-bromo-6-ethoxy-2,3-dihydro-1H-pyrido[2,3-b][1,4]oxazine

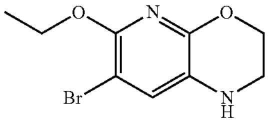

7-bromo-6-ethoxy-2,3-dihydro-1H-pyrido[2,3-b][1,4]oxazine (500 mg, crude) was prepared in a manner similar to that described in Example 1 step 3 from 7-bromo-6-ethoxy-1H-pyrido[2,3-b][1,4]oxazin-2(3H)-one. The crude material was used in next step without purification. LC-MS $(M+H)^+$=259.0, 261.0.

Step 7: tert-butyl 7-bromo-6-ethoxy-2,3-dihydro-1H-pyrido[2,3-b][1,4]oxazine-1-carboxylate

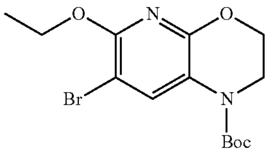 [SMILES: CCOc1nc2c(cc1Br)N(C(=O)OC(C)(C)C)CCO2]

The title compound of Step 7 (400 mg) was prepared in a manner similar to that described in Example 1 step 4 from 7-bromo-6-ethoxy-2,3-dihydro-1H-pyrido[2,3-b][1,4]oxazine. LC-MS $(M+H)^+$=359.1, 361.1.

Step 8: tert-butyl 6-ethoxy-7-(4-fluorobenzyl)-2,3-dihydro-1H-pyrido[2,3-b][1,4]oxazine-1-carboxylate

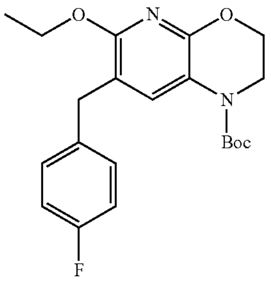 [SMILES: CCOc1nc2c(cc1Cc1ccc(F)cc1)N(C(=O)OC(C)(C)C)CCO2]

The title compound of Step 8 (300 mg) was prepared in a manner similar to that described in Example 1 step 7 from tert-butyl 7-bromo-6-ethoxy-2,3-dihydro-1H-pyrido[2,3-b][1,4]oxazine-1-carboxylate and (4-fluorobenzyl)zinc(II) chloride. LC-MS $(M+H)^+$=389.2.

Step 9: 6-ethoxy-7-(4-fluorobenzyl)-2,3-dihydro-1H-pyrido[2,3-b][1,4]oxazine

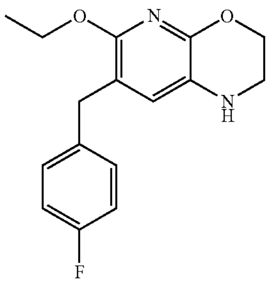 [SMILES: CCOc1nc2c(cc1Cc1ccc(F)cc1)NCCO2]

The title compound of Step 9 (210 mg) was prepared in a manner similar to that described in Example 1 step 8 from tert-butyl 6-ethoxy-7-(4-fluorobenzyl)-2,3-dihydro-1H-pyrido[2,3-b][1,4]oxazine-1-carboxylate. LC-MS $(M+H)^+$=289.1.

Step 10: 2-chloro-1-(6-ethoxy-7-(4-fluorobenzyl)-2,3-dihydro-1H-pyrido[2,3-b][1,4]oxazin-1-yl)ethan-1-one

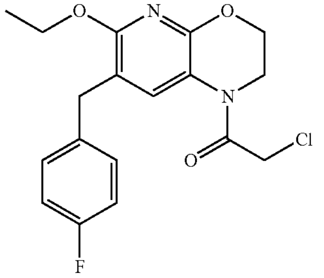 [SMILES: CCOc1nc2c(cc1Cc1ccc(F)cc1)N(C(=O)CCl)CCO2]

The title compound of Step 10 (120 mg) was prepared in a manner similar to that described in Example 1 step 9 from 6-ethoxy-7-(4-fluorobenzyl)-2,3-dihydro-1H-pyrido[2,3-b][1,4]oxazine and 2-chloroacetyl chloride. LC-MS $(M+H)^+$=365.1.

Step 11: tert-butyl (2R,5S)-4-(2-(6-ethoxy-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

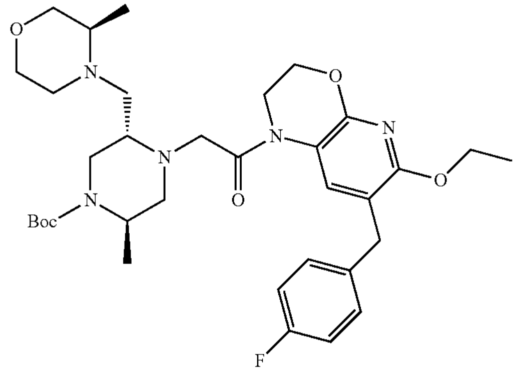 [SMILES: CCOc1nc2c(cc1Cc1ccc(F)cc1)N(C(=O)CN1C[C@@H](C)N(C(=O)OC(C)(C)C)C[C@@H]1CN1CCOC[C@H]1C)CCO2]

The title compound of Step 11 (100 mg) was prepared in a manner similar to that described in Example 1 step 18 from 2-chloro-1-(6-ethoxy-7-(4-fluorobenzyl)-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=642.4.

Step 12: 1-(6-ethoxy-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 17)

Compound 17 as formic acid salt was prepared in a manner similar to that described in Example 1 step 19 from tert-butyl (2R,5S)-4-(2-(6-ethoxy-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 17 (53 mg) as free base. $^1H$ NMR (400 MHz, DMSO-d6) δ 8.25 (s, 1H), 7.20-7.17 (m, 2H), 7.10-7.06 (m, 2H), 4.37-4.27 (m, 2H), 4.18 (q, J=8.0 Hz, 2H), 3.93-3.70 (m, 6H), 3.50-3.39 (m, 3H), 3.22-3.03 (m, 5H), 3.00-2.77 (m, 4H), 2.70-2.54 (m, 2H), 2.05-2.01 (m, 1H), 1.92-1.87 (m, 1H), 1.23 (t, J=8.0 Hz, 3H), 1.14 (d, J=8.0 Hz, 3H), 0.92-0.86 (m, 3H). LC-MS $(M+H)^+$=542.3.

Example 18: 1-(8-(4-fluorobenzyl)-3,4-dihydropyrido[2,3-b][1,4]oxazepin-1(2H)-yl)-2-((2R,5R)-5-methyl-2-(((R)-3-methylmorpholino)methyl)piperazin-1-yl)ethan-1-one (Compound 18)

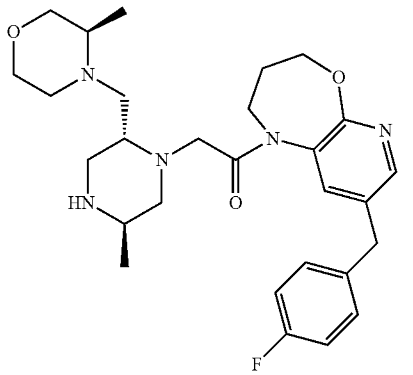 [SMILES: C[C@@H]1CN(CC(=O)N2CCCOc3ncc(Cc4ccc(F)cc4)cc32)[C@@H](CN2CCOC[C@H]2C)CN1]

Step 1: N-(3-((3,5-dibromopyridine-2-v1)oxy)propyl)-4-methylbenzenesulfonamide

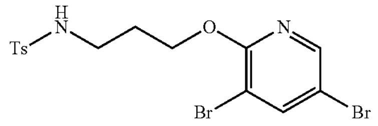 [SMILES: Cc1ccc(S(=O)(=O)NCCCOc2ncc(Br)cc2Br)cc1]

To the solution of N-(3-hydroxypropyl)-4-methylbenzenesulfonamide (7.6 g, 33 mmol) in THF (150 mL) under nitrogen at 0° C. was added NaH (1.44 g, 60%, 36 mmol) and stirred for 30 min. Then 3,5-dibromo-2-fluoropyridine (7.65 g, 30 mmol) was added in portions and stirred at 70°

C. for overnight. The reaction was quenched with water and the resulting mixture was extracted with EtOAc (80 mL×3). The combined organic layers were washed with brine, dried over $Na_2SO_4$, filtered and evaporated. The residue was purified by silica gel column chromatography (PE: EtOAc=2:1) to give the title product (2.4 g, 17% yield). LC-MS $(M+H)^+$=464.9.

Step 2: 8-bromo-1-tosyl-1,2,3,4-tetrahydropyrido[2,3-b][1,4]oxazepine

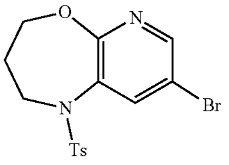 [SMILES: Cc1ccc(S(=O)(=O)N2CCCOc3ncc(Br)cc32)cc1]

To the mixture of N-(3-((3,5-dibromopyridin-2-yl)oxy)propyl)-4-methylbenzenesulfonamide (2.2 g, 4.74 mmol), picolinic acid (466 mg, 3.79 mmol), CuI (1.08 g, 5.69 mmol) and $K_2CO_3$ (1.96 g, 14.2 mmol) was added DMSO (20 mL). The mixture was stirred at 140° C. for 3 h under nitrogen atmosphere. The mixture was cooled, diluted with water and extracted with EtOAc (80 mL×3). The combined organic layers were washed with brine, dried over $Na_2SO_4$, filtered and evaporated. The residue was purified by silica gel column chromatography (PE:EtOAc=5:1) to afford the title product (1.03 g, 57% yield). LC-MS $(M+H)^+$=383.0, 385.0.

Step 3: 8-(4-fluorobenzyl)-1-tosyl-1,2,3,4-tetrahydropyrido[2,3-b][1,4]oxazepine

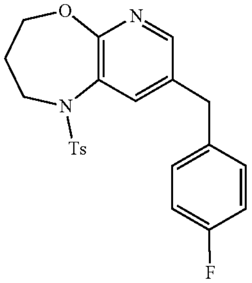 [SMILES: Cc1ccc(S(=O)(=O)N2CCCOc3ncc(Cc4ccc(F)cc4)cc32)cc1]

The title compound of Step 3 (630 mg) was prepared in a manner similar to that described in Example 1 step 7 from 8-bromo-1-tosyl-1,2,3,4-tetrahydropyrido[2,3-b][1,4]oxazepine and (4-fluorobenzyl)zinc(II) chloride. LC-MS $(M+H)^+$=413.1.

Step 4: 8-(4-fluorobenzyl)-1,2,3,4-tetrahydropyrido[2,3-b][1,4]oxazepine

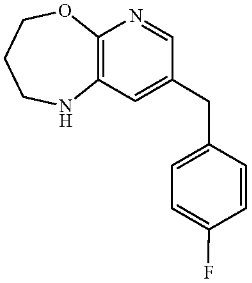 [SMILES: Fc1ccc(Cc2cnc3c(c2)NCCCO3)cc1]

To the solution of 8-(4-fluorobenzyl)-1-tosyl-1,2,3,4-tetrahydropyrido[2,3-b][1,4]oxazepine (350 mg, 0.85 mmol) in methanol (10 mL) at 80° C. was added Mg (204 mg, 8.5 mmol) in portions. The mixture was stirred at 80° C. for overnight. The precipitate was filtered off and the filtrate was evaporated. The residue was purified by silica gel column chromatography (DCM:MeOH=50:1) to afford the title product (80 mg, 36% yield). LC-MS $(M+H)^+$=259.1.

Step 5: 2-chloro-1-(8-(4-fluorobenzyl)-3,4-dihydropyrido[2,3-b][1,4]oxazepin-1(2H)-yl)ethan-1-one

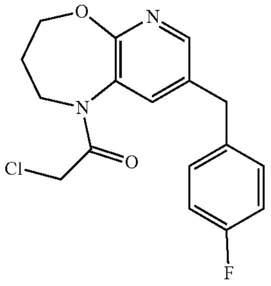 [SMILES: O=C(CCl)N1CCCOc2ncc(Cc3ccc(F)cc3)cc21]

The title compound of Step 5 (50 mg, crude) was prepared in a manner similar to that described in Example 1 step 9 from 8-(4-fluorobenzyl)-1,2,3,4-tetrahydropyrido[2,3-b][1,4]oxazepine and 2-chloroacetyl chloride. The crude material was used in next step directly without purification. LC-MS $(M+H)^+$=335.1.

Step 6: tert-butyl (2R,5S)-4-(2-(8-(4-fluorobenzyl)-3,4-dihydropyrido[2,3-b][1,4]oxazepin-1(2H)-yl)-2-oxoethyl)-2-methyl-5-(((R)-3-methylmorpholino)methyl)piperazine-1-carboxylate

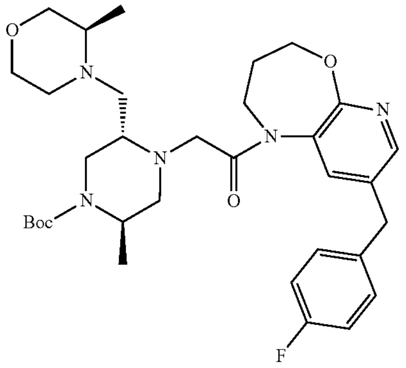 [SMILES: C[C@@H]1COCCN1C[C@H]1CN(C(=O)OC(C)(C)C)[C@H](C)CN1CC(=O)N1CCCOc2ncc(Cc3ccc(F)cc3)cc21]

The title compound of Step 6 (70 mg) was prepared in a manner similar to that described in Example 1 step 18 from 2-chloro-1-(8-(4-fluorobenzyl)-3,4-dihydropyrido[2,3-b][1,4]oxazepin-1(2H)-yl)ethan-1-one and tert-butyl (2R,5S)-2-methyl-5-(((R)-3-methylmorpholino)methyl)piperazine-1-carboxylate. LC-MS $(M+H)^+$=612.4.

Step 7: 1-(8-(4-fluorobenzyl)-3,4-dihydropyrido[2,3-b][1,4]oxazepin-1(2H)-yl)-2-((2R,5R)-5-methyl-2-(((R)-3-methylmorpholino)methyl)piperazin-1-yl)ethan-1-one (Compound 18)

Compound 18 as formic acid salt was prepared in a manner similar to that described in Example 1 step 19 from tert-butyl (2R,5S)-4-(2-(8-(4-fluorobenzyl)-3,4-dihydropyrido[2,3-b][1,4]oxazepin-1(2H)-yl)-2-oxoethyl)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 18 (25 mg) as free base. $^1H$ NMR (400 MHz, CD3OD) δ 8.14 (s, 1H), 7.77 (s, 1H), 7.29 (s, 2H), 7.06 (s, 2H), 4.70 (s, 1H), 4.46 (s, 1H), 4.19 (s, 1H), 4.01 (s, 2H), 3.90 (s, 1H), 3.58 (s, 1H), 3.45 (s, 1H), 3.04-2.63 (m, 9H), 2.52 (s, 1H), 2.34-2.21 (m, 3H), 2.09 (s, 1H), 1.88-1.77 (m, 2H), 1.58 (s, 1H), 1.01 (s, 3H), 0.84 (s, 3H). LC-MS $(M+H)^+$=512.3.

Example 19: 1-(7-(4-fluorobenzyl)-2-methyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 19)

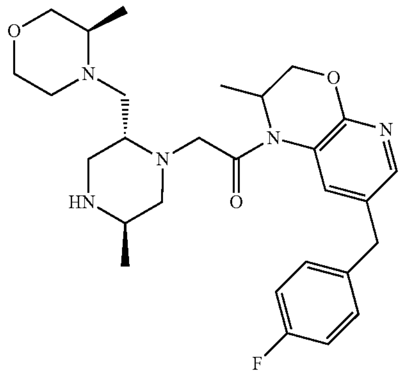 [SMILES: CC1COc2ncc(Cc3ccc(F)cc3)cc2N1C(=O)CN1C[C@@H](C)NC[C@@H]1CN1CCOC[C@H]1C]

Step 1: tert-butyl (1-((3,5-dibromopyridin-2-yl)oxy)propan-2-yl)carbamate

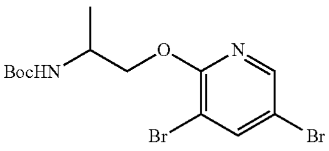 [SMILES: CC(COc1ncc(Br)cc1Br)NC(=O)OC(C)(C)C]

To the mixture of tert-butyl (1-hydroxypropan-2-yl)carbamate (2 g, 11.4 mmol) and 3,5-dibromo-2-fluoropyridine (2.6 g, 10.3 mmol) was added THF (40 mL). The mixture was cooled to 0° C. NaH (456 mg, 60% dispersion in mineral oil, 11.4 mmol) was added in portions. The new mixture was slowly warmed to room temperature and stirred for overnight.

The mixture was carefully quenched, diluted and extracted with EtOAc. The combined organic layers were dried, filtered and evaporated. The crude was purified by silica gel column chromatography (PE:EtOAc=8:1) to afford the title product (4 g, 95% yield). LC-MS $(M+H)^+$=409.0.

Step 2: tert-butyl 7-bromo-2-methyl-2,3-dihydro-1H-pyrido[2,3-b][1,4]oxazine-1-carboxylate

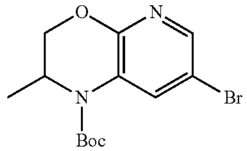 [SMILES: CC1COc2ncc(Br)cc2N1C(=O)OC(C)(C)C]

The title compound of Step 2 (300 mg) was prepared in a manner similar to that described in Example 18 step 2 from tert-butyl (1-((3,5-dibromopyridin-2-yl)oxy)propan-2-yl)carbamate. LC-MS $(M+H)^+$=329.0.

Step 3: tert-butyl 7-(4-fluorobenzyl)-2-methyl-2,3-dihydro-1H-pyrido[2,3-b][1,4]oxazine-1-carboxylate

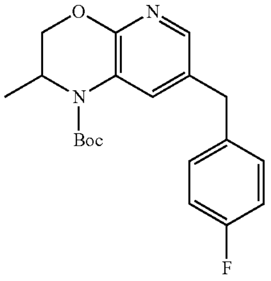 [SMILES: CC1COc2ncc(Cc3ccc(F)cc3)cc2N1C(=O)OC(C)(C)C]

The title compound of Step 3 (260 mg) was prepared in a manner similar to that described in Example 1 step 7 from tert-butyl 7-bromo-2-methyl-2,3-dihydro-1H-pyrido[2,3-b][1,4]oxazine-1-carboxylate and (4-fluorobenzyl)zinc(II) chloride. LC-MS $(M+H)^+$=359.2.

Step 4: 7-(4-fluorobenzyl)-2-methyl-2,3-dihydro-1H-pyrido[2,3-b][1,4]oxazine

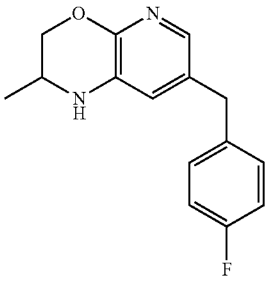 [SMILES: CC1COc2ncc(Cc3ccc(F)cc3)cc2N1]

The title compound of Step 4 (200 mg) was prepared in a manner similar to that described in Example 1 step 8 from tert-butyl 7-(4-fluorobenzyl)-2-methyl-2,3-dihydro-1H-pyrido[2,3-b][1,4]oxazine-1-carboxylate. The crude material was used in next step directly without purification. LC-MS $(M+H)^+$=259.1.

Step 5: 2-chloro-1-(7-(4-fluorobenzyl)-2-methyl-2,3-dihydro-1H-pyrido[2,3-b][1,4]oxazin-1-yl)ethan-1-one

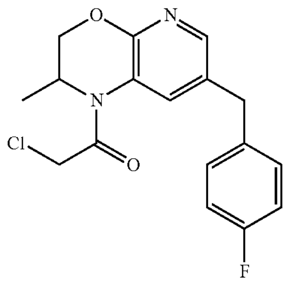 [SMILES: CC1COc2ncc(Cc3ccc(F)cc3)cc2N1C(=O)CCl]

The title compound of Step 5 (150 mg) was prepared in a manner similar to that described in Example 1 step 9 from 7-(4-fluorobenzyl)-2-methyl-2,3-dihydro-1H-pyrido[2,3-b][1,4]oxazine and 2-chloroacetyl chloride. LC-MS $(M+H)^+=335.1$.

Step 6: tert-butyl (2R,5S)-4-(2-(7-(4-fluorobenzyl)-2-methyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate

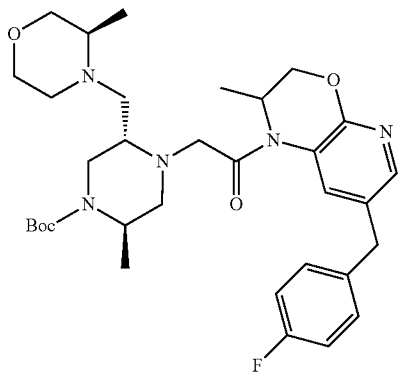 [SMILES: CC1COc2ncc(Cc3ccc(F)cc3)cc2N1C(=O)CN1C[C@@H](C)N(C(=O)OC(C)(C)C)C[C@@H]1CN1CCOC[C@H]1C]

The title compound of Step 6 (100 mg, mixture of diastereomers, 1/1 ratio) was prepared in a manner similar to that described in Example 1 step 18 from 2-chloro-1-(7-(4-fluorobenzyl)-2-methyl-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+=612.3$.

Step 7: 1-(7-(4-fluorobenzyl)-2-methyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 19)

Compound 19 (mixture of diastereomers, 1/1 ratio) as formic acid salt was prepared in a manner similar to that described in Example 1 step 19 from tert-butyl (2R,5S)-4-(2-(7-(4-fluorobenzyl)-2-methyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 19 (20 mg, mixture of diastereomers, 1/1 ratio) as free base. $^1H$ NMR (400 MHz, DMSO-d6) δ 8.25 (s, 1H), 7.84 (d, J=12.0 Hz, 1H), 7.30-7.22 (m, 2H), 7.16-7.09 (m, 2H), 4.77-4.67 (m, 1H), 4.35-4.19 (m, 2H), 4.07-4.03 (m, 1H), 3.88 (s, 2H), 3.59-3.46 (m, 3H), 2.98-2.51 (m, 8H), 2.33-2.17 (m, 3H), 2.06-1.89 (m, 2H), 1.76 (t, J=12.0 Hz, 1H), 1.19-1.12 (m, 3H), 0.91-0.82 (m, 6H). LC-MS $(M+H)^+=512.3$.

Example 19A: 1-((S)-7-(4-fluorobenzyl)-2-methyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 19A)

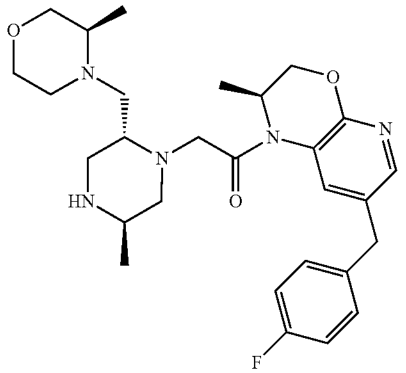

Compound 19A as formic acid salt was prepared in a manner similar to that described in Example 19 from chiral starting material tert-butyl (S)-(1-hydroxypropan-2-yl)carbamate in step 1 and tert-butyl (2R,5S)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 19A (23 mg) as free base. $^1H$ NMR (400 MHz, DMSO-d6) δ 8.22 (s, 1H), 7.82 (s, 1H), 7.26-7.22 (m, 2H), 7.13-7.08 (m, 2H), 4.74 (s, 1H), 4.32-4.29 (m, 1H), 4.19-4.16 (m, 1H), 4.05-4.00 (m, 1H), 3.85 (s, 2H), 3.49-3.45 (m, 3H), 3.29-3.23 (m, 1H), 2.95 (bro, 1H), 2.82-2.64 (m, 3H), 2.59-2.53 (m, 2H), 2.30-2.12 (m, 4H), 1.95 (t, J=12.0 Hz, 2H), 1.71 (d, J=8.0 Hz, 1H), 1.15-1.10 (m, 3H), 0.85-0.83 (m, 6H). LC-MS $(M+H)^+=512.5$.

Example 19B: 1-((R)-7-(4-fluorobenzyl)-2-methyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 19B)

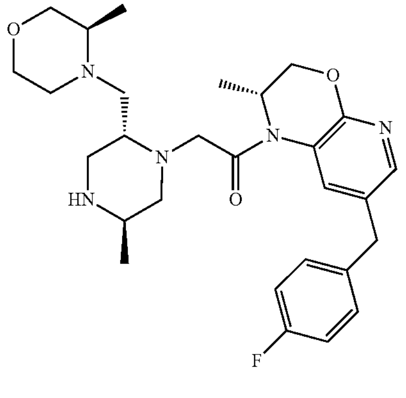 [SMILES: C[C@@H]1CN(CC(=O)N2c3cc(Cc4ccc(F)cc4)cnc3OC[C@H]2C)[C@@H](CN2CCOC[C@H]2C)CN1]

Compound 19B as formic acid salt was prepared in a manner similar to that described in Example 19 from chiral starting material tert-butyl (R)-(1-hydroxypropan-2-yl)carbamate in step 1 and tert-butyl (2R,5S)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 19B (15 mg) as free base. $^1H$ NMR (400 MHz, DMSO-d6) δ 8.25 (s, 1H), 7.83 (s, 1H), 7.27-7.24 (m, 2H), 7.14-7.09 (m, 2H), 4.67 (s, 1H), 4.38-4.19 (m, 3H), 3.88 (s, 2H), 3.58-3.51 (m, 2H), 3.31-3.16 (m, 2H), 3.00 (s, 1H), 2.88-2.72 (m, 3H), 2.63 (s, 2H), 2.32 (s, 2H), 2.17 (s, 2H), 2.00 (s, 2H), 1.79-1.76 (m, 1H), 1.21-1.11 (m, 3H), 0.93-0.81 (m, 6H). LC-MS $(M+H)^+$=512.5.

Example 20: 1-(7'-(4-fluorobenzyl)-1'H,3'H-spiro[cyclopropane-1,2'-pyrido[2,3-b][1,4]oxazin]-1'-yl)-2-42R,5R)-5-methyl-2-(((R)-3-methylmorpholino)methyl)piperazin-1-yl)ethan-1-one hydrochloride (Compound 20)

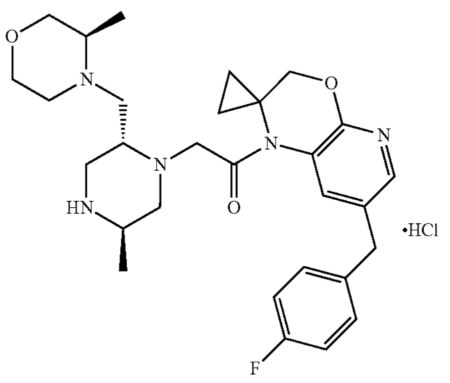 [SMILES: C[C@@H]1CN(CC(=O)N2c3cc(Cc4ccc(F)cc4)cnc3OCC23CC3)[C@@H](CN2CCOC[C@H]2C)CN1 ; Cl]

Step 1: tert-butyl (1-(((3,5-dibromopyridine-2-yl)oxy)methyl)cyclopropyl)carbamate

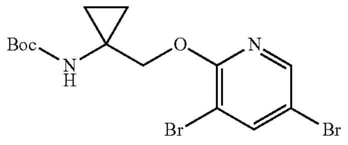 [SMILES: CC(C)(C)OC(=O)NC1(COc2ncc(Br)cc2Br)CC1]

The title compound of Step 1 (3.9 g) was prepared in a manner similar to that described in Example 19 step 1 from tert-butyl (1-(hydroxymethyl)cyclopropyl)carbamate and 3,5-dibromo-2-fluoropyridine. LC-MS $(M+H)^+$=423.0.

Step 2: tert-butyl 7'-bromo-1'H,3'H-spiro[cyclopropane-1,2'-pyrido[2,3-b][1,4]oxazine]-1'-carboxylate

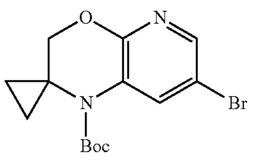 [SMILES: CC(C)(C)OC(=O)N1c2cc(Br)cnc2OCC12CC2]

To the mixture of tert-butyl (1-(((3,5-dibromopyridin-2-yl)oxy)methyl)cyclopropyl)carbamate (1.69 g, 4 mmol), CuI (762 mg, 4 mmol), picolinic acid (492 mg, 4 mmol) and $Cs_2CO_3$ (2.6 g, 8 mmol) was added DMSO (15 mL). The mixture was stirred at 120° C. for 2 h under nitrogen atmosphere. After cooling to room temperature, the mixture was treated with water and the resulting mixture was extracted with EtOAc (80 mL×3). The combined organic layers were washed with brine, dried over $Na_2SO_4$, filtered and evaporated. The residue was purified by silica gel column chromatography (PE/EtOAc=5:1) to give the title product (360 mg, 27% yield). LC-MS $(M+H)^+$=341.0, 343.0.

Step 3: tert-butyl 7'-(4-fluorobenzyl)-11-1,3'H-spiro[cyclopropane-1,2'-pyrido[2,3-b][1,4]oxazine]-1'-carboxylate

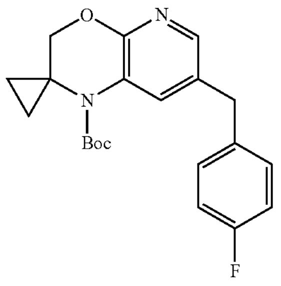 [SMILES: CC(C)(C)OC(=O)N1c2cc(Cc3ccc(F)cc3)cnc2OCC12CC2]

The title compound of Step 3 (230 mg) was prepared in a manner similar to that described in Example 1 step 7 from tert-butyl 7'-bromo-11-1,3'H-spiro[cyclopropane-1,2'-pyrido[2,3-b][1,4]oxazine]-1'-carboxylate and (4-fluorobenzyl)zinc(II) chloride. LC-MS $(M+H)^+$=371.1.

Step 4: 7'-(4-fluorobenzyl)-1'H,3'H-spiro[cyclopropane-1,2'-pyrido[2,3-b][1,4]oxazine]

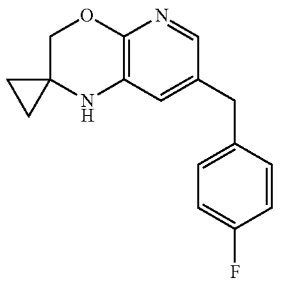 [SMILES: Fc1ccc(Cc2cnc3c(c2)NC2(CC2)CO3)cc1]

The title compound of Step 4 (45 mg) was prepared in a manner similar to that described in Example 1 step 8 from tert-butyl 7'-(4-fluorobenzyl)-1'H,3'H-spiro[cyclopropane-1,2'-pyrido[2,3-b][1,4]oxazine]-1'-carboxylate. LC-MS $(M+H)^+$=271.1.

Step 5: 2-chloro-1-(7'-(4-fluorobenzyl)-1'H,3'H-spiro[cyclopropane-1,2'-pyrido[2,3-b][1,4]oxazin]-1'-yl)ethan-1-one

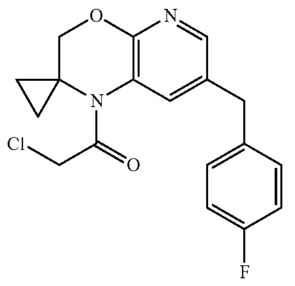 [SMILES: O=C(CCl)N1c2cc(Cc3ccc(F)cc3)cnc2OCC12CC2]

The title compound of Step 5 (60 mg, crude) was prepared in a manner similar to that described in Example 1 step 9 from 7'-(4-fluorobenzyl)-1'H,3'H-spiro[cyclopropane-1,2'-pyrido[2,3-b][1,4]oxazine] and 2-chloroacetyl chloride. The crude material was used in next step directly without purification. LC-MS $(M+H)^+$=347.1.

Step 6: tert-butyl (2R,5S)-4-(2-(7'-(4-fluorobenzyl)-1'H,3'H-spiro[cyclopropane-1,2'-pyrido[2,3-b][1,4]oxazin]-1'-yl)-2-oxoethyl)-2-methyl-5-(((R)-3-methylmorpholino)methyl)piperazine-1-carboxylate

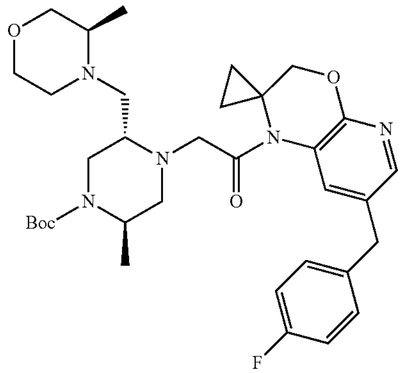 [SMILES: C[C@@H]1COCCN1C[C@H]1CN(C(=O)OC(C)(C)C)[C@H](C)CN1CC(=O)N1c2cc(Cc3ccc(F)cc3)cnc2OCC12CC2]

The title compound of Step 6 (100 mg) was prepared in a manner similar to that described in Example 1 step 18 from 2-chloro-1-(7'-(4-fluorobenzyl)-1'H,3'H-spiro[cyclopropane-1,2'-pyrido[2,3-b][1,4]oxazin]-1'-yl)ethan-1-one and tert-butyl (2R,5S)-2-methyl-5-(((R)-3-methylmorpholino)methyl)piperazine-1-carboxylate. LC-MS $(M+H)^+$=624.4.

Step 7: 1-(7'-(4-fluorobenzyl)-1'H,3'H-spiro[cyclopropane-1,2'-pyrido[2,3-b][1,4]oxazin]-1'-yl)-2-((2R,5R)-5-methyl-2-(((R)-3-methylmorpholino)methyl)piperazin-1-yl)ethan-1-one hydrochloride (Compound 20)

Compound 20 as formic acid salt was prepared in a manner similar to that described in Example 1 step 19 from tert-butyl (2R,5S)-4-(2-(7'-(4-fluorobenzyl)-1'H,3'H-spiro[cyclopropane-1,2'-pyrido[2,3-b][1,4]oxazin]-1'-yl)-2-oxoethyl)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was acidified with 1N HCl and lyophilized to afford compound 20 (23 mg) as its hydrochloride salt. $^1H$ NMR (400 MHz, DMSO-d6) δ 8.35 (s, 2H), 7.89 (d, J=2.2 Hz, 1H), 7.55 (d, J=1.9 Hz, 1H), 7.30-7.21 (m, 2H), 7.15-7.06 (m, 2H), 4.30 (s, 2H), 3.95-3.76 (m, 4H), 3.47 (d, J=11.3 Hz, 1H), 3.41 (d, J=8.4 Hz, 1H), 3.15-3.13 (m, 1H), 2.95 (s, 1H), 2.86-2.59 (m, 6H), 2.48-2.41 (m, 1H), 2.25 (t, J=11.2 Hz, 1H), 2.05 (s, 1H), 1.87 (t, J=10.3 Hz, 1H), 1.67 (d, J=13.3 Hz, 1H), 1.05 (s, 3H), 0.96-0.81 (m, 4H), 0.66 (s, 3H). LC-MS $(M+H)^+$=524.4.

Example 21: 1-(7-(4-fluorobenzyl)-6-(1-hydroxycyclopropyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 21)

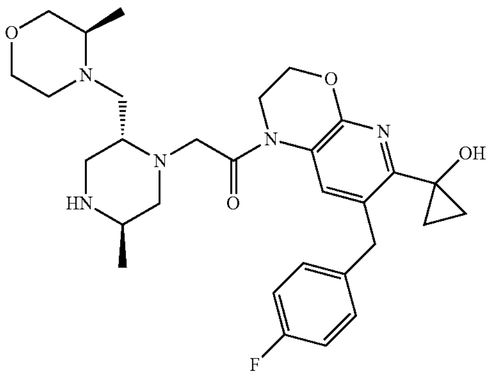 [SMILES: C[C@@H]1CN(CC(=O)N2CCOc3nc(C4(O)CC4)c(Cc4ccc(F)cc4)cc32)[C@@H](CN2CCOC[C@H]2C)CN1]

Step 1: tert-butyl 7-(4-fluorobenzyl)-6-(hydroxymethyl)-2,3-dihydro-1H-pyrido[2,3-b][1,4]oxazine-1-carboxylate

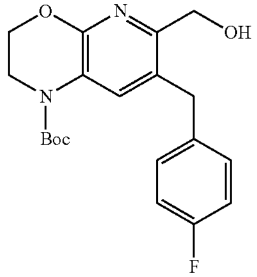 [SMILES: CC(C)(C)OC(=O)N1CCOc2nc(CO)c(Cc3ccc(F)cc3)cc21]

To the solution of tert-butyl 6-(acetoxymethyl)-7-(4-fluorobenzyl)-2,3-dihydro-1H-pyrido[2,3-b][1,4]oxazine-1-carboxylate (5 g, 12 mmol) was added THF/$H_2O$ (60 mL, v/v=1/1). The mixture was cooled to 0° C. $LiOH\cdot H_2O$ (1.0 g, 24 mmol) was added in portions. The mixture was stirred at room temperature for 2 h. The mixture was concentrated and extracted with EtOAc. The combined organic layers were dried, filtered and concentrated to afford the crude title product (4.5 g) which was directly used in next step without further purification. LC-MS $(M+H)^+$=375.2.

Step 2: 1-(tert-butoxycarbonyl)-7-(4-fluorobenzyl)-2,3-dihydro-1H-pyrido[2,3-b][1,4]oxazine-6-carboxylic acid

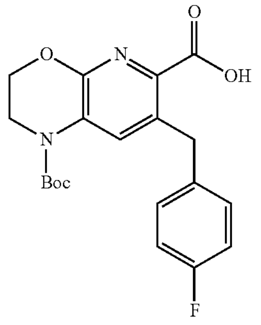 [SMILES: CC(C)(C)OC(=O)N1CCOc2nc(C(=O)O)c(Cc3ccc(F)cc3)cc21]

To the solution of tert-butyl 7-(4-fluorobenzyl)-6-(hydroxymethyl)-2,3-dihydro-1H-pyrido[2,3-b][1,4]oxazine-1-carboxylate (1.2 g, 3.2 mmol) and TEMPO (64 mg, 0.41 mmol) in MeCN (20 mL) was added a Phosphate Buffer (20 mL, pH=7.4). Then an aqueous solution of $NaClO_2$ (1.8 g, 15.9 mmol, 10 mL) and NaClO (1.2 g, 15.9 mmol, 10 mL) was added. The mixture was stirred at room temperature for overnight. The mixture was adjusted to pH 8 by addition of 1M NaOH. The mixture was poured into ice cooled saturated aqueous $Na_2S_2O_3$ solution and stirring was continued for 30 min. The pH was adjusted to pH=3 by addition of 1N HCl and the aqueous phase was extracted with DCM (30 mL×3). The combined organic layers were washed with brine, dried over $Na_2SO_4$, filtered and evaporated to give the crude title product (1.3 g) which was directly used in next step without further purification. LC-MS $(M+H)^+$=389.2.

Step 3: tert-butyl 7-(4-fluorobenzyl)-6-(methoxy(methyl)carbamoyl)-2,3-dihydro-1H-pyrido[2,3-b][1,4]oxazine-1-carboxylate

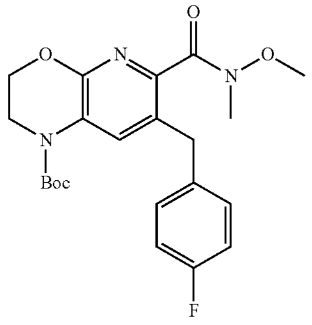 [SMILES: CON(C)C(=O)c1nc2c(cc1Cc1ccc(F)cc1)N(C(=O)OC(C)(C)C)CCO2]

The reaction mixture of 1-(tert-butoxycarbonyl)-7-(4-fluorobenzyl)-2,3-dihydro-1H-pyrido[2,3-b][1,4]oxazine-6-carboxylic acid (600 mg, 1.55 mmol), N,O-dimethylhydroxylamine hydrochloride (252 mg, 2.58 mmol), DIPEA (333 mg, 2.58 mmol) and HATU (589 mg, 1.55 mmol) in DMF (10 mL) was stirred at room temperature for overnight. The mixture was treated with water and extracted with EtOAc (30 mL×3). The combined organic layers were washed with brine, dried over $Na_2SO_4$, filtered and evaporated. The residue was purified by column chromatography (PE:EtOAc=2:1) to give the title product (640 mg, 98% yield). LC-MS $(M+H)^+$=432.2.

Step 4: tert-butyl 6-acetyl-7-(4-fluorobenzyl)-2,3-dihydro-1H-pyrido[2,3-b][1,4]oxazine-1-carboxylate

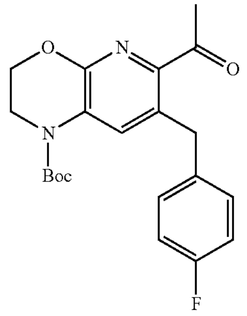 [SMILES: CC(=O)c1nc2c(cc1Cc1ccc(F)cc1)N(C(=O)OC(C)(C)C)CCO2]

To the solution of tert-butyl 7-(4-fluorobenzyl)-6-(methoxy(methyl)carbamoyl)-2,3-dihydro-1H-pyrido[2,3-b][1,4]oxazine-1-carboxylate (640 mg, 1.53 mmol) in THF (20 mL) under nitrogen at −78° C. was added MeLi (1.4 mL, 1.6 M in hexane, 2.24 mmol) and stirred for 2 h at the same temperature. The reaction was quenched with a saturated aqueous solution of $NH_4Cl$ and the mixture was extracted with EtOAc (20 mL×2). The combined organic layers were washed with brine, dried over $Na_2SO_4$, filtered and evaporated. The residue was purified by column chromatography (PE:EtOAc=2:1) to give the title product (380 mg, 64% yield). $^1H$ NMR (400 MHz, DMSO-d6) δ 8.14 (s, 1H), 7.17 (dd, J=8.1, 5.6 Hz, 2H), 7.08 (t, J=8.9 Hz, 2H), 4.37 (s, 2H), 4.24 (s, 2H), 3.84 (s, 2H), 2.50 (s, 3H), 1.42 (s, 9H). LC-MS $(M+H)^+$=387.1.

Step 5: tert-butyl 6-(1-((tert-butyldimethylsilyloxy)vinyl)-7-(4-fluorobenzyl)-2,3-dihydro-1H-pyrido[2,3-b][1,4]oxazine-1-carboxylate

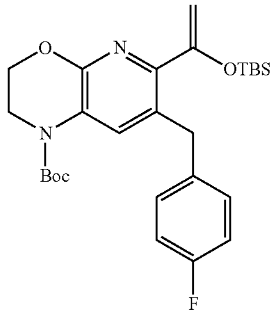 [SMILES: C=C(O[Si](C)(C)C(C)(C)C)c1nc2c(cc1Cc1ccc(F)cc1)N(C(=O)OC(C)(C)C)CCO2]

To the solution of tert-butyl 6-acetyl-7-(4-fluorobenzyl)-2,3-dihydro-1H-pyrido[2,3-b][1,4]oxazine-1-carboxylate (380 mg, 0.98 mmol) and $Et_3N$ (298 mg, 2.95 mmol) in DCM (20 mL) at 0° C. was added trifluoromethanesulfonic acid tert-butyldimethylsilyl ester (390 mg, 1.48 mmol) and stirred at room temperature for overnight. The mixture was diluted with DCM, washed with water and brine, dried over $Na_2SO_4$, filtered and evaporated. The residue was purified by column chromatography (PE:EtOAc=1:2) to give the title product (415 mg, 84% yield). $^1$H NMR (400 MHz, DMSO-d6) δ 7.92 (s, 1H), 7.18-7.05 (m, 4H), 4.56 (s, 1H), 4.52 (s, 1H), 4.31 (s, 2H), 4.06 (s, 2H), 3.78 (s, 2H), 1.38 (s, 9H), 0.87 (s, 9H), 0.11 (s, 6H). LC-MS $(M+H)^+$=501.1.

Step 6: 6-(1-((tert-butyldimethylsilyloxy)cyclopropyl)-7-(4-fluorobenzyl)-2,3-dihydro-1H-pyrido[2,3-b][1,4]oxazine

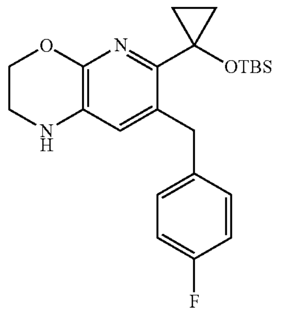 [SMILES: CC(C)(C)[Si](C)(C)OC1(c2nc3c(cc2Cc2ccc(F)cc2)NCCO3)CC1]

To the solution of $Et_2Zn$ (3.32 mL, 1 M solution in hexane, 3.32 mmol) in hexane under nitrogen at 0° C. was added $CH_2I_2$ (1.8 g, 6.64 mmol) and stirred for 30 min. Then a solution of tert-butyl 6-(1-((tert-butyldimethylsilyl)oxy)vinyl)-7-(4-fluorobenzyl)-2,3-dihydro-1H-pyrido[2,3-b][1,4]oxazine-1-carboxylate (415 mg, 0.83 mmol) in DCM (15 mL) was added dropwise and the mixture was stirred at 0° C. for 2 h. The reaction was quenched with a saturated aqueous solution of $NH_4Cl$ and extracted with DCM (20 mL×2). The combined organic layers were washed with brine, dried over $Na_2SO_4$, filtered and evaporated. The residue was purified by column chromatography (DCM:MeOH=20:1) to give the title product (180 mg, 52% yield). $^1$H NMR (400 MHz, DMSO-d6) δ 7.26-7.04 (m, 4H), 6.48 (s, 1H), 5.94 (s, 1H), 4.18 (s, 2H), 4.11 (s, 2H), 3.20 (s, 2H), 0.88 (d, J=5.6 Hz, 4H), 0.77 (s, 9H), 0.14 (s, 6H). LC-MS $(M+H)^+$=415.2.

Step 7: 1-(6-(1-((tert-butyldimethylsilyl)oxy)cyclopropyl)-7-(4-fluorobenzyl)-2,3-dihydro-1H-pyrido[2,3-b][1,4]oxazin-1-yl)-2-chloroethan-1-one

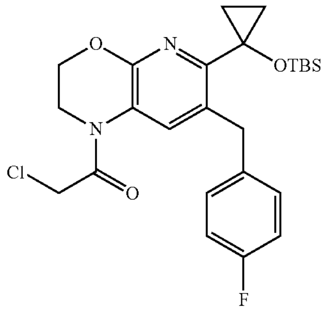 [SMILES: CC(C)(C)[Si](C)(C)OC1(c2nc3c(cc2Cc2ccc(F)cc2)N(C(=O)CCl)CCO3)CC1]

The title compound of Step 7 (210 mg, crude) was prepared in a manner similar to that described in Example 1 step 9 from 6-(1-((tert-butyldimethylsilyl)oxy)cyclopropyl)-7-(4-fluorobenzyl)-2,3-dihydro-1H-pyrido[2,3-b][1,4]oxazine and 2-chloroacetyl chloride. The crude material was used in next step directly without purification. LC-MS $(M+H)^+$=491.1.

Step 8: tert-butyl (2R,5S)-4-(2-(6-(1-((tert-butyldimethylsilyl)oxy)cyclopropyl)-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

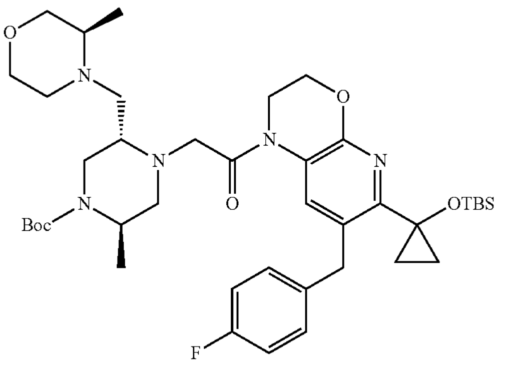 [SMILES: C[C@@H]1COCCN1C[C@H]1CN(C(=O)OC(C)(C)C)[C@H](C)CN1CC(=O)N1CCOc2nc(C3(O[Si](C)(C)C(C)(C)C)CC3)c(Cc3ccc(F)cc3)cc21]

The title compound of Step 8 (230 mg, 69% yield) was prepared in a manner similar to that described in Example 1 step 18 from 1-(6-(1-((tert-butyldimethylsilyl)oxy)cyclopropyl)-7-(4-fluorobenzyl)-2,3-dihydro-1H-pyrido[2,3-b][1,4]oxazin-1-yl)-2-chloroethan-1-one and tert-butyl (2R,5S)-2-methyl-5-(((R)-3-methylmorpholino)methyl)piperazine-1-carboxylate. LC-MS $(M+H)^+$=768.4.

Step 9: 1-(7-(4-fluorobenzyl)-6-(1-hydroxycyclopropyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 21)

To the solution of tert-butyl (2R,5S)-4-(2-(6-(1-((tert-butyldimethylsilyl)oxy)cyclopropyl)-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate (230 mg, 0.3 mmol) in methanol (3 mL) was added HCl solution in 1,4-dioxane (3 mL, 4M) at 0° C. The mixture was stirred at room temperature for 4 h. The solvent was evaporated and the residue was washed with aq. $NaHCO_3$ solution, extracted with EA. The combined organic layers were dried, filtered and concentrated. The residue was purified by silica gel column chromatography (DCM:MeOH=10:1) to give the title product (60 mg, 36% yield). $^1$H NMR (400 MHz, DMSO-d6) δ 8.22 (s, 1H), 7.24 (s, 2H), 7.10 (t, J=8.0 Hz, 2H), 6.03 (s, 1H), 4.43-4.23 (m, 3H), 4.15 (d, J=15.5 Hz, 1H), 3.97-3.93 (m, 2H), 3.74 (s, 1H), 3.61 (d, J=15.7 Hz, 1H), 3.45 (d, J=10.1 Hz, 1H), 3.36 (s, 1H), 3.17-3.12 (m, 1H), 2.28-2.78 (m, 4H), 2.66 (d, J=9.9 Hz, 2H), 2.56 (d, J=10.6 Hz, 1H), 2.33-2.30 (m, 2H), 2.12 (s, 1H), 1.93 (s, 1H), 1.74 (d, J=10.7 Hz, 1H), 0.90-0.83 (m, 10H). LC-MS $(M+H)^+$=554.3.

Example 22: 2-42R,5R)-24(3R,5R)-3,5-dimethylmorpholino)methyl)-5-methylpiperazin-1-yl)-1-(((S)-7-(4-fluorobenzyl)-2-methyl-2,3-dihydro-1H-pyrido[2,3-b][1,4]oxazin-1-yl)ethan-1-one (Compound 22)

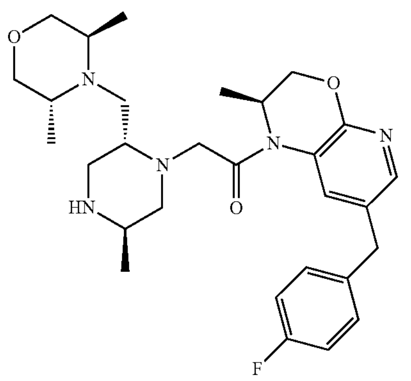 [SMILES: C[C@@H]1CN(CC(=O)N2c3cc(Cc4ccc(F)cc4)cnc3OC[C@@H]2C)[C@@H](CN2[C@H](C)COC[C@H]2C)CN1]

Compound as formic acid salt was prepared in a manner similar to that described in Example 19 from the corresponding chiral starting material tert-butyl (S)-(1-hydroxypropan-2-yl)carbamate in step 1 and tert-butyl (2R,5S)-5-(((3R,5R)-3,5-dimethylmorpholino)methyl)-2-methylpiperazine-1-carboxylate. The salt was neutralized with aq. $NaHCO_3$ and extracted with EtOAc. The combined organic layers were dried, filtered and concentrated. The residue was further lyophilized to afford compound 22 (224 mg, 41% yield) as free base. $^{1}$E NMR (400 MHz, DMSO-d6) δ 8.20 (s, 1H), 7.85 (s, 1H), 7.30-7.18 (m, 2H), 7.17-7.06 (m, 2H), 4.81-4.63 (m, 1H), 4.38-4.27 (m, 1H), 4.25-4.14 (m, 1H), 3.98-3.90 (m, 1H), 3.87 (s, 2H), 3.53-3.38 (m, 3H), 3.16-3.02 (m, 2H), 2.99-2.88 (m, 1H), 2.84-2.74 (m, 1H), 2.73-2.64 (m, 2H), 2.63-2.54 (m, 2H), 2.26 (t, J=10.7 Hz, 1H), 2.13 (t, J=10.8 Hz, 1H), 2.08-1.88 (m, 2H), 1.17 (d, J=6.0 Hz, 3H), 0.93-0.76 (m, 9H). LC-MS $(M+H)^+$=526.6.

Example 23: 1-(((S)-2-((benzyloxy)methyl)-7-(4-fluorobenzyl)-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 23)

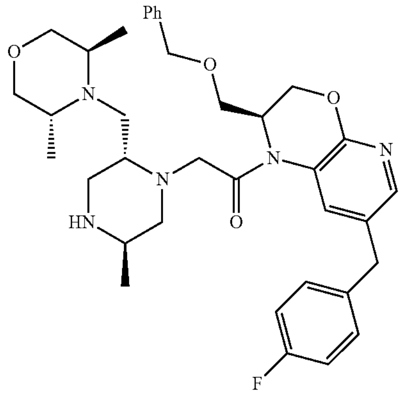 [SMILES: C[C@@H]1CN(CC(=O)N2c3cc(Cc4ccc(F)cc4)cnc3OC[C@@H]2COCc2ccccc2)[C@@H](CN2[C@H](C)COC[C@H]2C)CN1]

Step 1: tert-butyl (S)-(1-(benzyloxy)-3-((3,5-dibromopyridin-2-yl)oxy)propan-2-yl)carbamate

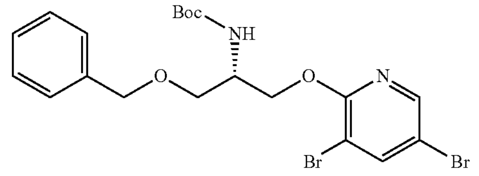 [SMILES: CC(C)(C)OC(=O)N[C@@H](COCc1ccccc1)COc1ncc(Br)cc1Br]

The title compound of step 1 (19 g, 95% yield) was prepared in a manner similar to that described in Example 19 step 1 from tert-butyl (R)-(1-(benzyloxy)-3-hydroxypropan-2-yl)carbamate and 3,5-dibromo-2-fluoropyridine. LC-MS $(M+H)^+$=515.0.

Step 2: tert-butyl (S)-2-((benzyloxy)methyl)-7-bromo-2,3-dihydro-1H-pyrido[2,3-b][1,4]oxazine-1-carboxylate

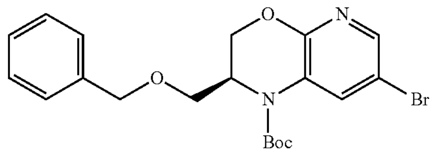 [SMILES: CC(C)(C)OC(=O)N1c2cc(Br)cnc2OC[C@@H]1COCc1ccccc1]

The title compound of step 2 (2.5 g, 38% yield) was prepared in a manner similar to that described in Example 18 step 2 from tert-butyl (S)-(1-(benzyloxy)-3-((3,5-dibromopyridin-2-yl)oxy)propan-2-yl)carbamate. LC-MS $(M+H)^+$=435.0.

Step 3: tert-butyl (S)-2-((benzyloxy)methyl)-7-(4-fluorobenzyl)-2,3-dihydro-1H-pyrido[2,3-b][1,4]oxazine-1-carboxylate

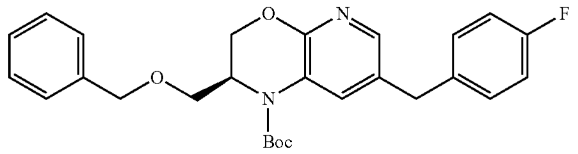 [SMILES: CC(C)(C)OC(=O)N1c2cc(Cc3ccc(F)cc3)cnc2OC[C@@H]1COCc1ccccc1]

The title compound of step 3 (1.5 g, 56% yield) was prepared in a manner similar to that described in Example 1 step 7 from tert-butyl (S)-2-((benzyloxy)methyl)-7-bromo-2,3-dihydro-1H-pyrido[2,3-b][1,4]oxazine-1-carboxylate and (4-fluorobenzyl)zinc(II) chloride. LC-MS $(M+H)^+$=465.2.

Step 4: (S)-2-((benzyloxy)methyl)-7-((4-fluorobenzyl)-2,3-dihydro-1H-pyrido[2,3-b][1,4]oxazine

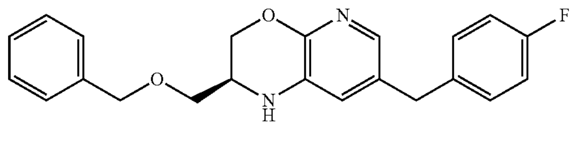 [SMILES: Fc1ccc(Cc2cnc3c(c2)N[C@@H](COCc2ccccc2)CO3)cc1]

The title compound of step 4 (1.1 g, 94% yield) was prepared in a manner similar to that described in Example 1 step 8 from tert-butyl (S)-2-((benzyloxy)methyl)-7-(4-fluorobenzyl)-2,3-dihydro-1H-pyrido[2,3-b][1,4]oxazine-1-carboxylate. LC-MS $(M+H)^+$=365.2.

Step 5: (S)-1-(2-((benzyloxy)methyl)-7-(4-fluorobenzyl)-2,3-dihydro-1H-pyrido[2,3-b][1,4]oxazin-1-yl)-2-chloroethan-1-one

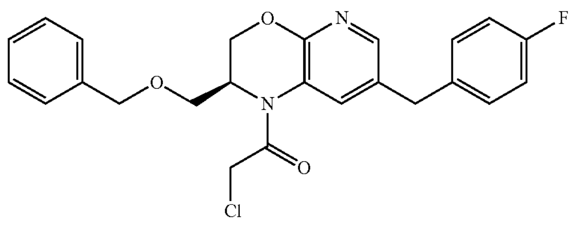 [SMILES: O=C(CCl)N1c2cc(Cc3ccc(F)cc3)cnc2OC[C@@H]1COCc1ccccc1]

The title compound of step 5 (750 mg, 56% yield) was prepared in a manner similar to that described in Example 1 step 9 from (S)-2-((benzyloxy)methyl)-7-(4-fluorobenzyl)-2,3-dihydro-1H-pyrido[2,3-b][1,4]oxazine and 2-chloroacetyl chloride. LC-MS $(M+H)^+$=441.1.

Step 6: tert-butyl (2R,5S)-4-(2-((S)-2-((benzyloxy)methyl)-7-(4-fluorobenzyl)-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

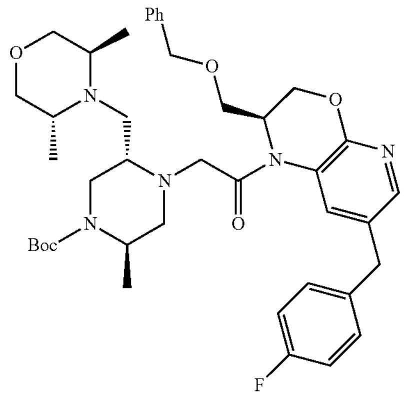 [SMILES: C[C@@H]1CN(CC(=O)N2c3cc(Cc4ccc(F)cc4)cnc3OC[C@@H]2COCc2ccccc2)[C@@H](CN2[C@H](C)COC[C@H]2C)CN1C(=O)OC(C)(C)C]

The title compound of step 6 (520 mg, 86% yield) was prepared in a manner similar to that described in Example 1 step 18 from (S)-1-(2-((benzyloxy)methyl)-7-(4-fluorobenzyl)-2,3-dihydro-1H-pyrido[2,3-b][1,4]oxazin-1-yl)-2-chloroethan-1-one and tert-butyl (2R,5S)-5-(((3R,5R)-3,5-dimethylmorpholino)methyl)-2-methylpiperazine-1-carboxylate. LC-MS $(M+H)^+$=732.4.

Step 7: 1-((S)-2-((benzyloxy)methyl)-7-(4-fluorobenzyl)-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 23)

Compound 23 as formic acid salt was prepared in a manner similar to that described in Example 1 step 19 from tert-butyl (2R,5S)-4-(2-((S)-2-((benzyloxy)methyl)-7-(4-fluorobenzyl)-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. The salt was neutralized with aq. $NaHCO_3$ and extracted with EtOAc. The combined organic layers were dried, filtered and concentrated. The residue was furtherly lyophilized to afford compound 23 (210 mg, 47% yield) as free base. $^1H$ NMR (400 MHz, DMSO-d6) δ 8.31 (s, 1H), 7.83 (s, 1H), 7.3-7.23 (m, 5H), 7.23-7.16 (m, 2H), 7.15-7.08 (m, 2H), 4.97 (brs, 1H), 4.58-4.52 (m, 1H), 4.51-4.39 (m, 2H), 4.27-4.20 (m, 1H), 4.19-4.11 (m, 1H), 3.88 (s, 2H), 3.55-3.49 (m, 1H), 3.48-3.41 (m, 3H), 3.31-3.24 (m, 2H), 3.11 (brs, 2H), 3.05-2.98 (m, 1H), 2.83-2.72 (m, 1H), 2.68-2.53 (m, 4H), 2.38 (brs, 1H), 2.27-2.17 (m, 1H), 2.08-1.98 (m, 1H), 1.98-1.90 (m, 1H), 0.85 (d, J=4.5 Hz, 3H), 0.80 (d, J=5.6 Hz, 6H). LC-MS $(M+H)^+$=632.4.

Example 24: 2-42R,5R)-24(3R,5R)-3,5-dimethylmorpholino)methyl)-5-methylpiperazin yl)-1-(((S)-7-(4-fluorobenzyl)-6-(hydroxymethyl)-2-methyl-2,3-dihydro-1H-pyrido[2,3-b][1,4]oxazin-1-yl)ethan-1-one (Compound 24)

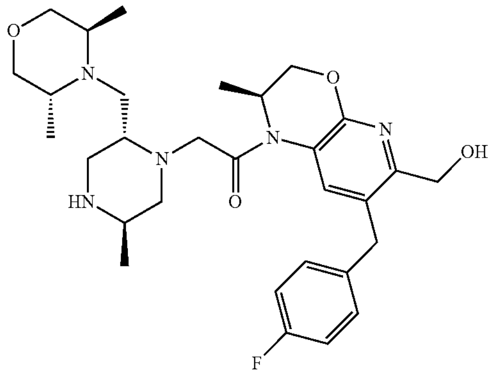 [SMILES: C[C@@H]1CN(CC(=O)N2c3cc(Cc4ccc(F)cc4)c(CO)nc3OC[C@@H]2C)[C@@H](CN2[C@H](C)COC[C@H]2C)CN1]

Step 1: tert-butyl (S)-(1-((3,5-dibromo-6-methylpyridin-2-yl)oxy)propan-2-yl)carbamate

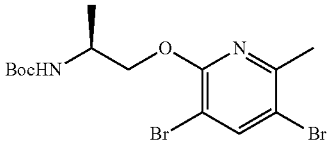

The title compound of step 1 (4.2 g, 75% yield) was prepared in a manner similar to that described in Example 19 step 1 from tert-butyl (S)-(1-hydroxypropan-2-yl)carbamate and 3,5-dibromo-2-fluoro-6-methylpyridine. LC-MS $(M+H)^+$=423.0.

Step 2: tert-butyl (S)-7-bromo-2,6-dimethyl-2,3-dihydro-1H-pyrido[2,3-b][1,4]oxazine-1-carboxylate

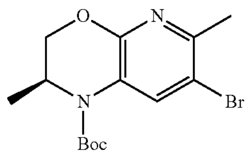 [SMILES: Cc1nc2c(cc1Br)N(C(=O)OC(C)(C)C)[C@@H](C)CO2]

The title compound of step 2 (890 mg, 15% yield) was prepared in a manner similar to that described in Example 18 step 2 from tert-butyl (S)-(1-((3,5-dibromo-6-methylpyridin-2-yl)oxy)propan-2-yl)carbamate. LC-MS $(M+H)^+$ =343.1.

Step 3: tert-butyl (S)-7-(4-fluorobenzyl)-2,6-dimethyl-2,3-dihydro-1H-pyrido[2,3-b][1,4]oxazine-1-carboxylate

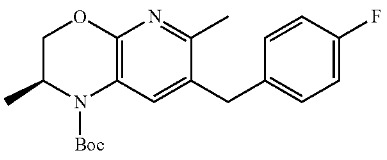 [SMILES: Cc1nc2c(cc1Cc1ccc(F)cc1)N(C(=O)OC(C)(C)C)[C@@H](C)CO2]

The title compound of step 3 (1.0 g, 90% yield) was prepared in a manner similar to that described in Example 1 step 7 from tert-butyl (S)-7-bromo-2,6-dimethyl-2,3-dihydro-1H-pyrido[2,3-b][1,4]oxazine-1-carboxylate and (4-fluorobenzyl)zinc(II) chloride. LC-MS $(M+H)^+$=373.

Step 4: (S)-1-(tert-butoxycarbonyl)-7-(4-fluorobenzyl)-2,6-dimethyl-2,3-dihydro-1H-pyrido[2,3-b][1,4] oxazine 5-oxide

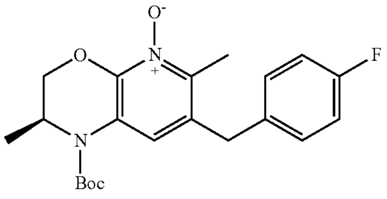

The title compound of step 4 (900 mg, 65% yield) was prepared in a manner similar to that described in Example 1 step 5 from tert-butyl (S)-7-(4-fluorobenzyl)-2,6-dimethyl-2,3-dihydro-1H-pyrido[2,3-b][1,4]oxazine-1-carboxylate and 3-chlorobenzoperoxoic acid. LC-MS $(M+H)^+$=389.2.

Step 5: tert-butyl (S)-6-(acetoxymethyl)-7-(4-fluorobenzyl)-2-methyl-2,3-dihydro-1H-pyrido[2,3-b][1,4]oxazine-1-carboxylate

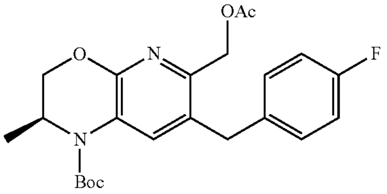 [SMILES: CC(=O)OCc1nc2c(cc1Cc1ccc(F)cc1)N(C(=O)OC(C)(C)C)[C@@H](C)CO2]

The title compound of step 5 (855 mg, 86% yield) was prepared in a manner similar to that described in Example 8 step 2 from (S)-1-(tert-butoxycarbonyl)-7-(4-fluorobenzyl)-2,6-dimethyl-2,3-dihydro-1H-pyrido[2,3-b][1,4]oxazine 5-oxide and $Ac_2O$. LC-MS $(M+H)^+$=431.2.

Step 6: (S)-(7-(4-fluorobenzyl)-2-methyl-2,3-dihydro-1H-pyrido[2,3-b][1,4]oxazin-6-yl)methyl acetate

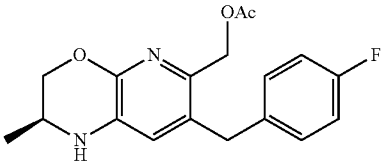 [SMILES: CC(=O)OCc1nc2c(cc1Cc1ccc(F)cc1)N[C@@H](C)CO2]

The title compound of step 6 (462 mg, 70% yield) was prepared in a manner similar to that described in Example 1 step 8 from tert-butyl (S)-6-(acetoxymethyl)-7-(4-fluorobenzyl)-2-methyl-2,3-dihydro-1H-pyrido[2,3-b][1,4] oxazine-1-carboxylate. LC-MS $(M+H)^+$=331.1.

Step 7: (S)-(1-(2-chloroacetyl)-7-(4-fluorobenzyl)-2-methyl-2,3-dihydro-1H-pyrido[2,3-b][1,4]oxazin-6-yl)methyl acetate

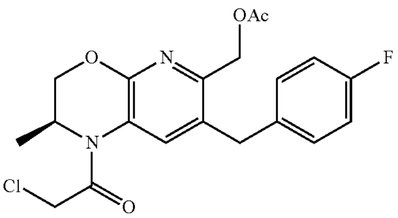 [SMILES: CC(=O)OCc1nc2c(cc1Cc1ccc(F)cc1)N(C(=O)CCl)[C@@H](C)CO2]

The title compound of step 7 (570 mg, 90% yield) was prepared in a manner similar to that described in Example 1 step 9 from (S)-(7-(4-fluorobenzyl)-2-methyl-2,3-dihydro-1H-pyrido[2,3-b][1,4]oxazin-6-yl)methyl acetate and 2-chloroacetyl chloride. LC-MS $(M+H)^+$=407.1.

Step 8: tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

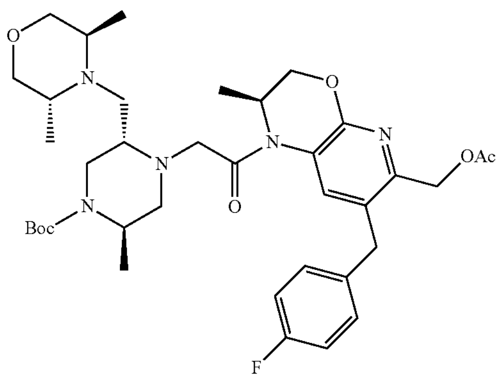 [SMILES: CC(=O)OCc1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 8 (252 mg, 51% yield) was prepared in a manner similar to that described in Example 1 step 18 from (S)-(1-(2-chloroacetyl)-7-(4-fluorobenzyl)-2-methyl-2,3-dihydro-1H-pyrido[2,3-b][1,4]oxazin-6-yl) methyl acetate and tert-butyl (2R,5S)-5-(((3R,5R)-3,5-dimethylmorpholino)methyl)-2-methylpiperazine-1-carboxylate. LC-MS $(M+H)^+$=698.5.

Step 9: tert-butyl (2R,5S)-5-(((3R,5R)-3,5-dimethylmorpholino)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate

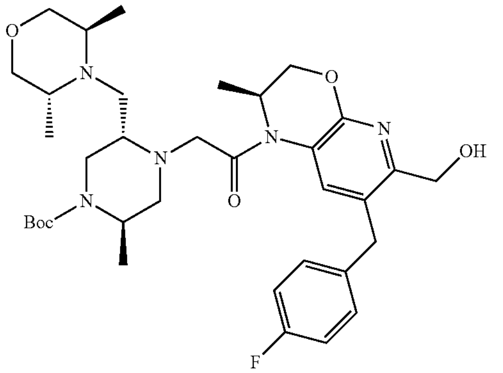 [SMILES: C[C@@H]1CN(CC(=O)N2c3cc(Cc4ccc(F)cc4)c(CO)nc3OC[C@@H]2C)[C@@H](CN2[C@H](C)COC[C@H]2C)CN1C(=O)OC(C)(C)C]

The title compound of step 9 (240 mg, 100% yield) was prepared in a manner similar to that described in Example 8 step 4 from tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. LC-MS $(M+H)^+$=656.5

Step 10: 2-42R,5R)-2-(((3R,5R)-3,5-dimethylmorpholino)methyl)-5-methylpiperazin-1-yl)-1-4S)-7-(4-fluorobenzyl)-6-(hydroxymethyl)-2-methyl-2,3-dihydro-1H-pyrido[2,3-b][1,4]oxazin-1-yl)ethan-1-one (Compound 24)

Compound 24 as formic acid salt was prepared in a manner similar to that described in Example 1 step 19 from tert-butyl (2R,5S)-5-(((3R,5R)-3,5-dimethylmorpholino) methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate. The salt was neutralized with aq. $NaHCO_3$ and extracted with EtOAc. The combined organic layers were dried, filtered and concentrated. The residue was further lyophilized to afford compound 24 (97 mg, 48% yield) as free base. $^1$H NMR (400 MHz, DMSO-d6) δ 8.12 (s, 1H), 7.28-7.17 (m, 2H), 7.16-7.04 (m, 2H), 5.15-5.01 (m, 1H), 4.72 (s, 1H), 4.50-4.37 (m, 2H), 4.33 (d, J=10.6 Hz, 1H), 4.20 (d, J=10.9 Hz, 1H), 3.97 (s, 2H), 3.94-3.83 (m, 1H), 3.54-3.37 (m, 3H), 3.18-3.02 (m, 2H), 2.97-2.88 (m, 1H), 2.82-2.71 (m, 1H), 2.71-2.63 (m, 2H), 2.62-2.53 (m, 2H), 2.31-2.19 (m, 1H), 2.18-2.05 (m, 1H), 2.02-1.89 (m, 2H), 1.19 (d, J=5.7 Hz, 3H), 0.92-0.75 (m, 9H). LC-MS $(M+H)^+$=556.6.

Example 25: 1-((S)-7-(4-fluorobenzyl)-6-(hydroxymethyl)-2-methyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 25)

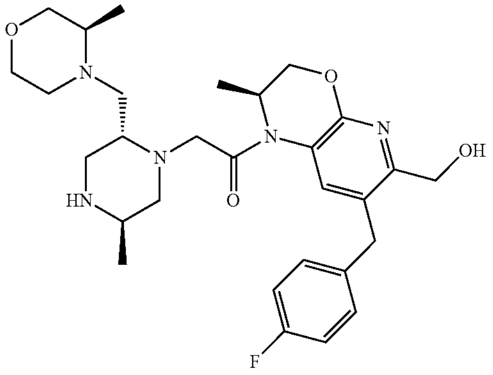 [SMILES: C[C@@H]1CN(CC(=O)N2c3cc(Cc4ccc(F)cc4)c(CO)nc3OC[C@@H]2C)[C@@H](CN2CCOC[C@H]2C)CN1]

Step 1: tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-2-methyl-5-(((R)-3-methylmorpholino)methyl) piperazine-1-carboxylate

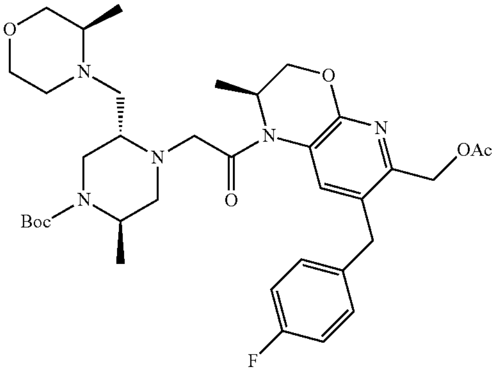 [SMILES: CC(=O)OCc1nc2c(cc1Cc1ccc(F)cc1)N(C(=O)CN1C[C@@H](C)N(C(=O)OC(C)(C)C)C[C@@H]1CN1CCOC[C@H]1C)[C@@H](C)CO2]

The title compound in step 1 (259 mg, 54% yield) was prepared in a manner similar to that described in Example 1 step 18 from (S)-(1-(2-chloroacetyl)-7-(4-fluorobenzyl)-2-methyl-2,3-dihydro-1H-pyrido[2,3-b][1,4]oxazin-6-yl) methyl acetate and tert-butyl (2R,5S)-2-methyl-5-(((R)-3-methylmorpholino)methyl)piperazine-1-carboxylate. LC-MS $(M+H)^+$=684.5.

Step 2: tert-butyl (2R,5S)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methyl-5-(((R)-3-methylmorpholino)methyl) piperazine-1-carboxylate

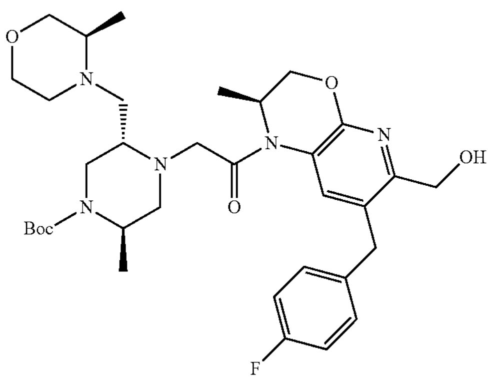 [SMILES: C[C@@H]1COCCN1C[C@H]1CN(C(=O)OC(C)(C)C)[C@H](C)CN1CC(=O)N1c2cc(Cc3ccc(F)cc3)c(CO)nc2OC[C@@H]1C]

The title compound of step 2 (240 mg, 90% yield) was prepared in a manner similar to that described in Example 8 step 4 from tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate. LC-MS $(M+H)^+$=642.5.

Step 3: 1-((S)-7-(4-fluorobenzyl)-6-(hydroxymethyl)-2-methyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 25)

Compound 25 as formic acid salt was prepared in a manner similar to that described in Example 1 step 19 from tert-butyl (2R,5S)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate. The salt was neutralized with aq.

$NaHCO_3$ and extracted with EtOAc. The combined organic layers were dried, filtered and concentrated. The residue was further lyophilized to afford compound 25 (103 mg, 51% yield) as free base. $^1H$ NMR (400 MHz, DMSO-d6) δ 8.18 (s, 1H), 7.26-7.17 (m, 2H), 7.16-7.06 (m, 2H), 5.12-5.04 (m, 1H), 4.77 (s, 1H), 4.50-4.37 (m, 2H), 4.37-4.28 (m, 1H), 4.26-4.15 (m, 1H), 4.07-4.00 (m, 1H), 3.97 (s, 2H), 3.56-3.40 (m, 3H), 3.31-3.24 (m, 1H), 3.05-2.92 (m, 1H), 2.88-2.53 (m, 6H), 2.36-2.23 (m, 1H), 2.23-2.07 (m, 2H), 2.03-1.84 (m, 2H), 1.79-1.67 (m, 1H), 1.16 (d, J=5.9 Hz, 3H), 0.93-0.77 (m, 6H). LC-MS $(M+H)^+$=542.5.

Example 26: 1-((S)-2-cyclopropyl-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 26)

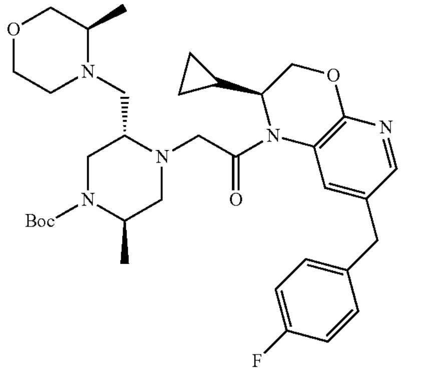 [SMILES: C[C@@H]1COCCN1C[C@H]1CN(C(=O)OC(C)(C)C)[C@H](C)CN1CC(=O)N1c2cc(Cc3ccc(F)cc3)cnc2OC[C@@H]1C1CC1]

Step 1: (S)-2-amino-2-cyclopropylethan-1-ol

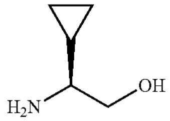

(S)-2-amino-2-cyclopropylacetic acid (6.9 g, 60 mmol) in anhydrous THF (190 mL) was added $LiAlH_4$ (4.56 g, 120 mmol) slowly at 0° C. The resulting solution was stirred at room temperature for 1 h. The reaction was quenched by water (20 mL) and extracted with EtOAc (100 mL*3). The combined EtOAc phase was dried over $Na_2SO_4$, filtered and evaporated in vacuo to give crude product (6.4 g) which was used in next step without further purification. LC-MS $(M+H)^+$=102.0.

Step 2: (S)-1-cyclopropyl-2-((3,5-dibromopyridin-2-yl)oxy)ethan-1-amine

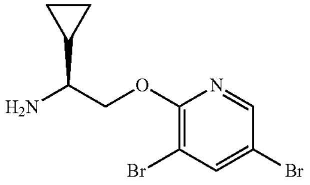 [SMILES: N[C@H](COc1ncc(Br)cc1Br)C1CC1]

3,5-dibromo-2-fluoropyridine (5 g, 20 mmol) and (S)-2-amino-2-cyclopropylethan-1-ol (2.5 g, 25 mmol) in anhydrous THF (100 mL) was added NaH (2 g, 60%, 50 mmol) slowly at 0° C. The resulting solution was stirred at room temperature for 1 h. The reaction was quenched by water (20 mL) and extracted with EtOAc (100 mL*3). The combined EtOAc phase was dried over $Na_2SO_4$, filtered and evaporated in vacuo. The residue was purified by silica gel chromatography (DCM:MeOH=10:1) to give the product (6.5 g, 97% yield for 2 steps). LC-MS $(M+H)^+$=334.9, 336.9.

Step 3: tert-butyl (S)-(1-cyclopropyl-2-((3,5-dibromopyridin-2-yl)oxy)ethyl)carbamate

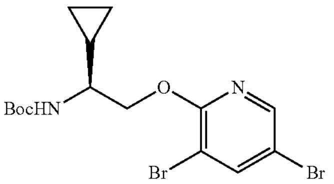 [SMILES: CC(C)(C)OC(=O)N[C@H](COc1ncc(Br)cc1Br)C1CC1]

(S)-1-cyclopropyl-2-((3,5-dibromopyridin-2-yl)oxy)ethan-1-amine (6.5 g, 19.3 mmol), $(Boc)_2O$ (6.3 g, 29 mmol), DMAP (0.1 g, 0.82 mmol) and $Et_3N$ (5.8 g, 58 mmol) in DCM (100 mL) was stirred at room temperature for 12 hours. The reaction was washed with water (50 mL), extracted with DCM (50 mL*3), the combined DCM phase was dried over $Na_2SO_4$, filtered and evaporated in vacuo. The residue was purified by silica gel chromatography (PE:EtOAc=5:1) to give the product (6.5 g, 77% yield). LC-MS $(M+H)^+$=434.9, 436.9.

Step 4: tert-butyl (S)-7-bromo-2-cyclopropyl-2,3-dihydro-1H-pyrido[2,3-b][1,4]oxazine-1-carboxylate

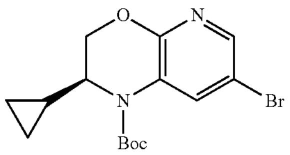 [SMILES: CC(C)(C)OC(=O)N1c2cc(Br)cnc2OC[C@@H]1C1CC1]

The title compound of step 4 (1.2 g, 26% yield) was prepared in a manner similar to that described in Example 18 step 2 from tert-butyl (S)-(1-cyclopropyl-2-((3,5-dibromopyridin-2-yl)oxy)ethyl)carbamate. LC-MS $(M+H)^+$=355.0, 357.0.

Step 5: tert-butyl (S)-2-cyclopropyl-7-(4-fluorobenzyl)-2,3-dihydro-1H-pyrido[2,3-b][1,4]oxazine-1-carboxylate

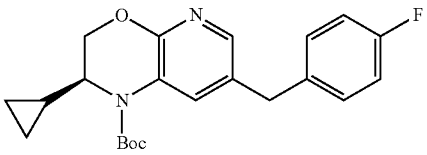 [SMILES: CC(C)(C)OC(=O)N1c2cc(Cc3ccc(F)cc3)cnc2OC[C@@H]1C1CC1]

The title compound of step 5 (0.8 g, 62% yield) was prepared in a manner similar to that described in Example 1 step 7 from tert-butyl (S)-7-bromo-2-cyclopropyl-2,3-dihydro-1H-pyrido[2,3-b][1,4]oxazine-1-carboxylate and (4-fluorobenzyl)zinc(II) chloride. LC-MS $(M+H)^+$=385.2.

Step 6: (S)-2-cyclopropyl-7-(4-fluorobenzyl)-2,3-dihydro-1H-pyrido[2,3-b][1,4]oxazine

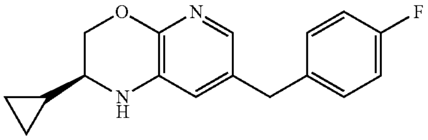 [SMILES: Fc1ccc(Cc2cnc3c(c2)N[C@@H](C2CC2)CO3)cc1]

The title compound of step 6 (0.6 g, 100% yield) was prepared in a manner similar to that described in Example 1 step 8 from tert-butyl (S)-2-cyclopropyl-7-(4-fluorobenzyl)-2,3-dihydro-1H-pyrido[2,3-b][1,4]oxazine-1-carboxylate. LC-MS $(M+H)^+$=285.0.

Step 7: (S)-2-chloro-1-(2-cyclopropyl-7-(4-fluorobenzyl)-2,3-dihydro-1H-pyrido[2,3-b][1,4]oxazin-1-yl)ethan-1-one

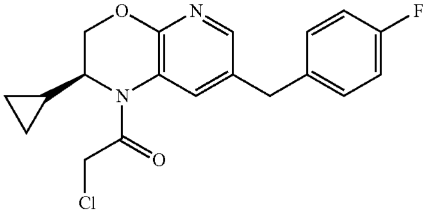 [SMILES: O=C(CCl)N1c2cc(Cc3ccc(F)cc3)cnc2OC[C@@H]1C1CC1]

The title compound of step 7 (520 mg, 68% yield) was prepared in a manner similar to that described in Example 1 step 9 from (S)-2-cyclopropyl-7-(4-fluorobenzyl)-2,3-dihydro-1H-pyrido[2,3-b][1,4]oxazine and 2-chloroacetyl chloride. LC-MS $(M+H)^+$=361.1.

Step 8: tert-butyl (2R,5S)-4-(2-((S)-2-cyclopropyl-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

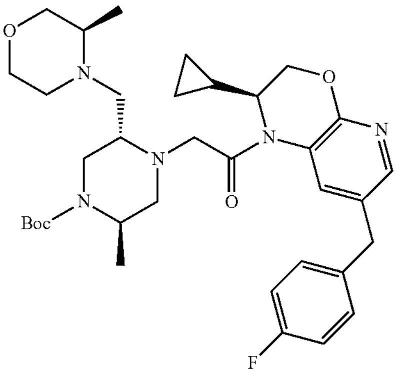 [SMILES: C[C@@H]1COCCN1C[C@H]1CN(C(=O)OC(C)(C)C)[C@H](C)CN1CC(=O)N1c2cc(Cc3ccc(F)cc3)cnc2OC[C@@H]1C1CC1]

The title compound of step 8 (300 mg, 66% yield) was prepared in a manner similar to that described in Example 1 step 18 from (S)-2-chloro-1-(2-cyclopropyl-7-(4-fluorobenzyl)-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$638.9.

Step 9: 1-((S)-2-cyclopropyl-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 26)

Compound 26 as formic acid salt was prepared in a manner similar to that described in Example 1 step 19 from tert-butyl (2R,5S)-4-(2-((S)-2-cyclopropyl-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 26 (190 mg, 75% yield) as free base. 1H NMR (400 MHz, DMSO-d6) δ 8.11 (s, 1H), 7.86 (d, J=1.8 Hz, 1H), 7.29-7.25 (m, 2H), 7.15-7.10 (m, 2H), 4.49-4.46 (m, 1H), 4.24-4.21 (m, 1H), 4.14-4.00 (m, 2H), 3.89 (s, 2H), 3.56-5.48 (m, 2H), 3.40-3.37 (m, 2H), 3.02 (brs, 1H), 2.85-2.82 (m, 1H), 2.71 (brs, 2H), 2.58-2.54 (m, 3H), 2.35-2.09 (m, 3H), 2.04 (brs, 1H), 1.77 (s, 1H), 0.85 (d, J=6.1 Hz, 3H), 0.80 (brs, 4H), 0.52 (d, J=5.9 Hz, 1H), 0.44 (s, 3H). LC-MS $(M+H)^+$=538.9.

Example 27: 1-((S)-2-cyclopropyl-7-(4-fluorobenzyl)-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 27)

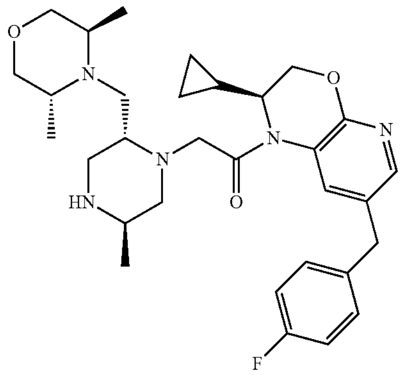 [SMILES: C[C@@H]1CN(CC(=O)N2c3cc(Cc4ccc(F)cc4)cnc3OC[C@@H]2C2CC2)[C@@H](CN2[C@H](C)COC[C@H]2C)CN1]

Step 1: tert-butyl (2R,5S)-4-(2-((S)-2-cyclopropyl-7-(4-fluorobenzyl)-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

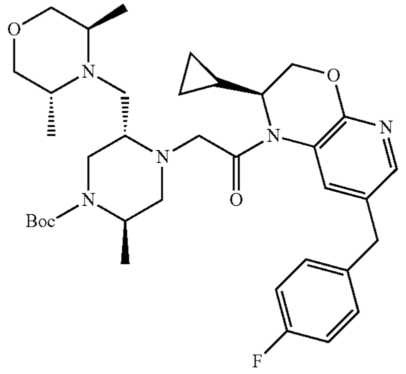 [SMILES: C[C@@H]1CN(CC(=O)N2c3cc(Cc4ccc(F)cc4)cnc3OC[C@@H]2C2CC2)[C@@H](CN2[C@H](C)COC[C@H]2C)CN1C(=O)OC(C)(C)C]

The title compound of step 1 (300 mg, 64% yield) was prepared in a manner similar to that described in Example 1 step 18 from (S)-2-chloro-1-(2-cyclopropyl-7-(4-fluorobenzyl)-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=652.9.

Step 2: 1-(((S)-2-cyclopropyl-7-(4-fluorobenzyl)-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan one (Compound 27)

Compound 27 as formic acid salt was prepared in a manner similar to that described in Example 1 step 19 from tert-butyl (2R,5S)-4-(2-((S)-2-cyclopropyl-7-(4-fluorobenzyl)-2,3-dihydro-1H-pyrido[2,3-b][1,4]oxazin-1-yl)-2-oxoethyl)-54(3R,5R)-3,5-dimethylmorpholino)methyl)-2-methylpiperazine-1-carboxylate. The salt was neutralized with aq. $NaHCO_3$ and extracted with EtOAc. The combined organic layers were dried, filtered and concentrated. The residue was further lyophilized to afford compound 27 (210 mg, 83% yield) as free base. $^1$H NMR (400 MHz, DMSO-d6) δ 8.11 (s, 1H), 7.87 (s, 1H), 7.28-7.25 (m, 2H), 7.12 (t, J=8.8 Hz, 2H), 4.49-4.47 (m, 1H), 4.23-4.21 (m, 1H), 4.11-4.09 (m, 1H), 3.96-3.93 (m, 1H), 3.89 (s, 2H), 3.50-3.48 (m, 2H), 3.25 (s, 1H), 3.15 (brs, 2H), 3.04-3.01 (m, 1H), 2.76-2.68 (m, 3H), 2.52 (brs, 2H), 2.40 (brs, 1H), 2.22-2.19 (m, 1H), 2.07-2.02 (m, 1H), 1.96-1.91 (m, 1H), 0.84 (brs, 10H), 0.53-0.51 (m, 2H), 0.45 (s, 2H). LC-MS $(M+H)^+$=552.9.

Example 28: 1-((S)-2-ethyl-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 28)

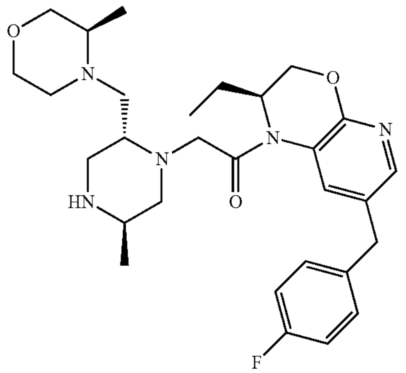 [SMILES: CC[C@H]1COc2ncc(Cc3ccc(F)cc3)cc2N1C(=O)CN1C[C@@H](C)NC[C@@H]1CN1CCOC[C@H]1C]

Step 1: tert-butyl (S)-(1-((3,5-dibromopyridin-2-yl)oxy)butan-2-yl)carbamate

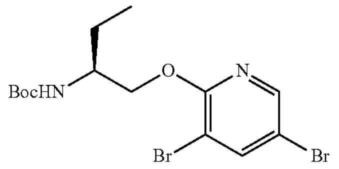 [SMILES: CC[C@@H](COc1ncc(Br)cc1Br)NC(=O)OC(C)(C)C]

The title compound of step 1 (12 g, 94% yield) was prepared in a manner similar to that described in Example 19 step 1 from tert-butyl (S)-(1-hydroxybutan-2-yl)carbamate and 3,5-dibromo-2-fluoropyridine. LC-MS $(M+H)^+$=423.0.

Step 2: tert-butyl (S)-7-bromo-2-ethyl-2,3-dihydro-1H-pyrido[2,3-b][1,4]oxazine-1-carboxylate

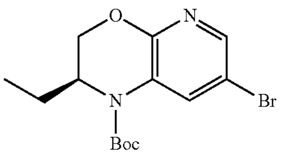 [SMILES: CC[C@H]1COc2ncc(Br)cc2N1C(=O)OC(C)(C)C]

The title compound of step 2 (1.1 g, 11% yield) was prepared in a manner similar to that described in Example 19 step 2 from tert-butyl (S)-(1-((3,5-dibromopyridin-2-yl)oxy)butan-2-yl)carbamate. LC-MS $(M+H)^+$=343.1.

Step 3: tert-butyl (S)-2-ethyl-7-(4-fluorobenzyl)-2,3-dihydro-1H-pyrido[2,3-b][1,4]oxazine carboxylate

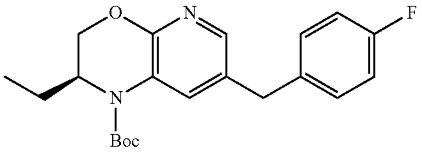 [SMILES: CC[C@H]1COc2ncc(Cc3ccc(F)cc3)cc2N1C(=O)OC(C)(C)C]

The title compound of step 3 (1 g, 82% yield) was prepared in a manner similar to that described in Example 1 step 7 from tert-butyl (S)-7-bromo-2-ethyl-2,3-dihydro-1H-pyrido[2,3-b][1,4]oxazine-1-carboxylate and (4-fluorobenzyl)zinc(II) chloride. LC-MS $(M+H)^+$=373.2.

Step 4: (S)-2-ethyl-7-(4-fluorobenzyl)-2,3-dihydro-1H-pyrido[2,3-b][1,4]oxazine

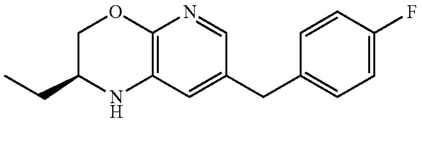 [SMILES: CC[C@H]1COc2ncc(Cc3ccc(F)cc3)cc2N1]

The title compound of step 4 (700 mg, 95% yield) was prepared in a manner similar to that described in Example 1 step 8 from tert-butyl (S)-2-ethyl-7-(4-fluorobenzyl)-2,3-dihydro-1H-pyrido[2,3-b][1,4]oxazine-1-carboxylate. LC-MS $(M+H)^+$=273.2.

Step 5: (S)-2-chloro-1-(2-ethyl-7-(4-fluorobenzyl)-2,3-dihydro-1H-pyrido[2,3-b][1,4]oxazin-1-yl)ethan-1-one

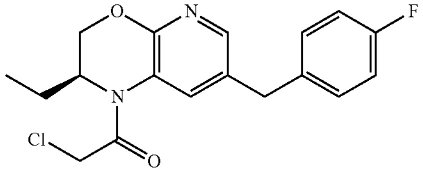 [SMILES: CC[C@H]1COc2ncc(Cc3ccc(F)cc3)cc2N1C(=O)CCl]

The title compound of step 5 (550 mg, 61% yield) was prepared in a manner similar to that described in Example 1 step 9 from (S)-2-ethyl-7-(4-fluorobenzyl)-2,3-dihydro-1H-pyrido[2,3-b][1,4]oxazine and 2-chloroacetyl chloride. LC-MS $(M+H)^+$=349.2.

Step 6: tert-butyl (2R,5S)-4-(2-((S)-2-ethyl-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

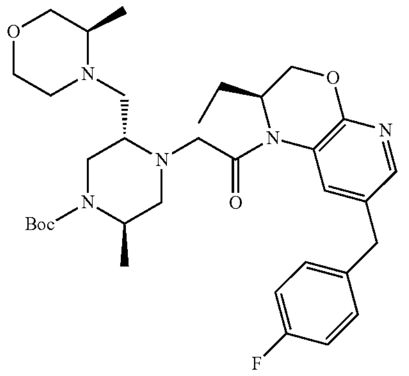 [SMILES: CC[C@H]1COc2ncc(Cc3ccc(F)cc3)cc2N1C(=O)CN1C[C@@H](C)N(C(=O)OC(C)(C)C)C[C@@H]1CN1CCOC[C@H]1C]

The title compound of step 6 (760 mg, 77% yield) was prepared in a manner similar to that described in Example 1 step 18 from (S)-2-chloro-1-(2-ethyl-7-(4-fluorobenzyl)-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=626.4.

Step 7: 1-(((S)-2-ethyl-7-(4-fluorobenzyl)-2,3-dihydro-1H-pyrido[2,3-b][1,4]oxazin-1-yl) ((2R,5R)-5-methyl-2-(((R)-3-methylmorpholino)methyl)piperazin-1-yl)ethan-1-one (Compound 28)

Compound 28 as formic acid salt was prepared in a manner similar to that described in Example 1 step 19 from tert-butyl (2R,5S)-4-(2-((S)-2-ethyl-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate. The salt was neutralized with aq. $NaHCO_3$and extracted with EtOAc. The combined organic layers were dried, filtered and concentrated. The residue was further lyophilized to afford compound 28 (290 mg, 45% yield) as free base. $^1H$ NMR (400 MHz, DMSO-d6) δ 8.16 (s, 1H), 7.84 (s, 1H), 7.25 (dd, J=8.4, 5.6 Hz, 2H), 7.12 (t, J=8.8 Hz, 2H), 4.45 (d, J=11.7 Hz, 2H), 4.20 (d, J=11.3 Hz, 1H), 4.09

(d, J=14.4 Hz, 1H), 3.88 (s, 2H), 3.51 (s, 2H), 3.42 (d, J=15.9 Hz, 1H), 2.99 (s, 1H), 2.82 (d, J=9.9 Hz, 2H), 2.73 (d, J=11.5 Hz, 1H), 2.71-2.56 (m, 4H), 2.27 (t, J=10.8 Hz, 1H), 2.16 (s, 2H), 2.00 (s, 1H), 1.76 (s, 1H), 1.46 (s, 2H), 0.87-0.81 (m, 9H). LC-MS $(M+H)^+$=526.5.

Example 29: 1-((S)-2-benzyl-7-(4-fluorobenzyl)-2,3-dihydro-1H-pyrido[2,3-b][1,4]oxazin-1-yl)-2-42R,5R)-5-methyl-2-(((R)-3-methylmorpholino)methyl)piperazin-1-yl)ethan-1-one (Compound 29)

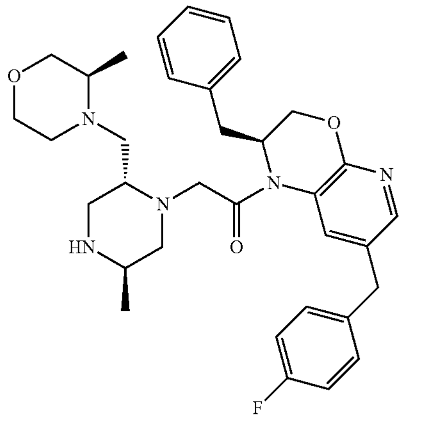 [SMILES: C[C@@H]1CN(CC(=O)N2c3cc(Cc4ccc(F)cc4)cnc3OC[C@@H]2Cc2ccccc2)[C@@H](CN2CCOC[C@H]2C)CN1]

Step 1: tert-butyl (S)-(1-((3,5-dibromopyridin-2-yl)oxy)-3-phenylpropan-2-yl)carbamate

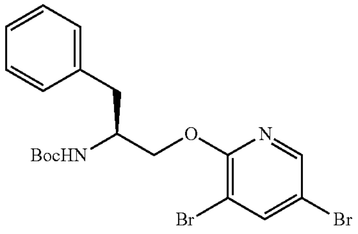 [SMILES: CC(C)(C)OC(=O)N[C@H](COc1ncc(Br)cc1Br)Cc1ccccc1]

To a solution of tert-butyl N-[(2S)-1-hydroxy-3-phenylpropan-2-yl]carbamate (4.7 g, 18.9 mmol) and 3,5-dibromo-2-fluoropyridine (4.4 g, 17.1 mmol) in THF (80 mL) was added NaH (865 mg, 21.6 mmol, 60%) in portions at 0° C. under nitrogen atmosphere. The resulting mixture was stirred for 5 h at room temperature under nitrogen atmosphere. When the reaction was done, the reaction was then quenched by the addition of water (60 mL). The resulting solution was extracted with ethyl acetate (60 mL×3). The organic phases were combined, washed with brine and dried over $Na_2SO_4$. The solvent was concentrated under reduced pressure and the residue was purified by flash chromatography (DCM:EtOAc=3:1) to yield the title product (9.9 g, 73% yield). LC-MS $(M+H)^+$=485.0.

Step 2: tert-butyl (S)-2-benzyl-7-bromo-2,3-dihydro-1H-pyrido[2,3-b][1,4]oxazine carboxylate

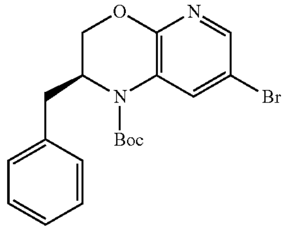 [SMILES: CC(C)(C)OC(=O)N1c2cc(Br)cnc2OC[C@@H]1Cc1ccccc1]

To a solution of tert-butyl (S)-(1-((3,5-dibromopyridin-2-yl)oxy)-3-phenylpropan-2-yl)carbamate (1.5 g, 3.1 mmol) in THF (10 mL) was added CuI (190 mg, 1.0 mmol), $Cs_2CO_3$ (2.1 g, 6.4 mmol), and DMEDA (105 mg, 1.3 mmol) at room temperature. The resulting mixture was stirred for 16 h at 80° C. under nitrogen atmosphere. When the reaction was done, the resulting mixture was filtered, the filter cake was washed with DCM (2×10 mL). The filtrate was concentrated under reduced pressure and the residue was purified by flash chromatography (PE:EtOAc=5:1) to yield the title product (260 mg, 20% yield). LC-MS $(M+H)^+$=405.1.

Step 3: tert-butyl (S)-2-benzyl-7-(4-fluorobenzyl)-2,3-dihydro-1H-pyrido[2,3-b][1,4]oxazine-1-carboxylate

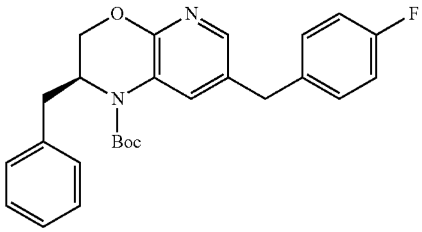 [SMILES: CC(C)(C)OC(=O)N1c2cc(Cc3ccc(F)cc3)cnc2OC[C@@H]1Cc1ccccc1]

To a solution of tert-butyl (S)-2-benzyl-7-bromo-2,3-dihydro-1H-pyrido[2,3-b][1,4]oxazine-1-carboxylate (260 mg, 0.6 mmol), chloro[(4-fluorophenyl)methyl]zinc (180 mg, 0.8 mmol), and $Pd(t\text{-}Bu_3P)_2$ (14 mg, 0.03 mmol) in THF (10 mL) was stirred for 2 h at 60° C. under nitrogen atmosphere. When the reaction was done, the reaction was then quenched by the addition of MeOH (5 mL). The resulting mixture was concentrated under reduced pressure. The resulting mixture was diluted with DCM (10 mL). The resulting mixture was filtered, the filter cake was washed with DCM (2×10 mL). The solvent was concentrated under reduced pressure and the residue was purified by flash chromatography (PE:EtOAc=3:1) to yield the title product (200 mg, 81% yield). LC-MS $(M+H)^+$=435.2.

Step 4: (S)-2-benzyl-7-(4-fluorobenzyl)-2,3-dihydro-1H-pyrido[2,3-b][1,4]oxazine

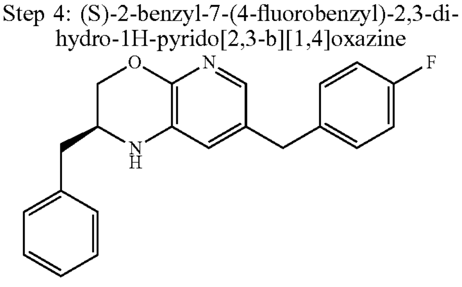

To a solution of tert-butyl (S)-2-benzyl-7-(4-fluorobenzyl)-2,3-dihydro-1H-pyrido[2,3-b][1,4]oxazine-1-carboxylate (200 mg, 0.5 mmol) in DCM (5 mL) was added HCl (g) in 1,4-dioxane (1.2 mL, 4.8 mmol, 4M) dropwise at 0° C. The resulting mixture was stirred for 3 h at room temperature. When the reaction was done, the resulting mixture was concentrated under reduced pressure. The resulting mixture was diluted with sat. $NaHCO_3$ (15 mL) and extracted with EtOAc (2×20 mL). The organic phases were combined, washed with brine and dried over $Na_2SO_4$. The solvent was concentrated under reduced pressure and the residue was purified by flash chromatography (PE:EtOAc=1:1) to yield the title product (120 mg, 78% yield). LC-MS $(M+H)^+$=335.0.

Step 5: (S)-1-(2-benzyl-7-(4-fluorobenzyl)-2,3-dihydro-1H-pyrido[2,3-b][1,4]oxazin-1-yl)-2-chloroethan-1-one

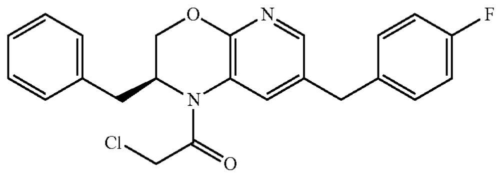 [SMILES: O=C(CCl)N1c2cc(Cc3ccc(F)cc3)cnc2OC[C@@H]1Cc1ccccc1]

The title compound of Step 5 (83 mg, crude) was prepared in a manner similar to that described in Example 1 step 9 from (S)-2-benzyl-7-(4-fluorobenzyl)-2,3-dihydro-1H-pyrido[2,3-b][1,4]oxazine and 2-chloroacetyl chloride. The crude material was used in next step directly without purification. LC-MS $(M+H)^+$=411.0.

Step 6: tert-butyl (2R,5S)-4-(2-((S)-2-benzyl-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

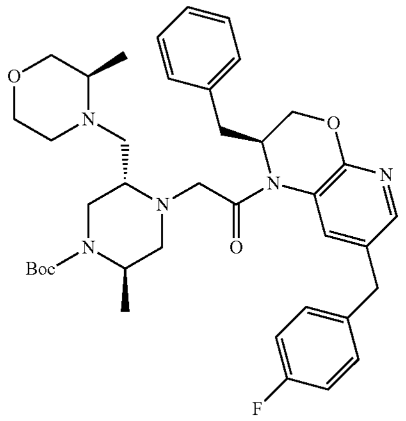 [SMILES: C[C@@H]1COCCN1C[C@H]1CN(C(=O)OC(C)(C)C)[C@H](C)CN1CC(=O)N1c2cc(Cc3ccc(F)cc3)cnc2OC[C@@H]1Cc1ccccc1]

The title compound of Step 6 (90 mg, 64% yield) was prepared in a manner similar to that described in Example 1 step 18 from (S)-1-(2-benzyl-7-(4-fluorobenzyl)-2,3-dihydro-1H-pyrido[2,3-b][1,4]oxazin-1-yl)-2-chloroethan-1-one and tert-butyl (2R,5S)-2-methyl-5-(((R)-3-methylmorpholino)methyl)piperazine-1-carboxylate. LC-MS $(M+H)^+$=688.4.

Step 7: 1-((S)-2-benzyl-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 29)

To a solution of tert-butyl (2R,5S)-4-(2-((S)-2-benzyl-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate (90 mg, 0.13 mmol) in DCM (3 mL) was added HCl (g) in 1,4-dioxane (0.5 mL, 2 mmol, 4 M) dropwise at 0° C. The resulting mixture was stirred for 3 h at room temperature. When the reaction was done, the resulting mixture was concentrated under reduced pressure. The resulting mixture was diluted with sat. $NaHCO_3$ solution (10 mL). The resulting mixture was extracted with EtOAc (2×15 mL). The organic phases were combined, washed with brine and dried over $Na_2SO_4$. The solvent was concentrated under reduced pressure and the residue was purified by prep-HPLC under the following conditions: column,)(Bridge Shield RP18 OBD Column, 30×150 mm, 5 um; mobile phase, acetonitrile in water (with 10 mmol/L $NH_4HCO_3$ and 0.1% $NH_3 \cdot H_2O$), 25% to 55% gradient in 8 min; detector, UV 254 nm. The title compound (29 mg, 38% yield) was obtained. $^1H$ NMR (400 MHz, DMSO-d6) δ 8.24 (s, 1H), 7.92 (s, 1H), 7.34-7.25 (m, 2H), 7.26 (s, 3H), 7.21-7.10 (m, 2H), 7.08 (s, 2H), 4.76 (s, 1H), 4.37 (d, J=11.2 Hz, 1H), 4.28-4.20 (m, 1H), 3.93 (d, J=2.2 Hz, 2H), 3.69 (s, 1H), 3.51 (s, 2H), 3.37 (d, J=9.4 Hz, 2H), 3.00 (s, 1H), 2.88 (s, 2H), 2.87-2.78 (m, 1H), 2.64-2.57 (m, 4H), 2.44-2.28 (m, 2H), 2.29-2.07 (m, 2H), 1.99 (s, 1H), 1.84 (t, J=10.6 Hz, 1H), 1.71-1.64 (m, 1H), 0.82 (d, J=6.2 Hz, 6H). LC-MS $(M+H)^+$=588.2.

Example 30: 1-((S)-7-(4-fluorobenzyl)-2-(p-tolyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 30)

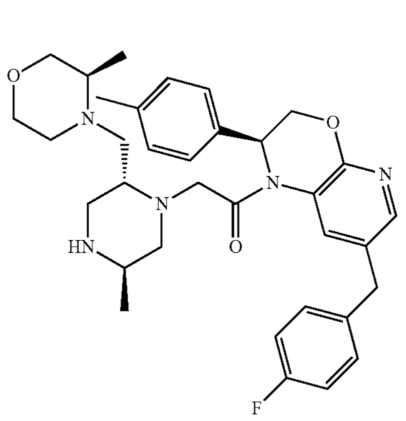 [SMILES: Cc1ccc([C@H]2COc3ncc(Cc4ccc(F)cc4)cc3N2C(=O)CN2C[C@@H](C)NC[C@@H]2CN2CCOC[C@H]2C)cc1]

Step 1: (S)-2-amino-2-(p-tolyl)ethan-1-ol

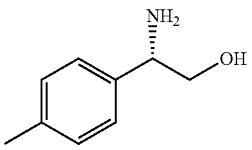

To a solution of (S)-amino(4-methylphenyl)acetic acid (1.9 g, 11.5 mmol) in THF (30 mL) was added $LiAlH_4$ (17.5 mL, 17.5 mmol, 1M) dropwise at 0° C. under nitrogen atmosphere. The resulting mixture was stirred for 16 h at 70° C. under nitrogen atmosphere. When the reaction was done, the reaction was then quenched by the addition of NaOH (2M) at 0° C. The resulting mixture was filtered, the filter cake was washed with THF (2×10 mL). The filtrate was concentrated under reduced pressure. The aqueous layer was extracted with $CH_2C_{12}$ (2×30 mL). The organic phases were combined, washed with brine and dried over $Na_2SO_4$. The solvent was concentrated under reduced pressure to yield the title compound (800 mg, 46% yield). LC-MS $(M+H)^+$=152.2.

Step 2: tert-butyl (S)-(2-hydroxy-1-(p-tolyl)ethyl) carbamate

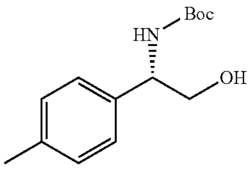 [SMILES: Cc1ccc([C@@H](CO)NC(=O)OC(C)(C)C)cc1]

To a solution of (S)-2-amino-2-(p-tolyl)ethan-1-ol (800 mg, 5.3 mmol) and TEA (1.4 g, 13.2 mmol) in THF (20 mL) was added $Boc_2O$ (1.7 g, 7.9 mmol) in portions at 0° C. under nitrogen atmosphere. The resulting mixture was stirred for 5 h at room temperature under nitrogen atmosphere. When the reaction was done, the reaction was then quenched by the addition of sat. $NaHCO_3$ (20 mL) at room temperature. The resulting solution was extracted with $CH_2Cl_2$ (2×30 mL). The organic phases were combined, washed with brine and dried over $Na_2SO_4$. The solvent was concentrated under reduced pressure and the residue was purified by flash chromatography (DCM:MeOH=10:1) to yield the title compound (850 mg, 64% yield). LC-MS $(M+H)^+$=252.1.

Step 3: tert-butyl (S)-(2-((3,5-dibromopyridin-2-yl) oxy)-1-(p-tolyl)ethyl)carbamate

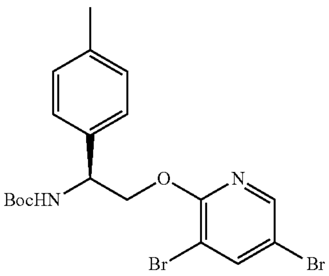 [SMILES: Cc1ccc([C@@H](COc2ncc(Br)cc2Br)NC(=O)OC(C)(C)C)cc1]

The title compound of step 3 (1.3 g, 86% yield) was prepared in a manner similar to that described in Example 29 step 1 from tert-butyl (S)-(2-hydroxy-1-(p-tolyl)ethyl)carbamate and 3,5-dibromo-2-fluoropyridine. LC-MS $(M+H)^+$=485.0.

Step 4: tert-butyl (S)-7-bromo-2-(p-tolyl)-2,3-dihydro-1H-pyrido[2,3-b][1,4]oxazine-1-carboxylate

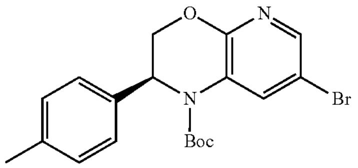 [SMILES: Cc1ccc([C@H]2COc3ncc(Br)cc3N2C(=O)OC(C)(C)C)cc1]

The title compound of step 4 (350 mg, 31% yield) was prepared in a manner similar to that described in Example 29 step 2 from tert-butyl (S)-(2-((3,5-dibromopyridin-2-yl) oxy)-1-(p-tolyl)ethyl)carbamate. LC-MS $(M+H)^+$=405.2.

Step 5: tert-butyl (S)-7-(4-fluorobenzyl)-2-(p-tolyl)-2,3-dihydro-1H-pyrido[2,3-b][1,4]oxazine-1-carboxylate

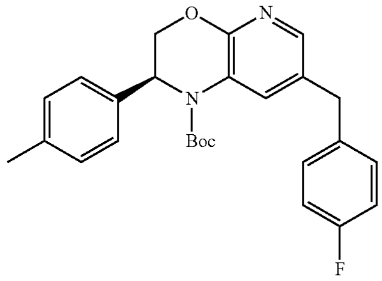 [SMILES: Cc1ccc([C@H]2COc3ncc(Cc4ccc(F)cc4)cc3N2C(=O)OC(C)(C)C)cc1]

The title compound of step 5 (275 mg, 73% yield) was prepared in a manner similar to that described in Example 29 step 3 from tert-butyl (S)-7-bromo-2-(p-tolyl)-2,3-dihydro-1H-pyrido[2,3-b][1,4]oxazine-1-carboxylate and (4-fluorobenzyl)zinc(II) chloride. LC-MS $(M+H)^+$=435.3.

Step 6: (S)-7-(4-fluorobenzyl)-2-(p-tolyl)-2,3-dihydro-1H-pyrido[2,3-b][1,4]oxazine

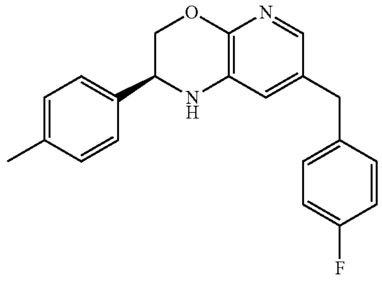 [SMILES: Cc1ccc([C@H]2COc3ncc(Cc4ccc(F)cc4)cc3N2)cc1]

The title compound of step 6 (180 mg, 84% yield) was prepared in a manner similar to that described in Example 29 step 4 from tert-butyl (S)-7-(4-fluorobenzyl)-2-(p-tolyl)-2,3-dihydro-1H-pyrido[2,3-b][1,4]oxazine-1-carboxylate. LC-MS $(M+H)^+$=335.1.

Step 7: (S)-2-chloro-1-(7-(4-fluorobenzyl)-2-(p-tolyl)-2,3-dihydro-1H-pyrido[2,3-b][1,4]oxazin-1-yl) ethan-1-one

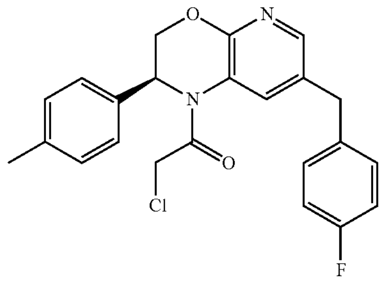 [SMILES: Cc1ccc([C@H]2COc3ncc(Cc4ccc(F)cc4)cc3N2C(=O)CCl)cc1]

The title compound of step 7 (162 mg, 73% yield) was prepared in a manner similar to that described in Example 1 step 9 from (S)-7-(4-fluorobenzyl)-2-(p-tolyl)-2,3-dihydro-1H-pyrido[2,3-b][1,4]oxazine and 2-chloroacetyl chloride. LC-MS $(M+H)^+$=411.2.

Step 8: tert-butyl (2R,5S)-4-(2-((S)-7-(4-fluorobenzyl)-2-(p-tolyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

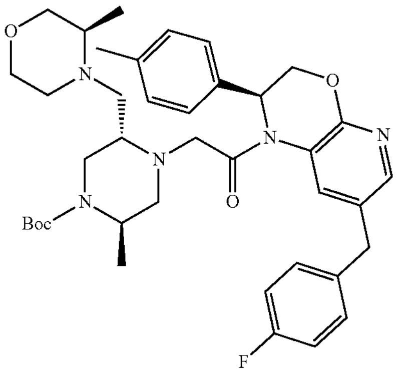 [SMILES: Cc1ccc([C@H]2COc3ncc(Cc4ccc(F)cc4)cc3N2C(=O)CN2C[C@@H](C)N(C(=O)OC(C)(C)C)C[C@@H]2CN2CCOC[C@H]2C)cc1]

The title compound of step 8 (90 mg, 64% yield) was prepared in a manner similar to that described in Example 1 step 18 from (S)-2-chloro-1-(7-(4-fluorobenzyl)-2-(p-tolyl)-2,3-dihydro-1H-pyrido[2,3-b][1,4]oxazin-1-yl)ethan-1-one and tert-butyl (2R,5S)-2-methyl (((R)-3-methylmorpholino) methyl)piperazine-1-carboxylate. LC-MS $(M+H)^+$=688.4.

Step 9: 1-((S)-7-(4-fluorobenzyl)-2-(p-tolyl)-2,3-dihydro-1H-pyrido[2,3-b][1,4]oxazin-1-yl) ((2R,5R)-5-methyl-2-(((R)-3-methylmorpholino)methyl) piperazin-1-yl)ethan-1-one (Compound 30)

To a solution of tert-butyl (2R,5S)-4-(2-((S)-7-(4-fluorobenzyl)-2-(p-tolyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate (90 mg, 0.13 mmol) in DCM (3 mL) was added HCl (g) in 1,4-dioxane (0.5 mL, 2 mmol, 4 M) dropwise at 0° C. The resulting mixture was stirred for 3 h at room temperature. When the reaction was done, the resulting mixture was concentrated under reduced pressure. The resulting mixture was diluted with sat. $NaHCO_3$ solution (10 mL). The resulting mixture was extracted with EtOAc (2×15 mL). The organic phases were combined, washed with brine and dried over $Na_2SO_4$. The solvent was concentrated under reduced pressure and the residue was purified by prep-HPLC under the following conditions: column,)(Bridge Shield RP18 OBD Column, 30×150 mm, 5 um; mobile phase, acetonitrile in water (with 10 mmol/L $NH_4HCO_3$ and 0.1% $NH_3 \cdot H_2O$), 25% to 55% gradient in 8 min; detector, UV 254 nm. The title compound (29 mg, 38% yield) was obtained. $^1H$ NMR (400 MHz, DMSO-d6) δ 8.24 (s, 1H), 7.92 (s, 1H), 7.34-7.25 (m, 2H), 7.26 (s, 3H), 7.21-7.10 (m, 2H), 7.08 (s, 2H), 4.76 (s, 1H), 4.37 (d, J=11.2 Hz, 1H), 4.28-4.20 (m, 1H), 3.93 (d, J=2.2 Hz, 2H), 3.69 (s, 1H), 3.51 (s, 2H), 3.37 (d, J=9.4 Hz, 2H), 3.00 (s, 1H), 2.88 (s, 2H), 2.87-2.78 (m, 1H), 2.64-2.57 (m, 4H), 2.44-2.28 (m, 2H), 2.29-2.07 (m, 2H), 1.99 (s, 1H), 1.84 (t, J=10.6 Hz, 1H), 1.71-1.64 (m, 1H), 0.82 (d, J=6.2 Hz, 6H). LC-MS $(M+H)^+$=588.2.

Example 31: (S)-7-(4-fluorobenzyl)-2-methyl-1-(2-((2R,5R)-5-methyl-2-(((R)-3-methylmorpholino) methyl)piperazin-1-yl)acetyl)-2,3-dihydro-1H-pyrido[2,3-b][1,4]oxazine-6-carboxamide (Compound 31)

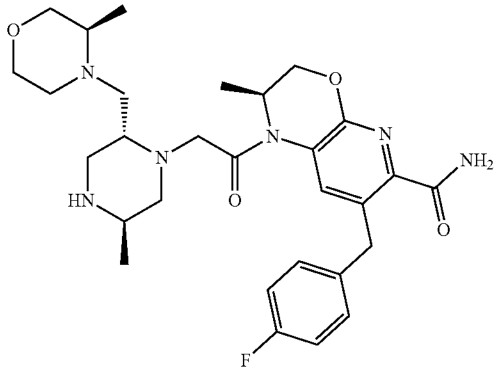 [SMILES: C[C@@H]1CN(CC(=O)N2c3cc(Cc4ccc(F)cc4)c(C(N)=O)nc3OC[C@@H]2C)[C@@H](CN2CCOC[C@H]2C)CN1]

Step 1: tert-butyl (S)-7-(4-fluorobenzyl)-6-(hydroxymethyl)-2-methyl-2,3-dihydro-1H-pyrido[2,3-b][1,4]oxazine-1-carboxylate

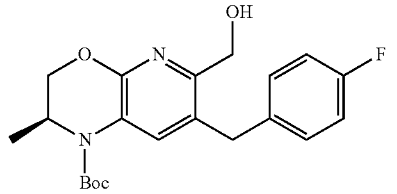 [SMILES: C[C@H]1COc2nc(CO)c(Cc3ccc(F)cc3)cc2N1C(=O)OC(C)(C)C]

The title compound of step 1 (3 g, 90% yield) was prepared in a manner similar to that described in Example 21 step 1 from tert-butyl (S)-6-(acetoxymethyl)-7-(4-fluorobenzyl)-2-methyl-2,3-dihydro-1H-pyrido[2,3-b][1,4] oxazine-1-carboxylate. LC-MS $(M+H)^+$=389.2.

Step 2: (S)-1-(tert-butoxycarbonyl)-7-(4-fluorobenzyl)-2-methyl-2,3-dihydro-1H-pyrido[2,3-b][1,4]oxazine-6-carboxylic acid

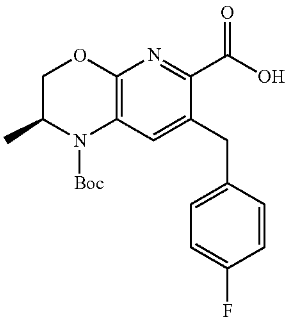 [SMILES: C[C@H]1COc2nc(C(=O)O)c(Cc3ccc(F)cc3)cc2N1C(=O)OC(C)(C)C]

The title compound of step 2 (2 g, crude) was prepared in a manner similar to that described in Example 21 step 2 from tert-butyl (S)-7-(4-fluorobenzyl)-6-(hydroxymethyl)-2-methyl-2,3-dihydro-1H-pyrido[2,3-b][1,4]oxazine-1-carboxylate. LC-MS $(M+H)^+$=403.2.

Step 3: tert-butyl (S)-6-carbamoyl-7-(4-fluorobenzyl)-2-methyl-2,3-dihydro-1H-pyrido[2,3-b][1,4]oxazine-1-carboxylate

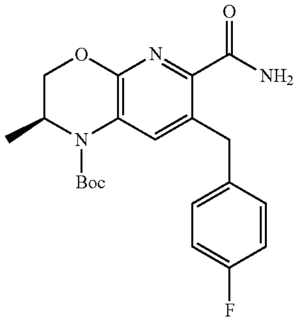 [SMILES: C[C@H]1COc2nc(C(N)=O)c(Cc3ccc(F)cc3)cc2N1C(=O)OC(C)(C)C]

The reaction mixture of (S)-1-(tert-butoxycarbonyl)-7-(4-fluorobenzyl)-2-methyl-2,3-dihydro-1H-pyrido[2,3-b][1,4]oxazine-6-carboxylic acid (430 mg, 1.1 mmol), $NH_4Cl$ (289 mg, 5.3 mmol), DIPEA (276 mg, 2.1 mmol) and HATU (407 mg, 1.1 mmol) in DMF (8 mL) was stirred at room temperature for overnight. The mixture was treated with water and extracted with EtOAc (30 mL×3). The combined organic layers were washed with brine, dried over $Na_2SO_4$, filtered and evaporated. The residue was purified by column chromatography (PE:EtOAc=2:1) to give the title product (340 mg, 79% yield). LC-MS $(M+H)^+$=402.1.

Step 4: (S)-7-(4-fluorobenzyl)-2-methyl-2,3-dihydro-1H-pyrido[2,3-b][1,4]oxazine-6-carboxamide

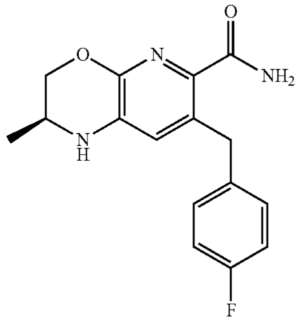 [SMILES: C[C@H]1COc2nc(C(N)=O)c(Cc3ccc(F)cc3)cc2N1]

The title compound of step 4 (255 mg, 100% yield) was prepared in a manner similar to that described in Example 1 step 8 from tert-butyl (S)-6-carbamoyl-7-(4-fluorobenzyl)-2-methyl-2,3-dihydro-1H-pyrido[2,3-b][1,4]oxazine-1-carboxylate. LC-MS $(M+H)^+$=302.1.

Step 5: (S)-1-(2-chloroacetyl)-7-(4-fluorobenzyl)-2-methyl-2,3-dihydro-1H-pyrido[2,3-b][1,4]oxazine-6-carboxamide

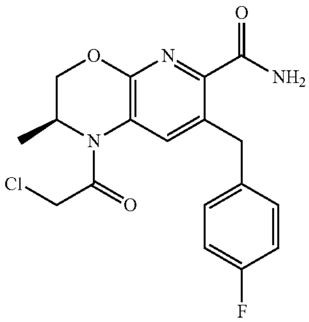 [SMILES: C[C@H]1COc2nc(C(N)=O)c(Cc3ccc(F)cc3)cc2N1C(=O)CCl]

The title compound of step 5 (200 mg, 62% yield) was prepared in a manner similar to that described in Example 1 step 9 from (S)-7-(4-fluorobenzyl)-2-methyl-2,3-dihydro-1H-pyrido[2,3-b][1,4]oxazine-6-carboxamide and 2-chloroacetyl chloride. LC-MS $(M+H)^+$=378.1.

Step 6: tert-butyl (2R,5S)-4-(24S)-6-carbamoyl-7-(4-fluorobenzyl)-2-methyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate

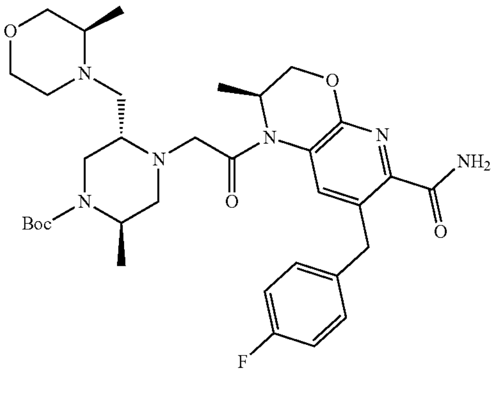 [SMILES: C[C@@H]1COCCN1C[C@H]1CN(C(=O)OC(C)(C)C)[C@H](C)CN1CC(=O)N1c2cc(Cc3ccc(F)cc3)c(C(N)=O)nc2OC[C@@H]1C]

The title compound of step 6 (150 mg, 88% yield) was prepared in a manner similar to that described in Example 1 step 18 from (S)-1-(2-chloroacetyl)-7-(4-fluorobenzyl)-2-methyl-2,3-dihydro-1H-pyrido[2,3-b][1,4]oxazine-6-carboxamide and tert-butyl (2R,5S)-2-methyl-5-(((R)-3-methylmorpholino)methyl)piperazine-1-carboxylate. LC-MS $(M+H)^+$=655.3.

Step 7: (S)-7-(4-fluorobenzyl)-2-methyl-1-(2-((2R,5R)-5-methyl-2-(((R)-3-methylmorpholino)methyl)piperazin-1-yl)acetyl)-2,3-dihydro-1H-pyrido[2,3-b][1,4]oxazine-6-carboxamide (Compound 31)

Compound 31 as formic acid salt was prepared in a manner similar to that described in Example 1 step 19 from tert-butyl (2R,5S)-4-(2-((S)-6-carbamoyl-7-(4-fluorobenzyl)-2-methyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate. The salt was neutralized with aq. $NaHCO_3$ and extracted with EtOAc. The combined organic layers were dried, filtered and concentrated. The residue was further lyophilized to afford compound 31 (53 mg, 41% yield) as free base. $^1$H NMR (400 MHz, DMSO-d6) δ 8.37 (s, 1H), 7.80 (s, 1H), 7.44 (s, 1H), 7.30-7.17 (m, 2H), 7.08 (t, J=8.8 Hz, 2H), 4.79 (s, 1H), 4.39-4.26 (m, 4H), 4.07 (d, J=15.6 Hz, 1H), 3.55-3.45 (m, 3H), 3.30-3.17 (m, 1H), 2.97 (t, J=9.7 Hz, 1H), 2.83-2.72 (m, 4H), 2.60-2.56 (m, 2H), 2.37-2.06 (m, 4H), 1.96 (t, J=9.4 Hz, 1H), 1.74 (d, J=11.6 Hz, 1H), 1.19 (d, J=6.4 Hz, 3H), 0.86 (d, J=5.8 Hz, 6H). LC-MS $(M+H)^+$=555.5.

Example 32: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 32)

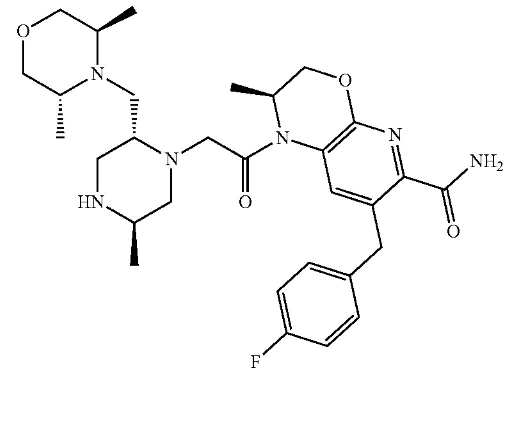 [SMILES: C[C@@H]1CN(CC(=O)N2c3cc(Cc4ccc(F)cc4)c(C(N)=O)nc3OC[C@@H]2C)[C@@H](CN2[C@H](C)COC[C@H]2C)CN1]

Step 1: tert-butyl (2R,5S)-4-(2-((S)-6-carbamoyl-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

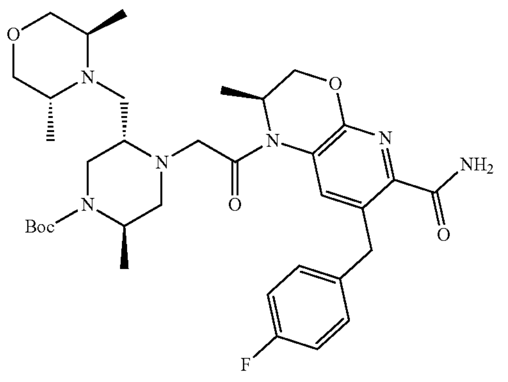 [SMILES: C[C@@H]1CN(CC(=O)N2c3cc(Cc4ccc(F)cc4)c(C(N)=O)nc3OC[C@@H]2C)[C@@H](CN2[C@H](C)COC[C@H]2C)CN1C(=O)OC(C)(C)C]

The title compound of step 1 (100 mg, 60% yield) was prepared in a manner similar to that described in Example 1 step 18 from (S)-1-(2-chloroacetyl)-7-(4-fluorobenzyl)-2-methyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=669.3.

Step 2: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 32)

Compound 32 as formic acid salt was prepared in a manner similar to that described in Example 1 step 19 from tert-butyl (2R,5S)-4-(2-((S)-6-carbamoyl-7-(4-fluorobenzyl) methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. The salt was neutralized with aq. $NaHCO_3$ and extracted with EtOAc. The combined organic layers were dried, filtered and concentrated. The residue was further lyophilized to afford compound 32 (15 mg, 17% yield) as free base. $^1$H NMR (400 MHz, DMSO-d6) δ 8.32 (s, 1H), 7.80 (s, 1H), 7.44 (s, 1H), 7.22 (s, 2H), 7.08 (t, J=8.8 Hz, 2H), 4.75 (s, 1H), 4.43-4.21 (m, 4H), 3.96 (d, J=15.4 Hz, 1H), 3.52 (d, J=15.3 Hz, 1H), 3.42 (d, J=9.2 Hz, 2H), 3.08 (s, 2H), 2.94 (d, J=10.5 Hz, 1H), 2.77 (d, J=8.4 Hz, 1H), 2.71-2.55 (m, 5H), 2.30-2.18 (m, 2H), 1.96 (d, J=8.6 Hz, 1H), 1.24-1.18 (m, 4H), 0.87 (d, J=5.8 Hz, 3H), 0.83 (d, J=6.0 Hz, 6H). LC-MS $(M+H)^+$=569.5.

Example 33: 1-(((S)-7-(4-fluorobenzyl)-2-isobutyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 33)

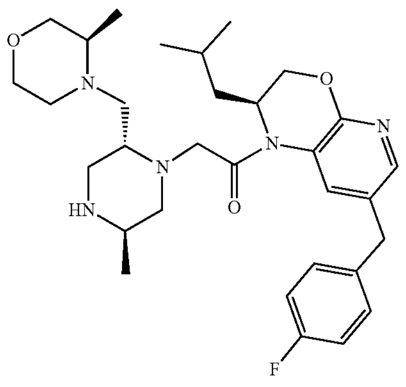 [SMILES: CC(C)C[C@H]1COc2ncc(Cc3ccc(F)cc3)cc2N1C(=O)CN1C[C@@H](C)NC[C@@H]1CN1CCOC[C@H]1C]

Step 1: tert-butyl (S)-(1-((3,5-dibromopyridin-2-yl)oxy)-4-methylpentan-2-yl)carbamate

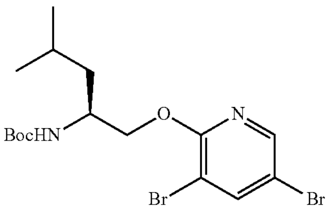 [SMILES: CC(C)C[C@@H](COc1ncc(Br)cc1Br)NC(=O)OC(C)(C)C]

The title compound of step 1 (6 g, 83% yield) was prepared in a manner similar to that described in Example 29 step 1 from tert-butyl (S)-(1-hydroxy-4-methylpentan-2-yl)carbamate and 3,5-dibromo-2-fluoropyridine. LC-MS $(M+H)^+$=451.0.

Step 2: tert-butyl (S)-7-bromo-2-isobutyl-2,3-dihydro-1H-pyrido[2,3-b][1,4]oxazine-1-carboxylate

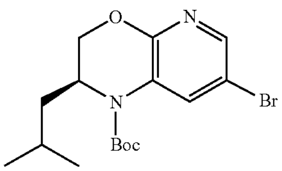 [SMILES: CC(C)C[C@H]1COc2ncc(Br)cc2N1C(=O)OC(C)(C)C]

The title compound of step 2 (760 mg, 15% yield) was prepared in a manner similar to that described in Example 29 step 2 from tert-butyl (S)-(1-((3,5-dibromopyridin-2-yl)oxy)-4-methylpentan-2-yl)carbamate. LC-MS $(M+H)^+$=371.1.

Step 3: tert-butyl (S)-7-(4-fluorobenzyl)-2-isobutyl-2,3-dihydro-1H-pyrido[2,3-b][1,4]oxazine-1-carboxylate

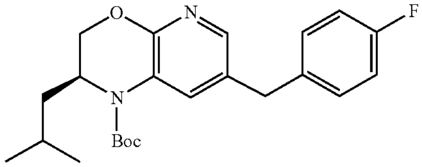 [SMILES: CC(C)C[C@H]1COc2ncc(Cc3ccc(F)cc3)cc2N1C(=O)OC(C)(C)C]

The title compound of step 3 (600 mg, 69% yield) was prepared in a manner similar to that described in Example 29 step 3 from tert-butyl (S)-7-bromo-2-isobutyl-2,3-dihydro-1H-pyrido[2,3-b][1,4]oxazine-1-carboxylate and (4-fluorobenzyl)zinc(II) chloride. LC-MS $(M+H)^+$=401.2

Step 4: (S)-7-(4-fluorobenzyl)-2-isobutyl-2,3-dihydro-1H-pyrido[2,3-b][1,4]oxazine

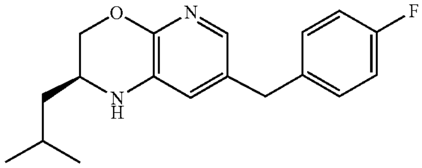 [SMILES: CC(C)C[C@H]1COc2ncc(Cc3ccc(F)cc3)cc2N1]

The title compound of step 4 (350 mg, 91% yield) was prepared in a manner similar to that described in Example 29 step 4 from tert-butyl (S)-7-(4-fluorobenzyl)-2-isobutyl-2,3-dihydro-1H-pyrido[2,3-b][1,4]oxazine-1-carboxylate. LC-MS $(M+H)^+$=301.1.

Step 5: (S)-2-chloro-1-(7-(4-fluorobenzyl)-2-isobutyl-2,3-dihydro-1H-pyrido[2,3-b][1,4]oxazin-1-yl)ethan-1-one

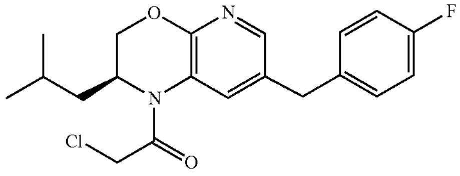 [SMILES: CC(C)C[C@H]1COc2ncc(Cc3ccc(F)cc3)cc2N1C(=O)CCl]

The title compound of step 5 (330 mg, 90% yield) was prepared in a manner similar to that described in Example 1 step 9 from (S)-7-(4-fluorobenzyl)-2-isobutyl-2,3-dihydro-1H-pyrido[2,3-b][1,4]oxazine and 2-chloroacetyl chloride. LC-MS $(M+H)^+$=377.1.

Step 6: tert-butyl (2R,5S)-4-(2-((S)-7-(4-fluorobenzyl)-2-isobutyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate

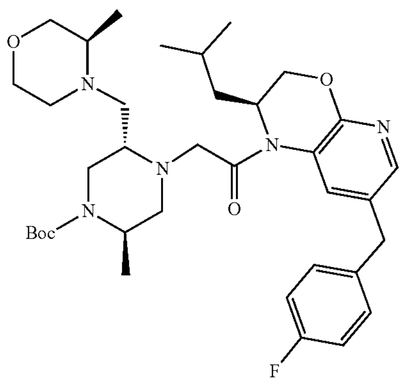 [SMILES: CC(C)C[C@H]1COc2ncc(Cc3ccc(F)cc3)cc2N1C(=O)CN1C[C@@H](C)N(C(=O)OC(C)(C)C)C[C@@H]1CN1CCOC[C@H]1C]

The title compound of step 6 (300 mg, 57% yield) was prepared in a manner similar to that described in Example 1 step 18 from (S)-2-chloro-1-(7-(4-fluorobenzyl)-2-isobutyl-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=654.5.

Step 7: 1-((S)-7-(4-fluorobenzyl)-2-isobutyl-2,3-dihydro-1H-pyrido[2,3-b][1,4]oxazin-1-yl) ((2R,5R)-5-methyl-2-(((R)-3-methylmorpholino)methyl)piperazin-1-yl)ethan-1-one (Compound 33)

Compound 33 (13 mg, 6% yield) was prepared in a manner similar to that in Example 29 step 7 from tert-butyl (2R,5S)-4-(2-((S)-7-(4-fluorobenzyl)-2-isobutyl-2,3-dihydro-1H-pyrido[2,3-b][1,4]oxazin-1-yl)-2-oxoethyl)-2-methyl-5-(((R)-3-methylmorpholino)methyl)piperazine carboxylate. $^1$H NMR (300 MHz, DMSO-d6) δ 8.09 (s, 1H), 7.83 (d, J=2.1 Hz, 1H), 7.28-.16 (m, 2H), 7.16-7.04 (m, 2H), 4.65-4.11 (m, 3H), 3.99 (d, J=15.9 Hz, 1H), 3.86 (s, 2H), 2.92 (s, 2H), 2.82-2.65 (m, 4H), 2.58-2.49 (m, 2H), 2.36-2.14 (m, 3H), 2.11-1.87 (m, 3H), 1.66 (s, 3H), 1.28 (d, J=34.5 Hz, 3H), 0.91-0.80 (m, 12H). LC-MS $(M+H)^+$=554.4.

Example 34: 2-42R,5R)-2-(((3R,5R)-3,5-dimethylmorpholino)methyl)-5-methylpiperazin-1-yl)-1-(((S)-7-(4-fluorobenzyl)-2-(methoxymethyl)-2,3-dihydro-1H-pyrido[2,3-b][1,4]oxazin-1-yl)ethan-1-one (Compound 34)

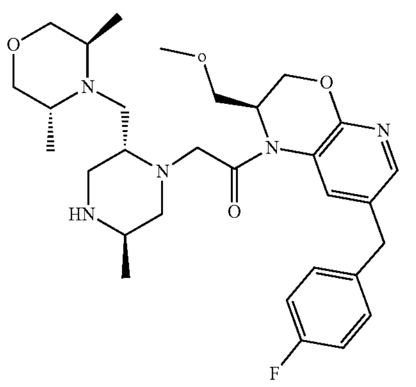

Step 1: tert-butyl (S)-(1-(benzyloxy)-3-((3-bromo-5-chloropyridin-2-yl)oxy)propan-2-yl)carbamate

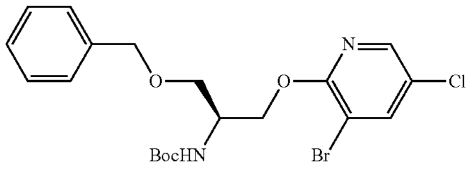 [SMILES: CC(C)(C)OC(=O)N[C@@H](COCc1ccccc1)COc1ncc(Cl)cc1Br]

The title compound of step 1 (19.5 g, 78% yield) was prepared in a manner similar to that described in Example 29 step 1 from tert-butyl (R)-(1-(benzyloxy)-3-hydroxypropan-2-yl)carbamate and 3-bromo-5-chloro-2-fluoropyridine. LC-MS $(M+H)^+$=471.0.

Step 2: tert-butyl (S)-2-((benzyloxy)methyl)-7-chloro-2,3-dihydro-1H-pyrido[2,3-b][1,4]oxazine-1-carboxylate

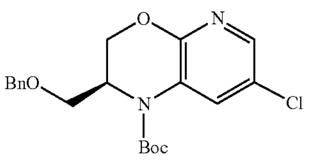 [SMILES: CC(C)(C)OC(=O)N1c2cc(Cl)cnc2OC[C@@H]1COCc1ccccc1]

To a solution of tert-butyl (S)-(1-(benzyloxy)-3-((3-bromo-5-chloropyridin-2-yl)oxy)propan-2-yl)carbamate (19.5 g, 41.9 mmol) in dioxane (200 mL) was added XantPhos (4.9 g, 8.4 mmol), $Cs_2CO_3$ (41.0 g, 125.9 mmol), and $Pd_2(dba)_3$ (3.8 g, 4.2 mmol). The resulting mixture was stirred for 4 h at 100° C. under nitrogen atmosphere. When the reaction was done, the reaction was then quenched by the addition of water (200 mL). The resulting solution was extracted with ethyl acetate (250 mL×2). The organic phases were combined, washed with brine and dried over $Na_2SO_4$. The solvent was concentrated under reduced pressure and the residue was purified by flash chromatography (PE: EtOAc=5:1) to yield the title compound (14.3 g, 87% yield). LC-MS $(M+H)^+$=391.1.

Step 3: tert-butyl (S)-2-((benzyloxy)methyl)-7-(4-fluorobenzyl)-2,3-dihydro-1H-pyrido[2,3-b][1,4]oxazine-1-carboxylate

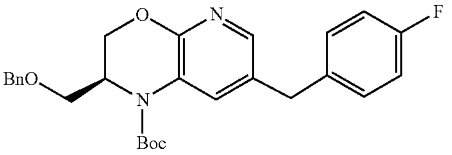 [SMILES: CC(C)(C)OC(=O)N1c2cc(Cc3ccc(F)cc3)cnc2OC[C@@H]1COCc1ccccc1]

To a solution of tert-butyl (S)-2-((benzyloxy)methyl)-7-chloro-2,3-dihydro-1H-pyrido[2,3-b][1,4]oxazine-1-carboxylate (14.3 g, 36.6 mmol), [1,3-bis[2,6-bis(propan-2-yl)phenyl]-2,3-dihydro-1H-imidazol-2-yl]dichloro(3-chloropyridin-1-ium-1-yl)palladium (1.2 g, 1.8 mmol) and LiBr (9.5 g, 109.7 mmol) in THF (200 mL) and NMP (300 mL) were added chloro[(4-fluorophenyl)methyl]zinc (15.4 g, 73.2 mmol) under nitrogen atmosphere. The resulting mixture was stirred for 4 h at room temperature under nitrogen atmosphere. When the reaction was done, the reaction was then quenched by the addition of 2.5% w/w citric acid (600 mL). The resulting solution was extracted with ethyl acetate (600 mL×3). The organic phases were combined, washed with brine and dried over $Na_2SO_4$. The solvent was concentrated under reduced pressure and the residue was purified by flash chromatography (PE:EtOAc=1:1) to yield the title compound (15 g, 74% yield). LC-MS $(M+H)^+$=465.2.

Step 4: tert-butyl (S)-7-(4-fluorobenzyl)-2-(hydroxymethyl)-2,3-dihydro-1H-pyrido[2,3-b][1,4]oxazine-1-carboxylate

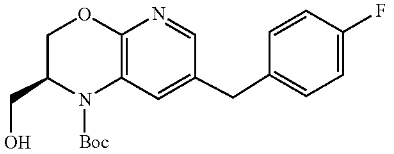 [SMILES: CC(C)(C)OC(=O)N1c2cc(Cc3ccc(F)cc3)cnc2OC[C@@H]1CO]

To a solution of tert-butyl (S)-2-((benzyloxy)methyl)-7-(4-fluorobenzyl)-2,3-dihydro-1H-pyrido[2,3-b][1,4]oxazine-1-carboxylate (15 g, 32.3 mmol) in MeOH (150 mL) and AcOH (30 mL) was added Pd/C (8.6 g, 8.0 mmol, 10%). The resulting mixture was stirred for 18 h at room temperature under hydrogen atmosphere. When the reaction was done, the mixture was filtered through a Celite pad and concentrated under reduced pressure. The residue was basified to pH=8 with sat. $NaHCO_3$ solution. The resulting mixture was extracted with $CH_2Cl_2$ (200 mL×3). The organic phases were combined, washed with brine and dried over $Na_2SO_4$. The solvent was concentrated under reduced pressure and the residue was purified by flash chromatography eluting with (DCM:MeOH=10:1) to yield the title compound (11.0 g, 90% yield). LC-MS $(M+H)^+$=375.1.

Step 5: tert-butyl (R)-7-(4-fluorobenzyl)-2-(((methylsulfonyl)oxy)methyl)-2,3-dihydro-1H-pyrido[2,3-b][1,4]oxazine-1-carboxylate

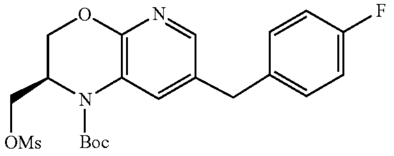 [SMILES: CC(C)(C)OC(=O)N1c2cc(Cc3ccc(F)cc3)cnc2OC[C@@H]1COS(C)(=O)=O]

To a solution of tert-butyl (S)-7-(4-fluorobenzyl)-2-(hydroxymethyl)-2,3-dihydro-1H-pyrido[2,3-b][1,4]oxazine-1-carboxylate (2.5 g, 6.7 mmol) and TEA (1.3 g, 13.3 mmol) in DCM (40 mL) were added MsCl (1.2 g, 10.0 mmol) at 0° C. The resulting mixture was stirred for 6 h at room temperature under nitrogen atmosphere. When the reaction was done, the resulting mixture was concentrated under reduced pressure. The residue was purified by flash chromatography (PE:EtOAc=4:1) to yield the title compound (3 g, 92% yield). LC-MS $(M+H)^+$=453.0.

Step 6: (R)-(7-(4-fluorobenzyl)-2,3-dihydro-1H-pyrido[2,3-b][1,4]oxazin-2-yl)methyl methanesulfonate

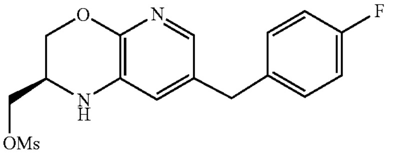 [SMILES: CS(=O)(=O)OC[C@H]1COc2ncc(Cc3ccc(F)cc3)cc2N1]

The title compound of step 6 (2 g, 85% yield) was prepared in a manner similar to that described in Example 29 step 4 from tert-butyl (R)-7-(4-fluorobenzyl)-2-(((methylsulfonyl)oxy)methyl)-2,3-dihydro-1H-pyrido[2,3-b][1,4]oxazine-1-carboxylate. LC-MS $(M+H)^+$=353.1.

Step 7: (S)-7-(4-fluorobenzyl)-2-(methoxymethyl)-2,3-dihydro-1H-pyrido[2,3-b][1,4]oxazine

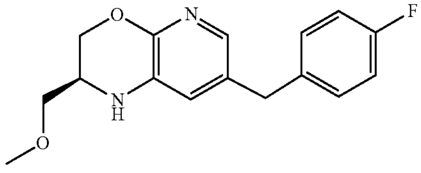 [SMILES: COC[C@H]1COc2ncc(Cc3ccc(F)cc3)cc2N1]

To a solution of (R)-(7-(4-fluorobenzyl)-2,3-dihydro-1H-pyrido[2,3-b][1,4]oxazin-2-yl)methyl methanesulfonate (280 mg, 0.8 mmol) and NaOMe (430 mg, 7.9 mmol) in MeOH (15 mL) was stirred for 16 h at 80° C. under nitrogen atmosphere. When the reaction was done, the resulting mixture was concentrated under reduced pressure. The resulting mixture was diluted with water (15 mL) and extracted with ethyl acetate (20 mL×3). The organic phases were combined, washed with brine and dried over $Na_2SO_4$. The solvent was concentrated under reduced pressure and the residue was purified by flash chromatography (DCM:EtOAc=2:3) to yield the title compound (170 mg, 74% yield). LC-MS $(M+H)^+$=289.1.

Step 8: (S)-2-chloro-1-(7-(4-fluorobenzyl)-2-(methoxymethyl)-2,3-dihydro-1H-pyrido[2,3-b][1,4]oxazin-1-yl)ethan-1-one

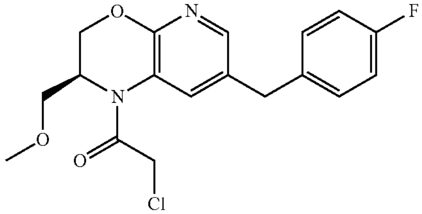 [SMILES: COC[C@H]1COc2ncc(Cc3ccc(F)cc3)cc2N1C(=O)CCl]

The title compound of step 8 (110 mg, 81% yield) was prepared in a manner similar to that described in Example 1 step 9 from (S)-7-(4-fluorobenzyl)-2-(methoxymethyl)-2,3-dihydro-1-H-pyrido[2,3-b][1,4]oxazine and 2-chloroacetyl chloride. LC-MS $(M+H)^+$=365.0.

Step 9: tert-butyl (2R,5S)-5-(((3R,5R)-3,5-dimethylmorpholino)methyl)-4-(2-((S)-7-(4-fluorobenzyl)-2-(methoxymethyl)-2,3-dihydro-1H-pyrido[2,3-b][1,4]oxazin-1-yl)-2-oxoethyl)-2-methylpiperazine-1-carboxylate

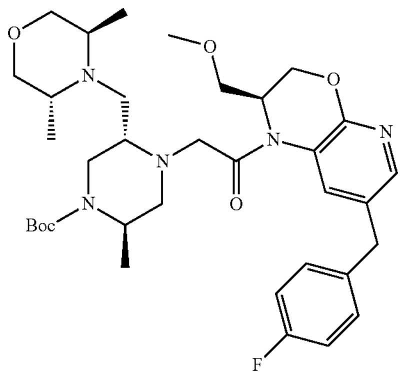 [SMILES: COC[C@H]1COc2ncc(Cc3ccc(F)cc3)cc2N1C(=O)CN1C[C@@H](C)N(C(=O)OC(C)(C)C)C[C@@H]1CN1[C@H](C)COC[C@H]1C]

The title compound of step 9 (42 mg, 45% yield) was prepared in a manner similar to that described in Example 1 step 18 from (S)-2-chloro-1-(7-(4-fluorobenzyl)-2-(methoxymethyl)-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=656.4.

Step 10: 2-((2R,5R)-2-(((3R,5R)-3,5-dimethylmorpholino)methyl)-5-methylpiperazin-1-yl)-1-((S)-7-(4-fluorobenzyl)-2-(m ethoxymethyl)-2,3-dihydro-1H-pyrido[2,3-b][1,4]oxazin-1-yl)ethan-1-one (Compound 34)

Compound 34 (30 mg, 85% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-(m ethoxymethyl)-2,3-dihydro-1H-pyrido[2,3-b][1,4]oxazin-1-yl)-2-oxoethyl)-2-methylpiperazine-1-carboxylate. 1H NMR (300 MHz, DMSO-d6) δ 8.27 (s, 1H), 7.84 (s, 1H), 7.30-7.18 (m, 2H), 7.18-7.05 (m, 2H), 4.88 (s, 1H), 4.50 (d, J=11.4 Hz, 1H), 4.20 (d, J=11.4, 2.7 Hz, 1H), 4.08 (d, J=15.0 Hz, 1H), 3.87 (s, 2H), 3.53-3.43 (m, 2H), 3.41-3.32 (m, 3H), 3.23 (s, 3H), 3.21-3.09 (m, 2H), 3.06-2.96 (m, 1H), 2.87-2.62 (m, 4H), 2.59-2.50 (m, 2H), 2.46-2.39 (m, 1H), 2.30-2.17 (m, 1H), 2.17-2.04 (m, 1H), 2.01-1.88 (m, 1H), 0.91-0.79 (m, 9H). LC-MS $(M+H)^+$=556.3.

Example 35: 1-((S)-7-(4-fluorobenzyl)-2-(methoxymethyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 35)

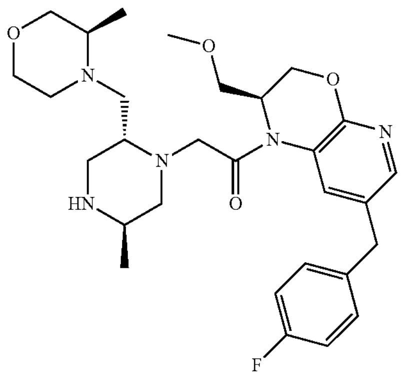 [SMILES: COC[C@H]1COc2ncc(Cc3ccc(F)cc3)cc2N1C(=O)CN1C[C@@H](C)NC[C@@H]1CN1CCOC[C@H]1C]

Step 1: tert-butyl (2R,5S)-4-(2-((S)-7-(4-fluorobenzyl)-2-(methoxymethyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

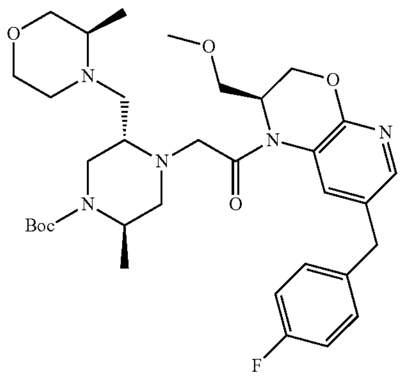 [SMILES: COC[C@H]1COc2ncc(Cc3ccc(F)cc3)cc2N1C(=O)CN1C[C@@H](C)N(C(=O)OC(C)(C)C)C[C@@H]1CN1CCOC[C@H]1C]

The title compound of step 1 (115 mg, 59% yield) was prepared in a manner similar to that described in Example 1 step 18 from (S)-2-chloro-1-(7-(4-fluorobenzyl)-2-(methoxymethyl)-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=642.5.

Step 2: 1-((S)-7-(4-fluorobenzyl)-2-(methoxymethyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 35)

Compound 35 (57 mg, 59% yield) was prepared in a manner similar to that described in Example 29 step 7 from tert-butyl (2R,5S)-4-(2-((S)-7-(4-fluorobenzyl)-2-(methoxymethyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate. $^1$H NMR (300

MHz, Chloroform-d) δ 8.48 (s, 1H), 7.84 (s, 1H), 7.23-7.10 (m, 2H), 7.06-6.92 (m, 2H), 5.11 (t, J=7.5 Hz, 1H), 4.66-4.53 (m, 2H), 4.23 (dd, J=11.3, 2.8 Hz, 1H), 3.89 (s, 2H), 3.76-3.51 (m, 3H), 3.51-3.29 (m, 2H), 3.30 (s, 3H), 3.27-3.09 (m, 2H), 3.09-2.88 (m, 2H), 2.87-2.74 (m, 2H), 2.78-2.65 (m, 1H), 2.62-2.54 (m, 1H), 2.53 (s, 2H), 2.39-2.28 (m, 1H), 2.23-2.02 (m, 2H), 1.96-1.85 (m, 1H), 1.02 (d, J=6.3 Hz, 3H), 0.96 (d, J=6.3 Hz, 3H). LC-MS $(M+H)^+$=542.3.

Example 36: 2-42R,5R)-2-(((3R,5R)-3,5-dimethylmorpholino)methyl)-5-methylpiperazin-1-yl)-1-(((S)-2-(ethoxymethyl)-7-(4-fluorobenzyl)-2,3-dihydro-1H-pyrido[2,3-b][1,4]oxazin-1-yl)ethan-1-one (Compound 36)

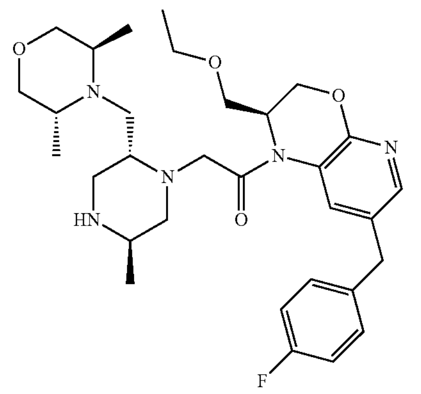 [SMILES: CCOC[C@H]1COc2ncc(Cc3ccc(F)cc3)cc2N1C(=O)CN1C[C@@H](C)NC[C@@H]1CN1[C@H](C)COC[C@H]1C]

Step 1: (S)-2-(ethoxymethyl)-7-(4-fluorobenzyl)-2,3-dihydro-1H-pyrido[2,3-b][1,4]oxazine

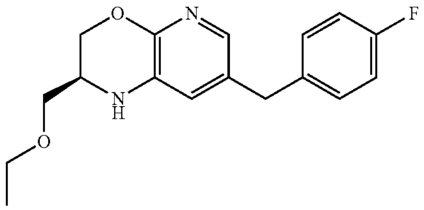 [SMILES: CCOC[C@H]1COc2ncc(Cc3ccc(F)cc3)cc2N1]

The title compound of step 1 (140 mg, 66% yield) was prepared in a manner similar to that described in Example 34 step 7 from (R)-(7-(4-fluorobenzyl)-2,3-dihydro-1H-pyrido[2,3-b][1,4]oxazin-2-yl)methyl methanesulfonate and sodium ethoxide. LC-MS $(M+H)^+$=303.3.

Step 2: (S)-2-chloro-1-(2-(ethoxymethyl)-7-(4-fluorobenzyl)-2,3-dihydro-1H-pyrido[2,3-b][1,4]oxazin-1-yl)ethan-1-one

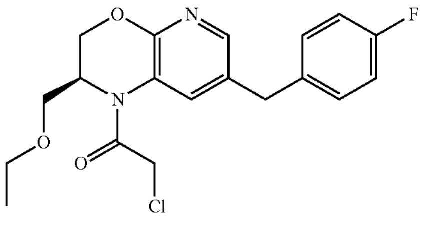 [SMILES: CCOC[C@H]1COc2ncc(Cc3ccc(F)cc3)cc2N1C(=O)CCl]

The title compound of step 2 (95 mg, 54% yield) was prepared in a manner similar to that described in Example 1 step 9 from (S)-2-(ethoxymethyl)-7-(4-fluorobenzyl)-2,3-dihydro-1H-pyrido[2,3-b][1,4]oxazine and 2-chloroacetyl chloride. LC-MS $(M+H)^+$=379.1.

Step 3: tert-butyl (2R,5S)-5-(((3R,5R)-3,5-dimethylmorpholino)methyl)-4-(2-((S)-2-(ethoxymethyl)-7-(4-fluorobenzyl)-2,3-dihydro-1H-pyrido[2,3-b][1,4]oxazin-1-yl)-2-oxoethyl)-2-methylpiperazine-1-carboxylate

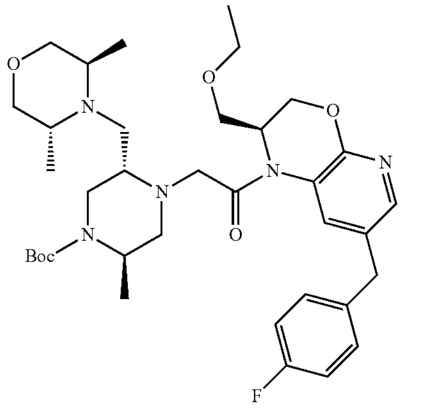 [SMILES: CCOC[C@H]1COc2ncc(Cc3ccc(F)cc3)cc2N1C(=O)CN1C[C@@H](C)N(C(=O)OC(C)(C)C)C[C@@H]1CN1[C@H](C)COC[C@H]1C]

The title compound of step 3 (155 mg, 77% yield) was prepared in a manner similar to that described in Example 1 step 18 from (S)-2-chloro-1-(2-(ethoxymethyl)-7-(4-fluorobenzyl)-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=670.4.

Step 4: 2-42R,5R)-24(3R,5R)-3,5-dimethylmorpholino)methyl)-5-methylpiperazin-1-yl)-1-((S)-2-(ethoxymethyl)-7-(4-fluorobenzyl)-2,3-dihydro-1H-pyrido[2,3-b][1,4]oxazin-1-yl)ethan-1-one (Compound 36)

Compound 36 (21 mg, 15% yield) was prepared in a manner similar to that in Example 29 step 7 from tert-butyl (2R,5S)-5-(((3R,5R)-3,5-dimethylmorpholino)methyl)-4-(2-((S)-2-(ethoxymethyl)-7-(4-fluorobenzyl)-2,3-dihydro-1H-pyrido[2,3-b][1,4]oxazin-1-yl) oxoethyl)-2-methylpiperazine-1-carboxylate. $^1$H NMR (300 MHz, Chloroform-d) δ 8.50 (s, 1H), 7.83 (s, 1H), 7.21-7.11 (m, 2H), 6.98 (t, J=8.5 Hz, 2H), 5.09 (t, J=7.4 Hz, 1H), 4.62 (d, J=11.3 Hz, 1H), 4.52 (d, J=13.7 Hz, 1H), 4.24 (d, J=11.4, 2.8 Hz, 1H), 3.89 (s, 2H), 3.63 (d, J=10.9, 3.0 Hz, 2H), 3.56-3.46 (m, 1H), 3.51-3.37 (m, 3H), 3.42-3.26 (m, 2H), 3.21 (d, J=10.5 Hz, 1H), 3.12 (d, J=13.7 Hz, 1H), 2.98-2.87 (m, 1H), 2.86-2.77 (m, 3H), 2.72 (d, J=11.5, 2.9 Hz, 1H), 2.58-2.41 (m, 2H), 2.18-2.00 (m, 2H), 1.14 (t, J=7.0 Hz, 3H), 1.02 (d, J=6.2 Hz, 3H), 0.96 (d, J=6.4 Hz, 6H). LC-MS $(M+H)^+$=570.5.

Example 37: 1-(((S)-2-(ethoxymethyl)-7-(4-fluorobenzyl)-2,3-dihydro-1H-pyrido[2,3-b][1,4]oxazin-1-yl)-2-42R,5R)-5-methyl-2-(((R)-3-methylmorpholino)methyl)piperazin-1-yl)ethan-1-one (Compound 37)

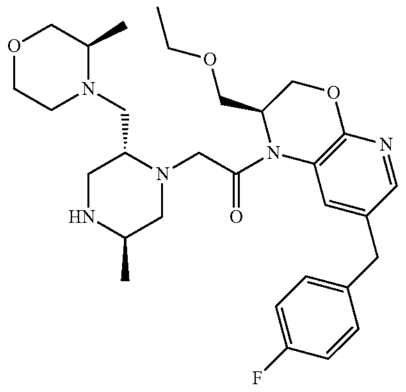 [SMILES: CCOC[C@H]1COc2ncc(Cc3ccc(F)cc3)cc2N1C(=O)CN1C[C@@H](C)NC[C@@H]1CN1CCOC[C@H]1C]

Step 1: tert-butyl (2R,5S)-4-(2-((S)-2-(ethoxymethyl)-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

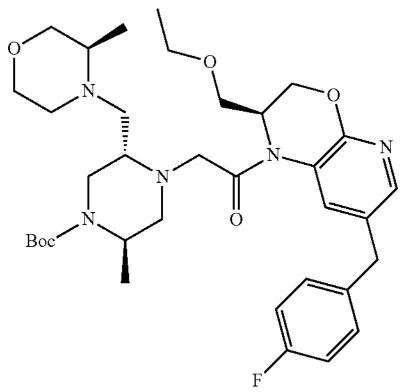 [SMILES: CCOC[C@H]1COc2ncc(Cc3ccc(F)cc3)cc2N1C(=O)CN1C[C@@H](C)N(C(=O)OC(C)(C)C)C[C@@H]1CN1CCOC[C@H]1C]

The title compound of step 1 (150 mg, 85% yield) was prepared in a manner similar to that described in Example 1 step 18 from (S)-2-chloro-1-(2-(ethoxymethyl)-7-(4-fluorobenzyl)-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=656.4.

Step 2: 1-((S)-2-(ethoxymethyl)-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 37)

Compound 37 (40 mg, 47% yield) was prepared in a manner similar to that described in Example 29 step 7 from tert-butyl (2R,5S)-4-(2-((S)-2-(ethoxymethyl)-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate. $^1H$ NMR (300 MHz, DMSO-d6) δ 8.27 (s, 1H), 7.83 (s, 1H), 7.29-7.17 (m, 2H), 7.17-7.02 (m, 2H), 4.79 (s, 1H), 4.48 (dd, J=11.5, 1.3 Hz, 1H), 4.27-4.10 (m, 2H), 3.86 (s, 2H), 3.60-3.47 (m, 2H), 3.44-3.17 (m, 7H), 3.07-2.92 (m, 2H), 2.86-2.56 (m, 5H), 2.44-2.25 (m, 2H), 2.22-2.16 (m, 1H), 2.15-2.03 (m, 1H), 1.87-1.77 (m, 1H), 1.02 (t, J=7.0 Hz, 3H), 0.93 (d, J=6.2 Hz, 3H), 0.81 (s, 3H). LC-MS $(M+H)^+$=556.3.

Example 38: 1-((S)-7-(4-fluorobenzyl)-2-(isopropoxymethyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 38)

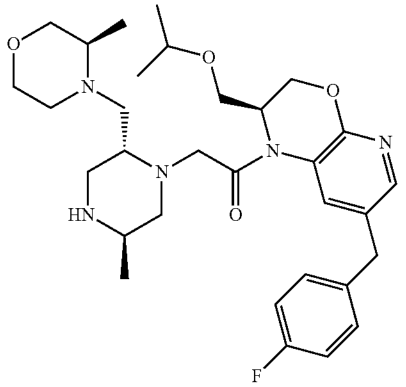 [SMILES: CC(C)OC[C@H]1COc2ncc(Cc3ccc(F)cc3)cc2N1C(=O)CN1C[C@@H](C)NC[C@@H]1CN1CCOC[C@H]1C]

Step 1: (S)-7-(4-fluorobenzyl)-2-(isopropoxymethyl)-2,3-dihydro-1H-pyrido[2,3-b][1,4]oxazine

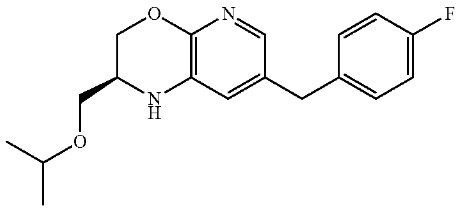 [SMILES: CC(C)OC[C@H]1COc2ncc(Cc3ccc(F)cc3)cc2N1]

The title compound of step 1 (240 mg, 87% yield) was prepared in a manner similar to that described in Example 34 step 7 from (R)-(7-(4-fluorobenzyl)-2,3-dihydro-1H-pyrido[2,3-b][1,4]oxazin-2-yl)methyl methanesulfonate and sodium isopropoxide. LC-MS $(M+H)^+$=317.1.

Step 2: (S)-2-chloro-1-(7-(4-fluorobenzyl)-2-(isopropoxymethyl)-2,3-dihydro-1H-pyrido[2,3-b][1,4]oxazin-1-yl)ethan-1-one

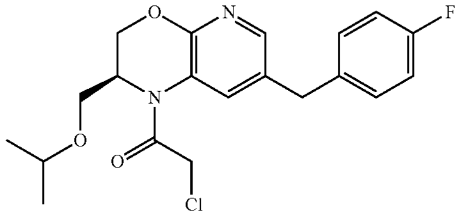 [SMILES: CC(C)OC[C@H]1COc2ncc(Cc3ccc(F)cc3)cc2N1C(=O)CCl]

The title compound of step 2 (225 mg, 90% yield) was prepared in a manner similar to that described in Example 1 step 9 from (S)-7-(4-fluorobenzyl)-2-(isopropoxymethyl)-2,3-dihydro-1H-pyrido[2,3-b][1,4]oxazine and 2-chloroacetyl chloride. LC-MS $(M+H)^+$=393.0.

Step 3: tert-butyl (2R,5S)-4-(2-((S)-7-(4-fluorobenzyl)-2-(isopropoxymethyl)-2,3-dihydro-1H-pyrido[2,3-b][1,4]oxazin-1-yl)-2-oxoethyl)-2-methyl-5-(((R)-3-methyl morpholino)methyl)piperazine-1-carboxylate

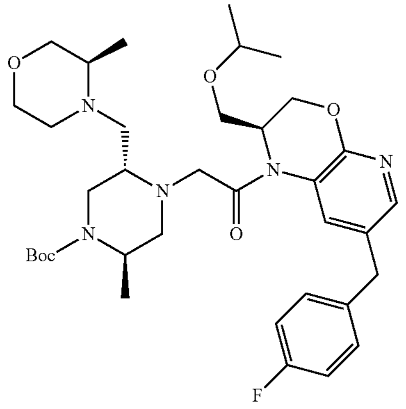 [SMILES: CC(C)OC[C@H]1COc2ncc(Cc3ccc(F)cc3)cc2N1C(=O)CN1C[C@@H](C)N(C(=O)OC(C)(C)C)C[C@@H]1CN1CCOC[C@H]1C]

The title compound of step 3 (150 mg, 86% yield) was prepared in a manner similar to that described in Example 1 step 18 from (S)-2-chloro-1-(7-(4-fluorobenzyl)-2-(isopropoxymethyl)-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=670.4.

Step 4: 1-((S)-7-(4-fluorobenzyl)-2-(isopropoxymethyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 38)

Compound 38 (63 mg, 73% yield) was prepared in a manner similar to that described in Example 29 step 7 from tert-butyl (2R,5S)-4-(2-((S)-7-(4-fluorobenzyl)-2-(isopropoxymethyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate. $^1H$ NMR (300 MHz, Chloroform-d) δ 8.50 (s, 1H), 7.83 (s, 1H), 7.20-7.09 (m, 2H), 7.04-6.91 (m, 2H), 4.99-4.93 (m, 1H), 4.66-4.52 (m, 2H), 4.23 (d, J=11.3, 2.9 Hz, 1H), 3.88 (s, 2H), 3.74-3.34 (m, 6H), 3.26-3.01 (m, 2H), 3.00-2.88 (m, 1H), 2.87-2.67 (m, 3H), 2.62-2.50 (m, 2H), 2.33 (s, 1H), 2.25-2.03 (m, 2H), 2.01 (s, 1H), 1.95-1.85 (m, 1H), 1.09 (d, J=6.1 Hz, 3H), 1.06-0.99 (m, 6H), 0.96 (d, J=6.3 Hz, 3H). LC-MS $(M+H)^+$=570.3.

Example 39: 2-((2R,5R)-2-(((3R,5R)-3,5-dimethylmorpholino)methyl)-5-methylpiperazin-1-yl)-1-((S)-7-(4-fluorobenzyl)-2-(isopropoxymethyl)-2,3-dihydro-1H-pyrido[2,3-b][1,4]oxazin-1-yl)ethan-1-one (Compound 39)

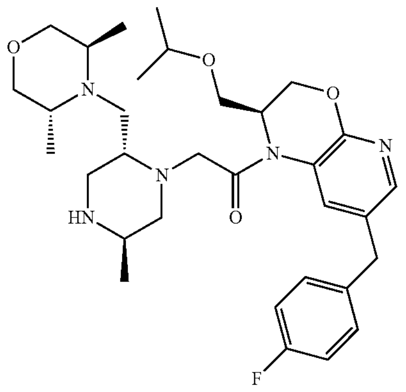 [SMILES: CC(C)OC[C@H]1COc2ncc(Cc3ccc(F)cc3)cc2N1C(=O)CN1C[C@@H](C)NC[C@@H]1CN1[C@H](C)COC[C@H]1C]

Step 1: tert-butyl (2R,5S)-5-(((3R,5R)-3,5-dimethylmorpholino)methyl)-4-(2-((S)-7-(4-fluorobenzyl)-2-(isopropoxymethyl)-2,3-dihydro-1H-pyrido[2,3-b][1,4]oxazin-1-yl)-2-oxoethyl)-2-methylpiperazine-1-carboxylate

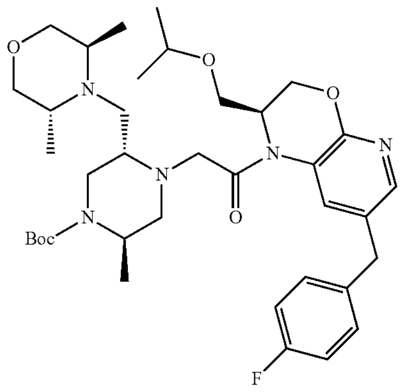 [SMILES: CC(C)OC[C@H]1COc2ncc(Cc3ccc(F)cc3)cc2N1C(=O)CN1C[C@@H](C)N(C(=O)OC(C)(C)C)C[C@@H]1CN1[C@H](C)COC[C@H]1C]

The title compound of step 1 (150 mg, 86% yield) was prepared in a manner similar to that described in Example 1 step 18 from (S)-2-chloro-1-(7-(4-fluorobenzyl)-2-(isopropoxymethyl)-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=684.4.

Step 2: 242R,5R)-2-(((3R,5R)-3,5-dimethylmorpholino)methyl)-5-methylpiperazin-1-yl)-1-((S)-7-(4-fluorobenzyl)-2-(isopropoxymethyl)-2,3-dihydro-1H-pyrido[2,3-b][1,4]oxazin-1-yl)ethan-1-one (Compound 39)

Compound 39 (60 mg, 72% yield) was prepared in a manner similar to that in Example 29 step 7 from tert-butyl (2R,5S)-5-(((3R,5R)-3,5-dimethylmorpholino)methyl)-4-(24S)-7-(4-fluorobenzyl)-2-(isopropoxymethyl)-2,3-dihydro-1H-pyrido[2,3-b][1,4]oxazin-1-yl)-2-oxoethyl)-2-methylpiperazine-1-carboxylate. $^1$H NMR (300 MHz, Chloroform-d) δ 8.51 (s, 1H), 7.83 (s, 1H), 7.20-7.09 (m, 2H), 7.03-6.91 (m, 2H), 5.05-4.96 (m, 1H), 4.65-4.47 (m, 2H), 4.27-4.19 (m, 1H), 3.88 (s, 2H), 3.68-3.57 (m, 2H), 3.55-3.36 (m, 3H), 3.36-3.26 (m, 2H), 3.22 (d, J=9.8 Hz, 1H), 3.10 (d, J=13.7 Hz, 1H), 2.98-2.87 (m, 1H), 2.85-2.66 (m, 3H), 2.57-2.44 (m, 2H), 2.16-2.02 (m, 2H), 1.10 (d, J=6.1 Hz, 3H), 1.05-0.99 (m, 6H), 0.96 (d, J=6.4 Hz, 6H). LC-MS $(M+H)^+$=584.3.

Example 40: 2-((2R,5R)-2-(((3R,5R)-3,5-dimethylmorpholino)methyl)-5-methylpiperazin-1-yl)-1-((S)-7-(4-fluorobenzyl)-2-(phenoxymethyl)-2,3-dihydro-1H-pyrido[2,3-b][1,4]oxazin-1-yl)ethan-1-one (Compound 40)

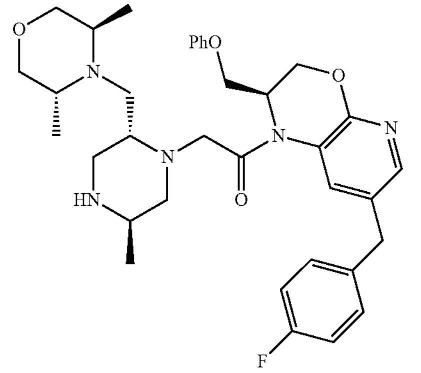 [SMILES: C[C@@H]1CN(CC(=O)N2c3cc(Cc4ccc(F)cc4)cnc3OC[C@@H]2COc2ccccc2)[C@@H](CN2[C@H](C)COC[C@H]2C)CN1]

Step 1: (S)-7-(4-fluorobenzyl)-2-(phenoxymethyl)-2,3-dihydro-1H-pyrido[2,3-b][1,4]oxazine

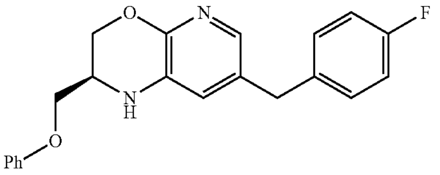 [SMILES: Fc1ccc(Cc2cnc3c(c2)N[C@@H](COc2ccccc2)CO3)cc1]

The title compound of step 1 (240 mg, 80% yield) was prepared in a manner similar to that described in Example 34 step 7 from (R)-(7-(4-fluorobenzyl)-2,3-dihydro-1H-pyrido[2,3-b][1,4]oxazin-2-yl)methyl methanesulfonate and sodium phenolate. LC-MS $(M+H)^+$=351.0.

Step 2: (S)-2-chloro-1-(7-(4-fluorobenzyl)-2-(phenoxymethyl)-2,3-dihydro-1H-pyrido[2,3-b][1,4]oxazin-1-yl)ethan-1-one

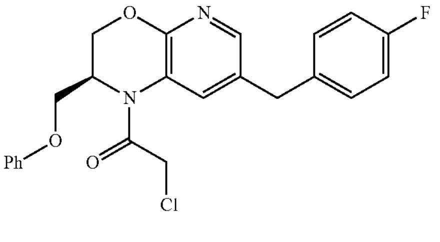 [SMILES: O=C(CCl)N1c2cc(Cc3ccc(F)cc3)cnc2OC[C@@H]1COc1ccccc1]

The title compound of step 2 (160 mg, 80% yield) was prepared in a manner similar to that described in Example 1 step 9 from (S)-7-(4-fluorobenzyl)-2-(phenoxymethyl)-2,3-dihydro-1H-pyrido[2,3-b][1,4]oxazine and 2-chloroacetyl chloride. LC-MS $(M+H)^+$=427.2.

Step 3: tert-butyl (2R,5S)-5-(((3R,5R)-3,5-dimethylmorpholino)methyl)-4-(2-((S)-7-(4-fluorobenzyl)-2-(phenoxymethyl)-2,3-dihydro-1H-pyrido[2,3-b][1,4]oxazin-1-yl)-2-oxoethyl)-2-methylpiperazine-1-carboxylate

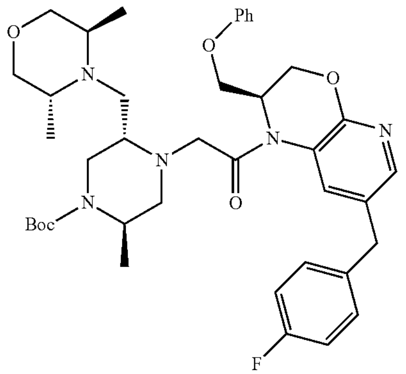 [SMILES: C[C@@H]1CN(CC(=O)N2c3cc(Cc4ccc(F)cc4)cnc3OC[C@@H]2COc2ccccc2)[C@@H](CN2[C@H](C)COC[C@H]2C)CN1C(=O)OC(C)(C)C]

The title compound of step 3 (100 mg, 46% yield) was prepared in a manner similar to that described in Example 1 step 18 from (S)-2-chloro-1-(7-(4-fluorobenzyl)-2-(phenoxymethyl)-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=718.5.

Step 4: 2-((2R,5R)-2-(((3R,5R)-3,5-dimethylmorpholino)methyl)-5-methylpiperazin-1-yl)-1-((S)-7-(4-fluorobenzyl)-2-(phenoxymethyl)-2,3-dihydro-1H-pyrido[2,3-b][1,4]oxazin-1-yl)ethan-1-one (Compound 40)

Compound 40 (48 mg, 56% yield) was prepared in a manner similar to that in Example 29 step 7 from tert-butyl (2R,5S)-5-(((3R,5R)-3,5-dimethylmorpholino)methyl)-4-(2-((S)-7-(4-fluorobenzyl)-2-(phenoxymethyl)-2,3-dihydro-1H-pyrido[2,3-b][1,4]oxazin-1-yl)-2-oxoethyl)-2-methylpiperazine-1-carboxylate. $^1$H NMR (300 MHz, Chloroform-d) δ 8.47 (s, 1H), 7.84 (s, 1H), 7.30-7.19 (m, 2H), 7.19-7.09 (m, 2H), 7.03-6.91 (m, 3H), 6.85-6.76 (m, 2H), 5.41 (s, 1H), 4.78-4.61 (m, 2H), 4.38-4.30 (m, 1H), 4.13-3.95 (m, 2H), 3.88 (s, 2H), 3.65-3.55 (m, 2H), 3.34-3.23 (m, 2H), 3.23-3.10 (m, 2H), 2.97-2.85 (m, 1H), 2.76 (s, 4H), 2.57-2.43 (m, 2H), 2.17-2.01 (m, 2H), 1.01 (d, J=6.2 Hz, 3H), 0.89 (d, J=6.4 Hz, 6H). LC-MS $(M+H)^+$=618.5.

Example 41: 1-(((S)-7-(4-fluorobenzyl)-2-(phenoxymethyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 41)

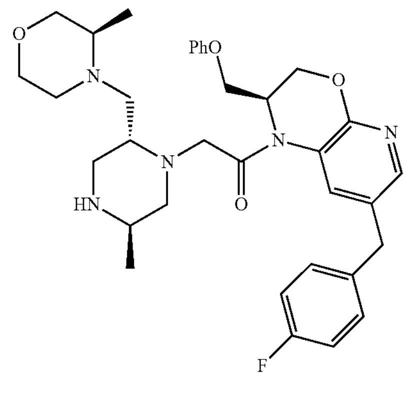 [SMILES: C[C@@H]1CN(CC(=O)N2c3cc(Cc4ccc(F)cc4)cnc3OC[C@@H]2COc2ccccc2)[C@@H](CN2CCOC[C@H]2C)CN1]

Step 1: tert-butyl (2R,5S)-4-(2-((S)-7-(4-fluorobenzyl)-2-(phenoxymethyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

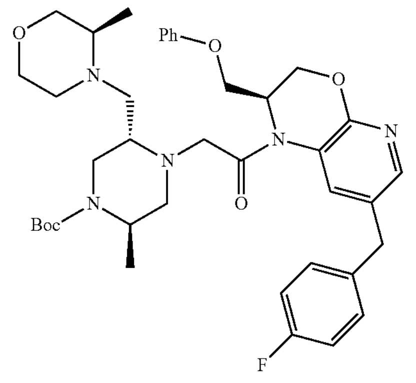 [SMILES: C[C@@H]1COCCN1C[C@H]1CN(C(=O)OC(C)(C)C)[C@H](C)CN1CC(=O)N1c2cc(Cc3ccc(F)cc3)cnc2OC[C@@H]1COc1ccccc1]

The title compound of step 1 (97 mg, 46% yield) was prepared in a manner similar to that described in Example 1 step 18 from (S)-2-chloro-1-(7-(4-fluorobenzyl)-2-(phenoxymethyl)-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=704.5.

Step 2: 1-4S)-7-(4-fluorobenzyl)-2-(phenoxymethyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 41)

Compound 41 (45 mg, 49% yield) was prepared in a manner similar to that described in Example 29 step 7 from tert-butyl (2R,5S)-4-(2-((S)-7-(4-fluorobenzyl)-2-(phenoxymethyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate. $^1$H NMR (300 MHz, Chloroform-d) δ 8.47 (s, 1H), 7.84 (s, 1H), 7.30-7.19 (m, 2H), 7.19-7.09 (m, 2H), 7.03-6.91 (m, 3H), 6.87-6.75 (m, 2H), 5.41 (t, J=7.5 Hz, 1H), 4.74 (dd, J=11.5, 1.5 Hz, 2H), 4.38-4.30 (m, 1H), 4.11-3.92 (m, 2H), 3.88 (s, 2H), 3.73-3.63 (m, 1H), 3.63-3.48 (m, 2H), 3.21-3.09 (m, 2H), 3.06-2.86 (m, 2H), 2.82-2.68 (m, 3H), 2.56 (t, J=10.9 Hz, 1H), 2.48 (s, 1H), 2.29 (s, 1H), 2.20-1.98 (m, 3H), 1.96-1.84 (m, 1H), 1.01 (d, J=6.3 Hz, 3H), 0.86 (d, J=6.3 Hz, 3H). LC-MS $(M+H)^+$=604.4.

Example 42: 1-(((S)-2-cyclohexyl-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 42)

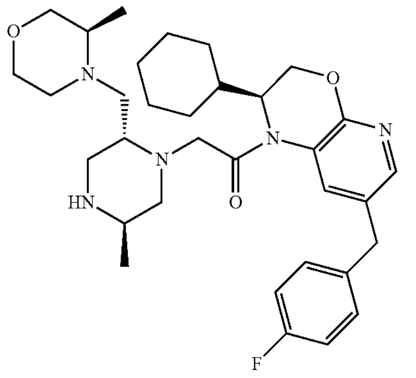 [SMILES: C[C@@H]1CN(CC(=O)N2c3cc(Cc4ccc(F)cc4)cnc3OC[C@@H]2C2CCCCC2)[C@@H](CN2CCOC[C@H]2C)CN1]

Step 1: 3-bromo-2-fluoro-5-(4-fluorobenzyl)pyridine

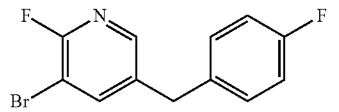 [SMILES: Fc1ccc(Cc2cnc(F)c(Br)c2)cc1]

To a solution of 3,5-dibromo-2-fluoropyridine (9.5 g, 37.2 mmol), XantPhos (650 mg, 1.1 mmol,) and $Pd_2(dba)_3$ (70 mg, 0.07 mmol) in THF (75 mL) was added chloro[(4-fluorophenyl)methyl]zinc (74.6 mL, 37.3 mmol, 0.5 M solution in THF) dropwise over 5 min at room temperature. The resulting mixture was stirred for 6 h at 40° C. under nitrogen atmosphere. When the reaction was done, the resulting mixture was concentrated under reduced pressure and the residue was purified by flash chromatography (PE: EtOAc=20:1) to yield the title compound (2.8 g, 31% yield). LC-MS $(M+H)^+$=284.0.

Step 2: tert-butyl (S)-(2-((3-bromo-5-(4-fluorobenzyl)pyridin-2-yl)oxy)-1-cyclohexylethyl)carbamate

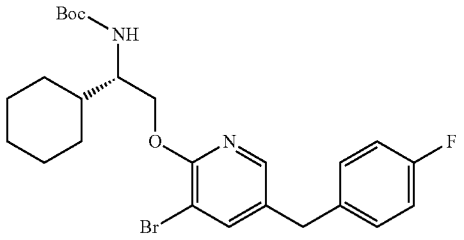 [SMILES: CC(C)(C)OC(=O)N[C@H](COc1ncc(Cc2ccc(F)cc2)cc1Br)C1CCCCC1]

The title compound of step 2 (270 mg, 63% yield) was prepared in a manner similar to that described in Example 29 step 1 from 3-bromo-2-fluoro-5-(4-fluorobenzyl)pyridine and tert-butyl (S)-(1-cyclohexyl-2-hydroxyethyl)carbamate. LC-MS $(M+H)^+$=507.1.

Step 3: tert-butyl (S)-2-cyclohexyl-7-(4-fluorobenzyl)-2,3-dihydro-1H-pyrido[2,3-b][1,4]oxazine-1-carboxylate

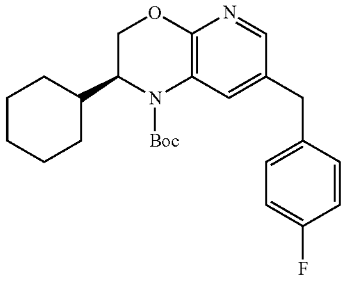 [SMILES: CC(C)(C)OC(=O)N1c2cc(Cc3ccc(F)cc3)cnc2OC[C@@H]1C1CCCCC1]

The title compound of step 3 (195 mg, 86% yield) was prepared in a manner similar to that described in Example 34 step 2 from tert-butyl (S)-(2-((3-bromo-5-(4-fluorobenzyl) pyridin yl)oxy)-1-cyclohexylethyl)carbamate. LC-MS $(M+H)^+$=427.3.

Step 4: (S)-2-cyclohexyl-7-(4-fluorobenzyl)-2,3-dihydro-1H-pyrido[2,3-b][1,4]oxazine

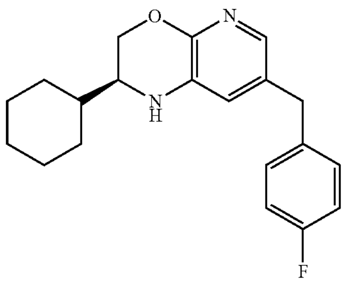 [SMILES: Fc1ccc(Cc2cnc3c(c2)N[C@@H](C2CCCCC2)CO3)cc1]

The title compound of step 4 (130 mg, 89% yield) was prepared in a manner similar to that described in Example 29 step 4 from tert-butyl (S)-2-cyclohexyl-7-(4-fluorobenzyl)-2,3-dihydro-1H-pyrido[2,3-b][1,4]oxazine-1-carboxylate. LC-MS $(M+H)^+$=327.1.

Step 5: (S)-2-chloro-1-(2-cyclohexyl-7-(4-fluorobenzyl)-2,3-dihydro-1H-pyrido[2,3-b][1,4]oxazin-1-yl)ethan-1-one

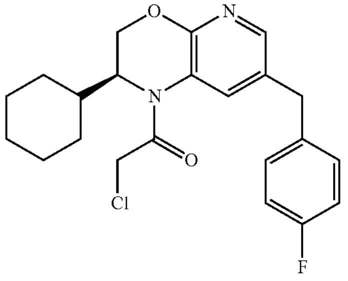 [SMILES: O=C(CCl)N1c2cc(Cc3ccc(F)cc3)cnc2OC[C@@H]1C1CCCCC1]

The title compound of step 5 (105 mg, 88% yield) was prepared in a manner similar to that described in Example 1 step 9 from (S)-2-cyclohexyl-7-(4-fluorobenzyl)-2,3-dihydro-1H-pyrido[2,3-b][1,4]oxazine and 2-chloroacetyl chloride. LC-MS $(M+H)^+$=403.2.

Step 6: tert-butyl (2R,5S)-4-(2-((S)-2-cyclohexyl-7-(4-fluorobenzyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

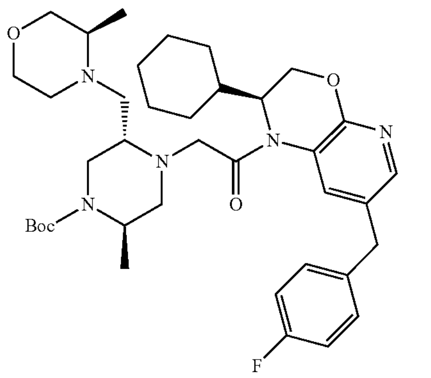 [SMILES: C[C@@H]1COCCN1C[C@H]1CN(C(=O)OC(C)(C)C)[C@H](C)CN1CC(=O)N1c2cc(Cc3ccc(F)cc3)cnc2OC[C@@H]1C1CCCCC1]

The title compound of step 6 (40 mg, 30% yield) was prepared in a manner similar to that described in Example 1 step 18 from (S)-2-chloro-1-(2-cyclohexyl-7-(4-fluorobenzyl)-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=680.5.

Step 7: 1-((S)-2-cyclohexyl-7-(4-fluorobenzyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 42)

Compound 42 (12 mg, 24% yield) was prepared in a manner similar to that described in Example 29 step 7 from tert-butyl (2R,5S)-4-(2-((S)-2-cyclohexyl-7-(4-fluorobenzyl)-2,3-dihydro-1H-pyrido[2,3-b][1,4]oxazin-1-yl)-2-oxoethyl)-2-methyl-5-(((R)-3-methylmorpholino)methylpiperazine-1-carboxylate. $^1H$ NMR (300 MHz, Chloroform-d) δ 8.26 (s, 1H), 7.83 (s, 1H), 7.18-7.08 (m, 2H), 7.04-6.92 (m, 2H), 4.67 (d, J=11.3 Hz, 1H), 4.53-4.30 (m, 2H), 4.17 (dd, J=11.3, 2.7 Hz, 1H), 3.90 (s, 2H), 3.74-3.45 (m, 3H), 3.19 (s, 1H), 3.04 (d, J=8.4 Hz, 2H), 2.89-2.65 (m, 4H), 2.53 (d, J=7.7 Hz, 2H), 2.34 (s, 3H), 2.15 (s, 2H), 2.02-1.89 (m, 3H), 1.79-1.70 (m, 1H), 1.39 (s, 1H), 1.26-0.63 (m, 12H). LC-MS $(M+H)^+$=580.5.

Example 43: 1-((S)-2-cyclohexyl-7-(4-fluorobenzyl)-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 43)

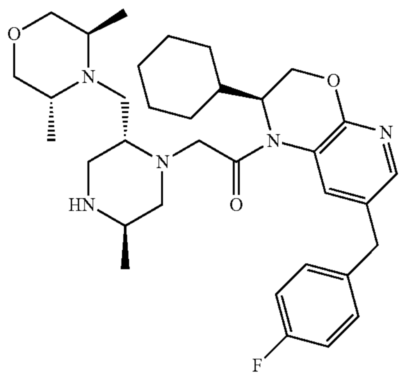 [SMILES: C[C@@H]1CN(CC(=O)N2c3cc(Cc4ccc(F)cc4)cnc3OC[C@@H]2C2CCCCC2)[C@@H](CN2[C@H](C)COC[C@H]2C)CN1]

Step 1: tert-butyl (2R,5S)-4-(2-((S)-2-cyclohexyl-7-(4-fluorobenzyl)-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

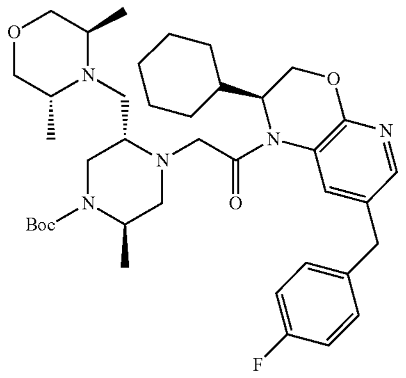 [SMILES: C[C@@H]1CN(CC(=O)N2c3cc(Cc4ccc(F)cc4)cnc3OC[C@@H]2C2CCCCC2)[C@@H](CN2[C@H](C)COC[C@H]2C)CN1C(=O)OC(C)(C)C]

The title compound of step 1 (61 mg, 41% yield) was prepared in a manner similar to that described in Example 1 step 18 from (S)-2-chloro-1-(2-cyclohexyl-7-(4-fluorobenzyl)-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=694.4.

Step 2: 1-((S)-2-cyclohexyl-7-(4-fluorobenzyl)-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 43)

Compound 43 (15 mg, 27% yield) was prepared in a manner similar to that in Example 29 step 7 from tert-butyl (2R,5S)-4-(2-((S)-2-cyclohexyl-7-(4-fluorobenzyl)-2,3-dihydro-1H-pyrido[2,3-b][1,4]oxazin-1-yl)-2-oxoethyl)-5-(((3R,5R)-3,5-dimethylmorpholino)methyl) methylpiperazine-1-carboxylate. $^1H$ NMR (300 MHz, Chloroform-d) δ 8.26 (s, 1H), 7.84 (s, 1H), 7.14 (t, J=7.1 Hz, 2H), 6.98 (t, J=8.6 Hz, 2H), 4.68 (d, J=11.3 Hz, 1H), 4.38 (s, 2H), 4.22-4.12 (m, 1H), 3.90 (s, 2H), 3.62 (d, J=10.9 Hz, 2H), 3.36-3.21 (m, 3H), 3.13-2.96 (m, 1H), 2.80 (s, 4H), 2.69 (d, J=11.3 Hz, 1H), 2.47 (d, J=10.1 Hz, 2H), 2.25-1.92 (m, 4H), 1.77-1.53 (m, 3H), 1.49-1.36 (m, 1H), 1.15-1.11 (m, 2H), 1.06-0.86 (m, 13H). LC-MS $(M+H)^+$=594.3.

Example 44: 2-42R,5R)-24(3R,5R)-3,5-dimethylmorpholino)methyl)-5-methylpiperazin-1-yl)-1-((S)-7-(4-fluorobenzyl)-2-phenyl-2,3-dihydro-1H-pyrido[2,3-b][1,4]oxazin-1-yl)ethan-1-one (Compound 44)

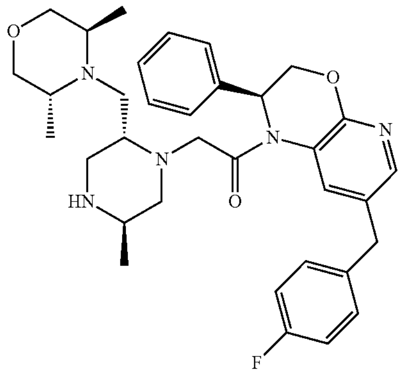 [SMILES: C[C@@H]1CN(CC(=O)N2c3cc(Cc4ccc(F)cc4)cnc3OC[C@@H]2c2ccccc2)[C@@H](CN2[C@H](C)COC[C@H]2C)CN1]

Step 1: tert-butyl (S)-(2-((3-bromo-5-chloropyridin-2-yl)oxy)-1-phenylethyl)carbamate

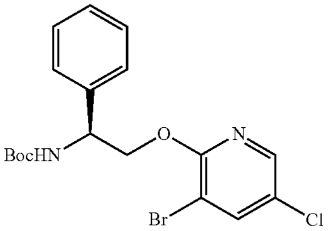 [SMILES: CC(C)(C)OC(=O)N[C@H](COc1ncc(Cl)cc1Br)c1ccccc1]

The title compound of step 1 (2.1 g, 38% yield) was prepared in a manner similar to that described in Example 34 step 1 from tert-butyl (S)-(2-hydroxy-1-phenylethyl)carbamate and 3-bromo-5-chloro-2-fluoropyridine. LC-MS $(M+H)^+$=427.0.

Step 2: tert-butyl (S)-7-chloro-2-phenyl-2,3-dihydro-1H-pyrido[2,3-b][1,4]oxazine-1-carboxylate

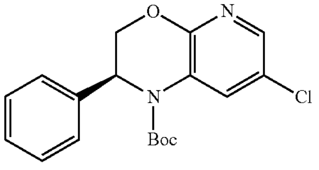 [SMILES: CC(C)(C)OC(=O)N1c2cc(Cl)cnc2OC[C@@H]1c1ccccc1]

The title compound of step 2 (1.5 g, 88% yield) was prepared in a manner similar to that described in Example 34 step 2 from tert-butyl (S)-(2-((3-bromo-5-chloropyridin-2-yl)oxy)-1-phenylethyl)carbamate. LC-MS $(M+H)^+$=347.1.

Step 3: tert-butyl (S)-7-(4-fluorobenzyl)-2-phenyl-2,3-dihydro-1H-pyrido[2,3-b][1,4]oxazine-1-carboxylate

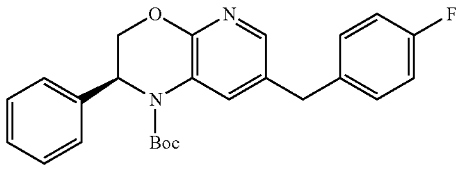 [SMILES: CC(C)(C)OC(=O)N1c2cc(Cc3ccc(F)cc3)cnc2OC[C@@H]1c1ccccc1]

The title compound of step 3 (750 mg, 41% yield) was prepared in a manner similar to that described in Example 34 step 3 from tert-butyl (S)-7-chloro-2-phenyl-2,3-dihydro-1H-pyrido[2,3-b][1,4]oxazine-1-carboxylate. LC-MS $(M+H)^+$=421.1.

Step 4: (S)-7-(4-fluorobenzyl)-2-phenyl-2,3-dihydro-1H-pyrido[2,3-b][1,4]oxazine

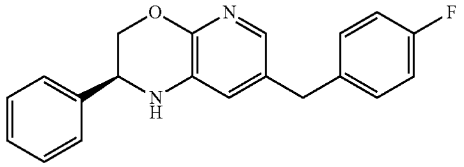 [SMILES: Fc1ccc(Cc2cnc3c(c2)N[C@@H](c2ccccc2)CO3)cc1]

The title compound of step 4 (550 mg, 96% yield) was prepared in a manner similar to that described in Example 29 step 4 from tert-butyl (S)-7-(4-fluorobenzyl)-2-phenyl-2,3-dihydro-1H-pyrido[2,3-b][1,4]oxazine-1-carboxylate. LC-MS $(M+H)^+$=321.1.

Step 5: (S)-2-chloro-1-(7-(4-fluorobenzyl)-2-phenyl-2,3-dihydro-1H-pyrido[2,3-b][1,4]oxazin-1-yl)ethan-1-one

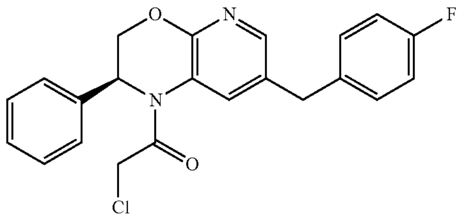 [SMILES: O=C(CCl)N1c2cc(Cc3ccc(F)cc3)cnc2OC[C@@H]1c1ccccc1]

The title compound of step 5 (350 mg, 51% yield) was prepared in a manner similar to that described in Example 1 step 9 from (S)-7-(4-fluorobenzyl)-2-phenyl-2,3-dihydro-1H-pyrido[2,3-b][1,4]oxazine and 2-chloroacetyl chloride. LC-MS $(M+H)^+$=397.1.

Step 6: tert-butyl (2R,5S)-5-(((3R,5R)-3,5-dimethylmorpholino)methyl)-4-(2-((S)-7-(4-fluorobenzyl)-2-phenyl-2,3-dihydro-1H-pyrido[2,3-b][1,4]oxazin-1-yl)-2-oxoethyl)-2-methylpiperazine-1-carboxylate

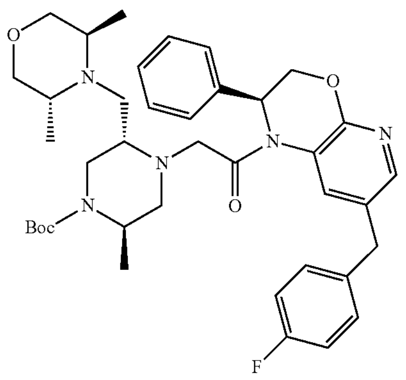 [SMILES: C[C@@H]1CN(CC(=O)N2c3cc(Cc4ccc(F)cc4)cnc3OC[C@@H]2c2ccccc2)[C@@H](CN2[C@H](C)COC[C@H]2C)CN1C(=O)OC(C)(C)C]

The title compound of step 6 (150 mg, 57% yield) was prepared in a manner similar to that described in Example 1 step 18 from (S)-2-chloro-1-(7-(4-fluorobenzyl)-2-phenyl-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=688.4.

Step 7: 2-((2R,5R)-24(3R,5R)-3,5-dimethylmorpholino)methyl)-5-methylpiperazin-1-yl)-1-((S)-7-(4-fluorobenzyl)-2-phenyl-2,3-dihydro-1H-pyrido[2,3-b][1,4]oxazin-1-yl)ethan-1-one (Compound 44)

Compound 44 (51 mg, 66% yield) was prepared in a manner similar to that in Example 29 step 7 from tert-butyl (2R,5S)-5-(((3R,5R)-3,5-dimethylmorpholino)methyl)-4-(24S)-7-(4-fluorobenzyl)-2-phenyl-2,3-dihydro-1H-pyrido[2,3-b][1,4]oxazin-1-yl)-2-oxoethyl) methylpiperazine-1-carboxylate. $^1$H NMR (300 MHz, DMSO-d6) δ 8.62 (s, 1H), 7.82 (d, J=2.1 Hz, 1H), 7.39-7.27 (m, 3H), 7.24-7.11 (m, 4H), 7.08-6.94 (m, 2H), 6.01 (s, 1H), 4.86 (d, J=11.7, 1.9 Hz, 1H), 4.57-4.47 (m, 1H), 4.29 (d, J=14.4 Hz, 1H), 3.92 (s, 2H), 3.55 (dd, J=11.0, 2.9 Hz, 2H), 3.31 (d, J=11.6 Hz, 1H), 3.25-3.14 (m, 3H), 2.96 (d, J=9.0 Hz, 1H), 2.82 (dd, J=11.9, 2.9 Hz, 1H), 2.74-2.65 (m, 1H), 2.69-2.63 (m, 3H), 2.63-2.44 (m, 2H), 2.37 (t, J=11.3 Hz, 1H), 2.07-1.95 (m, 1H), 1.18 (d, J=6.3 Hz, 3H), 0.78 (d, J=6.3 Hz, 6H). LC-MS $(M+H)^+$=588.3.

Example 45: 1-(((S)-7-(4-fluorobenzyl)-2-phenyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 45)

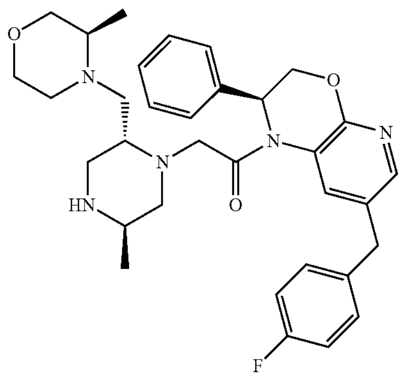 [SMILES: C[C@@H]1CN(CC(=O)N2c3cc(Cc4ccc(F)cc4)cnc3OC[C@@H]2c2ccccc2)[C@@H](CN2CCOC[C@H]2C)CN1]

Step 1: tert-butyl (2R,5S)-4-(2-((S)-7-(4-fluorobenzyl)-2-phenyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate

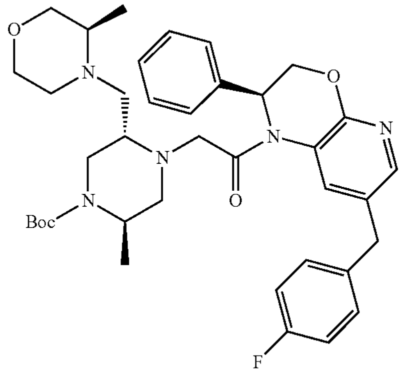 [SMILES: C[C@@H]1COCCN1C[C@H]1CN(C(=O)OC(C)(C)C)[C@H](C)CN1CC(=O)N1c2cc(Cc3ccc(F)cc3)cnc2OC[C@@H]1c1ccccc1]

The title compound of step 1 (150 mg, 58% yield) was prepared in a manner similar to that described in Example 1 step 18 from (S)-2-chloro-1-(7-(4-fluorobenzyl)-2-phenyl-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=674.4.

Step 2: 1-((S)-7-(4-fluorobenzyl)-2-phenyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 45)

Compound 45 (44 mg, 35% yield) as free base was prepared in a manner similar to that in Example 29 step 7 from tert-butyl (2R,5S)-4-(2-((S)-7-(4-fluorobenzyl)-2-phenyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate. $^1$H NMR (300 MHz, Chloroform-d) δ 8.63 (s, 1H), 7.80 (s, 1H), 7.35-7.11 (m, 7H), 7.06-6.95 (m, 2H), 6.23 (s, 1H), 4.94 (d, J=11.5, 1.9 Hz, 1H), 4.54 (d, J=11.6, 3.0 Hz, 2H), 3.92 (s, 2H), 3.60 (d, J=11.5 Hz, 1H), 3.54-3.47 (m, 1H), 3.51-3.42 (m, 1H), 3.18-3.10 (m, 1H), 3.08-2.99 (m, 1H), 2.98 (dd, J=11.4, 2.3 Hz, 1H), 2.89-2.76 (m, 2H), 2.76-2.67 (m, 2H), 2.55 (t, J=10.9 Hz, 1H), 2.50 (s, 1H), 2.22-2.17 (m, 1H), 2.09 (t, J=10.9 Hz, 1H), 2.01-1.91 (m, 1H), 1.83 (dd, J=13.4, 3.1 Hz, 1H), 1.04 (d, J=6.2 Hz, 3H), 0.58 (d, J=6.3 Hz, 3H). LC-MS $(M+H)^+$=574.3.

Example 46: 2-((2R,5R)-2-(((3R,5R)-3,5-dimethylmorpholino)methyl)-5-methylpiperazin-1-yl)-1-((S)-7-(4-fluorobenzyl)-2-isopropyl-2,3-dihydro-1H-pyrido[2,3-b][1,4]oxazin-1-yl)ethan-1-one (Compound 46)

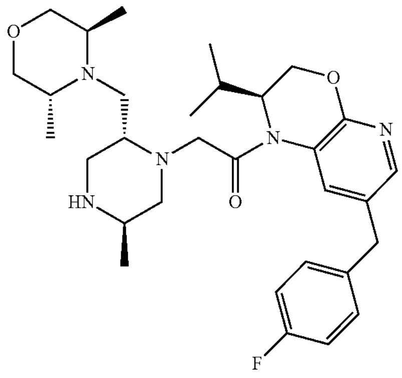 [SMILES: CC(C)[C@H]1COc2ncc(Cc3ccc(F)cc3)cc2N1C(=O)CN1C[C@@H](C)NC[C@@H]1CN1[C@H](C)COC[C@H]1C]

Step 1: tert-butyl (S)-(1-((3-bromo-5-(4-fluorobenzyl)pyridin-2-yl)oxy)-3-methylbutan-2-v1)carbamate

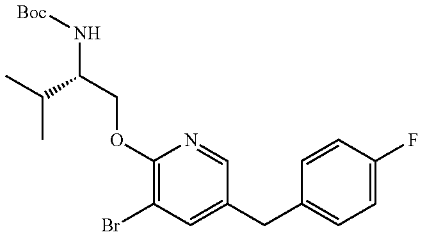 [SMILES: CC(C)[C@@H](COc1ncc(Cc2ccc(F)cc2)cc1Br)NC(=O)OC(C)(C)C]

The title compound of step 1 (2.4 g, 75% yield) was prepared in a manner similar to that described in Example 29 step 1 from 3-bromo-2-fluoro-5-(4-fluorobenzyl)pyridine and tert-butyl (S)-(1-hydroxy-3-methylbutan-2-yl)carbamate. LC-MS $(M+H)^+$=467.1.

Step 2: tert-butyl (S)-7-(4-fluorobenzyl)-2-isopropyl-2,3-dihydro-1H-pyrido[2,3-b][1,4]oxazine-1-carboxylate

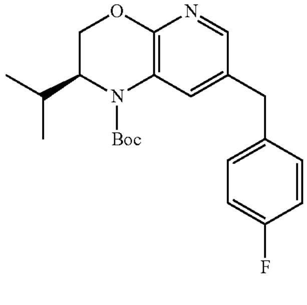 [SMILES: CC(C)[C@H]1COc2ncc(Cc3ccc(F)cc3)cc2N1C(=O)OC(C)(C)C]

The title compound of step 2 (370 mg, 95% yield) was prepared in a manner similar to that described in Example 34 step 2 from tert-butyl (S)-(1-((3-bromo-5-(4-fluorobenzyl) pyridin yl)oxy)-3-methylbutan-2-yl)carbamate. LC-MS $(M+H)^+$=387.2.

Step 3: (S)-7-(4-fluorobenzyl)-2-isopropyl-2,3-dihydro-1H-pyrido[2,3-b][1,4]oxazine

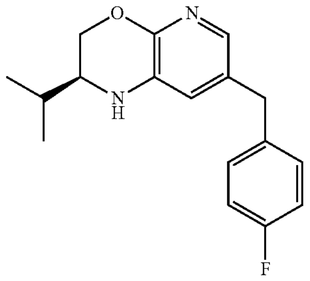 [SMILES: CC(C)[C@H]1COc2ncc(Cc3ccc(F)cc3)cc2N1]

The title compound of step 3 (240 mg, 92% yield) was prepared in a manner similar to that described in Example 29 step 4 from tert-butyl (S)-7-(4-fluorobenzyl)-2-isopropyl-2,3-dihydro-1H-pyrido[2,3-b][1,4]oxazine-1-carboxylate. LC-MS $(M+H)^+$=287.1.

Step 4: (S)-2-chloro-1-(7-(4-fluorobenzyl)-2-isopropyl-2,3-dihydro-1H-pyrido[2,3-b][1,4]oxazin-1-yl) ethan-1-one

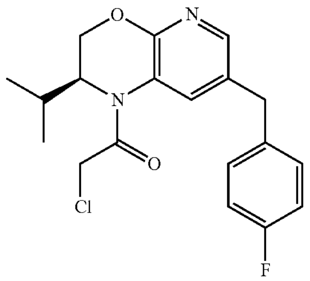 [SMILES: CC(C)[C@H]1COc2ncc(Cc3ccc(F)cc3)cc2N1C(=O)CCl]

The title compound of step 4 (250 mg, 83% yield) was prepared in a manner similar to that described in Example 1 step 9 from (S)-7-(4-fluorobenzyl)-2-isopropyl-2,3-dihydro-1H-pyrido[2,3-b][1,4]oxazine and 2-chloroacetyl chloride. LC-MS $(M+H)^+$=363.1.

Step 5: tert-butyl (2R,5S)-5-(((3R,5R)-3,5-dimethylmorpholino)methyl)-4-(2-((S)-7-(4-fluorobenzyl)-2-isopropyl-2,3-dihydro-1H-pyrido[2,3-b][1,4]oxazin-1-yl)-2-oxoethyl)-2-methylpiperazine-1-carboxylate

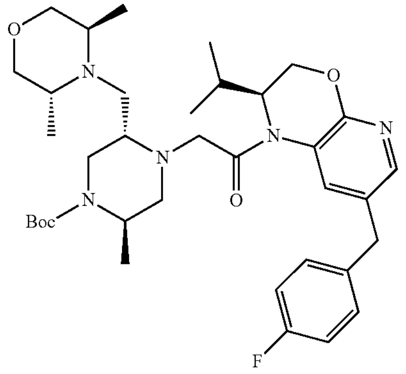

The title compound of step 5 (95 mg, 45% yield) was prepared in a manner similar to that described in Example 1 step 18 from (S)-2-chloro-1-(7-(4-fluorobenzyl)-2-isopropyl-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=654.3.

Step 6: 2-((2R,5R)-2-(((3R,5R)-3,5-dimethylmorpholino)methyl)-5-methylpiperazin-1-yl)-1-((S)-7-(4-fluorobenzyl)-2-isopropyl-2,3-dihydro-1H-pyrido[2,3-b][1,4]oxazin-1-yl)ethan-1-one (Compound 46)

Compound 46 (30 mg, 31% yield) was prepared in a manner similar to that described in Example 29 step 7 from tert-butyl (2R,5S)-5-(((3R,5R)-3,5-dimethylmorpholino) methyl)-4-(2-((S)-7-(4-fluorobenzyl)-2-isopropyl-2,3-dihydro-1H-pyrido[2,3-b][1,4]oxazin-1-yl) oxoethyl)-2-methylpiperazine-1-carboxylate. $^1H$ NMR (300 MHz, Chloroform-d) δ 8. 8.26 (s, 1H), 7.83 (s, 1H), 7.19-7.08 (m, 2H), 7.03-6.92 (m, 2H), 4.66 (d, J=11.2 Hz, 1H), 4.38 (s, 1H), 4.25-4.15 (m, 1H), 3.90 (s, 2H), 3.66-3.57 (m, 2H), 3.33-3.27 (m, 2H), 3.21 (s, 1H), 2.78 (s, 4H), 2.72-2.62 (m, 1H), 2.58-2.24 (m, 2H), 2.15-2.02 (m, 1H), 2.02-1.89 (m, 4H), 1.06 (d, J=6.4 Hz, 3H), 1.03-0.84 (m, 12H). LC-MS $(M+H)^+$=554.4.

Example 47: 1-(((S)-7-(4-fluorobenzyl)-2-isopropyl-2,3-dihydro-1H-pyrido[2,3-b][1,4]oxazin-1-yl)-2-((2R,5R)-5-methyl-2-(((R)-3-methylmorpholino) methyl)piperazin-1-yl)ethan-1-one (Compound 47)

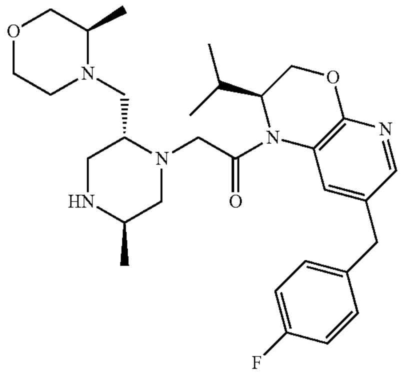 [SMILES: CC(C)[C@H]1COc2ncc(Cc3ccc(F)cc3)cc2N1C(=O)CN1C[C@@H](C)NC[C@@H]1CN1CCOC[C@H]1C]

Step 1: tert-butyl (2R,5S)-4-(2-((S)-7-(4-fluorobenzyl)-2-isopropyl-2,3-dihydro-1H-pyrido[2,3-b][1,4] oxazin-1-yl)-2-oxoethyl)-2-methyl-5-(((R)-3-methylmorpholino)methyl)piperazine-1-carboxylate

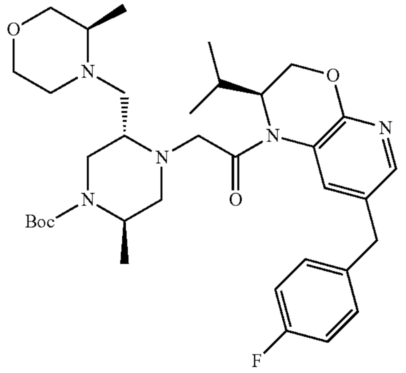 [SMILES: CC(C)[C@H]1COc2ncc(Cc3ccc(F)cc3)cc2N1C(=O)CN1C[C@@H](C)N(C(=O)OC(C)(C)C)C[C@@H]1CN1CCOC[C@H]1C]

The title compound of step 1 (95 mg, 45% yield) was prepared in a manner similar to that described in Example 1 step 18 from (S)-2-chloro-1-(7-(4-fluorobenzyl)-2-isopropyl-2,3-dihydro-1H-pyrido[2,3-b][1,4]oxazin-1-yl)ethan-1-one and tert-butyl (2R,5S)-2-methyl-5-(((R)-3-methylmorpholino)methyl)piperazine-1-carboxylate. LC-MS $(M+H)^+$=640.3.

Step 2: 1-((S)-7-(4-fluorobenzyl)-2-isopropyl-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 47)

Compound 47 (36 mg, 44% yield) was prepared in a manner similar to that described in Example 29 step 7 from tert-butyl (2R,5S)-4-(2-((S)-7-(4-fluorobenzyl)-2-isopropyl-2,3-dihydro-1H-pyrido[2,3-b][1,4]oxazin-1-yl)-2-oxoethyl)-2-methyl-5-(((R)-3-methylmorpholino)methyl)piperazine-1-carboxylate. $^1$H NMR (300 MHz, Chloroform-d) δ 8.26 (s, 1H), 7.87-7.80 (m, 1H), 7.19-7.08 (m, 2H), 7.05-6.92 (m, 2H), 4.65 (dd, J=11.4, 1.4 Hz, 1H), 4.59-4.28 (m, 2H), 4.27-4.16 (m, 1H), 3.90 (s, 2H), 3.75-3.49 (m, 3H), 3.26-2.96 (m, 3H), 2.90-2.63 (m, 4H), 2.60-2.40 (m, 2H), 2.33 (s, 1H), 2.15 (s, 1H), 2.05-1.76 (m, 4H), 1.02 (dd, J=19.5, 6.4 Hz, 6H), 0.90 (s, 6H). LC-MS $(M+H)^+$=540.5.

Example 48: 2-42R,5R)-2-((3,3-dimethylmorpholino)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 48)

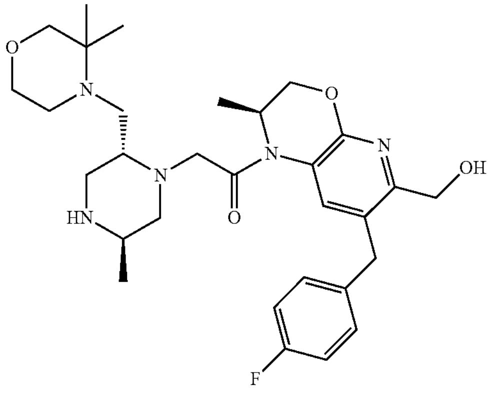 [SMILES: C[C@@H]1CN(CC(=O)N2c3cc(Cc4ccc(F)cc4)c(CO)nc3OC[C@@H]2C)[C@@H](CN2CCOCC2(C)C)CN1]

Step 1: tert-butyl (2R,5S)-4-benzyl-5-((3,3-dimethylmorpholino)methyl)-2-methylpiperazine-1-carboxylate

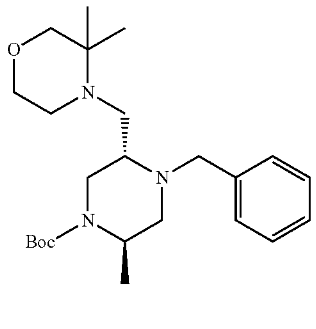 [SMILES: C[C@@H]1CN(Cc2ccccc2)[C@@H](CN2CCOCC2(C)C)CN1C(=O)OC(C)(C)C]

The title compound of step 1 (500 mg, 81% yield) was prepared in a manner similar to that described in Example 1 step 16 from 3,3-dimethylmorpholine and tert-butyl (2R,5R)-4-benzyl-5-(chloromethyl)-2-methylpiperazine-1-carboxylate. LC-MS $(M+H)^+$=418.4.

Step 2: tert-butyl (2R,5S)-5-((3,3-dimethylmorpholino)methyl)-2-methylpiperazine-1-carboxylate

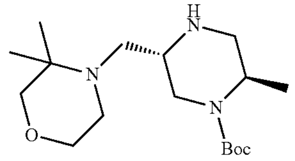

The title compound of step 2 (350 mg, crude) was prepared in a manner similar to that described in Example 1 step 17 from tert-butyl (2R,5S)-4-benzyl-5-((3,3-dimethylmorpholino)methyl)-2-methylpiperazine-1-carboxylate. LC-MS $(M+H)^+$=328.3.

Step 3: tert-butyl (2R,5S)-4-(24S)-6-(acetoxymethyl)-7-(4-fluorobenzyl)-2-methyl-2,3-dihydro-1H-pyrido[2,3-b][1,4]oxazin-1-yl)-2-oxoethyl)-5-((3,3-dimethylmorpholino)methyl)-2-methylpiperazine-1-carboxylate

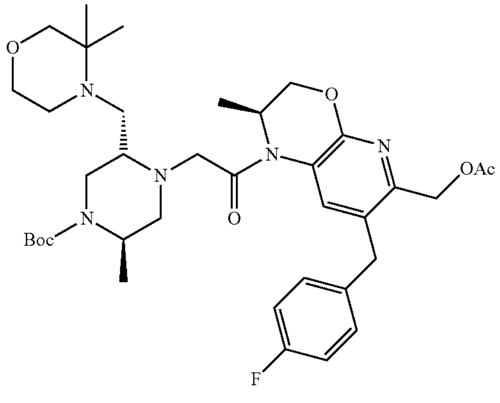

The title compound of step 3 (550 mg, 59% yield for 2 steps) was prepared in a manner similar to that described in Example 1 step 18 from (S)-(1-(2-chloroacetyl)-7-(4-fluorobenzyl)-2-methyl-2,3-dihydro-1H-pyrido[2,3-b][1,4]oxazin-6-yl)methyl acetate and tert-butyl (2R,5S)-5-((3,3-dimethylmorpholino)methyl)-2-methylpiperazine-1-carboxylate. LC-MS $(M+H)^+$=698.4.

Step 4: ((S)-1-(2-((2R,5R)-2-((3,3-dimethylmorpholino)methyl)-5-methylpiperazin-1-yl)acetyl)-7-(4-fluorobenzyl)-2-methyl-2,3-dihydro-1H-pyrido[2,3-b][1,4]oxazin-6-yl)methyl acetate

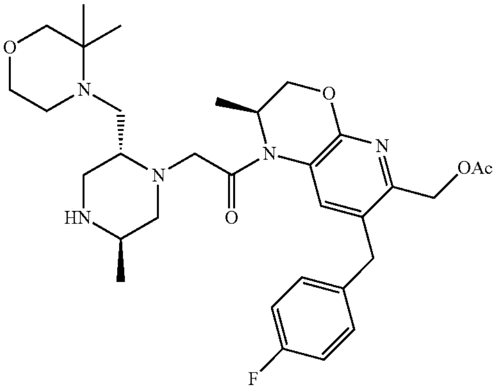 [SMILES: CC(=O)OCc1nc2c(cc1Cc1ccc(F)cc1)N(C(=O)CN1C[C@@H](C)NC[C@@H]1CN1CCOCC1(C)C)[C@@H](C)CO2]

The title compound of step 4 (120 mg, 70% yield) was prepared in a manner similar to that described in Example 1 step 8 from tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-((3,3-dimethylmorpholino)methyl)-2-methylpiperazine-1-carboxylate. LC-MS $(M+H)^+$=598.4.

Step 5: 242R,5R)-2-((3,3-dimethylmorpholino)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 48)

To a solution of ((S)-1-(242R,5R)-2-((3,3-dimethylmorpholino)methyl)-5-methylpiperazin-1-yl)acetyl)-7-(4-fluorobenzyl)-2-methyl-2,3-dihydro-1H-pyrido[2,3-b][1,4]oxazin-6-yl)methyl acetate (120 mg, 0.2 mmol) in THF (5 mL) was added LiOH (10 mg, 0.4 mmol) in $H_2O$ (5 mL). The resulting mixture was stirred for 1 h at room temperature. When the reaction was done, the resulting mixture was concentrated under reduced pressure. The residue was purified by prep-HPLC under the following conditions: column, XBridge Shield RP18 OBD Column, 30×150 mm, 5 um; mobile phase, acetonitrile in water (with 10 mmol/L $NH_4HCO_3$ and 0.1% $NH_3 \cdot H_2O$), 23% to 53% gradient in 8 min; detector, UV 254 nm. The title compound (47 mg, 42% yield) was obtained. $^1H$ NMR (300 MHz, Chloroform-d) δ 8.39 (brs, 1H), 7.14-7.03 (m, 2H), 7.03-6.91 (m, 2H), 4.95 (s, 1H), 4.64-4.47 (m, 2H), 4.45-4.35 (m, 1H), 4.35-4.24 (m, 1H), 4.19-4.08 (m, 1H), 3.82 (s, 2H), 3.68-3.60 (m, 2H), 3.33-3.07 (m, 4H), 2.89-2.76 (m, 1H), 2.76-2.67 (m, 1H), 2.57-2.40 (m, 4H), 2.44-2.36 (m, 1H), 2.23-2.01 (m, 2H), 1.36-1.28 (m, 3H), 1.05-0.98 (m, 3H), 0.98-0.89 (m, 6H). LC-MS $(M+H)^+$=556.3.

Example 49: 2-42R,5R)-24(2S,5R)-2,5-dimethylmorpholino)methyl)-5-methylpiperazin-1-yl)-1-(((S)-7-((4-fluorobenzyl)-6-(hydroxymethyl)-2-methyl-2,3-dihydro-1H-pyrido[2,3-b][1,4]oxazin-1-yl)ethan-1-one (Compound 49)

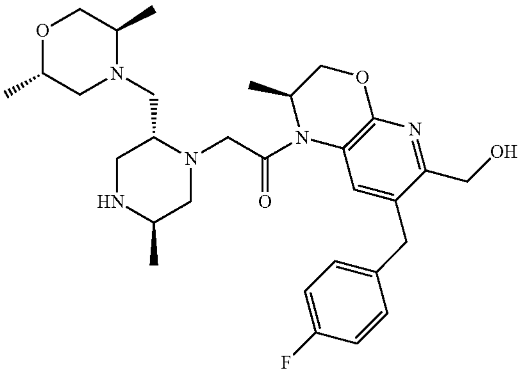 [SMILES: C[C@@H]1CN(CC(=O)N2c3cc(Cc4ccc(F)cc4)c(CO)nc3OC[C@@H]2C)[C@@H](CN2C[C@H](C)OC[C@H]2C)CN1]

Step 1: tert-butyl (2R,5S)-4-benzyl-5-(((2S,5R)-2,5-dimethylmorpholino)methyl)-2-methylpiperazine-1-carboxylate

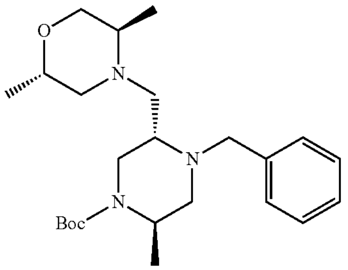 [SMILES: C[C@@H]1CO[C@@H](C)CN1C[C@H]1CN(C(=O)OC(C)(C)C)[C@H](C)CN1Cc1ccccc1]

The title compound of step 1 (460 mg, 51% yield) was prepared in a manner similar to that described in Example 1 step 16 from (2S,5R)-dimethylmorpholine and tert-butyl (2R,5R)-4-benzyl-5-(chloromethyl)-2-methylpiperazine-1-carboxylate. LC-MS $(M+H)^+$=418.3.

Step 2: tert-butyl (2R,5S)-5-(((2S,5R)-2,5-dimethylmorpholino)methyl)-2-methylpiperazine-1-carboxylate

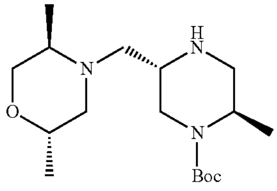 [SMILES: C[C@@H]1CO[C@@H](C)CN1C[C@H]1CN(C(=O)OC(C)(C)C)[C@H](C)CN1]

The title compound of step 2 (280 mg, 78% yield) was prepared in a manner similar to that described in Example 1 step 17 from tert-butyl (2R,5S)-4-benzyl-5-(((2S,5R)-2,5-dimethylmorpholino)methyl)-2-methylpiperazine-1-carboxylate. LC-MS $(M+H)^+$=328.3. Step 3: tert-butyl (2R, 5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((2S,5R)-2,5-dimethylmorpholino)methyl)-2-methylpiperazine-1-carboxylate

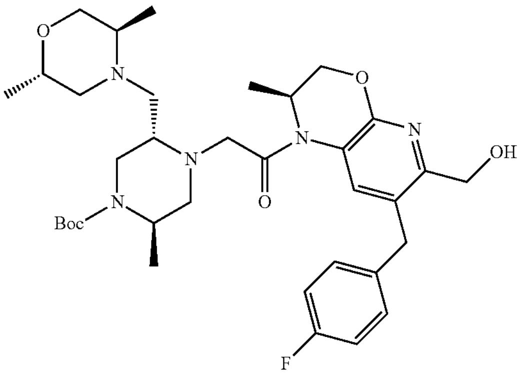 [SMILES: C[C@@H]1CO[C@@H](C)CN1C[C@H]1CN(C(=O)OC(C)(C)C)[C@H](C)CN1CC(=O)N1c2cc(Cc3ccc(F)cc3)c(CO)nc2OC[C@@H]1C]

The title compound of step 3 (150 mg, 62% yield) was prepared in a manner similar to that described in Example 1 step 18 from (S)-(1-(2-chloroacetyl)-7-(4-fluorobenzyl)-2-methyl-2,3-dihydro-1H-pyrido[2,3-b][1,4]oxazin-6-yl) methyl acetate and tert-butyl (2R,5S)-5-(((2 S,5R)-2,5-dimethylmorpholino)methyl)-2-methylpiperazine-1-carboxylate. LC-MS $(M+H)^+$=698.3.

Step 4: tert-butyl (2R,5S)-5-(((2S,5R)-2,5-dimethylmorpholino)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate

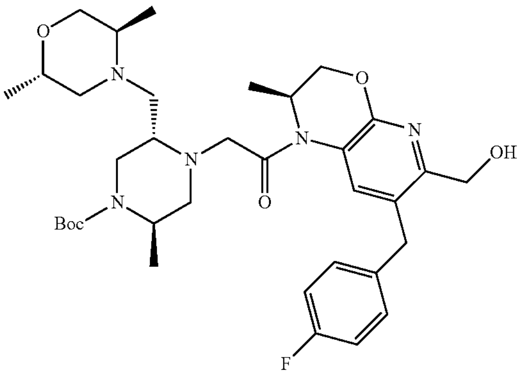 [SMILES: C[C@@H]1CO[C@@H](C)CN1C[C@H]1CN(C(=O)OC(C)(C)C)[C@H](C)CN1CC(=O)N1c2cc(Cc3ccc(F)cc3)c(CO)nc2OC[C@@H]1C]

The title compound of step 4 (130 mg, 92% yield) was prepared in a manner similar to that described in Example 8 step 4 from tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((2S,5R)-2,5-dimethylmorpholino)methyl)-2-methylpiperazine-1-carboxylate. LC-MS $(M+H)^+$=656.3.

Step 5: 2-42R,5R)-24(2S,5R)-2,5-dimethylmorpholino)methyl)-5-methylpiperazin-1-yl)-1-4S)-7-(4-fluorobenzyl)-6-(hydroxymethyl)-2-methyl-2,3-dihydro-1H-pyrido[2,3-b][1,4]oxazin-1-yl)ethan-1-one (Compound 49)

Compound 49 as formic acid salt was prepared in a manner similar to that described in Example 1 step 19 from tert-butyl (2R,5S)-5-(((2S,5R)-2,5-dimethylmorpholino) methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate. The salt was neutralized with aq. $NaHCO_3$ and extracted with EtOAc. The combined organic layers were dried, filtered and concentrated. The residue was further lyophilized to afford compound 49 (15 mg, 14% yield) as free base. $^1H$ NMR (400 MHz, DMSO-d6) δ 8.22 (s, 1H), 7.21-7.17 (m, 2H), 7.14-7.09 (m, 2H), 5.07 (t, J=5.6 Hz, 1H), 4.79 (s, 1H), 4.43-4.32 (m, 3H), 4.22-4.20 (m, 1H), 4.06-4.00 (m, 2H), 3.95-3.91 (m, 1H), 3.57-3.55 (m, 1H), 3.50-3.47 (m, 1H), 3.39-3.37 (m, 1H), 3.01-2.96 (m, 1H), 2.89-2.86 (m, 2H), 2.77-2.74 (m, 1H), 2.71 (brs, 2H), 2.60 (brs, 1H), 2.55 (brs, 1H), 2.32-2.27 (m, 1H), 2.21-2.18 (m, 1H), 1.96 (brs, 1H), 1.64-1.55 (m, 2H), 1.16 (d, J=6.4 Hz, 3H), 0.97 (d, J=6.2 Hz, 3H), 0.86 (d, J=6.2 Hz, 6H). LC-MS $(M+H)^+$=556.5.

Example 50: 2-42R,5R)-2-((7-oxa-4-azaspiro[2.5]octan-4-yl)methyl)-5-methylpiperazin-1-yl)-1-(S)-7-(4-fluorobenzyl)-6-(hydroxymethyl)-2-methyl-2,3-dihydro-1H-pyrido[2,3-b][1,4]oxazin-1-yl)ethan-1-one (Compound 50)

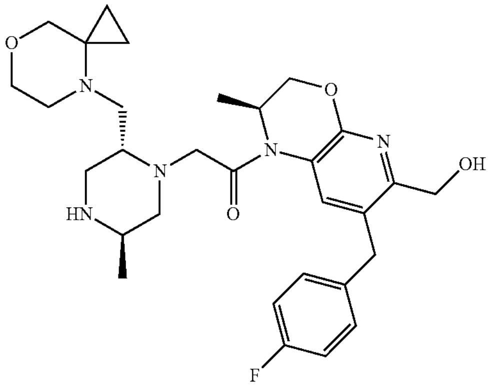 [SMILES: C[C@@H]1CN(CC(=O)N2c3cc(Cc4ccc(F)cc4)c(CO)nc3OC[C@@H]2C)[C@@H](CN2CCOCC23CC3)CN1]

Step 1: tert-butyl (2R,5S)-5-((7-oxa-4-azaspiro[2.5]octan-4-yl)methyl)-4-benzyl-2-methylpiperazine-1-carboxylate

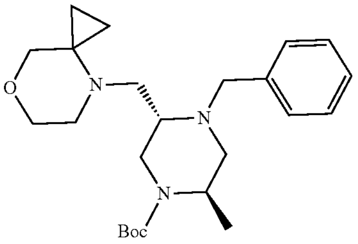 [SMILES: C[C@@H]1CN(Cc2ccccc2)[C@@H](CN2CCOCC23CC3)CN1C(=O)OC(C)(C)C]

The title compound of step 1 (500 mg, 81% yield) was prepared in a manner similar to that described in Example 1 step 16 from tert-butyl (2R,5R)-4-benzyl-5-(chloromethyl)-2-methylpiperazine-1-carboxylate and 7-oxa-4-azaspiro[2.5]octane. LC-MS $(M+H)^+$=416.3.

Step 2: tert-butyl (2R,5S)-5-((7-oxa-4-azaspiro[2.5]octan-4-yl)methyl)-2-methylpiperazine-1-carboxylate

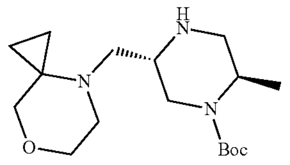 [SMILES: C[C@@H]1CN[C@@H](CN2CCOCC23CC3)CN1C(=O)OC(C)(C)C]

The title compound of step 2 (320 mg, crude) was prepared in a manner similar to that described in Example 1 step 17 from tert-butyl (2R,55)-5-((7-oxa-4-azaspiro[2.5]octan-4-yl)methyl)-4-benzyl-2-methylpiperazine-1-carboxylate. LC-MS $(M+H)^+$=326.2.

Step 3: tert-butyl (2R,5S)-5-((7-oxa-4-azaspiro[2.5]octan-4-yl)methyl)-4-(24S)-6-(acetoxymethyl)-7-(4-fluorobenzyl)-2-methyl-2,3-dihydro-1H-pyrido[2,3-b][1,4]oxazin-1-yl)-2-oxoethyl)-2-methylpiperazine-1-carboxylate

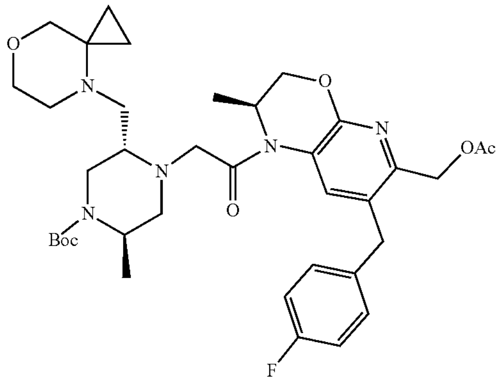 [SMILES: CC(=O)OCc1nc2c(cc1Cc1ccc(F)cc1)N(C(=O)CN1C[C@@H](C)N(C(=O)OC(C)(C)C)C[C@@H]1CN1CCOCC13CC3)[C@@H](C)CO2]

The title compound of step 3 (448 mg, 53% yield for 2 steps) was prepared in a manner similar to that described in Example 1 step 18 from (S)-(1-(2-chloroacetyl)-7-(4-fluorobenzyl) methyl-2,3-dihydro-1H-pyrido[2,3-b][1,4]oxazin-6-yl)methyl acetate and tert-butyl (2R,5S)-5-((7-oxa-4-azaspiro[2.5]octan-4-yl)methyl)-2-methylpiperazine-1-carboxylate. LC-MS $(M+H)^+$=696.4.

Step 4: tert-butyl (2R,5S)-5-((7-oxa-4-azaspiro[2.5]octan-4-yl)methyl)-4-(24S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate

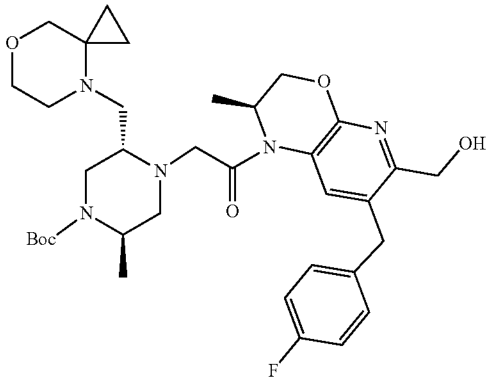 [SMILES: C[C@@H]1CN(CC(=O)N2c3cc(Cc4ccc(F)cc4)c(CO)nc3OC[C@@H]2C)[C@@H](CN2CCOCC23CC3)CN1C(=O)OC(C)(C)C]

The title compound of step 4 (240 mg, crude) was prepared in a manner similar to that described in Example 8 step 4 from tert-butyl (2R,55)-5-((7-oxa-4-azaspiro[2.5]octan-4-yl)methyl)-4-(24S)-6-(acetoxymethyl)-7-(4-fluorobenzyl)-2-methyl-2,3-dihydro-1H-pyrido[2,3-b][1,4]oxazin-1-yl)-2-oxoethyl)-2-methylpiperazine-1-carboxylate. LC-MS $(M+H)^+$=654.4.

Step 5: 2-((2R,5R)-2-((7-oxa-4-azaspiro[2.5]octan-4-yl)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 50)

Compound 50 (25 mg, 11% yield) was prepared in a manner similar to that described in Example 29 step 7 from tert-butyl (2R,5S)-5-((7-oxa-4-azaspiro[2.5]octan-4-yl) methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate. $^1$H NMR (300 MHz, Chloroform-d) δ 8.40 (brs, 1H), 7.15-7.04 (m, 2H), 7.04-6.92 (m, 2H), 4.91 (s, 1H), 4.66-4.47 (m, 2H), 4.44-4.24 (m, 2H), 4.18-4.07 (m, 1H), 3.83 (s, 2H), 3.69-3.63 (m, 2H), 3.43-3.30 (m, 2H), 3.20-2.98 (m, 2H), 2.89-2.76 (m, 4H), 2.76-2.66 (m, 1H), 2.55-2.34 (m, 3H), 2.18-2.05 (m, 1H), 1.36-1.27 (m, 3H), 1.05-0.97 (m, 3H), 0.64-0.41 (m, 4H). LC-MS $(M+H)^+$=554.4.

Example 51: 2-42R,5R)-2-(((R)-3-ethylmorpholino) methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 51)

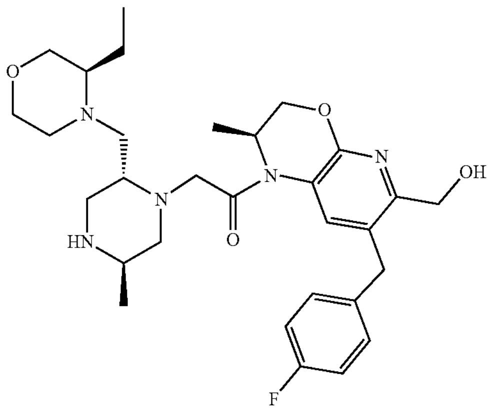 [SMILES: CC[C@@H]1COCCN1C[C@H]1CN[C@H](C)CN1CC(=O)N1c2cc(Cc3ccc(F)cc3)c(CO)nc2OC[C@@H]1C]

Step 1: tert-butyl (2R,5S)-4-benzyl-5-(((R)-3-ethylmorpholino)methyl)-2-methylpiperazine-1-carboxylate

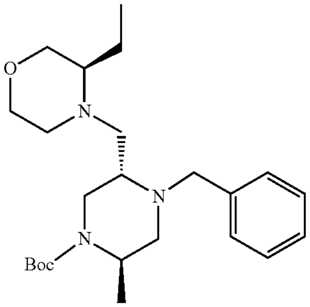 [SMILES: CC[C@@H]1COCCN1C[C@H]1CN(C(=O)OC(C)(C)C)[C@H](C)CN1Cc1ccccc1]

The title compound of step 1 (550 mg, 89% yield) was prepared in a manner similar to that described in Example 1 step 16 from (R)-3-ethylmorpholine and tert-butyl (2R,5R)-4-benzyl-5-(chloromethyl)-2-methylpiperazine-1-carboxylate. LC-MS $(M+H)^+$=418.3.

Step 2: tert-butyl (2R,5S)-5-(((R)-3-ethylmorpholino)methyl)-2-methylpiperazine-1-carboxylate

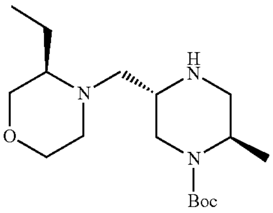 [SMILES: CC[C@@H]1COCCN1C[C@H]1CN(C(=O)OC(C)(C)C)[C@H](C)CN1]

The title compound of step 2 (350 mg, crude) was prepared in a manner similar to that described in Example 1 step 17 from tert-butyl (2R,5S)-4-benzyl-5-(((R)-3-ethylmorpholino)methyl)-2-methylpiperazine-1-carboxylate. LC-MS $(M+H)^+$=328.3.

Step 3: tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((R)-3-ethylmorpholino)methyl)-2-methylpiperazine-1-carboxylate

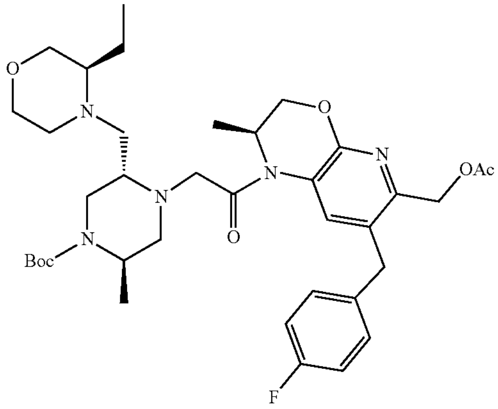 [SMILES: CC[C@@H]1COCCN1C[C@H]1CN(C(=O)OC(C)(C)C)[C@H](C)CN1CC(=O)N1c2cc(Cc3ccc(F)cc3)c(COC(C)=O)nc2OC[C@@H]1C]

The title compound of step 3 (534 mg, 58% yield for 2 steps) was prepared in a manner similar to that described in Example 1 step 18 from tert-butyl (2R,55)-5-(((R)-3-ethylmorpholino)methyl)-2-methylpiperazine-1-carboxylate and (S)-(1-(2-chloroacetyl)-7-(4-fluorobenzyl)-2-methyl-2,3-dihydro-1H-pyrido[2,3-b][1,4]oxazin-6-yl)methyl acetate. LC-MS $(M+H)^+$=698.4.

Step 4: tert-butyl (2R,5S)-5-(((R)-3-ethylmorpholino)methyl)-4-(2-((S)-7-(4-fluorobenzyl) (hydroxymethyl)-2-methyl-2,3-dihydro-1H-pyrido[2,3-b][1,4]oxazin-1-yl)-2-oxoethyl)-2-methylpiperazine-1-carboxylate

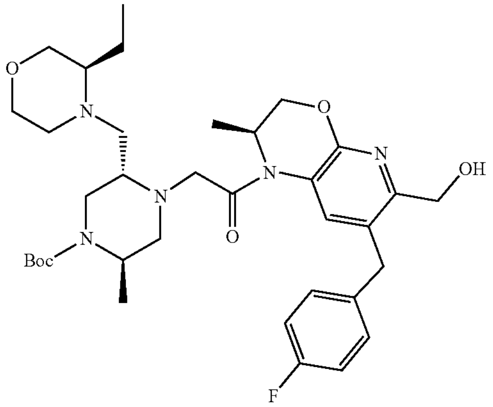 [SMILES: CC[C@@H]1COCCN1C[C@H]1CN(C(=O)OC(C)(C)C)[C@H](C)CN1CC(=O)N1c2cc(Cc3ccc(F)cc3)c(CO)nc2OC[C@@H]1C]

The title compound of step 4 (250 mg, 88% yield) was prepared in a manner similar to that described in Example 8 step 4 from tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((R)-3-ethylmorpholino)methyl)-2-methylpiperazine-1-carboxylate. LC-MS $(M+H)^+$=656.4.

Step 5: 2-((2R,5R)-2-(((R)-3-ethylmorpholino)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 51)

Compound 51 (52 mg, 24% yield) was prepared in a manner similar to that in Example 29 step 7 from tert-butyl (2R,5S)-5-(((R)-3-ethylmorpholino)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate. $^1H$ NMR (400 MHz, Chloroform-d) δ 8.49 (brs, 1H), 7.16-7.08 (m, 2H), 7.05-6.95 (m, 2H), 5.01 (s, 1H), 4.67-4.52 (m, 2H), 4.52-4.36 (m, 2H), 4.36-4.26 (m, 1H), 3.85 (s, 2H), 3.79-3.65 (m, 2H), 3.59-3.50 (m, 1H), 3.37-3.21 (m, 2H), 3.05-2.99 (m, 1H), 2.98-2.89 (m, 1H), 2.88-2.83 (m, 2H), 2.79-2.70 (m, 1H), 2.68-2.54 (m, 2H), 2.21-2.12 (m, 3H), 2.02-1.94 (m, 1H), 1.70-1.54 (m, 1H), 1.36-1.29 (m, 4H), 1.07-1.00 (m, 3H), 0.92-0.84 (m, 3H). LC-MS $(M+H)^+$=556.4.

Example 52: 1-((S)-7-(4-fluorobenzyl)-6-(hydroxymethyl)-2-methyl-2,3-dihydro-1H-pyrido[2,3-b][1,4]oxazin-1-yl)-2-((2R,5R)-2-(4R)-3-(methoxymethyl)morpholino)methyl)-5-methylpiperazin-1-yl)ethan-1-one (Compound 52)

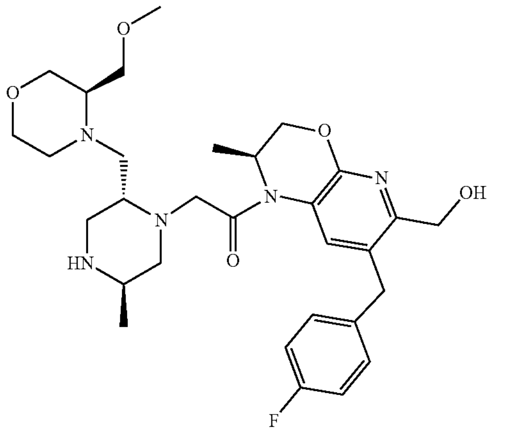 [SMILES: COC[C@@H]1COCCN1C[C@H]1CN[C@H](C)CN1CC(=O)N1c2cc(Cc3ccc(F)cc3)c(CO)nc2OC[C@@H]1C]

Step 1: tert-butyl (2R,5S)-4-benzyl-5-(((R)-3-(methoxymethyl)morpholino)methyl) methylpiperazine-1-carboxylate

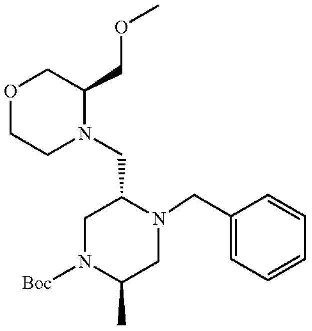 [SMILES: COC[C@@H]1COCCN1C[C@H]1CN(C(=O)OC(C)(C)C)[C@H](C)CN1Cc1ccccc1]

The title compound of step 1 (500 mg, 78% yield) was prepared in a manner similar to that described in Example 1 step 16 from (R)-3-(methoxymethyl)morpholine and tert-butyl (2R,5R)-4-benzyl-5-(chloromethyl)-2-methylpiperazine-1-carboxylate. LC-MS $(M+H)^+$=434.3.

Step 2: tert-butyl (2R,5S)-5-(4R)-3-(methoxymethyl)morpholino)methyl)-2-methylpiperazine-1-carboxylate

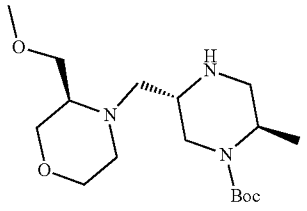

The title compound of step 2 (300 mg, crude) was prepared in a manner similar to that described in Example 1 step 17 from tert-butyl (2R,55)-4-benzyl-5-(((R)-3-(methoxymethyl)morpholino)methyl)-2-methylpiperazine-1-carboxylate. LC-MS $(M+H)^+$=344.2.

Step 3: tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((R)-3-(methoxymethyl)morpholino)methyl)-2-methylpiperazine-1-carboxylate

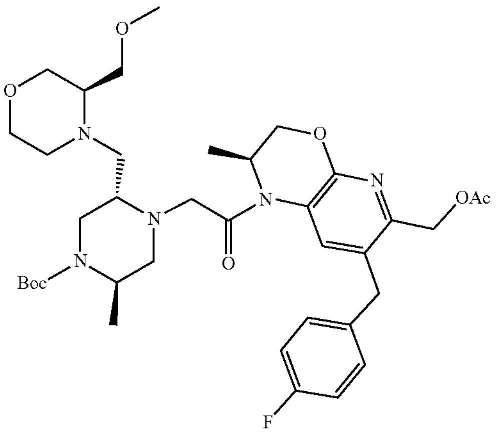 [SMILES: COC[C@@H]1COCCN1C[C@H]1CN(C(=O)OC(C)(C)C)[C@H](C)CN1CC(=O)N1c2cc(Cc3ccc(F)cc3)c(COC(C)=O)nc2OC[C@@H]1C]

The title compound of step 3 (425 mg, 51% yield for 2 steps) was prepared in a manner similar to that described in Example 1 step 18 from tert-butyl (2R,5S)-5-(((R)-3-(methoxymethyl)morpholino)methyl)-2-methylpiperazine-1-carboxylate and (S)-(1-(2-chloroacetyl)-7-(4-fluorobenzyl)-2-methyl-2,3-dihydro-1H-pyrido[2,3-b][1,4]oxazin-6-yl)methyl acetate. LC-MS $(M+H)^+$=714.4.

Step 4: tert-butyl (2R,5S)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-5-(((R)-3-(methoxymethyl)morpholino)methyl)-2-methylpiperazine-1-carboxylate

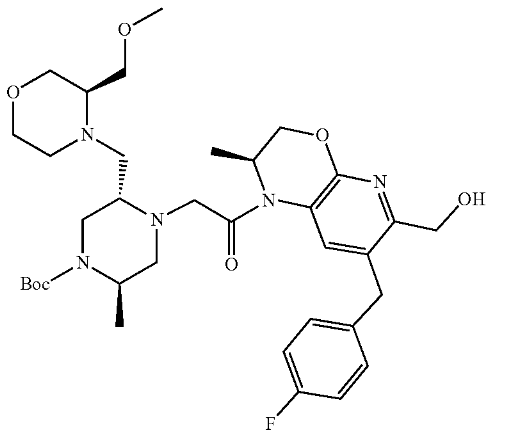 [SMILES: COC[C@@H]1COCCN1C[C@H]1CN(C(=O)OC(C)(C)C)[C@H](C)CN1CC(=O)N1c2cc(Cc3ccc(F)cc3)c(CO)nc2OC[C@@H]1C]

The title compound of step 4 (170 mg, 60% yield) was prepared in a manner similar to that described in Example 8 step 4 from tert-butyl (2R,55)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((R)-3-(methoxymethyl)morpholino)methyl)-2-methylpiperazine-1-carboxylate. LC-MS $(M+H)^+$=672.4.

Step 5: 1-((S)-7-(4-fluorobenzyl)-6-(hydroxymethyl)-2-methyl-2,3-dihydro-1H-pyrido[2,3-b][1,4]oxazin-1-yl)-2-((2R,5R)-2-(((R)-3-(methoxymethyl)morpholino)methyl)-5-methylpiperazin-1-yl)ethan-1-one (Compound 52)

Compound 52 (45 mg, 26% yield) as free base was prepared in a manner similar to that in Example 29 step 7 from tert-butyl (2R,5S)-4-(24S)-7-(4-fluorobenzyl)-6-(hydroxymethyl)-2-methyl-2,3-dihydro-1H-pyrido[2,3-b][1,4]oxazin-1-yl)-2-oxoethyl)-5-(((R)-3-(methoxymethyl)morpholino)methyl)-2-methylpiperazine-1-carboxylate. $^1$NMR (300 MHz, Chloroform-d) δ 8.41 (brs, 1H), 7.17-7.06 (m, 2H), 7.06-6.94 (m, 2H), 4.97 (s, 1H), 4.68-4.46 (m, 3H), 4.45-4.27 (m, 2H), 3.86 (s, 2H), 3.77-3.60 (m, 2H), 3.58-3.42 (m, 3H), 3.39-3.33 (m, 2H), 3.26 (s, 3H), 3.14-2.83 (m, 4H), 2.83-2.51 (m, 3H), 2.41 (s, 1H), 2.32-1.91 (m, 3H), 1.36-1.28 (m, 3H), 1.07-0.99 (m, 3H). LC-MS $(M+H)^+$=572.4.

Example 53: 2-42R,5R)-2-((R)-3-(ethoxymethyl)morpholino)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 53)

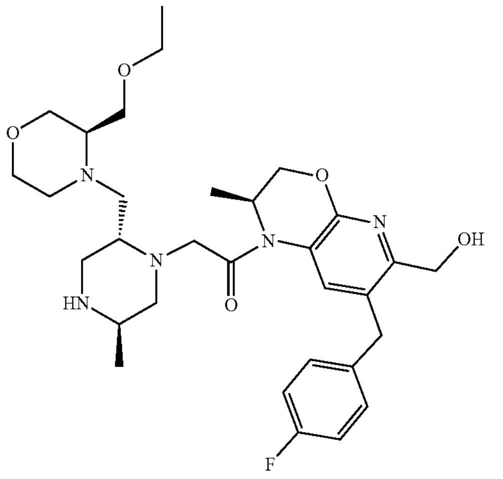 [SMILES: CCOC[C@@H]1COCCN1C[C@H]1CN[C@H](C)CN1CC(=O)N1c2cc(Cc3ccc(F)cc3)c(CO)nc2OC[C@@H]1C]

Step 1: (R)-4-benzyl-3-(ethoxymethyl)morpholine

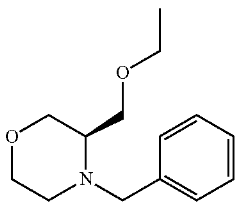 [SMILES: CCOC[C@@H]1COCCN1Cc1ccccc1]

To a solution of [(3R)-4-benzylmorpholin-3-yl]methanol (395 mg, 1.9 mmol) and iodoethane (740 mg, 4.7 mmol) in DMF (6 mL) was added NaH (96 mg, 4 mmol) in portions at 0° C. under nitrogen atmosphere. The resulting mixture was stirred for 4 h at 80° C. under nitrogen atmosphere. When the reaction was done, the reaction was quenched with $H_2O$ at room temperature. The resulting mixture was extracted with EtOAc (2×25 mL). The organic phases were combined, washed with brine and dried over $Na_2SO_4$. The solvent was removed under reduced pressure and the residue was purified by flash chromatography (PE:EtOAc=4:1) to yield the title compound (342 mg, 76% yield). LC-MS $(M+H)^+$=236.0.

Step 2: (R)-3-(ethoxymethyl)morpholine

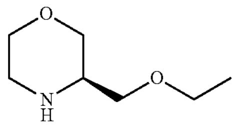

To a solution of (R)-4-benzyl-3-(ethoxymethyl)morpholine (342 mg, 1.4 mmol) in MeOH (12 mL) was added Pd/C (300 mg, 0.3 mmol, 10%) under nitrogen atmosphere. The mixture was hydrogenated at room temperature for 16 h under hydrogen atmosphere using a hydrogen balloon. When the reaction was done, the mixture was filtered through a Celite pad and concentrated under reduced pressure to yield the title compound (210 mg, crude). LC-MS $(M+H)^+$=146.3.

Step 3: tert-butyl (2R,5S)-4-benzyl-5-(((R)-3-(ethoxymethyl)morpholino)methyl)-2-methylpiperazine-1-carboxylate

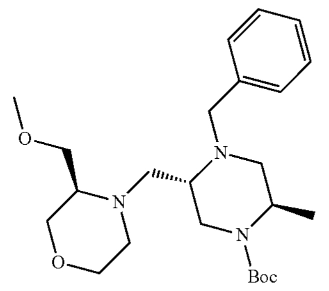

The title compound of step 3 (338 mg, 51% yield for 2 steps) was prepared in a manner similar to that described in Example 1 step 16 from (R)-3-(ethoxymethyl)morpholine and tert-butyl (2R,5R)-4-benzyl-5-(chloromethyl)-2-methylpiperazine-1-carboxylate. LC-MS $(M+H)^+$=448.3.

Step 4: tert-butyl (2R,5S)-5-(((R)-3-(ethoxymethyl)morpholino)methyl)-2-methylpiperazine-1-carboxylate

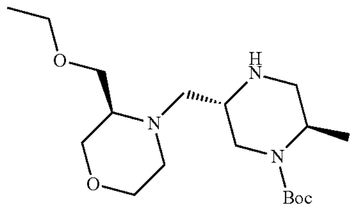 [SMILES: CCOC[C@@H]1COCCN1C[C@H]1CN(C(=O)OC(C)(C)C)[C@H](C)CN1]

The title compound of step 4 (280 mg, crude) was prepared in a manner similar to that described in Example 1 step 17 from tert-butyl (2R,5S)-4-benzyl-5-(((R)-3-(ethoxymethyl)morpholino)methyl)-2-methylpiperazine-1-carboxylate. LC-MS $(M+H)^+$=358.3.

Step 5: tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((R)-3-(ethoxymethyl)morpholino)methyl)-2-methylpiperazine-1-carboxylate

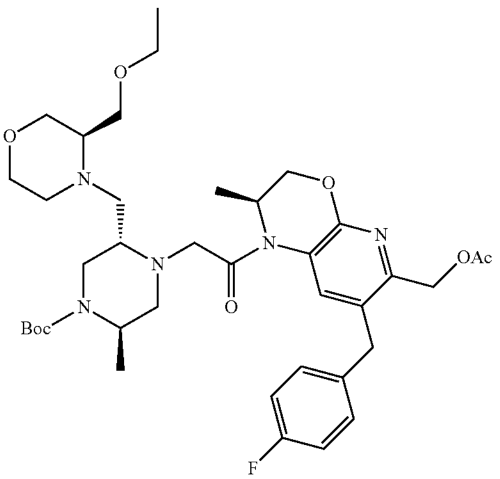 [SMILES: CCOC[C@@H]1COCCN1C[C@H]1CN(C(=O)OC(C)(C)C)[C@H](C)CN1CC(=O)N1c2cc(Cc3ccc(F)cc3)c(COC(C)=O)nc2OC[C@@H]1C]

The title compound of step 5 (307 mg, 55% yield for 2 steps) was prepared in a manner similar to that described in Example 1 step 18 from tert-butyl (2R,5S)-5-(((R)-3-(ethoxymethyl)morpholino)methyl)-2-methylpiperazine-1-carboxylate and (S)-(1-(2-chloroacetyl)-7-(4-fluorobenzyl)-2-methyl-2,3-dihydro-1H-pyrido[2,3-b][1,4]oxazin-6-yl) methyl acetate. LC-MS $(M+H)^+$=728.4.

Step 6: tert-butyl (2R,5S)-5-(4R)-3-(ethoxymethyl) morpholino)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate

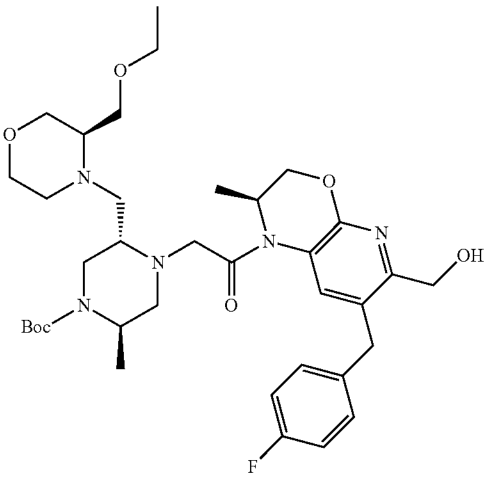 [SMILES: CCOC[C@@H]1COCCN1C[C@H]1CN(C(=O)OC(C)(C)C)[C@H](C)CN1CC(=O)N1c2cc(Cc3ccc(F)cc3)c(CO)nc2OC[C@@H]1C]

The title compound of step 6 (101 mg, 87% yield) was prepared in a manner similar to that described in Example 8 step 4 from tert-butyl (2R,5S)-4-(2-((S)-6-(acetoxymethyl)-7-(4-fluorobenzyl)-2-methyl-2,3-dihydro-1H-pyrido[2,3-b]

[1,4]oxazin-1-yl)-2-oxoethyl)-5-(((R)-3-(ethoxymethyl)morpholino)methyl)-2-methylpiperazine-1-carboxylate. LC-MS $(M+H)^+$=686.5.

Step 7: 2-42R,5R)-2-(((R)-3-(ethoxymethyl)morpholino)methyl)-5-methylpiperazin-1-yl) ((S)-7-(4-fluorobenzyl)-6-(hydroxymethyl)-2-methyl-2,3-dihydro-1H-pyrido[2,3-b][1,4]oxazin-1-yl)ethan-1-one (Compound 53)

Compound 53 (54 mg, 42% yield) was prepared in a manner similar to that in Example 29 step 7 from tert-butyl (2R,5S)-5-(((R)-3-(ethoxymethyl)morpholino)methyl)-4-(24S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 8.19 (brs, 1H), 7.26-7.17 (m, 2H), 7.17-7.07 (m, 2H), 5.12-5.04 (m, 1H), 4.75 (s, 1H), 4.49-4.30 (m, 3H), 4.25-4.17 (m, 1H), 4.02-3.93 (m, 3H), 3.68-3.53 (m, 2H), 3.46-3.33 (m, 4H), 3.32-3.23 (m, 2H), 2.90-2.81 (m, 1H), 2.81-2.73 (m, 3H), 2.66-2.53 (m, 2H), 2.34-2.18 (m, 3H), 2.08-1.98 (m, 1H), 1.96-1.87 (m, 1H), 1.21-1.15 (m, 3H), 1.10-1.02 (m, 3H), 0.89-0.83 (m, 3H). LC-MS $(M+H)^+$=586.4.

Example 54: 1-((S)-7-(4-fluorobenzyl)-6-(hydroxymethyl)-2-methyl-2,3-dihydro-1H-pyrido[2,3-b][1,4]oxazin-1-yl)-2-((2R,5R)-2-(((R)-3-(hydroxymethyl)morpholino)methyl)-5-methylpiperazin-1-yl)ethan-1-one (Compound 54)

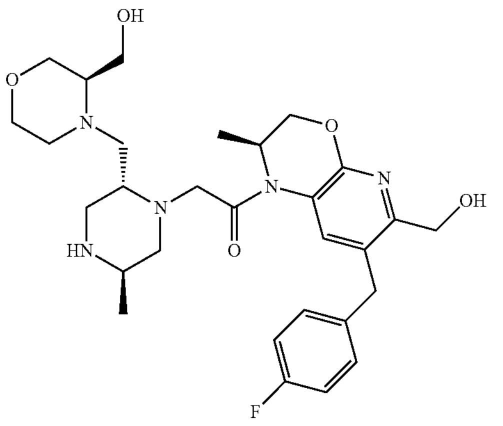 [SMILES: C[C@@H]1CN(CC(=O)N2c3cc(Cc4ccc(F)cc4)c(CO)nc3OC[C@@H]2C)[C@@H](CN2CCOC[C@H]2CO)CN1]

Step 1: (S)-4-benzyl-3-(((tert-butyldimethylsilyl)oxy)methyl)morpholine

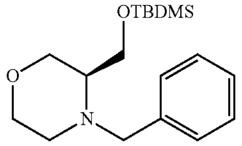 [SMILES: CC(C)(C)[Si](C)(C)OC[C@@H]1COCCN1Cc1ccccc1]

To a solution of [(3R)-4-benzylmorpholin-3-yl]methanol (425 mg, 2.1 mmol) and Imidazole (350 mg, 5.2 mmol) in DMF (10 mL) was added TBDMSCl (375 mg, 2.5 mmol) in portions at room temperature under nitrogen atmosphere. The resulting mixture was stirred for 16 h at room temperature under nitrogen atmosphere. When the reaction was done, the reaction was quenched with $H_2O$ at room temperature. The resulting mixture was extracted with EtOAc (2×30 mL). The organic phases were combined, washed with brine and dried over $Na_2SO_4$. The solvent was removed under reduced pressure and the residue was purified by flash chromatography (PE:EtOAc=4:1) to yield the title compound (342 mg, 76% yield). LC-MS $(M+H)^+$=322.2.

Step 2: (S)-3-(((tert-butyldimethylsilyl)oxy)methyl)morpholine

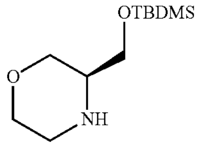 [SMILES: CC(C)(C)[Si](C)(C)OC[C@@H]1COCCN1]

The title compound of step 2 (200 mg, crude) was prepared in a manner similar to that described in Example 53 step 2 from (S)-4-benzyl-3-(((tert-butyldimethylsilyl)oxy)methyl)morpholine. LC-MS $(M+H)^+$=232.2.

Step 3: tert-butyl (2R,5S)-4-benzyl-5-((S)-3-(((tert-butyldimethylsilyloxy)methyl)morpholino)methyl)-2-methylpiperazine-1-carboxylate

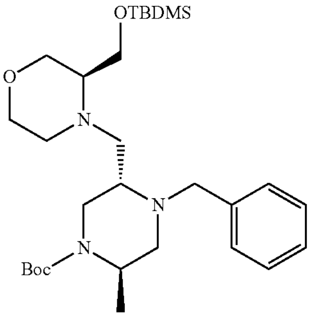 [SMILES: C[C@@H]1CN(Cc2ccccc2)[C@@H](CN2CCOC[C@H]2CO[Si](C)(C)C(C)(C)C)CN1C(=O)OC(C)(C)C]

The title compound of step 3 (281 mg, 49% yield for 2 steps) was prepared in a manner similar to that described in Example 1 step 16 from (S)-3-(((tert-butyldimethylsilyl)oxy)methyl)morpholine and tert-butyl (2R,5R)-4-benzyl-5-(chloromethyl)-2-methylpiperazine-1-carboxylate. LC-MS $(M+H)^+$=534.4.

Step 4: tert-butyl (2R,5S)-5-(((S)-3-(((tert-butyldimethylsilyl)oxy)methyl)morpholino)methyl)-2-methylpiperazine-1-carboxylate

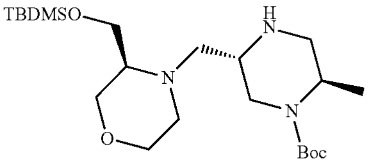 [SMILES: C[C@@H]1CN[C@@H](CN2CCOC[C@H]2CO[Si](C)(C)C(C)(C)C)CN1C(=O)OC(C)(C)C]

The title compound of step 4 (220 mg, crude) was prepared in a manner similar to that described in Example 1 step 17 from tert-butyl (2R,5S)-4-benzyl-5-(((S)-3-(((tert-butyldimethylsilyl)oxy)methyl)morpholino)methyl)-2-methylpiperazine-1-carboxylate. LC-MS $(M+H)^+$=444.3.

Step 5: tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-((S)-3-(((tert-butyl dimethylsilyl)oxy)methyl)morpholino)methyl)-2-methylpiperazine-1-carboxylate

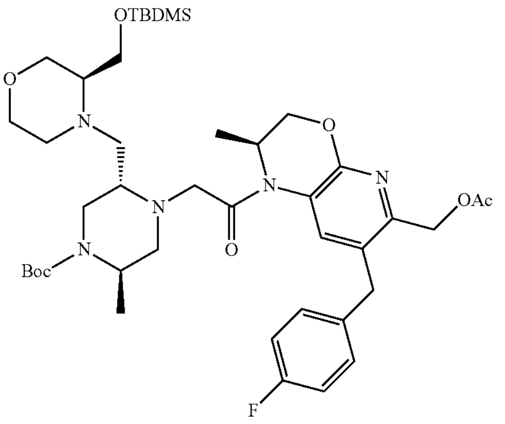 [SMILES: CC(=O)OCc1nc2c(cc1Cc1ccc(F)cc1)N(C(=O)CN1C[C@@H](C)N(C(=O)OC(C)(C)C)C[C@@H]1CN1CCOC[C@H]1CO[Si](C)(C)C(C)(C)C)[C@@H](C)CO2]

The title compound of step 5 (250 mg, 58% yield for 2 steps) was prepared in a manner similar to that described in Example 1 step 18 from tert-butyl (2R,5S)-5-(4S)-3-(((tert-butyldimethylsilypoxy)methyl)morpholino)methyl)-2-methylpiperazine-1-carboxylate and (S)-(1-(2-chloroacetyl)-7-(4-fluorobenzyl)-2-methyl-2,3-dihydro-1H-pyrido[2,3-b][1,4]oxazin-6-yl)methyl acetate. LC-MS $(M+H)^+$=814.5.

Step 6: tert-butyl (2R,5S)-5-((S)-3-(((tert-butyldimethylsilyl)oxy)methyl)morpholino)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate

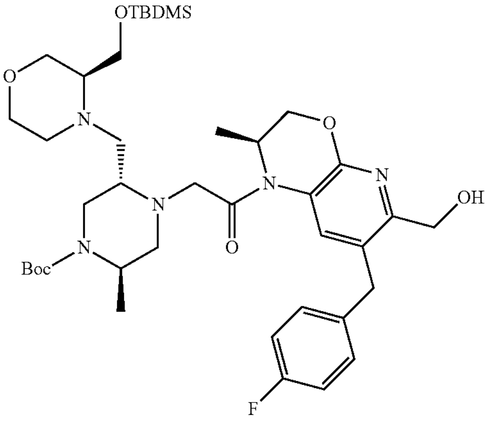 [SMILES: C[C@@H]1CN(CC(=O)N2c3cc(Cc4ccc(F)cc4)c(CO)nc3OC[C@@H]2C)[C@@H](CN2CCOC[C@H]2CO[Si](C)(C)C(C)(C)C)CN1C(=O)OC(C)(C)C]

The title compound of step 6 (162 mg, 68% yield) was prepared in a manner similar to that described in Example 8 step 4 from tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((S)-3-(((tert-butyldimethylsilyl)oxy)methyl)morpholino)methyl)-2-methylpiperazine-1-carboxylate. LC-MS $(M+H)^+$=772.4.

Step 7: 1-((S)-7-(4-fluorobenzyl)-6-(hydroxymethyl)-2-methyl-2,3-dihydro-1H-pyrido[2,3-b][1,4]oxazin-1-yl)-2-((2R,5R)-2-(((R)-3-(hydroxymethyl)morpholino)methyl)-5-methylpiperazin-1-yl)ethan-1-one (Compound 54)

Compound 54 (70 mg, 59% yield) was prepared in a manner similar to that described in Example 29 step 7 from tert-butyl (2R,5S)-5-(((S)-3-(((tert-butyldimethylsilyl)oxy)methyl)morpholino)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate. $^1$H NMR (400 MHz, Chloroform-d) δ 8.43 (brs, 1H), 7.16-7.07 (m, 2H), 7.05-6.96 (m, 2H), 4.88 (s, 1H), 4.67-4.51 (m, 2H), 4.49-4.29 (m, 3H), 3.96-3.67 (m, 6H), 3.65-3.48 (m, 3H), 3.30-3.22 (m, 1H), 3.13-3.00 (m, 2H), 2.99-2.86 (m, 2H), 2.84-2.77 (m, 1H), 2.67-2.63 (m, 2H), 2.40-2.35 (m, 1H), 2.31-2.21 (m, 1H), 2.18-2.08 (m, 2H), 1.35-1.29 (m, 3H), 1.08-1.02 (m, 3H). LC-MS $(M+H)^+$=558.3.

Example 55: 2-42R,5R)-2-(((S)-3-(difluoromethyl)morpholino)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 55)

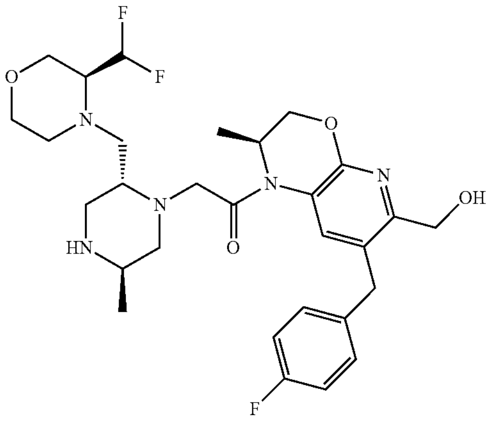 [SMILES: C[C@@H]1CN(CC(=O)N2c3cc(Cc4ccc(F)cc4)c(CO)nc3OC[C@@H]2C)[C@@H](CN2CCOC[C@H]2C(F)F)CN1]

Step 1: (S)-4-benzylmorpholine-3-carbaldehyde

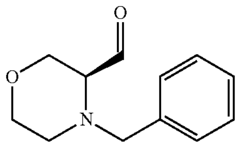 [SMILES: O=C[C@@H]1COCCN1Cc1ccccc1]

To a solution of DMSO (1.95 mL, 27.5 mmol) in DCM (10 mL) was added oxalyl chloride (1.16 mL, 13.6 mmol) in DCM (5 mL) dropwise at −78° C. under nitrogen atmosphere. The resulting mixture was stirred for 15 min at −78° C. under nitrogen atmosphere. To the above mixture was added [(3R)-4-benzylmorpholin-3-yl]methanol (950 mg, 4.6 mmol) in DCM (5 mL) dropwise over 30 min at −78° C. The resulting mixture was stirred for additional 30 min at −78° C. To the above mixture was added TEA (7.60 mL, 54.7 mmol) dropwise over 10 min at −78° C. The resulting mixture was stirred for additional 1 h at −78° C. When the reaction was done, the reaction was quenched with sat. $NaHCO_3$ at room temperature. The resulting mixture was extracted with DCM (2×50 mL). The organic phases were combined, washed with brine and dried over $Na_2SO_4$. The solvent was removed under reduced pressure and the residue was purified by flash chromatography (PE:EtOAc=3:1) to yield the title compound (455 mg, 48% yield). LC-MS $(M+H)^+$=206.2.

Step 2: (S)-4-benzyl-3-(difluoromethyl)morpholine

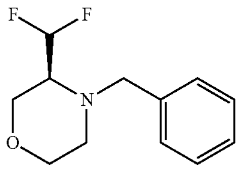 [SMILES: FC(F)[C@@H]1COCCN1Cc1ccccc1]

To a solution of (S)-4-benzylmorpholine-3-carbaldehyde (455 mg, 2.2 mmol) in DCM was added Diethylaminosulphur trifluoride (345 mg, 2.2 mmol) dropwise at 0° C. under nitrogen atmosphere. The resulting mixture was stirred for 2 h at room temperature under nitrogen atmosphere. When the reaction was done, the reaction was quenched with sat. $NaHCO_3$ at room temperature. The resulting mixture was extracted with DCM (2×30 mL). The organic phases were combined, washed with brine and dried over $Na_2SO_4$. The solvent was removed under reduced pressure and the residue was purified by flash chromatography (PE:EtOAc=2:1) to yield the title compound (260 mg, 51% yield). LC-MS $(M+H)^+$=228.1.

Step 3: (S)-3-(difluoromethyl)morpholine hydrochloride

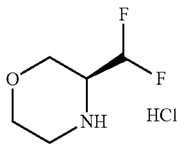

To a solution of (S)-4-benzyl-3-(difluoromethyl)morpholine (260 mg, 1.1 mmol) in MeOH (12 mL) was added Pd/C (250 mg, 0.2 mmol, 10%) under nitrogen atmosphere. The mixture was hydrogenated at room temperature for 16 h under hydrogen atmosphere using a hydrogen balloon. When the reaction was done, the mixture was filtered through a Celite pad. To the above mixture was added HCl in dioxane (2 mL, 8 mmol, 4 M) dropwise at room temperature. The resulting mixture was stirred for additional 30 min at room temperature. The resulting mixture was concentrated under reduced pressure to yield the title compound (200 mg, crude) which was used in next step without purification. LC-MS $(M+H)^+$=138.1.

Step 4: tert-butyl (2R,5S)-4-benzyl-5-(((S)-3-(difluoromethyl)morpholino)methyl)-2-methylpiperazine-1-carboxylate

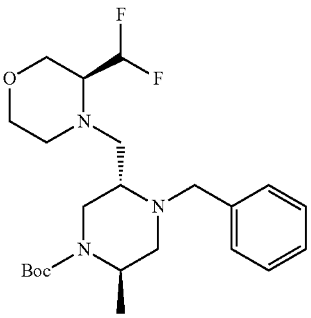 [SMILES: C[C@@H]1CN(Cc2ccccc2)[C@@H](CN2CCOC[C@H]2C(F)F)CN1C(=O)OC(C)(C)C]

The title compound of step 4 (225 mg, 44% yield for 2 steps) was prepared in a manner similar to that described in Example 1 step 16 from (S)-3-(difluoromethyl)morpholine hydrochloride and tert-butyl (2R,5R)-4-benzyl-5-(chloromethyl)-2-methylpiperazine-1-carboxylate. LC-MS $(M+H)^+$=440.3.

Step 5: tert-butyl (2R,5S)-5-(((S)-3-(difluoromethyl)morpholino)methyl)-2-methylpiperazine-1-carboxylate

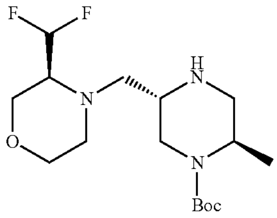 [SMILES: C[C@@H]1CN[C@@H](CN2CCOC[C@H]2C(F)F)CN1C(=O)OC(C)(C)C]

The title compound of step 5 (180 mg, crude) was prepared in a manner similar to that described in Example 1 step 17 from tert-butyl (2R,5S)-4-benzyl-5-(((S)-3-(difluoromethyl)morpholino)methyl)-2-methylpiperazine-1-carboxylate. LC-MS $(M+H)^+$=350.2.

Step 6: tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((S)-3-(difluoromethyl)morpholino)methyl)-2-methylpiperazine-1-carboxylate

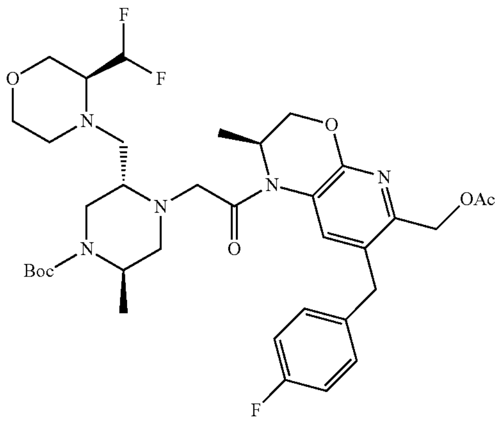 [SMILES: CC(=O)OCc1nc2c(cc1Cc1ccc(F)cc1)N(C(=O)CN1C[C@@H](C)N(C(=O)OC(C)(C)C)C[C@@H]1CN1CCOC[C@H]1C(F)F)[C@@H](C)CO2]

The title compound of step 6 (220 mg, 59% yield for 2 steps) was prepared in a manner similar to that described in Example 1 step 18 from tert-butyl (2R,5S)-5-(((S)-3-(difluoromethyl)morpholino)methyl)-2-methylpiperazine-1-carboxylate and (S)-(1-(2-chloroacetyl)-7-(4-fluorobenzyl)-2-methyl-2,3-dihydro-1H-pyrido[2,3-b][1,4]oxazin-6-yl) methyl acetate. LC-MS $(M+H)^+$=720.4.

Step 7: tert-butyl (2R,5S)-5-(((S)-3-(difluoromethyl) morpholino)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate

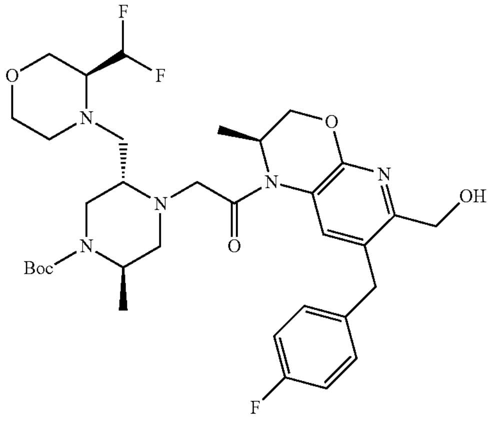 [SMILES: C[C@@H]1CN(CC(=O)N2c3cc(Cc4ccc(F)cc4)c(CO)nc3OC[C@@H]2C)[C@@H](CN2CCOC[C@H]2C(F)F)CN1C(=O)OC(C)(C)C]

The title compound of step 7 (134 mg, 65% yield) was prepared in a manner similar to that described in Example 8 step 4 from tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((S)-3-(difluoromethyl) morpholino)methyl)-2-methylpiperazine-1-carboxylate. LC-MS $(M+H)^+$=678.3.

Step 8: 2-((2R,5R)-2-(((S)-3-(difluoromethyl)morpholino)methyl)-5-methylpiperazin-1-yl)-1-4S)-7-(4-fluorobenzyl)-6-(hydroxymethyl)-2-methyl-2,3-dihydro-1H-pyrido[2,3-b][1,4]oxazin-1-yl)ethan-1-one (Compound 55)

Compound 55 (53 mg, 46% yield) was prepared in a manner similar to that in Example 29 step 7 from tert-butyl (2R,5S)-5-(((S)-3-(difluoromethyl)morpholino)methyl)-4-(2-((S)-7-(4-fluorobenzyl)-6-(hydroxymethyl)-2-methyl-2,3-dihydro-1H-pyrido[2,3-b][1,4]oxazin-1-yl) oxoethyl)-2-methylpiperazine-1-carboxylate. $^1H$ NMR (400 MHz, Chloroform-d) δ 8.41 (brs, 1H), 7.14-7.04 (m, 2H), 7.03-6.92 (m, 2H), 6.32-5.87 (m, 1H), 5.06-4.77 (m, 1H), 4.64-4.50 (m, 2H), 4.44-4.35 (m, 1H), 4.35-4.25 (m, 1H), 4.10-4.02 (m, 1H), 3.83 (s, 2H), 3.82-3.57 (m, 4H), 3.23-3.07 (m, 2H), 2.95-2.79 (m, 3H), 2.78-2.64 (m, 2H), 2.62-2.36 (m, 4H), 2.19-2.07 (m, 1H), 1.35-1.23 (m, 3H), 1.06-0.99 (m, 3H). LC-MS $(M+H)^+$=578.4.

Example 56: 2-42R,5R)-2-((8-oxa-5-azaspiro[3.5] nonan-5-yl)methyl)-5-methylpiperazin yl)-1-(((S)-7-(4-fluorobenzyl)-6-(hydroxymethyl)-2-methyl-2,3-dihydro-1H-pyrido[2,3-b][1,4]oxazin-1-yl)ethan-1-one (Compound 56)

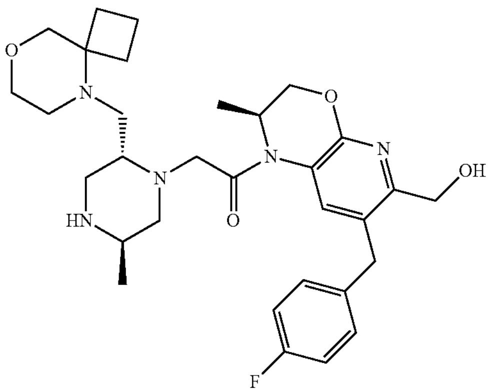 [SMILES: C[C@@H]1CN(CC(=O)N2c3cc(Cc4ccc(F)cc4)c(CO)nc3OC[C@@H]2C)[C@@H](CN2CCOCC23CCC3)CN1]

Step 1: tert-butyl (2R,5S)-5-((8-oxa-5-azaspiro[3.5] nonan-5-yl)methyl)-4-benzyl-2-methylpiperazine-1-carboxylate

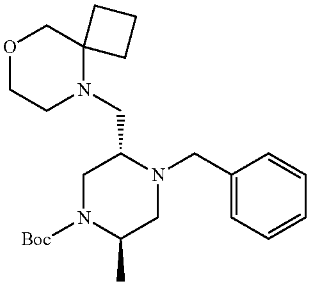 [SMILES: C[C@@H]1CN(Cc2ccccc2)[C@@H](CN2CCOCC23CCC3)CN1C(=O)OC(C)(C)C]

The title compound of step 1 (500 mg, 78% yield) was prepared in a manner similar to that described in Example 1 step 16 from 8-oxa-5-azaspiro[3.5]nonane and tert-butyl (2R,5R)-4-benzyl-5-(chloromethyl)-2-methylpiperazine-1-carboxylate. LC-MS $(M+H)^+$=430.3.

Step 2: tert-butyl (2R,5S)-5-((8-oxa-5-azaspiro[3.5] nonan-5-yl)methyl)-2-methylpiperazine-1-carboxylate

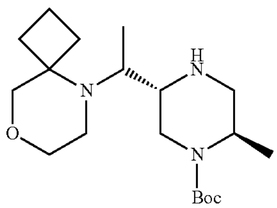 [SMILES: CC([C@H]1CN(C(=O)OC(C)(C)C)[C@H](C)CN1)N1CCOCC12CCC2]

The title compound of step 2 (300 mg, crude) was prepared in a manner similar to that described in Example 1 step 17 from tert-butyl (2R,5S)-5-((8-oxa-5-azaspiro[3.5]

nonan-5-yl)methyl)-4-benzyl-2-methylpiperazine-1-carboxylate. LC-MS $(M+H)^+$=340.3.

Step 3: tert-butyl (2R,5S)-5-((8-oxa-5-azaspiro[3.5]nonan-5-yl)methyl)-4-(2-((S)-6-(acetoxymethyl)-744-fluorobenzyl)-2-methyl-2,3-dihydro-1H-pyrido[2,3-b][1,4]oxazin-1-yl)-2-oxoethyl)-2-methylpiperazine-1-carboxylate

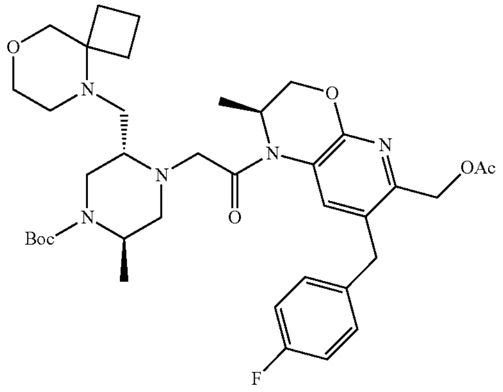 [SMILES: CC(=O)OCc1nc2c(cc1Cc1ccc(F)cc1)N(C(=O)CN1C[C@@H](C)N(C(=O)OC(C)(C)C)C[C@@H]1CN1CCOCC13CCC3)[C@@H](C)CO2]

The title compound of step 3 (350 mg, 42% yield for 2 steps) was prepared in a manner similar to that described in Example 1 step 18 from tert-butyl (2R,5S)-5-((8-oxa-5-azaspiro[3.5]nonan-5-yl)methyl)-2-methylpiperazine-1-carboxylate and (S)-(1-(2-chloroacetyl)-7-(4-fluorobenzyl)-2-methyl-2,3-dihydro-1H-pyrido[2,3-b][1,4]oxazin-6-yl)methyl acetate. LC-MS $(M+H)^+$=710.4.

Step 4: tert-butyl (2R,5S)-5-((8-oxa-5-azaspiro[3.5]nonan-5-yl)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate

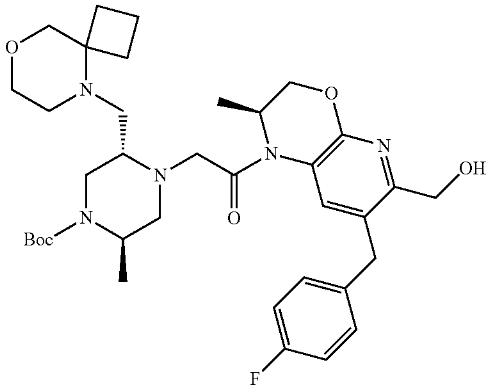 [SMILES: C[C@@H]1CN(CC(=O)N2c3cc(Cc4ccc(F)cc4)c(CO)nc3OC[C@@H]2C)[C@@H](CN2CCOCC23CCC3)CN1C(=O)OC(C)(C)C]

The title compound of step 4 (250 mg, 75% yield) was prepared in a manner similar to that described in Example 8 step 4 from tert-butyl (2R,55)-5-((8-oxa-5-azaspiro[3.5]nonan-5-yl)methyl)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-2-methylpiperazine-1-carboxylate. LC-MS $(M+H)^+$=668.4.

Step 5: 2-((2R,5R)-2-((8-oxa-5-azaspiro[3.5]nonan-5-yl)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 56)

Compound 56 (59 mg, 28% yield) was prepared in a manner similar to that described in Example 29 step 7 from tert-butyl (2R,5S)-5-((8-oxa-5-azaspiro[3.5]nonan-5-yl)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate. $^1H$ NMR (300 MHz, Chloroform-d) δ 8.45 (brs, 1H), 7.17-7.06 (m, 2H), 7.06-6.93 (m, 2H), 4.97 (s, 1H), 4.66-4.50 (m, 2H), 4.47-4.37 (m, 1H), 4.37-4.24 (m, 2H), 3.85 (s, 2H), 3.72-3.56 (m, 3H), 3.48-3.38 (m, 1H), 3.22-3.08 (m, 2H), 2.93-2.66 (m, 3H), 2.63-2.32 (m, 4H), 2.32-2.20 (m, 1H), 2.17-2.00 (m, 3H), 1.87-1.49 (m, 4H), 1.37-1.29 (m, 3H), 1.07-0.99 (m, 3H). LC-MS $(M+H)^+$=568.3.

Example 57: 1-((S)-7-(4-fluorobenzyl)-6-(hydroxymethyl)-2-(methoxymethyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 57)

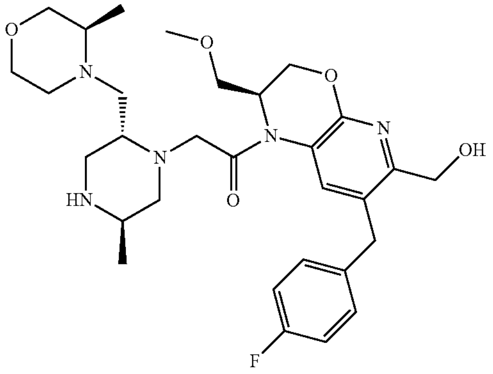 [SMILES: COC[C@H]1COc2nc(CO)c(Cc3ccc(F)cc3)cc2N1C(=O)CN1C[C@@H](C)NC[C@@H]1CN1CCOC[C@H]1C]

Step 1: tert-butyl (S)-(1-(benzyloxy)-3-((3,5-dibromo-6-methylpyridin-2-yl)oxy)propan-2-yl)carbamate

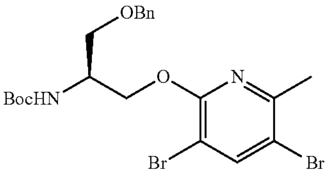 [SMILES: Cc1nc(OC[C@H](COCc2ccccc2)NC(=O)OC(C)(C)C)c(Br)cc1Br]

The title compound of step 1 (9.8 g, 99% yield) was prepared in a manner similar to that described in Example 19 step 1 from tert-butyl (R)-(1-(benzyloxy)-3-hydroxypropan-2-yl)carbamate and 3,5-dibromo-2-chloro-6-methylpyridine. LC-MS $(M+H)^+$=529.0.

Step 2: tert-butyl (S)-2-((benzyloxy)methyl)-7-bromo-6-methyl-2,3-dihydro-1H-pyrido[2,3-b][1,4]oxazine-1-carboxylate

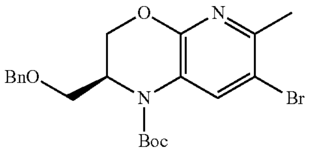 [SMILES: Cc1nc2c(cc1Br)N(C(=O)OC(C)(C)C)[C@@H](COCc1ccccc1)CO2]

The title compound of step 2 (4 g, 74% yield) was prepared in a manner similar to that described in Example 34 step 2 from tert-butyl (S)-(1-(benzyloxy)-3-((3,5-dibromo-6-methylpyridin-2-yl)oxy)propan-2-yl)carbamate. LC-MS $(M+H)^+$=449.1.

Step 3: tert-butyl (S)-2-((benzyloxy)methyl)-7-(4-fluorobenzyl)-6-methyl-2,3-dihydro-1H-pyrido[2,3-b][1,4]oxazine-1-carboxylate

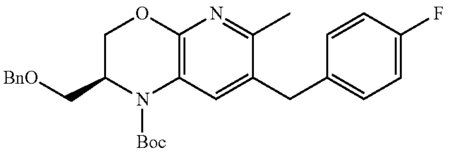 [SMILES: Cc1nc2c(cc1Cc1ccc(F)cc1)N(C(=O)OC(C)(C)C)[C@@H](COCc1ccccc1)CO2]

The title compound of step 3 (2.9 g, 91% yield) was prepared in a manner similar to that described in Example 1 step 7 from tert-butyl (S)-2-((benzyloxy)methyl)-7-bromo-6-methyl-2,3-dihydro-1H-pyrido[2,3-b][1,4]oxazine-1-carboxylate and (4-fluorobenzyl)zinc(II) chloride. LC-MS $(M+H)^+$=479.2.

Step 4: tert-butyl (S)-7-(4-fluorobenzyl)-2-(hydroxymethyl)-6-methyl-2,3-dihydro-1H-pyrido[2,3-b][1,4]oxazine-1-carboxylate

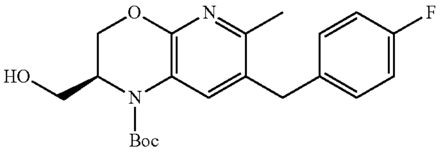 [SMILES: Cc1nc2c(cc1Cc1ccc(F)cc1)N(C(=O)OC(C)(C)C)[C@@H](CO)CO2]

The title compound of step 4 (2 g, 84% yield) was prepared in a manner similar to that described in Example 34 step 4 from tert-butyl (S)-2-((benzyloxy)methyl)-7-(4-fluorobenzyl)-6-methyl-2,3-dihydro-1H-pyrido[2,3-b][1,4]oxazine-1-carboxylate. LC-MS $(M+H)^+$=389.2.

Step 5: tert-butyl (R)-7-(4-fluorobenzyl)-6-methyl-2-(((methylsulfonyloxy)methyl)-2,3-dihydro-1H-pyrido[2,3-b][1,4]oxazine-1-carboxylate

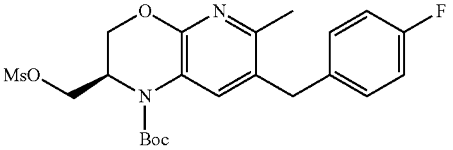

The title compound of step 5 (2.3 g, 99% yield) was prepared in a manner similar to that described in Example 34 step 5 from tert-butyl (S)-7-(4-fluorobenzyl)-2-(hydroxymethyl)-6-methyl-2,3-dihydro-1H-pyrido[2,3-b][1,4]oxazine-1-carboxylate and MsCl. LC-MS $(M+H)^+$=467.2.

Step 6: (R)-(7-(4-fluorobenzyl)-6-methyl-2,3-dihydro-1H-pyrido[2,3-b][1,4]oxazin-2-yl)methyl methanesulfonate

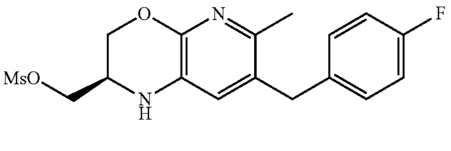 [SMILES: Cc1nc2c(cc1Cc1ccc(F)cc1)N[C@@H](COS(C)(=O)=O)CO2]

The title compound of step 6 (1.4 g, 75% yield) was prepared in a manner similar to that described in Example 34 step 6 from tert-butyl (R)-7-(4-fluorobenzyl)-6-methyl-2-(((methylsulfonyl)oxy)methyl)-2,3-dihydro-1H-pyrido[2,3-b][1,4]oxazine-1-carboxylate. LC-MS $(M+H)^+$=367.1.

Step 7: (S)-7-(4-fluorobenzyl)-2-(methoxymethyl)-6-methyl-2,3-dihydro-1H-pyrido[2,3-b][1,4]oxazine

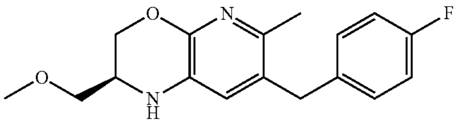 [SMILES: COC[C@H]1COc2nc(C)c(Cc3ccc(F)cc3)cc2N1]

The title compound of step 7 (665 mg, 58% yield) was prepared in a manner similar to that described in Example 34 step 7 from (R)-(7-(4-fluorobenzyl)-6-methyl-2,3-dihydro-1H-pyrido[2,3-b][1,4]oxazin-2-yl)methyl methanesulfonate and sodium methoxide. LC-MS $(M+H)^+$=303.1.

Step 8: tert-butyl (S)-7-(4-fluorobenzyl)-2-(methoxymethyl)-6-methyl-2,3-dihydro-1H-pyrido[2,3-b][1,4]oxazine-1-carboxylate

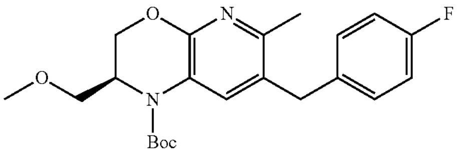 [SMILES: COC[C@H]1COc2nc(C)c(Cc3ccc(F)cc3)cc2N1C(=O)OC(C)(C)C]

The title compound of step 8 (590 mg, 79% yield) was prepared in a manner similar to that described in Example 1 step 4 from (S)-7-(4-fluorobenzyl)-2-(methoxymethyl)-6-methyl-2,3-dihydro-1H-pyrido[2,3-b][1,4]oxazine. LC-MS $(M+H)^+$=403.2.

Step 9: (S)-1-(tert-butoxycarbonyl)-7-(4-fluorobenzyl)-2-(methoxymethyl)-6-methyl-2,3-dihydro-1H-pyrido[2,3-b][1,4]oxazine 5-oxide

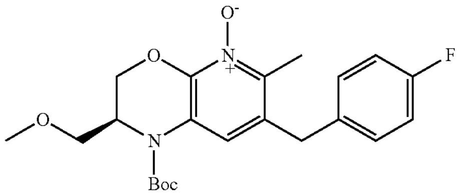 [SMILES: COC[C@H]1COc2c(cc(Cc3ccc(F)cc3)c(C)[n+]2[O-])N1C(=O)OC(C)(C)C]

The title compound of step 9 (457 mg, 74% yield) was prepared in a manner similar to that described in Example 1 step 5 from tert-butyl (S)-7-(4-fluorobenzyl)-2-(methoxymethyl)-6-methyl-2,3-dihydro-1H-pyrido[2,3-b][1,4]oxazine-1-carboxylate. LC-MS $(M+H)^+$=419.2.

Step 10: tert-butyl (S)-6-(acetoxymethyl)-7-(4-fluorobenzyl)-2-(methoxymethyl)-2,3-dihydro-1H-pyrido[2,3-b][1,4]oxazine-1-carboxylate

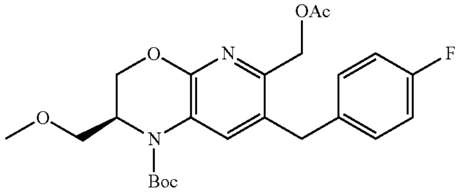 [SMILES: COC[C@H]1COc2nc(COC(C)=O)c(Cc3ccc(F)cc3)cc2N1C(=O)OC(C)(C)C]

The title compound of step 10 (409 mg, 93% yield) was prepared in a manner similar to that described in Example 8 step 2 from (S)-1-(tert-butoxycarbonyl)-7-(4-fluorobenzyl)-2-(m ethoxymethyl)-6-methyl-2,3-dihydro-1H-pyrido[2,3-b][1,4]oxazine 5-oxide. LC-MS $(M+H)^+$=461.2.

Step 11: (S)-(7-(4-fluorobenzyl)-2-(methoxymethyl)-2,3-dihydro-1H-pyrido[2,3-b][1,4]oxazin-6-yl)methyl acetate

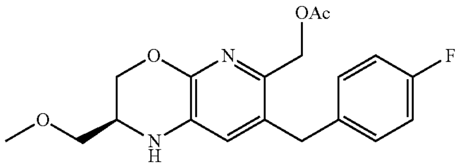 [SMILES: COC[C@H]1COc2nc(COC(C)=O)c(Cc3ccc(F)cc3)cc2N1]

The title compound of step 11 (298 mg, 98% yield) was prepared in a manner similar to that described in Example 1 step 8 from tert-butyl (S)-6-(acetoxymethyl)-7-(4-fluorobenzyl)-2-(methoxymethyl)-2,3-dihydro-1H-pyrido[2,3-b][1,4]oxazine-1-carboxylate. LC-MS $(M+H)^+$=361.1.

Step 12: (S)-(1-(2-chloroacetyl)-7-(4-fluorobenzyl)-2-(methoxymethyl)-2,3-dihydro-1H-pyrido[2,3-b][1,4]oxazin-6-yl)methyl acetate

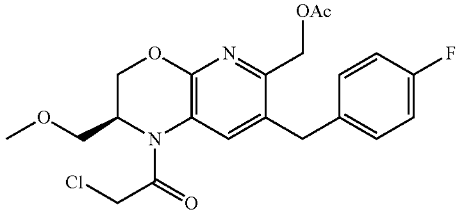 [SMILES: COC[C@H]1COc2nc(COC(C)=O)c(Cc3ccc(F)cc3)cc2N1C(=O)CCl]

The title compound of step 12 (400 mg, crude) was prepared in a manner similar to that described in Example 1 step 9 from (S)-(7-(4-fluorobenzyl)-2-(methoxymethyl)-2,3-dihydro-1H-pyrido[2,3-b][1,4]oxazin-6-yl)methyl acetate and 2-chloroacetyl chloride. LC-MS $(M+H)^+$=437.1.

Step 13: tert-butyl (2R,5S)-4-(2-((S)-6-(acetoxymethyl)-7-(4-fluorobenzyl)-2-(methoxymethyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

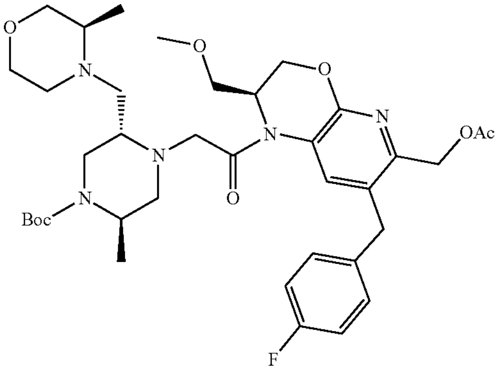 [SMILES: COC[C@H]1COc2nc(COC(C)=O)c(Cc3ccc(F)cc3)cc2N1C(=O)CN1C[C@@H](C)N(C(=O)OC(C)(C)C)C[C@@H]1CN1CCOC[C@H]1C]

The title compound of step 13 (400 mg, crude) was prepared in a manner similar to that described in Example 1 step 18 from (S)-(1-(2-chloroacetyl)-7-(4-fluorobenzyl)-2-(methoxymethyl)-2,3-dihydro-1H-pyrido[2,3-b][1,4]oxazin-6-yl)methyl acetate and tert-butyl (2R,5S)-2-methyl-5-(((R)-3-methylmorpholino)methyl)piperazine-1-carboxylate. LC-MS $(M+H)^+$=714.4.

Step 14: tert-butyl (2R,5S)-4-(2-((S)-7-(4-fluorobenzyl)-6-(hydroxymethyl)-2-(methoxymethyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate

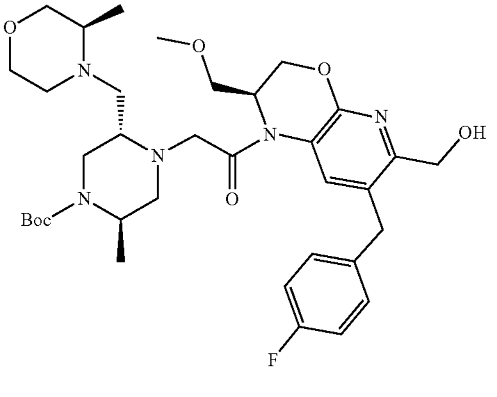 [SMILES: COC[C@H]1COc2nc(CO)c(Cc3ccc(F)cc3)cc2N1C(=O)CN1C[C@@H](C)N(C(=O)OC(C)(C)C)C[C@@H]1CN1CCOC[C@H]1C]

The title compound of step 14 (110 mg, 61% yield) was prepared in a manner similar to that described in Example 8 step 4 from tert-butyl (2R,5S)-4-(2-((S)-6-(acetoxymethyl)-7-(4-fluorobenzyl)-2-(methoxymethyl)-2,3-dihydro-1H-pyrido[2,3-b][1,4]oxazin-1-yl)-2-oxoethyl)-2-methyl-5-(((R)-3-methylmorpholino)methyl)piperazine-1-carboxylate. LC-MS $(M+H)^+$=672.4.

Step 15: 1-((S)-7-(4-fluorobenzyl)-6-(hydroxymethyl)-2-(methoxymethyl)-2,3-dihydro-1H-pyrido[2,3-b][1,4]oxazin-1-yl)-2-((2R,5R)-5-methyl-2-(((R)-3-methylmorpholino)methyl)piperazin-1-yl)ethan-1-one (Compound 57)

Compound 57 (20 mg, 15% yield) was prepared in a manner similar to that described in Example 29 step 7 from tert-butyl (2R,5S)-4-(2-((S)-7-(4-fluorobenzyl)-6-(hydroxymethyl) (methoxymethyl)-2,3-dihydro-1H-pyrido[2,3-b][1,4]oxazin-1-yl)-2-oxoethyl)-2-methyl (((R)-3-methylmorpholino)methyl)piperazine-1-carboxylate. $^1$H NMR (300 MHz, DMSO-d6) δ 8.22 (brs, 1H), 7.25-7.14 (m, 2H), 7.17-7.04 (m, 2H), 5.14-5.04 (m, 1H), 4.85 (s, 1H), 4.54-4.45 (m, 1H), 4.45-4.33 (m, 2H), 4.25-4.09 (m, 2H), 3.96 (s, 2H), 3.54-3.45 (m, 2H), 3.49-3.33 (m, 1H), 3.30-3.24 (m, 2H), 3.21 (s, 3H), 3.07-2.95 (m, 1H), 2.93-2.74 (m, 2H), 2.73-2.53 (m, 4H), 2.39-2.12 (m, 3H), 2.10-1.96 (m, 1H), 1.82-1.71 (m, 1H), 1.22 (s, 1H), 0.92-0.85 (m, 3H), 0.85-0.79 (m, 3H). LC-MS $(M+H)^+$=572.0.

Example 58: 2-((2R,5R)-2-(((3R,5R)-3,5-dimethylmorpholino)methyl)-5-methylpiperazin-1-yl)-1-((S)-7-(4-fluorobenzyl)-6-(hydroxymethyl)-2-(methoxymethyl)-2,3-dihydro-1H-pyrido[2,3-b][1,4]oxazin-1-yl)ethan-1-one (Compound 58)

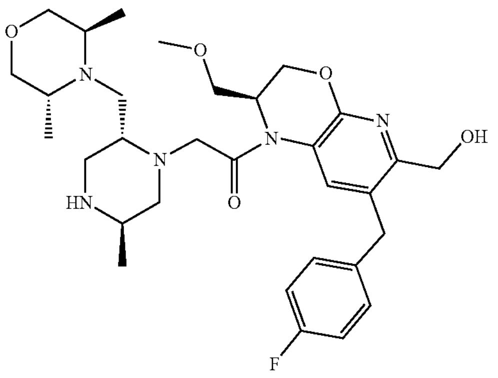 [SMILES: COC[C@H]1COc2nc(CO)c(Cc3ccc(F)cc3)cc2N1C(=O)CN1C[C@@H](C)NC[C@@H]1CN1[C@H](C)COC[C@H]1C]

Step 1: tert-butyl (2R,5S)-4-(2-((S)-6-(acetoxymethyl)-7-(4-fluorobenzyl)-2-(methoxymethyl)-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

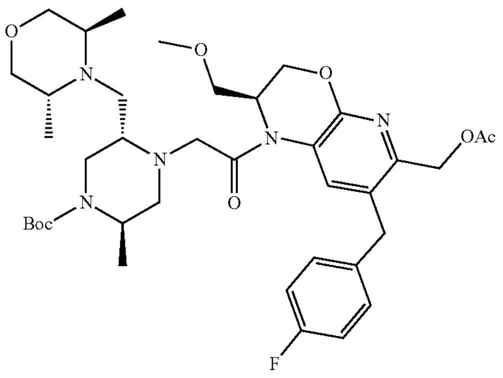 [SMILES: COC[C@H]1COc2nc(COC(C)=O)c(Cc3ccc(F)cc3)cc2N1C(=O)CN1C[C@@H](C)N(C(=O)OC(C)(C)C)C[C@@H]1CN1[C@H](C)COC[C@H]1C]

The title compound of step 1 (400 mg, crude) was prepared in a manner similar to that described in Example 1 step 18 from (S)-(1-(2-chloroacetyl)-7-(4-fluorobenzyl)-2-(methoxymethyl)-2,3-dihydro-1H-pyrido[2,3-b][1,4]oxazin-6-yl)methyl acetate and tert-butyl (2R,5S)-5-(((3R,5R)-3,5-dimethylmorpholino)methyl)-2-methylpiperazine-1-carboxylate. LC-MS $(M+H)^+$=728.4

Step 2: tert-butyl (2R,5S)-5-(((3R,5R)-3,5-dimethylmorpholino)methyl)-4-(2-((S)-7-(4-fluorobenzyl)-6-(hydroxymethyl)-2-(methoxymethyl)-2,3-dihydro-1H-pyrido[2,3-b][1,4]oxazin-1-yl)-2-oxoethyl)-2-methylpiperazine-1-carboxylate

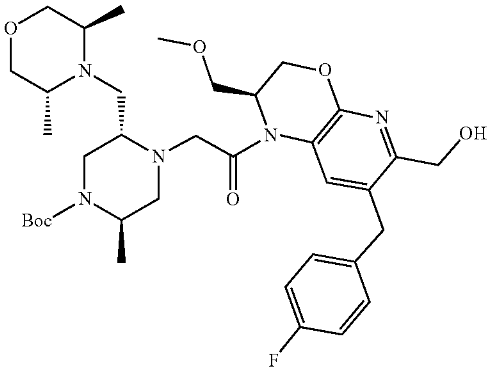 [SMILES: COC[C@H]1COc2nc(CO)c(Cc3ccc(F)cc3)cc2N1C(=O)CN1C[C@@H](C)N(C(=O)OC(C)(C)C)C[C@@H]1CN1[C@H](C)COC[C@H]1C]

The title compound of step 2 (109 mg, 59% yield) was prepared in a manner similar to that described in Example 8 step 4 from tert-butyl (2R,5S)-4-(2-((S)-6-(acetoxymethyl)-7-(4-fluorobenzyl)-2-(methoxymethyl)-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. LC-MS $(M+H)^+$=686.4.

Step 3: 242R,5R)-2-(((3R,5R)-3,5-dimethylmorpholino)methyl)-5-methylpiperazin-1-yl)-1-4S)-7-(4-fluorobenzyl)-6-(hydroxymethyl)-2-(methoxymethyl)-2,3-dihydro-1H-pyrido[2,3-b][1,4]oxazin-1-yl)ethan-1-one (Compound 58)

Compound 58 (29 mg, 32% yield) was prepared in a manner similar to that in Example 29 step 7 from tert-butyl (2R,5S)-5-(((3R,5R)-3,5-dimethylmorpholino)methyl)-4-(2-((S)-7-(4-fluorobenzyl)-6-(hydroxymethyl)-2-(methoxymethyl)-2,3-dihydro-1H-pyrido[2,3-b][1,4]oxazin-1-yl)-2-oxoethyl)-2-methylpiperazine-1-carboxylate. $^{1}$H NMR (400 MHz, DMSO-d6) δ 8.20 (brs, 1H), 7.25-7.17 (m, 2H), 7.21-7.07 (m, 2H), 5.13-5.06 (m, 1H), 4.86 (s, 1H), 4.55-4.36 (m, 3H), 4.26-4.18 (m, 1H), 4.09-3.95 (m, 3H), 3.52-3.44 (m, 2H), 3.43-3.38 (m, 2H), 3.24 (s, 3H), 3.19-3.11 (m, 2H), 3.09-2.98 (m, 1H), 2.84-2.75 (m, 1H), 2.73-2.51 (m, 5H), 2.50-2.44 (m, 1H), 2.30-2.20 (m, 1H), 2.19-2.10 (m, 1H), 2.00-1.90 (m, 1H), 0.90-0.80 (m, 9H). LC-MS $(M+H)^+$=586.3.

Example 59: 1-4S)-7-(4-fluorobenzyl)-6-(hydroxymethyl)-2-methyl-2,3-dihydro-1H-pyrido[2,3-b][1,4]oxazin-1-yl)-2-((2R,5R)-2-(((S)-3-(isopropoxymethyl)morpholino)methyl)-5-methylpiperazin-1-yl)ethan-1-one (Compound 59)

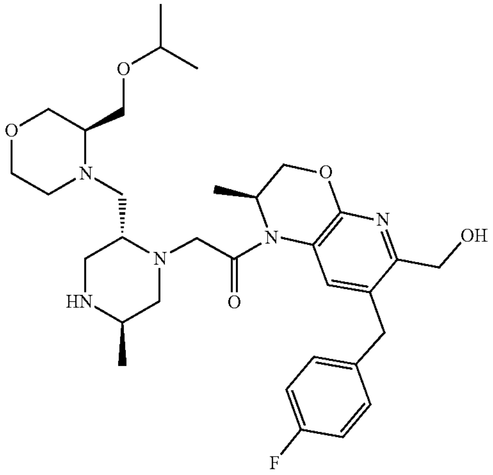 [SMILES: CC(C)OC[C@@H]1COCCN1C[C@H]1CN[C@H](C)CN1CC(=O)N1c2cc(Cc3ccc(F)cc3)c(CO)nc2OC[C@@H]1C]

Step 1: (S)-(4-benzylmorpholin-3-yl)methyl methanesulfonate

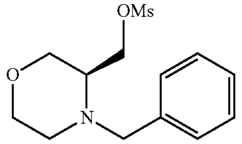 [SMILES: CS(=O)(=O)OC[C@@H]1COCCN1Cc1ccccc1]

The title compound of step 1 (335 mg, 61% yield) was prepared in a manner similar to that described in Example 34 step 5 from (R)-(4-benzylmorpholin-3-yl)methanol and MsCl. LC-MS $(M+H)^+$=286.1.

Step 2: (S)-4-benzyl-3-(isopropoxymethyl)morpholine

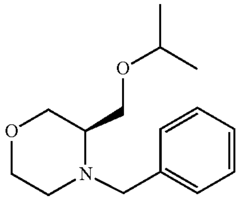 [SMILES: CC(C)OC[C@@H]1COCCN1Cc1ccccc1]

The title compound of step 2 (230 mg, 78% yield) was prepared in a manner similar to that described in Example 34 step 7 from (S)-(4-benzylmorpholin-3-yl)methyl methanesulfonate and sodium isopropoxide. LC-MS $(M+H)^+$=250.2.

Step 3: (S)-3-(isopropoxymethyl)morpholine

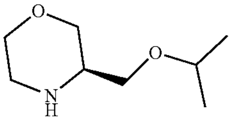

The title compound of step 3 (160 mg, crude) was prepared in a manner similar to that described in Example 53 step 2 from (S)-4-benzyl-3-(isopropoxymethyl)morpholine. LC-MS $(M+H)^+$=160.1.

Step 4: tert-butyl (2R,5S)-4-benzyl-5-(((S)-3-(isopropoxymethyl)morpholino)methyl)-2-methylpiperazine-1-carboxylate

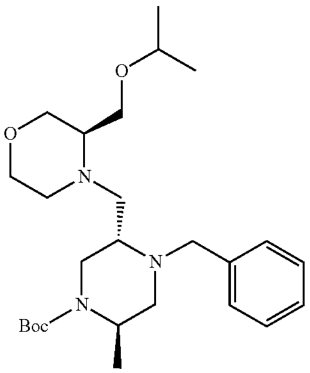 [SMILES: CC(C)OC[C@@H]1COCCN1C[C@H]1CN(C(=O)OC(C)(C)C)[C@H](C)CN1Cc1ccccc1]

The title compound of step 4 (310 mg, 46% yield for 2 steps) was prepared in a manner similar to that described in Example 1 step 16 from (S)-3-(isopropoxymethyl)morpholine and tert-butyl (2R,5R)-4-benzyl-5-(chloromethyl)-2-methylpiperazine-1-carboxylate. LC-MS $(M+H)^+$=462.3.

Step 5: tert-butyl (2R,5S)-5-(((S)-3-(isopropoxymethyl)morpholino)methyl)-2-methylpiperazine-1-carboxylate

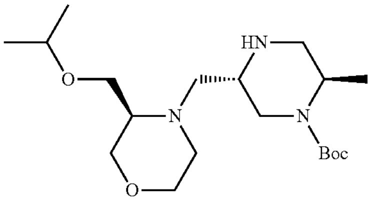 [SMILES: CC(C)OC[C@@H]1COCCN1C[C@H]1CN(C(=O)OC(C)(C)C)[C@H](C)CN1]

The title compound of step 5 (250 mg, crude) was prepared in a manner similar to that described in Example 1 step 17 from tert-butyl (2R,5S)-4-benzyl-5-(((S)-3-(isopropoxymethyl)morpholino)methyl)-2-methylpiperazine-1-carboxylate. LC-MS $(M+H)^+$=372.3.

Step 6: tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((S)-3-(isopropoxymethyl)morpholino)methyl)-2-methylpiperazine-1-carboxylate

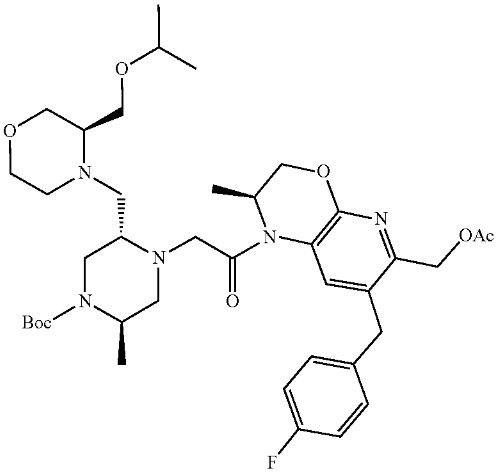 [SMILES: CC(=O)OCc1nc2c(cc1Cc1ccc(F)cc1)N(C(=O)CN1C[C@@H](C)N(C(=O)OC(C)(C)C)C[C@@H]1CN1CCOC[C@H]1COC(C)C)[C@@H](C)CO2]

The title compound of step 6 (130 mg, 52% yield for 2 steps) was prepared in a manner similar to that described in Example 1 step 18 from tert-butyl (2R,5S)-5-(((S)-3-(isopropoxymethyl)morpholino)methyl)-2-methylpiperazine-1-carboxylate and (S)-(1-(2-chloroacetyl)-7-(4-fluorobenzyl)-2-methyl-2,3-dihydro-1H-pyrido[2,3-b][1,4]oxazin-6-yl) methyl acetate. LC-MS $(M+H)^+$=742.4.

Step 7: tert-butyl (2R,5S)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-5-(((S)-3-(isopropoxymethyl)morpholino)methyl)-2-methylpiperazine-1-carboxylate

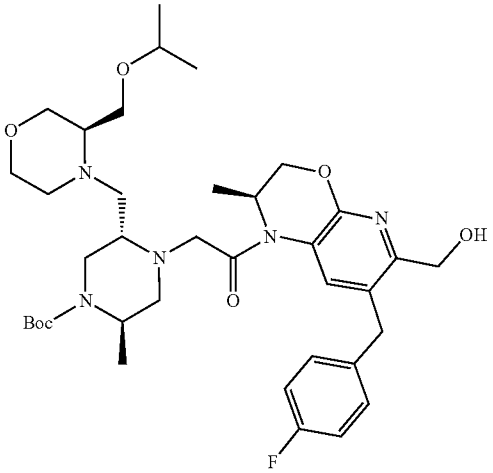 [SMILES: CC(C)OC[C@@H]1COCCN1C[C@H]1CN(C(=O)OC(C)(C)C)[C@H](C)CN1CC(=O)N1c2cc(Cc3ccc(F)cc3)c(CO)nc2OC[C@@H]1C]

The title compound of step 7 (90 mg, 74% yield) was prepared in a manner similar to that described in Example 8 step 4 from tert-butyl (2R,55)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(((S)-3-(isopropoxymethyl)morpholino)methyl)-2-methylpiperazine-1-carboxylate. LC-MS $(M+H)^+$=700.5.

Step 8: 1-(((S)-7-(4-fluorobenzyl)-6-(hydroxymethyl)-2-methyl-2,3-dihydro-1H-pyrido[2,3-b][1,4]oxazin-1-yl)-2-((2R,5R)-2-(((S)-3-(isopropoxymethyl)morpholino)methyl)-5-methylpiperazin-1-yl)ethan-1-one (Compound 59)

Compound 59 (54 mg, 70% yield) was prepared in a manner similar to that described in Example 29 step 7 from tert-butyl (2R,5S)-4-(2-((S)-7-(4-fluorobenzyl)-6-(hydroxymethyl) methyl-2,3-dihydro-1H-pyrido[2,3-b][1,4]oxazin-1-yl)-2-oxoethyl)-5-(((S)-3-(isopropoxymethyl)morpholino)methyl)-2-methylpiperazine-1-carboxylate. $^1$H NMR (400 MHz, Chloroform-d) δ 8.40 (brs, 1H), 7.13-7.05 (m, 2H), 7.03-6.93 (m, 2H), 5.03 (s, 1H), 4.63-4.47 (m, 2H), 4.42-4.21 (m, 3H), 3.84 (s, 2H), 3.75-3.67 (m, 1H), 3.66-3.59 (m, 1H), 3.56-3.37 (m, 6H), 3.02-2.92 (m, 2H), 2.92-2.82 (m, 2H), 2.78-2.67 (m, 2H), 2.64-2.54 (m, 1H), 2.43 (s, 1H), 2.19-2.15 (m, 3H), 1.93-1.81 (m, 1H), 1.33-1.23 (m, 3H), 1.13-1.07 (m, 6H), 1.04-0.98 (m, 3H). LC-MS $(M+H)^+$=600.3.

Example 60: 1-((S)-7-(2,4-difluorobenzyl)-6-(hydroxymethyl)-2-methyl-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 60)

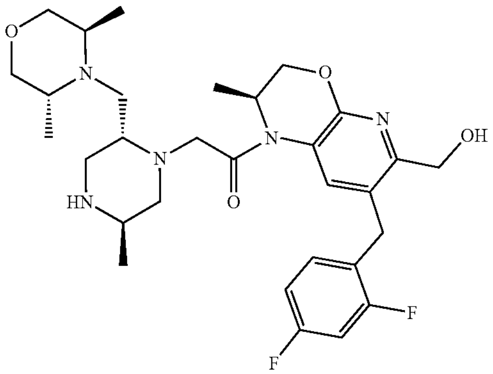 [SMILES: C[C@@H]1CN(CC(=O)N2c3cc(Cc4ccc(F)cc4F)c(CO)nc3OC[C@@H]2C)[C@@H](CN2[C@H](C)COC[C@H]2C)CN1]

Step 1: tert-butyl (S)-7-(2,4-difluorobenzyl)-2,6-dimethyl-2,3-dihydro-1H-pyrido[2,3-b][1,4]oxazine-1-carboxylate

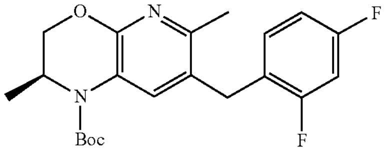 [SMILES: Cc1nc2c(cc1Cc1ccc(F)cc1F)N(C(=O)OC(C)(C)C)[C@@H](C)CO2]

The title compound of step 1 (1.5 g, 94% yield) was prepared in a manner similar to that described in Example 1 step 7 from tert-butyl (S)-7-bromo-2,6-dimethyl-2,3-dihydro-1H-pyrido[2,3-b][1,4]oxazine-1-carboxylate and (2,4-difluorobenzyl)zinc(II) chloride. LC-MS $(M+H)^+=$ 391.2.

Step 2: (S)-1-(tert-butoxycarbonyl)-7-(2,4-difluorobenzyl)-2,6-dimethyl-2,3-dihydro-1H-pyrido[2,3-b][1,4]oxazine 5-oxide

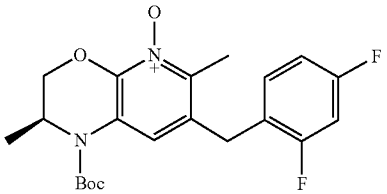

The title compound of step 2 (590 mg, 47% yield) was prepared in a manner similar to that described in Example 1 step 5 from tert-butyl (S)-7-(2,4-difluorobenzyl)-2,6-dimethyl-2,3-dihydro-1H-pyrido[2,3-b][1,4]oxazine-1-carboxylate. LC-MS $(M+H)^+=407.2$.

Step 3: tert-butyl (S)-6-(acetoxymethyl)-7-(2,4-difluorobenzyl)-2-methyl-2,3-dihydro-1H-pyrido[2,3-b][1,4]oxazine-1-carboxylate

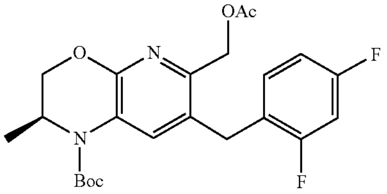 [SMILES: CC(=O)OCc1nc2c(cc1Cc1ccc(F)cc1F)N(C(=O)OC(C)(C)C)[C@@H](C)CO2]

The title compound of step 3 (540 mg, 75% yield) was prepared in a manner similar to that described in Example 8 step 2 from (S)-1-(tert-butoxycarbonyl)-7-(2,4-difluorobenzyl)-2,6-dimethyl-2,3-dihydro-1H-pyrido[2,3-b][1,4]oxazine 5-oxide. LC-MS $(M+H)^+=449.2$.

Step 4: (S)-(7-(2,4-difluorobenzyl)-2-methyl-2,3-dihydro-1H-pyrido[2,3-b][1,4]oxazin-6-yl)methyl acetate

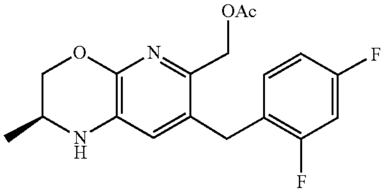 [SMILES: CC(=O)OCc1nc2c(cc1Cc1ccc(F)cc1F)N[C@@H](C)CO2]

The title compound of step 4 (150 mg, 96% yield) was prepared in a manner similar to that described in Example 1 step 8 from tert-butyl (S)-6-(acetoxymethyl)-7-(2,4-difluorobenzyl)-2-methyl-2,3-dihydro-1H-pyrido[2,3-b][1,4]oxazine-1-carboxylate. LC-MS $(M+H)^+=349.2$.

Step 5: (S)-(1-(2-chloroacetyl)-7-(2,4-difluorobenzyl)-2-methyl-2,3-dihydro-1H-pyrido[2,3-b][1,4]oxazin-6-yl)methyl acetate

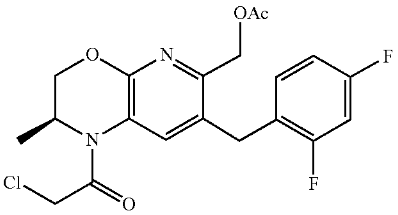 [SMILES: CC(=O)OCc1nc2c(cc1Cc1ccc(F)cc1F)N(C(=O)CCl)[C@@H](C)CO2]

The title compound of step 5 (180 mg, crude) was prepared in a manner similar to that described in Example 1 step 9 from (S)-(7-(2,4-difluorobenzyl)-2-methyl-2,3-dihydro-1H-pyrido[2,3-b][1,4]oxazin-6-yl)methyl acetate and 2-chloroacetyl chloride. LC-MS $(M+H)^+=425.1$.

Step 6: tert-butyl (2R,5S)-4-(2-((S)-6-(acetoxymethyl)-7-(2,4-difluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

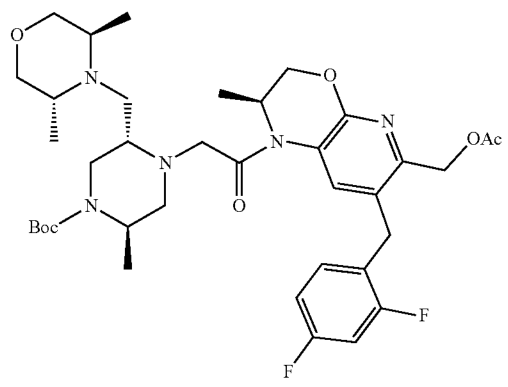 [SMILES: CC(=O)OCc1nc2c(cc1Cc1ccc(F)cc1F)N(C(=O)CN1C[C@@H](C)N(C(=O)OC(C)(C)C)C[C@@H]1CN1[C@H](C)COC[C@H]1C)[C@@H](C)CO2]

The title compound of step 6 (274 mg, 91% yield) was prepared in a manner similar to that described in Example 1 step 18 from (S)-(1-(2-chloroacetyl)-7-(2,4-difluorobenzyl)-2-methyl-2,3-dihydro-1H-pyrido[2,3-b][1,4]oxazin-6-yl) methyl acetate and tert-butyl (2R,5S)-5-(((3R,5R)-3,5-dimethylmorpholino)methyl)-2-methylpiperazine-1-carboxylate. LC-MS $(M+H)^+$=716.4.

Step 7: tert-butyl (2R,5S)-4-(2-((S)-7-(2,4-difluorobenzyl)-6-(hydroxymethyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

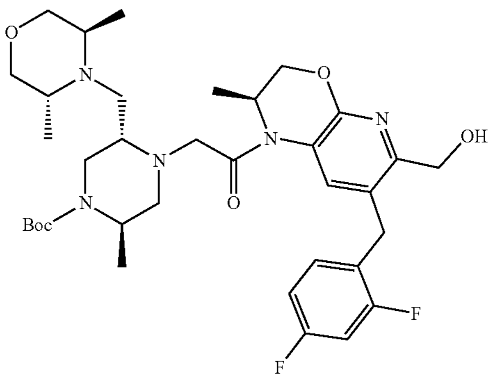 [SMILES: C[C@@H]1CN(CC(=O)N2c3cc(Cc4ccc(F)cc4F)c(CO)nc3OC[C@@H]2C)[C@@H](CN2[C@H](C)COC[C@H]2C)CN1C(=O)OC(C)(C)C]

The title compound of step 7 (218 mg, 84% yield) was prepared in a manner similar to that described in Example 8 step 4 from tert-butyl (2R,5S)-4-(2-((S)-6-(acetoxymethyl)-7-(2,4-difluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. LC-MS $(M+H)^+$=674.4.

Step 8: 1-(((S)-7-(2,4-difluorobenzyl)-6-(hydroxymethyl)-2-methyl-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 60)

Compound 60 (88 mg, 47% yield) was prepared in a manner similar to that described in Example 29 step 7 from tert-butyl (2R,5S)-4-(2-((S)-7-(2,4-difluorobenzyl)-6-(hydroxymethyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. NMR (400 MHz, Chloroform-d) δ 8.41 (brs, 1H), 7.11-7.01 (m, 1H), 6.89-6.78 (m, 2H), 5.06-5.00 (m, 1H), 4.69-4.57 (m, 2H), 4.51-4.26 (m, 3H), 3.91-3.77 (m, 2H), 3.67-3.59 (m, 2H), 3.37-3.23 (m, 3H), 3.15-3.08 (m, 1H), 2.94-2.77 (m, 4H), 2.76-2.68 (m, 1H), 2.66-2.51 (m, 2H), 2.23-2.11 (m, 2H), 1.37-1.30 (m, 3H), 1.06-1.02 (m, 3H), 1.00-0.94 (m, 6H). LC-MS $(M+H)^+$=574.3.

Example 61: (S)-1-(2-((2R,5R)-2-((3,3-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 61)

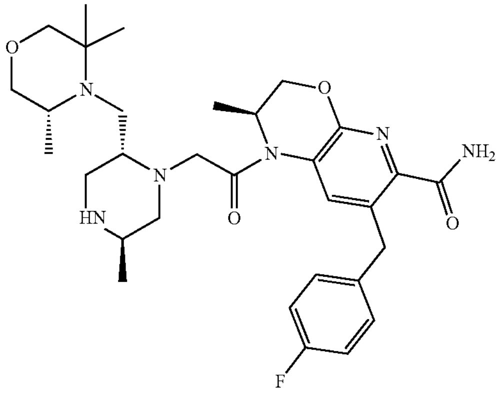 [SMILES: C[C@@H]1CN(CC(=O)N2c3cc(Cc4ccc(F)cc4)c(C(N)=O)nc3OC[C@@H]2C)[C@@H](CN2[C@H](C)COCC2(C)C)CN1]

Step 1: tert-butyl (2R,5S)-4-(2-((S)-6-carbamoyl-7-(4-fluorobenzyl)-2-methyl-2,3-dihydro-1H-pyrido[2,3-b][1,4]oxazin-1-yl)-2-oxoethyl)-5-((3,3-dimethylmorpholino)methyl) methylpiperazine-1-carboxylate

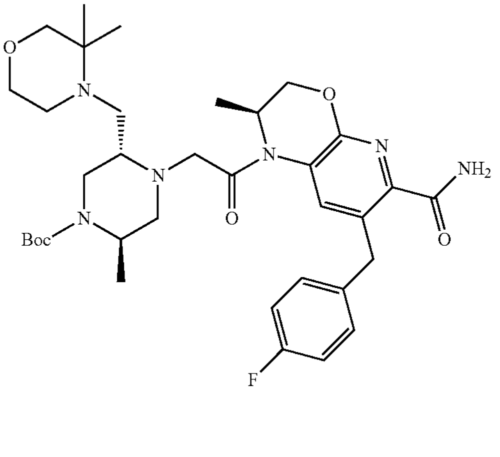 [SMILES: C[C@@H]1CN(CC(=O)N2c3cc(Cc4ccc(F)cc4)c(C(N)=O)nc3OC[C@@H]2C)[C@@H](CN2CCOCC2(C)C)CN1C(=O)OC(C)(C)C]

The title compound of step 1 (400 mg, 65% yield) was prepared in a manner similar to that described in Example 1 step 18 from (S)-1-(2-chloroacetyl)-7-(4-fluorobenzyl)-2-methyl-2,3-dihydro-1H-pyrido[2,3-b][1,4]oxazine-6-carboxamide and tert-butyl (2R,5S)-5-((3,3-dimethylmorpholino)methyl)-2-methylpiperazine-1-carboxylate. LC-MS $(M+H)^+$=669.4.

Step 2: (5)-1-(24(2R,5R)-2-((3,3-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 61)

Compound 61 (64 mg, 18% yield) was prepared in a manner similar to that in Example 29 step 7 from tert-butyl (2R,5S)-4-(2-((S)-6-carbamoyl-7-(4-fluorobenzyl)-2-methyl-2,3-dihydro-1H-pyrido[2,3-b][1,4]oxazin-1-yl)-2-oxoethyl)-5-((3,3-dimethylmorpholino)methyl)-2-methylpiperazine-1-carboxylate. $^1H$ NMR (300 MHz, Chloroform-d) δ 8.44 (brs, 1H), 7.63 (s, 1H), 7.28-7.16 (m, 2H), 7.02-6.89 (m, 2H), 5.44 (d, J=4.3 Hz, 1H), 5.01-4.92 (m, 1H), 4.58-4.45 (m, 2H), 4.42-4.25 (m, 2H), 4.20-4.09 (m, 1H), 3.68-3.59 (m, 2H), 3.33-3.08 (m, 4H), 2.89-2.76 (m, 1H), 2.75-2.66 (m, 1H), 2.60-2.34 (m, 5H), 2.22-1.99 (m, 2H), 1.37-1.28 (m, 3H), 1.06-0.98 (m, 3H), 1.06-0.86 (m, 9H). LC-MS $(M+H)^+$=569.3.

Example 62: (S)-7-(4-fluorobenzyl)-1-(2-((2R,5R)-2-(((S)-3-(isopropoxymethyl)morpholino)methyl)-5-methylpiperazin-1-yl)acetyl)-2-methyl-2,3-dihydro-1H-pyrido[2,3-b][1,4]oxazine-6-carboxamide (Compound 62)

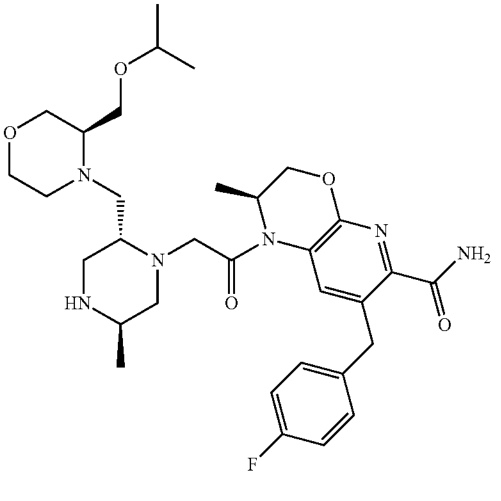 [SMILES: CC(C)OC[C@@H]1COCCN1C[C@H]1CN[C@H](C)CN1CC(=O)N1c2cc(Cc3ccc(F)cc3)c(C(N)=O)nc2OC[C@@H]1C]

Step 1: tert-butyl (2R,5S)-4-(2-((S)-6-carbamoyl-7-(4-fluorobenzyl)-2-methyl-2,3-dihydro-1H-pyrido[2,3-b][1,4]oxazin-1-yl)-2-oxoethyl)-5-(((S)-3-(isopropoxymethyl)morpholino)methyl)-2-methylpiperazine-1-carboxylate

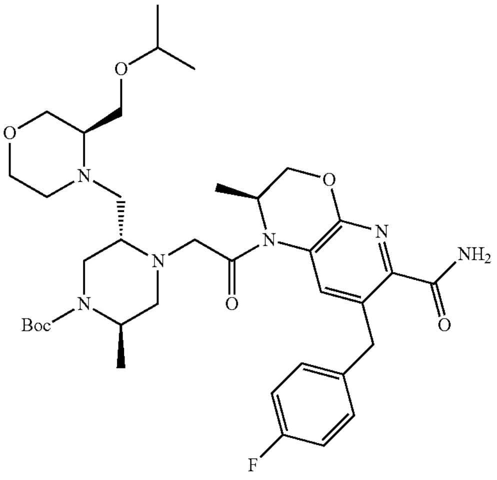 [SMILES: CC(C)OC[C@@H]1COCCN1C[C@H]1CN(C(=O)OC(C)(C)C)[C@H](C)CN1CC(=O)N1c2cc(Cc3ccc(F)cc3)c(C(N)=O)nc2OC[C@@H]1C]

The title compound of step 1 (60 mg, 63% yield) was prepared in a manner similar to that described in Example 1 step 18 from (S)-1-(2-chloroacetyl)-7-(4-fluorobenzyl)-2-methyl-2,3-dihydro-1H-pyrido[2,3-b][1,4]oxazine-6-carboxamide and tert-butyl (2R,5S)-5-(((S)-3-(isopropoxymethyl)morpholino)methyl)-2-methylpiperazine-1-carboxylate. LC-MS $(M+H)^+$=713.4.

Step 2: (S)-7-(4-fluorobenzyl)-1-(2-((2R,5R)-2-(((S)-3-(isopropoxymethyl)morpholino)methyl)-5-methylpiperazin-1-yl)acetyl)-2-methyl-2,3-dihydro-1H-pyrido[2,3-b][1,4]oxazine-6-carboxamide (Compound 62)

Compound 62 (11 mg, 22% yield) was prepared in a manner similar to that in Example 29 step 7 from tert-butyl (2R,5S)-4-(2-((S)-6-carbamoyl-7-(4-fluorobenzyl)-2-methyl-2,3-dihydro-1H-pyrido[2,3-b][1,4]oxazin-1-yl)-2-oxoethyl)-5-(((S)-3-(isopropoxymethyl)morpholino)methyl)-2-methylpiperazine-1-carboxylate. $^1H$ NMR (400 MHz, DMSO-d6) δ 8.36 (brs, 1H), 7.80 (s, 1H), 7.42 (s, 1H), 7.28-7.18 (m, 2H), 7.13-7.01 (m, 2H), 4.81-4.74 (m, 1H), 4.45-4.31 (m, 3H), 4.31-4.21 (m, 1H), 4.04-3.95 (m, 1H), 3.78-3.69 (m, 1H), 3.58-3.51 (m, 1H), 3.49-3.35 (m, 3H), 3.29-3.18 (m, 3H), 2.91-2.72 (m, 4H), 2.67-2.59 (m, 1H), 2.59-2.52 (m, 1H), 2.33-2.28 (m, 2H), 2.28-2.21 (m, 1H), 2.07-1.98 (m, 1H), 1.97-1.90 (m, 1H), 1.26-1.17 (m, 3H), 1.07-1.00 (m, 6H), 0.92-0.84 (m, 3H). LC-MS $(M+H)^+$=613.4.

Example 63: (S)—N-cyclopropyl-1-(2-42R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 63)

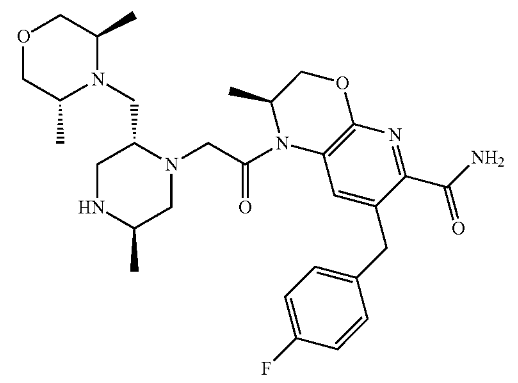 [SMILES: C[C@@H]1CN(CC(=O)N2c3cc(Cc4ccc(F)cc4)c(C(N)=O)nc3OC[C@@H]2C)[C@@H](CN2[C@H](C)COC[C@H]2C)CN1]

Step 1: tert-butyl (S)-6-(cyclopropylcarbamoyl)-7-(4-fluorobenzyl)-2-methyl-2,3-dihydro-1H-pyrido[2,3-b][1,4]oxazine-1-carboxylate

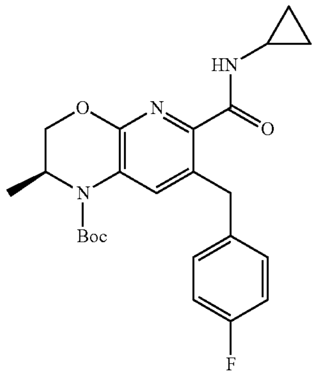 [SMILES: C[C@H]1COc2nc(C(=O)NC3CC3)c(Cc3ccc(F)cc3)cc2N1C(=O)OC(C)(C)C]

The title compound of step 1 (5.1 g, 95% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and cyclopropanamine. LC-MS $(M+H)^+=442.4$.

Step 2: (S)—N-cyclopropyl-7-(4-fluorobenzyl)-2-methyl-2,3-dihydro-1H-pyrido[2,3-b][1,4]oxazine-6-carboxamide

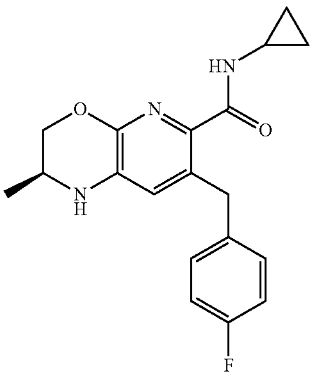 [SMILES: C[C@H]1COc2nc(C(=O)NC3CC3)c(Cc3ccc(F)cc3)cc2N1]

The title compound of step 2 (3.3 g, 84% yield) was prepared in a manner similar to that described in Example 1 step 8 from tert-butyl (S)-6-(cyclopropylcarbamoyl)-7-(4-fluorobenzyl)-2-methyl-2,3-dihydro-1H-pyrido[2,3-b][1,4]oxazine-1-carboxylate. LC-MS $(M+H)^+=342.5$.

Step 3: (S)-1-(2-chloroacetyl)-N-cyclopropyl-7-(4-fluorobenzyl)-2-methyl-2,3-dihydro-1H-pyrido[2,3-b][1,4]oxazine-6-carboxamide

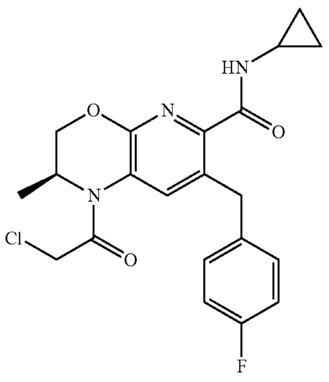 [SMILES: C[C@H]1COc2nc(C(=O)NC3CC3)c(Cc3ccc(F)cc3)cc2N1C(=O)CCl]

The title compound of step 3 (3.2 g, 79% yield) was prepared in a manner similar to that described in Example 1 step 9 from (S)—N-cyclopropyl-7-(4-fluorobenzyl)-2-methyl-2,3-dihydro-1H-pyrido[2,3-b][1,4]oxazine-6-carboxamide and 2-chloroacetyl chloride. LC-MS $(M+H)^+=418.4$.

Step 4: tert-butyl (2R,5S)-4-(2-((S)-6-(cyclopropylcarbamoyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

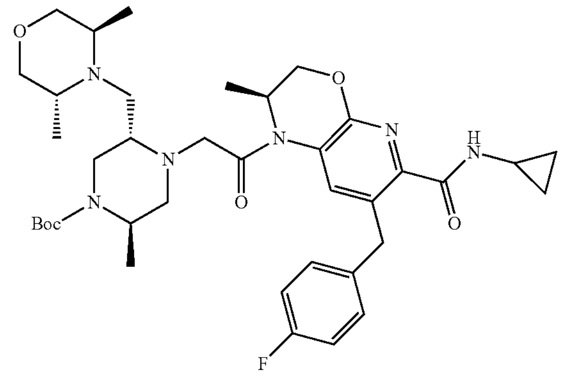 [SMILES: C[C@@H]1CN(CC(=O)N2c3cc(Cc4ccc(F)cc4)c(C(=O)NC4CC4)nc3OC[C@@H]2C)[C@@H](CN2[C@H](C)COC[C@H]2C)CN1C(=O)OC(C)(C)C]

The title compound of step 4 (220 mg, 65% yield) was prepared in a manner similar to that described in Example 1 step 18 from (S)-1-(2-chloroacetyl)-N-cyclopropyl-7-(4-fluorobenzyl)-2-methyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=709.5.

Step 5: (S)—N-cyclopropyl-1-(2-42R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 63)

Compound 63 as formic acid salt was prepared in a manner similar to that described in Example 1 step 19 from tert-butyl (2R,5S)-4-(2-((S)-6-(cyclopropylcarbamoyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. The salt was neutralized with aq. $NaHCO_3$ solution and extracted with EtOAc. The combined EtOAc layers were dried, filtered and concentrated. The residue was further lyophilized to afford compound 63 (68 mg, 36% yield) as free base. $^1$H NMR (400 MHz, DMSO-d6) δ 8.38 (s, 1H), 8.32 (s, 1H), 7.26-7.19 (m, 2H), 7.11-7.06 (m, 2H), 4.73 (s, 1H), 4.36 (d, J=8.0 Hz, 1H), 4.25 (s, 3H), 3.94 (d, J=12.0 Hz, 1H), 3.55 (d, J=16.0 Hz, 1H), 3.41 (d, J=12.0 Hz, 2H), 3.07 (s, 2H), 2.94 (d, J=12.0 Hz, 2H), 2.81-2.57 (m, 7H), 2.33-2.22 (m, 2H), 1.98-1.94 (m, 1H), 1.23-1.16 (m, 3H), 0.89-0.79 (m, 9H), 0.69-0.63 (m, 2H), 0.59-0.53 (m, 2H). LC-MS $(M+H)^+$=609.6.

Example 64: (5)-1-(242R,5R)-2-(((3R,5R)-3,5-dimethylmorpholino)methyl)-5-methylpiperazin-1-yl)acetyl)-7-(4-fluorobenzyl)-2-methyl-N-(2,2,2-trifluoroethyl)-2,3-dihydro-1H-pyrido[2,3-b][1,4]oxazine-6-carboxamide (Compound 64)

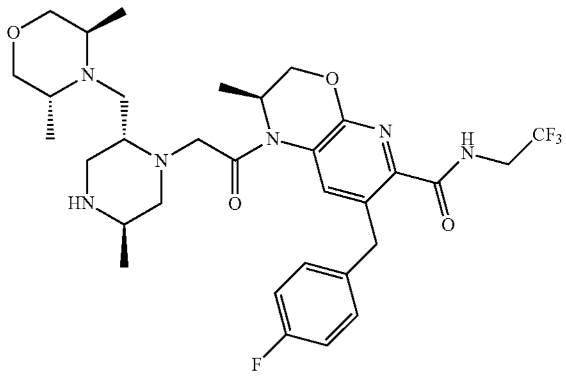 [SMILES: C[C@@H]1CN(CC(=O)N2c3cc(Cc4ccc(F)cc4)c(C(=O)NCC(F)(F)F)nc3OC[C@@H]2C)[C@@H](CN2[C@H](C)COC[C@H]2C)CN1]

Step 1: tert-butyl (S)-7-(4-fluorobenzyl)-2-methyl-6-((2,2,2-trifluoroethyl)carbamoyl)-2,3-dihydro-1H-pyrido[2,3-b][1,4]oxazine-1-carboxylate

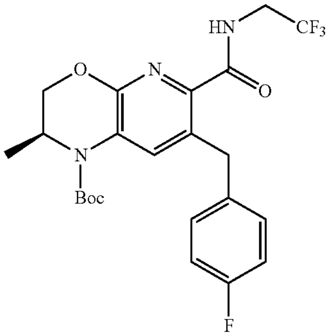 [SMILES: C[C@H]1COc2nc(C(=O)NCC(F)(F)F)c(Cc3ccc(F)cc3)cc2N1C(=O)OC(C)(C)C]

The title compound of step 1 (220 mg, 98% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and 2,2,2-trifluoroethan-1-amine. LC-MS $(M+H)^+$=484.2.

Step 2: (S)-7-(4-fluorobenzyl)-2-methyl-N-(2,2,2-trifluoroethyl)-2,3-dihydro-1H-pyrido[2,3-b][1,4]oxazine-6-carboxamide

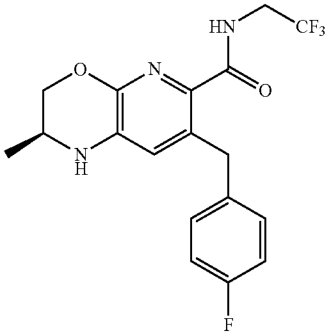 [SMILES: C[C@H]1COc2nc(C(=O)NCC(F)(F)F)c(Cc3ccc(F)cc3)cc2N1]

The title compound of step 2 (130 mg, 80% yield) was prepared in a manner similar to that described in Example 1 step 8 from tert-butyl (S)-7-(4-fluorobenzyl)-2-methyl-6-((2,2,2-trifluoroethyl)carbamoyl)-2,3-dihydro-1H-pyrido[2,3-b][1,4]oxazine-1-carboxylate. LC-MS $(M+H)^+=384.1$.

Step 3: (S)-1-(2-chloroacetyl)-7-(4-fluorobenzyl)-2-methyl-N-(2,2,2-trifluoroethyl)-2,3-dihydro-1H-pyrido[2,3-b][1,4]oxazine-6-carboxamide

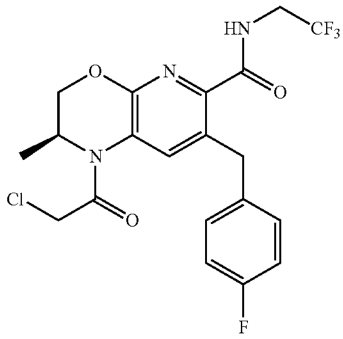 [SMILES: C[C@H]1COc2nc(C(=O)NCC(F)(F)F)c(Cc3ccc(F)cc3)cc2N1C(=O)CCl]

The title compound of step 3 (120 mg, 70% yield) was prepared in a manner similar to that described in Example 1 step 9 from (S)-7-(4-fluorobenzyl)-2-methyl-N-(2,2,2-trifluoroethyl)-2,3-dihydro-1H-pyrido[2,3-b][1,4]oxazine-6-carboxamide and 2-chloroacetyl chloride. LC-MS $(M+H)^+=460.2$.

Step 4: tert-butyl (2R,5S)-5-(((3R,5R)-3,5-dimethylmorpholino)methyl)-4-(2-((S)-7-(4-fluorobenzyl)-2-methyl-6-((2,2,2-trifluoroethyl)carbamoyl)-2,3-dihydro-1H-pyrido[2,3-b][1,4]oxazin-1-yl)-2-oxoethyl)-2-methylpiperazine-1-carboxylate

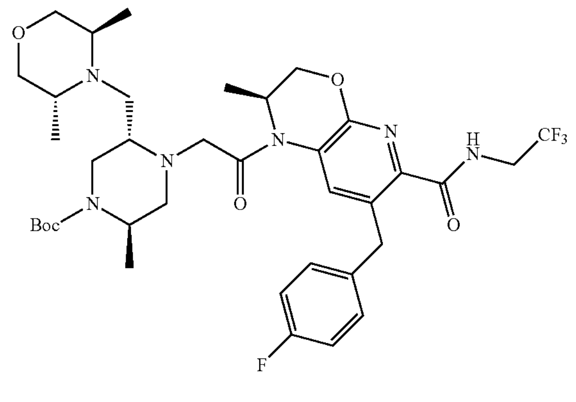 [SMILES: C[C@@H]1CN(CC(=O)N2c3cc(Cc4ccc(F)cc4)c(C(=O)NCC(F)(F)F)nc3OC[C@@H]2C)[C@@H](CN2[C@H](C)COC[C@H]2C)CN1C(=O)OC(C)(C)C]

The title compound of step 4 (130 mg, 61% yield) was prepared in a manner similar to that described in Example 1 step 18 from (S)-1-(2-chloroacetyl)-7-(4-fluorobenzyl)-2-methyl-N-(2,2,2-trifluoroethyl)-2,3-dihydro-1H-pyrido[2,3-b][1,4]oxazine-6-carboxamide and tert-butyl (2R,5S)-54(3R,5R)-3,5-dimethylmorpholino)methyl)-2-methylpiperazine-1-carboxylate. LC-MS $(M+H)^+=751.4$.

Step 5: (S)-1-(242R,5R)-2-(((3R,5R)-3,5-dimethylmorpholino)methyl)-5-methylpiperazin-1-yl)acetyl)-7-(4-fluorobenzyl)-2-methyl-N-(2,2,2-trifluoroethyl)-2,3-dihydro-1H-pyrido[2,3-b][1,4]oxazine-6-carboxamide (Compound 64)

Compound 64 as formic acid salt was prepared in a manner similar to that described in Example 1 step 19 from tert-butyl (2R,5S)-5-(((3R,5R)-3,5-dimethylmorpholino)methyl)-4-(2-((S)-7-(4-fluorobenzyl)-2-methyl-6-((2,2,2-trifluoroethyl)carbamoyl)-2,3-dihydro-1H-pyrido[2,3-b][1,4]oxazin-1-yl)-2-oxoethyl)-2-methylpiperazine-1-carboxylate. The salt was neutralized with aq. $NaHCO_3$ solution and extracted with EtOAc. The combined organic layers were dried, filtered and concentrated. The residue was further lyophilized to afford compound 64 (30 mg, 43% yield) as free base. $^1$H NMR (400 MHz, DMSO-d6) δ 9.03 (s, 1H), 8.38 (s, 1H), 7.25-7.18 (m, 2H), 7.10-7.07 (m, 2H), 4.73 (s, 1H), 4.40-4.31 (m, 4H), 4.02 (d, J=12.0 Hz, 1H), 3.65 (d, J=16.0 Hz, 1H), 3.42 (d, J=8.0 Hz, 1H), 3.08 (d, J=8.0 Hz, 3H), 2.85-2.78 (m, 3H), 2.67 (d, J=8.0 Hz, 3H), 2.43 (d, J=8.0 Hz, 2H), 2.01 (d, J=12.0 Hz, 1H), 1.22-1.17 (m, 3H), 1.00-0.94 (m, 3H), 0.88-0.81 (m, 6H). LC-MS $(M+H)^+=651.4$.

Example 65: (S)-1-(2-42R,5R)-2-(((3R,5R)-3,5-dimethylmorpholino)methyl) methylpiperazin-1-yl) acetyl)-N-ethyl-7-(4-fluorobenzyl)-2-methyl-2,3-dihydro-1H-pyrido[2,3-b][1,4]oxazine-6-carboxamide (Compound 65)

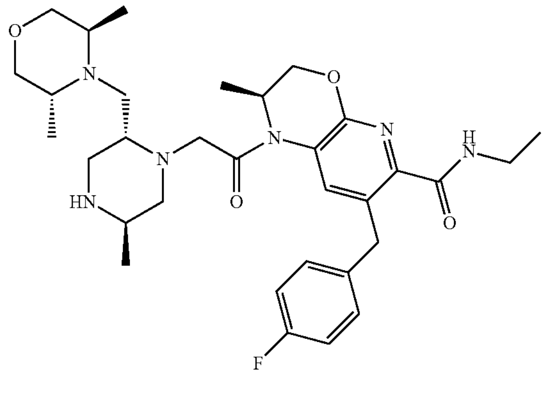 [SMILES: CCNC(=O)c1nc2c(cc1Cc1ccc(F)cc1)N(C(=O)CN1C[C@@H](C)NC[C@@H]1CN1[C@H](C)COC[C@H]1C)[C@@H](C)CO2]

Step 1: tert-butyl (S)-6-(ethylcarbamoyl)-7-(4-fluorobenzyl)-2-methyl-2,3-dihydro-1H-pyrido[2,3-b][1,4]oxazine-1-carboxylate

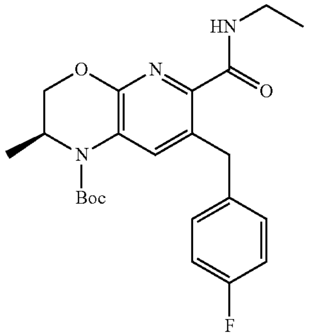 [SMILES: CCNC(=O)c1nc2c(cc1Cc1ccc(F)cc1)N(C(=O)OC(C)(C)C)[C@@H](C)CO2]

The title compound of step 1 (200 mg, 98% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and ethanamine. LC-MS $(M+H)^+$=430.2.

Step 2: (S)—N-ethyl-7-(4-fluorobenzyl)-2-methyl-2,3-dihydro-1H-pyrido[2,3-b][1,4]oxazine-6-carboxamide

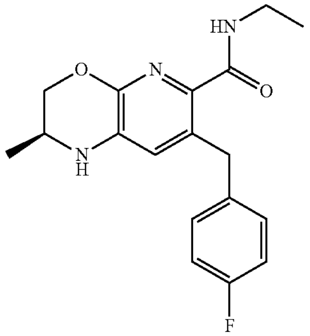 [SMILES: CCNC(=O)c1nc2c(cc1Cc1ccc(F)cc1)N[C@@H](C)CO2]

The title compound of step 2 (130 mg, 85% yield) was prepared in a manner similar to that described in Example 1 step 8 from tert-butyl (S)-6-(ethylcarbamoyl)-7-(4-fluorobenzyl)-2-methyl-2,3-dihydro-1H-pyrido[2,3-b][1,4]oxazine-1-carboxylate. LC-MS $(M+H)^+$=330.2.

Step 3: (S)-1-(2-chloroacetyl)-N-ethyl-7-(4-fluorobenzyl)-2-methyl-2,3-dihydro-1H-pyrido[2,3-b][1,4]oxazine-6-carboxamide

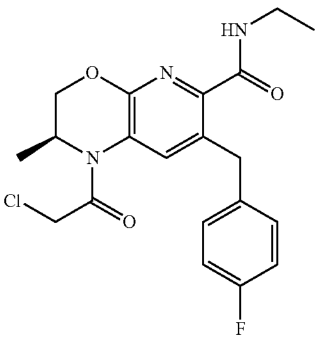 [SMILES: CCNC(=O)c1nc2c(cc1Cc1ccc(F)cc1)N(C(=O)CCl)[C@@H](C)CO2]

The title compound (110 mg, 69% yield) was prepared in a manner similar to that described in Example 1 step 9 from (S)—N-ethyl-7-(4-fluorobenzyl)-2-methyl-2,3-dihydro-1H-pyrido[2,3-b][1,4]oxazine-6-carboxamide and 2-chloroacetyl chloride. LC-MS $(M+H)^+$=406.2.

Step 4: tert-butyl (2R,5S)-5-(((3R,5R)-3,5-dimethylmorpholino)methyl)-4-(2-((S)-6-(ethyl carbamoyl)-7-(4-fluorobenzyl)-2-methyl-2,3-dihydro-1H-pyrido[2,3-b][1,4]oxazin-1-yl)-2-oxoethyl)-2-methylpiperazine-1-carboxylate

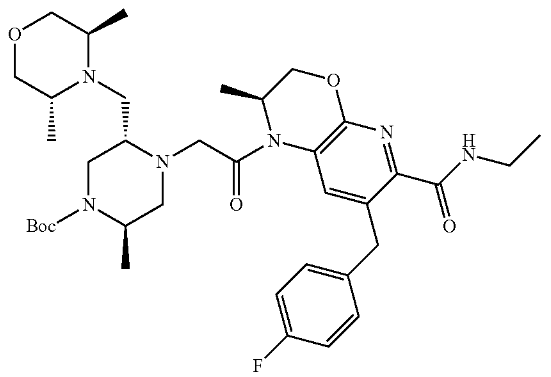 [SMILES: CCNC(=O)c1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (120 mg, 63% yield) was prepared in a manner similar to that described in Example 1 step 18 from (S)-1-(2-chloroacetyl)-N-ethyl-7-(4-fluorobenzyl)-2-methyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=697.4.

Step 5: (S)-1-(2-((2R,5R)-2-(((3R,5R)-3,5-dimethylmorpholino)methyl)-5-methylpiperazin-1-yl)acetyl)-N-ethyl-7-(4-fluorobenzyl)-2-methyl-2,3-dihydro-1H-pyrido[2,3-b][1,4]oxazine-6-carboxamide (Compound 65)

Compound 65 as formic acid salt was prepared in a manner similar to that described in Example 1 step 19 from tert-butyl (2R,5S)-5-(((3R,5R)-3,5-dimethylmorpholino)methyl)-4-(2-((S)-6-(ethylcarbamoyl)-7-(4-fluorobenzyl)-2-methyl-2,3-dihydro-1H-pyrido[2,3-b][1,4]oxazin-1-yl)-2-oxoethyl)-2-methylpiperazine-1-carboxylate. The salt was neutralized with aq. $NaHCO_3$ solution and extracted with EtOAc. The combined organic layers were dried, filtered and concentrated. The residue was further lyophilized to afford compound 65 (33 mg, 32% yield) as free base. $^1H$ NMR (400 MHz, DMSO-d6) δ 8.43 (s, 1H), 8.34 (s, 1H), 7.26-7.20 (m, 2H), 7.10-7.06 (m, 2H), 4.73 (s, 1H), 4.38-4.27 (m, 4H), 3.96 (d, J=16.0 Hz, 1H), 3.58 (d, J=16.0 Hz, 1H), 3.42 (d, J=12.0 Hz, 2H), 3.25 (s, 2H), 3.08 (s, 2H), 2.99 (d, J=8.0 Hz, 1H), 2.79-2.60 (m, 6H), 2.35-2.26 (m, 2H), 1.98 (d, J=12.0 Hz, 1H), 1.26-1.18 (m, 4H), 1.10-1.07 (m, 3H), 0.91 (s, 3H), 0.87-0.80 (m, 6H). LC-MS $(M+H)^+$=597.4.

Example 66: (S)-1-(2-42R,5R)-2-(((3R,5R)-3,5-dimethylmorpholino)methyl) methylpiperazin-1-yl) acetyl)-7-(4-fluorobenzyl)-N-(2-methoxyethyl)-2-methyl-2,3-dihydro-1H-pyrido[2,3-b][1,4]oxazine-6-carboxamide (Compound 66)

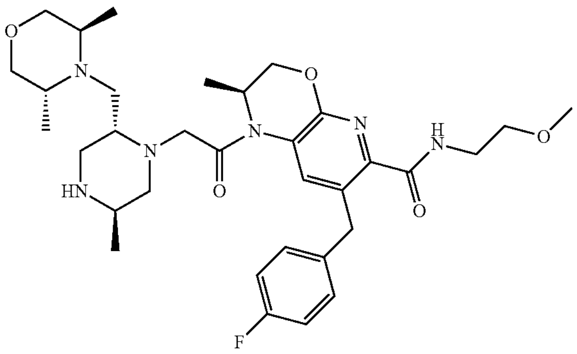 [SMILES: COCCNC(=O)c1nc2c(cc1Cc1ccc(F)cc1)N(C(=O)CN1C[C@@H](C)NC[C@@H]1CN1[C@H](C)COC[C@H]1C)[C@@H](C)CO2]

Step 1: tert-butyl (S)-7-(4-fluorobenzyl)-6-((2-methoxyethyl)carbamoyl)-2-methyl-2,3-dihydro-1H-pyrido[2,3-b][1,4]oxazine-1-carboxylate

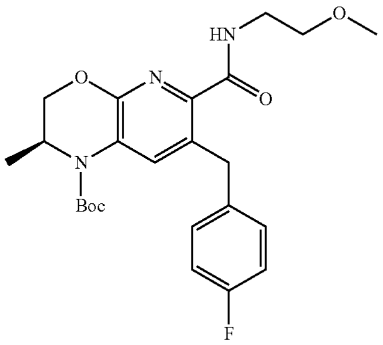

The title compound of step 1 (170 mg, 97% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and 2-methoxyethan-1-amine. LC-MS $(M+H)^+$=460.2.

Step 2: (S)-7-(4-fluorobenzyl)-N-(2-methoxyethyl)-2-methyl-2,3-dihydro-1H-pyrido[2,3-b][1,4]oxazine-6-carboxamide

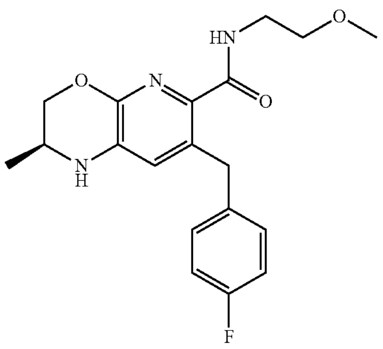

The title compound of step 2 (110 mg, 83% yield) was prepared in a manner similar to that described in Example 1 step 8 from tert-butyl (S)-7-(4-fluorobenzyl) methoxyethyl) carbamoyl)-2-methyl-2,3-dihydro-1H-pyrido[2,3-b][1,4] oxazine-1-carboxylate. LC-MS $(M+H)^+$=360.2.

Step 3: (S)-1-(2-chloroacetyl)-7-(4-fluorobenzyl)-N-(2-methoxyethyl)-2-methyl-2,3-dihydro-1H-pyrido [2,3-b][1,4]oxazine-6-carboxamide

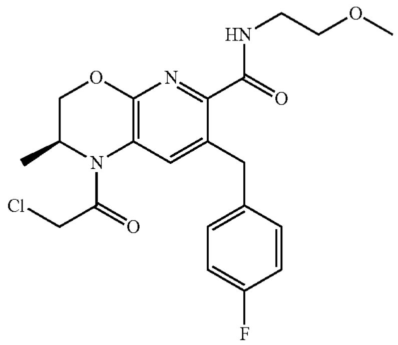

The title compound of step 3 (140 mg, 75% yield) was prepared in a manner similar to that described in Example 1 step 9 from (S)-7-(4-fluorobenzyl)-N-(2-methoxyethyl)-2-methyl-2,3-dihydro-1H-pyrido[2,3-b][1,4]oxazine-6-carboxamide and 2-chloroacetyl chloride. LC-MS $(M+H)^+$=436 2.

Step 4: tert-butyl (2R,5S)-5-(((3R,5R)-3,5-dimethylmorpholino)methyl)-4-(2-((S)-7-(4-fluorobenzyl)-6-((2-methoxyethyl)carbamoyl)-2-methyl-2,3-dihydro-1H-pyrido[2,3-b][1,4]oxazin-1-yl)-2-oxoethyl)-2-methylpiperazine-1-carboxylate

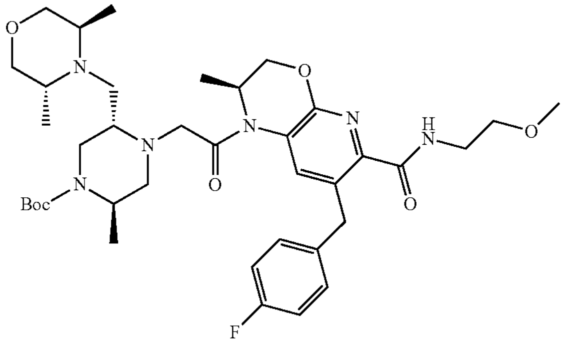 [SMILES: COCCNC(=O)c1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (160 mg, 67% yield) was prepared in a manner similar to that described in Example 1 step 18 from (S)-1-(2-chloroacetyl)-7-(4-fluorobenzyl)-N-(2-methoxyethyl)-2-methyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=727.4.

Step 5: (S)-1-(2-((2R,5R)-2-(((3R,5R)-3,5-dimethylmorpholino)methyl)-5-methylpiperazin-1-yl)acetyl)-7-(4-fluorobenzyl)-N-(2-methoxyethyl)-2-methyl-2,3-dihydro-1H-pyrido[2,3-b][1,4]oxazine-6-carboxamide (Compound 66)

Compound 66 as formic acid salt was prepared in a manner similar to that described in Example 1 step 19 from tert-butyl (2R,5S)-5-(((3R,5R)-3,5-dimethylmorpholino)methyl)-4-(2-4S)-7-(4-fluorobenzyl)-6-((2-methoxyethyl)carbamoyl)-2-methyl-2,3-dihydro-1H-pyrido[2,3-b][1,4]oxazin-1-yl)-2-oxoethyl)-2-methylpiperazine-1-carboxylate. The salt was neutralized with aq. $NaHCO_3$ solution and extracted with EtOAc. The combined organic layers were dried, filtered and concentrated. The residue was further lyophilized to afford compound 66 (56 mg, 48% yield) as free base. $^1$H NMR (400 MHz, DMSO-d6) δ 8.40 (s, 1H), 8.35 (s, 1H), 7.27-7.19 (m, 2H), 7.10-7.07 (m, 2H), 4.77 (s, 1H), 4.45-4.23 (m, 4H), 3.97 (d, J=16.0 Hz, 1H), 3.52 (d, J=16.0 Hz, 1H), 3.42 (s, 6H), 3.27 (s, 3H), 3.09 (s, 2H), 2.92 (d, J=12.0 Hz, 1H), 2.78-2.56 (m, 6H), 2.27 (t, J=12.0 Hz, 1H), 2.17 (t, J=12.0 Hz, 1H), 1.96 (d, J=12.0 Hz, 1H), 1.26-1.17 (m, 4H), 0.91-0.80 (m, 9H). LC-MS $(M+H)^+$=627.4.

Example 67: (S)-1-(2-((2R,5R)-2-(((3R,5R)-3,5-dimethylmorpholino)methyl)-5-methylpiperazin-1-yl)acetyl)-7-(4-fluorobenzyl)-N-(2-(2-methoxyethoxy)ethyl)-2-methyl-2,3-dihydro-1H-pyrido[2,3-b][1,4]oxazine-6-carboxamide (Compound 67)

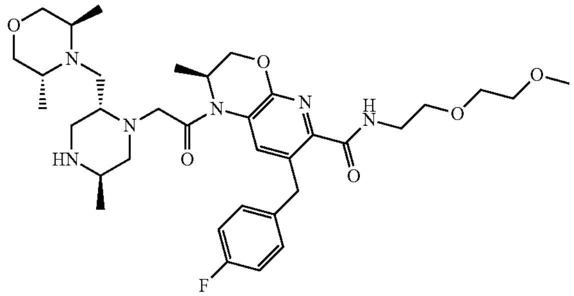 [SMILES: COCCOCCNC(=O)c1nc2c(cc1Cc1ccc(F)cc1)N(C(=O)CN1C[C@@H](C)NC[C@@H]1CN1[C@H](C)COC[C@H]1C)[C@@H](C)CO2]

Step 1: tert-butyl (S)-7-(4-fluorobenzyl)-6-((2-(2-methoxyethoxy)ethyl)carbamoyl)-2-methyl-2,3-dihydro-1H-pyrido[2,3-b][1,4]oxazine-1-carboxylate

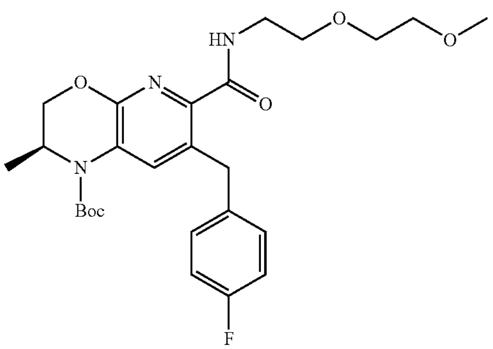

The title compound of step 1 (230 mg, 98% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and 2-(2-methoxyethoxy)ethan-1-amine. LC-MS $(M+H)^+$=504.2.

Step 2: (S)-7-(4-fluorobenzyl)-N-(2-(2-methoxyethoxy)ethyl)-2-methyl-2,3-dihydro-1H-pyrido[2,3-b][1,4]oxazine-6-carboxamide

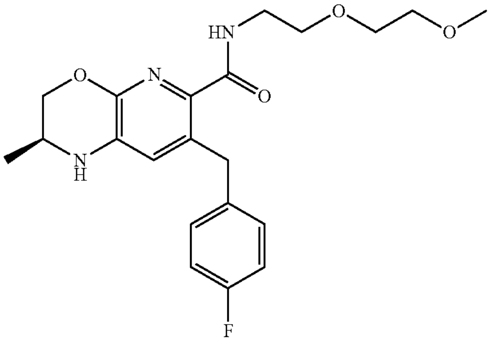

The title compound of step 2 (160 mg, 88% yield) was prepared in a manner similar to that described in Example 1 step 8 from tert-butyl (S)-7-(4-fluorobenzyl)-6-((2-(2-methoxyethoxy)ethyl)carbamoyl)-2-methyl-2,3-dihydro-1H-pyrido[2,3-b][1,4]oxazine-1-carboxylate. LC-MS $(M+H)^+$=404.2.

Step 3: (S)-1-(2-chloroacetyl)-7-(4-fluorobenzyl)-N-(2-(2-methoxyethoxy)ethyl)-2-methyl-2,3-dihydro-1H-pyrido[2,3-b][1,4]oxazine-6-carboxamide

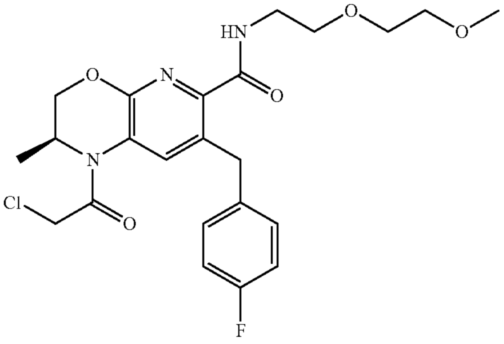

The title compound of step 3 (150 mg, 71% yield) was prepared in a manner similar to that described in Example 1 step 9 from (S)-7-(4-fluorobenzyl)-N-(2-(2-methoxyethoxy)ethyl)-2-methyl-2,3-dihydro-1H-pyrido[2,3-b][1,4]oxazine-6-carboxamide and 2-chloroacetyl chloride. LC-MS $(M+H)^+$=480.2.

Step 4: tert-butyl (2R,5S)-5-(((3R,5R)-3,5-dimethylmorpholino)methyl)-4-(2-((S)-7-(4-fluorobenzyl)-6-((2-(2-methoxyethoxy)ethyl)carbamoyl)-2-methyl-2,3-dihydro-1H-pyrido[2,3-b][1,4]oxazin-1-yl)-2-oxoethyl)-2-methylpiperazine-1-carboxylate

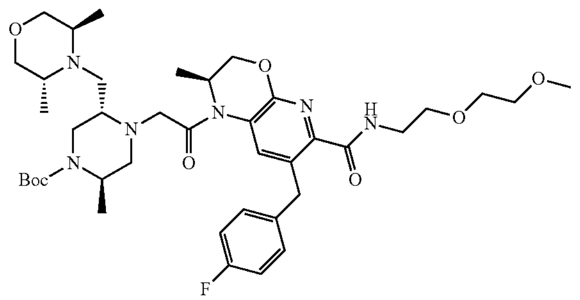 [SMILES: COCCOCCNC(=O)c1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (180 mg, 66% yield) was prepared in a manner similar to that described in Example 1 step 18 from (S)-1-(2-chloroacetyl)-7-(4-fluorobenzyl)-N-(2-(2-methoxyethoxy)ethyl)-2-methyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=771.4.

Step 5: (S)-1-(2-((2R,5R)-2-(((3R,5R)-3,5-dimethylmorpholino)methyl)-5-methylpiperazin-1-yl)acetyl)-7-(4-fluorobenzyl)-N-(2-(2-methoxyethoxy)ethyl)-2-methyl-2,3-dihydro-1H-pyrido[2,3-b][1,4]oxazine-6-carboxamide (Compound 67)

Compound 67 as formic acid salt was prepared in a manner similar to that described in Example 1 step 19 from tert-butyl (2R,5S)-5-(((3R,5R)-3,5-dimethylmorpholino)methyl)-4-(2-4S)-7-(4-fluorobenzyl)-6-((2-(2-methoxyethoxy)ethyl)carbamoyl)-2-methyl-2,3-dihydro-1H-pyrido[2,3-b][1,4]oxazin-1-yl)-2-oxoethyl)-2-methylpiperazine-1-carboxylate. The salt was neutralized with aq. $NaHCO_3$ solution and extracted with EA. The combined organic layers were dried, filtered and concentrated. The residue was further lyophilized to afford compound 67 (65 mg, 47% yield) as free base. $^1H$ NMR (400 MHz, DMSO-d6) δ 8.43 (s, 1H), 8.35 (s, 1H), 7.27-7.19 (m, 2H), 7.10-7.07 (m, 2H), 4.77 (s, 1H), 4.40-4.27 (m, 4H), 3.97 (d, J=16.0 Hz, 1H), 3.54-3.34 (m, 11H), 3.24 (s, 3H), 3.09 (s, 2H), 2.93 (d, J=8.0 Hz, 1H), 2.75 (d, J=12.0 Hz, 1H), 2.68 (s, 2H), 2.61-2.56 (m, 3H), 2.27 (t, J=12.0 Hz, 1H), 2.18 (t, J=8.0 Hz, 1H), 1.96 (d, J=12.0 Hz, 1H), 1.26-1.18 (m, 4H), 0.91-0.80 (m, 9H). LC-MS $(M+H)^+$=671.5.

Example 68: (S)-1-(2-((2R,5R)-2-(((3R,5R)-3,5-dimethylmorpholino)methyl)-5-methylpiperazin-1-yl)acetyl)-7-(4-fluorobenzyl)-N,2-dimethyl-2,3-dihydro-1H-pyrido[2,3-b][1,4]oxazine-6-carboxamide (Compound 68)

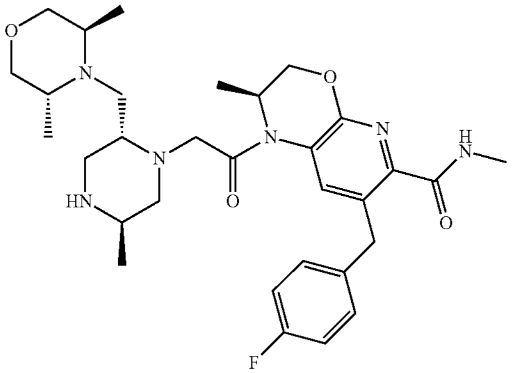

Step 1: tert-butyl (S)-7-(4-fluorobenzyl)-2-methyl-6-(methylcarbamoyl)-2,3-dihydro-1H-pyrido[2,3-b][1,4]oxazine-1-carboxylate

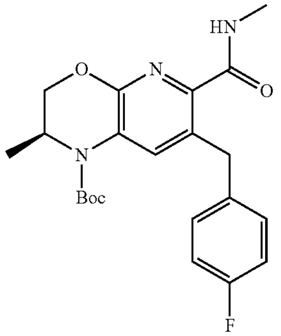 [SMILES: CNC(=O)c1nc2c(cc1Cc1ccc(F)cc1)N(C(=O)OC(C)(C)C)[C@@H](C)CO2]

The title compound of step 1 (258 mg, 96% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and methylamine. LC-MS $(M+H)^+$=416.2.

Step 2: (S)-7-(4-fluorobenzyl)-N,2-dimethyl-2,3-dihydro-1H-pyrido[2,3-b][1,4]oxazine-6-carboxamide

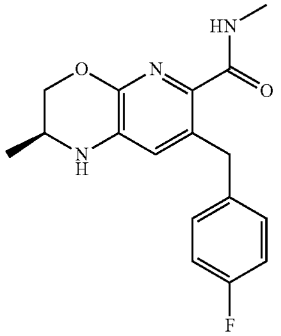

The title compound of step 2 (191 mg, 97% yield) was prepared in a manner similar to that described in Example 1 step 8 from tert-butyl (S)-7-(4-fluorobenzyl)-2-methyl (methylcarbamoyl)-2,3-dihydro-1H-pyrido[2,3-b][1,4] oxazine-1-carboxylate. LC-MS $(M+H)^+$=316.2.

Step 3: (5)-1-(2-chloroacetyl)-7-(4-fluorobenzyl)-N, 2-dimethyl-2,3-dihydro-1H-pyrido[2,3-b][1,4] oxazine-6-carboxamide

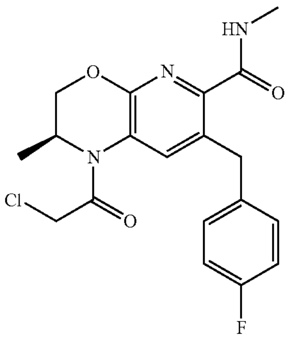

The title compound of step 3 (232 mg, 95% yield) was prepared in a manner similar to that described in Example 1 step 9 from (S)-7-(4-fluorobenzyl)-N,2-dimethyl-2,3-dihydro-1H-pyrido[2,3-b][1,4]oxazine-6-carboxamide and 2-chloroacetyl chloride. LC-MS $(M+H)^+$=392.2.

Step 4: tert-butyl (2R,5S)-5-(((3R,5R)-3,5-dimethylmorpholino)methyl)-4-(2-((S)-7-(4-fluorobenzyl)-2-methyl-6-(methylcarbamoyl)-2,3-dihydro-1H-pyrido [2,3-b][1,4]oxazin-1-yl)-2-oxoethyl)-2-methylpiperazine-1-carboxylate

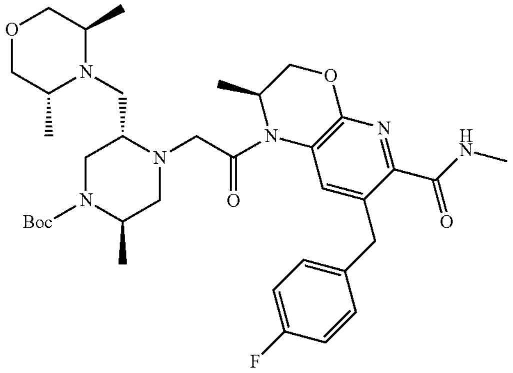 [SMILES: CNC(=O)c1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (184 mg, 62% yield) was prepared in a manner similar to that described in Example 1 step 18 from (S)-1-(2-chloroacetyl)-7-(4-fluorobenzyl)-N,2-dimethyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=683.5.

Step 5: (S)-1-(2-((2R,5R)-2-(((3R,5R)-3,5-dimethylmorpholino)methyl)-5-methyl piperazin-1-yl) acetyl)-7-(4-fluorobenzyl)-N,2-dimethyl-2,3-dihydro-1H-pyrido[2,3-b][1,4]oxazine-6-carboxamide (Compound 68)

Compound 68 (64 mg, 40% yield) was prepared in a manner similar to that described in Example 29 step 7 from tert-butyl (2R,5S)-5-(((3R,5R)-3,5-dimethylmorpholino) methyl)-4-(2-((S)-7-(4-fluorobenzyl)-2-methyl-6-(methylcarbamoyl)-2,3-dihydro-1H-pyrido[2,3-b][1,4]oxazin-1-yl)-2-oxoethyl)-2-methylpiperazine-1-carboxylate. $^1$H NMR (400 MHz, Chloroform-d) δ 8.44 (brs, 1H), 7.85-7.76 (m, 1H), 7.29-7.22 (m, 2H), 7.04-6.93 (m, 2H), 4.84-4.81 (m, 1H), 4.63-4.51 (m, 2H), 4.44-4.15 (m, 3H), 3.64-3.56 (m, 2H), 3.42-3.24 (m, 4H), 3.17-3.00 (m, 2H), 2.99-2.94 (m, 3H), 2.86-2.78 (m, 4H), 2.71-2.53 (m, 2H), 2.24-2.15 (m, 1H), 1.37-1.28 (m, 6H), 1.00-0.94 (m, 6H). LC-MS $(M+H)^+$=583.4.

Example 69: (S)-1-(2-((2R,5R)-2-(((3R,5R)-3,5-dimethylmorpholino)methyl)-5-methylpiperazin-1-yl)acetyl)-7-(4-fluorobenzyl)-N-isopropyl-2-methyl-2,3-dihydro-1H-pyrido[2,3-b][1,4]oxazine-6-carboxamide (Compound 69)

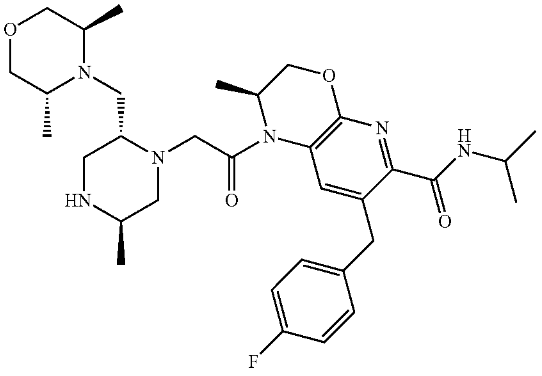 [SMILES: CC(C)NC(=O)c1nc2c(cc1Cc1ccc(F)cc1)N(C(=O)CN1C[C@@H](C)NC[C@@H]1CN1[C@H](C)COC[C@H]1C)[C@@H](C)CO2]

Step 1: tert-butyl (S)-7-(4-fluorobenzyl)-6-(isopropylcarbamoyl)-2-methyl-2,3-dihydro-1H-pyrido[2,3-b][1,4]oxazine-1-carboxylate

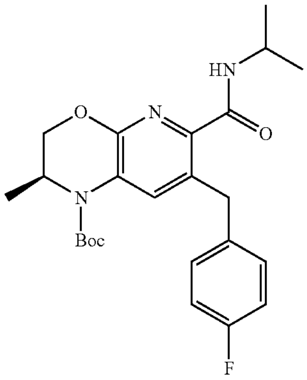 [SMILES: CC(C)NC(=O)c1nc2c(cc1Cc1ccc(F)cc1)N(C(=O)OC(C)(C)C)[C@@H](C)CO2]

The title compound of step 1 (273 mg, 95% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and isopropyl amine. LC-MS $(M+H)^+$=444.2.

Step 2: (S)-7-(4-fluorobenzyl)-N-isopropyl-2-methyl-2,3-dihydro-1H-pyrido[2,3-b][1,4]oxazine-6-carboxamide

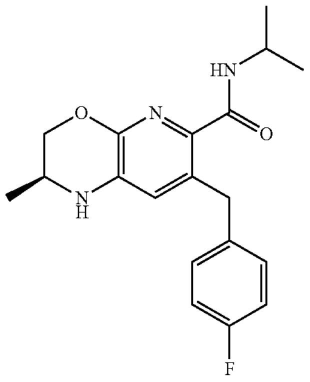 [SMILES: CC(C)NC(=O)c1nc2c(cc1Cc1ccc(F)cc1)N[C@@H](C)CO2]

The title compound of step 2 (185 mg, 87% yield) was prepared in a manner similar to that described in Example 1 step 8 from tert-butyl (S)-7-(4-fluorobenzyl)-6-(isopropylcarbamoyl)-2-methyl-2,3-dihydro-1H-pyrido[2,3-b][1,4]oxazine-1-carboxylate. LC-MS $(M+H)^+$=344.2.

Step 3: (S)-1-(2-chloroacetyl)-7-(4-fluorobenzyl)-N-isopropyl-2-methyl-2,3-dihydro-1H-pyrido[2,3-b][1,4]oxazine-6-carboxamide

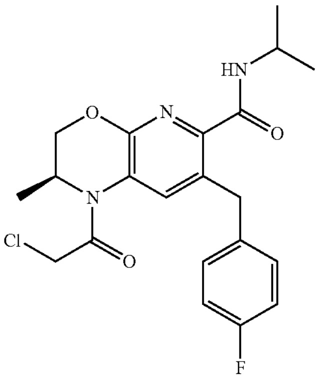 [SMILES: CC(C)NC(=O)c1nc2c(cc1Cc1ccc(F)cc1)N(C(=O)CCl)[C@@H](C)CO2]

The title compound of step 3 (223 mg, 98% yield) was prepared in a manner similar to that described in Example 1 step 9 from (S)-7-(4-fluorobenzyl)-N-isopropyl-2-methyl-2,3-dihydro-1H-pyrido[2,3-b][1,4]oxazine-6-carboxamide and 2-chloroacetyl chloride. LC-MS $(M+H)^+$=420.2.

Step 4: tert-butyl (2R,5S)-5-(((3R,5R)-3,5-dimethylmorpholino)methyl)-4-(2-((S)-7-(4-fluorobenzyl)-6-(isopropylcarbamoyl)-2-methyl-2,3-dihydro-1H-pyrido[2,3-b][1,4]oxazin-1-yl)-2-oxoethyl)-2-methylpiperazine-1-carboxylate

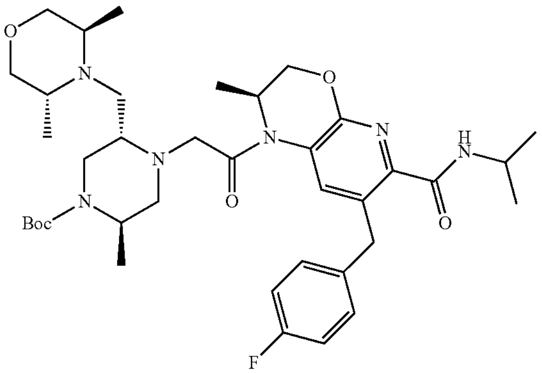

The title compound of step 4 (116 mg, 37% yield) was prepared in a manner similar to that described in Example 1 step 18 from (S)-1-(2-chloroacetyl)-7-(4-fluorobenzyl)-N-isopropyl-2-methyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=711.5.

Step 5: (S)-1-(2-42R,5R)-2-(((3R,5R)-3,5-dimethylmorpholino)methyl)-5-methylpiperazin-1-yl)acetyl)-7-(4-fluorobenzyl)-N-isopropyl-2-methyl-2,3-dihydro-1H-pyrido[2,3-b][1,4]oxazine-6-carboxamide (Compound 69)

Compound 69 (34 mg, 34% yield) was prepared in a manner similar to that described in Example 29 step 7 from tert-butyl (2R,5S)-5-(((3R,5R)-3,5-dimethylmorpholino)methyl)-4-(2-4S)-7-(4-fluorobenzyl)-6-(isopropylcarbamoyl)-2-methyl-2,3-dihydro-1H-pyrido[2,3-b][1,4]oxazin-1-yl)-2-oxoethyl)-2-methylpiperazine-1-carboxylate. $^1H$ NMR (400 MHz, Chloroform-d) δ 8.45 (brs, 1H), 7.65-7.58 (m, 1H), 7.30-7.22 (m, 2H), 7.03-6.95 (m, 2H), 4.75-4.73 (m, 1H), 4.57 (s, 2H), 4.45-4.37 (m, 1H), 4.34-4.11 (m, 3H), 3.64-3.56 (m, 2H), 3.51-3.36 (m, 2H), 3.32-3.28 (m, 2H), 3.23-3.19 (m, 2H), 2.91-2.79 (m, 4H), 2.77-2.62 (m, 2H), 2.25-2.16 (m, 1H), 1.44-1.38 (m, 3H), 1.34 (d, J=6.7 Hz, 3H), 1.30-1.23 (m, 6H), 1.00-0.94 (m, 6H). LC-MS $(M+H)^+$=611.3.

Example 70: (S)—N-(cyclopropylmethyl)-1-(2-((2R,5R)-2-(((3R,5R)-3, 5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 70)

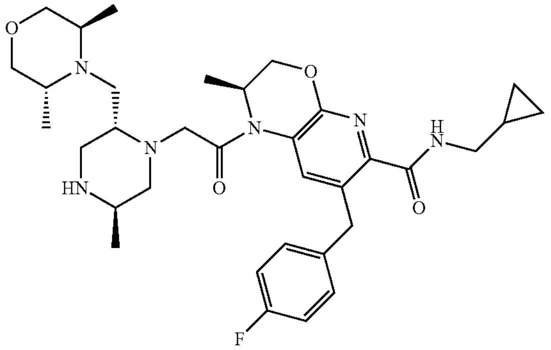 [SMILES: C[C@@H]1CN(CC(=O)N2c3cc(Cc4ccc(F)cc4)c(C(=O)NCC4CC4)nc3OC[C@@H]2C)[C@@H](CN2[C@H](C)COC[C@H]2C)CN1]

Step 1: tert-butyl (S)-6-((cyclopropylmethyl)carbamoyl)-7-(4-fluorobenzyl)-2-methyl-2,3-dihydro-1H-pyrido[2,3-b][1,4]oxazine-1-carboxylate

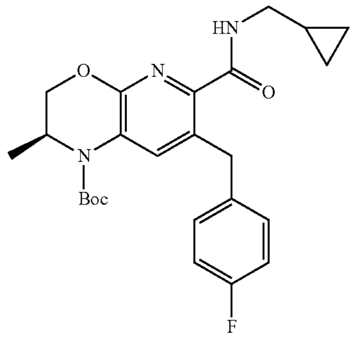 [SMILES: C[C@H]1COc2nc(C(=O)NCC3CC3)c(Cc3ccc(F)cc3)cc2N1C(=O)OC(C)(C)C]

The title compound of step 1 (290 mg, 98% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and cyclopropylmethanamine. LC-MS $(M+H)^+$= 456.2.

Step 2: (S)—N-(cyclopropylmethyl)-7-(4-fluorobenzyl)-2-methyl-2,3-dihydro-1H-pyrido[2,3-b][1,4]oxazine-6-carboxamide

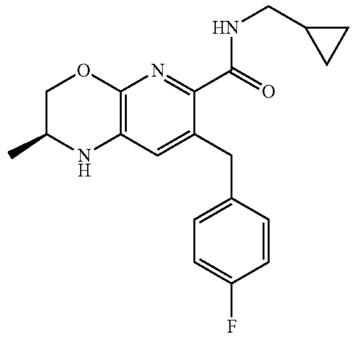 [SMILES: C[C@H]1COc2nc(C(=O)NCC3CC3)c(Cc3ccc(F)cc3)cc2N1]

The title compound of step 2 (182 mg, 71% yield) was prepared in a manner similar to that described in Example 1 step 8 from tert-butyl (S)-6-((cyclopropylmethyl)carbamoyl)-7-(4-fluorobenzyl)-2-methyl-2,3-dihydro-1H-pyrido[2,3-b][1,4]oxazine-1-carboxylate. LC-MS $(M+H)^+$=356.2.

Step 3: (S)-1-(2-chloroacetyl)-N-(cyclopropylmethyl)-7-(4-fluorobenzyl)-2-methyl-2,3-dihydro-1H-pyrido[2,3-b][1,4]oxazine-6-carboxamide

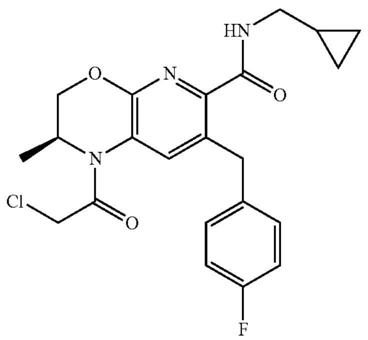 [SMILES: C[C@H]1COc2nc(C(=O)NCC3CC3)c(Cc3ccc(F)cc3)cc2N1C(=O)CCl]

The title compound of step 3 (216 mg, 96% yield) was prepared in a manner similar to that described in Example 1 step 9 from (S)—N-(cyclopropylmethyl)-7-(4-fluorobenzyl)-2-methyl-2,3-dihydro-1H-pyrido[2,3-b][1,4]oxazine-6-carboxamide and 2-chloroacetyl chloride. LC-MS $(M+H)^+$=432.2.

Step 4: tert-butyl (2R,5S)-4-(2-((S)-6-((cyclopropylmethyl)carbamoyl)-7-(4-fluorobenzyl)-2-methyl-2,3-dihydro-1H-pyrido[2,3-b][1,4]oxazin-1-yl)-2-oxoethyl)-54(3R,5R)-3,5-dimethylmorpholino)methyl)-2-methylpiperazine-1-carboxylate

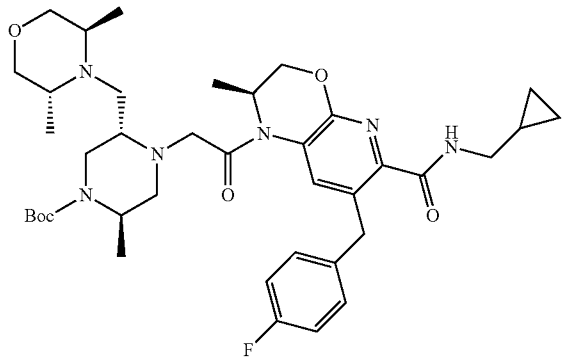 [SMILES: C[C@@H]1CN(CC(=O)N2c3cc(Cc4ccc(F)cc4)c(C(=O)NCC4CC4)nc3OC[C@@H]2C)[C@@H](CN2[C@H](C)COC[C@H]2C)CN1C(=O)OC(C)(C)C]

The title compound of step 4 (230 mg, 73% yield) was prepared in a manner similar to that described in Example 1 step 18 from (S)-1-(2-chloroacetyl)-N-(cyclopropylmethyl)-7-(4-fluorobenzyl)-2-methyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=723.5.

Step 5: (S)—N-(cyclopropylmethyl)-1-(2-((2R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 70)

Compound 70 (48 mg, 24% yield) was prepared in a manner similar to that described in Example 29 step 7 from tert-butyl (2R,5S)-4-(2-((S)-6-((cyclopropylmethyl)carbamoyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^1$H NMR (400 MHz, Chloroform-d) δ 8.40 (brs, 1H), 7.92-7.85 (m, 1H), 7.30-7.21 (m, 2H), 7.03-6.94 (m, 2H), 4.71 (s, 1H), 4.57 (s, 2H), 4.46-4.38 (m, 1H), 4.34-4.27 (m, 1H), 4.22 (s, 1H), 3.64-3.56 (m, 2H), 3.54-3.37 (m, 2H), 3.34-3.16 (m, 6H), 2.94-2.66 (m, 6H), 2.25-2.18 (m, 1H), 1.45 (d, J=6.4 Hz, 3H), 1.35 (d, J=6.7 Hz, 3H), 1.10-1.01 (m, 1H), 1.00-0.86 (m, 6H), 0.60-0.49 (m, 2H), 0.32-0.24 (m, 2H). LC-MS $(M+H)^+$=623.4.

Example 71: (S)-1-(2-42R,5R)-2-(((3R,5R)-3,5-dimethylmorpholino)methyl) methylpiperazin-1-yl) acetyl)-7-(4-fluorobenzyl)-N-(4-fluorophenyl)-2-methyl-2,3-dihydro-1H-pyrido[2,3-b][1,4]oxazine-6-carboxamide (Compound 71)

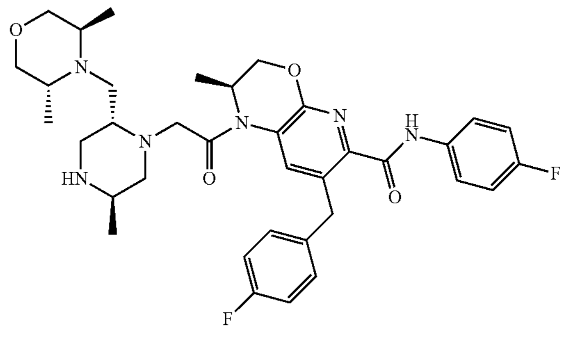 [SMILES: C[C@@H]1CN(CC(=O)N2c3cc(Cc4ccc(F)cc4)c(C(=O)Nc4ccc(F)cc4)nc3OC[C@@H]2C)[C@@H](CN2[C@H](C)COC[C@H]2C)CN1]

Step 1: tert-butyl (S)-7-(4-fluorobenzyl)-6-((4-fluorophenyl)carbamoyl)-2-methyl-2,3-dihydro-1H-pyrido[2,3-b][1,4]oxazine-1-carboxylate

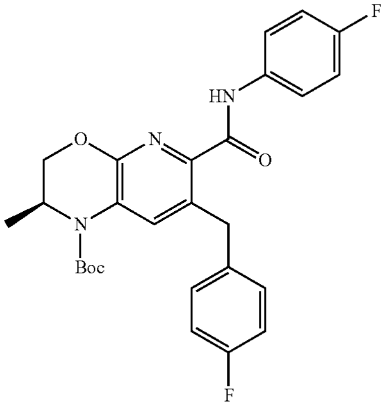 [SMILES: C[C@H]1COc2nc(C(=O)Nc3ccc(F)cc3)c(Cc3ccc(F)cc3)cc2N1C(=O)OC(C)(C)C]

The title compound of step 1 (328 mg, 76% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and 4-fluoroaniline. LC-MS $(M+H)^+=496.3$.

Step 2: (S)-7-(4-fluorobenzyl)-N-(4-fluorophenyl)-2-methyl-2,3-dihydro-1H-pyrido[2,3-b][1,4]oxazine-6-carboxamide

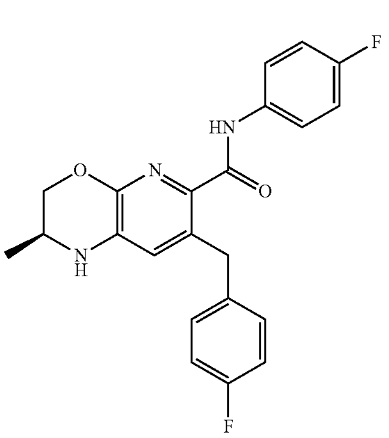 [SMILES: C[C@H]1COc2nc(C(=O)Nc3ccc(F)cc3)c(Cc3ccc(F)cc3)cc2N1]

The title compound of step 2 (250 mg, 95% yield) was prepared in a manner similar to that described in Example 1 step 8 from tert-butyl (S)-7-(4-fluorobenzyl)-6-((4-fluorophenyl)carbamoyl)-2-methyl-2,3-dihydro-1H-pyrido[2,3-b][1,4]oxazine-1-carboxylate. LC-MS $(M+H)^+=396.2$.

Step 3: (S)-1-(2-chloroacetyl)-7-(4-fluorobenzyl)-N-(4-fluorophenyl)-2-methyl-2,3-dihydro-1H-pyrido[2,3-b][1,4]oxazine-6-carboxamide

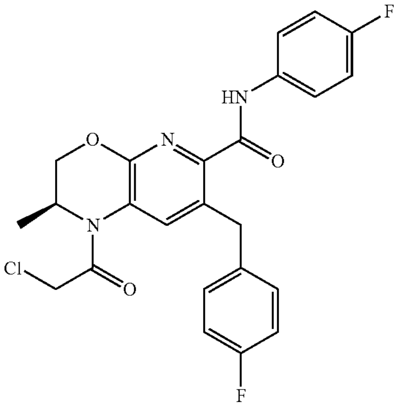 [SMILES: C[C@H]1COc2nc(C(=O)Nc3ccc(F)cc3)c(Cc3ccc(F)cc3)cc2N1C(=O)CCl]

The title compound of step 3 (200 mg, 67% yield) was prepared in a manner similar to that described in Example 1 step 9 from (S)-7-(4-fluorobenzyl)-N-(4-fluorophenyl)-2-methyl-2,3-dihydro-1H-pyrido[2,3-b][1,4]oxazine-6-carboxamide and 2-chloroacetyl chloride. LC-MS $(M+H)^+=472.2$.

Step 4: tert-butyl (2R,5S)-5-(((3R,5R)-3,5-dimethylmorpholino)methyl)-4-(2-((S)-7-(4-fluorobenzyl)-6-((4-fluorophenyl)carbamoyl)-2-methyl-2,3-dihydro-1H-pyrido[2,3-b][1,4]oxazin-1-yl)-2-oxoethyl)-2-methylpiperazine-1-carboxylate

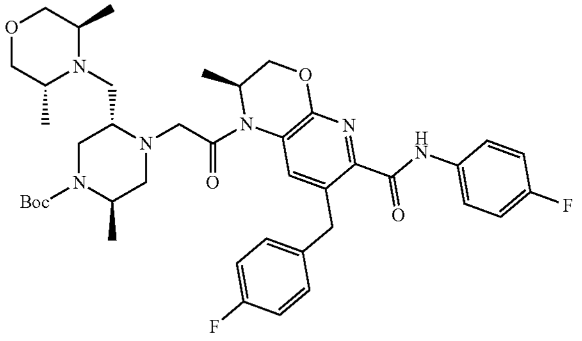 [SMILES: C[C@@H]1CN(CC(=O)N2c3cc(Cc4ccc(F)cc4)c(C(=O)Nc4ccc(F)cc4)nc3OC[C@@H]2C)[C@@H](CN2[C@H](C)COC[C@H]2C)CN1C(=O)OC(C)(C)C]

The title compound of step 4 (220 mg, 68% yield) was prepared in a manner similar to that described in Example 1 step 18 from (S)-1-(2-chloroacetyl)-7-(4-fluorobenzyl)-N-(4-fluorophenyl)-2-methyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+=763.6$.

Step 5: (S)-1-(2-((2R,5R)-2-(((3R,5R)-3,5-dimethylmorpholino)methyl)-5-methylpiperazin-1-yl)acetyl)-7-(4-fluorobenzyl)-N-(4-fluorophenyl)-2-methyl-2,3-dihydro-1H-pyrido[2,3-b][1,4]oxazine-6-carboxamide (Compound 71)

Compound 71 (66 mg, 34% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-6-((4-fluorophenyl)carbamoyl)-2-methyl-2,3-dihydro-1H-pyrido[2,3-b][1,4]oxazin-1-yl)-2-oxoethyl)-2-methylpiperazine-1-carboxylate. $^1H$ NMR (300 MHz, Chloroform-d) δ 9.66 (s, 1H), 8.35 (brs, 1H), 7.62-7.49 (m, 2H), 7.21-7.10 (m, 2H), 7.02-6.81 (m, 4H), 4.61-4.55 (m, 1H), 4.50 (s, 2H), 4.38-4.27 (m, 1H), 4.26-4.00 (m, 2H), 3.53-3.27 (m, 4H), 3.20-3.14 (m, 4H), 2.80-2.64 (m, 6H), 2.15-2.05 (m, 1H), 1.35 (d, J=6.4 Hz, 3H), 1.25 (d, J=6.7 Hz, 3H), 0.90-0.82 (m, 6H). LC-MS $(M+H)^+$=663.5.

Example 72: 2-42R,5R)-24(3R,5R)-3,5-dimethylmorpholino)methyl)-5-methylpiperazin-1-yl)-1-((S)-7-(4-fluorobenzyl)-2-methyl-6-(morpholine-4-carbonyl)-2,3-dihydro-1H-pyrido[2,3-b][1,4]oxazin-1-yl)ethan-1-one (Compound 72)

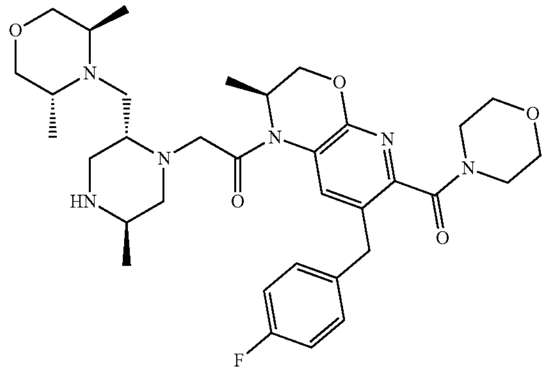 [SMILES: C[C@@H]1CN(CC(=O)N2c3cc(Cc4ccc(F)cc4)c(C(=O)N4CCOCC4)nc3OC[C@@H]2C)[C@@H](CN2[C@H](C)COC[C@H]2C)CN1]

Step 1: tert-butyl (S)-7-(4-fluorobenzyl)-2-methyl-6-(morpholine-4-carbonyl)-2,3-dihydro-1H-pyrido[2,3-b][1,4]oxazine-1-carboxylate

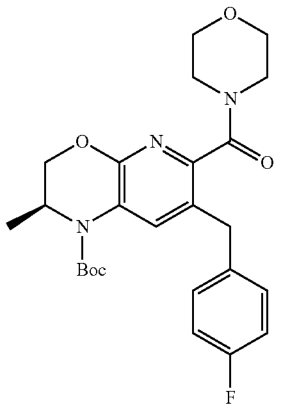 [SMILES: C[C@H]1COc2nc(C(=O)N3CCOCC3)c(Cc3ccc(F)cc3)cc2N1C(=O)OC(C)(C)C]

The title compound of step 1 (302 mg, 96% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and morpholine. LC-MS $(M+H)^+$=472.4.

Step 2: (S)-(7-(4-fluorobenzyl)-2-methyl-2,3-dihydro-1H-pyrido[2,3-b][1,4]oxazin-6-yl)(morpholino)methanone

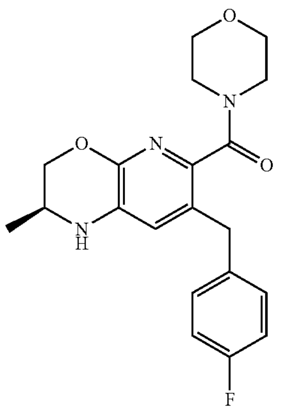 [SMILES: C[C@H]1COc2nc(C(=O)N3CCOCC3)c(Cc3ccc(F)cc3)cc2N1]

The title compound of step 2 (232 mg, 97% yield) was prepared in a manner similar to that described in Example 1 step 8 from tert-butyl (S)-7-(4-fluorobenzyl)-2-methyl-6-(morpholine-4-carbonyl)-2,3-dihydro-1H-pyrido[2,3-b][1,4]oxazine-1-carboxylate. LC-MS (M+H)=372.2.

Step 3: (S)-2-chloro-1-(7-(4-fluorobenzyl)-2-methyl-6-(morpholine-4-carbonyl)-2,3-dihydro-1H-pyrido[2,3-b][1,4]oxazin-1-yl)ethan-1-one

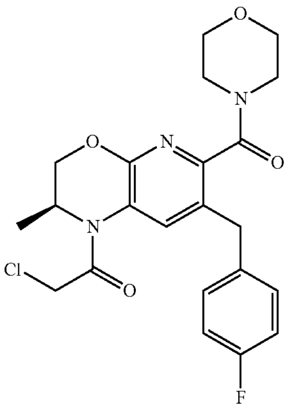 [SMILES: C[C@H]1COc2nc(C(=O)N3CCOCC3)c(Cc3ccc(F)cc3)cc2N1C(=O)CCl]

The title compound of step 3 (210 mg, 82% yield) was prepared in a manner similar to that described in Example 1 step 9 from (S)-(7-(4-fluorobenzyl)-2-methyl-2,3-dihydro-1H-pyrido[2,3-b][1,4]oxazin-6-yl)(morpholino)methanone and 2-chloroacetyl chloride. LC-MS $(M+H)^+$=448.1.

Step 4: tert-butyl (2R,5S)-5-(((3R,5R)-3,5-dimethylmorpholino)methyl)-4-(2-((S)-7-(4-fluorobenzyl)-2-methyl-6-(morpholine-4-carbonyl)-2,3-dihydro-1H-pyrido[2,3-b][1,4]oxazin-1-yl)-2-oxoethyl)-2-methylpiperazine-1-carboxylate

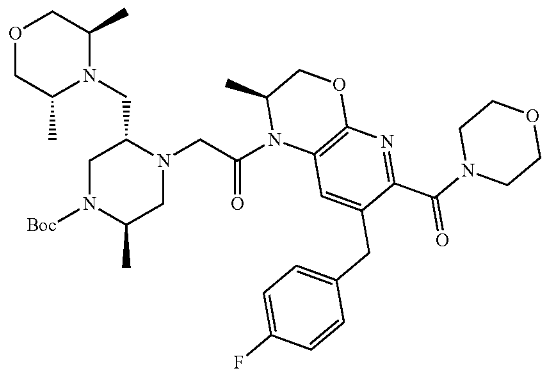 [SMILES: C[C@@H]1CN(CC(=O)N2c3cc(Cc4ccc(F)cc4)c(C(=O)N4CCOCC4)nc3OC[C@@H]2C)[C@@H](CN2[C@H](C)COC[C@H]2C)CN1C(=O)OC(C)(C)C]

The title compound of step 4 (180 mg, 52% yield) was prepared in a manner similar to that described in Example 1 step 18 from (S)-2-chloro-1-(7-(4-fluorobenzyl)-2-methyl-6-(morpholine-4-carbonyl)-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=739.4.

Step 5: 2-((2R,5R)-2-(((3R,5R)-3,5-dimethylmorpholino)methyl)-5-methylpiperazin-1-yl)-1-((S)-7-(4-fluorobenzyl)-2-methyl-6-(morpholine-4-carbonyl)-2,3-dihydro-1H-pyrido[2,3-b][1,4]oxazin-1-yl)ethan-1-one (Compound 72)

Compound 72 (74 mg, 47% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-(morpholine-4-carbonyl)-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 8.33 (brs, 1H), 7.23-7.09 (m, 4H), 4.81-4.75 (m, 1H), 4.41-4.33 (m, 1H), 4.31-4.23 (m, 1H), 4.02-3.94 (m, 1H), 3.93-3.80 (m, 2H), 3.60-3.52 (m, 5H), 3.52-3.39 (m, 3H), 3.34-3.19 (m, 2H), 3.16-3.06 (m, 2H), 3.04-2.89 (m, 3H), 2.85-2.75 (m, 1H), 2.74-2.67 (m, 2H), 2.65-2.52 (m, 3H), 2.34-2.24 (m, 1H), 2.23-2.13 (m, 1H), 2.03-1.94 (m, 1H), 1.22 (d, J=6.7 Hz, 3H), 0.92-0.83 (m, 9H). LC-MS $(M+H)^+$=639.5.

Example 73: (S)-1-(2-((2R,5R)-2-(((3R,5R)-3,5-dimethylmorpholino)methyl)-5-methylpiperazin-1-yl)acetyl)-7-(4-fluorobenzyl)-N-(2-hydroxyethyl)-2-methyl-2,3-dihydro-1H-pyrido[2,3-b][1,4]oxazine-6-carboxamide (Compound 73)

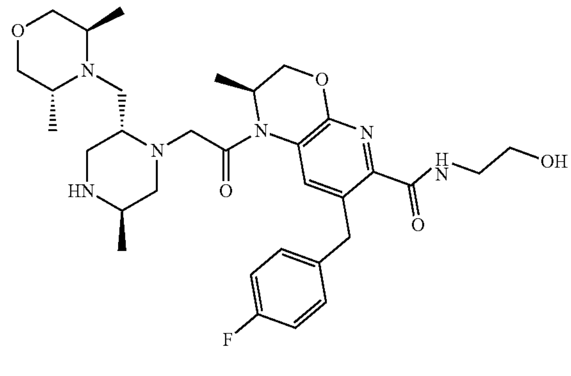 [SMILES: C[C@@H]1CN(CC(=O)N2c3cc(Cc4ccc(F)cc4)c(C(=O)NCCO)nc3OC[C@@H]2C)[C@@H](CN2[C@H](C)COC[C@H]2C)CN1]

Step 1: tert-butyl (S)-7-(4-fluorobenzyl)-6-((2-hydroxyethyl)carbamoyl)-2-methyl-2,3-dihydro-1H-pyrido[2,3-b][1,4]oxazine-1-carboxylate

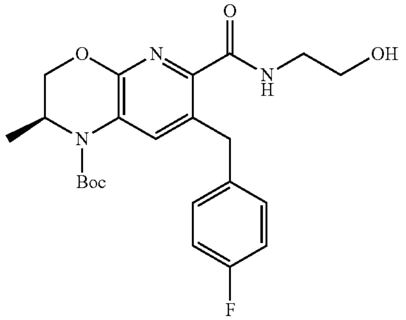 [SMILES: C[C@H]1COc2nc(C(=O)NCCO)c(Cc3ccc(F)cc3)cc2N1C(=O)OC(C)(C)C]

The title compound of step 1 (260 mg, 89% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and 2-aminoethane-1-ol. LC-MS $(M+H)^+$=446.2.

Step 2: (S)-7-(4-fluorobenzyl)-N-(2-hydroxyethyl)-2-methyl-2,3-dihydro-1H-pyrido[2,3-b][1,4]oxazine-6-carboxamide

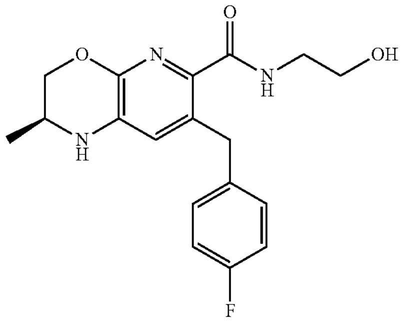 [SMILES: C[C@H]1COc2nc(C(=O)NCCO)c(Cc3ccc(F)cc3)cc2N1]

The title compound of step 2 (180 mg, 89% yield) was prepared in a manner similar to that described in Example 1 step 8 from tert-butyl (S)-7-(4-fluorobenzyl)-6-((2-hydroxyethyl)carbamoyl)-2-methyl-2,3-dihydro-1H-pyrido[2,3-b][1,4]oxazine-1-carboxylate. LC-MS $(M+H)^+$=346.2.

Step 3: (S)—N-(2-((tert-butyldimethylsilyl)oxy)ethyl)-7-(4-fluorobenzyl)-2-methyl-2,3-dihydro-1H-pyrido[2,3-b][1,4]oxazine-6-carboxamide

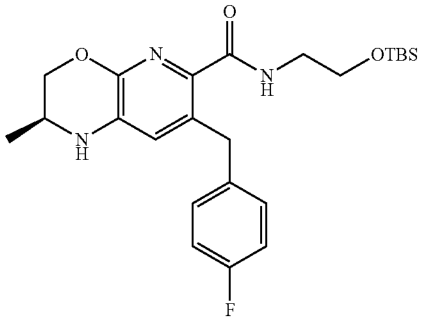 [SMILES: C[C@H]1COc2nc(C(=O)NCCO[Si](C)(C)C(C)(C)C)c(Cc3ccc(F)cc3)cc2N1]

The title compound of step 3 (190 mg, 79% yield) was prepared in a manner similar to that described in Example 54 step 1 from (S)-7-(4-fluorobenzyl)-N-(2-hydroxyethyl)-2-methyl-2,3-dihydro-1H-pyrido[2,3-b][1,4]oxazine-6-carboxamide and TBSCl. LC-MS $(M+H)^+$=460.2.

Step 4: (S)—N-(2-((tert-butyldimethylsilyl)oxy)ethyl)-1-(2-chloroacetyl)-7-(4-fluorobenzyl)-2-methyl-2,3-dihydro-1H-pyrido[2,3-b][1,4]oxazine-6-carboxamide

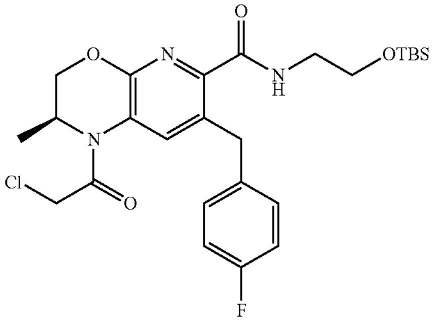 [SMILES: C[C@H]1COc2nc(C(=O)NCCO[Si](C)(C)C(C)(C)C)c(Cc3ccc(F)cc3)cc2N1C(=O)CCl]

The title compound of step 4 (167 mg, 75% yield) was prepared in a manner similar to that described in Example 1 step 9 from (S)—N-(2-((tert-butyldimethylsilyl)oxy)ethyl)-7-(4-fluorobenzyl)-2-methyl-2,3-dihydro-1H-pyrido[2,3-b][1,4]oxazine-6-carboxamide and 2-chloroacetyl chloride. LC-MS $(M+H)^+$=536.2.

Step 5: tert-butyl (2R,5S)-4-(2-((S)-6-((2-((tert-butyldimethylsilyloxy)ethyl)carbamoyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

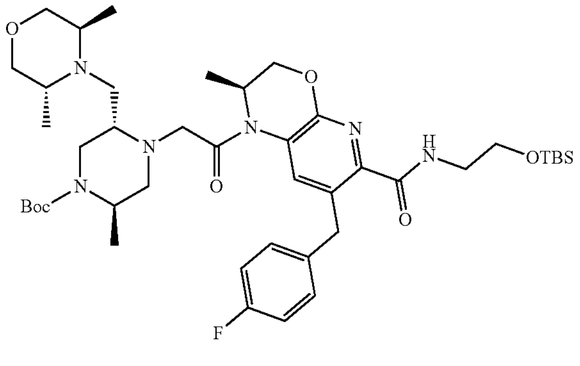 [SMILES: C[C@@H]1CN(CC(=O)N2c3cc(Cc4ccc(F)cc4)c(C(=O)NCCO[Si](C)(C)C(C)(C)C)nc3OC[C@@H]2C)[C@@H](CN2[C@H](C)COC[C@H]2C)CN1C(=O)OC(C)(C)C]

The title compound of step 5 (82 mg, 32% yield) was prepared in a manner similar to that described in Example 1 step 18 from (S)—N-(2-((tert-butyldimethylsilyl)oxy)ethyl)-1-(2-chloroacetyl)-7-(4-fluorobenzyl)-2-methyl-2,3-dihydro-1H-pyrido[2,3-b][1,4]oxazine carboxamide and tert-butyl (2R,5S)-5-(((3R,5R)-3,5-dimethylmorpholino)methyl)-2-methylpiperazine-1-carboxylate. LC-MS $(M+H)^+$=827.5.

Step 6: (S)-1-(2-((2R,5R)-2-(((3R,5R)-3,5-dimethylmorpholino)methyl)-5-methylpiperazin-1-yl)acetyl)-7-(4-fluorobenzyl)-N-(2-hydroxyethyl)-2-methyl-2,3-dihydro-1H-pyrido[2,3-b][1,4]oxazine-6-carboxamide (Compound 73)

Compound 73 (8 mg, 12% yield) was prepared in a manner similar to that described in Example 29 step 7 from tert-butyl (2R,5S)-4-(2-((S)-6-((2-((tert-butyldimethylsilyl)oxy)ethyl)carbamoyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^1$H NMR (400 MHz, DMSO-d6) δ 8.41-8.33 (m, 2H), 7.29-7.19 (m, 2H), 7.13-7.03 (m, 2H), 4.82-4.73 (m, 2H), 4.41-4.25 (m, 4H), 4.01-3.93 (m, 1H), 3.56-3.39 (m, 5H), 3.36-3.33 (m, 1H), 3.31-3.28 (m, 1H), 3.14-3.05 (m, 2H), 2.97-2.89 (m, 1H), 2.82-2.73 (m, 1H), 2.73-2.66 (m, 2H), 2.65-2.53 (m, 3H), 2.33-2.22 (m, 1H), 2.21-2.11 (m, 1H), 2.01-1.92 (m, 1H), 1.22 (d, J=6.7 Hz, 3H), 0.90-0.81 (m, 9H). LC-MS $(M+H)^+$=613.4.

Example 74: 2-((2R,5R)-2-(((3R,5R)-3,5-dimethylmorpholino)methyl)-5-methylpiperazin-1-yl)-1-((S)-7-(4-fluorobenzyl)-6-(3-hydroxyazetidine-1-carbonyl)-2-methyl-2,3-dihydro-1H-pyrido[2,3-b][1,4]oxazin-1-yl)ethan-1-one (Compound 74)

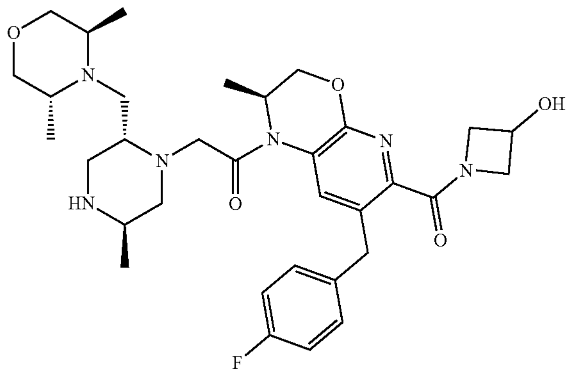 [SMILES: C[C@@H]1CN(CC(=O)N2c3cc(Cc4ccc(F)cc4)c(C(=O)N4CC(O)C4)nc3OC[C@@H]2C)[C@@H](CN2[C@H](C)COC[C@H]2C)CN1]

Step 1: tert-butyl (S)-7-(4-fluorobenzyl)-6-(3-hydroxyazetidine-1-carbonyl)-2-methyl-2,3-dihydro-1H-pyrido[2,3-b][1,4]oxazine-1-carboxylate

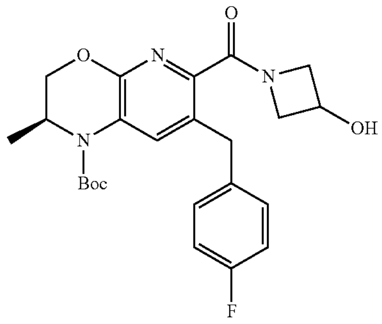 [SMILES: C[C@H]1COc2nc(C(=O)N3CC(O)C3)c(Cc3ccc(F)cc3)cc2N1C(=O)OC(C)(C)C]

The title compound of step 1 (280 mg, 93% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and azetidin-3-ol. LC-MS $(M+H)^+$=458.2.

Step 2: (S)-(7-(4-fluorobenzyl)-2-methyl-2,3-dihydro-1H-pyrido[2,3-b][1,4]oxazin-6-yl)(3-hydroxy azetidin-1-yl)methanone

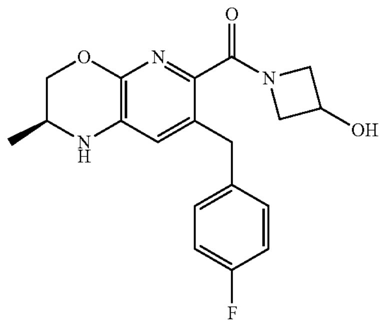 [SMILES: C[C@H]1COc2nc(C(=O)N3CC(O)C3)c(Cc3ccc(F)cc3)cc2N1]

The title compound of step 2 (180 mg, 89% yield) was prepared in a manner similar to that described in Example 1 step 8 from tert-butyl (S)-7-(4-fluorobenzyl)-6-(3-hydroxyazetidine-1-carbonyl)-2-methyl-2,3-dihydro-1H-pyrido[2,3-b][1,4]oxazine-1-carboxylate. LC-MS $(M+H)^+$=358.1.

Step 3: (S)-(3-((tert-butyldimethylsilyl)oxy)azetidin-1-yl)(7-(4-fluorobenzyl)-2-methyl-2,3-dihydro-1H-pyrido[2,3-b][1,4]oxazin-6-yl)methanone

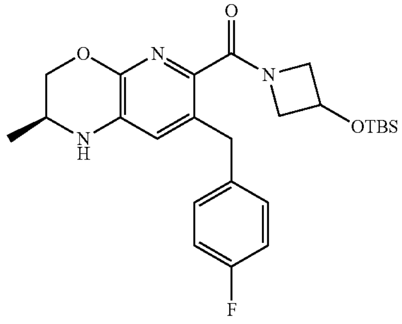 [SMILES: C[C@H]1COc2nc(C(=O)N3CC(O[Si](C)(C)C(C)(C)C)C3)c(Cc3ccc(F)cc3)cc2N1]

The title compound of step 3 (180 mg, 84% yield) was prepared in a manner similar to that described in Example 54 step 1 from (S)-(7-(4-fluorobenzyl)-2-methyl-2,3-dihydro-1H-pyrido[2,3-b][1,4]oxazin-6-yl)(3-hydroxyazetidin-1-yl) methanone and TBSCl. LC-MS $(M+H)^+$=472.2.

Step 4: (S)-1-(6-(3-((tert-butyldimethylsilyl)oxy) azetidine-1-carbonyl)-7-(4-fluorobenzyl)-2-methyl-2,3-dihydro-1H-pyrido[2,3-b][1,4]oxazin-1-yl)-2-chloroethan-1-one

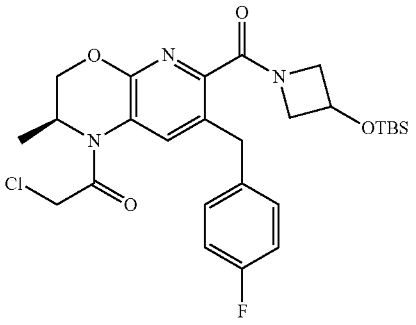 [SMILES: C[C@H]1COc2nc(C(=O)N3CC(O[Si](C)(C)C(C)(C)C)C3)c(Cc3ccc(F)cc3)cc2N1C(=O)CCl]

The title compound of step 4 (150 mg, 71% yield) was prepared in a manner similar to that described in Example 1 step 9 from (S)-(3-((tert-butyldimethylsilyl)oxy)azetidin-1-yl)(7-(4-fluorobenzyl)-2-methyl-2,3-dihydro-1H-pyrido[2,3-b][1,4]oxazin-6-yl)methanone and 2-chloroacetyl chloride. LC-MS $(M+H)^+$=548.3.

Step 5: tert-butyl (2R,5S)-4-(2-((S)-6-(3-((tert-butyldimethylsilyl)oxy)azetidine-1-carbonyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

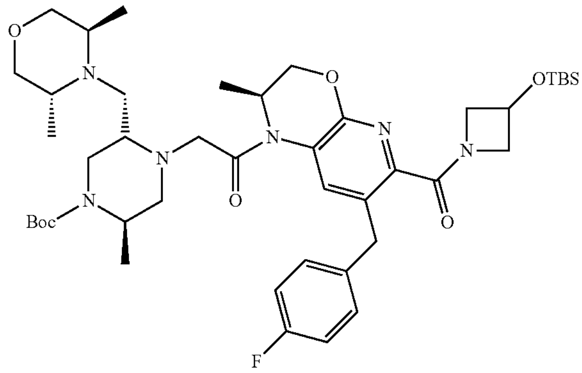

The title compound of step 5 (130 mg, 56% yield) was prepared in a manner similar to that described in Example 1 step 18 from (S)-1-(6-(3-((tert-butyldimethylsilyl)oxy)azetidine-1-carbonyl)-7-(4-fluorobenzyl)-2-methyl-2,3-dihydro-1H-pyrido[2,3-b][1,4]oxazin-1-yl)-2-chloroethan-1-one and tert-butyl (2R,5S)-5-(((3R,5R)-3,5-dimethylmorpholino)methyl)-2-methylpiperazine-1-carboxylate. LC-MS $(M+H)^+$=839.4.

Step 6: 2-((2R,5R)-2-(((3R,5R)-3,5-dimethylmorpholino)methyl)-5-methylpiperazin-1-yl)-1-((S)-7-(4-fluorobenzyl)-6-(3-hydroxyazetidine-1-carbonyl)-2-methyl-2,3-dihydro-1H-pyrido[2,3-b][1,4]oxazin-1-yl)ethan-1-one (Compound 74)

Compound 74 (28 mg, 29% yield) was prepared in a manner similar to that described in Example 29 step 7 from tert-butyl (2R,5S)-4-(2-((S)-6-(3-((tert-butyldimethylsilyl)oxy)azetidine-1-carbonyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^{1}$H NMR (400 MHz, DMSO-d6) δ 8.31 (s, 1H), 7.26-7.18 (m, 2H), 7.17-7.06 (m, 2H), 5.75-5.67 (m, 1H), 4.81-4.75 (m, 1H), 4.43-4.33 (m, 2H), 4.31-4.22 (m, 1H), 4.22-4.09 (m, 2H), 4.09-3.91 (m, 4H), 3.85-3.67 (m, 2H), 3.54-3.40 (m, 3H), 3.14-3.06 (m, 2H), 2.97-2.89 (m, 1H), 2.83-2.74 (m, 1H), 2.74-2.63 (m, 2H), 2.62-2.52 (m, 2H), 2.32-2.22 (m, 1H), 2.20-2.09 (m, 1H), 2.06-1.92 (m, 2H), 1.20 (d, J=6.6 Hz, 3H), 0.90-0.81 (m, 9H). LC-MS $(M+H)^+$=625.3.

Example 75: (5)-1-(2-((2R,5R)-2-(((3R,5R)-3,5-dimethylmorpholino)methyl)-5-methylpiperazin-1-yl)acetyl)-7-(4-fluorobenzyl)-2-methyl-N-(2-morpholinoethyl)-2,3-dihydro-1H-pyrido[2,3-b][1,4]oxazine-6-carboxamide (Compound 75)

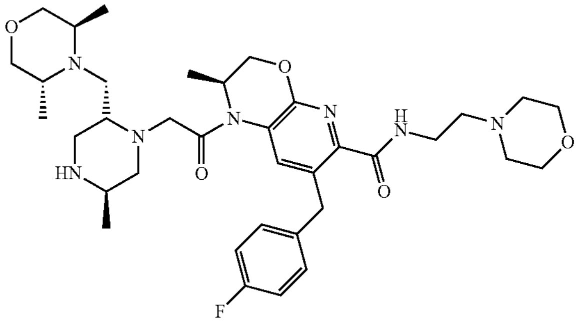

Step 1: 1-(tert-butyl) 6-methyl (S)-7-(4-fluorobenzyl)-2-methyl-2,3-dihydro-1H-pyrido[2,3-b][1,4]oxazine-1,6-dicarboxylate

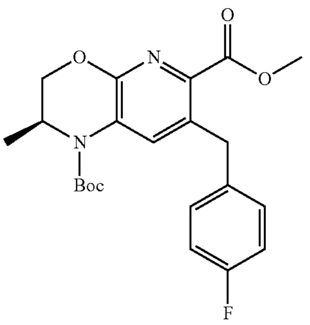

To a solution of (S)-1-(tert-butoxycarbonyl)-7-(4-fluorobenzyl)-2-methyl-2,3-dihydro-1H-pyrido[2,3-b][1,4]oxazine-6-carboxylic acid (100 mg, 0.16 mmol) and oxalic dichloride (157 mg, 1.24 mmol) in DCM (6 mL) was added DMF (0.01 mL, 0.13 mmol) dropwise at room temperature. The resulting mixture was stirred for 30 min at room temperature. When the reaction was done, the resulting mixture was concentrated under vacuum. The residue was dissolved in MeOH (10 mL). The resulting mixture was stirred for overnight at room temperature under nitrogen atmosphere. When the reaction was done, the resulting mixture was concentrated under reduced pressure to yield the title compound (63 mg, 93% yield). LC-MS $(M+H)^+$=417.2.

Step 2: methyl (S)-7-(4-fluorobenzyl)-2-methyl-2,3-dihydro-1H-pyrido[2,3-b][1,4]oxazine-6-carboxylate

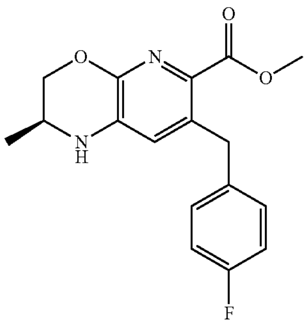

The title compound of step 2 (47 mg, 98% yield) was prepared in a manner similar to that described in Example 1 step 8 from 1-(tert-butyl) 6-methyl (S)-7-(4-fluorobenzyl)-2-methyl-2,3-dihydro-1H-pyrido[2,3-b][1,4]oxazine-1,6-dicarboxylate. LC-MS $(M+H)^+$=317.1.

Step 3: methyl (S)-1-(2-chloroacetyl)-7-(4-fluorobenzyl)-2-methyl-2,3-dihydro-1H-pyrido[2,3-b][1,4]oxazine-6-carboxylate

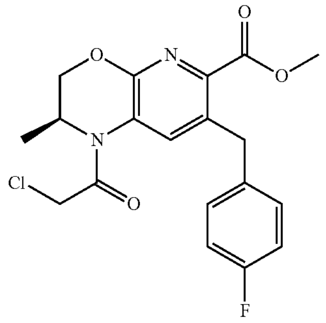

The title compound of step 3 (55 mg, 92% yield) was prepared in a manner similar to that described in Example 1 step 9 from methyl (S)-7-(4-fluorobenzyl)-2-methyl-2,3-dihydro-1H-pyrido[2,3-b][1,4]oxazine-6-carboxylate and 2-chloroacetyl chloride. LC-MS $(M+H)^+$=393.1.

Step 4: methyl (S)-1-(2-((2S,5R)-4-(tert-butoxycarbonyl)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxylate

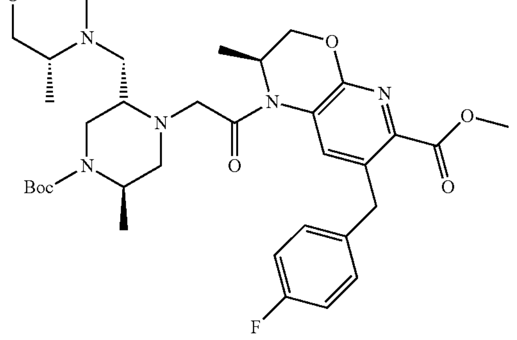

The title compound of step 4 (71 mg, 74% yield) was prepared in a manner similar to that described in Example 1 step 18 from methyl (S)-1-(2-chloroacetyl)-7-(4-fluorobenzyl)-2-methyl-2,3-dihydro-1H-pyrido[2,3-b][1,4]oxazine-6-carboxylate and tert-butyl (2R,5S)-5-(((3R,5R)-3,5-dimethylmorpholino)methyl)-2-methylpiperazine-1-carboxylate. LC-MS $(M+H)^+$=684.4.

Step 5: (S)-1-(2-((2S,5R)-4-(tert-butoxycarbonyl)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxylic acid

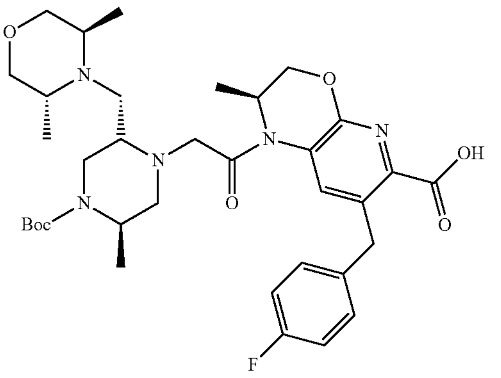

The title compound of step 5 (22 mg, 30% yield) was prepared in a manner similar to that described in Example 8 step 4 from methyl (S)-1-(2-((2S,5R)-4-(tert-butoxycarbonyl)-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxylate. LC-MS $(M+H)^+$=670.3.

Step 6: tert-butyl (2R,5S)-5-(((3R,5R)-3,5-dimethylmorpholino)methyl)-4-(2-((S)-7-(4-fluorobenzyl)-2-methyl-6-((2-morpholinoethyl)carbamoyl)-2,3-dihydro-1H-pyrido[2,3-b][1,4]oxazin-1-yl)-2-oxoethyl)-2-methylpiperazine-1-carboxylate

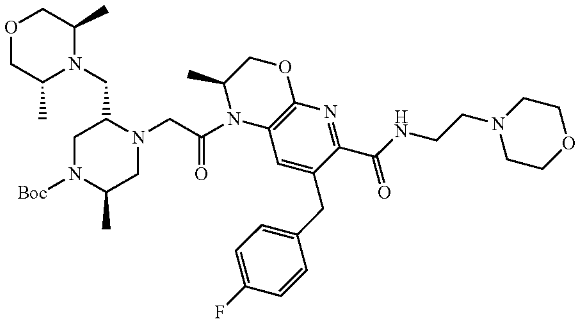

The title compound of step 6 (10 mg, 37% yield) was prepared in a manner similar to that described in Example 31 step 3 from (S)-1-(2-((2S,5R)-4-(tert-butoxycarbonyl)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxylic acid and 2-morpholinoethan-1-amine. LC-MS $(M+H)^+$=782.5.

Step 7: (S)-1-(2-42R,5R)-2-(((3R,5R)-3,5-dimethylmorpholino)methyl)-5-methylpiperazin-1-yl)acetyl)-7-(4-fluorobenzyl)-2-methyl-N-(2-morpholinoethyl)-2,3-dihydro-1H-pyrido[2,3-b][1,4]oxazine-6-carboxamide (Compound 75)

Compound 75 (3 mg, 39% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-((2-morpholinoethyl)carbamoyl)-2,3-dihydro-1H-pyrido[2,3-b][1,4]oxazin-1-yl)-2-oxoethyl)-2-methylpiperazine-1-carboxylate. $^1H$ NMR (300 MHz, Chloroform-d) δ 8.50 (brs, 1H), 8.05-7.97 (m, 1H), 7.33-7.20 (m, 2H), 7.04-6.91 (m, 2H), 5.09-5.00 (m, 1H), 4.63-4.43 (m, 2H), 4.47-4.37 (m, 2H), 4.37-4.27 (m, 1H), 3.80-3.70 (m, 4H), 3.66-3.47 (m, 4H), 3.36-3.23 (m, 3H), 3.13-3.04 (m, 1H), 2.93-2.77 (m, 4H), 2.74-2.63 (m, 1H), 2.63-2.47 (m, 8H), 2.22-2.09 (m, 2H), 1.35 (d, J=6.7 Hz, 3H), 1.07-0.92 (m, 9H). LC-MS $(M+H)^+$=682.5.

Example 76: (5)-1-(2-((2R,5R)-2-(((3R,5R)-3,5-dimethylmorpholino)methyl)-5-methylpiperazin-1-yl)acetyl)-7-(4-fluorobenzyl)-2-methyl-N-(tetrahydro-2H-pyran-4-yl)-2,3-dihydro-1H-pyrido[2,3-b][1,4]oxazine-6-carboxamide (Compound 76)

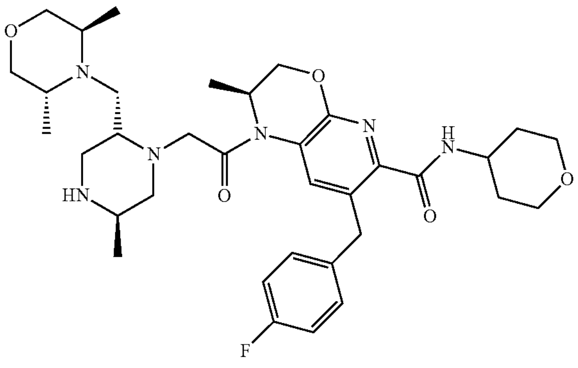

Step 1: (S)-1-((3,5-dibromo-6-methylpyridin-2-yl)oxy)propan-2-amine

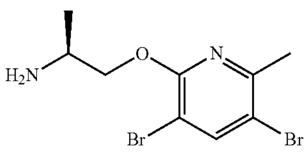

The title compound of step 1 (56.7 g, crude) was prepared in a manner similar to that described in Example 26 step 2 from 3,5-dibromo-2-chloro-6-methylpyridine and (S)-2-aminopropan-1-ol. LC-MS $(M+H)^+$=322.9.

Step 2: benzyl (S)-(1-((3,5-dibromo-6-methylpyridin-2-yl)oxy)propan-2-yl)carbamate

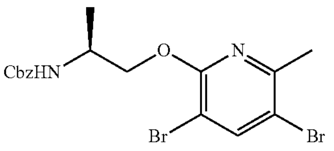 [SMILES: Cc1nc(OC[C@H](C)NC(=O)OCc2ccccc2)c(Br)cc1Br]

$K_2CO_3$ (53.2 g, 385.9 mol) in $H_2O$ (250 mL) was added to a solution of (S)-1-((3,5-dibromo-6-methylpyridin-2-yl)oxy)propan-2-amine (56.7 g, crude) in EtOAc (250 mL), the resulting solution was cooled to 0° C. by ice-water bath. CbzCl (29.9 g, 175.4 mmol) was added dropwise at 0° C., the resulting solution was warmed to room temperature and stirred for 1 hour. The organic phase was separated and washed with brine (100 mL), $H_2O$ (100 mL), dried over $Na_2SO_4$, and concentrated in vacuo to afford crude product, which was stirred in petroleum ether (100 mL) for 1 hour. White solid was collected by filtration and dried in vacuo to give the title product (70.8 g, 88% yield for 2 steps). LC-MS $(M+H)^+$=457.0.

Step 3: benzyl (S)-7-bromo-2,6-dimethyl-2,3-dihydro-1H-pyrido[2,3-b][1,4]oxazine-1-carboxylate

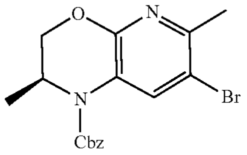 [SMILES: Cc1nc2c(cc1Br)N(C(=O)OCc1ccccc1)[C@@H](C)CO2]

To a solution of benzyl (S)-(1-((3,5-dibromo-6-methylpyridin-2-yl)oxy)propan-2-yl)carbamate (70.8 g, 155.3 mmol) in dioxane (300 mL) was added XantPhos (8.9 g, 15.4 mmol), $Cs_2CO_3$ (151.9 g, 465.9 mmol), and $Pd_2(dba)_3$ (7.0 g, 7.7 mmol). The resulting mixture was stirred for 12 h at 100° C. under nitrogen atmosphere. When the reaction was done, the reaction was then quenched by the addition of water (200 mL). The resulting solution was extracted with ethyl acetate (250 mL×2). The organic phases were combined, washed with brine and dried over $Na_2SO_4$. The solvent was concentrated under reduced pressure and the residue was purified by flash chromatography (PE:EtOAc=5:1) to yield the title compound (52 g, 90% yield). LC-MS $(M+H)^+$=377.0.

Step 4: benzyl (S)-7-(4-fluorobenzyl)-2,6-dimethyl-2,3-dihydro-1H-pyrido[2,3-b][1,4]oxazine-1-carboxylate

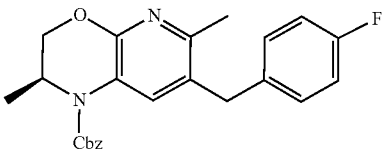 [SMILES: Cc1nc2c(cc1Cc1ccc(F)cc1)N(C(=O)OCc1ccccc1)[C@@H](C)CO2]

The title compound of step 4 (43.3 g, 77% yield) was prepared in a manner similar to that described in Example 1 step 7 from benzyl (S)-7-bromo-2,6-dimethyl-2,3-dihydro-1H-pyrido[2,3-b][1,4]oxazine-1-carboxylate and (4-fluorobenzyl)zinc(II) chloride. LC-MS $(M+H)^+$=407.2.

Step 5: (S)-1-((benzyloxy)carbonyl)-7-(4-fluorobenzyl)-2,6-dimethyl-2,3-dihydro-1H-pyrido[2,3-b][1,4]oxazine 5-oxide

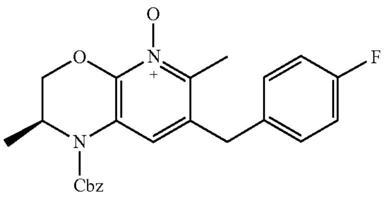

The title compound of step 5 (34.2 g, 76% yield) was prepared in a manner similar to that described in Example 1 step 5 from benzyl (S)-7-(4-fluorobenzyl)-2,6-dimethyl-2,3-dihydro-1H-pyrido[2,3-b][1,4]oxazine-1-carboxylate. LC-MS $(M+H)^+$=423.3.

Step 6: benzyl (S)-6-(acetoxymethyl)-7-(4-fluorobenzyl)-2-methyl-2,3-dihydro-1H-pyrido[2,3-b][1,4]oxazine-1-carboxylate

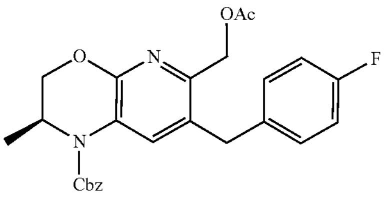 [SMILES: CC(=O)OCc1nc2c(cc1Cc1ccc(F)cc1)N(C(=O)OCc1ccccc1)[C@@H](C)CO2]

The title compound of step 6 (23.1 g, 62% yield) was prepared in a manner similar to that described in Example 8 step 2 from (S)-1-((benzyloxy)carbonyl)-7-(4-fluorobenzyl)-2,6-dimethyl-2,3-dihydro-1H-pyrido[2,3-b][1,4] oxazine 5-oxide. LC-MS $(M+H)^+$=465.2.

Step 7: benzyl (S)-7-(4-fluorobenzyl)-6-(hydroxymethyl)-2-methyl-2,3-dihydro-1H-pyrido[2,3-b][1,4]oxazine-1-carboxylate

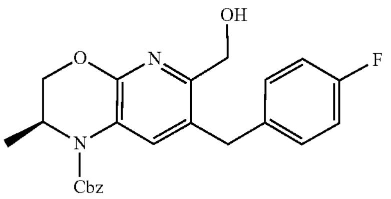 [SMILES: C[C@H]1COc2nc(CO)c(Cc3ccc(F)cc3)cc2N1C(=O)OCc1ccccc1]

The title compound of step 7 (4 g, 88% yield) was prepared in a manner similar to that described in Example 8 step 4 from benzyl (S)-6-(acetoxymethyl)-7-(4-fluorobenzyl) methyl-2,3-dihydro-1H-pyrido[2,3-b][1,4]oxazine-1-carboxylate. LC-MS $(M+H)^+$=423.2.

Step 8: benzyl (S)-7-(4-fluorobenzyl)-6-formyl-2-methyl-2,3-dihydro-1H-pyrido[2,3-b][1,4]oxazine-1-carboxylate

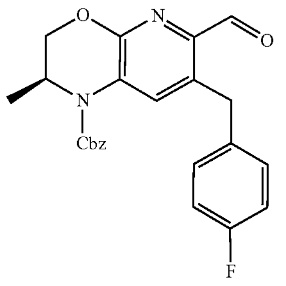 [SMILES: C[C@H]1COc2nc(C=O)c(Cc3ccc(F)cc3)cc2N1C(=O)OCc1ccccc1]

Benzyl (S)-7-(4-fluorobenzyl)-6-(hydroxymethyl)-2-methyl-2,3-dihydro-1H-pyrido[2,3-b][1,4]oxazine-1-carboxylate (4 g, 9.5 mmol) in DCM (150 mL) was added Dess-Martin Periodinane (6.0 g, 14.2 mmol), the resulting solution was stirred at room temperature for 5 hours. Water (50 mL) was added to the reaction mixture and filtered through a pad of kieselguhr, the organic layer was separated and dried over $Na_2SO_4$, filtered and concentrated. The residue was purified by silica gel column chromatography (PE:EtOAc=4:1) to afford the title product (3.7 g, 93% yield). LC-MS $(M+H)^+$=421.3.

Step 9: (S)-1-((benzyloxy)carbonyl)-7-(4-fluorobenzyl)-2-methyl-2,3-dihydro-1H-pyrido[2,3-b][1,4]oxazine-6-carboxylic acid

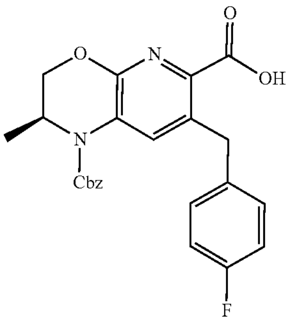 [SMILES: C[C@H]1COc2nc(C(=O)O)c(Cc3ccc(F)cc3)cc2N1C(=O)OCc1ccccc1]

benzyl (S)-7-(4-fluorobenzyl)-6-formyl-2-methyl-2,3-dihydro-1H-pyrido[2,3-b][1,4]oxazine-1-carboxylate (3.7 g, 87.9 mmol) in 1,4-dioxane (40 mL) and $H_2O$ (15 mL) was added $NH_3SO_3$ (1.1 g, 11.4 mmol), followed by addition of $NaClO_2$ (1.03 g, 11.4 mmol) slowly, the resulting solution was stirred at room temperature for 1 hour. The reaction mixture was added $H_2O$ (20 mL) and extracted with EtOAc (50 mL*3). The combined organic phase was washed with water (50 mL) and brine (50 mL), dried over $Na_2SO_4$, concentrated in vacuo to afford crude product. The residue was stirred in 50 mL of PE/EtOAc mixture (v/v=10/1) for 2 hours, solid was precipitated and collected by filtration, furtherly dried in vacuo to afford the title product (3.4 g, 89% yield). LC-MS $(M+H)^+$=437.4.

Step 10: benzyl (S)-7-(4-fluorobenzyl)-2-methyl-6-((tetrahydro-2H-pyran-4-yl)carbamoyl)-2,3-dihydro-1H-pyrido[2,3-b][1,4]oxazine-1-carboxylate

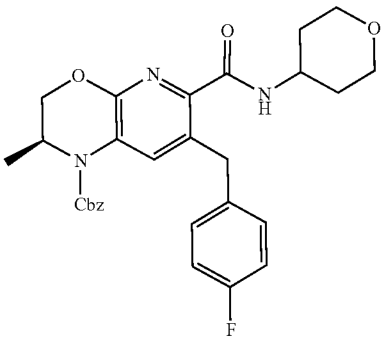 [SMILES: C[C@H]1COc2nc(C(=O)NC3CCOCC3)c(Cc3ccc(F)cc3)cc2N1C(=O)OCc1ccccc1]

The title compound of step 10 (500 mg, crude) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and tetrahydro-2H-pyran-4-amine. LC-MS $(M+H)^+$=520.4.

Step 11: (S)-7-(4-fluorobenzyl)-2-methyl-N-(tetrahydro-2H-pyran-4-yl)-2,3-dihydro-1H-pyrido[2,3-b][1,4]oxazine-6-carboxamide

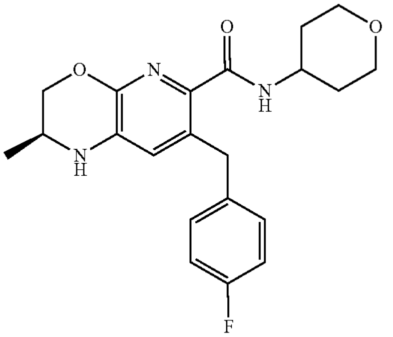 [SMILES: C[C@H]1COc2nc(C(=O)NC3CCOCC3)c(Cc3ccc(F)cc3)cc2N1]

The title compound of step 11 (387 mg, crude) was prepared in a manner similar to that described in Example 1 step 17 from benzyl (S)-7-(4-fluorobenzyl)-2-methyl-6-((tetrahydro-2H-pyran-4-yl)carbamoyl)-2,3-dihydro-1H-pyrido[2,3-b][1,4]oxazine-1-carboxylate. LC-MS $(M+H)^+$=386.3.

Step 12: (S)-1-(2-chloroacetyl)-7-(4-fluorobenzyl)-2-methyl-N-(tetrahydro-2H-pyran-4-yl)-2,3-dihydro-1H-pyrido[2,3-b][1,4]oxazine-6-carb oxamide

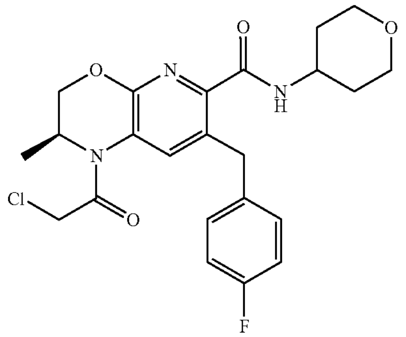 [SMILES: C[C@H]1COc2nc(C(=O)NC3CCOCC3)c(Cc3ccc(F)cc3)cc2N1C(=O)CCl]

The title compound of step 12 (370 mg, crude) was prepared in a manner similar to that described in Example 1 step 9 from (S)-7-(4-fluorobenzyl)-2-methyl-N-(tetrahydro-2H-pyran-4-yl)-2,3-dihydro-1H-pyrido[2,3-b][1,4]oxazine-6-carboxamide and 2-chloroacetyl chloride. LC-MS $(M+H)^+=462.3$.

Step 13: tert-butyl (2R,5S)-5-(((3R,5R)-3,5-dimethylmorpholino)methyl)-4-((2-4S)-7-(4-fluorobenzyl)-2-methyl-6-((tetrahydro-2H-pyran-4-yl)carbamoyl)-2,3-dihydro-1H-pyrido[2,3-b][1,4]oxazin-1-yl)-2-oxoethyl)-2-methylpiperazine-1-carboxylate

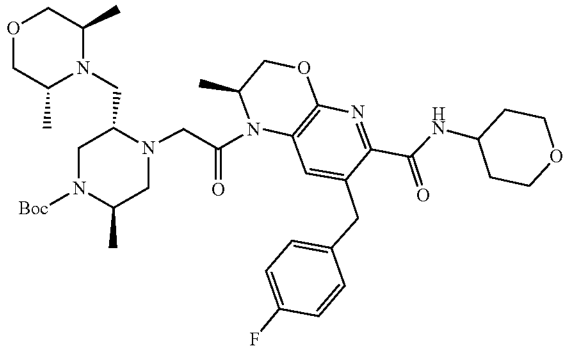 [SMILES: C[C@@H]1CN(CC(=O)N2c3cc(Cc4ccc(F)cc4)c(C(=O)NC4CCOCC4)nc3OC[C@@H]2C)[C@@H](CN2[C@H](C)COC[C@H]2C)CN1C(=O)OC(C)(C)C]

The title compound of step 13 (473 mg, 78% yield) was prepared in a manner similar to that described in Example 1 step 18 from (S)-1-(2-chloroacetyl)-7-(4-fluorobenzyl)-2-methyl-N-(tetrahydro-2H-pyran-4-yl)-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+=753.6$.

Step 14: (S)-1-(2-((2R,5R)-2-(((3R,5R)-3,5-dimethylmorpholino)methyl)-5-methylpiperazin-1-yl) acetyl)-7-(4-fluorobenzyl)-2-methyl-N-(tetrahydro-2H-pyran-4-yl)-2,3-dihydro-1H-pyrido[2,3-b][1,4] oxazine-6-carboxamide (Compound 76)

Compound 76 (190 mg, 46% yield) was prepared in a manner similar to that described in Example 29 step 7 from tert-butyl (2R,5S)-5-(((3R,5R)-3,5-dimethylmorpholino)methyl)-4-(2-4S)-7-(4-fluorobenzyl)-2-methyl-6-((tetrahydro-2H-pyran-4-yl)carbamoyl)-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 8.41-8.22 (m, 2H), 7.29-7.17 (m, 2H), 7.14-7.01 (m, 2H), 4.76 (s, 1H), 4.43-4.33 (m, 1H), 4.31-4.19 (m, 3H), 4.00-3.90 (m, 2H), 3.89-3.79 (m, 2H), 3.58-3.47 (m, 1H), 3.47-3.36 (m, 5H), 3.08 (s, 2H), 2.98-2.86 (m, 1H), 2.82-2.73 (m, 1H), 2.67 (s, 2H), 2.62-2.53 (m, 3H), 2.26 (t, J=10.0 Hz, 1H), 2.16 (t, J=10.0 Hz, 1H), 2.00-1.90 (m, 1H), 1.76-1.65 (m, 2H), 1.64-1.49 (m, 2H), 1.21 (s, 3H), 0.92-0.76 (m, 9H). LC-MS $(M+H)^+=653.7$.

Example 77: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N-((tetrahydro-2H-pyran-4-yl)methyl)-2,3-dihydro-1H-pyrido[2,3-b][1,4]oxazine-6-carboxamide (Compound 77)

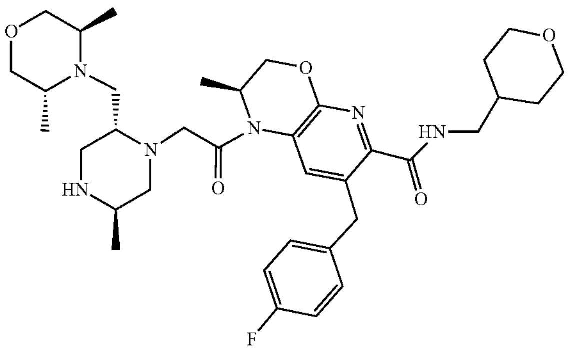 [SMILES: C[C@@H]1CN(CC(=O)N2c3cc(Cc4ccc(F)cc4)c(C(=O)NCC4CCOCC4)nc3OC[C@@H]2C)[C@@H](CN2[C@H](C)COC[C@H]2C)CN1]

Step 1: benzyl (S)-7-(4-fluorobenzyl)-2-methyl-6-(((tetrahydro-2H-pyran yl)methyl)carbamoyl)-2,3-dihydro-1H-pyrido[2,3-b][1,4]oxazine-1-carboxylate

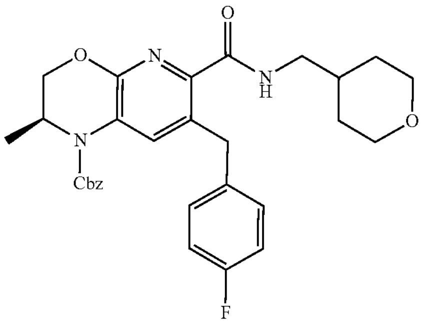 [SMILES: C[C@H]1COc2nc(C(=O)NCC3CCOCC3)c(Cc3ccc(F)cc3)cc2N1C(=O)OCc1ccccc1]

The title compound of step 1 (500 mg, crude) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and (tetrahydro-2H-pyran-4-yl)methanamine. LC-MS $(M+H)^+=534.0$.

Step 2: (S)-7-(4-fluorobenzyl)-2-methyl-N-((tetrahydro-2H-pyran-4-yl)methyl)-2,3-dihydro-1H-pyrido[2,3-b][1,4]oxazine-6-carboxamide

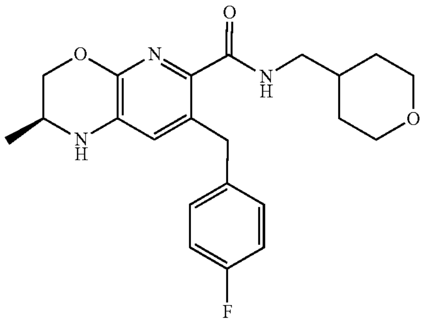 [SMILES: C[C@H]1COc2nc(C(=O)NCC3CCOCC3)c(Cc3ccc(F)cc3)cc2N1]

The title compound of step 2 (350 mg, crude) was prepared in a manner similar to that described in Example 1 step 17 from benzyl (S)-7-(4-fluorobenzyl)-2-methyl-6-(((tetrahydro-2H-pyran-4-yl)methyl)carbamoyl)-2,3-dihydro-1H-pyrido[2,3-b][1,4]oxazine-1-carboxylate. LC-MS $(M+H)^+$=400.3.

Step 3: (S)-1-(2-chloroacetyl)-7-(4-fluorobenzyl)-2-methyl-N-((tetrahydro-2H-pyran-4-yl)methyl)-2,3-dihydro-1H-pyrido[2,3-b][1,4]oxazine-6-carboxamide

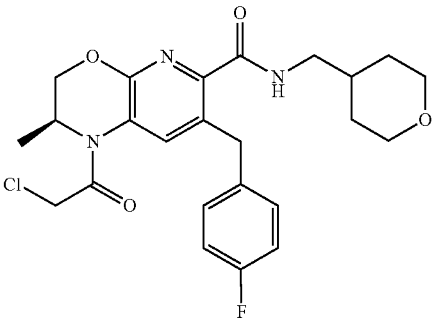 [SMILES: C[C@H]1COc2nc(C(=O)NCC3CCOCC3)c(Cc3ccc(F)cc3)cc2N1C(=O)CCl]

The title compound of step 3 (370 mg, crude) was prepared in a manner similar to that described in Example 1 step 9 from (S)-7-(4-fluorobenzyl)-2-methyl-N-((tetrahydro-2H-pyran-4-yl)methyl)-2,3-dihydro-1H-pyrido[2,3-b][1,4]oxazine-6-carboxamide and 2-chloroacetyl chloride. LC-MS $(M+H)^+$=476.3.

Step 4: tert-butyl (2R,5S)-5-(((3R,5R)-3,5-dimethylmorpholino)methyl)-4-(2-((S)-7-(4-fluorobenzyl)-2-methyl-6-(((tetrahydro-2H-pyran-4-yl)methyl)carbamoyl)-2,3-dihydro-1H-pyrido[2,3-b][1,4]oxazin-1-yl)-2-oxoethyl)-2-methylpiperazine-1-carboxylate

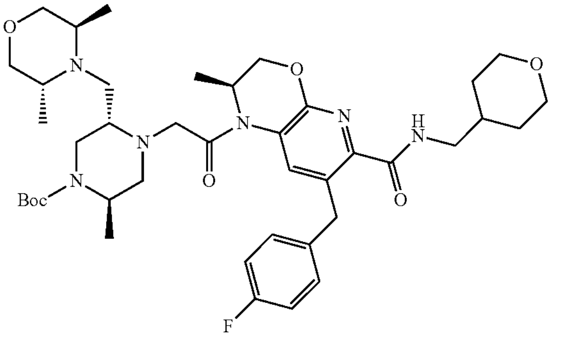 [SMILES: C[C@@H]1CN(CC(=O)N2c3cc(Cc4ccc(F)cc4)c(C(=O)NCC4CCOCC4)nc3OC[C@@H]2C)[C@@H](CN2[C@H](C)COC[C@H]2C)CN1C(=O)OC(C)(C)C]

The title compound of step 4 (340 mg, 57% yield) was prepared in a manner similar to that described in Example 1 step 18 from (S)-1-(2-chloroacetyl)-7-(4-fluorobenzyl)-2-methyl-N-((tetrahydro-2H-pyran-4-yl)methyl)-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=767.5.

Step 5: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N-((tetrahydro-2H-pyran-4-yl)methyl)-2,3-dihydro-1H-pyrido[2,3-b][1,4]oxazine-6-carboxamide (Compound 77)

Compound 77 (154 mg, 52% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-(((tetrahydro-2H-pyran-4-yl)methyl)carbamoyl)-2,3-dihydro-1H-pyrido[2,3-b][1,4]oxazin-1-yl)-2-oxoethyl)-2-methylpiperazine-1-carboxylate. $^1H$ NMR (400 MHz, DMSO-d6) δ 8.44 (s, 1H), 8.34 (s, 1H), 7.21 (s, 2H), 7.14-7.00 (m, 2H), 4.77 (s, 1H), 4.43-4.33 (m, 1H), 4.32-4.20 (s, 3H), 4.03-3.90 (m, 1H), 3.88-3.75 (m, 2H), 3.57-3.47 (m, 1H), 3.47-3.37 (m, 2H), 3.33-3.28 (m, 1H), 3.28-3.18 (m, 2H), 3.17-3.00 (m, 4H), 2.97-2.86 (m, 1H), 2.83-2.73 (m, 1H), 2.73-2.63 (m, 2H), 2.63-2.53 (m, 3H), 2.25 (t, J=10.4 Hz, 1H), 2.15 (t, J=9.9 Hz, 1H), 2.01-1.91 (m, 1H), 1.73 (s, 1H), 1.56-1.44 (m, 2H), 1.21 (s, 3H), 1.18-1.05 (m, 2H), 0.93-0.75 (m, 9H). LC-MS $(M+H)^+$=667.8.

Example 78: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N—((R)-tetrahydrofuran-3-yl)-2,3-dihydro-1H-pyrido[2,3-b][1,4]oxazine-6-carboxamide (Compound 78)

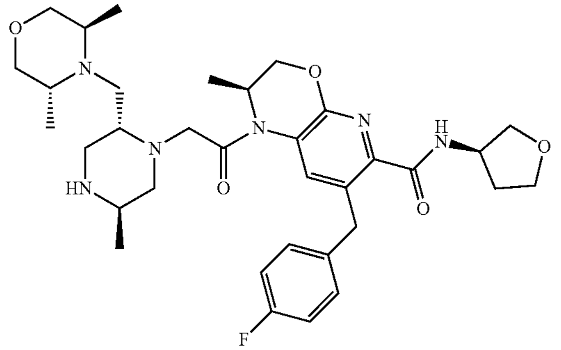 [SMILES: C[C@@H]1CN(CC(=O)N2c3cc(Cc4ccc(F)cc4)c(C(=O)N[C@@H]4CCOC4)nc3OC[C@@H]2C)[C@@H](CN2[C@H](C)COC[C@H]2C)CN1]

Step 1: benzyl (S)-7-(4-fluorobenzyl)-2-methyl-6-(((R)-tetrahydrofuran-3-yl)carbamoyl)-2,3-dihydro-1H-pyrido[2,3-b][1,4]oxazine-1-carboxylate

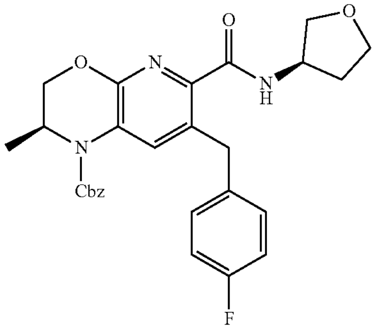 [SMILES: C[C@H]1COc2nc(C(=O)N[C@@H]3CCOC3)c(Cc3ccc(F)cc3)cc2N1C(=O)OCc1ccccc1]

The title compound of step 1 (500 mg, crude) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and (R)-tetrahydrofuran-3-amine. LC-MS $(M+H)^+=506.5$.

Step 2: (S)-7-(4-fluorobenzyl)-2-methyl-N—((R)-tetrahydrofuran-3-yl)-2,3-dihydro-1H-pyrido[2,3-b][1,4]oxazine-6-carboxamide

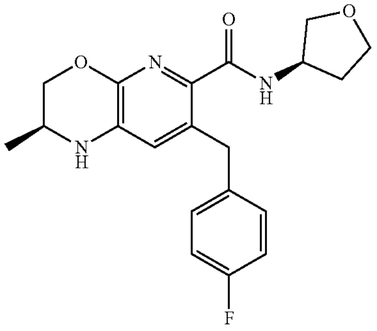 [SMILES: C[C@H]1COc2nc(C(=O)N[C@@H]3CCOC3)c(Cc3ccc(F)cc3)cc2N1]

The title compound of step 2 (390 mg, crude) was prepared in a manner similar to that described in Example 1 step 17 from benzyl (S)-7-(4-fluorobenzyl)-2-methyl-6-(((R)-tetrahydrofuran-3-yl)carbamoyl)-2,3-dihydro-1H-pyrido[2,3-b][1,4]oxazine-1-carboxylate. LC-MS $(M+H)^+=372.3$.

Step 3: (S)-1-(2-chloroacetyl)-7-(4-fluorobenzyl)-2-methyl-N—((R)-tetrahydrofuran-3-yl)-2,3-dihydro-1H-pyrido[2,3-b][1,4]oxazine-6-carboxamide

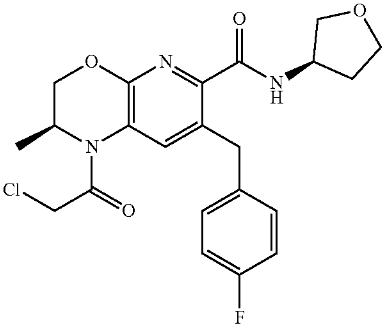 [SMILES: C[C@H]1COc2nc(C(=O)N[C@@H]3CCOC3)c(Cc3ccc(F)cc3)cc2N1C(=O)CCl]

The title compound of step 3 (347 mg, crude) was prepared in a manner similar to that described in Example 1 step 9 from (S)-7-(4-fluorobenzyl)-2-methyl-N—((R)-tetrahydrofuran-3-yl)-2,3-dihydro-1H-pyrido[2,3-b][1,4]oxazine-6-carboxamide and 2-chloroacetyl chloride. LC-MS $(M+H)^+=448.3$.

Step 4: tert-butyl (2R,5S)-5-(((3R,5R)-3,5-dimethylmorpholino)methyl)-4-(2-((S)-7-(4-fluorobenzyl)-2-methyl-6-(((R)-tetrahydrofuran-3-yl)carbamoyl)-2,3-dihydro-1H-pyrido[2,3-b][1,4]oxazin-1-yl)-2-oxoethyl)-2-methylpiperazine-1-carboxylate

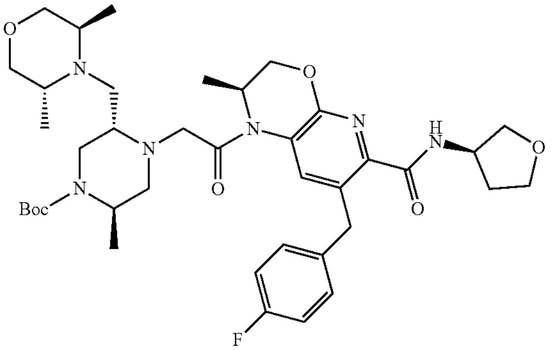 [SMILES: C[C@@H]1CN(CC(=O)N2c3cc(Cc4ccc(F)cc4)c(C(=O)N[C@@H]4CCOC4)nc3OC[C@@H]2C)[C@@H](CN2[C@H](C)COC[C@H]2C)CN1C(=O)OC(C)(C)C]

The title compound of step 4 (360 mg, 62% yield) was prepared in a manner similar to that described in Example 1 step 18 from (S)-1-(2-chloroacetyl)-7-(4-fluorobenzyl)-2-methyl-N—((R)-tetrahydrofuran-3-yl)-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+=739.5$.

Step 5: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N—((R)- tetrahydrofuran-3-yl)-2,3-dihydro-1H-pyrido[2,3-b][1,4]oxazine-6-carboxamide (Compound 78)

Compound 78 (160 mg, 51% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-(((R)-tetrahydrofuran-3-yl)carbamoyl)-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 8.47 (s, 1H), 8.34 (s, 1H), 7.23 (s, 2H), 7.14-7.02 (m, 2H), 4.76 (s, 1H), 4.47-4.33 (m, 2H), 4.32-4.18 (m, 3H), 4.02-3.90 (m, 1H), 3.87-3.76 (m, 2H), 3.76-3.66 (m, 1H), 3.59-3.48 (m, 2H), 3.47-3.38 (m, 2H), 3.33-3.28 (m, 1H), 3.08 (s, 2H), 2.97-2.85 (m, 1H), 2.83-2.72 (m, 1H), 2.67 (s, 2H), 2.62-2.53 (m, 3H), 2.25 (t, J=10.3 Hz, 1H), 2.20-2.07 (m, 2H), 2.01-1.93 (m, 1H), 1.92-1.81 (m, 1H), 1.21 (s, 3H), 0.91-0.77 (m, 9H). LC-MS $(M+H)^+$=639.7.

Example 79: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N—((S)-tetrahydrofuran-3-yl)-2,3-dihydro-1H-pyrido[2,3-b][1,4]oxazine-6-carboxamide (Compound 79)

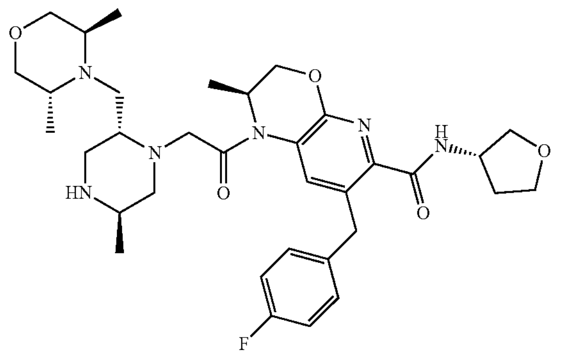 [SMILES: C[C@@H]1CN(CC(=O)N2c3cc(Cc4ccc(F)cc4)c(C(=O)N[C@H]4CCOC4)nc3OC[C@@H]2C)[C@@H](CN2[C@H](C)COC[C@H]2C)CN1]

Step 1: benzyl (S)-7-(4-fluorobenzyl)-2-methyl-6-(((S)-tetrahydrofuran-3-yl)carbamoyl)-2,3-dihydro-1H-pyrido[2,3-b][1,4]oxazine-1-carboxylate

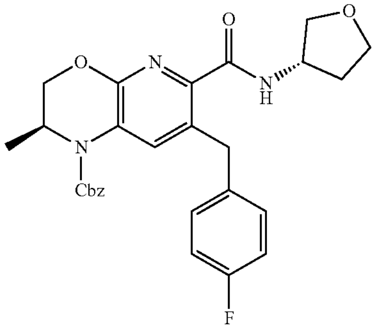 [SMILES: C[C@H]1COc2nc(C(=O)N[C@H]3CCOC3)c(Cc3ccc(F)cc3)cc2N1C(=O)OCc1ccccc1]

The title compound of step 1 (500 mg, crude) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and (S)-tetrahydrofuran-3-amine. LC-MS $(M+H)^+$=506.5.

Step 2: (S)-7-(4-fluorobenzyl)-2-methyl-N—((S)-tetrahydrofuran-3-yl)-2,3-dihydro-1H-pyrido[2,3-b][1,4]oxazine-6-carboxamide

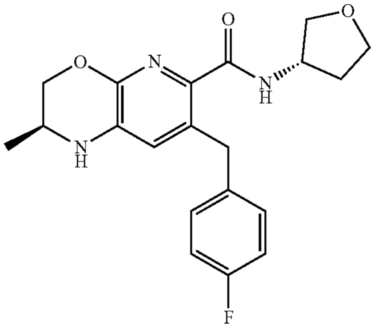 [SMILES: C[C@H]1COc2nc(C(=O)N[C@H]3CCOC3)c(Cc3ccc(F)cc3)cc2N1]

The title compound of step 2 (467 mg, crude) was prepared in a manner similar to that described in Example 1 step 17 from benzyl (S)-7-(4-fluorobenzyl)-2-methyl-6-(((S)-tetrahydrofuran-3-yl)carbamoyl)-2,3-dihydro-1H-pyrido[2,3-b][1,4]oxazine-1-carboxylate. LC-MS $(M+H)^+$=372.3.

Step 3: (S)-1-(2-chloroacetyl)-7-(4-fluorobenzyl)-2-methyl-N—((S)-tetrahydrofuran-3-yl)-2,3-dihydro-1H-pyrido[2,3-b][1,4]oxazine-6-carboxamide

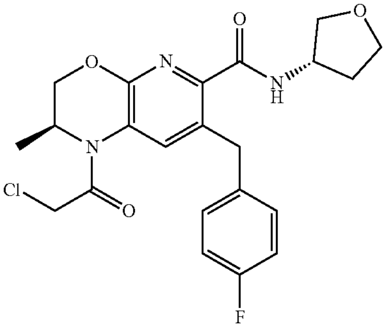 [SMILES: C[C@H]1COc2nc(C(=O)N[C@H]3CCOC3)c(Cc3ccc(F)cc3)cc2N1C(=O)CCl]

The title compound of step 3 (350 mg, 62% yield) was prepared in a manner similar to that described in Example 1 step 9 from (S)-7-(4-fluorobenzyl)-2-methyl-N—((S)-tetrahydrofuran-3-yl)-2,3-dihydro-1H-pyrido[2,3-b][1,4]oxazine-6-carboxamide and 2-chloroacetyl chloride. LC-MS $(M+H)^+$=448.3.

Step 4: tert-butyl (2R,5S)-5-(((3R,5R)-3,5-dimethylmorpholino)methyl)-4-(2-((S)-7-(4-fluorobenzyl)-2-methyl-6-(((S)-tetrahydrofuran-3-yl)carbamoyl)-2,3-dihydro-1H-pyrido[2,3-b][1,4]oxazin-1-yl)-2-oxoethyl)-2-methylpiperazine-1-carboxylate

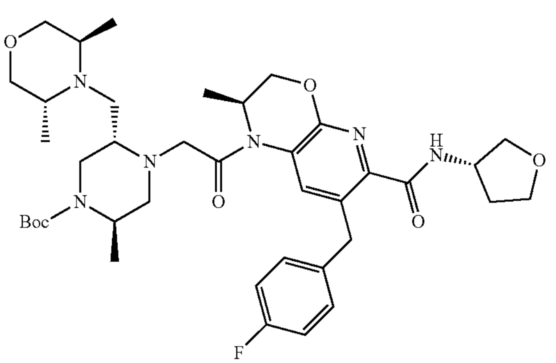 [SMILES: C[C@@H]1CN(CC(=O)N2c3cc(Cc4ccc(F)cc4)c(C(=O)N[C@H]4CCOC4)nc3OC[C@@H]2C)[C@@H](CN2[C@H](C)COC[C@H]2C)CN1C(=O)OC(C)(C)C]

The title compound of step 4 (438 mg, 76% yield) was prepared in a manner similar to that described in Example 1 step 18 from (S)-1-(2-chloroacetyl)-7-(4-fluorobenzyl)-2-methyl-N—((S)-tetrahydrofuran-3-yl)-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=739.8.

Step 5: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N—((S)-tetrahydrofuran-3-yl)-2,3-dihydro-1H-pyrido[2,3-b][1,4]oxazine-6-carboxamide (Compound 79)

Compound 79 (170 mg, 45% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-(((S)-tetrahydrofuran-3-yl)carbamoyl)-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 8.47 (d, J=7.1 Hz, 1H), 8.34 (s, 1H), 7.27-7.18 (m, 2H), 7.13-7.04 (m, 2H), 4.76 (d, J=6.5 Hz, 1H), 4.45-4.33 (m, 2H), 4.31-4.18 (m, 3H), 4.02-3.90 (m, 1H), 3.87-3.77 (m, 2H), 3.74-3.65 (m, 1H), 3.59-3.48 (m, 2H), 3.46-3.38 (m, 2H), 3.33-3.28 (m, 1H), 3.15-3.01 (m, 2H), 2.96-2.86 (m, 1H), 2.82-2.73 (m, 1H), 2.72-2.63 (m, 2H), 2.63-2.53 (m, 3H), 2.26 (t, J=10.9 Hz, 1H), 2.21-2.08 (m, 2H), 2.00-1.92 (m, 1H), 1.92-1.82 (m, 1H), 1.21 (d, J=6.6 Hz, 3H), 0.92-0.76 (m, 9H). LC-MS $(M+H)^+$=639.7.

Example 80: (S)-1-(2-((2R,5R)-2-(((3R,5R)-3,5-dimethylmorpholino)methyl)-5-methylpiperazin-1-yl)acetyl)-7-(4-fluorobenzyl)-N,N,2-trimethyl-2,3-dihydro-1H-pyrido[2,3-b][1,4]oxazine-6-carboxamide (Compound 80)

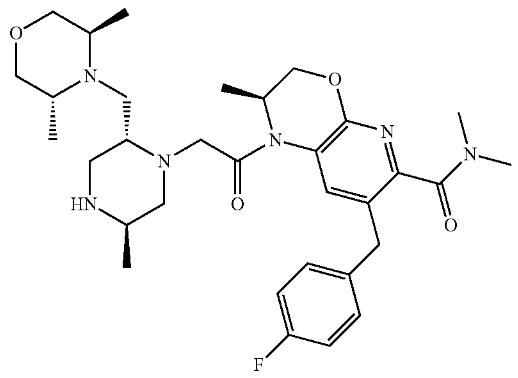 [SMILES: C[C@@H]1CN(CC(=O)N2c3cc(Cc4ccc(F)cc4)c(C(=O)N(C)C)nc3OC[C@@H]2C)[C@@H](CN2[C@H](C)COC[C@H]2C)CN1]

Step 1: benzyl (S)-6-(dimethylcarbamoyl)-7-(4-fluorobenzyl)-2-methyl-2,3-dihydro-1H-pyrido[2,3-b][1,4]oxazine-1-carboxylate

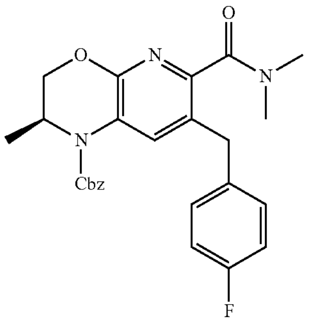

The title compound of step 1 (500 mg, crude) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and dimethylamine. LC-MS $(M+H)^+$=464.2.

Step 2: (S)-7-(4-fluorobenzyl)-N,N,2-trimethyl-2,3-dihydro-1H-pyrido[2,3-b][1,4]oxazine-6-carboxamide

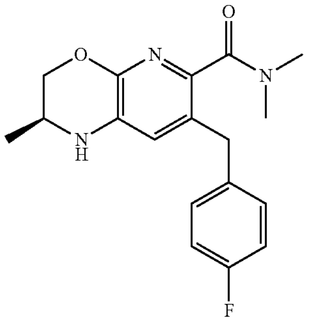

The title compound of step 2 (429 mg, crude) was prepared in a manner similar to that described in Example 1 step 17 from benzyl (S)-6-(dimethylcarbamoyl)-7-(4-fluorobenzyl)-2-methyl-2,3-dihydro-1H-pyrido[2,3-b][1,4]oxazine-1-carboxylate. LC-MS $(M+H)^+$=330.1.

Step 3: (S)-1-(2-chloroacetyl)-7-(4-fluorobenzyl)-N,N,2-trimethyl-2,3-dihydro-1H-pyrido[2,3-b][1,4]oxazine-6-carboxamide

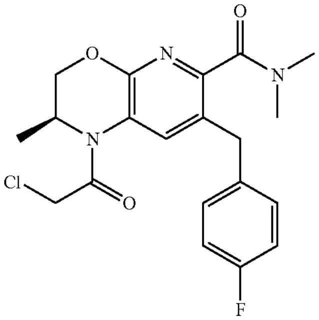

The title compound of step 3 (348 mg, 66% yield) was prepared in a manner similar to that described in Example 1 step 9 from (S)-7-(4-fluorobenzyl)-N,N,2-trimethyl-2,3-dihydro-1H-pyrido[2,3-b][1,4]oxazine-6-carboxamide and 2-chloroacetyl chloride. LC-MS $(M+H)^+$=406.2.

Step 4: tert-butyl (2R,5S)-4-(2-((S)-6-(dimethylcarbamoyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

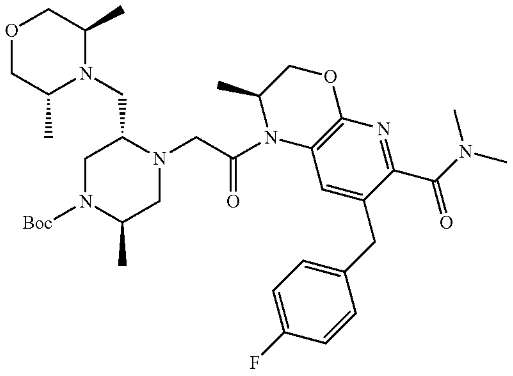

The title compound of step 4 (460 mg, 77% yield) was prepared in a manner similar to that described in Example 1 step 18 from (S)-1-(2-chloroacetyl)-7-(4-fluorobenzyl)-N,N,2-trimethyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=697.5.

Step 5: (S)-1-(24(2R,5R)-2-(((3R,5R)-3,5-dimethylmorpholino)methyl)-5-methylpiperazin-1-yl)acetyl)-7-(4-fluorobenzyl)-N,N,2-trimethyl-2,3-dihydro-1H-pyrido[2,3-b][1,4]oxazine-6-carboxamide (Compound 80)

Compound 80 (120 mg, 30% yield) was prepared in a manner similar to that described in Example 29 step 7 from tert-butyl (2R,5S)-4-(2-((S)-6-(dimethylcarbamoyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^1$H NMR (400 MHz, DMSO-d6) δ 8.31 (s, 1H), 7.23-7.15 (m, 2H), 7.15-7.05 (m, 2H), 4.77 (d, J=5.9 Hz, 1H), 4.41-4.32 (m, 1H), 4.30-4.21 (m, 1H), 4.01-3.90 (m, 1H), 3.86-3.74 (m, 2H), 3.57-3.40 (m, 3H), 3.33-3.26 (m, 1H), 3.16-3.02 (m, 2H), 2.98-2.86 (m, 4H), 2.84-2.74 (m, 1H), 2.74-2.65 (m, 2H), 2.63-2.53 (m, 3H), 2.51 (s, 3H), 2.26 (t, J=10.9 Hz, 1H), 2.16 (t, J=10.9 Hz, 1H), 2.02-1.92 (m, 1H), 1.20 (d, J=6.5 Hz, 3H), 0.93-0.76 (m, 9H). LC-MS $(M+H)^+$=597.5.

Example 81: 2-42R,5R)-2-(((3R,5R)-3,5-dimethylmorpholino)methyl)-5-methylpiperazin-1-yl)-1-((S)-7-(4-fluorobenzyl)-6-hydroxy-2-methyl-2,3-dihydro-1H-pyrido[2,3-b][1,4]oxazin-1-yl)ethan-1-one (Compound 81)

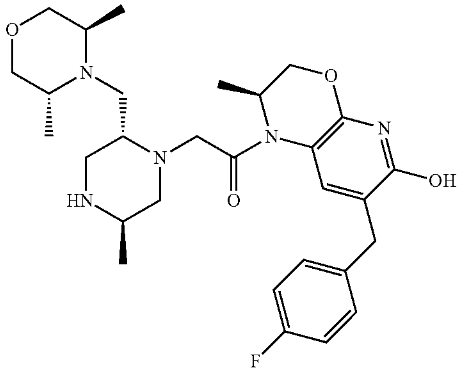 [SMILES: C[C@@H]1CN(CC(=O)N2c3cc(Cc4ccc(F)cc4)c(O)nc3OC[C@@H]2C)[C@@H](CN2[C@H](C)COC[C@H]2C)CN1]

Step 1: tert-butyl (S)-(1-((3-bromo-5-chloropyridin-2-yl)oxy)propan-2-yl)carbamate

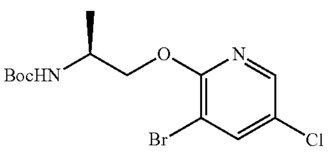 [SMILES: C[C@@H](COc1ncc(Cl)cc1Br)NC(=O)OC(C)(C)C]

The title compound of step 1 (18.0 g, 87% yield) was prepared in a manner similar to that described in Example 29 step 1 from tert-butyl (S)-(1-hydroxypropan-2-yl)carbamate and 3-bromo-5-chloro-2-fluoropyridine. LC-MS $(M+H)^+$=365.0.

Step 2: tert-butyl (S)-7-chloro-2-methyl-2,3-dihydro-1H-pyrido[2,3-b][1,4]oxazine-1-carboxylate

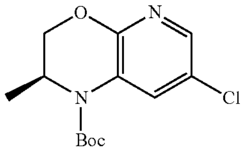 [SMILES: C[C@H]1COc2ncc(Cl)cc2N1C(=O)OC(C)(C)C]

The title compound of step 2 (13.9 g, 94% yield) was prepared in a manner similar to that described in Example 34 step 2 from tert-butyl (S)-(1-((3-bromo-5-chloropyridin-2-yl)oxy)propan-2-yl)carbamate. LC-MS $(M+H)^+$=285.1.

Step 3: tert-butyl (S)-7-(4-fluorobenzyl)-2-methyl-2,3-dihydro-1H-pyrido[2,3-b][1,4]oxazine-1-carboxylate

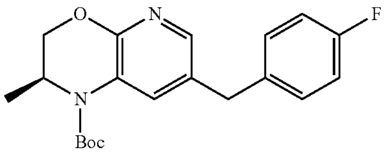 [SMILES: C[C@H]1COc2ncc(Cc3ccc(F)cc3)cc2N1C(=O)OC(C)(C)C]

The title compound of step 3 (4.6 g, 73% yield) was prepared in a manner similar to that described in Example 34 step 3 from tert-butyl (S)-7-chloro-2-methyl-2,3-dihydro-1H-pyrido[2,3-b][1,4]oxazine-1-carboxylate and (4-fluorobenzyl)zinc(II) chloride. LC-MS $(M+H)^+$=359.1.

Step 4: (S)-1-(tert-butoxycarbonyl)-7-(4-fluorobenzyl)-2-methyl-2,3-dihydro-1H-pyrido[2,3-b][1,4]oxazine 5-oxide

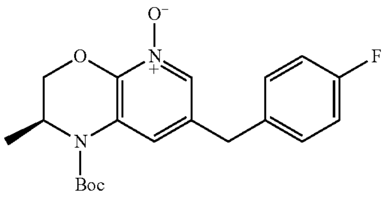 [SMILES: C[C@H]1COc2c(cc(Cc3ccc(F)cc3)c[n+]2[O-])N1C(=O)OC(C)(C)C]

The title compound of step 4 (2.1 g, 43% yield) was prepared in a manner similar to that described in Example 1 step 5 from tert-butyl (S)-7-(4-fluorobenzyl)-2-methyl-2,3-dihydro-1H-pyrido[2,3-b][1,4]oxazine-1-carboxylate. LC-MS $(M+H)^+$=375.1.

Step 5: tert-butyl (S)-6-acetoxy-7-(4-fluorobenzyl)-2-methyl-2,3-dihydro-1H-pyrido[2,3-b][1,4]oxazine-1-carboxylate

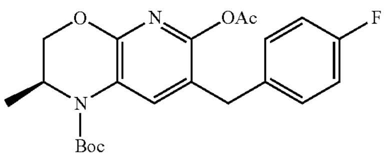 [SMILES: CC(=O)Oc1nc2c(cc1Cc1ccc(F)cc1)N(C(=O)OC(C)(C)C)[C@@H](C)CO2]

The title compound of step 5 (1.5 g, 61% yield) was prepared in a manner similar to that described in Example 9 step 2 from (S)-1-(tert-butoxycarbonyl)-7-(4-fluorobenzyl)-2-methyl-2,3-dihydro-1H-pyrido[2,3-b][1,4]oxazine 5-oxide. LC-MS $(M+H)^+$=417.1.

Step 6: (S)-7-(4-fluorobenzyl)-2-methyl-2,3-dihydro-1H-pyrido[2,3-b][1,4]oxazin-6-yl acetate

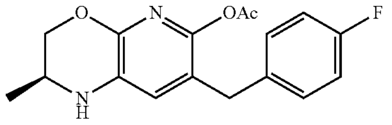 [SMILES: CC(=O)Oc1nc2c(cc1Cc1ccc(F)cc1)N[C@@H](C)CO2]

The title compound of step 6 (63 mg, 20% yield) was prepared in a manner similar to that described in Example 1 step 8 from tert-butyl (S)-6-acetoxy-7-(4-fluorobenzyl)-2-methyl-2,3-dihydro-1H-pyrido[2,3-b][1,4]oxazine-1-carboxylate. LC-MS $(M+H)^+$=317.1.

Step 7: (S)-1-(2-chloroacetyl)-7-(4-fluorobenzyl)-2-methyl-2,3-dihydro-1H-pyrido[2,3-b][1,4]oxazin-6-yl acetate

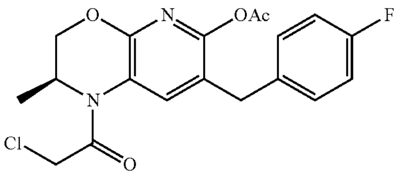 [SMILES: CC(=O)Oc1nc2c(cc1Cc1ccc(F)cc1)N(C(=O)CCl)[C@@H](C)CO2]

The title compound of step 7 (66 mg, 85% yield) was prepared in a manner similar to that described in Example 1 step 9 from (S)-7-(4-fluorobenzyl)-2-methyl-2,3-dihydro-1H-pyrido[2,3-b][1,4]oxazin-6-yl acetate and 2-chloroacetyl chloride. LC-MS $(M+H)^+$=393.1.

Step 8: tert-butyl (2R,5S)-5-(((3R,5R)-3,5-dimethylmorpholino)methyl)-4-(2-((S)-7-(4-fluorobenzyl)-6-hydroxy-2-methyl-2,3-dihydro-1H-pyrido[2,3-b][1,4]oxazin-1-yl)-2-oxoethyl)-2-methylpiperazine-1-carboxylate

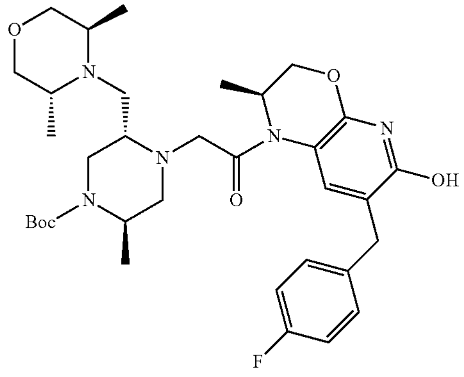 [SMILES: C[C@@H]1CN(CC(=O)N2c3cc(Cc4ccc(F)cc4)c(O)nc3OC[C@@H]2C)[C@@H](CN2[C@H](C)COC[C@H]2C)CN1C(=O)OC(C)(C)C]

The compound of step 8 (80 mg, 74% yield) was prepared in a manner similar to that described in Example 1 step 18 from (S)-1-(2-chloroacetyl)-7-(4-fluorobenzyl)-2-methyl-2,3-dihydro-1H-pyrido[2,3-b][1,4]oxazin-6-yl acetate and tert-butyl (2R,5S)-5-(((3R,5R)-3,5-dimethylmorpholino)methyl)-2-methylpiperazine-1-carboxylate. LC-MS $(M+H)^+$=642.4.

Step 9: 242R,5R)-2-(((3R,5R)-3,5-dimethylmorpholino)methyl)-5-methylpiperazin-1-yl)-1-((S)-7-(4-fluorobenzyl)-6-hydroxy-2-methyl-2,3-dihydro-1H-pyrido[2,3-b][1,4]oxazin-1-yl)ethan-1-one (Compound 81)

Compound 81 (41 mg, 60% yield) was prepared in a manner similar to that described in ((S)-7-(4-fluorobenzyl)-6-hydroxy-2-methyl-2,3-dihydro-1H-pyrido[2,3-b][1,4]oxazin-1-yl) oxoethyl)-2-methylpiperazine-1-carboxylate. $^1$H NMR (400 MHz, Chloroform-d) δ 8.18 (brs, 1H), 7.29-7.23 (m, 2H), 7.04-6.95 (m, 2H), 4.93 (s, 1H), 4.39-4.23 (m, 3H), 3.95-3.79 (m, 2H), 3.66-3.58 (m, 2H), 3.33-3.29 (m, 2H), 3.26-3.18 (m, 1H), 3.16-3.09 (m, 1H), 2.84-2.80 (m, 4H), 2.75-2.67 (m, 1H), 2.61-2.49 (m, 2H), 2.23-2.09 (m, 2H), 1.33-1.25 (m, 3H), 1.07-1.01 (m, 3H), 0.99-0.93 (m, 6H). LC-MS $(M+H)^+$=542.3.

Example 82: (S)-1-(242R,5R)-2-(((S)-3-(difluoromethyl)morpholino)methyl)-5-methylpiperazin-1-yl) acetyl)-7-(4-fluorobenzyl)-2-methyl-2,3-dihydro-1H-pyrido[2,3-b][1,4]oxazine-6-carboxamide (Compound 82)

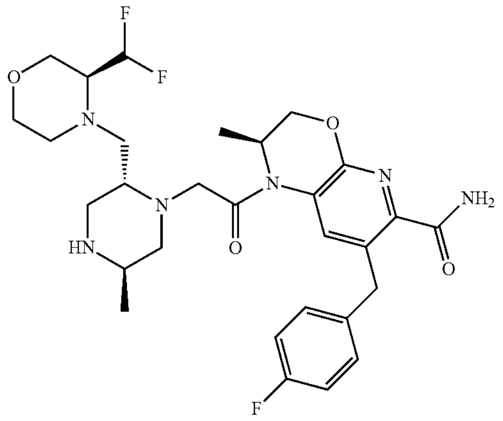 [SMILES: C[C@@H]1CN(CC(=O)N2c3cc(Cc4ccc(F)cc4)c(C(N)=O)nc3OC[C@@H]2C)[C@@H](CN2CCOC[C@H]2C(F)F)CN1]

Step 1: tert-butyl (2R,5S)-4-(24S)-6-carbamoyl-7-(4-fluorobenzyl)-2-methyl-2,3-dihydro-1H-pyrido[2,3-b][1,4]oxazin-1-yl)-2-oxoethyl)-5-(((S)-3-(difluoromethyl)morpholino)methyl)-2-methylpiperazine-1-carboxylate

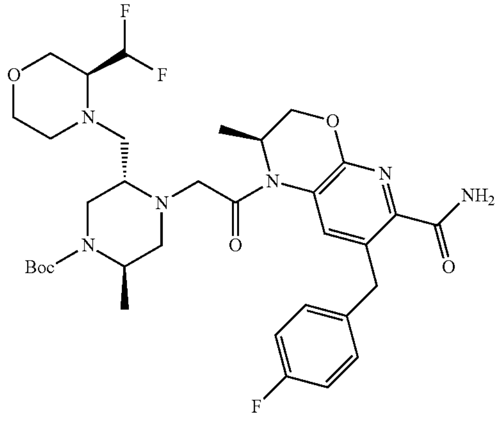 [SMILES: C[C@@H]1CN(CC(=O)N2c3cc(Cc4ccc(F)cc4)c(C(N)=O)nc3OC[C@@H]2C)[C@@H](CN2CCOC[C@H]2C(F)F)CN1C(=O)OC(C)(C)C]

The title compound of step 1 (195 mg, 52% yield) was prepared in a manner similar to that described in Example 1 step 18 from (S)-1-(2-chloroacetyl)-7-(4-fluorobenzyl)-2-methyl-2,3-dihydro-1H-pyrido[2,3-b][1,4]oxazine-6-carboxamide and tert-butyl (2R,5S)-5-(((S)-3-(difluoromethyl)morpholino)methyl)-2-methylpiperazine-1-carboxylate. LC-MS $(M+H)^+$=691.4.

Step 2: (5)-1-(242R,5R)-2-(((S)-3-(difluoromethyl)morpholino)methyl)-5-methylpiperazin-1-yl)acetyl)-7-(4-fluorobenzyl)-2-methyl-2,3-dihydro-1H-pyrido[2,3-b][1,4]oxazine carboxamide (Compound 82)

Compound 82 (41 mg, 24% yield) was prepared in a manner similar to that described in Example 29 step 7 from tert-butyl (2R,5S)-4-(2-((S)-6-carbamoyl-7-(4-fluorobenzyl) methyl-2,3-dihydro-1H-pyrido[2,3-b][1,4]oxazin-1-yl)-2-oxoethyl)-5-(((S)-3-(difluoromethyl)morpholino)methyl)-2-methylpiperazine-1-carboxylate. $^1$H NMR (400 MHz, DMSO-d6) δ 8.37 (brs, 1H), 7.80 (s, 1H), 7.43 (s, 1H), 7.29-7.19 (m, 2H), 7.14-7.01 (m, 2H), 6.52-6.07 (m, 1H), 4.83-4.72 (m, 1H), 4.44-4.32 (m, 2H), 4.32-4.22 (m, 2H), 4.00-3.89 (m, 1H), 3.66-3.27 (m, 5H), 2.94-2.85 (m, 3H), 2.74-2.56 (m, 4H), 2.46-2.21 (m, 3H), 2.18-1.99 (m, 1H), 1.26-1.16 (m, 3H), 0.92-0.84 (m, 3H). LC-MS $(M+H)^+$=591.3.

Example 83: (S)-7-(2,4-difluorobenzyl)-1-(24(2R,5R)-2-(((3R,5R)-3,5-dimethylmorpholino)methyl)-5-methylpiperazin-1-yl)acetyl)-2-methyl-2,3-dihydro-1H-pyrido[2,3-b][1,4]oxazine-6-carboxamide (Compound 83)

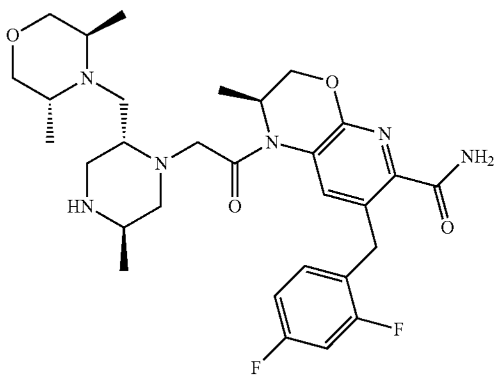 [SMILES: C[C@@H]1CN(CC(=O)N2c3cc(Cc4ccc(F)cc4F)c(C(N)=O)nc3OC[C@@H]2C)[C@@H](CN2[C@H](C)COC[C@H]2C)CN1]

Step 1: tert-butyl (S)-7-(2,4-difluorobenzyl)-6-(hydroxymethyl)-2-methyl-2,3-dihydro-1H-pyrido[2,3-b][1,4]oxazine-1-carboxylate

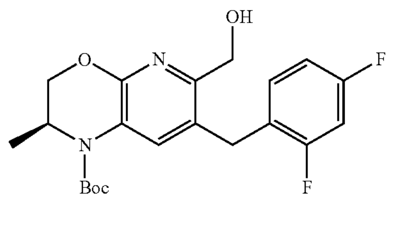

The title compound of step 1 (217 mg, 96% yield) was prepared in a manner similar to that described in Example 8 step 4 from tert-butyl (S)-6-(acetoxymethyl)-7-(2,4-difluorobenzyl)-2-methyl-2,3-dihydro-1H-pyrido[2,3-b][1,4]oxazine-1-carboxylate. LC-MS $(M+H)^+$=407.0.

Step 2: (S)-1-(tert-butoxycarbonyl)-7-(2,4-difluorobenzyl)-2-methyl-2,3-dihydro-1H-pyrido[2,3-b][1,4]oxazine-6-carboxylic acid

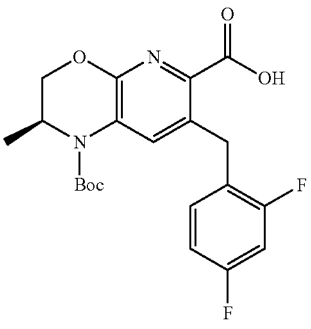 [SMILES: C[C@H]1COc2nc(C(=O)O)c(Cc3ccc(F)cc3F)cc2N1C(=O)OC(C)(C)C]

The title compound of step 2 (186 mg, 86% yield) was prepared in a manner similar to that described in Example 21 step 2 from tert-butyl (S)-7-(2,4-difluorobenzyl)-6-(hydroxymethyl)-2-methyl-2,3-dihydro-1H-pyrido[2,3-b][1,4]oxazine-1-carboxylate. LC-MS $(M+H)^+$=421.2.

Step 3: tert-butyl (S)-6-carbamoyl-7-(2,4-difluorobenzyl)-2-methyl-2,3-dihydro-1H-pyrido[2,3-b][1,4]oxazine-1-carboxylate

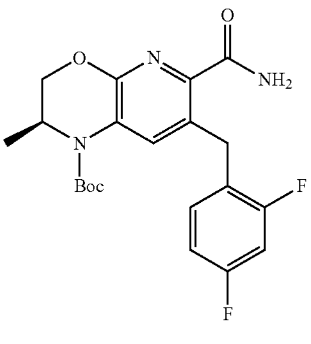

The title compound of step 3 (176 mg, 95% yield) was prepared in a manner similar to that described in Example 31 step 3 from (S)-1-(tert-butoxycarbonyl)-7-(2,4-difluorobenzyl)-2-methyl-2,3-dihydro-1H-pyrido[2,3-b][1,4]oxazine-6-carboxylic acid and $NH_4Cl$. LC-MS $(M+H)^+$=420.3.

Step 4: (S)-7-(2,4-difluorobenzyl)-2-methyl-2,3-dihydro-1H-pyrido[2,3-b][1,4]oxazine-6-carboxamide

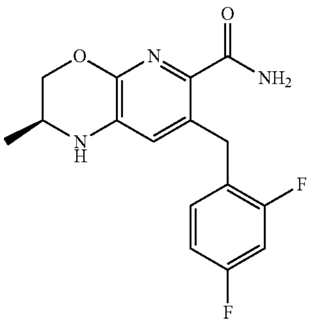 [SMILES: C[C@H]1COc2nc(C(N)=O)c(Cc3ccc(F)cc3F)cc2N1]

The title compound of step 4 (60 mg, 45% yield) was prepared in a manner similar to that described in Example 1 step 8 from tert-butyl (S)-6-carbamoyl-7-(2,4-difluorobenzyl)-2-methyl-2,3-dihydro-1H-pyrido[2,3-b][1,4]oxazine-1-carboxylate. LC-MS $(M+H)^+$=320.2.

Step 5: (S)-1-(2-chloroacetyl)-7-(2,4-difluorobenzyl)-2-methyl-2,3-dihydro-1H-pyrido[2,3-b][1,4]oxazine-6-carboxamide

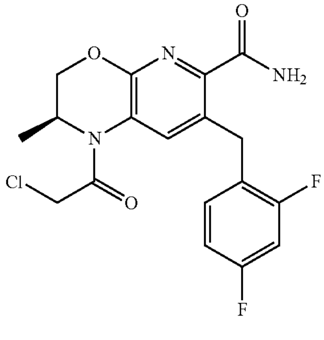 [SMILES: C[C@H]1COc2nc(C(N)=O)c(Cc3ccc(F)cc3F)cc2N1C(=O)CCl]

The title compound of step 5 (71 mg, 95% yield) was prepared in a manner similar to that described in Example 1 step 9 from (S)-7-(2,4-difluorobenzyl)-2-methyl-2,3-dihydro-1H-pyrido[2,3-b][1,4]oxazine-6-carboxamide and 2-chloroacetyl chloride. LC-MS $(M+H)^+$=396.2.

Step 6: tert-butyl (2R,5S)-4-(2-((S)-6-carbamoyl-7-(2,4-difluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

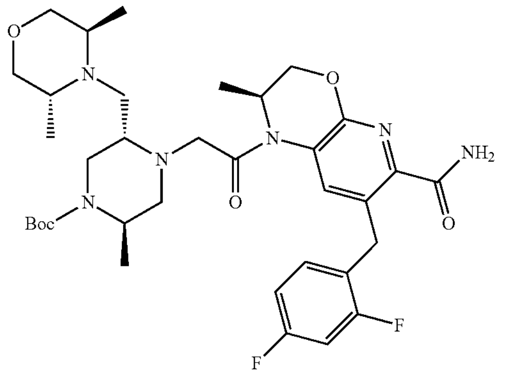 [SMILES: C[C@@H]1CN(CC(=O)N2c3cc(Cc4ccc(F)cc4F)c(C(N)=O)nc3OC[C@@H]2C)[C@@H](CN2[C@H](C)COC[C@H]2C)CN1C(=O)OC(C)(C)C]

The title compound of step 6 (150 mg, 73% yield) was prepared in a manner similar to that described in Example 1 step 18 from (S)-1-(2-chloroacetyl)-7-(2,4-difluorobenzyl)-2-methyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=687.3.

Step 7: (S)-7-(2,4-difluorobenzyl)-1-(2-((2R,5R)-2-(((3R,5R)-3,5-dimethylmorpholino)methyl)-5-methylpiperazin-1-yl)acetyl)-2-methyl-2,3-dihydro-1H-pyrido[2,3-b][1,4]oxazine-6-carboxamide (Compound 83)

Compound 83 (15 mg, 11% yield) was prepared in a manner similar to that described in Example 29 step 7 from tert-butyl (2R,5S)-4-(2-((S)-6-carbamoyl-7-(2,4-difluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^1H$ NMR (400 MHz, Chloroform-d) δ 8.49 (brs, 1H), 7.75-7.58 (m, 1H), 7.33-7.22 (m, 2H), 6.87-6.76 (m, 2H), 5.43 (s, 1H), 5.08-5.02 (m, 1H), 4.63-4.50 (m, 2H), 4.45-4.18 (m, 3H), 3.66-3.58 (m, 2H), 3.43-3.22 (m, 3H), 3.17-3.09 (m, 1H), 2.92-2.79 (m, 4H), 2.74-2.63 (m, 2H), 2.61-2.51 (m, 1H), 2.27-2.11 (m, 2H), 1.38-1.26 (m, 3H), 1.09-1.03 (m, 3H), 1.01-0.94 (m, 6H). LC-MS $(M+H)^+$=587.3.

Example 84A & 84B: 24(2R,5R)-2-(((R)-3-cyclopropylmorpholino)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one and 2-((2R,5R)-2-(((S)-3-cyclopropylmorpholino)methyl)-5-methylpiperazin-1-yl)-1-4S)-7-(4-fluorobenzyl)-6-(hydroxymethyl)-2-methyl-2,3-dihydro-1H-pyrido[2,3-b][1,4]oxazin-1-yl)ethan-1-one (Compound 84A & 84B)

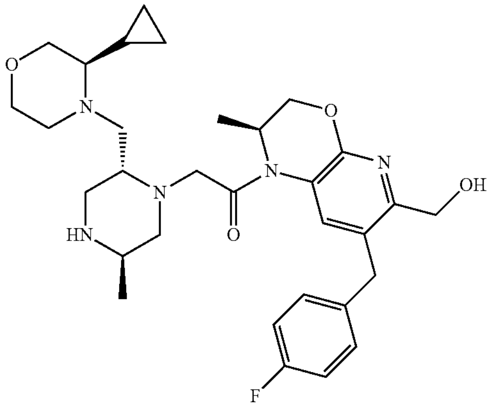

and

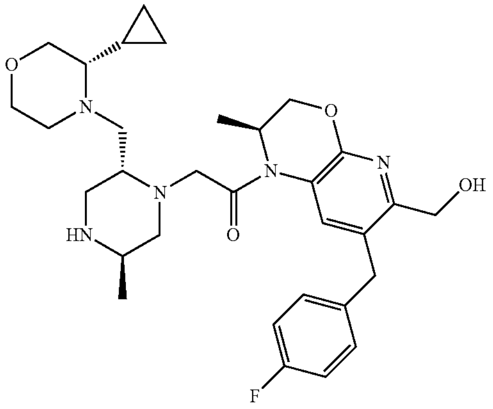

Step 1: tert-butyl (2R,5S)-4-benzyl-5-((3-cyclopropylmorpholino)methyl)-2-methylpiperazine-1-carboxylate

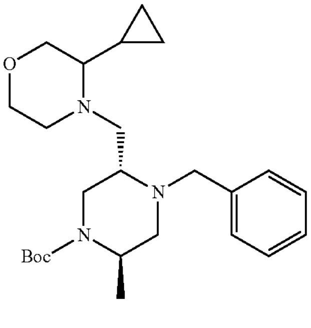 [SMILES: C[C@@H]1CN(Cc2ccccc2)[C@@H](CN2CCOCC2C2CC2)CN1C(=O)OC(C)(C)C]

The title compound of step 1 (365 mg, 73% yield) was prepared in a manner similar to that described in Example 1 step 16 from tert-butyl (2R,5R)-4-benzyl-5-(chloromethyl)-

2-methylpiperazine-1-carboxylate and 3-cyclopropylmorpholine. LC-MS $(M+H)^+$=430.4.

Step 2: tert-butyl (2R,5S)-5-((3-cyclopropylmorpholino)methyl)-2-methylpiperazine-1-carboxylate

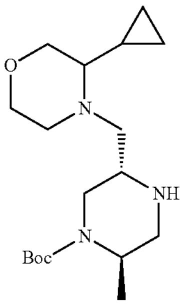 [SMILES: C[C@@H]1CN[C@@H](CN2CCOCC2C2CC2)CN1C(=O)OC(C)(C)C]

The title compound of step 2 (260 mg, crude) was prepared in a manner similar to that described in Example 1 step 17 from tert-butyl (2R,5S)-4-benzyl-5-((3-cyclopropylmorpholino)methyl)-2-methylpiperazine-1-carboxylate LC-MS $(M+H)^+$=340.3.

Step 3: tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-((3-cyclopropylmorpholino)methyl)-2-methylpiperazine-1-carboxylate

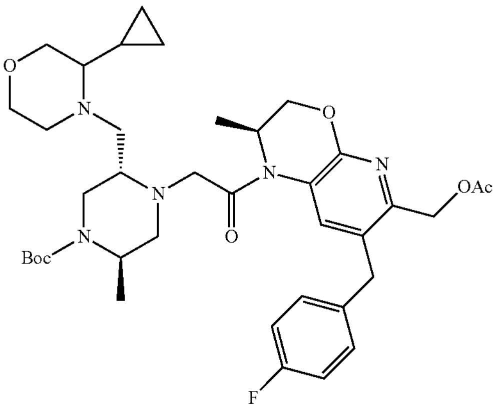 [SMILES: CC(=O)OCc1nc2c(cc1Cc1ccc(F)cc1)N(C(=O)CN1C[C@@H](C)N(C(=O)OC(C)(C)C)C[C@@H]1CN1CCOCC1C1CC1)[C@@H](C)CO2]

The title compound of step 3 (400 mg, 66% for 2 steps) was prepared in a manner similar to that described in Example 1 step 18 from (S)-(1-(2-chloroacetyl)-7-(4-fluorobenzyl)-2-methyl-2,3-dihydro-1H-pyrido[2,3-b][1,4]oxazin-6-yl)methyl acetate and tert-butyl (2R,5S)-5-((3-cyclopropylmorpholino)methyl)-2-methylpiperazine-1-carboxylate LC-MS $(M+H)^+$=710.3.

Step 4: tert-butyl (2R,5S)-5-((3-cyclopropylmorpholino)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl) methylpiperazine-1-carboxylate

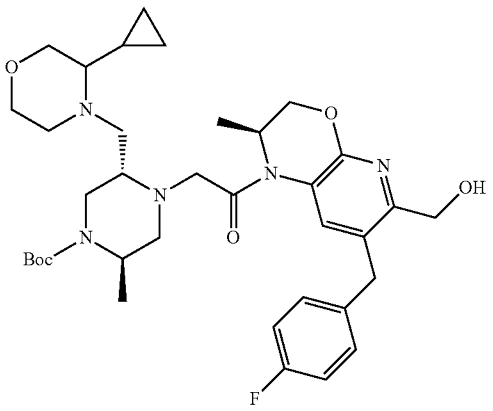 [SMILES: C[C@@H]1CN(CC(=O)N2c3cc(Cc4ccc(F)cc4)c(CO)nc3OC[C@@H]2C)[C@@H](CN2CCOCC2C2CC2)CN1C(=O)OC(C)(C)C]

The title compound of step 4 (300 mg, 80% yield) was prepared in a manner similar to that described in Example 8 step 4 from tert-butyl (2R,55)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-((3-cyclopropylmorpholino)methyl)-2-methylpiperazine-1-carboxylate. LC-MS $(M+H)^+$=668.5

Step 5: 2-((2R,5R)-2-(((R)-3-cyclopropylmorpholino)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one and 2-((2R,5R)-2-(((S)-3-cyclopropylmorpholino)methyl)-5-methylpiperazin-1-yl)-1-(((S)-7-(4-fluorobenzyl)-6-(hydroxymethyl)-2-methyl-2,3-dihydro-1H-pyrido[2,3-b][1,4]oxazin-1-yl)ethan-1-one (Compound 84A & 84B)

Compound 84A & 84B mixture was prepared in a manner similar to that described in Example 29 step 7 from tert-butyl (2R,5S)-5-((3-cyclopropylmorpholino)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate. The mixture of isomers was furtherly purified by chiral HPLC to afford diastereomeric pure 84A & 84B. The analytical chiral HPLC conditions were as follows: CHIRALPAK ID-3, 0.46×5 cm, 3.0 um. Mobile phase: (Hex:DCM=3:1) (0.5% 2M $NM_3$-MeOH): IPA, 1 mL/min in 9 min. Example 84A (21 mg, 11% yield): $^1H$ NMR (400 MHz, Chloroform-d) δ 8.45 (brs, 1H), 7.16-7.08 (m, 2H), 7.05-6.95 (m, 2H), 5.05 (s, 1H), 4.67-4.46 (m, 3H), 4.43-4.29 (m, 2H), 3.93-3.83 (m, 3H), 3.82-3.69 (m, 2H), 3.57-3.41 (m, 2H), 3.38-3.29 (m, 2H), 3.06-2.99 (m, 1H), 2.95-2.88 (m, 2H), 2.79-2.71 (m, 2H), 2.69-2.58 (m, 1H), 2.29-2.19 (m, 1H), 2.14-2.04 (m, 1H), 1.96-1.88 (m, 1H), 1.33-1.25 (m, 4H), 1.11-1.04 (m, 3H), 0.72-0.68 (m, 1H), 0.51-0.47 (m, 2H), 0.34-0.26 (m, 1H), 0.13-0.08 (m, 1H). LC-MS $(M+H)^+$=568.3. Chiral HPLC: tR=1.813 min.

Example 84B (22 mg, 11% yield): $^{1}$H NMR (400 MHz, Chloroform-d) δ 8.43 (brs, 1H), 7.17-7.08 (m, 2H), 7.05-6.95 (m, 2H), 5.02 (s, 1H), 4.67-4.51 (m, 2H), 4.45-4.24 (m, 2H), 4.06-3.98 (m, 2H), 3.87-3.83 (m, 2H), 3.82-3.70 (m, 2H), 3.62-3.52 (m, 1H), 3.44-3.35 (m, 2H), 3.13-3.08 (m, 2H), 2.82-2.74 (m, 3H), 2.60-2.52 (m, 2H), 2.37-2.32 (m, 1H), 2.21-2.15 (m, 2H), 1.37-1.32 (m, 4H), 1.10-1.04 (m, 3H), 0.69-0.58 (m, 1H), 0.56-0.35 (m, 2H), 0.17-0.03 (m, 2H). LC-MS $(M+H)^+$ =568.3. Chiral HPLC: tR=2.367 min.

Example 85: 2-((2R,5R)-2-(((1S,4S)-2-oxa-5-azabicyclo[2.2.1]heptan-5-yl)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 85)

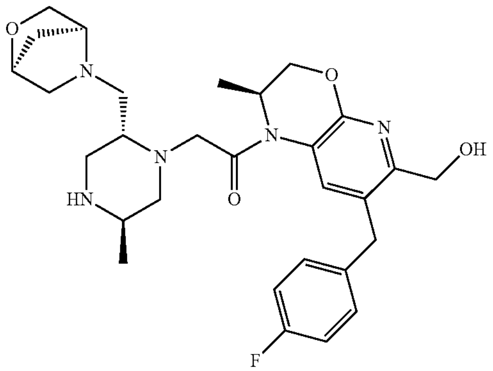 [SMILES: C[C@@H]1CN(CC(=O)N2c3cc(Cc4ccc(F)cc4)c(CO)nc3OC[C@@H]2C)[C@@H](CN2C[C@@H]3C[C@H]2CO3)CN1]

Step 1: tert-butyl (2R,5S)-5-(((1S,4S)-2-oxa-5-azabicyclo[2.2.1]heptan-5-yl)methyl)-4-benzyl-2-methylpiperazine-1-carboxylate

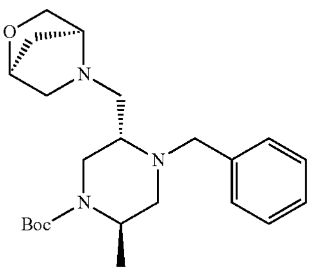 [SMILES: C[C@@H]1CN(Cc2ccccc2)[C@@H](CN2C[C@@H]3C[C@H]2CO3)CN1C(=O)OC(C)(C)C]

The title compound of step 1 (335 mg, 58% yield) was prepared in a manner similar to that described in Example 1 step 16 from tert-butyl (2R,5R)-4-benzyl-5-(chloromethyl)-2-methylpiperazine-1-carboxylate and (1S,4S)-2-oxa-5-azabicyclo[2.2.1]heptane hydrochloride. LC-MS $(M+H)^+$=402.2.

Step 2: tert-butyl (2R,5S)-5-(((1S,4S)-2-oxa-5-azabicyclo[2.2.1]heptan-5-yl)methyl)-2-methylpiperazine-1-carboxylate

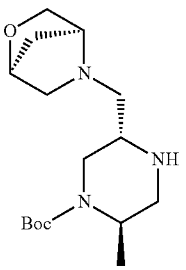 [SMILES: C[C@@H]1CN[C@@H](CN2C[C@@H]3C[C@H]2CO3)CN1C(=O)OC(C)(C)C]

The title compound of step 2 (200 mg, crude) was prepared in a manner similar to that described in Example 1 step 17 from tert-butyl (2R,5S)-5-(((1S,4S)-2-oxa-5-azabicyclo[2.2.1]heptan-5-yl)methyl)-4-benzyl-2-methylpiperazine-1-carboxylate. LC-MS $(M+H)^+$=312.2.

Step 3: tert-butyl (2R,5S)-5-(((1S,4S)-2-oxa-5-azabicyclo[2.2.1]heptan-5-yl)methyl)-4-(24S)-6-(acetoxymethyl)-7-(4-fluorobenzyl)-2-methyl-2,3-dihydro-1H-pyrido[2,3-b][1,4]oxazin yl)-2-oxoethyl)-2-methylpiperazine-1-carboxylate

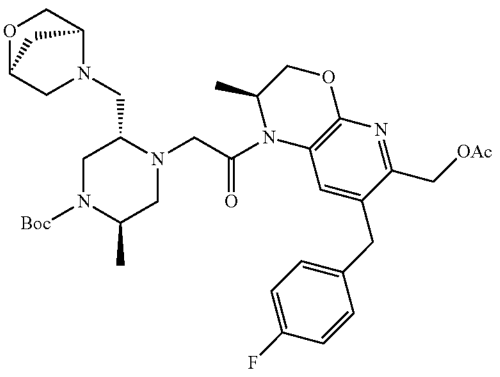 [SMILES: CC(=O)OCc1nc2c(cc1Cc1ccc(F)cc1)N(C(=O)CN1C[C@@H](C)N(C(=O)OC(C)(C)C)C[C@@H]1CN1C[C@@H]3C[C@H]1CO3)[C@@H](C)CO2]

The title compound of step 3 (270 mg, 47% yield for 2 steps) was prepared in a manner similar to that described in Example 1 step 18 from (S)-(1-(2-chloroacetyl)-7-(4-fluorobenzyl)-2-methyl-2,3-dihydro-1H-pyrido[2,3-b][1,4]oxazin-6-yl)methyl acetate and tert-butyl (2R,5S)-5-(((1S,4S)-2-oxa-5-azabicyclo[2.2.1]heptan-5-yl)methyl)-2-methylpiperazine-1-carboxylate. LC-MS $(M+H)^+$=682.4.

Step 4: tert-butyl (2R,5S)-5-(((1S,4S)-2-oxa-5-azabicyclo[2.2.1]heptan-5-yl)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate

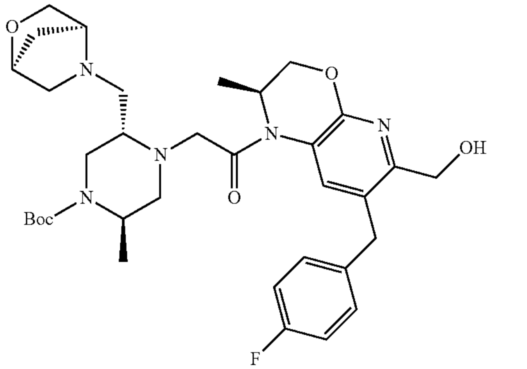 [SMILES: C[C@@H]1CN(CC(=O)N2c3cc(Cc4ccc(F)cc4)c(CO)nc3OC[C@@H]2C)[C@@H](CN2C[C@@H]3C[C@H]2CO3)CN1C(=O)OC(C)(C)C]

The title compound of step 4 (335 mg, 58% yield) was prepared in a manner similar to that described in Example 8 step 4 from tert-butyl (2R,5S)-5-0(1S,4S)-2-oxa-5-azabicyclo[2.2.1]heptan-5-yl)methyl)-4-(24S)-6-(acetoxymethyl)-7-(4-fluorobenzyl)-2-methyl-2,3-dihydro-1H-pyrido[2,3-b][1,4]oxazin-1-yl)-2-oxoethyl)-2-methylpiperazine-1-carboxylate. LC-MS $(M+H)^+$=640.4.

Step 5: 2-((2R,5R)-2-(((1S,45)-2-oxa-5-azabicyclo[2.2.1]heptan-5-yl)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 85)

Compound 85 (38 mg, 34% yield) was prepared in a manner similar to that described in Example 29 step 7 from tert-butyl (2R,55)-5-(((1 S,4S)-2-oxa-5-azabicyclo[2.2.1]heptan-5-yl)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 8.19 (brs, 1H), 7.26-7.17 (m, 2H), 7.17-7.07 (m, 2H), 5.11-5.04 (m, 1H), 4.79-4.75 (m, 1H), 4.50-4.36 (m, 2H), 4.36-4.28 (m, 1H), 4.26-4.16 (m, 2H), 4.00-3.92 (m, 3H), 3.73 (s, 1H), 3.43-3.34 (m, 3H), 2.90-2.82 (m, 1H), 2.75-2.63 (m, 2H), 2.62-2.52 (m, 2 H), 2.35-2.15 (m, 5H), 1.55-1.47 (m, 1H), 1.40-1.34 (m, 1H), 1.14 (d, J=6.7 Hz, 3H), 0.86 (d, J=6.2 Hz, 3H). LC-MS $(M+H)^+$=540.3.

Example 86: 2-42R,5R)-2-((3-oxa-8-azabicyclo[3.2.1]octan-8-yl)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 86)

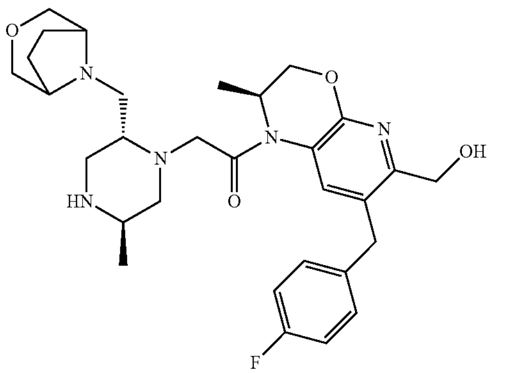 [SMILES: C[C@@H]1CN(CC(=O)N2c3cc(Cc4ccc(F)cc4)c(CO)nc3OC[C@@H]2C)[C@@H](CN2C3CCC2COC3)CN1]

Step 1: tert-butyl (2R,5S)-5-((3-oxa-8-azabicyclo[3.2.1]octan-8-yl)methyl)-4-benzyl-2-methylpiperazine-1-carboxylate

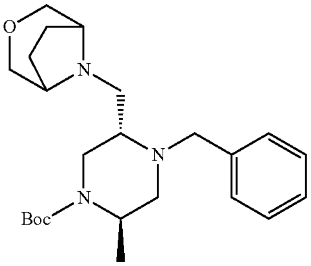 [SMILES: C[C@@H]1CN(Cc2ccccc2)[C@@H](CN2C3CCC2COC3)CN1C(=O)OC(C)(C)C]

The title compound of step 1 (413 mg, 70% yield) was prepared in a manner similar to that described in Example 1 step 16 from tert-butyl (2R,5R)-4-benzyl-5-(chloromethyl)-2-methylpiperazine-1-carboxylate and 3-oxa-8-azabicyclo[3.2.1]octane hydrochloride. LC-MS $(M+H)^+$=416.3.

Step 2: tert-butyl (2R,5S)-5-((3-oxa-8-azabicyclo[3.2.1]octan-8-yl)methyl)-2-methylpiperazine-1-carboxylate

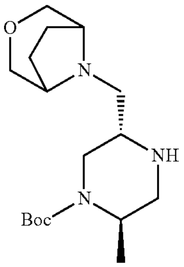

The title compound of step 2 (250 mg, crude) was prepared in a manner similar to that described in Example 1 step 17 from tert-butyl (2R,5S)-5-((3-oxa-8-azabicyclo[3.2.1]octan-8-yl)methyl)-4-benzyl-2-methylpiperazine-1-carboxylate. LC-MS $(M+H)^+$=326.2.

Step 3: tert-butyl (2R,5S)-5-((3-oxa-8-azabicyclo[3.2.1]octan-8-yl)methyl)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-2-methylpiperazine-1-carboxylate

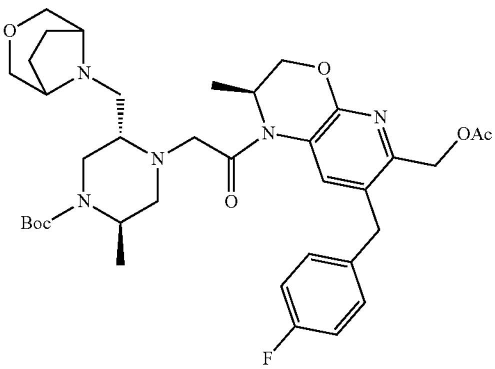 [SMILES: CC(=O)OCc1nc2c(cc1Cc1ccc(F)cc1)N(C(=O)CN1C[C@@H](C)N(C(=O)OC(C)(C)C)C[C@@H]1CN1C3CCC1COC3)[C@@H](C)CO2]

The title compound of step 3 (257 mg, 37% yield for 2 steps) was prepared in a manner similar to that described in Example 1 step 18 from (S)-(1-(2-chloroacetyl)-7-(4-fluorobenzyl)-2-methyl-2,3-dihydro-1H-pyrido[2,3-b][1,4]oxazin-6-yl)methyl acetate and tert-butyl (2R,5S)-5-43-oxa-8-azabicyclo[3.2.1]octan-8-yl)methyl)-2-methylpiperazine-1-carboxylate. LC-MS $(M+H)^+$=696.5.

Step 4: tert-butyl (2R,5S)-5-((3-oxa-8-azabicyclo[3.2.1]octan-8-yl)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate

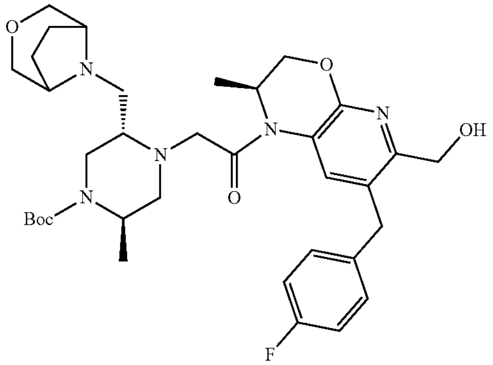 [SMILES: C[C@@H]1CN(CC(=O)N2c3cc(Cc4ccc(F)cc4)c(CO)nc3OC[C@@H]2C)[C@@H](CN2C3CCC2COC3)CN1C(=O)OC(C)(C)C]

The title compound of step 4 (110 mg, 75% yield) was prepared in a manner similar to that described in Example 8 step 4 from tert-butyl (2R,5S)-5-((3-oxa-8-azabicyclo[3.2.1]octan-8-yl)methyl)-4-(24S)-6-(acetoxymethyl)-7-(4-fluorobenzyl)-2-methyl-2,3-dihydro-1H-pyrido[2,3-b][1,4]oxazin-1-yl)-2-oxoethyl)-2-methylpiperazine-1-carboxylate. LC-MS $(M+H)^+$=654.4.

Step 5: 2-42R,5R)-2-((3-oxa-8-azabicyclo[3.2.1]octan-8-yl)methyl)-5-methylpiperazin-1-yl)-1-((S)-7-(4-fluorobenzyl)-6-(hydroxymethyl)-2-methyl-2,3-dihydro-1H-pyrido[2,3-b][1,4]oxazin-1-yl)ethan-1-one (Compound 86)

Compound 86 (50 mg, 53% yield) was prepared in a manner similar to that described in Example 29 step 7 from tert-butyl (2R,5S)-5-((3-oxa-8-azabicyclo[3.2.1]octan-8-yl)methyl)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate. NMR (400 MHz, DMSO-d6) δ 8.15 (brs, 1H), 7.25-7.16 (m, 2H), 7.16-7.07 (m, 2H), 5.10-5.06 (m, 1H), 4.77-4.71 (m, 1H), 4.48-4.38 (m, 2H), 4.37-4.30 (m, 1H), 4.23-4.15 (m, 1H), 4.03-3.95 (m, 3H), 3.46-3.35 (m, 3H), 3.33-3.23 (m, 2H), 3.06-2.98 (m, 1H), 2.96-2.84 (m, 2H), 2.65-2.56 (m, 2H), 2.43-2.36 (m, 2H), 2.33-2.23 (m, 1H), 2.11-2.01 (m, 1H), 1.98-1.88 (m, 1H), 1.74-1.58 (m, 4H), 1.17 (d, J=6.7 Hz, 3H), 0.88 (d, J=6.1 Hz, 3H). LC-MS $(M+H)^+$=554.4.

Example 87: 2-42R,5R)-24(3R,5R)-3,5-dimethylmorpholino)methyl)-5-methylpiperazin-1-yl)-1-((S)-6-ethoxy-7-(4-fluorobenzyl)-2-methyl-2,3-dihydro-1H-pyrido[2,3-b][1,4]oxazin-1-yl)ethan-1-one (Compound 87)

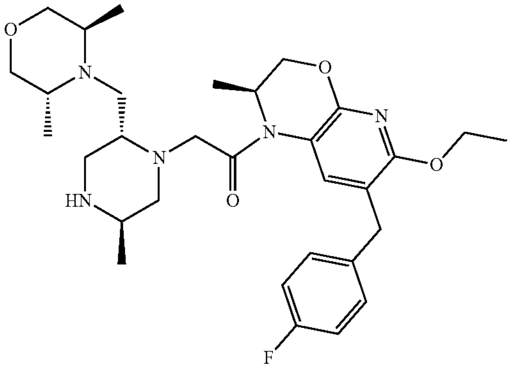 [SMILES: CCOc1nc2c(cc1Cc1ccc(F)cc1)N(C(=O)CN1C[C@@H](C)NC[C@@H]1CN1[C@H](C)COC[C@H]1C)[C@@H](C)CO2]

Step 1: tert-butyl (S)-7-(4-fluorobenzyl)-6-hydroxy-2-methyl-2,3-dihydro-1H-pyrido[2,3-b][1,4]oxazine-1-carboxylate

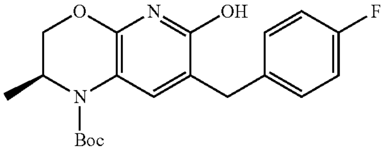 [SMILES: C[C@H]1COc2nc(O)c(Cc3ccc(F)cc3)cc2N1C(=O)OC(C)(C)C]

The title compound of step 1 (880 mg, 80% yield) was prepared in a manner similar to that described in Example 8 step 4 from tert-butyl (S)-6-acetoxy-7-(4-fluorobenzyl)-2-methyl-2,3-dihydro-1H-pyrido[2,3-b][1,4]oxazine-1-carboxylate. LC-MS $(M+H)^+$=375.2.

Step 2: tert-butyl (S)-6-ethoxy-7-(4-fluorobenzyl)-2-methyl-2,3-dihydro-1H-pyrido[2,3-b][1,4]oxazine-1-carboxylate

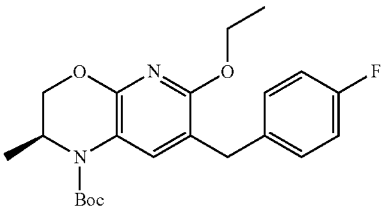 [SMILES: CCOc1nc2c(cc1Cc1ccc(F)cc1)N(C(=O)OC(C)(C)C)[C@@H](C)CO2]

To a solution of tert-butyl (S)-7-(4-fluorobenzyl)-6-hydroxy-2-methyl-2,3-dihydro-1H-pyrido[2,3-b][1,4]oxazine-1-carboxylate (0.5 g, 1.34 mmol) and ethyl iodide (1.2 g, 7.63 mmol) in $CHCl_3$ (10 mL) were added $Ag_2CO_3$ (420 mg, 1.53 mmol) at room temperature. The resulting mixture was stirred for 3 h at 70° C. under nitrogen atmosphere. When the reaction was done, the mixture was allowed to cool down to room temperature. The resulting mixture was filtered, the filter cake was washed with $CH_2Cl_2$ (10 mL×3). The filtrate was concentrated under reduced pressure. The residue was purified by silica gel column chromatography (PE: EtOAc=3:1) to yield the title compound (400 mg, 74% yield). LC-MS $(M+H)^+$=403.2.

Step 3: (S)-6-ethoxy-7-(4-fluorobenzyl)-2-methyl-2,3-dihydro-1H-pyrido[2,3-b][1,4]oxazine

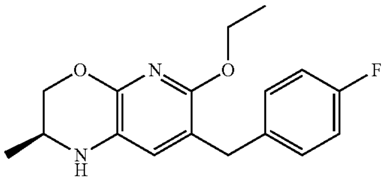 [SMILES: CCOc1nc2c(cc1Cc1ccc(F)cc1)N[C@@H](C)CO2]

The title compound of step 3 (350 mg, 71% yield) was prepared in a manner similar to that described in Example 1 step 8 from tert-butyl (S)-6-ethoxy-7-(4-fluorobenzyl)-2-methyl-2,3-dihydro-1H-pyrido[2,3-b][1,4]oxazine-1-carboxylate. LC-MS $(M+H)^+$=303.1.

Step 4: (S)-2-chloro-1-(6-ethoxy-7-(4-fluorobenzyl)-2-methyl-2,3-dihydro-1H-pyrido[2,3-b][1,4]oxazin-1-yl)ethan-1-one

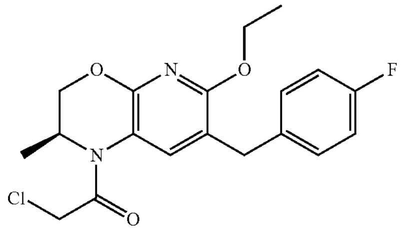 [SMILES: CCOc1nc2c(cc1Cc1ccc(F)cc1)N(C(=O)CCl)[C@@H](C)CO2]

The title compound of step 4 (350 mg, 79% yield) was prepared in a manner similar to that described in Example 1 step 9 from (S)-6-ethoxy-7-(4-fluorobenzyl)-2-methyl-2,3-dihydro-1H-pyrido[2,3-b][1,4]oxazine and 2-chloroacetyl chloride. LC-MS $(M+H)^+$=379.1.

Step 5: tert-butyl (2R,5S)-5-(((3R,5R)-3,5-dimethylmorpholino)methyl)-4-(2-((S)-6-ethoxy-7-(4-fluorobenzyl)-2-methyl-2,3-dihydro-1H-pyrido[2,3-b][1,4]oxazin-1-yl)-2-oxoethyl)-2-methylpiperazine-1-carboxylate

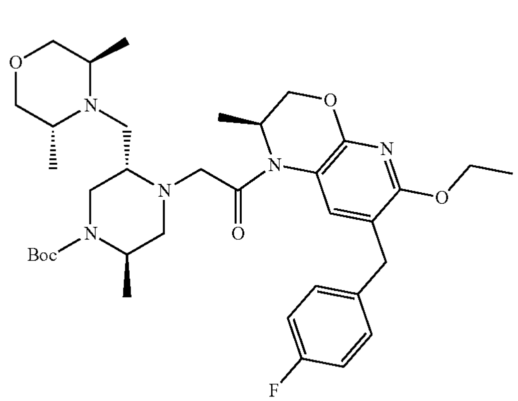 [SMILES: CCOc1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 5 (287 mg, 54% yield) was prepared in a manner similar to that described in Example 1 step 18 from (S)-2-chloro-1-(6-ethoxy-7-(4-fluorobenzyl)-2-methyl-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=670.5.

Step 6: 242R,5R)-24(3R,5R)-3,5-dimethylmorpholino)methyl)-5-methylpiperazin-1-yl)-1-((S)-6-ethoxy-7-(4-fluorobenzyl)-2-methyl-2,3-dihydro-1H-pyrido[2,3-b][1,4]oxazin-1-yl)ethan-1-one (Compound 87)

Compound 87 (54 mg, 22% yield) was prepared in a manner similar to that described in Example 29 step 7 from tert-butyl (2R,5S)-54(3R,5R)-3,5-dimethylmorpholino) methyl)-4-(2-4S)-6-ethoxy-7-(4-fluorobenzyl)-2-methyl-2,3-dihydro-1H-pyrido[2,3-b][1,4]oxazin-1-yl) oxoethyl)-2-methylpiperazine-1-carboxylate. $^1$H NMR (300 MHz, Chloroform-d) δ 8.15 (brs, 1H), 7.14-7.04 (m, 2H), 6.91-6.79 (m, 2H), 4.82 (s, 1H), 4.30-4.05 (m, 5H), 3.79-3.62 (m, 2 H), 3.56-3.45 (m, 2H), 3.22-3.05 (m, 3H), 3.03-2.94 (m, 1H), 2.74-2.57 (m, 5H), 2.44 (s, 2H), 2.09-1.96 (m, 2H), 1.28-1.13 (m, 6H), 0.94-0.77 (m, 9H). LC-MS $(M+H)^+$=570.5.

Example 88: (S)-1-(2-42R,5R)-2-((7-oxa-4-azaspiro[2.5]octan-4-yl)methyl) methylpiperazin-1-yl) acetyl)-7-(4-fluorobenzyl)-2-methyl-2,3-dihydro-1H-pyrido[2,3-b][1,4]oxazine-6-carboxamide (Compound 88)

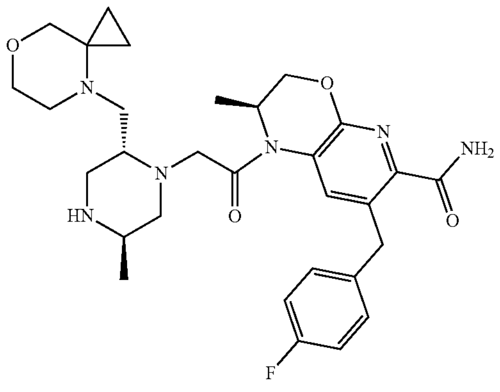 [SMILES: C[C@@H]1CN(CC(=O)N2c3cc(Cc4ccc(F)cc4)c(C(N)=O)nc3OC[C@@H]2C)[C@@H](CN2CCOCC23CC3)CN1]

Step 1: tert-butyl (2R,5S)-5-((7-oxa-4-azaspiro[2.5]octan-4-yl)methyl)-4-(2-((S)-6-carbamoyl-7-(4-fluorobenzyl)-2-methyl-2,3-dihydro-1H-pyrido[2,3-b][1,4]oxazin-1-yl)-2-oxoethyl)-2-methylpiperazine-1-carboxylate

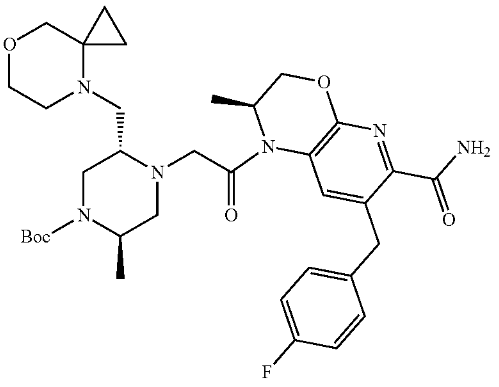 [SMILES: C[C@@H]1CN(CC(=O)N2c3cc(Cc4ccc(F)cc4)c(C(N)=O)nc3OC[C@@H]2C)[C@@H](CN2CCOCC23CC3)CN1C(=O)OC(C)(C)C]

The title compound of step 1 (476 mg, 97% yield) was prepared in a manner similar to that described in Example 1 step 18 from (S)-1-(2-chloroacetyl)-7-(4-fluorobenzyl)-2-methyl-2,3-dihydro-1H-pyrido[2,3-b][1,4]oxazine-6-carboxamide and tert-butyl (2R,5S)-5-((7-oxa-4-azaspiro[2.5]octan-4-yl)methyl)-2-methylpiperazine-1-carboxylate. LC-MS $(M+H)^+$=667.4.

Step 2: (S)-1-(2-((2R,5R)-2-((7-oxa-4-azaspiro[2.5]octan-4-yl)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 88)

Compound 88 (52 mg, 12% yield) was prepared in a manner similar to that described in Example 29 step 7 from tert-butyl (2R,5S)-5-((7-oxa-4-azaspiro[2.5]octan-4-yl)methyl)-4-(2-((S)-6-carbamoyl-7-(4-fluorobenzyl)-2-methyl-2,3-dihydro-1H-pyrido[2,3-b][1,4]oxazin-1-yl)-2-oxoethyl)-2-methylpiperazine-1-carboxylate. 411\11V1R (400 MHz, Chloroform-d) δ 8.47 (brs, 1H), 7.68-7.62 (m, 1H), 7.29-7.20 (m, 2H), 7.02-6.92 (m, 2H), 5.49-5.44 (m, 1H), 4.99-4.93 (m, 1H), 4.54 (s, 2H), 4.43-4.36 (m, 1H), 4.34-4.26 (m, 1H), 4.19-4.11 (m, 1H), 3.74-3.60 (m, 2H), 3.45-3.33 (m, 2H), 3.21-3.13 (m, 1H), 3.09-3.01 (m, 1H), 2.94-2.76 (m, 4H), 2.74-2.66 (m, 1H), 2.55-2.46 (m, 1H), 2.46-2.37 (m, 2H), 2.17-2.07 (m, 1H), 1.34 (d, J=6.8 Hz, 3H), 1.02 (d, J=6.2 Hz, 3H), 0.64-0.56 (m, 2H), 0.54-0.42 (m, 2H). LC-MS $(M+H)^+$=567.3.

Example 89: 2-((2R,5R)-2-(((3R,5R)-3,5-dimethylmorpholino)methyl)-5-methylpiperazin yl)-1-((S)-7-(4-fluorobenzyl)-6-(2-methoxy ethoxy)-2-methyl-2,3-dihydro-1H-pyrido[2,3-b][1,4]oxazin-1-yl)ethan-1-one (Compound 89)

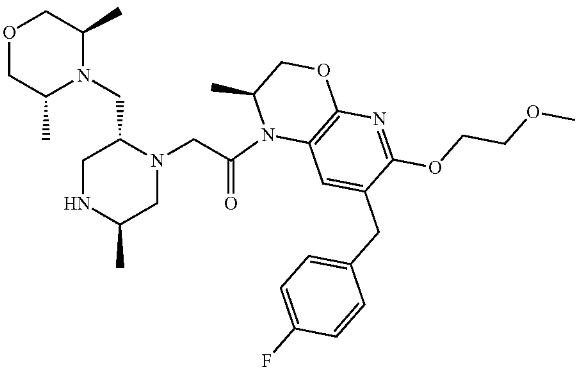 [SMILES: COCCOc1nc2c(cc1Cc1ccc(F)cc1)N(C(=O)CN1C[C@@H](C)NC[C@@H]1CN1[C@H](C)COC[C@H]1C)[C@@H](C)CO2]

Step 1: tert-butyl (S)-7-(4-fluorobenzyl)-6-(2-methoxyethoxy)-2-methyl-2,3-dihydro-1H-pyrido[2,3-b][1,4]oxazine-1-carboxylate

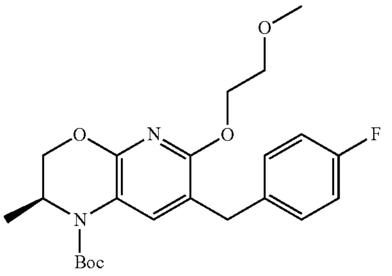 [SMILES: COCCOc1nc2c(cc1Cc1ccc(F)cc1)N(C(=O)OC(C)(C)C)[C@@H](C)CO2]

The title compound of step 1 (190 mg, 66% yield) was prepared in a manner similar to that described in Example 87 step 2 from tert-butyl (S)-7-(4-fluorobenzyl)-6-hydroxy-2-methyl-2,3-dihydro-1H-pyrido[2,3-b][1,4]oxazine-1-carboxylate and 2-bromoethyl methyl ether. LC-MS $(M+H)^+$=433.2.

Step 2: (S)-7-(4-fluorobenzyl)-6-(2-methoxyethoxy)-2-methyl-2,3-dihydro-1H-pyrido[2,3-b][1,4]oxazine

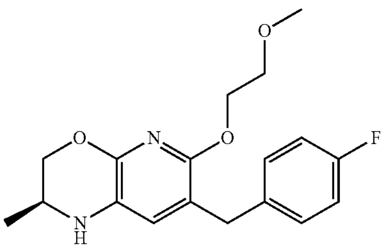 [SMILES: COCCOc1nc2c(cc1Cc1ccc(F)cc1)N[C@@H](C)CO2]

The title compound of step 2 (110 mg, 75% yield) was prepared in a manner similar to that described in Example 1 step 8 from tert-butyl (S)-7-(4-fluorobenzyl)-6-(2-methoxyethoxy)-2-methyl-2,3-dihydro-1H-pyrido[2,3-b][1,4]oxazine-1-carboxylate. LC-MS $(M+H)^+$=333.1.

Step 3: (S)-2-chloro-1-(7-(4-fluorobenzyl)-6-(2-methoxyethoxy)-2-methyl-2,3-dihydro-1H-pyrido[2,3-b][1,4]oxazin-1-yl)ethan-1-one

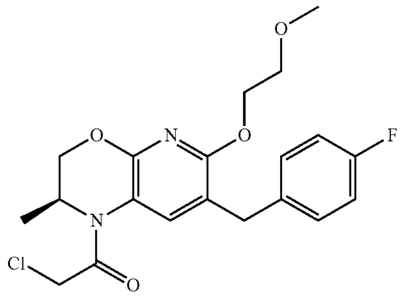 [SMILES: COCCOc1nc2c(cc1Cc1ccc(F)cc1)N(C(=O)CCl)[C@@H](C)CO2]

The title compound of step 3 (110 mg, 73% yield) was prepared in a manner similar to that described in Example 1 step 9 from (S)-7-(4-fluorobenzyl)-6-(2-methoxyethoxy)-2-methyl-2,3-dihydro-1H-pyrido[2,3-b][1,4]oxazine and 2-chloroacetyl chloride. LC-MS $(M+H)^+$=409.1.

Step 4: tert-butyl (2R,5S)-5-(((3R,5R)-3,5-dimethylmorpholino)methyl)-4-(2-((S)-7-(4-fluorobenzyl)-6-(2-methoxyethoxy)-2-methyl-2,3-dihydro-1H-pyrido[2,3-b][1,4]oxazin-1-yl)-2-oxoethyl)-2-methylpiperazine-1-carboxylate

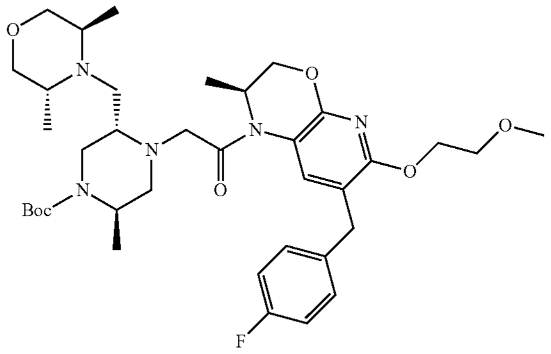 [SMILES: COCCOc1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (70 mg, 37% yield) was prepared in a manner similar to that described in Example 1 step 18 from (S)-2-chloro-1-(7-(4-fluorobenzyl)-6-(2-methoxyethoxy)-2-methyl-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=700.4.

Step 5: 2-((2R,5R)-2-(((3R,5R)-3,5-dimethylmorpholino)methyl)-5-methylpiperazin-1-yl)-1-((S)-7-(4-fluorobenzyl)-6-(2-methoxyethoxy)-2-methyl-2,3-dihydro-1H-pyrido[2,3-b][1,4]oxazin-1-yl)ethan-1-one (Compound 89)

Compound 89 (14 mg, 23% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-6-(2-methoxyethoxy)-2-methyl-2,3-dihydro-1H-pyrido[2,3-b][1,4]oxazin-1-yl)-2-oxoethyl)-2-methylpiperazine-1-carboxylate. $^1$H NMR (300 MHz, DMSO-d6) δ 8.10 (brs, 1H), 7.31-7.20 (m, 2H), 7.16-7.02 (m, 2H), 4.71 (s, 1H), 4.36-4.26 (m, 3H), 4.23-4.13 (m, 1H), 3.94-3.83 (m, 1H), 3.77 (s, 2H), 3.67-3.58 (m, 2H), 3.53-3.44 (m, 2H), 3.44-3.35 (m, 1H), 3.29 (s, 3H), 3.20-3.09 (m, 2H), 3.01-2.91 (m, 1H), 2.83-2.77 (m, 1H), 2.72-2.66 (m, 2H), 2.63-2.53 (m, 2H), 2.48-2.43 (m, 1H), 2.33-2.20 (m, 1H), 2.16-2.03 (m, 1H), 2.03-1.92 (m, 1H), 1.21-1.13 (m, 3H), 0.91-0.81 (m, 9H). LC-MS $(M+H)^+$=600.5.

Example 90: 2-((2R,5R)-2-(((3R,5R)-3,5-dimethylmorpholino)methyl)-5-methylpiperazin yl)-1-(((S)-7-(4-fluorobenzyl)-2-methyl-6-(2-morpholinoethoxy)-2,3-dihydro-1H-pyrido[2,3-b][1,4]oxazin-1-yl)ethan-1-one (Compound 90)

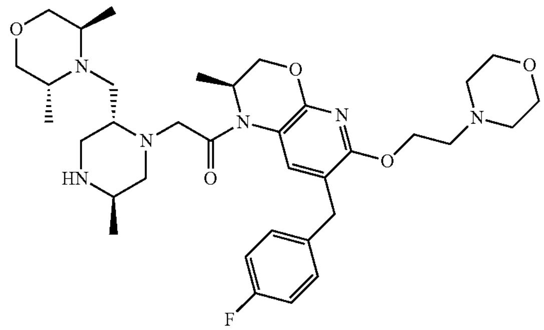 [SMILES: C[C@@H]1CN(CC(=O)N2c3cc(Cc4ccc(F)cc4)c(OCCN4CCOCC4)nc3OC[C@@H]2C)[C@@H](CN2[C@H](C)COC[C@H]2C)CN1]

Step 1: tert-butyl (S)-7-(4-fluorobenzyl)-2-methyl-6-(2-morpholinoethoxy)-2,3-dihydro-1H-pyrido[2,3-b][1,4]oxazine-1-carboxylate

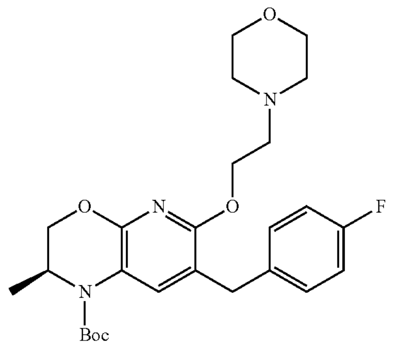 [SMILES: C[C@H]1COc2nc(OCCN3CCOCC3)c(Cc3ccc(F)cc3)cc2N1C(=O)OC(C)(C)C]

The title compound of step 1 (410 mg, 79% yield) was prepared in a manner similar to that described in Example 87 step 2 from tert-butyl (S)-7-(4-fluorobenzyl)-6-hydroxy-2-methyl-2,3-dihydro-1H-pyrido[2,3-b][1,4]oxazine-1-carboxylate and 4-(2-bromoethyl)morpholine. LC-MS $(M+H)^+$=488.2.

Step 2: (S)-7-(4-fluorobenzyl)-2-methyl-6-(2-morpholinoethoxy)-2,3-dihydro-1H-pyrido[2,3-b][1,4]oxazine

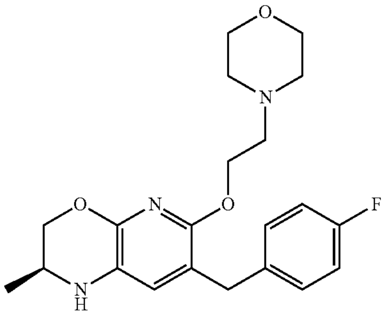 [SMILES: C[C@H]1COc2nc(OCCN3CCOCC3)c(Cc3ccc(F)cc3)cc2N1]

The title compound of step 2 (300 mg, 92% yield) was prepared in a manner similar to that described in Example 1 step 8 from tert-butyl (S)-7-(4-fluorobenzyl)-2-methyl-6-(2-morpholinoethoxy)-2,3-dihydro-1H-pyrido[2,3-b][1,4]oxazine-1-carboxylate. LC-MS $(M+H)^+$=388.1.

Step 3: (S)-2-chloro-1-(7-(4-fluorobenzyl)-2-methyl-6-(2-morpholinoethoxy)-2,3-dihydro-1H-pyrido[2,3-b][1,4]oxazin-1-yl)ethan-1-one

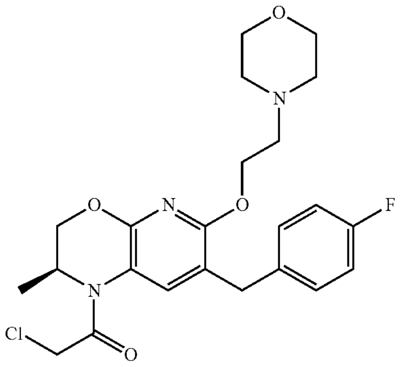 [SMILES: C[C@H]1COc2nc(OCCN3CCOCC3)c(Cc3ccc(F)cc3)cc2N1C(=O)CCl]

The title compound of step 3 (300 mg, 83% yield) was prepared in a manner similar to that described in Example 1 step 9 from (S)-7-(4-fluorobenzyl)-2-methyl-6-(2-morpholinoethoxy)-2,3-dihydro-1H-pyrido[2,3-b][1,4]oxazine and 2-chloroacetyl chloride. LC-MS $(M+H)^+$=464.2.

Step 4: tert-butyl (2R,5S)-5-(((3R,5R)-3,5-dimethylmorpholino)methyl)-4-(2-((S)-7-(4-fluorobenzyl)-2-methyl-6-(2-morpholinoethoxy)-2,3-dihydro-1H-pyrido[2,3-b][1,4]oxazin-1-yl)-2-oxoethyl)-2-methylpiperazine-1-carboxylate

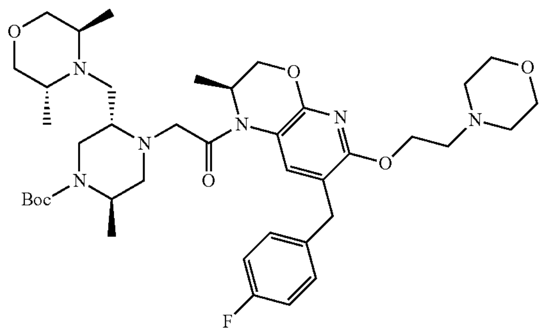 [SMILES: C[C@@H]1CN(CC(=O)N2c3cc(Cc4ccc(F)cc4)c(OCCN4CCOCC4)nc3OC[C@@H]2C)[C@@H](CN2[C@H](C)COC[C@H]2C)CN1C(=O)OC(C)(C)C]

The title compound of step 4 (120 mg, 52% yield) was prepared in a manner similar to that described in Example 1 step 18 from (S)-2-chloro-1-(7-(4-fluorobenzyl)-2-methyl-6-(2-morpholinoethoxy)-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=755.4.

Step 5: 2-((2R,5R)-24(3R,5R)-3,5-dimethylmorpholino)methyl)-5-methylpiperazin-1-yl)-1-((S)-7-(4-fluorobenzyl)-2-methyl-6-(2-morpholinoethoxy)-2,3-dihydro-1H-pyrido[2,3-b][1,4]oxazin-1-yl)ethan-1-one (Compound 90)

Compound 90 (48 mg, 46% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-(2-morpholinoethoxy)-2,3-dihydro-1H-pyrido[2,3-b][1,4]oxazin-1-yl)-2-oxoethyl)-2-methylpiperazine-1-carboxylate. $^1H$ NMR (300 MHz, DMSO-d6) δ 8.11 (brs, 1H), 7.28-7.17 (m, 2H), 7.16-7.03 (m, 2H), 4.74-4.68 (m, 1H), 4.37-4.24 (m, 3H), 4.23-4.13 (m, 1H), 3.95-3.84 (m, 1H), 3.77 (s, 2H), 3.57-3.30 (m, 7H), 3.21-3.10 (m, 2H), 3.01-2.90 (m, 1H), 2.85-2.68 (m, 3H), 2.67-2.60 (m, 3H), 2.59-2.54 (m, 1H), 2.49-2.44 (m, 1H), 2.43-2.35 (m, 4H), 2.34-2.20 (m, 1H), 2.16-2.02 (m, 1H), 2.02-1.91 (m, 1H), 1.27-1.13 (m, 3H), 0.91-0.82 (m, 9H). LC-MS $(M+H)^+$=655.4.

Example 91A & B: 1-((S)-7-(4-fluorobenzyl)-6-(hydroxymethyl)-2-methyl-2,3-dihydro-1H-pyrido[2,3-b][1,4]oxazin-1-yl)-2-((2R,5R)-5-methyl-2-(((S)-3-(trifluoromethyl)morpholino)methyl)piperazin-1-yl)ethan-1-one and 1-((S)-7-(4-fluorobenzyl)-6-(hydroxymethyl)-2-methyl-2,3-dihydro-1H-pyrido[2,3-b][1,4]oxazin-1-yl)-2-((2R,5R)-5-methyl-2-(((R)-3-(trifluoromethyl)morpholino)methyl)piperazin-1-yl)ethan-1-one (Compound 91A & 91B)

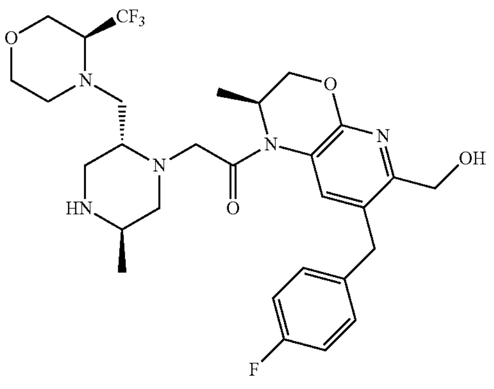

and

-continued

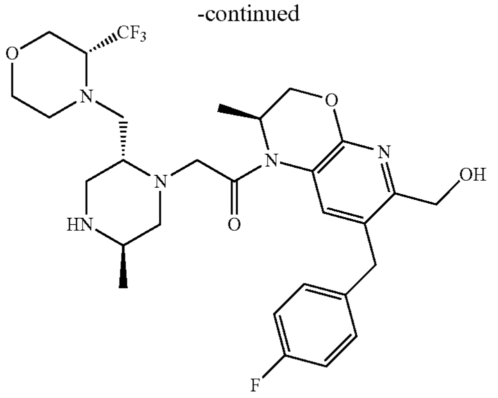

Step 1: tert-butyl (2R,5R)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(hydroxymethyl)-2-methylpiperazine-1-carboxylate

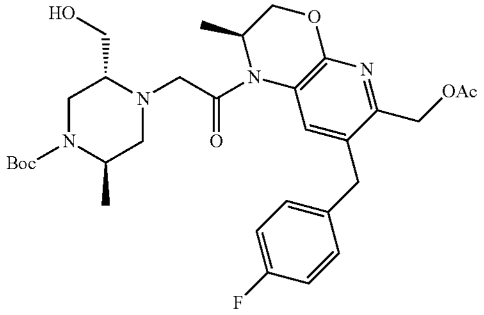

The title compound of step 1 (911 mg, 98% yield) was prepared in a manner similar to that described in Example 1 step 18 from (S)-(1-(2-chloroacetyl)-7-(4-fluorobenzyl)-2-methyl-2,3-dihydro-1H-pyrido[2,3-b][1,4]oxazin-6-yl) methyl acetate and tert-butyl (2R,5R)-5-(hydroxymethyl)-2-methylpiperazine-1-carboxylate. LC-MS $(M+H)^+=601.4$.

Step 2: tert-butyl (2R,5R)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(chloromethyl)-2-methylpiperazine-1-carboxylate

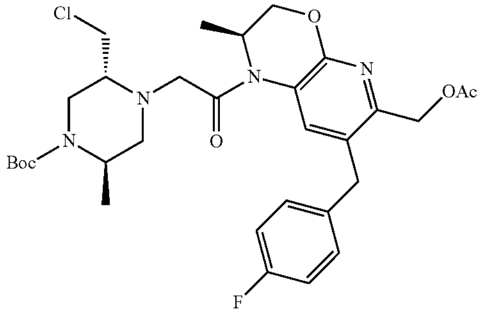 [SMILES: CC(=O)OCc1nc2c(cc1Cc1ccc(F)cc1)N(C(=O)CN1C[C@@H](C)N(C(=O)OC(C)(C)C)C[C@@H]1CCl)[C@@H](C)CO2]

The title compound of step 2 (670 mg, 71% yield) was prepared in a manner similar to that described in Example 1 step 15 from tert-butyl (2R,5R)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl) (hydroxymethyl)-2-methylpiperazine-1-carboxylate. LC-MS $(M+H)^+=619.3$.

Step 3: tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-2-methyl-5-((3-(trifluoromethyl)morpholino)methyl) piperazine-1-carboxylate

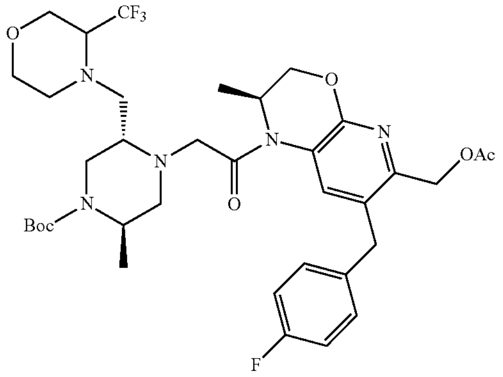 [SMILES: CC(=O)OCc1nc2c(cc1Cc1ccc(F)cc1)N(C(=O)CN1C[C@@H](C)N(C(=O)OC(C)(C)C)C[C@@H]1CN1CCOCC1C(F)(F)F)[C@@H](C)CO2]

The title compound of step 3 (23 mg, 6% yield) was prepared in a manner similar to that described in Example 1 step 16 from tert-butyl (2R,5R)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(chloromethyl)-2-methylpiperazine-1-carboxylate and 3-(trifluoromethyl) morpholine hydrochloride. LC-MS $(M+H)^+=738.4$.

Step 4: tert-butyl (2R,5S)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methyl-5-((3-(trifluoromethyl)morpholino)methyl) piperazine-1-carboxylate

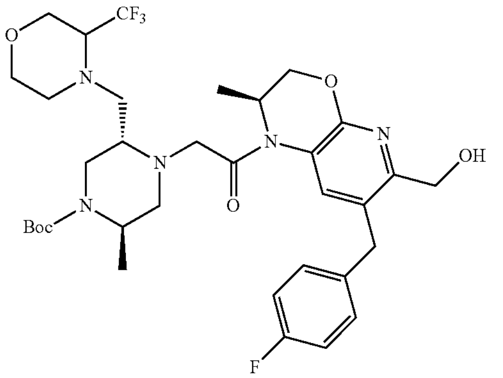 [SMILES: C[C@@H]1CN(CC(=O)N2c3cc(Cc4ccc(F)cc4)c(CO)nc3OC[C@@H]2C)[C@@H](CN2CCOCC2C(F)(F)F)CN1C(=O)OC(C)(C)C]

The title compound of step 4 (16 mg, 75% yield) was prepared in a manner similar to that described in Example 8 step 4 from tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-2-methyl-5-((3-(trifluoromethyl)morpholino)methyl)piperazine-1-carboxylate. LC-MS $(M+H)^+=696.4$.

Step 5: 1-((S)-7-(4-fluorobenzyl)-6-(hydroxymethyl)-2-methyl-2,3-dihydro-1H-pyrido[2,3-b][1,4]oxazin-1-yl)-2-((2R,5R)-5-methyl-2-(((S)-3-(trifluoromethyl)morpholino)methyl)piperazin-1-yl)ethan-1-one and 1-((S)-7-(4-fluorobenzyl)-6-(hydroxymethyl)-2-methyl-2,3-dihydro-1H-pyrido[2,3-b][1,4]oxazin-1-yl)-2-((2R,5R) methyl-2-(((R)-3-(trifluoromethyl)morpholino)methyl)piperazin-1-yl)ethan-1-one (Compound 91A & 91B)

Compound 91A & 91B mixture was prepared in a manner similar to that described in Example 29 step 7 from tert-butyl (2R,5S)-4-(2-((S)-7-(4-fluorobenzyl)-6-(hydroxymethyl)-2-methyl-2,3-dihydro-1H-pyrido[2,3-b][1,4]oxazin-1-yl)-2-oxoethyl)-2-methyl-5-((3-(trifluoromethyl)morpholino)methyl)piperazine-1-carboxylate. The isomer mixture was furtherly purified by chiral-HPLC to afford the diastereomeric pure 91A & 91B with the following conditions: Column, XBridge Prep OBD C18 Column, 19*250 mm, 5 um; mobile phase, Water (10 mmol/L $NH_4HCO_3$+0.1% $NH_3 \cdot H_2O$) and ACN (20% up to 50% in 8 min); Detector, UV 254 nm.

Compound 91A (6 mg, 52% yield): $^1H$ NMR (400 MHz, Chloroform-d) δ 8.47 (brs, 1H), 7.16-7.08 (m, 2H), 7.05-6.95 (m, 2H), 4.91-4.87 (m, 1H), 4.66-4.52 (m, 2H), 4.44-4.36 (m, 1H), 4.35-4.27 (m, 1H), 4.04-3.92 (m, 2H), 3.84 (s, 2H), 3.80-3.72 (m, 2H), 3.66-3.56 (m, 1H), 3.24-3.17 (m, 2H), 3.09-3.04 (m, 3H), 2.87-2.83 (m, 1H), 2.80-2.72 (m, 1H), 2.63-2.37 (m, 5H), 2.23-2.13 (m, 1H), 1.36-1.30 (m, 3H), 1.05 (d, J=6.3 Hz, 3H). LC-MS $(M+H)^+$=596.3. Chiral HPLC: tR=1.060 min.

Compound 91B (2 mg, 12% yield): $^1H$ NMR (400 MHz, Chloroform-d) δ 8.47 (brs, 1H),7.15-7.07 (m, 2H), 7.05-6.96 (m, 2H), 4.66-4.51 (m, 2H), 4.43-4.30 (m, 2H), 4.08-3.94 (m, 1H), 3.86 (s, 2H), 3.81-3.64 (m, 3H), 3.61-3.50 (m, 3H), 3.30-3.19 (m, 2H), 3.18-3.09 (m, 3H), 3.08-2.72 (m, 5H), 2.64-2.57 (m, 1H), 2.50-2.43 (m, 1H), 1.32 (s, 3H), 1.07 (d, J=6.3 Hz, 3H). LC-MS $(M+H)^+$=596.2. Chiral HPLC: tR=1.173 min.

Example 92: 2-((2R,5R)-2-(((3R,5R)-3,5-dimethylmorpholino)methyl)-5-methylpiperazin-1-yl)-1-(((S)-7-(4-fluorobenzyl)-2-methyl-6-(morpholinomethyl)-2,3-dihydro-1H-pyrido[2,3-b][1,4]oxazin-1-yl)ethan-1-one (Compound 92)

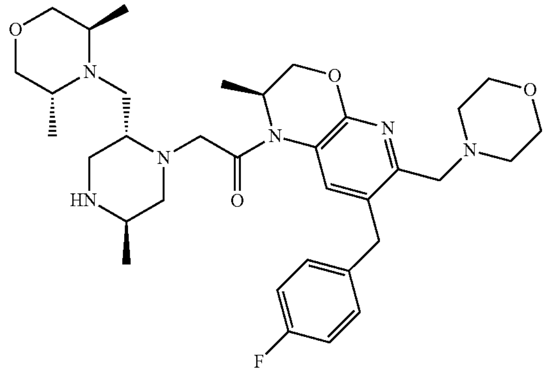 [SMILES: C[C@@H]1CN(CC(=O)N2c3cc(Cc4ccc(F)cc4)c(CN4CCOCC4)nc3OC[C@@H]2C)[C@@H](CN2[C@H](C)COC[C@H]2C)CN1]

Step 1: benzyl (S)-7-(4-fluorobenzyl)-2-methyl-6-(morpholinomethyl)-2,3-dihydro-1H-pyrido[2,3-b][1,4]oxazine-1-carboxylate

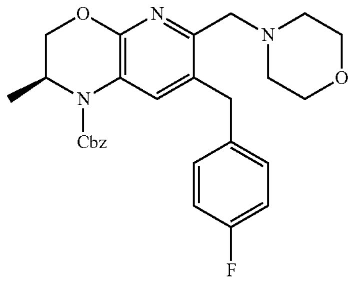 [SMILES: C[C@H]1COc2nc(CN3CCOCC3)c(Cc3ccc(F)cc3)cc2N1C(=O)OCc1ccccc1]

To a solution of benzyl (S)-7-(4-fluorobenzyl)-6-formyl-2-methyl-2,3-dihydro-1H-pyrido[2,3-b][1,4]oxazine-1-carboxylate (550 mg, 1.31 mmol) and morpholine (227 mg, 2.62 mmol) in MeOH (22 mL) was added $NaBH_3CN$ (411 mg, 6.54 mmol) in portions at room temperature. The resulting mixture was stirred for 2 h at room temperature. When the reaction was done, the reaction was then quenched by the addition of sat. $NaHCO_3$ at room temperature. The resulting mixture was extracted with DCM (40 mL×2). The organic phases were combined, washed with brine and dried over $Na_2SO_4$. The resulting mixture was concentrated under reduced pressure. The residue was purified by silica gel column chromatography (DCM:EtOAc=1:1) yield the title compound (225 mg, 35% yield). LC-MS $(M+H)^+$=492.3.

Step 2: (S)-7-(4-fluorobenzyl)-2-methyl-6-(morpholinomethyl)-2,3-dihydro-1H-pyrido[2,3-b][1,4]oxazine

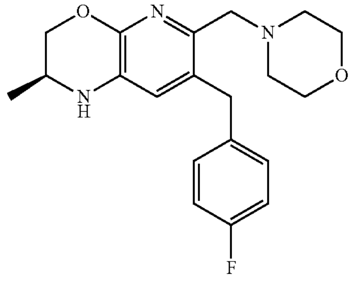 [SMILES: C[C@H]1COc2nc(CN3CCOCC3)c(Cc3ccc(F)cc3)cc2N1]

To a solution of benzyl (S)-7-(4-fluorobenzyl)-2-methyl-6-(morpholinomethyl)-2,3-dihydro-1H-pyrido[2,3-b][1,4]oxazine-1-carboxylate (225 mg, 0.46 mmol) in DCM (10 mL) was added $BCl_3$ in DCM (5 mL, 5 mmol, 1M) in portions at 0° C. under nitrogen atmosphere. The resulting mixture was stirred for 1 h at room temperature under nitrogen atmosphere. When the reaction was done, the reaction was then quenched by the addition of sat. $NaHCO_3$ at room temperature. The resulting mixture was extracted with DCM (40 mL×2). The organic phases were combined, washed with brine and dried over $Na_2SO_4$. The resulting mixture was concentrated under reduced pressure. The residue was purified by silica gel column chromatography (DCM:MeOH=10:1) to yield the title compound (150 mg, 89% yield). LC-MS $(M+H)^+$=358.3

Step 3: (S)-2-chloro-1-(7-(4-fluorobenzyl)-2-methyl-6-(morpholinomethyl)-2,3-dihydro-1H-pyrido[2,3-b][1,4]oxazin-1-yl)ethan-1-one

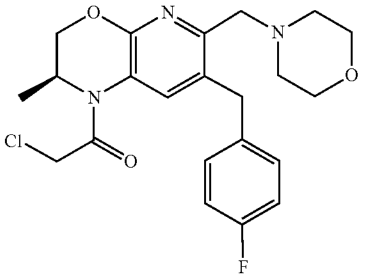 [SMILES: C[C@H]1COc2nc(CN3CCOCC3)c(Cc3ccc(F)cc3)cc2N1C(=O)CCl]

The title compound of step 3 (112 mg, 61% yield) was prepared in a manner similar to that described in Example 1 step 9 from (S)-7-(4-fluorobenzyl)-2-methyl-6-(morpholinomethyl)-2,3-dihydro-1H-pyrido[2,3-b][1,4]oxazine and 2-chloroacetyl chloride. LC-MS $(M+H)^+$=434.2.

Step 4: tert-butyl (2R,5S)-5-(((3R,5R)-3,5-dimethylmorpholino)methyl)-4-(2-((S)-7-(4-fluorobenzyl)-2-methyl-6-(morpholinomethyl)-2,3-dihydro-1H-pyrido[2,3-b][1,4]oxazin-1-yl)-2-oxoethyl)-2-methylpiperazine-1-carboxylate

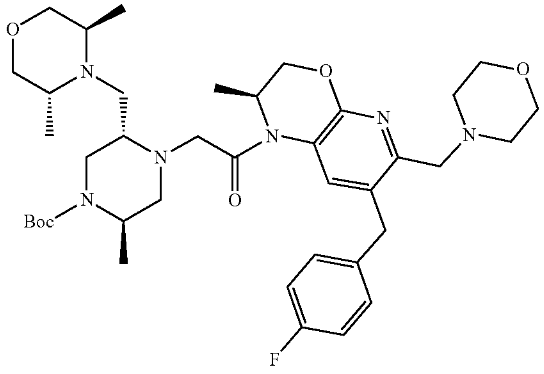 [SMILES: C[C@@H]1CN(CC(=O)N2c3cc(Cc4ccc(F)cc4)c(CN4CCOCC4)nc3OC[C@@H]2C)[C@@H](CN2[C@H](C)COC[C@H]2C)CN1C(=O)OC(C)(C)C]

The title compound of step 4 (132 mg, 70% yield) was prepared in a manner similar to that described in Example 1 step 18 from (S)-2-chloro-1-(7-(4-fluorobenzyl)-2-methyl-6-(morpholinomethyl)-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=725.5.

Step 5: 2-42R,5R)-24(3R,5R)-3,5-dimethylmorpholino)methyl)-5-methylpiperazin-1-yl)-1-((S)-7-(4-fluorobenzyl)-2-methyl-6-(morpholinomethyl)-2,3-dihydro-1H-pyrido[2,3-b][1,4]oxazin-1-yl)ethan-1-one (Compound 92)

Compound 92 (36 mg, 31% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-(morpholinomethyl)-2,3-dihydro-1H-pyrido[2,3-b][1,4]oxazin-1-yl)-2-oxoethyl)-2-methylpiperazine-1-carboxylate. $^{1}$H $N_1$V1R (400 MHz, DMSO-d6) δ 8.13 (brs, 1H), 7.25-7.16 (m, 2H), 7.16-7.06 (m, 2H), 4.76-4.70 (m, 1H), 4.35-4.25 (m, 1H), 4.25-4.17 (m, 1H), 4.10-3.97 (m, 2H), 3.95-3.87 (m, 1H), 3.53-3.41 (m, 8H), 3.38-3.34 (m, 2H), 3.14-3.05 (m, 2H), 2.97-2.89 (m, 1H), 2.80-2.72 (m, 1H), 2.71-2.62 (m, 2H), 2.61-2.49 (m, 2H), 2.42-2.21 (m, 5H), 2.18-2.05 (m, 1H), 2.00-1.91 (m, 1H), 1.17 (d, J=6.6 Hz, 3H), 0.94-0.78 (m, 9H). LC-MS $(M+H)^+$=625.3.

Example 93: (S)-1-(2-((2R,5R)-2-(((3R,5R)-3,5-dimethylmorpholino)methyl) methylpiperazin-1-yl) acetyl)-7-(4-fluorobenzyl)-2-methyl-N—(((S)-tetrahydrofuranyl)methyl)-2,3-dihydro-1H-pyrido[2,3-b][1,4]oxazine-6-carboxamide (Compound 93)

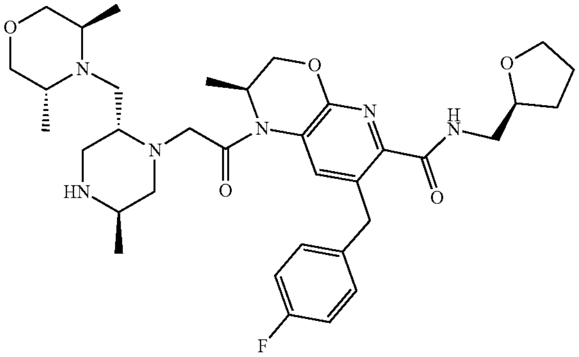 [SMILES: C[C@@H]1CN(CC(=O)N2c3cc(Cc4ccc(F)cc4)c(C(=O)NC[C@@H]4CCCO4)nc3OC[C@@H]2C)[C@@H](CN2[C@H](C)COC[C@H]2C)CN1]

Step 1: benzyl (S)-7-(4-fluorobenzyl)-2-methyl-6-((((S)-tetrahydrofuran-2-yl)methyl)carbamoyl)-2,3-dihydro-1H-pyrido[2,3-b][1,4]oxazine-1-carboxylate

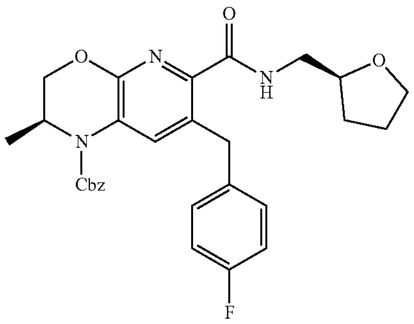 [SMILES: C[C@H]1COc2nc(C(=O)NC[C@@H]3CCCO3)c(Cc3ccc(F)cc3)cc2N1C(=O)OCc1ccccc1]

The title compound of step 1 (351 mg, 73% yield) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and (S)-(tetrahydrofuran-2-yl)methanamine. LC-MS $(M+H)^+$=520.2.

Step 2: (S)-7-(4-fluorobenzyl)-2-methyl-N—(((S)-tetrahydrofuran-2-yl)methyl)-2,3-dihydro-1H-pyrido[2,3-b][1,4]oxazine-6-carboxamide

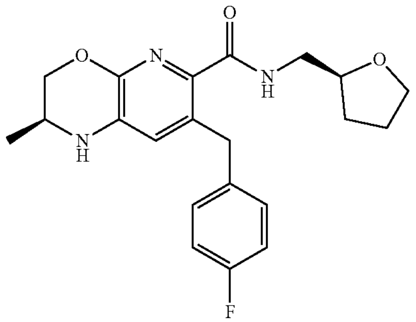 [SMILES: C[C@H]1COc2nc(C(=O)NC[C@@H]3CCCO3)c(Cc3ccc(F)cc3)cc2N1]

The title compound of step 2 (210 mg, 80% yield) was prepared in a manner similar to that described in Example 1 step 17 from benzyl (S)-7-(4-fluorobenzyl)-2-methyl-6-((((S)-tetrahydrofuran-2-yl)methyl)carbamoyl)-2,3-dihydro-1H-pyrido[2,3-b][1,4]oxazine-1-carboxylate. LC-MS $(M+H)^+$=386.1.

Step 3: (S)-1-(2-chloroacetyl)-7-(4-fluorobenzyl)-2-methyl —N—(((S)-tetrahydrofuran yl)methyl)-2,3-dihydro-1H-pyrido[2,3-b][1,4]oxazine-6-carboxamide

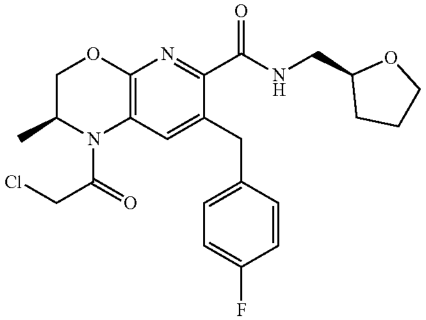 [SMILES: C[C@H]1COc2nc(C(=O)NC[C@@H]3CCCO3)c(Cc3ccc(F)cc3)cc2N1C(=O)CCl]

The title compound of step 3 (150 mg, 83% yield) was prepared in a manner similar to that described in Example 1 step 9 from (S)-7-(4-fluorobenzyl)-2-methyl-N—(((S)-tetrahydrofuran-2-yl)methyl)-2,3-dihydro-1H-pyrido[2,3-b][1,4]oxazine-6-carboxamide and 2-chloroacetyl chloride. LC-MS $(M+H)^+$=462.3.

Step 4: tert-butyl (2R,5S)-5-(((3R,5R)-3,5-dimethylmorpholino)methyl)-4-(2-((S)-7-(4-fluorobenzyl)-2-methyl-6-((((S)-tetrahydrofuran-2-yl)methyl)carbamoyl)-2,3-dihydro-1H-pyrido[2,3-b][1,4]oxazin-1-yl)-2-oxoethyl)-2-methylpiperazine-1-carboxylate

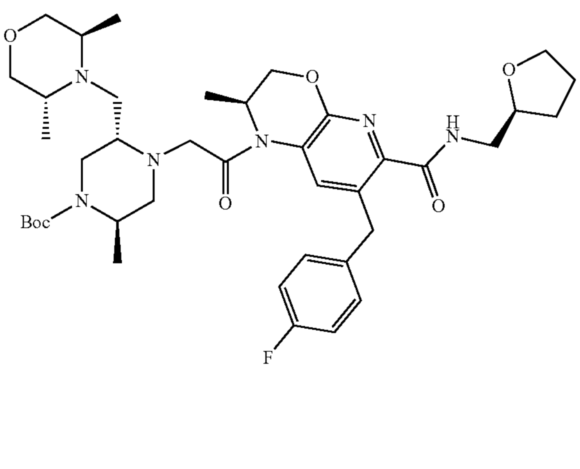 [SMILES: C[C@@H]1CN(CC(=O)N2c3cc(Cc4ccc(F)cc4)c(C(=O)NC[C@@H]4CCCO4)nc3OC[C@@H]2C)[C@@H](CN2[C@H](C)COC[C@H]2C)CN1C(=O)OC(C)(C)C]

The title compound of step 4 (66 mg, 27% yield) was prepared in a manner similar to that described in Example 1 step 18 from (S)-1-(2-chloroacetyl)-7-(4-fluorobenzyl)-2-methyl-N—(((S)-tetrahydrofuran-2-yl)methyl)-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=753.4.

Step 5: (S)-1-(24(2R,5R)-2-(((3R,5R)-3,5-dimethylmorpholino)methyl)-5-methylpiperazin-1-yl)acetyl)-7-(4-fluorobenzyl)-2-methyl-N—(((S)-tetrahydrofuran-2-yl)methyl)-2,3-dihydro-1H-pyrido[2,3-b][1,4]oxazine-6-carboxamide (Compound 93)

Compound 93 (16 mg, 28% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-4-(((S)-tetrahydrofuran-2-yl)methyl)carbamoyl)-2,3-dihydro-1H-pyrido[2,3-b][1,4]oxazin-1-yl)-2-oxoethyl)-2-methylpiperazine-1-carboxylate. $^1H$ NMR (400 MHz, DMSO-d6) δ 8.38-8.33 (m, 2H), 7.27-7.19 (m, 2H), 7.13-7.03 (m, 2H), 4.82-4.75 (m, 1H), 4.43-4.19 (m, 4H), 4.02-3.89 (m, 2H), 3.83-3.73 (m, 1H), 3.68-3.58 (m, 1H), 3.55-3.47 (m, 1H), 3.47-3.40 (m, 2H), 3.32-3.21 (m, 2H), 3.14-3.05 (m, 2H), 2.96-2.89 (m, 1H), 2.82-2.73 (m, 1H), 2.71-2.64 (m, 2H), 2.64-2.53 (m, 3H), 2.32-2.21 (m, 1H), 2.20-2.10 (m, 1H), 2.01-1.92 (m, 1H), 1.92-1.75 (m, 3H), 1.60-1.50 (m, 1H), 1.27-1.14 (m, 3H), 0.90-0.81 (m, 9H). LC-MS $(M+H)^+$=653.5.

Example 94: (S)-1-(2-42R,5R)-2-(((3R,5R)-3,5-dimethylmorpholino)methyl) methylpiperazin-1-yl)acetyl)-7-(4-fluorobenzyl)-2-methyl-N—(((R)-tetrahydrofuran-2-yl)methyl)-2,3-dihydro-1H-pyrido[2,3-b][1,4]oxazine-6-carboxamide (Compound 94)

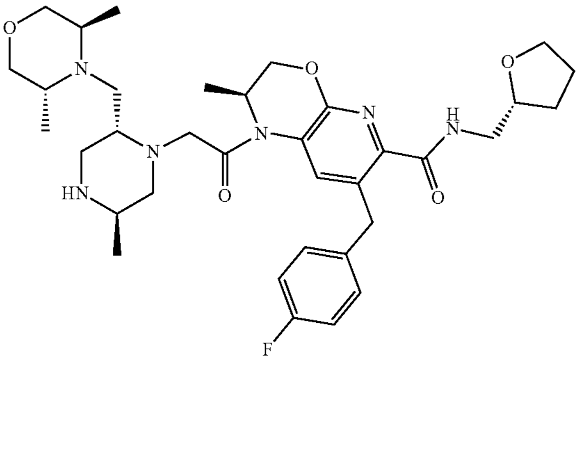 [SMILES: C[C@@H]1CN(CC(=O)N2c3cc(Cc4ccc(F)cc4)c(C(=O)NC[C@H]4CCCO4)nc3OC[C@@H]2C)[C@@H](CN2[C@H](C)COC[C@H]2C)CN1]

Step 1: benzyl (S)-7-(4-fluorobenzyl)-2-methyl-6-4-((((R)-tetrahydrofuran-2-yl)methyl)carbamoyl)-2,3-dihydro-1H-pyrido[2,3-b][1,4]oxazine-1-carboxylate

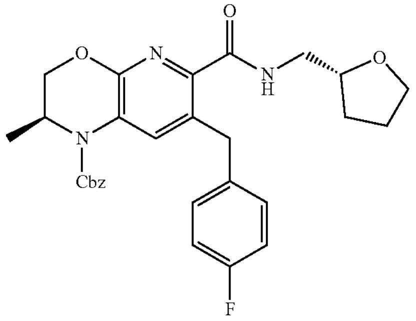 [SMILES: C[C@H]1COc2nc(C(=O)NC[C@H]3CCCO3)c(Cc3ccc(F)cc3)cc2N1C(=O)OCc1ccccc1]

The title compound of step 1 (432 mg, 97% yield) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and (R)-(tetrahydrofuran-2-yl)methanamine. LC-MS $(M+H)^+$=520.3.

Step 2: (S)-7-(4-fluorobenzyl)-2-methyl-N—(((R)-tetrahydrofuran-2-yl)methyl)-2,3-dihydro-1H-pyrido[2,3-b][1,4]oxazine-6-carboxamide

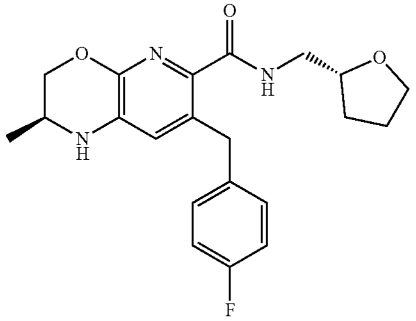 [SMILES: C[C@H]1COc2nc(C(=O)NC[C@H]3CCCO3)c(Cc3ccc(F)cc3)cc2N1]

The title compound of step 2 (150 mg, 46% yield) was prepared in a manner similar to that described in Example 1 step 17 from benzyl (S)-7-(4-fluorobenzyl)-2-methyl-6-((((R)-tetrahydrofuran-2-yl)methyl)carbamoyl)-2,3-dihydro-1H-pyrido[2,3-b][1,4]oxazine carboxylate. LC-MS $(M+H)^+$=386.3.

Step 3: (S)-1-(2-chloroacetyl)-7-(4-fluorobenzyl)-2-methyl-N—(((R)-tetrahydrofuran yl)methyl)-2,3-dihydro-1H-pyrido[2,3-b][1,4]oxazine-6-carboxamide

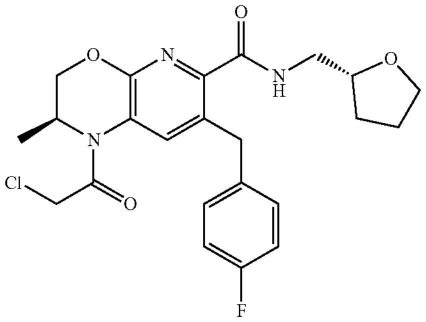 [SMILES: C[C@H]1COc2nc(C(=O)NC[C@H]3CCCO3)c(Cc3ccc(F)cc3)cc2N1C(=O)CCl]

The title compound of step 3 (105 mg, 58% yield) was prepared in a manner similar to that described in Example 1 step 9 from (S)-7-(4-fluorobenzyl)-2-methyl-N—(((R)-tetrahydrofuran-2-yl)methyl)-2,3-dihydro-1H-pyrido[2,3-b][1,4]oxazine-6-carboxamide and 2-chloroacetyl chloride. LC-MS $(M+H)^+$=462.3.

Step 4: tert-butyl (2R,5S)-54(3R,5R)-3,5-dimethylmorpholino)methyl)-4-(2-((S)-7-(4-fluorobenzyl)-2-methyl-6-(((R)-tetrahydrofuran-2-yl)methyl)carbamoyl)-2,3-dihydro-1H-pyrido[2,3-b][1,4]oxazin-1-yl)-2-oxoethyl)-2-methylpiperazine-1-carboxylate

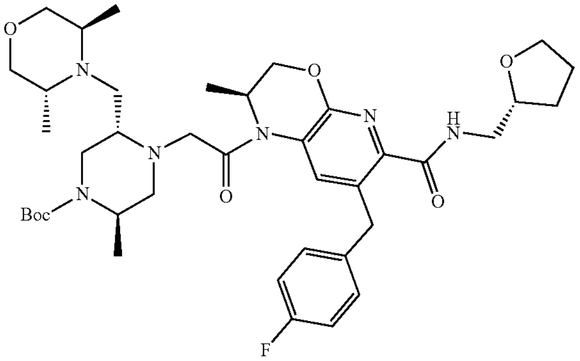 [SMILES: C[C@@H]1CN(CC(=O)N2c3cc(Cc4ccc(F)cc4)c(C(=O)NC[C@H]4CCCO4)nc3OC[C@@H]2C)[C@@H](CN2[C@H](C)COC[C@H]2C)CN1C(=O)OC(C)(C)C]

The title compound of step 4 (160 mg, 93% yield) was prepared in a manner similar to that described in Example 1 step 18 from (S)-1-(2-chloroacetyl)-7-(4-fluorobenzyl)-2-methyl-N—(((R)-tetrahydrofuran-2-yl)methyl)-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=753.5.

Step 5: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N—(((R)-tetrahydrofuran-2-yl)methyl)-2,3-dihydro-1H-pyrido[2,3-b][1,4]oxazine-6-carboxamide (Compound 94)

Compound 94 (68 mg, 49% yield) was prepared in a manner similar to that described in Example 29 step 7 from tert-butyl (2R,5S)-54(3R,5R)-3,5-dimethylmorpholino)methyl)-4-(2-4S)-7-(4-fluorobenzyl)-2-methyl-6-((((R)-tetrahydrofuran-2-yl)methyl)carbamoyl)-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 8.39-8.32 (m, 2H), 7.27-7.18 (m, 2H), 7.13-7.03 (m, 2H), 4.84-4.75 (m, 1H), 4.46-4.24 (m, 4H), 4.03-3.89 (m, 2H), 3.83-3.74 (m, 1H), 3.68-3.58 (m, 1H), 3.55-3.47 (m, 1H), 3.47-3.36 (m, 2H), 3.30-3.20 (m, 2H), 3.14-3.05 (m, 2H), 3.00-2.89 (m, 1H), 2.82-2.74 (m, 1H), 2.74-2.65 (m, 2H), 2.69-2.53 (m, 3H), 2.32-2.22 (m, 1H), 2.20-2.10 (m, 1H), 2.05-2.01 (m, 1H), 2.01-1.93 (m, 1H), 1.93-1.73 (m, 3H), 1.61-1.48 (m, 1H), 1.22 (d, J=6.7 Hz, 3H), 0.90-0.81 (m, 9H). LC-MS $(M+H)^+$=653.5.

Example 95: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N—((S)-tetrahydrofuran-3-yl)methyl)-2,3-dihydro-1H-pyrido[2,3-b][1,4]oxazine-6-carboxamide (Compound 95)

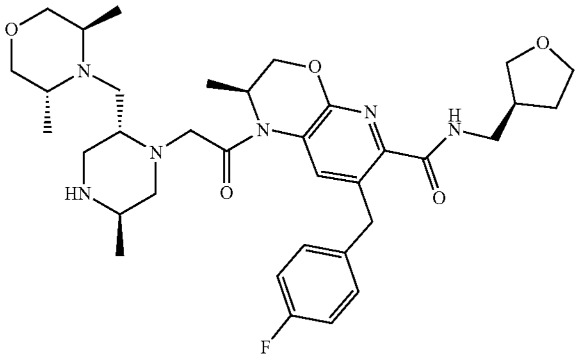 [SMILES: C[C@@H]1CN(CC(=O)N2c3cc(Cc4ccc(F)cc4)c(C(=O)NC[C@@H]4CCOC4)nc3OC[C@@H]2C)[C@@H](CN2[C@H](C)COC[C@H]2C)CN1]

Step 1: benzyl (S)-7-(4-fluorobenzyl)-2-methyl-6-((((S)-tetrahydrofuran-3-yl)methyl)carbamoyl)-2,3-dihydro-1H-pyrido[2,3-b][1,4]oxazine-1-carboxylate

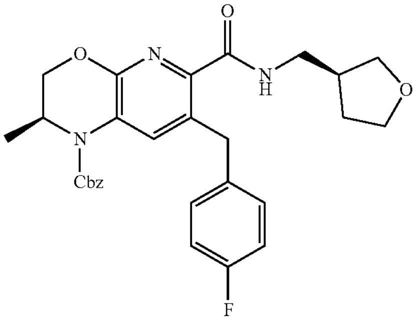 [SMILES: C[C@H]1COc2nc(C(=O)NC[C@@H]3CCOC3)c(Cc3ccc(F)cc3)cc2N1C(=O)OCc1ccccc1]

The title compound of step 1 (400 mg, 84% yield) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and (S)-(tetrahydrofuran-3-yl)methanamine. LC-MS $(M+H)^+=520.1$.

Step 2: (S)-7-(4-fluorobenzyl)-2-methyl-N—(((S)-tetrahydrofuran-3-yl)methyl)-2,3-dihydro-1H-pyrido[2,3-b][1,4]oxazine-6-carboxamide

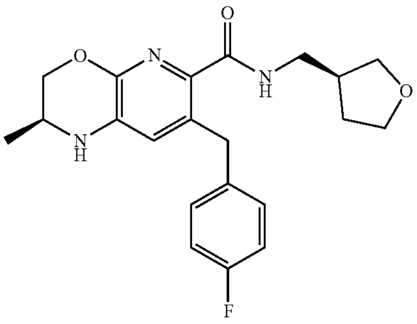 [SMILES: C[C@H]1COc2nc(C(=O)NC[C@@H]3CCOC3)c(Cc3ccc(F)cc3)cc2N1]

The title compound of step 2 (180 mg, 80% yield) was prepared in a manner similar to that described in Example 1 step 17 from benzyl (S)-7-(4-fluorobenzyl)-2-methyl-6-((((S)-tetrahydrofuran-3-yl)methyl)carbamoyl)-2,3-dihydro-1H-pyrido[2,3-b][1,4]oxazine-1-carboxylate. LC-MS $(M+H)^+=386.0$.

Step 3: (S)-1-(2-chloroacetyl)-7-(4-fluorobenzyl)-2-methyl-N—(((S)-tetrahydrofuran yl)methyl)-2,3-dihydro-1H-pyrido[2,3-b][1,4]oxazine-6-carboxamide

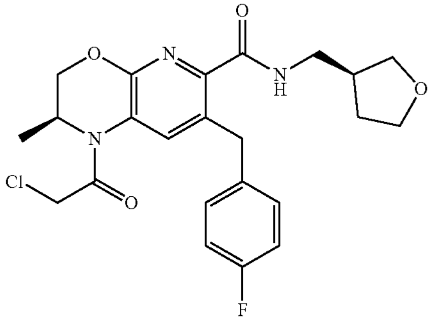 [SMILES: C[C@H]1COc2nc(C(=O)NC[C@@H]3CCOC3)c(Cc3ccc(F)cc3)cc2N1C(=O)CCl]

The title compound of step 3 (135 mg, 63% yield) was prepared in a manner similar to that described in Example 1 step 9 from (S)-7-(4-fluorobenzyl)-2-methyl-N—(((S)-tetrahydrofuran-3-yl)methyl)-2,3-dihydro-1H-pyrido[2,3-b][1,4]oxazine-6-carboxamide and 2-chloroacetyl chloride. LC-MS $(M+H)^+=462.0$.

Step 4: tert-butyl (2R,5S)-5-(((3R,5R)-3,5-dimethylmorpholino)methyl)-4-(2-((S)-7-(4-fluorobenzyl)-2-methyl-6-((((S)-tetrahydrofuran-3-yl)methyl)carbamoyl)-2,3-dihydro-1H-pyrido[2,3-b][1,4]oxazin-1-yl)-2-oxoethyl)-2-methylpiperazine-1-carboxylate

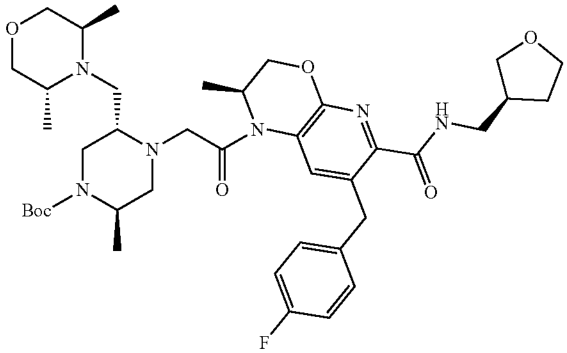 [SMILES: C[C@@H]1CN(CC(=O)N2c3cc(Cc4ccc(F)cc4)c(C(=O)NC[C@@H]4CCOC4)nc3OC[C@@H]2C)[C@@H](CN2[C@H](C)COC[C@H]2C)CN1C(=O)OC(C)(C)C]

The title compound of step 4 (120 mg, 49% yield) was prepared in a manner similar to that described in Example 1 step 18 from (S)-1-(2-chloroacetyl)-7-(4-fluorobenzyl)-2-methyl-N—(((S)-tetrahydrofuran-3-yl)methyl)-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+=753.2$.

Step 5: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N—(((S)-tetrahydrofuran-3-yl)methyl)-2,3-dihydro-1H-pyrido[2,3-b][1,4]oxazine-6-carboxamide (Compound 95)

Compound 95 (13 mg, 12% yield) was prepared in a manner similar to that described in Example 29 step 7 from tert-butyl (2R,5S)-5-(((3R,5R)-3,5-dimethylmorpholino)methyl)-4-(2-4S)-7-(4-fluorobenzyl)-2-methyl-6-(((S)-tetrahydrofuran-3-yl)methyl)carbamoyl)-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 8.55 (t, J=6.1 Hz, 1H), 8.34 (brs, 1H), 7.26-7.17 (m, 2H), 7.12-7.02 (m, 2H), 4.80-4.74 (m, 1H), 4.42-4.34 (m, 1H), 4.31-4.26 (m, 3H), 4.01-3.93 (m, 1H), 3.77-3.67 (m, 1H), 3.67-3.55 (m, 2H), 3.55-3.47 (m, 1H), 3.47-3.38 (m, 3H), 3.26-3.16 (m, 2H), 3.13-3.04 (m, 2H), 2.97-2.89 (m, 1H), 2.82-2.73 (m, 1H), 2.72-2.65 (m, 2H), 2.65-2.53 (m, 3H), 2.49-2.39 (m, 1H), 2.31-2.22 (m, 1H), 2.22-2.12 (m, 1H), 2.01-1.92 (m, 1H), 1.94-1.81 (m, 1H), 1.62-1.50 (m, 1H), 1.22 (d, J=6.7 Hz, 3H), 0.90-0.81 (m, 9H). LC-MS $(M+H)^+$=653.5.

Example 96: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N—(((R)-tetrahydrofuran-3-yl)methyl)-2,3-dihydro-1H-pyrido[2,3-b][1,4]oxazine-6-carboxamide (Compound 96)

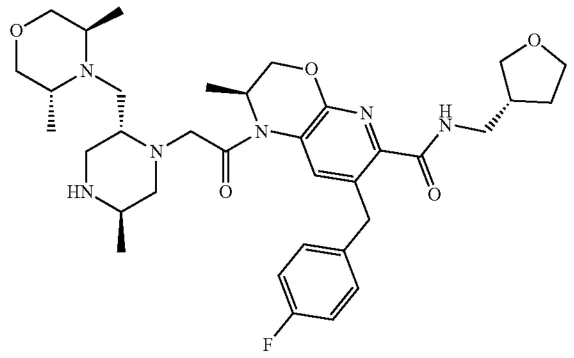 [SMILES: C[C@@H]1CN(CC(=O)N2c3cc(Cc4ccc(F)cc4)c(C(=O)NC[C@H]4CCOC4)nc3OC[C@@H]2C)[C@@H](CN2[C@H](C)COC[C@H]2C)CN1]

Step 1: benzyl (S)-7-(4-fluorobenzyl)-2-methyl-6-((((R)-tetrahydrofuran-3-yl)methyl)carbamoyl)-2,3-dihydro-1H-pyrido[2,3-b][1,4]oxazine-1-carboxylate

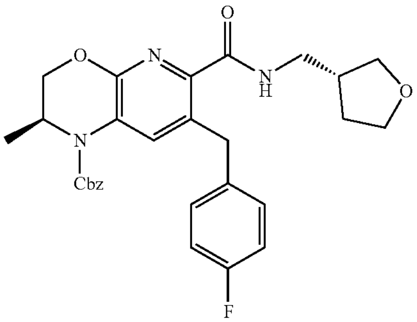 [SMILES: C[C@H]1COc2nc(C(=O)NC[C@H]3CCOC3)c(Cc3ccc(F)cc3)cc2N1C(=O)OCc1ccccc1]

The title compound of step 1 (330 mg, 92% yield) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and (R)-(tetrahydrofuran-3-yl)methanamine. LC-MS $(M+H)^+$=520.1.

Step 2: (S)-7-(4-fluorobenzyl)-2-methyl-N—(((R)-tetrahydrofuran-3-yl)methyl)-2,3-dihydro-1H-pyrido[2,3-b][1,4]oxazine-6-carboxamide

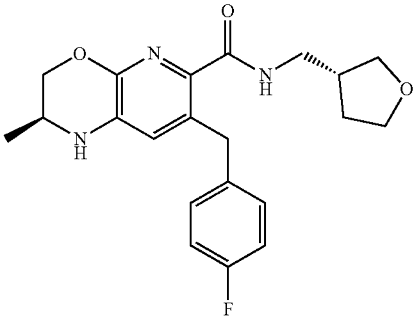 [SMILES: C[C@H]1COc2nc(C(=O)NC[C@H]3CCOC3)c(Cc3ccc(F)cc3)cc2N1]

The title compound of step 2 (130 mg, 53% yield) was prepared in a manner similar to that described in Example 1 step 17 from benzyl (S)-7-(4-fluorobenzyl)-2-methyl-6-((((R)-tetrahydrofuran-3-yl)methyl)carbamoyl)-2,3-dihydro-1H-pyrido[2,3-b][1,4]oxazine carboxylate. LC-MS $(M+H)^+$=386.3.

Step 3: (S)-1-(2-chloroacetyl)-7-(4-fluorobenzyl)-2-methyl-N—(((R)-tetrahydrofuran yl)methyl)-2,3-dihydro-1H-pyrido[2,3-b][1,4]oxazine-6-carboxamide

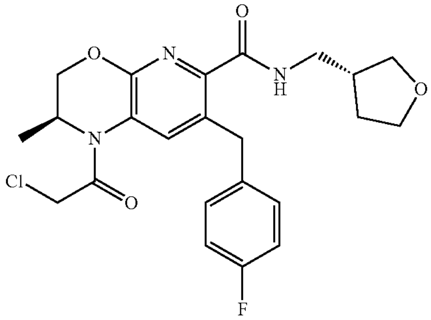 [SMILES: C[C@H]1COc2nc(C(=O)NC[C@H]3CCOC3)c(Cc3ccc(F)cc3)cc2N1C(=O)CCl]

The title compound of step 3 (140 mg, 89% yield) was prepared in a manner similar to that described in Example 1 step 9 from (S)-7-(4-fluorobenzyl)-2-methyl-N—(((R)-tetrahydrofuran-3-yl)methyl)-2,3-dihydro-1H-pyrido[2,3-b][1,4]oxazine-6-carb oxamide and 2-chloroacetyl chloride. LC-MS $(M+H)^+$=462.0.

Step 4: tert-butyl (2R,5S)-5-(((3R,5R)-3,5-dimethylmorpholino)methyl)-4-(2-((S)-7-(4-fluorobenzyl)-2-methyl-6-((((R)-tetrahydrofuran-3-yl)methyl)carbamoyl)-2,3-dihydro-1H-pyrido[2,3-b][1,4]oxazin-1-yl)-2-oxoethyl)-2-methylpiperazine-1-carboxylate

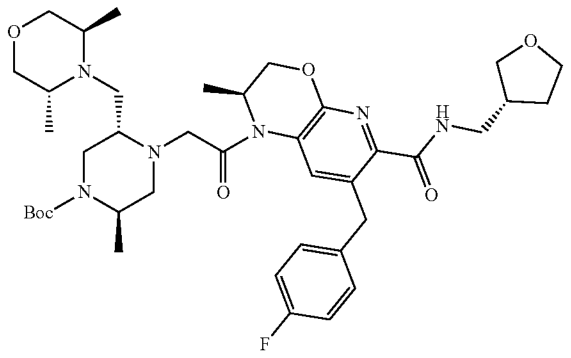 [SMILES: C[C@@H]1CN(CC(=O)N2c3cc(Cc4ccc(F)cc4)c(C(=O)NC[C@H]4CCOC4)nc3OC[C@@H]2C)[C@@H](CN2[C@H](C)COC[C@H]2C)CN1C(=O)OC(C)(C)C]

The title compound of step 4 (87 mg, 38% yield) was prepared in a manner similar to that described in Example 1 step 18 from (S)-1-(2-chloroacetyl)-7-(4-fluorobenzyl)-2-methyl-N—(((R)-tetrahydrofuran-3-yl)methyl)-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=753.4.

Step 5: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N—((R)-tetrahydrofuran-3-yl)methyl)-2,3-dihydro-1H-pyrido[2,3-b][1,4]oxazine-6-carboxamide (Compound 96)

Compound 96 (37 mg, 49% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-(((R)-tetrahydrofuran-3-yl)methyl)carbamoyl)-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 8.56 (t, J=6.1 Hz, 1H), 8.35 (s, 1H), 7.26-7.18 (m, 2H), 7.13-7.03 (m, 2H), 4.83-4.73 (m, 1H), 4.42-4.35 (m, 1H), 4.31-4.25 (m, 3H), 4.02-3.93 (m, 1H), 3.77-3.68 (m, 1H), 3.68-3.56 (m, 2H), 3.56-3.48 (m, 1H), 3.48-3.39 (m, 3H), 3.30-3.17 (m, 2H), 3.14-3.05 (m, 2H), 2.98-2.90 (m, 1H), 2.83-2.74 (m, 1H), 2.73-2.64 (m, 2H), 2.63-2.55 (m, 2H), 2.50-2.40 (m, 1H), 2.33-2.23 (m, 1H), 2.23-2.13 (m, 1H), 2.02-1.94 (m, 1H), 1.94-1.82 (m, 1H), 1.63-1.50 (m, 1H), 1.22 (d, J=6.7 Hz, 3H), 0.91-0.81 (m, 9H). LC-MS $(M+H)^+$=653.5.

Example 97: (S)—N-(2-(dimethylamino)ethyl)-1-(2-((2R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 97)

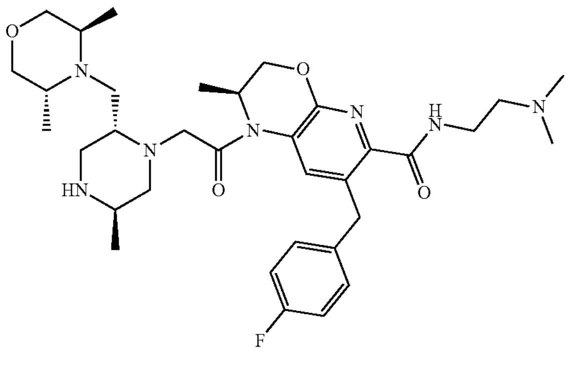 [SMILES: C[C@@H]1CN(CC(=O)N2c3cc(Cc4ccc(F)cc4)c(C(=O)NCCN(C)C)nc3OC[C@@H]2C)[C@@H](CN2[C@H](C)COC[C@H]2C)CN1]

Step 1: benzyl (S)-6-((2-(dimethylamino)ethyl)carbamoyl)-7-(4-fluorobenzyl)-2-methyl-2,3-dihydro-1H-pyrido[2,3-b][1,4]oxazine-1-carboxylate

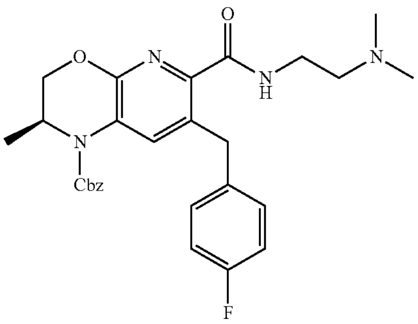

the title compound of step 1 (400 mg, 86% yield) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and N1,N1-dimethylethane-1,2-diamine. LC-MS $(M+H)^+$=507.1.

Step 2: (S)—N-(2-(dimethylamino)ethyl)-7-(4-fluorobenzyl)-2-methyl-2,3-dihydro-1H-pyrido[2,3-b][1,4]oxazine-6-carboxamide

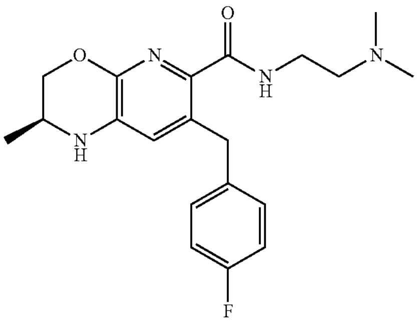

The title compound of step 2 (200 mg, 68% yield) was prepared in a manner similar to that described in Example 1 step 17 from benzyl (S)-6-((2-(dimethylamino)ethyl)carbamoyl)-7-(4-fluorobenzyl)-2-methyl-2,3-dihydro-1H-pyrido[2,3-b][1,4]oxazine-1-carboxylate. LC-MS $(M+H)^+$=373.0.

Step 3: (S)-1-(2-chloroacetyl)-N-(2-(dimethylamino)ethyl)-7-(4-fluorobenzyl)-2-methyl-2,3-dihydro-1H-pyrido[2,3-b][1,4]oxazine-6-carboxamide

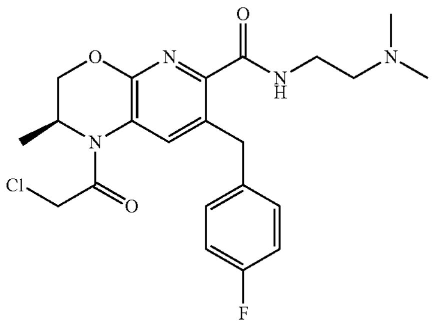

The title compound of step 3 (52 mg, 21% yield) was prepared in a manner similar to that described in Example 1 step 9 from (S)—N-(2-(dimethylamino)ethyl)-7-(4-fluorobenzyl)-2-methyl-2,3-dihydro-1H-pyrido[2,3-b][1,4]oxazine-6-carboxamide and 2-chloroacetyl chloride. LC-MS $(M+H)^+$=449.3.

Step 4: tert-butyl (2R,5S)-4-(2-((S)-6-((2-(dimethylamino)ethyl)carbamoyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

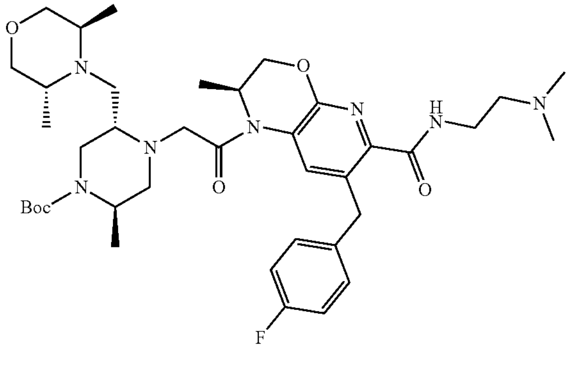 [SMILES: C[C@@H]1CN(CC(=O)N2c3cc(Cc4ccc(F)cc4)c(C(=O)NCCN(C)C)nc3OC[C@@H]2C)[C@@H](CN2[C@H](C)COC[C@H]2C)CN1C(=O)OC(C)(C)C]

The title compound of step 4 (39 mg, 45% yield) was prepared in a manner similar to that described in Example 1 step 18 from (S)-1-(2-chloroacetyl)-N-(2-(dimethylamino)ethyl)-7-(4-fluorobenzyl)-2-methyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=740.2.

Step 5: (S)—N-(2-(dimethylamino)ethyl)-1-(2-((2R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 97)

Compound 97 (0.5 mg, 2% yield) was prepared in a manner similar to that described in Example 29 step 7 from tert-butyl (2R,5S)-4-(2-((S)-6-((2-(dimethylamino)ethyl)carbamoyl)-7-(4-fluorobenzyl)-2-methyl-2,3-dihydro-1H-pyrido[2,3-b][1,4]oxazin-1-yl)-2-oxoethyl)-(((3R,5R)-3,5-dimethylmorpholino)methyl)-2-methylpiperazine-1-carboxylate. $^1$H NMR (300 MHz, DMSO-d6) δ 8.39-8.27 (m, 2H), 7.29-7.18 (m, 2H), 7.15-7.02 (m, 2H), 4.83-4.74 (m, 1H), 4.44-4.33 (m, 3H), 4.33-4.24 (m, 1H), 4.04-3.92 (m, 1H), 3.57-3.37 (m, 4H), 3.20-3.04 (m, 2H), 2.98-2.89 (m, 1H), 2.83-2.53 (m, 6H), 2.43-2.33 (m, 2H), 2.32-2.07 (m, 9H), 2.03-1.91 (m, 1H), 1.24-1.20 (m, 3H), 0.91-0.80 (m, 9H). LC-MS $(M+H)^+$=640.5.

Example 98: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N-((1-methylpiperidin-4-yl)methyl)-2,3-dihydro-1H-pyrido[2,3-b][1,4]oxazine-6-carb oxamide (Compound 98)

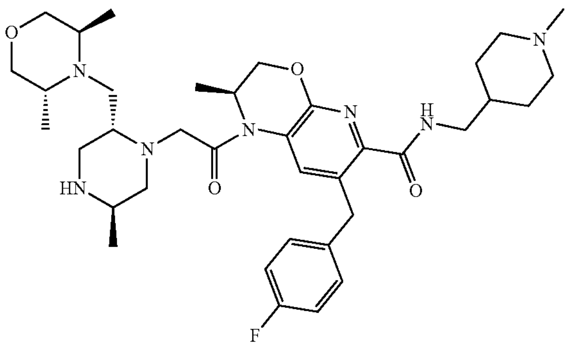 [SMILES: C[C@@H]1CN(CC(=O)N2c3cc(Cc4ccc(F)cc4)c(C(=O)NCC4CCN(C)CC4)nc3OC[C@@H]2C)[C@@H](CN2[C@H](C)COC[C@H]2C)CN1]

Step 1: benzyl (S)-7-(4-fluorobenzyl)-2-methyl-6-(((1-methylpiperidin-4-yl)methyl)carbamoyl)-2,3-dihydro-1H-pyrido[2,3-b][1,4]oxazine-1-carboxylate

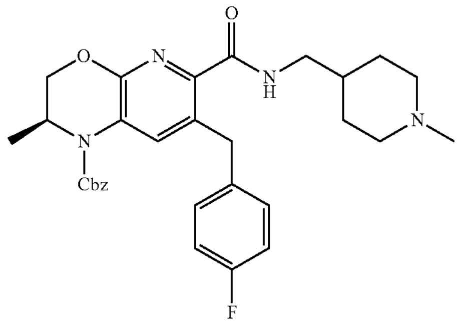

The title compound of step 1 (400 mg, 79% yield) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and (1-methylpiperidin-4-yl)methanamine. LC-MS $(M+H)^+$=547.2.

Step 2: (S)-7-(4-fluorobenzyl)-2-methyl-N-((1-methylpiperidin-4-yl)methyl)-2,3-dihydro-1H-pyrido[2,3-b][1,4]oxazine-6-carboxamide

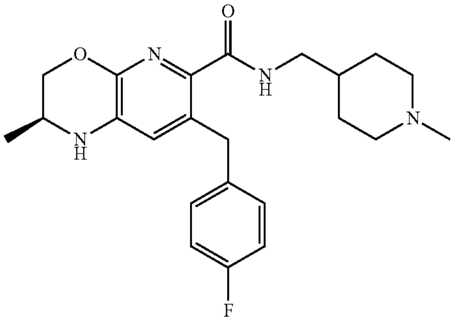

The title compound of step 2 (200 mg, 66% yield) was prepared in a manner similar to that described in Example 1 step 17 from benzyl (S)-7-(4-fluorobenzyl)-2-methyl-6-(((1-methylpiperidin-4-yl)methyl)carbamoyl)-2,3-dihydro-1H-pyrido[2,3-b][1,4]oxazine carboxylate. LC-MS $(M+H)^+$=413.1.

Step 3: (S)-1-(2-chloroacetyl)-7-(4-fluorobenzyl)-2-methyl-N-((1-methylpiperidin-4-yl)methyl)-2,3-dihydro-1H-pyrido[2,3-b][1,4]oxazine-6-carboxamide

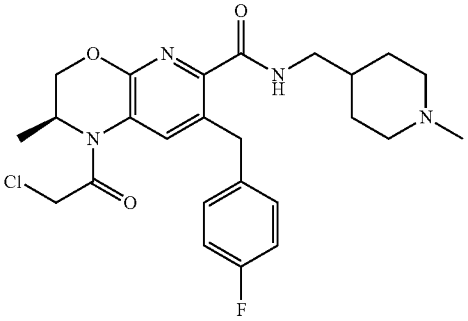 [SMILES: C[C@H]1COc2nc(C(=O)NCC3CCN(C)CC3)c(Cc3ccc(F)cc3)cc2N1C(=O)CCl]

The title compound of step 3 (77 mg, 32% yield) was prepared in a manner similar to that described in Example 1 step 9 from (S)-7-(4-fluorobenzyl)-2-methyl-N-((1-methylpiperidin-4-yl)methyl)-2,3-dihydro-1H-pyrido[2,3-b][1,4]oxazine-6-carboxamide and 2-chloroacetyl chloride. LC-MS $(M+H)^+$=489.2.

Step 4: tert-butyl (2R,5S)-5-(((3R,5R)-3,5-dimethylmorpholino)methyl)-4-(2-((S)-7-(4-fluorobenzyl)-2-methyl-6-(((1-methylpiperidin-4-yl)methyl)carbamoyl)-2,3-dihydro-1H-pyrido[2,3-b][1,4]oxazin-1-yl)-2-oxoethyl)-2-methylpiperazine-1-carboxylate

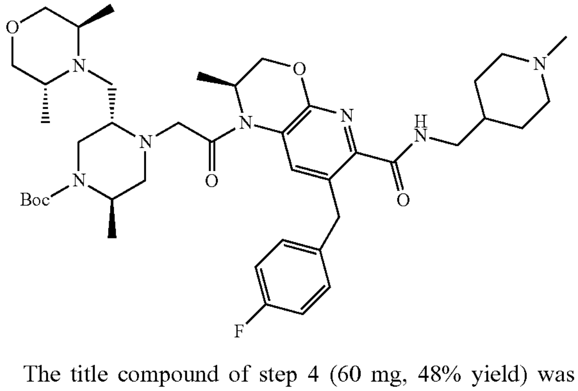

The title compound of step 4 (60 mg, 48% yield) was prepared in a manner similar to that described in Example 1 step 18 from (S)-1-(2-chloroacetyl)-7-(4-fluorobenzyl)-2-methyl-N-((1-methylpiperidin-4-yl)methyl)-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=780.3.

Step 5: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N-((l-methylpiperidin-4-yl)methyl)-2,3-dihydro-1H-pyrido[2,3-b][1,4]oxazine-6-carboxamide (Compound 98)

Compound 98 (6 mg, 10% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-(((1-methylpiperidin-4-yl)methyl)carbamoyl)-2,3-dihydro-1H-pyrido[2,3-b][1,4]oxazin-1-yl)-2-oxoethyl)-2-methylpiperazine-1-carboxylate. $^1$H NMR (300 MHz, DMSO-d6) δ 8.44-8.32 (m, 2H), 7.30-7.16 (m, 2H), 7.14-7.00 (m, 2H), 4.83-4.74 (m, 1H), 4.43-4.20 (m, 4H), 4.04-3.92 (m, 1H), 3.60-3.39 (m, 3H), 3.16-3.04 (m, 4H), 2.99-2.88 (m, 1H), 2.84-2.65 (m, 5H), 2.63-2.54 (m, 3H), 2.36-2.15 (m, 2H), 2.13 (s, 3H), 2.04-1.91 (m, 1H), 1.84-1.70 (m, 2H), 1.61-1.51 (m, 2H), 1.51-1.35 (m, 1H), 1.22 (d, J=6.7 Hz, 3H), 1.17-1.07 (m, 2H), 0.95-0.81 (m, 9H). LC-MS $(M+H)^+$=680.4.

Example 99: (S)-1-(24(2R,5R)-2-(((3R,5R)-3,5-dimethylmorpholino)methyl)-5-methylpiperazin-1-yl)acetyl)-7-(4-fluorobenzyl)-2-methyl-N-(2-(4-methylpiperazin-1-acetyl)-2,3-dihydro-1H-pyrido[2,3-b][1,4]oxazine-6-carboxamide (Compound 99)

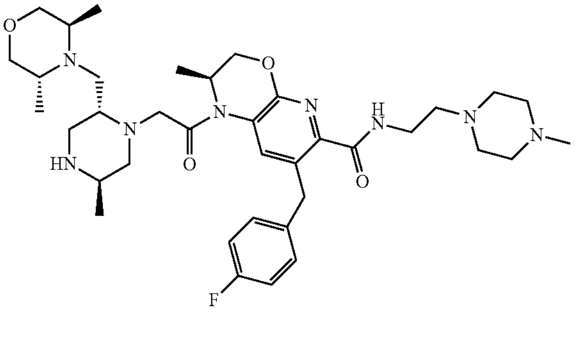 [SMILES: C[C@@H]1CN(CC(=O)N2c3cc(Cc4ccc(F)cc4)c(C(=O)NCCN4CCN(C)CC4)nc3OC[C@@H]2C)[C@@H](CN2[C@H](C)COC[C@H]2C)CN1]

Step 1: benzyl (S)-7-(4-fluorobenzyl)-2-methyl-6-((2-(4-methylpiperazin-1-yl)ethyl)carbamoyl)-2,3-dihydro-1H-pyrido[2,3-b][1,4]oxazine-1-carboxylate

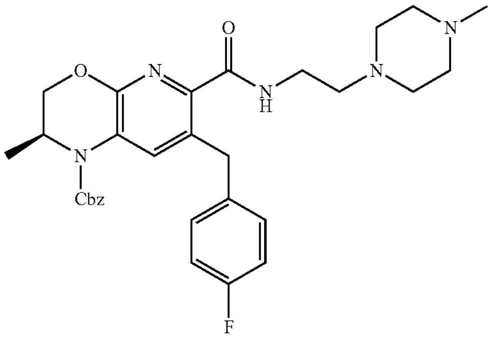

The title compound of step 1 (330 mg, 64% yield) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and 2-(4-methylpiperazin-1-yl)ethan-1-amine. LC-MS $(M+H)^+$=562.3.

Step 2: (S)-7-(4-fluorobenzyl)-2-methyl-N-(2-(4-methylpiperazin-1-yl)ethyl)-2,3-dihydro-1H-pyrido[2,3-b][1,4]oxazine-6-carboxamide

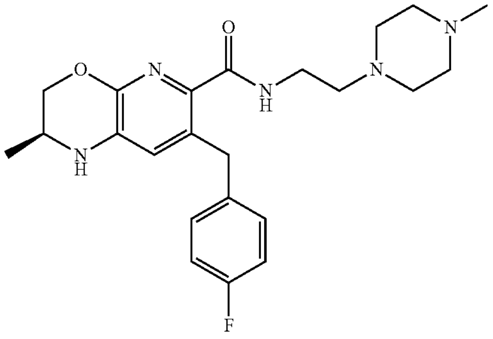

The title compound of step 2 (220 mg, 87% yield) was prepared in a manner similar to that described in Example 1 step 17 from benzyl (S)-7-(4-fluorobenzyl)-2-methyl-6-((2-(4-methylpiperazin-1-yl)ethyl)carbamoyl)-2,3-dihydro-1H-pyrido[2,3-b][1,4]oxazine carboxylate. LC-MS $(M+H)^+$=428.1.

Step 3: (S)-1-(2-chloroacetyl)-7-(4-fluorobenzyl)-2-methyl-N-(2-(4-methylpiperazin yl)ethyl)-2,3-dihydro-1H-pyrido[2,3-b][1,4]oxazine-6-carboxamide

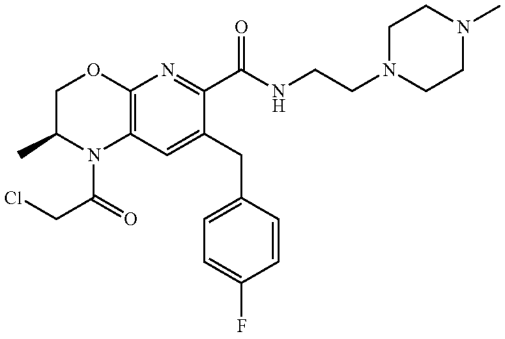 [SMILES: C[C@H]1COc2nc(C(=O)NCCN3CCN(C)CC3)c(Cc3ccc(F)cc3)cc2N1C(=O)CCl]

The title compound of step 3 (108 mg, 41% yield) was prepared in a manner similar to that described in Example 1 step 9 from (S)-7-(4-fluorobenzyl)-2-methyl-N-(2-(4-methylpiperazin-1-yl)ethyl)-2,3-dihydro-1H-pyrido[2,3-b][1,4]oxazine-6-carboxamide and 2-chloroacetyl chloride. LC-MS $(M+H)^+$=504.2.

Step 4: tert-butyl (2R,5S)-5-(((3R,5R)-3,5-dimethylmorpholino)methyl)-4-(2-((S)-7-(4-fluorobenzyl)-2-methyl-6-((2-(4-methylpiperazin-1-yl)ethyl)carbamoyl)-2,3-dihydro-1H-pyrido[2,3-b][1,4]oxazin-1-yl)-2-oxoethyl)-2-methylpiperazine-1-carboxylate

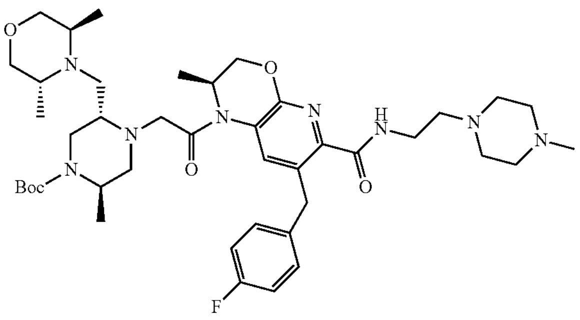 [SMILES: C[C@@H]1CN(CC(=O)N2c3cc(Cc4ccc(F)cc4)c(C(=O)NCCN4CCN(C)CC4)nc3OC[C@@H]2C)[C@@H](CN2[C@H](C)COC[C@H]2C)CN1C(=O)OC(C)(C)C]

The title compound of step 4 (80 mg, 46% yield) was prepared in a manner similar to that described in Example 1 step 18 from (S)-1-(2-chloroacetyl)-7-(4-fluorobenzyl)-2-methyl-N-(2-(4-methylpiperazin-1-yl)ethyl)-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=795.4.

Step 5: (S)-1-(2-((2R,5R)-2-(((3R,5R)-3,5-dimethylmorpholino)methyl)-5-methylpiperazin-1-yl)acetyl)-7-(4-fluorobenzyl)-2-methyl-N-(2-(4-methylpiperazin-1-yl)ethyl)-2,3-dihydro-1H-pyrido[2,3-b][1,4]oxazine-6-carboxamide (Compound 99)

Compound 99 (4.3 mg, 6% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-((2-(4-methylpiperazin-1-yl)ethyl)carbamoyl)-2,3-dihydro-1H- pyrido[2,3-b][1,4]oxazin-1-yl)-2-oxoethyl)-2-methylpiperazine-1-carboxylate. $^1$H NMR (400 MHz, DMSO-d6) δ 8.38-8.32 (m, 2H), 7.29-7.17 (m, 2H), 7.15-7.02 (m, 2H), 4.81-4.76 (m, 1H), 4.44-4.24 (m, 4H), 4.03-3.92 (m, 1H), 3.58-3.48 (m, 1H), 3.48-3.35 (m, 2H), 3.39-3.30 (m, 3H), 3.15-3.03 (m, 2H), 3.00-2.90 (m, 1H), 2.80-2.65 (m, 4H), 2.63-2.54 (m, 2H), 2.48-2.37 (m, 5H), 2.35-2.16 (m, 6H), 2.13 (s, 3H), 2.04-1.91 (m, 1H), 1.22 (d, J=6.7 Hz, 3H), 0.92-0.80 (m, 9H). LC-MS $(M+H)^+$=695.4.

Example 100: 2-((2R,5R)-2-(((3R,5R)-3,5-dimethylmorpholino)methyl)-5-methylpiperazin-1-yl)-1-((S)-7-(4-fluorobenzyl)-6-((S)-3-fluoropyrrolidine-1-carbonyl)-2-methyl-2,3-dihydro-1H-pyrido[2,3-b][1,4]oxazin-1-yl)ethan-1-one (Compound 100)

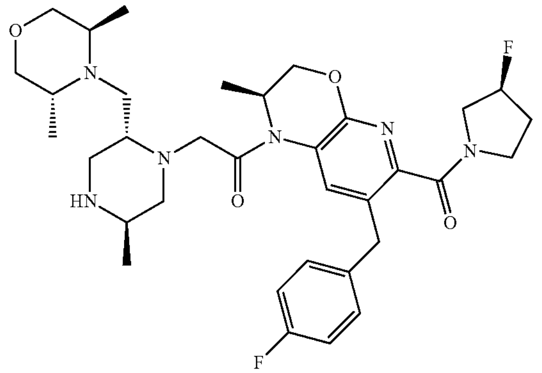 [SMILES: C[C@@H]1CN(CC(=O)N2c3cc(Cc4ccc(F)cc4)c(C(=O)N4CC[C@H](F)C4)nc3OC[C@@H]2C)[C@@H](CN2[C@H](C)COC[C@H]2C)CN1]

Step 1: benzyl (S)-7-(4-fluorobenzyl)-6-(((S)-3-fluoropyrrolidine-1-carbonyl)-2-methyl-2,3-dihydro-1H-pyrido[2,3-b][1,4]oxazine-1-carboxylate

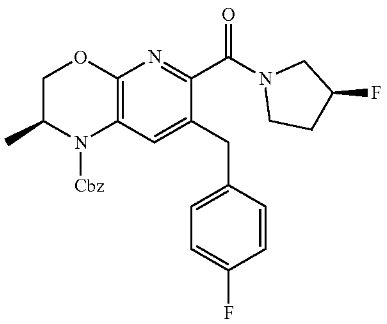 [SMILES: C[C@H]1COc2nc(C(=O)N3CC[C@H](F)C3)c(Cc3ccc(F)cc3)cc2N1C(=O)OCc1ccccc1]

The title compound of step 1 (304 mg, 76% yield) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and (S)-3-fluoropyrrolidine. LC-MS $(M+H)^+$=508.2.

Step 2: ((S)-7-(4-fluorobenzyl)-2-methyl-2,3-dihydro-1H-pyrido[2,3-b][1,4]oxazin-6-yl)((S)-3-fluoropyrrolidin-1-yl)methanone

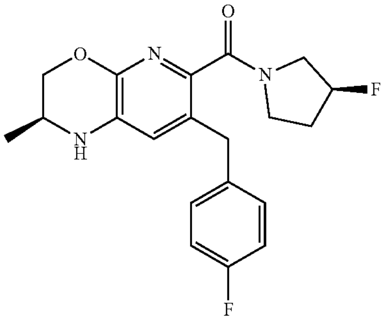 [SMILES: C[C@H]1COc2nc(C(=O)N3CC[C@H](F)C3)c(Cc3ccc(F)cc3)cc2N1]

The title compound of step 2 (200 mg, 89% yield) was prepared in a manner similar to that described in Example 1 step 17 from benzyl (S)-7-(4-fluorobenzyl)-6-((S)-3-fluoropyrrolidine-1-carbonyl)-2-methyl-2,3-dihydro-1H-pyrido[2,3-b][1,4]oxazine-1-carboxylate. LC-MS $(M+H)^+$=374.0.

Step 3: 2-chloro-1-((S)-7-(4-fluorobenzyl)-6-((S)-3-fluoropyrrolidine-1-carbonyl)-2-methyl-2,3-dihydro-1H-pyrido[2,3-b][1,4]oxazin-1-yl)ethan-1-one

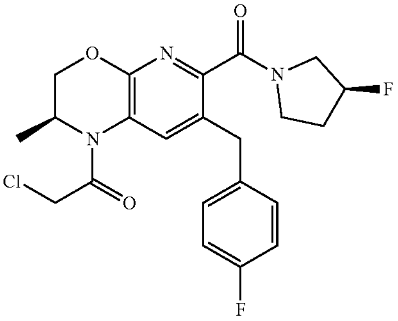 [SMILES: C[C@H]1COc2nc(C(=O)N3CC[C@H](F)C3)c(Cc3ccc(F)cc3)cc2N1C(=O)CCl]

The title compound of step 3 (210 mg, 87% yield) was prepared in a manner similar to that described in Example 1 step 9 from ((S)-7-(4-fluorobenzyl)-2-methyl-2,3-dihydro-1H-pyrido[2,3-b][1,4]oxazin-6-yl)((S)-3-fluoropyrrolidin-1-yl)methanone and 2-chloroacetyl chloride. LC-MS $(M+H)^+$=450.0.

Step 4: tert-butyl (2R,5S)-5-(((3R,5R)-3,5-dimethylmorpholino)methyl)-4-(2-((S)-7-(4-fluorobenzyl)-6-((S)-3-fluoropyrrolidine-1-carbonyl)-2-methyl-2,3-dihydro-1H-pyrido[2,3-b][1,4]oxazin-1-yl)-2-oxoethyl)-2-methylpiperazine-1-carboxylate

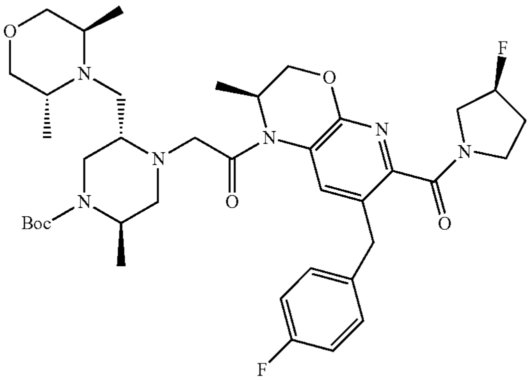 [SMILES: C[C@@H]1CN(CC(=O)N2c3cc(Cc4ccc(F)cc4)c(C(=O)N4CC[C@H](F)C4)nc3OC[C@@H]2C)[C@@H](CN2[C@H](C)COC[C@H]2C)CN1C(=O)OC(C)(C)C]

The title compound of step 4 (80 mg, 16% yield) was prepared in a manner similar to that described in Example 1 step 18 from 2-chloro-1-((S)-7-(4-fluorobenzyl)-6-((S)-3-fluoropyrrolidine-1-carbonyl)-2-methyl-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=741.5.

Step 5: 2-((2R,5R)-2-(((3R,5R)-3,5-dimethylmorpholino)methyl)-5-methylpiperazin-1-yl)-1-((S)-7-(4-fluorobenzyl)-6-(((S)-3-fluoropyrrolidine-1-carbonyl)-2-methyl-2,3-dihydro-1H-pyrido[2,3-b][1,4]oxazin-1-yl)ethan-1-one (Compound 100)

Compound 100 (14 mg, 29% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-6-(((S)-3-fluoropyrrolidine-1-carbonyl)-2-methyl-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 8.34 (s, 1H), 7.23-7.14 (m, 2H), 7.13-7.03 (m, 2H), 5.44-5.11 (m, 1H), 4.81-4.77 (m, 1H), 4.40-4.33 (m, 1H), 4.31-4.23 (m, 1H), 4.02-3.94 (m, 1H), 3.94-3.82 (m, 2H), 3.78-3.58 (m, 2H), 3.53-3.36 (m, 4H), 3.22-3.06 (m, 4H), 2.98-2.90 (m, 1H), 2.84-2.75 (m, 1H), 2.74-2.67 (m, 2H), 2.65-2.52 (m, 2H), 2.32-2.22 (m, 1H), 2.19-2.01 (m, 2H), 2.00-1.89 (m, 2H), 1.21 (d, J=6.7 Hz, 3H), 0.90-0.82 (m, 9H). LC-MS $(M+H)^+$=641.5.

Example 101: 2-((2R,5R)-2-(((3R,5R)-3,5-dimethylmorpholino)methyl)-5-methylpiperazin-1-yl)-1-((S)-7-(4-fluorobenzyl)-6-((R)-3-fluoropyrrolidine-1-carbonyl)-2-methyl-2,3-dihydro-1H-pyrido[2,3-b][1,4]oxazin-1-yl)ethan-1-one (Compound 101)

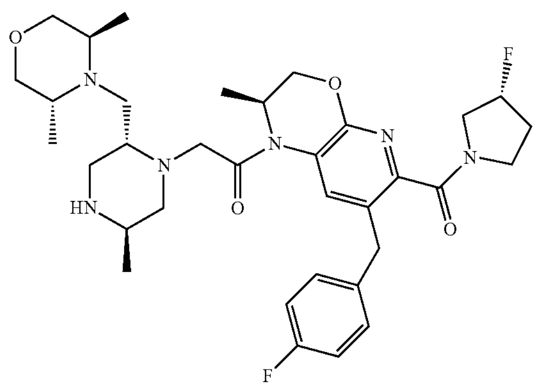 [SMILES: C[C@@H]1CN(CC(=O)N2c3cc(Cc4ccc(F)cc4)c(C(=O)N4CC[C@@H](F)C4)nc3OC[C@@H]2C)[C@@H](CN2[C@H](C)COC[C@H]2C)CN1]

Step 1: benzyl (S)-7-(4-fluorobenzyl)-6-((R)-3-fluoropyrrolidine-1-carbonyl)-2-methyl-2,3-dihydro-1H-pyrido[2,3-b][1,4]oxazine-1-carboxylate

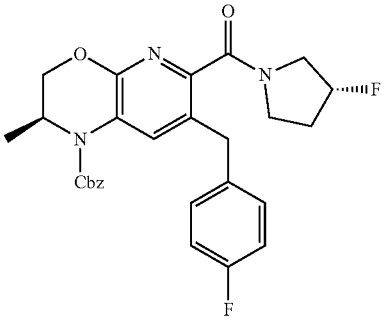 [SMILES: C[C@H]1COc2nc(C(=O)N3CC[C@@H](F)C3)c(Cc3ccc(F)cc3)cc2N1C(=O)OCc1ccccc1]

The title compound of step 1 (427 mg, 98% yield) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and (R)-3-fluoropyrrolidine. LC-MS $(M+H)^+$=508.2.

Step 2: ((S)-7-(4-fluorobenzyl)-2-methyl-2,3-dihydro-1H-pyrido[2,3-b][1,4]oxazin-6-yl)((R)-3-fluoropyrrolidin-1-yl)methanone

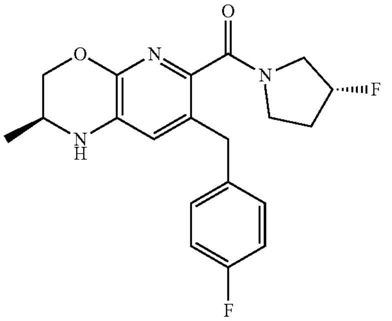 [SMILES: C[C@H]1COc2nc(C(=O)N3CC[C@@H](F)C3)c(Cc3ccc(F)cc3)cc2N1]

The title compound of step 2 (171 mg, 54% yield) was prepared in a manner similar to that described in Example 1 step 17 from benzyl (S)-7-(4-fluorobenzyl)-6-((R)-3-fluoropyrrolidine-1-carbonyl)-2-methyl-2,3-dihydro-1H-pyrido[2,3-b][1,4]oxazine-1-carboxylate. LC-MS $(M+H)^+$=374.2.

Step 3: 2-chloro-1-((S)-7-(4-fluorobenzyl)-6-((R)-3-fluoropyrrolidine-1-carbonyl)-2-methyl-2,3-dihydro-1H-pyrido[2,3-b][1,4]oxazin-1-yl)ethan-1-one

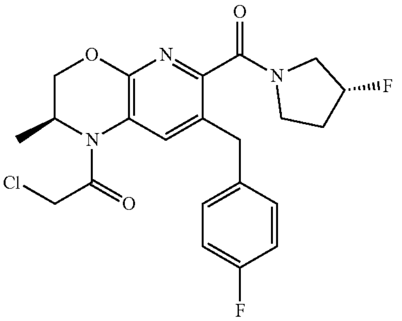 [SMILES: C[C@H]1COc2nc(C(=O)N3CC[C@@H](F)C3)c(Cc3ccc(F)cc3)cc2N1C(=O)CCl]

The title compound of step 3 (179 mg, 87% yield) was prepared in a manner similar to that described in Example 1 step 9 from ((S)-7-(4-fluorobenzyl)-2-methyl-2,3-dihydro-1H-pyrido[2,3-b][1,4]oxazin-6-yl)((R)-3-fluoropyrrolidin-1-yl)methanone and 2-chloroacetyl chloride. LC-MS $(M+H)^+$=450.3.

Step 4: tert-butyl (2R,5S)-5-(((3R,5R)-3,5-dimethylmorpholino)methyl)-4-(2-((S)-7-(4-fluorobenzyl)-6-((R)-3-fluoropyrrolidine-1-carbonyl)-2-methyl-2,3-dihydro-1H-pyrido[2,3-b][1,4]oxazin-1-yl)-2-oxoethyl)-2-methylpiperazine-1-carboxylate

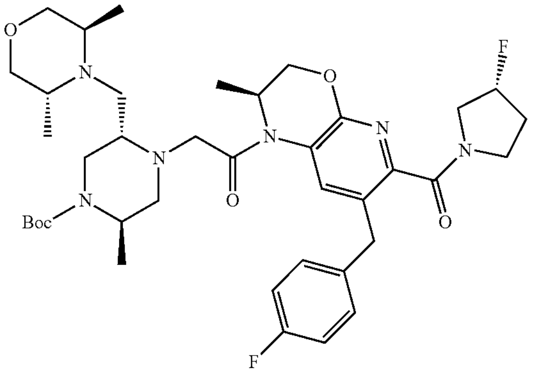 [SMILES: C[C@@H]1CN(CC(=O)N2c3cc(Cc4ccc(F)cc4)c(C(=O)N4CC[C@@H](F)C4)nc3OC[C@@H]2C)[C@@H](CN2[C@H](C)COC[C@H]2C)CN1C(=O)OC(C)(C)C]

The title compound of step 4 (126 mg, 42% yield) was prepared in a manner similar to that described in Example 1 step 18 from 2-chloro-1-((S)-7-(4-fluorobenzyl)-6-((R)-3-fluoropyrrolidine-1-carbonyl)-2-methyl-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=741.3.

Step 5: 2-((2R,5R)-2-(((3R,5R)-3,5-dimethylmorpholino)methyl)-5-methylpiperazin-1-yl)-1-((S)-7-(4-fluorobenzyl)-6-((R)-3-fluoropyrrolidine-1-carbonyl)-2-methyl-2,3-dihydro-1H-pyrido[2,3-b][1,4]oxazin-1-yl)ethan-1-one (Compound 101)

Compound 101 (49 mg, 45% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-6-((R)-3-fluoropyrrolidine-1-carbonyl)-2-methyl-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 8.39-8.33 (m, 1H), 7.24-7.15 (m, 2H), 7.15-7.03 (m, 2H), 5.43-5.10 (m, 1 H), 4.85-4.75 (m, 1H), 4.41-4.33 (m, 1H), 4.32-4.23 (m, 1H), 4.07-3.85 (m, 3H), 3.72-3.59 (m, 1H), 3.56-3.38 (m, 4H), 3.27-3.15 (m, 1H), 3.18-2.99 (m, 3H), 2.98-2.90 (m, 1H), 2.85-2.75 (m, 1H), 2.75-2.67 (m, 2H), 2.66-2.53 (m, 3H), 2.33-2.23 (m, 1H), 2.21-2.11 (m, 1H), 2.09-1.94 (m, 3H), 1.22 (d, J=6.7 Hz, 3H), 0.91-0.83 (m, 9H). LC-MS $(M+H)^+$=641.5.

Example 102: 2-((2R,5R)-2-(((3R,5R)-3,5-dimethylmorpholino)methyl)-5-methylpiperazin-1-yl)-1-(((S)-7-(4-fluorobenzyl)-2-methyl-6-(piperidine-1-carbonyl)-2,3-dihydro-1H-pyrido[2,3-b][1,4]oxazin-1-yl)ethan-1-one (Compound 102)

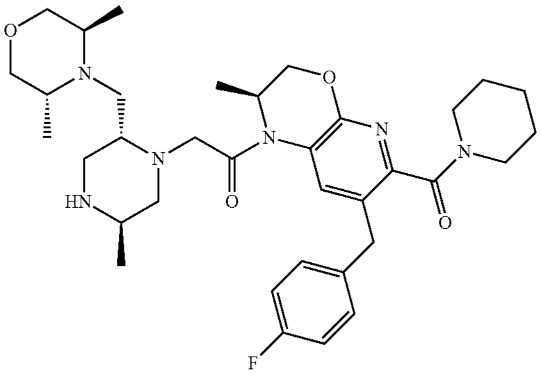 [SMILES: C[C@@H]1CN(CC(=O)N2c3cc(Cc4ccc(F)cc4)c(C(=O)N4CCCCC4)nc3OC[C@@H]2C)[C@@H](CN2[C@H](C)COC[C@H]2C)CN1]

Step 1: benzyl (S)-7-(4-fluorobenzyl)-2-methyl-6-(piperidine-1-carbonyl)-2,3-dihydro-1H-pyrido[2,3-b][1,4]oxazine-1-carboxylate

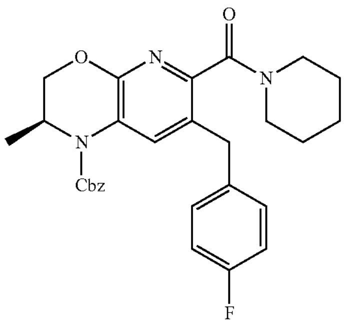 [SMILES: C[C@H]1COc2nc(C(=O)N3CCCCC3)c(Cc3ccc(F)cc3)cc2N1C(=O)OCc1ccccc1]

The title compound of step 1 (220 mg, 95% yield) was prepared in a manner similar to that described in Example 31 step 3 from (S)-1-((benzyloxy)carbonyl)-7-(4-fluorobenzyl)-2-methyl-2,3-dihydro-1H-pyrido[2,3-b][1,4]oxazine-6-carboxylic acid and piperidine. LC-MS $(M+H)^+$=504.2.

Step 2: (S)-(7-(4-fluorobenzyl)-2-methyl-2,3-dihydro-1H-pyrido[2,3-b][1,4]oxazin-6-yl)(piperidin-1-yl)methanone

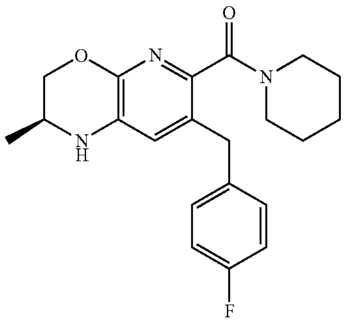 [SMILES: C[C@H]1COc2nc(C(=O)N3CCCCC3)c(Cc3ccc(F)cc3)cc2N1]

The title compound of step 2 (120 mg, 74% yield) was prepared in a manner similar to that described in Example 1 step 17 from benzyl (S)-7-(4-fluorobenzyl)-2-methyl-6-(piperidine carbonyl)-2,3-dihydro-1H-pyrido[2,3-b][1,4]oxazine-1-carboxylate. LC-MS (M+H)$^+$=370.0.

Step 3: (S)-2-chloro-1-(7-(4-fluorobenzyl)-2-methyl-6-(piperidine-1-carbonyl)-2,3-dihydro-1H-pyrido[2,3-b][1,4]oxazin-1-yl)ethan-1-one

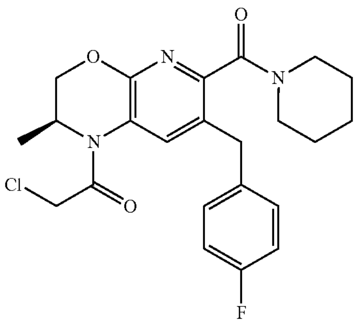 [SMILES: C[C@H]1COc2nc(C(=O)N3CCCCC3)c(Cc3ccc(F)cc3)cc2N1C(=O)CCl]

The title compound of step 3 (100 mg, 69% yield) was prepared in a manner similar to that described in Example 1 step 9 from (S)-(7-(4-fluorobenzyl)-2-methyl-2,3-dihydro-1H-pyrido[2,3-b][1,4]oxazin-6-yl)(piperidin-1-yl)methanone and 2-chloroacetyl chloride. LC-MS (M+H)$^+$=446.1.

Step 4: tert-butyl (2R,5S)-5-(((3R,5R)-3,5-dimethylmorpholino)methyl)-4-(2-((S)-7-(4-fluorobenzyl)-2-methyl-6-(piperidine-1-carbonyl)-2,3-dihydro-1H-pyrido[2,3-b][1,4]oxazin-1-yl)-2-oxoethyl)-2-methylpiperazine-1-carboxylate

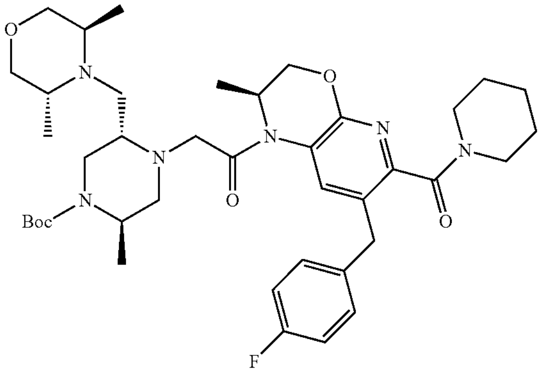 [SMILES: C[C@@H]1CN(CC(=O)N2c3cc(Cc4ccc(F)cc4)c(C(=O)N4CCCCC4)nc3OC[C@@H]2C)[C@@H](CN2[C@H](C)COC[C@H]2C)CN1C(=O)OC(C)(C)C]

The title compound of step 4 (70 mg, 42% yield) was prepared in a manner similar to that described in Example 1 step 18 from (S)-2-chloro-1-(7-(4-fluorobenzyl)-2-methyl-6-(piperidine-1-carbonyl)-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS (M+H)$^+$=737.4.

Step 5: 2-((2R,5R)-2-(((3R,5R)-3,5-dimethylmorpholino)methyl)-5-methylpiperazin-1-yl)-1-((S)-7-(4-fluorobenzyl)-2-methyl-6-(piperidine-1-carbonyl)-2,3-dihydro-1H-pyrido[2,3-b][1,4]oxazin-1-yl)ethan-1-one (Compound 102)

Compound 102 (16 mg, 27% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-2-methyl-6-(piperidine-1-carbonyl)-2,3-dihydro-1H-pyrido[2,3-b][1,4]oxazin-1-yl)-2-oxoethyl)-2-methylpiperazine-1-carboxylate. $^1$H NMR (300 MHz, DMSO-d6) δ 8.29 (s, 1H), 7.25-7.14 (m, 2H), 7.19-7.06 (m, 2H), 4.80-4.78 (m, 1H), 4.41-4.22 (m, 2H), 3.97 (d, J=15.3 Hz, 1H), 3.83 (s, 2H), 3.60-3.37 (m, 6H), 3.16-3.05 (m, 2H), 2.99-2.88 (m, 3H), 2.85-2.53 (m, 5H), 2.35-2.21 (m, 1H), 2.21-2.09 (m, 1H), 2.04-1.91 (m, 1H), 1.54-1.48 (m, 4H), 1.35-1.17 (m, 5H), 0.92-0.81 (m, 9H). LC-MS (M+H)$^+$=637.4.

Example 103: 1-(((S)-6-(4,4-difluoropiperidine-1-carbonyl)-7-(4-fluorobenzyl)-2-methyl-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 103)

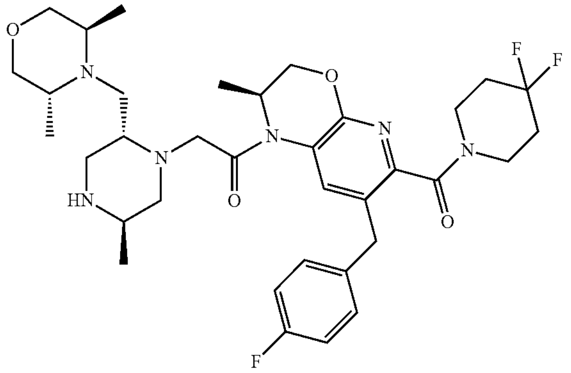 [SMILES: C[C@@H]1CN(CC(=O)N2c3cc(Cc4ccc(F)cc4)c(C(=O)N4CCC(F)(F)CC4)nc3OC[C@@H]2C)[C@@H](CN2[C@H](C)COC[C@H]2C)CN1]

Step 1: tert-butyl (S)-6-(4,4-difluoropiperidine-1-carbonyl)-7-(4-fluorobenzyl)-2-methyl-2,3-dihydro-1H-pyrido[2,3-b][1,4]oxazine-1-carboxylate

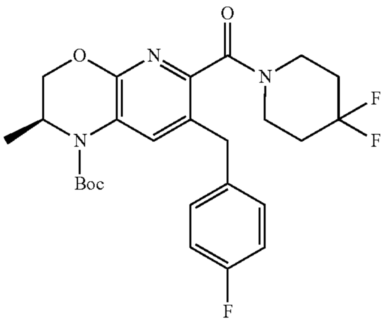 [SMILES: C[C@H]1COc2nc(C(=O)N3CCC(F)(F)CC3)c(Cc3ccc(F)cc3)cc2N1C(=O)OC(C)(C)C]

The title compound of step 1 (500 mg, crude) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and 4,4-difluoropiperidine. LC-MS (M+H)$^+$=506.4.

Step 2: (S)-(4,4-difluoropiperidin-1-yl)(7-(4-fluorobenzyl)-2-methyl-2,3-dihydro-1H-pyrido[2,3-b][1,4]oxazin-6-yl)methanone

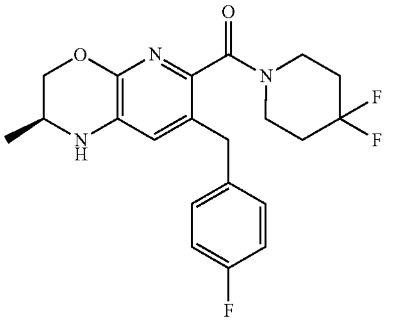 [SMILES: C[C@H]1COc2nc(C(=O)N3CCC(F)(F)CC3)c(Cc3ccc(F)cc3)cc2N1]

The title compound of step 2 (338 mg, 77% yield for 2 steps) was prepared in a manner similar to that described in Example 1 step 8 from tert-butyl (S)-6-(4,4-difluoropiperidine-1-carbonyl)-7-(4-fluorobenzyl)-2-methyl-2,3-dihydro-1H-pyrido[2,3-b][1,4]oxazine-1-carboxylate. LC-MS $(M+H)^+$=406.4.

Step 3: (S)-2-chloro-1-(6-(4,4-difluoropiperidine-1-carbonyl)-7-(4-fluorobenzyl)-2-methyl-2,3-dihydro-1H-pyrido[2,3-b][1,4]oxazin-1-yl)ethan-1-one

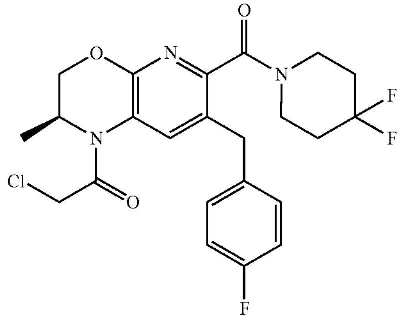 [SMILES: C[C@H]1COc2nc(C(=O)N3CCC(F)(F)CC3)c(Cc3ccc(F)cc3)cc2N1C(=O)CCl]

The title compound of step 3 (350 mg, 87% yield) was prepared in a manner similar to that described in Example 1 step 9 from (S)-(4,4-difluoropiperidin-1-yl)(7-(4-fluorobenzyl)-2-methyl-2,3-dihydro-1H-pyrido[2,3-b][1,4]oxazin-6-yl)methanone and 2-chloroacetyl chloride. LC-MS $(M+H)^+$=482.3.

Step 4: tert-butyl (2R,5S)-4-(2-((S)-6-(4,4-difluoropiperidine-1-carbonyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

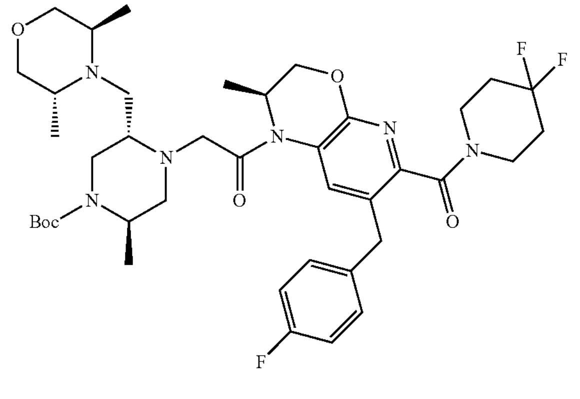 [SMILES: C[C@@H]1CN(CC(=O)N2c3cc(Cc4ccc(F)cc4)c(C(=O)N4CCC(F)(F)CC4)nc3OC[C@@H]2C)[C@@H](CN2[C@H](C)COC[C@H]2C)CN1C(=O)OC(C)(C)C]

The title compound of step 4 (530 mg, 94% yield) was prepared in a manner similar to that described in Example 1 step 18 from (S)-2-chloro-1-(6-(4,4-difluoropiperidine-1-carbonyl)-7-(4-fluorobenzyl)-2-methyl-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=773.9.

Step 5: 1-((S)-6-(4,4-difluoropiperidine-1-carbonyl)-7-(4-fluorobenzyl)-2-methyl-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 103)

Compound 103 (16 mg, 27% yield) was prepared in a manner similar to that described in Example 29 step 7 from tert-butyl (2R,5S)-4-(2-((S)-6-(4,4-difluoropiperidine-1-carbonyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^1$H NMR (300 MHz, DMSO-d6) δ 8.29 (s, 1H), 7.25-7.14 (m, 2H), 7.19-7.06 (m, 2H), 4.80-4.78 (m, 1H), 4.41-4.22 (m, 2H), 3.97 (d, J=15.3 Hz, 1H), 3.83 (s, 2H), 3.60-3.37 (m, 6H), 3.16-3.05 (m, 2H), 2.99-2.88 (m, 3H), 2.85-2.53 (m, 5H), 2.35-2.21 (m, 1H), 2.21-2.09 (m, 1H), 2.04-1.91 (m, 1H), 1.54-1.48 (m, 4H), 1.35-1.17 (m, 5H), 0.92-0.81 (m, 9H). LC-MS $(M+H)^+$=673.4. Example 104: 242R,5R)-2-(((3R,5R)-3,5-dimethylmorpholino)methyl)-5-methylpiperazin yl)-1-((S)-7-(4-fluorobenzyl)-2-methyl-6-(4-methylpiperazine-1-carbonyl)-2,3-dihydro-1H-pyrido[2,3-b][1,4]oxazin-1-yl)ethan-1-one (Compound 104)

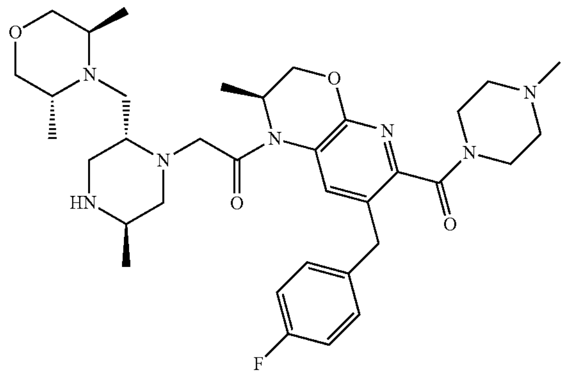 [SMILES: C[C@@H]1CN(CC(=O)N2c3cc(Cc4ccc(F)cc4)c(C(=O)N4CCN(C)CC4)nc3OC[C@@H]2C)[C@@H](CN2[C@H](C)COC[C@H]2C)CN1]

Step 1: tert-butyl (S)-7-(4-fluorobenzyl)-2-methyl-6-(4-methylpiperazine-1-carbonyl)-2,3-dihydro-1H-pyrido[2,3-b][1,4]oxazine-1-carboxylate

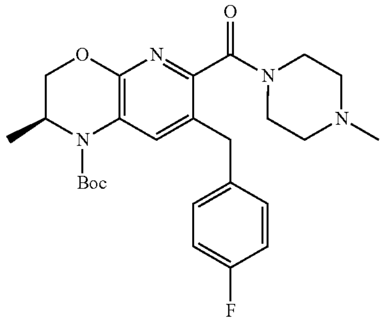

The title compound of step 1 (121 mg, 77% yield) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and 1-methylpiperazine. LC-MS $(M+H)^+$=485.3.

Step 2: (S)-(7-(4-fluorobenzyl)-2-methyl-2,3-dihydro-1H-pyrido[2,3-b][1,4]oxazin-6-yl)(4-methylpiperazin-1-yl)methanone

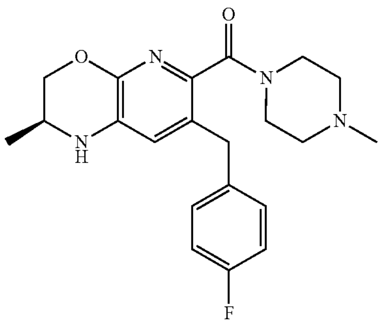

The title compound of step 2 (78 mg, 81% yield) was prepared in a manner similar to that described in Example 1 step 8 from tert-butyl (S)-7-(4-fluorobenzyl)-2-methyl-6-(4-methylpiperazine-1-carbonyl)-2,3-dihydro-1H-pyrido[2,3-b][1,4]oxazine-1-carboxylate. LC-MS $(M+H)^+$=385.2.

Step 3: (S)-2-chloro-1-(7-(4-fluorobenzyl)-2-methyl-6-(4-methylpiperazine-1-carbonyl)-2,3-dihydro-1H-pyrido[2,3-b][1,4]oxazin-1-yl)ethan-1-one

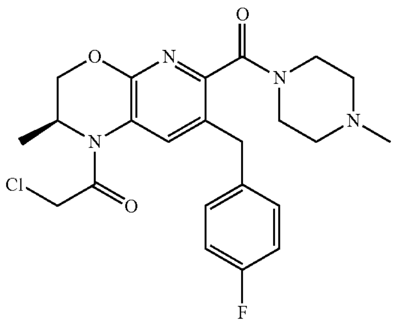 [SMILES: C[C@H]1COc2nc(C(=O)N3CCN(C)CC3)c(Cc3ccc(F)cc3)cc2N1C(=O)CCl]

The title compound of step 3 (90 mg, 96% yield) was prepared in a manner similar to that described in Example 1 step 9 from (S)-(7-(4-fluorobenzyl)-2-methyl-2,3-dihydro-1H-pyrido[2,3-b][1,4]oxazin-6-yl)(4-methylpiperazin-1-yl) methanone and 2-chloroacetyl chloride. LC-MS $(M+H)^+$=461.2.

Step 4: tert-butyl (2R,5S)-5-(((3R,5R)-3,5-dimethylmorpholino)methyl)-4-(2-((S)-7-(4-fluorobenzyl)-2-methyl-6-(4-methylpiperazine-1-carbonyl)-2,3-dihydro-1H-pyrido[2,3-b][1,4]oxazin-1-yl)-2-oxoethyl)-2-methylpiperazine-1-carboxylate

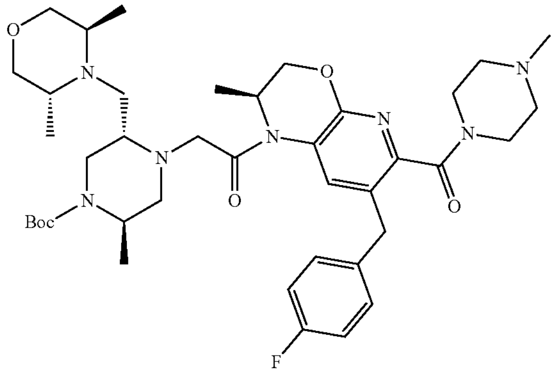 [SMILES: C[C@@H]1CN(CC(=O)N2c3cc(Cc4ccc(F)cc4)c(C(=O)N4CCN(C)CC4)nc3OC[C@@H]2C)[C@@H](CN2[C@H](C)COC[C@H]2C)CN1C(=O)OC(C)(C)C]

The title compound of step 4 (67 mg, 46% yield) was prepared in a manner similar to that described in Example 1 step 18 from (S)-2-chloro-1-(7-(4-fluorobenzyl)-2-methyl-6-(4-methylpiperazine-1-carbonyl)-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=752.5.

Step 5: 2-((2R,5R)-2-(((3R,5R)-3,5-dimethylmorpholino)methyl)-5-methylpiperazin-1-yl)-1-4S)-7-(4-fluorobenzyl)-2-methyl-6-(4-methylpiperazine-1-carbonyl)-2,3-dihydro-1H-pyrido[2,3-b][1,4]oxazin-1-yl)ethan-1-one (Compound 104)

Compound 104 (19 mg, 32% yield) was prepared in a manner similar to that described in Example 29 step 7 from tert-butyl (2R,5S)-5-(((3R,5R)-3,5-dimethylmorpholino) methyl)-4-(2-4S)-7-(4-fluorobenzyl)-2-methyl-6-(4-methylpiperazine-1-carbonyl)-2,3-dihydro-1H-pyrido[2,3-b][1,4]oxazin-1-yl)-2-oxoethyl)-2-methylpiperazine-1-carboxylate. $^1H$ NMR (400 MHz, DMSO-d6) δ 8.32 (s, 1H), 7.22-7.15 (m, 2H), 7.15-7.08 (m, 2H), 4.85-4.75 (m, 1H), 4.40-4.33 (m, 1H), 4.31-4.23 (m, 1H), 3.98 (d, J=15.2 Hz, 1H), 3.91-3.78 (m, 2H), 3.62-3.41 (m, 5H), 3.20-3.07 (m, 2H), 3.02-2.88 (m, 3H), 2.85-2.75 (m, 1H), 2.74-2.66 (m, 2H), 2.63-2.53 (m, 2H), 2.34-2.20 (m, 3H), 2.20-2.14 (m, 1H), 2.12 (s, 3H), 2.05-1.84 (m, 4H), 1.22 (d, J=6.7 Hz, 3H), 0.91-0.83 (m, 9H). LC-MS $(M+H)^+$=652.3.

Example 105: 1-((S)-7-(4-fluorobenzyl)-6-(hydroxymethyl)-2-methyl-2,3-dihydro-1H-pyrido[2,3-b][1,4]oxazin-1-yl)-2-((2R,5R)-5-methyl-2-(((2R,6R)-2,4,6-trimethylpiperazine-1-yl)methyl)piperazin-1-yl)ethan-1-one (Compound 105)

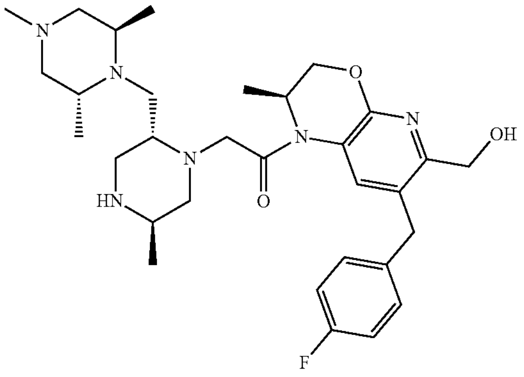 [SMILES: C[C@@H]1CN(CC(=O)N2c3cc(Cc4ccc(F)cc4)c(CO)nc3OC[C@@H]2C)[C@@H](CN2[C@H](C)CN(C)C[C@H]2C)CN1]

Step 1: (9H-fluoren-9-yl)methyl (3R,5R)-3,5-dimethylpiperazine-1-carboxylate

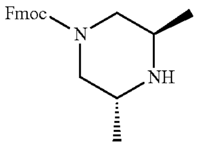

To a solution of (2R,6R)-2,6-dimethylpiperazine dihydrochloride (2.0 g, 10.7 mmol) and DIEA (1.7 g, 12.8 mmol) in DCM (30 mL) was added 9-fluorenylmethyloxycarbonyl chloride (2.8 g, 10.7 mmol) in portions at 0° C. under nitrogen atmosphere. The resulting mixture was stirred for 2 h at room temperature under nitrogen atmosphere. When the reaction was done, the resulting mixture was concentrated under reduced pressure. The residue was purified by flash chromatography eluting with MeOH in DCM (0% to 40% gradient) to yield the title compound (2.5 g, 69% yield). LC-MS $(M+H)^+$=337.2.

Step 2: 4-((9H-fluoren-9-yl)methyl) 1-benzyl (2R,6R)-2,6-dimethylpiperazine-1,4-dicarboxylate

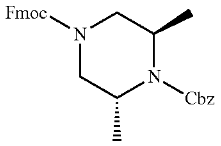

To a solution of (9H-fluoren-9-yl)methyl (3R,5R)-3,5-dimethylpiperazine-1-carboxylate (450 mg, 1.34 mmol) and DIEA (260 mg, 2.02 mmol) in DCM (20 mL) was added Cbz-Cl (275 mg, 1.62 mmol) dropwise at 0° C. under nitrogen atmosphere. The resulting mixture was stirred for 2 h at room temperature under nitrogen atmosphere. When the reaction was done, the reaction was then quenched by the addition of sat. $NaHCO_3$ at room temperature. The resulting mixture was extracted with DCM (30 mL×2). The organic phases were combined, washed with brine and dried over $Na_2SO_4$. The resulting mixture was concentrated under reduced pressure. The residue was purified by flash chromatography eluting with EtOAc in PE (0% to 70% gradient) to yield the title compound (275 mg, 43% yield). LC-MS $(M+H)^+$=471.2.

Step 3: benzyl (2R,6R)-2,6-dimethylpiperazine-1-carboxylate

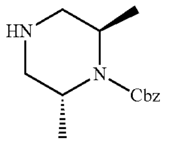 [SMILES: C[C@@H]1CNC[C@@H](C)N1C(=O)OCc1ccccc1]

To a solution of 4-((9H-fluoren-9-yl)methyl) 1-benzyl (2R,6R)-2,6-dimethylpiperazine-1,4-dicarboxylate (275 mg, 0.58 mmol) in DCM (3 mL) was added piperidine (10% in DCM, 3 mL) dropwise at room temperature under nitrogen atmosphere. The resulting mixture was stirred for 3 h at room temperature under nitrogen atmosphere. When the reaction was done, the reaction was then quenched by the addition of sat. $NaHCO_3$ at room temperature. The resulting mixture was extracted with DCM (15 mL×2). The organic phases were combined, washed with brine and dried over $Na_2SO_4$. The resulting mixture was concentrated under reduced pressure. The residue was purified by flash chromatography eluting with MeOH in DCM (0% to 20% gradient) to yield the title compound (68 mg, 47% yield). LC-MS $(M+H)^+$=249.1.

Step 4: benzyl (2R,6R)-2,4,6-trimethylpiperazine-1-carboxylate

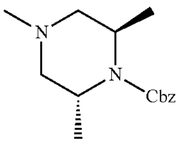 [SMILES: C[C@@H]1CN(C)C[C@@H](C)N1C(=O)OCc1ccccc1]

The title compound of step 4 (67 mg, 95% yield) was prepared in a manner similar to that described in Example 92 step 1 from benzyl (2R,6R)-2,6-dimethylpiperazine-1-carboxylate and formaldehyde aqueous solution. LC-MS $(M+H)^+$=263.0.

Step 5: (3R,5R)-1,3,5-trimethylpiperazine hydrochloride

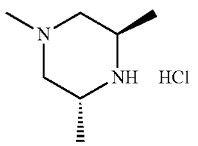

The title compound of step 5 (40 mg, crude) was prepared in a manner similar to that described in Example 1 step 17 from benzyl (2R,6R)-2,4,6-trimethylpiperazine-1-carboxylate. LC-MS $(M+H)^+$=129.2.

Step 6: tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-2-methyl-54(2R,6R)-2,4,6-trimethylpiperazin-1-yl)methyl)piperazine-1-carboxylate

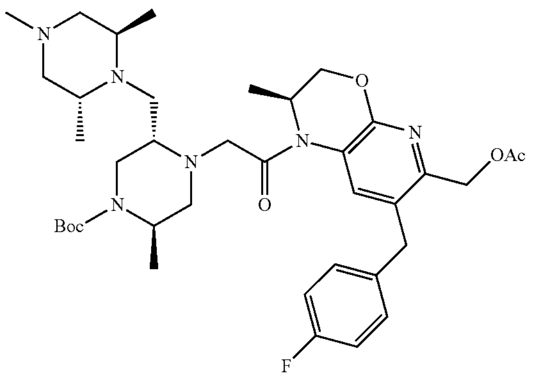 [SMILES: CC(=O)OCc1nc2c(cc1Cc1ccc(F)cc1)N(C(=O)CN1C[C@@H](C)N(C(=O)OC(C)(C)C)C[C@@H]1CN1[C@H](C)CN(C)C[C@H]1C)[C@@H](C)CO2]

The title compound of step 6 (80 mg, 46% for 2 steps) was prepared in a manner similar to that described in Example 1 step 18 from (3R,5R)-1,3,5-trimethylpiperazine hydrochloride and tert-butyl(2R,5R)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-5-(chloromethyl)-2-methylpiperazine carboxylate. LC-MS $(M+H)^+$=711.3.

Step 7: 1-((S)-7-(4-fluorobenzyl)-6-(hydroxymethyl)-2-methyl-2,3-dihydro-1H-pyrido[2,3-b][1,4]oxazin-1-yl)-2-((2R,5R)-5-methyl-2-(((2R,6R)-2,4,6-trimethylpiperazin-1-yl)methyl)piperazin-1-yl)ethan-1-one (Compound 105)

To a solution of tert-butyl (2R,5S)-4-(2-((S)-6-(acetoxymethyl)-7-(4-fluorobenzyl)-2-methyl-2,3-dihydro-1H-pyrido[2,3-b][1,4]oxazin-1-yl)-2-oxoethyl)-2-methyl-5-(((2R,6R)-2,4,6-trimethylpiperazin-1-yl)methyl)piperazine-1-carboxylate (80 mg, 0.11 mmol) in MeOH (2 mL) was added HCl in MeOH (0.5 mL, 2 mmol, 4 M solution) dropwise at 0° C. The resulting mixture was stirred for 2 h at 60° C. When the reaction was done, the resulting mixture was concentrated under reduced pressure. The resulting mixture was diluted with sat.$NaHCO_3$ (10 mL). The resulting mixture was extracted with DCM (2×15 mL). The organic phases were combined, washed with brine and dried over $Na_2SO_4$. The solvent was concentrated under reduced pressure and the residue was purified in a manner similar to that described in Example 29 step 7 to obtain compound 105 (23 mg, 35% yield). $^1$H NMR (400 MHz, DMSO-d6) δ 8.12 (s, 1H), 7.24-7.15 (m, 2H), 7.15-7.05 (m, 2H), 5.08 (t, J=5.6 Hz, 1H), 4.70 (s, 1H), 4.48-4.36 (m, 2H), 4.36-4.29 (m, 1H), 4.25-4.17 (m, 1H), 4.05-3.95 (m, 2H), 3.95-3.84 (m, 1H), 3.49 (d, J=15.3 Hz, 1H), 2.99-2.91 (m, 1H), 2.76-2.72 (m, 3H), 2.67-2.54 (m, 3H), 2.31-2.11 (m, 4H), 1.99 (s, 3H), 1.96-1.79 (m, 3H), 1.18 (d, J=6.7 Hz, 3H), 0.91-0.85 (m, 9H). LC-MS $(M+H)^+$=569.3.

Example 106: 2-((2R,5R)-2-(((3R,5R)-3,5-dimethylmorpholino)methyl)-5-methylpiperazin-1-yl)-1-(((S)-7-(4-fluorobenzyl)-2-methyl-6-morpholino-2,3-dihydro-1H-pyrido[2,3-b][1,4]oxazin-1-yl)ethan-1-one (Compound 106)

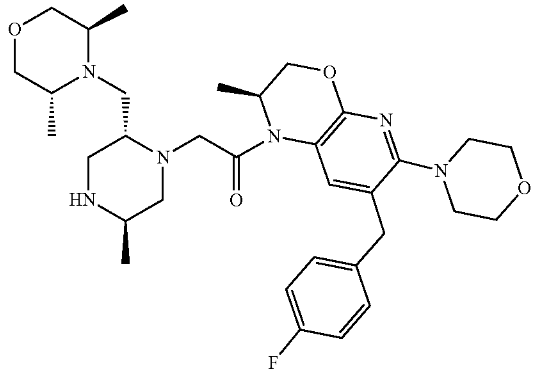 [SMILES: C[C@@H]1CN(CC(=O)N2c3cc(Cc4ccc(F)cc4)c(N4CCOCC4)nc3OC[C@@H]2C)[C@@H](CN2[C@H](C)COC[C@H]2C)CN1]

Step 1: tert-butyl (S)-7-(4-fluorobenzyl)-2-methyl-6-morpholino-2,3-dihydro-1H-pyrido[2,3-b][1,4]oxazine

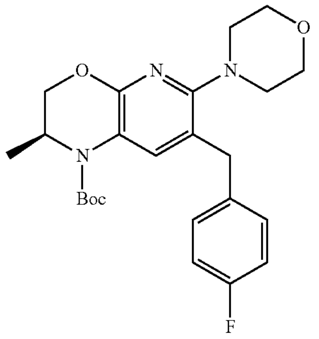 [SMILES: C[C@H]1COc2nc(N3CCOCC3)c(Cc3ccc(F)cc3)cc2N1C(=O)OC(C)(C)C]

To a solution of morpholine (57 mg, 0.63 mmol) and DIEA (263 mg, 1.93 mmol) in DCM (3 mL) was added (S)-1-(tert-butoxycarbonyl)-7-(4-fluorobenzyl)-2-methyl-2,3-dihydro-1H-pyrido[2,3-b][1,4]oxazine 5-oxide (189 mg, 0.48 mmol), and PyBrOP (331 mg, 0.68 mmol) at room temperature under nitrogen atmosphere. The resulting mixture was stirred for 16 h at room temperature under nitrogen atmosphere. When the reaction was done, the reaction was then quenched by the addition of water at room temperature. The resulting mixture was extracted with DCM (30 mL×2). The organic phases were combined, washed with brine and dried over $Na_2SO_4$. The resulting mixture was concentrated under reduced pressure. The residue was purified by flash chromatography eluting with EtOAc in PE (0% to 50% gradient) to yield the title compound (117 mg, 52% yield). LC-MS $(M+H)^+$=444.2.

Step 2: (S)-7-(4-fluorobenzyl)-2-methyl-6-morpholino-2,3-dihydro-1H-pyrido[2,3-b][1,4]oxazine

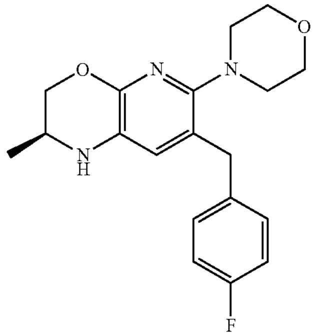 [SMILES: C[C@H]1COc2nc(N3CCOCC3)c(Cc3ccc(F)cc3)cc2N1]

The title compound of step 2 (62 mg, 75% yield) was prepared in a manner similar to that described in Example 1 step 8 from tert-butyl (S)-7-(4-fluorobenzyl)-2-methyl-6-morpholino-2,3-dihydro-1H-pyrido[2,3-b][1,4]oxazine-1-carboxylate. LC-MS $(M+H)^+$=344.3.

Step 3: (S)-2-chloro-1-(7-(4-fluorobenzyl)-2-methyl-6-morpholino-2,3-dihydro-1H-pyrido[2,3-b][1,4]oxazin-1-yl)ethan-1-one

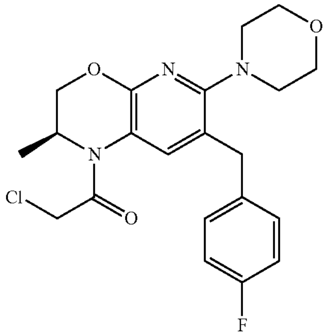 [SMILES: C[C@H]1COc2nc(N3CCOCC3)c(Cc3ccc(F)cc3)cc2N1C(=O)CCl]

The title compound of step 3 (60 mg, 76% yield) was prepared in a manner similar to that described in Example 1 step 9 from (S)-7-(4-fluorobenzyl)-2-methyl-6-morpholino-2,3-dihydro-1H-pyrido[2,3-b][1,4]oxazine and 2-chloroacetyl chloride. LC-MS $(M+H)^+$=420.1.

Step 4: tert-butyl (2R,5S)-5-(((3R,5R)-3,5-dimethylmorpholino)methyl)-4-(2-((S)-7-(4fluorobenzyl)-2-methyl-6-morpholino-2,3-dihydro-1H-pyrido[2,3-b][1,4]oxazin-1-yl)-2-oxoethyl)-2-methylpiperazine-1-carboxylate

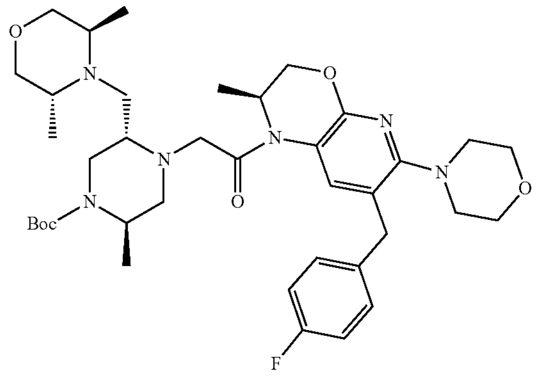 [SMILES: C[C@@H]1CN(CC(=O)N2c3cc(Cc4ccc(F)cc4)c(N4CCOCC4)nc3OC[C@@H]2C)[C@@H](CN2[C@H](C)COC[C@H]2C)CN1C(=O)OC(C)(C)C]

The title compound of step 4 (54 mg, 53% yield) was prepared in a manner similar to that described in Example 1 step 18 from (S)-2-chloro-1-(7-(4-fluorobenzyl)-2-methyl-6-morpholino-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=711.4.

Step 5: 2-((2R,5R)-2-(((3R,5R)-3,5-dimethylmorpholino)methyl)-5-methylpiperazin-1-yl)-1-((S)-7-(4-fluorobenzyl)-2-methyl-6-morpholino-2,3-dihydro-1H-pyrido[2,3-b][1,4]oxazin-1-yl)ethan-1-one (Compound 106)

Compound 106 (2.0 mg, 4.3% yield) was prepared in a manner similar to that described in Example 29 step 7 from tert-butyl (2R,5S)-5-(((3R,5R)-3,5-dimethylmorpholino)methyl)-4-(2-4S)-7-(4-fluorobenzyl)-2-methyl-6-morpholino-2,3-dihydro-1H-pyrido[2,3-b][1,4]oxazin-1-yl)-2-oxoethyl)-2-methylpiperazine-1-carboxylate. $^1H$ NMR (300 MHz, DMSO-d6) δ 8.01 (s, 1H), 7.27-7.16 (m, 2H), 7.19-7.06 (m, 2H), 4.81-4.69 (m, 1H), 4.36-4.26 (m, 1H), 4.24-4.14 (m, 1H), 4.00-3.82 (m, 3H), 3.76-3.61 (m, 4H), 3.52-3.39 (m, 3H), 3.17-3.06 (m, 2H), 3.04-2.83 (m, 6H), 2.75 (s, 1H), 2.70-2.51 (m, 4H), 2.33-2.20 (m, 1H), 2.16-2.03 (m, 1H), 2.02-1.90 (m, 1H), 1.17 (d, J=6.5 Hz, 3H), 0.91-0.80 (m, 9H). LC-MS $(M+H)^+$=611.5.

Example 107: 2-((2R,5R)-2-(((3R,5R)-3,5-dimethylmorpholino)methyl)-5-methylpiperazin-1-yl)-1-(((S)-7-(4-fluorobenzyl)-6-(2-hydroxyethoxy)-2-methyl-2,3-dihydro-1H-pyrido[2,3-b][1,4]oxazin-1-yl)ethan-1-one (Compound 107)

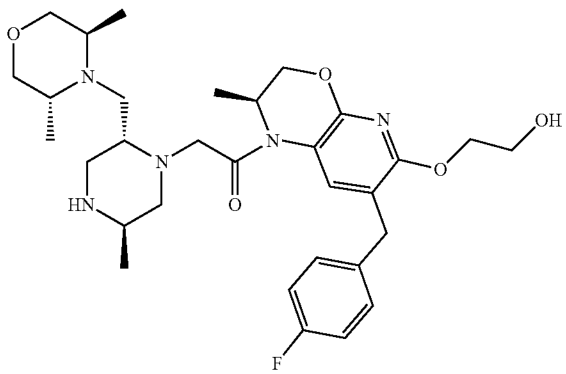 [SMILES: C[C@@H]1CN(CC(=O)N2c3cc(Cc4ccc(F)cc4)c(OCCO)nc3OC[C@@H]2C)[C@@H](CN2[C@H](C)COC[C@H]2C)CN1]

Step 1: (S)-7-(4-fluorobenzyl)-2-methyl-2,3-dihydro-1H-pyrido[2,3-b][1,4]oxazine

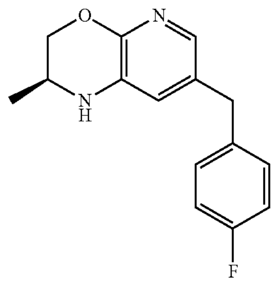 [SMILES: C[C@H]1COc2ncc(Cc3ccc(F)cc3)cc2N1]

The title compound of step 1 (5.8 g, 89% yield) was prepared in a manner similar to that described in Example 1 step 8 from tert-butyl (S)-7-(4-fluorobenzyl)-2-methyl-2,3-dihydro-1H-pyrido[2,3-b][1,4]oxazine-1-carboxylate. LC-MS $(M+H)^+$=259.2.

Step 2: (S)-6-bromo-7-(4-fluorobenzyl)-2-methyl-2,3-dihydro-1H-pyrido[2,3-b][1,4]oxazine

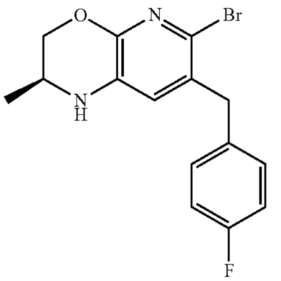 [SMILES: C[C@H]1COc2nc(Br)c(Cc3ccc(F)cc3)cc2N1]

The title compound of step 2 (6.8 g, 90% yield) was prepared in a manner similar to that described in Example 4 step 1 from (S)-7-(4-fluorobenzyl)-2-methyl-2,3-dihydro-1H-pyrido[2,3-b][1,4]oxazine. LC-MS $(M+H)^+$=337.1.

Step 3: tert-butyl (S)-6-bromo-7-(4-fluorobenzyl)-2-methyl-2,3-dihydro-1H-pyrido[2,3-b][1,4]oxazine-1-carboxylate

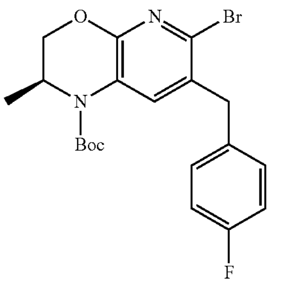 [SMILES: C[C@H]1COc2nc(Br)c(Cc3ccc(F)cc3)cc2N1C(=O)OC(C)(C)C]

The title compound of step 3 (7.0 g, 80% yield) was prepared in a manner similar to that described in Example 4 step 2 from (S)-6-bromo-7-(4-fluorobenzyl)-2-methyl-2,3-dihydro-1H-pyrido[2,3-b][1,4]oxazine. LC-MS $(M+H)^+$=437.1.

Step 4: tert-butyl (S)-7-(4-fluorobenzyl)-6-(2-hydroxyethoxy)-2-methyl-2,3-dihydro-1H-pyrido[2,3-b][1,4]oxazine-1-carboxylate

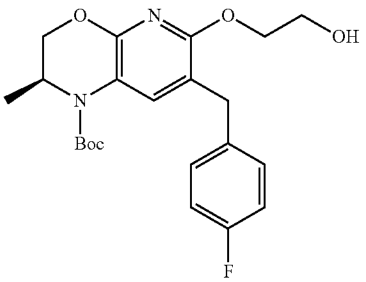 [SMILES: C[C@H]1COc2nc(OCCO)c(Cc3ccc(F)cc3)cc2N1C(=O)OC(C)(C)C]

To a solution of tert-butyl (S)-6-bromo-7-(4-fluorobenzyl)-2-methyl-2,3-dihydro-1H-pyrido[2,3-b][1,4]oxazine-1-carboxylate (400 mg, 0.92 mmol) and ethane-1,2-diol (114 mg, 1.83 mmol) in dioxane (30 mL) were added $Pd_2(dba)_3$ (84 mg, 0.09 mmol), Xantphos (106 mg, 0.18 mmol) and $Cs_2CO_3$ (631 mg, 1.83 mmol). The mixture was refluxed for 16 h under nitrogen. The mixture was cooled to room temperature and diluted with EtOAc (30 mL), washed with brine (20 mL), dried over sodium sulfate, concentrated under reduced pressure. The residue was purified by silica gel column chromatography (eluent with PE:EtOAc=1:1) to give title compound (280 mg, 73%) as a solid. LC-MS $(M+H)^+$=418.9.

Step 5: (S)-2-((7-(4-fluorobenzyl)-2-methyl-2,3-dihydro-1H-pyrido[2,3-b][1,4]oxazin-6-yloxy)ethan-1-ol

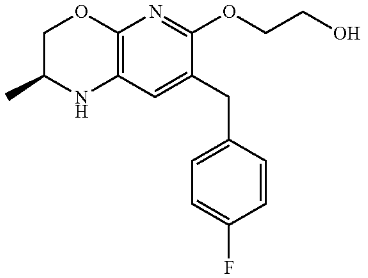 [SMILES: C[C@H]1COc2nc(OCCO)c(Cc3ccc(F)cc3)cc2N1]

The title compound of step 2 (50 mg, 20% yield) was prepared in a manner similar to that described in Example 1 step 8 from tert-butyl (S)-7-(4-fluorobenzyl)-6-(2-hydroxyethoxy)-2-methyl-2,3-dihydro-1H-pyrido[2,3-b][1,4]oxazine-1-carboxylate. LC-MS $(M+H)^+$=318.9.

Step 6: (S)-6-(2-((tert-butyldimethylsilyl)oxy)ethoxy)-7-(4-fluorobenzyl)-2-methyl-2,3-dihydro-1H-pyrido[2,3-b][1,4]oxazine

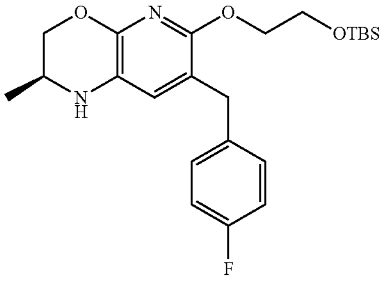 [SMILES: C[C@H]1COc2nc(OCCO[Si](C)(C)C(C)(C)C)c(Cc3ccc(F)cc3)cc2N1]

The title compound of step 3 (60 mg, 88% yield) was prepared in a manner similar to that described in Example 54 step 1 from (S)-2-((7-(4-fluorobenzyl)-2-methyl-2,3-dihydro-1H-pyrido[2,3-b][1,4]oxazin-6-yloxy)ethan-1-ol and TBSCl. LC-MS $(M+H)^+$=433.3.

Step 7: (S)-1-(6-(2-((tert-butyldimethylsilyl)oxy) ethoxy)-7-(4-fluorobenzyl)-2-methyl-2,3-dihydro-1H-pyrido[2,3-b][1,4]oxazin-1-yl)-2-chloroethan-1-one

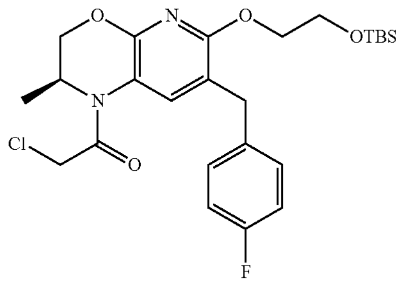 [SMILES: C[C@H]1COc2nc(OCCO[Si](C)(C)C(C)(C)C)c(Cc3ccc(F)cc3)cc2N1C(=O)CCl]

The title compound of step 4 (60 mg, 86% yield) was prepared in a manner similar to that described in Example 1 step 9 from (S)-6-(2-((tert-butyldimethylsilyl)oxy)ethoxy)-7-(4-fluorobenzyl)-2-methyl-2,3-dihydro-1H-pyrido[2,3-b][1,4]oxazine and 2-chloroacetyl chloride. LC-MS $(M+H)^+$=509.3.

Step 8: tert-butyl (2R,5S)-4-(2-((S)-6-(2-((tert-butyldimethylsilyl)oxy)ethoxy)-7-(4-fluorobenzyl)-2-methyl-2,3-dihydro-1H-pyrido[2,3-b][1,4]oxazin-1-yl)-2-oxoethyl)-5-4(3R,5R)-3,5-dimethylmorpholino)methyl)-2-methylpiperazine-1-carboxylate

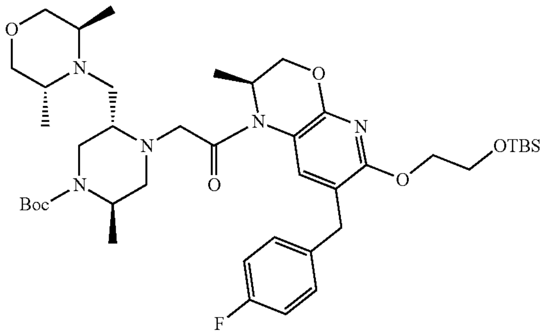 [SMILES: C[C@@H]1CN(CC(=O)N2c3cc(Cc4ccc(F)cc4)c(OCCO[Si](C)(C)C(C)(C)C)nc3OC[C@@H]2C)[C@@H](CN2[C@H](C)COC[C@H]2C)CN1C(=O)OC(C)(C)C]

The title compound of step 5 (90 mg, 96% yield) was prepared in a manner similar to that described in Example 1 step 18 from (S)-1-(6-(2-((tert-butyldimethylsilyl)oxy) ethoxy)-7-(4-fluorobenzyl)-2-methyl-2,3-dihydro-1H-pyrido[2,3-b][1,4]oxazin-1-yl)-2-chloroethan-1-one and tert-butyl (2R,5S)-5-(((3R,5R)-3,5-dimethylmorpholino) methyl)-2-methylpiperazine-1-carboxylate. LC-MS $(M+H)^+$=800.9.

Step 9: 242R,5R)-2-(((3R,5R)-3,5-dimethylmorpholino)methyl)-5-methylpiperazin-1-yl)-1-((S)-7-(4-fluorobenzyl)-6-(2-hydroxyethoxy)-2-methyl-2,3-dihydro-1H-pyrido[2,3-b][1,4]oxazin-1-yl)ethan-1-one (Compound 107)

Compound 107 (40 mg, 62% yield) was prepared in a manner similar to that described in Example 29 step 7 from tert-butyl (2R,5S)-4-(2-((S)-6-(2-((tert-butyldimethylsilyl) oxy)ethoxy)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^1$H NMR (400 MHz, DMSO-d6) δ 8.06 (s, 1H), 7.26 (brs, 2H), 7.09 (brs, 2H), 4.81 (s, 1H), 4.67 (s, 1H), 4.31-4.28 (m, 1H), 4.18 (s, 3H), 3.88-3.84 (m, 1H), 3.79 (brs, 2H), 3.68 (brs, 2H), 3.45-3.41 (m, 4H), 3.13 (brs, 2H), 2.98-2.96 (m, 1H), 2.79 (brs, 1H), 2.67 (brs, 3H), 2.60-2.57 (m, 2H), 2.31-2.28 (m, 1H), 2.13 (brs, 1H), 1.95 (brs, 1H), 1.16 (s, 3H), 0.97-0.72 (m, 9H). LC-MS $(M+H)^+$=586.5.

Example 108: 2-((2R,5R)-2-(((3R,5R)-3,5-dimethylmorpholino)methyl)-5-methylpiperazin yl)-1-(((S)-7-(4-fluorobenzyl)-6-((2-methoxyethyl)amino)-2-methyl-2,3-dihydro-1H-pyrido[2,3-b][1,4]oxazin-1-yl)ethan-1-one (Compound 108)

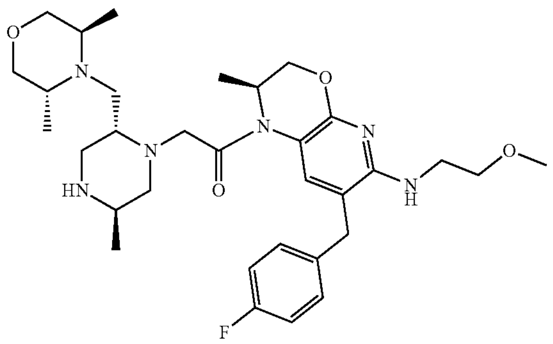 [SMILES: COCCNc1nc2c(cc1Cc1ccc(F)cc1)N(C(=O)CN1C[C@@H](C)NC[C@@H]1CN1[C@H](C)COC[C@H]1C)[C@@H](C)CO2]

Step 1: tert-butyl (S)-7-(4-fluorobenzyl)-6-((2-methoxyethyl)amino)-2-methyl-2,3-dihydro-1H-pyrido[2,3-b][1,4]oxazine-1-carboxylate

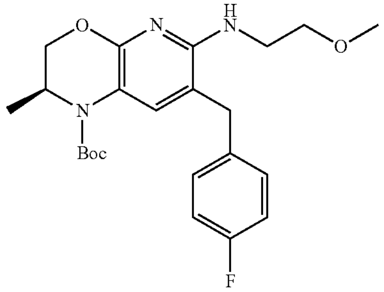

The title compound of step 1 (287 mg, 28% yield) was prepared in a manner similar to that described in Example 106 step 1 from (S)-1-(tert-butoxycarbonyl)-7-(4-fluorobenzyl)-2-methyl-2,3-dihydro-1H-pyrido[2,3-b][1,4]oxazine 5-oxide and 2-methoxyethan-1-amine. LC-MS $(M+H)^+$=432.3.

Step 2: (S)-7-(4-fluorobenzyl)-N-(2-methoxyethyl)-2-methyl-2,3-dihydro-1H-pyrido[2,3-b][1,4]oxazin-6-amine

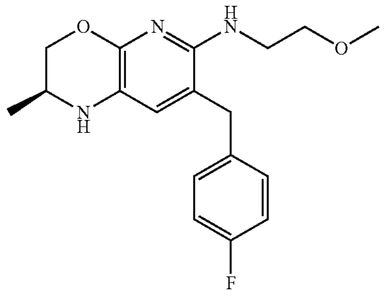

The title compound of step 2 (115 mg, 52% yield) was prepared in a manner similar to that described in Example 1 step 8 from tert-butyl (S)-7-(4-fluorobenzyl)-6-((2-methoxyethyl)amino)-2-methyl-2,3-dihydro-1H-pyrido[2,3-b][1,4]oxazine-1-carboxylate. LC-MS $(M+H)^+=332.1$.

Step 3: (S)-2-chloro-1-(7-(4-fluorobenzyl)-6-((2-methoxyethyl)amino)-2-methyl-2,3-dihydro-1H-pyrido[2,3-b][1,4]oxazin-1-yl)ethan-1-one

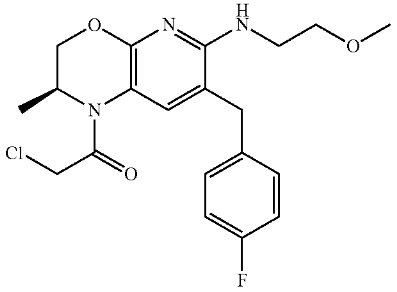

The title compound of step 3 (60 mg, 76% yield) was prepared in a manner similar to that described in Example 1 step 9 from (S)-7-(4-fluorobenzyl)-N-(2-methoxyethyl)-2-methyl-2,3-dihydro-1H-pyrido[2,3-b][1,4]oxazin-6-amine and 2-chloroacetyl chloride. LC-MS $(M+H)^+=408.2$.

Step 4: tert-butyl (2R,5S)-5-(((3R,5R)-3,5-dimethylmorpholino)methyl)-4-(2-((S)-7-(4-fluorobenzyl)-6-((2-methoxyethyl)amino)-2-methyl-2,3-dihydro-1H-pyrido[2,3-b][1,4]oxazin-1-yl)-2-oxoethyl)-2-methylpiperazine-1-carboxylate

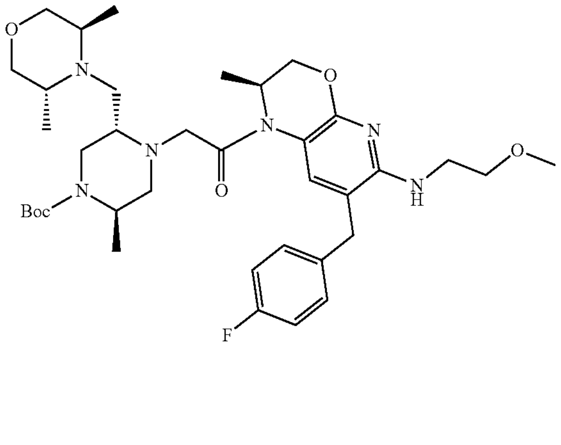 [SMILES: COCCNc1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (100 mg, 53% yield) was prepared in a manner similar to that described in Example 1 step 18 from (S)-2-chloro-1-(7-(4-fluorobenzyl)-64(2-methoxyethyl)amino)-2-methyl-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+=699.4$.

Step 5: 242R,5R)-24(3R,5R)-3,5-dimethylmorpholino)methyl)-5-methylpiperazin-1-yl)-1-4S)-7-(4-fluorobenzyl)-6-((2-methoxyethyl)amino)-2-methyl-2,3-dihydro-1H-pyrido[2,3-b][1,4]oxazin-1-yl)ethan-1-one (Compound 108)

Compound 108 (44 mg, 50% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-6-((2-methoxyethyl)amino)-2-methyl-2,3-dihydro-1H-pyrido[2,3-b][1,4]oxazin-1-yl)-2-oxoethyl)-2-methylpiperazine-1-carboxylate. $^1H$ NMR (400 MHz, DMSO-d6) δ 7.74 (brs, 1H), 7.26-7.17 (m, 2H), 7.17-7.06 (m, 2H), 5.87 (t, J=5.0, 3.9 Hz, 1H), 4.66-4.58 (m, 1H), 4.27-4.20 (m, 1H), 4.15-4.07 (m, 1H), 3.86-3.78 (m, 1H), 3.69 (s, 2H), 3.52-3.42 (m, 2H), 3.44-3.36 (m, 3H), 3.33-3.28 (m, 2H), 3.22 (s, 3H), 3.19-3.10 (m, 2H), 3.00-2.91 (m, 1H), 2.84-2.75 (m, 1H), 2.69-2.51 (m, 1H), 2.45-2.38 (m, 4H), 2.31-2.21 (m, 1H), 2.07-2.01 (m, 2H), 2.00-1.90 (m, 1H), 1.20-1.13 (m, 3H), 0.90-0.82 (m, 9H). LC-MS $(M+H)^+=599.3$.

Example 109: 2-((2R,5R)-2-(((3R,5R)-3,5-dimethylmorpholino)methyl)-5-methylpiperazin yl)-1-(((S)-7-(4-fluorobenzyl)-6-((2-hydroxy ethyl)amino)-2-methyl-2,3-dihydro-1H-pyrido[2,3-b][1,4]oxazin-1-yl)ethan-1-one

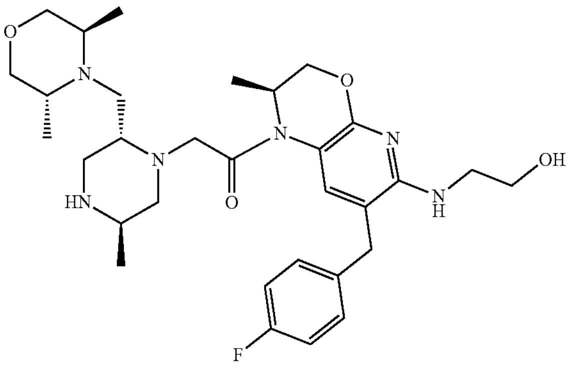 [SMILES: C[C@@H]1CN(CC(=O)N2c3cc(Cc4ccc(F)cc4)c(NCCO)nc3OC[C@@H]2C)[C@@H](CN2[C@H](C)COC[C@H]2C)CN1]

Step 1: tert-butyl (S)-7-(4-fluorobenzyl)-6-((2-hydroxyethyl)amino)-2-methyl-2,3-dihydro-1H-pyrido[2,3-b][1,4]oxazine-1-carboxylate

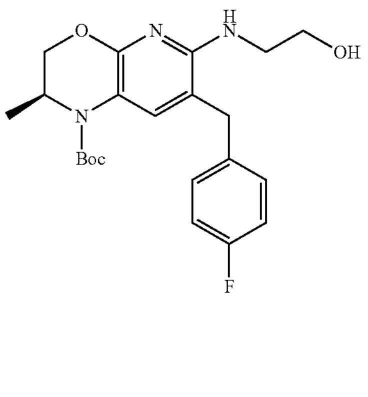 [SMILES: C[C@H]1COc2nc(NCCO)c(Cc3ccc(F)cc3)cc2N1C(=O)OC(C)(C)C]

The title compound of step 1 (201 mg, 20% yield) was prepared in a manner similar to that described in Example 106 step 1 from (S)-1-(tert-butoxycarbonyl)-7-(4-fluorobenzyl)-2-methyl-2,3-dihydro-1H-pyrido[2,3-b][1,4]oxazine 5-oxide and 2-aminoethan-1-ol. LC-MS $(M+H)^+$=418.2.

Step 2: (S)-2-((7-(4-fluorobenzyl)-2-methyl-2,3-dihydro-1H-pyrido[2,3-b][1,4]oxazin-6-yl)amino) ethan-1-ol

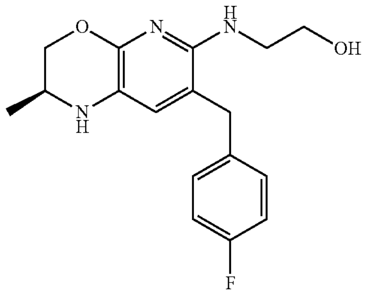 [SMILES: C[C@H]1COc2nc(NCCO)c(Cc3ccc(F)cc3)cc2N1]

The title compound of step 2 (70 mg, 45% yield) was prepared in a manner similar to that described in Example 1 step 8 from tert-butyl (S)-7-(4-fluorobenzyl)-6-((2-hydroxyethyl)amino)-2-methyl-2,3-dihydro-1H-pyrido[2,3-b][1,4] oxazine-1-carboxylate. LC-MS $(M+H)^+$=318.1.

Step 3: (S)—N-(2-((tert-butyldimethylsilyl)oxy) ethyl)-7-(4-fluorobenzyl)-2-methyl-2,3-dihydro-1H-pyrido[2,3-b][1,4]oxazin-6-amine

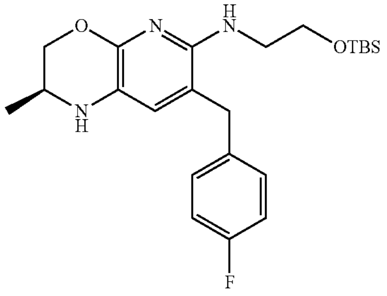 [SMILES: C[C@H]1COc2nc(NCCO[Si](C)(C)C(C)(C)C)c(Cc3ccc(F)cc3)cc2N1]

The title compound of step 3 (65 mg, 68% yield) was prepared in a manner similar to that described in Example 54 step 1 from (S)-2-((7-(4-fluorobenzyl)-2-methyl-2,3-dihydro-1H-pyrido[2,3-b][1,4]oxazin-6-yl)amino)ethan-1-ol and TBSCl. LC-MS $(M+H)^+$=432.3.

Step 4: (S)-1-(6-((2-((tert-butyldimethylsilyl)oxy) ethyl)amino)-7-(4-fluorobenzyl)-2-methyl-2,3-dihydro-1H-pyrido[2,3-b][1,4]oxazin-1-yl)-2-chloro-ethan-1-one

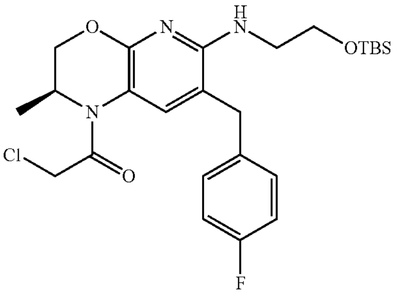 [SMILES: C[C@H]1COc2nc(NCCO[Si](C)(C)C(C)(C)C)c(Cc3ccc(F)cc3)cc2N1C(=O)CCl]

The title compound of step 4 (71 mg, 93% yield) was prepared in a manner similar to that described in Example 1 step 9 from (S)—N-(2-((tert-butyldimethylsilyl)oxy)ethyl)-7-(4-fluorobenzyl)-2-methyl-2,3-dihydro-1H-pyrido[2,3-b] [1,4]oxazin-6-amine and 2-chloroacetyl chloride. LC-MS $(M+H)^+$=508.3.

Step 5: tert-butyl (2R,5S)-4-(2-((S)-6-((2-((tert-butyldimethylsilyl)oxy)ethyl)amino)-7-(4-fluorobenzyl)-2-methyl-2,3-dihydro-1H-pyrido[2,3-b][1,4] oxazin-1-yl)-2-oxoethyl)-5-(((3R,5R)-3,5-dimethylmorpholino)methyl)-2-methylpiperazine-1-carboxylate

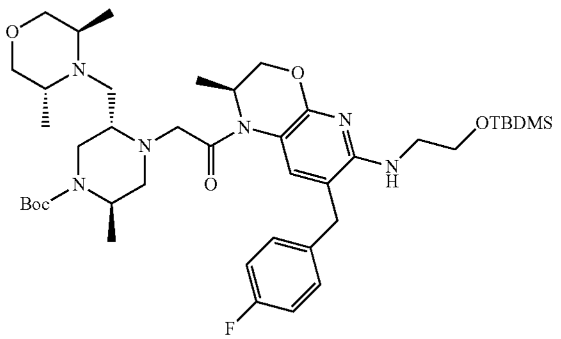 [SMILES: C[C@@H]1CN(CC(=O)N2c3cc(Cc4ccc(F)cc4)c(NCCO[Si](C)(C)C(C)(C)C)nc3OC[C@@H]2C)[C@@H](CN2[C@H](C)COC[C@H]2C)CN1C(=O)OC(C)(C)C]

The title compound of step 5 (60 mg, 53% yield) was prepared in a manner similar to that described in Example 1 step 18 from (S)-1-(64(2-((tert-butyldimethylsilyl)oxy) ethyl)amino)-7-(4-fluorobenzyl)-2-methyl-2,3-dihydro-1H-pyrido[2,3-b][1,4]oxazin-1-yl)-2-chloroethan-1-one and tert-butyl (2R,5S)-5-(((3R,5R)-3,5-dimethylmorpholino) methyl)-2-methylpiperazine-1-carboxylate. LC-MS $(M+H)^+$=799.5.

Step 6: 2-42R,5R)-24(3R,5R)-3,5-dimethylmorpholino)methyl)-5-methylpiperazin-1-yl) ((S)-7-(4-fluorobenzyl)-6-((2-hydroxyethyl)amino)-2-methyl-2,3-dihydro-1H-pyrido[2,3-b][1,4]oxazin-1-yl)ethan-1-one (Compound 109)

Compound 109 (20 mg, 46% yield) was prepared in a manner similar to that described in Example 29 step 7 from tert-butyl (2R,55)-4-(2-((S)-6-((2-((tert-butyldimethylsilyl)

oxy)ethyl)amino)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^1$H NMR (400 MHz, DMSO-d6) δ 7.70 (s, 1H), 7.26-7.18 (m, 2H), 7.17-7.06 (m, 2H), 5.86 (t, J=5.5 Hz, 1H), 4.69-4.64 (m, 1H), 4.27-4.20 (m, 1H), 4.15-4.07 (m, 1H), 3.81 (d, J=14.9 Hz, 1H), 3.69 (s, 2H), 3.52-3.44 (m, 4H), 3.40-3.32 (m, 3H), 3.18-3.10 (m, 2H), 3.00-2.92 (m, 1H), 2.83-2.75 (m, 1H), 2.69-2.52 (m, 4H), 2.45-2.37 (m, 1H), 2.31-2.21 (m, 1H), 2.09-2.02 (m, 1H), 2.00-1.90 (m, 1H), 1.19-1.13 (m, 3H), 0.90-0.81 (m, 9H). LC-MS $(M+H)^+$=585.3.

Example 110: 14S)-6-(cyclopropylamino)-7-(4-fluorobenzyl)-2-methyl-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 110)

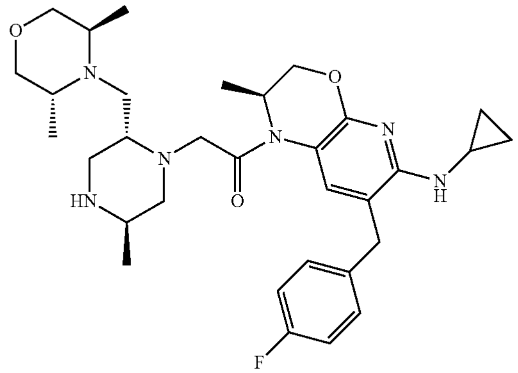 [SMILES: C[C@@H]1CN(CC(=O)N2c3cc(Cc4ccc(F)cc4)c(NC4CC4)nc3OC[C@@H]2C)[C@@H](CN2[C@H](C)COC[C@H]2C)CN1]

Step 1: tert-butyl (S)-6-(cyclopropylamino)-7-(4-fluorobenzyl)-2-methyl-2,3-dihydro-1H-pyrido[2,3-b][1,4]oxazine-1-carboxylate

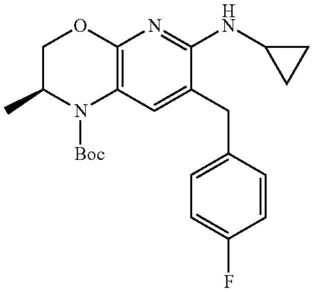 [SMILES: C[C@H]1COc2nc(NC3CC3)c(Cc3ccc(F)cc3)cc2N1C(=O)OC(C)(C)C]

The title compound of step 1 (164 mg, 18% yield) was prepared in a manner similar to that described in Example 106 step 1 from (S)-1-(tert-butoxycarbonyl)-7-(4-fluorobenzyl)-2-methyl-2,3-dihydro-1H-pyrido[2,3-b][1,4]oxazine 5-oxide and cyclopropyl amine. LC-MS $(M+H)^+$=414.1.

Step 2: (S)—N-cyclopropyl-7-(4-fluorobenzyl)-2-methyl-2,3-dihydro-1H-pyrido[2,3-b][1,4]oxazin-6-amine

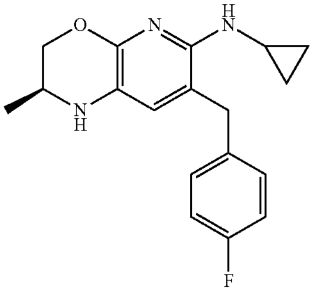 [SMILES: C[C@H]1COc2nc(NC3CC3)c(Cc3ccc(F)cc3)cc2N1]

The title compound of step 2 (80 mg, 63% yield) was prepared in a manner similar to that described in Example 1 step 8 from tert-butyl (S)-6-(cyclopropylamino)-7-(4-fluorobenzyl)-2-methyl-2,3-dihydro-1H-pyrido[2,3-b][1,4]oxazine-1-carboxylate. LC-MS $(M+H)^+$=314.3.

Step 3: (S)-2-chloro-1-(6-(cyclopropylamino)-7-(4-fluorobenzyl)-2-methyl-2,3-dihydro-1H-pyrido[2,3-b][1,4]oxazin-1-yl)ethan-1-one

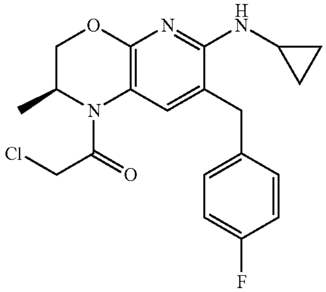 [SMILES: C[C@H]1COc2nc(NC3CC3)c(Cc3ccc(F)cc3)cc2N1C(=O)CCl]

The title compound of step 3 (77 mg, 78% yield) was prepared in a manner similar to that described in Example 1 step 9 from (S)—N-cyclopropyl-7-(4-fluorobenzyl)-2-methyl-2,3-dihydro-1H-pyrido[2,3-b][1,4]oxazin-6-amine and 2-chloroacetyl chloride. LC-MS $(M+H)^+$=390.1.

Step 4: tert-butyl (2R,5S)-4-(2-((S)-6-(cyclopropylamino)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

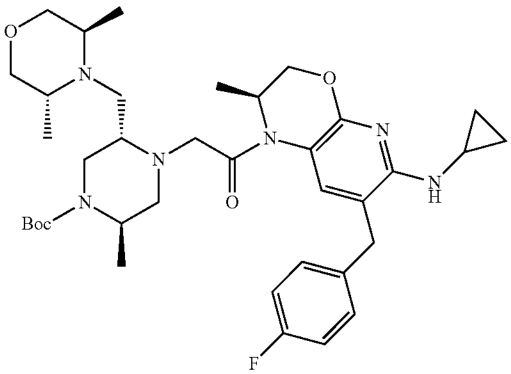 [SMILES: C[C@@H]1CN(CC(=O)N2c3cc(Cc4ccc(F)cc4)c(NC4CC4)nc3OC[C@@H]2C)[C@@H](CN2[C@H](C)COC[C@H]2C)CN1C(=O)OC(C)(C)C]

The title compound of step 4 (101 mg, 74% yield) was prepared in a manner similar to that described in Example 1 step 18 from (S)-2-chloro-1-(6-(cyclopropylamino)-7-(4-fluorobenzyl)-2-methyl-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine carboxylate. LC-MS $(M+H)^+$=681.4.

Step 5: 1-4S)-6-(cyclopropylamino)-7-(4-fluorobenzyl)-2-methyl-2,3-dihydro-1H-pyrido[2,3-b][1,4]oxazin-1-yl)-2-((2R,5R)-2-(((3R,5R)-3,5-dimethylmorpholino)methyl) methylpiperazin-1-yl)ethan-1-one (Compound 110)

Compound 110 (26 mg, 30% yield) was prepared in a manner similar to that described in Example 29 step 7 from tert-butyl (2R,5S)-4-(2-((S)-6-(cyclopropylamino)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^1$H NMR (300 MHz, DMSO-d6) δ 7.67 (s, 1H), 7.22-7.11 (m, 2H), 7.17-7.01 (m, 2H), 6.07 (s, 1H), 4.68-4.52 (m, 1H), 4.26-4.17 (m, 1H), 4.14-4.04 (m, 1H), 3.85-3.74 (m, 1H), 3.64 (s, 2H), 3.50-3.40 (m, 2H), 3.38-3.29 (m, 1H), 3.17-3.05 (m, 2H), 2.99-2.90 (m, 1H), 2.83-2.67 (m, 1H), 2.66-2.50 (m, 5H), 2.47-2.37 (m, 1H), 2.31-2.18 (m, 1H), 2.08-2.02 (m, 1H), 1.99-1.86 (m, 1H), 1.17-1.11 (m, 3H), 0.90-0.77 (m, 9H), 0.67-0.52 (m, 2H), 0.40-0.30 (m, 2H). LC-MS $(M+H)^+$=581.5.

Example 111: 2-((2R,5R)-2-(((3R,5R)-3,5-dimethylmorpholino)methyl)-5-methylpiperazin-1-yl)-1-((S)-6-(ethyl amino)-7-(4-fluorobenzyl)-2-methyl-2,3-dihydro-1H-pyrido[2,3-b][1,4]oxazin-1-yl)ethan-1-one (Compound 111)

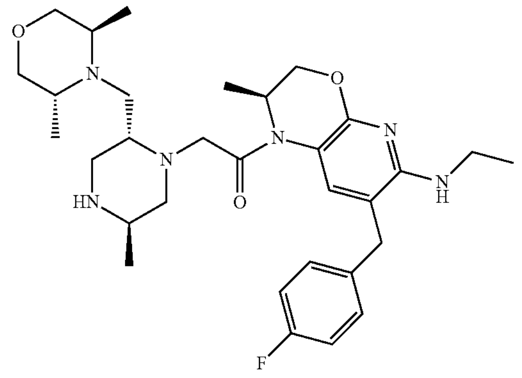 [SMILES: CCNc1nc2c(cc1Cc1ccc(F)cc1)N(C(=O)CN1C[C@@H](C)NC[C@@H]1CN1[C@H](C)COC[C@H]1C)[C@@H](C)CO2]

Step 1: tert-butyl (S)-6-(ethylamino)-7-(4-fluorobenzyl)-2-methyl-2,3-dihydro-1H-pyrido[2,3-b][1,4]oxazine-1-carboxylate

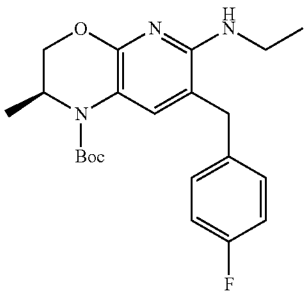 [SMILES: CCNc1nc2c(cc1Cc1ccc(F)cc1)N(C(=O)OC(C)(C)C)[C@@H](C)CO2]

The title compound of step 1 (104 mg, 19% yield) was prepared in a manner similar to that described in Example 106 step 1 from (S)-1-(tert-butoxycarbonyl)-7-(4-fluorobenzyl)-2-methyl-2,3-dihydro-1H-pyrido[2,3-b][1,4]oxazine 5-oxide and ethylamine hydrochloride. LC-MS $(M+H)^+$=402.2.

Step 2: (S)—N-ethyl-7-(4-fluorobenzyl)-2-methyl-2,3-dihydro-1H-pyrido[2,3-b][1,4]oxazin amine

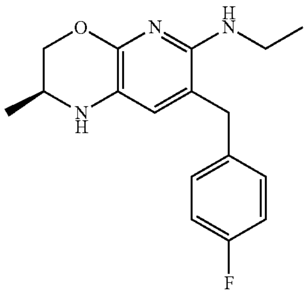 [SMILES: CCNc1nc2c(cc1Cc1ccc(F)cc1)N[C@@H](C)CO2]

The title compound of step 2 (45 mg, 57% yield) was prepared in a manner similar to that described in Example 1 step 8 from tert-butyl (S)-6-(ethylamino)-7-(4-fluorobenzyl)-2-methyl-2,3-dihydro-1H-pyrido[2,3-b][1,4]oxazine-1-carboxylate. LC-MS $(M+H)^+$=302.2.

Step 3: (S)-2-chloro-1-(6-(ethylamino)-7-(4-fluorobenzyl)-2-methyl-2,3-dihydro-1H-pyrido[2,3-b][1,4]oxazin-1-yl)ethan-1-one

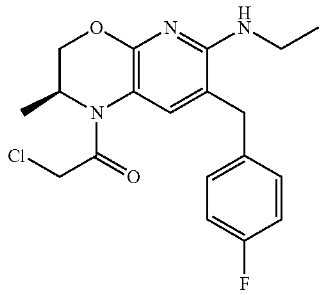 [SMILES: CCNc1nc2c(cc1Cc1ccc(F)cc1)N(C(=O)CCl)[C@@H](C)CO2]

The title compound of step 3 (50 mg, 88% yield) was prepared in a manner similar to that described in Example 1 step 9 from (S)—N-ethyl-7-(4-fluorobenzyl)-2-methyl-2,3-dihydro-1H-pyrido[2,3-b][1,4]oxazin-6-amine and 2-chloroacetyl chloride. LC-MS $(M+H)^+$=378.1.

Step 4: tert-butyl (2R,5S)-5-(((3R,5R)-3,5-dimethylmorpholino)methyl)-4-(2-((S)-6-(ethylamino)-7-(4-fluorobenzyl)-2-methyl-2,3-dihydro-1H-pyrido[2,3-b][1,4]oxazin-1-yl)-2-oxoethyl)-2-methylpiperazine-1-carboxylate

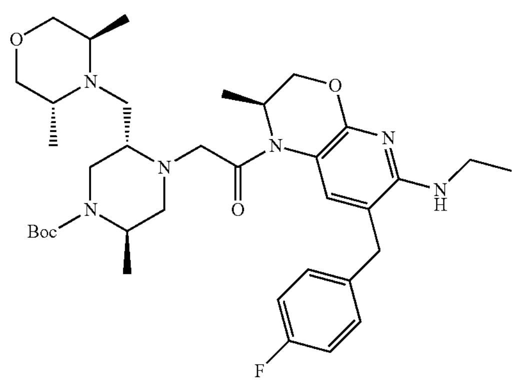 [SMILES: CCNc1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (50 mg, 57% yield) was prepared in a manner similar to that described in Example 1 step 18 from (S)-2-chloro-1-(6-(ethylamino)-7-(4-fluorobenzyl)-2-methyl-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=669.1.

Step 5: 242R,5R)-24(3R,5R)-3,5-dimethylmorpholino)methyl)-5-methylpiperazin-1-yl) ((S)-6-(ethylamino)-7-(4-fluorobenzyl)-2-methyl-2,3-dihydro-1H-pyrido[2,3-b][1,4]oxazin-1-yl)ethan-1-one (Compound 111)

Compound 111 (24 mg, 56% yield) was prepared in a manner similar to that described in Example 29 step 7 from tert-butyl (2R,5S)-5-(((3R,5R)-3,5-dimethylmorpholino) methyl)-4-(2-((S)-6-(ethylamino)-7-(4-fluorobenzyl)-2-methyl-2,3-dihydro-1H-pyrido[2,3-b][1,4]oxazin yl)-2-oxoethyl)-2-methylpiperazine-1-carboxylate. $^1$H NMR (300 MHz, DMSO-d6) δ 7.67 (brs, 1H), 7.25-7.15 (m, 2H), 7.15-7.03 (m, 2H), 5.87 (t, J=5.5 Hz, 1H), 4.62-4.56 (m, 1H), 4.25-4.16 (m, 1H), 4.13-4.03 (m, 1H), 3.84-3.73 (m, 1H), 3.66 (s, 2H), 3.51-3.40 (m, 2H), 3.35-3.16 (m, 3H), 3.16-3.06 (m, 2H), 2.98-2.89 (m, 1H), 2.83-2.68 (m, 1H), 2.672.53 (m, 4H), 2.42-2.36 (m, 1H), 2.30-2.17 (m, 1H), 2.12-1.81 (m, 2H), 1.16-1.01 (m, 6H), 0.89-0.75 (m, 9H). LC-MS $(M+H)^+$=569.4.

Example 112: 2-((2R,5R)-2-(((3R,5R)-3,5-dimethylmorpholino)methyl)-5-methylpiperazin-1-yl)-1-((S)-7-(4-fluorobenzyl)-2-methyl-6-((2,2,2-trifluoroethyl) amino)-2,3-dihydro-1H-pyrido[2,3-b][1,4]oxazin-1-yl)ethan-1-one (Compound 112)

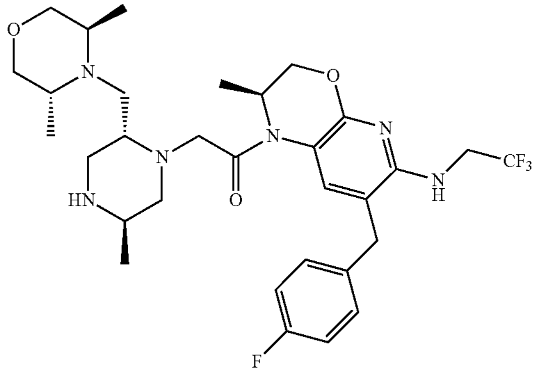 [SMILES: C[C@@H]1CN(CC(=O)N2c3cc(Cc4ccc(F)cc4)c(NCC(F)(F)F)nc3OC[C@@H]2C)[C@@H](CN2[C@H](C)COC[C@H]2C)CN1]

Step 1: benzyl (S)-6-((tert-butoxycarbonyl)amino)-7-(4-fluorobenzyl)-2-methyl-2,3-dihydro-1H-pyrido [2,3-b][1,4]oxazine-1-carboxylate

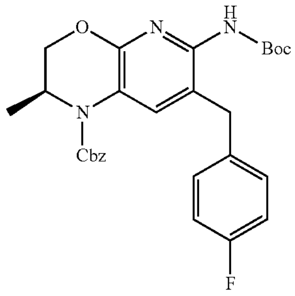 [SMILES: C[C@H]1COc2nc(NC(=O)OC(C)(C)C)c(Cc3ccc(F)cc3)cc2N1C(=O)OCc1ccccc1]

To a solution of (S)-1-((benzyloxy)carbonyl)-7-(4-fluorobenzyl)-2-methyl-2,3-dihydro-1H-pyrido[2,3-b][1,4] oxazine-6-carboxylic acid (923 mg, 2.13 mmol) and TEA (335 mg, 3.26 mmol) in t-BuOH (10 mL) was added DPPA (720 mg, 2.61 mmol) at room temperature under nitrogen atmosphere. The resulting mixture was stirred for 1 h at 100° C. under nitrogen atmosphere. When the reaction was done, the mixture was allowed to cool down to room temperature. The reaction mixture was concentrated under reduced pressure. The residue was purified by flash chromatography eluting with EtOAc in DCM (0% to 10% gradient) to yield the title compound (537 mg, 50% yield). LC-MS $(M+H)^+$=508.2.

Step 2: benzyl (S)-6-amino-7-(4-fluorobenzyl)-2-methyl-2,3-dihydro-1H-pyrido[2,3-b][1,4]oxazine-1carboxylate

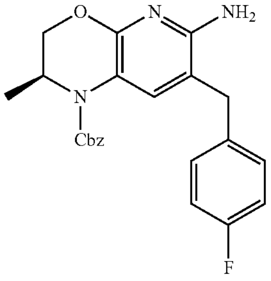 [SMILES: C[C@H]1COc2nc(N)c(Cc3ccc(F)cc3)cc2N1C(=O)OCc1ccccc1]

The title compound of step 2 (310 mg, 71% yield) was prepared in a manner similar to that described in Example 1 step 8 from benzyl (S)-6-((tert-butoxycarbonyl)amino)-7-(4-fluorobenzyl)-2-methyl-2,3-dihydro-1H-pyrido[2,3-b][1,4]oxazine-1-carboxylate. LC-MS $(M+H)^+$=408.3.

Step 3: benzyl (S)-7-(4-fluorobenzyl)-2-methyl-6-(2,2,2-trifluoroacetamido)-2,3-dihydro-1H-pyrido[2,3-b][1,4]oxazine-1-carboxylate

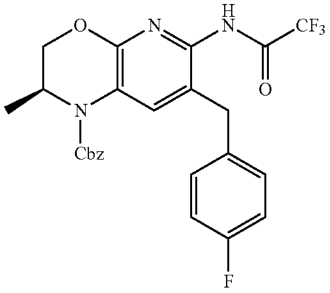 [SMILES: C[C@H]1COc2nc(NC(=O)C(F)(F)F)c(Cc3ccc(F)cc3)cc2N1C(=O)OCc1ccccc1]

At 0° C., to a solution of benzyl (S)-6-amino-7-(4-fluorobenzyl)-2-methyl-2,3-dihydro-1H-pyrido[2,3-b][1,4]oxazine-1-carboxylate (250 mg, 0.61 mmol) and Pyridine (195 mg, 1.21 mmol) in DCM (5 mL) was added TFAA (130 mg, 0.61 mmol) dropwise under nitrogen atmosphere. The resulting mixture was stirred for 1 h at 100° C. under nitrogen atmosphere. When the reaction was done, the mixture was allowed to cool down to room temperature. The reaction was then quenched by the addition of ice water (15 mL). The resulting solution was extracted with DCM (20 mL×3). The organic phases were combined, washed with brine and dried over $Na_2SO_4$. The residue was purified by flash chromatography eluting with EtOAc in DCM (0% to 10% gradient) to yield the title compound (128 mg, 64% yield). LC-MS $(M+H)^+$=504.2.

Step 4: benzyl (S)-7-(4-fluorobenzyl)-2-methyl-6-((2,2,2-trifluoroethyl)amino)-2,3-dihydro-1H-pyrido[2,3-b][1,4]oxazine-1-carboxylate

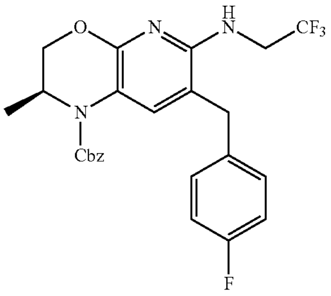 [SMILES: C[C@H]1COc2nc(NCC(F)(F)F)c(Cc3ccc(F)cc3)cc2N1C(=O)OCc1ccccc1]

At 0° C., to a solution of benzyl (S)-7-(4-fluorobenzyl)-2-methyl-6-(2,2,2-trifluoroacetamido)-2,3-dihydro-1H-pyrido[2,3-b][1,4]oxazine-1-carboxylate (100 mg, 0.20 mmol) in THF (2 mL) was added $BH_3$-THF (0.55 mL, 0.55 mmol, 1 M) dropwise under nitrogen atmosphere. The resulting mixture was stirred for 5 h at 50° C. under nitrogen atmosphere. When the reaction was done, the mixture was allowed to cool down to room temperature. The reaction was then quenched by the addition of MeOH (5 mL). The reaction mixture was concentrated under reduced pressure. The residue was purified by flash chromatography eluting with EtOAc in PE (0% to 25% gradient) to yield the title compound (95 mg, 97% yield). LC-MS $(M+H)^+$=490.3.

Step 5: (S)-7-(4-fluorobenzyl)-2-methyl-N-(2,2,2-trifluoroethyl)-2,3-dihydro-1H-pyrido[2,3-b][1,4]oxazin-6-amine

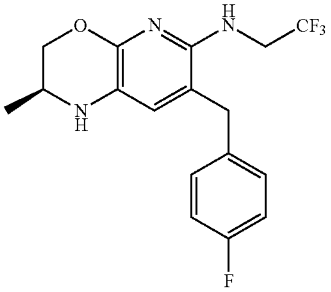 [SMILES: C[C@H]1COc2nc(NCC(F)(F)F)c(Cc3ccc(F)cc3)cc2N1]

The title compound of step 5 (58 mg, 84% yield) was prepared in a manner similar to that described in Example 1 step 17 from benzyl (S)-7-(4-fluorobenzyl)-2-methyl-6-((2,2,2-trifluoroethyl)amino)-2,3-dihydro-1H-pyrido[2,3-b][1,4]oxazine-1-carboxylate. LC-MS $(M+H)^+$=356.2

Step 6: (S)-2-chloro-1-(7-(4-fluorobenzyl)-2-methyl-6-((2,2,2-trifluoroethyl)amino)-2,3-dihydro-1H-pyrido[2,3-b][1,4]oxazin-1-yl)ethan-1-one

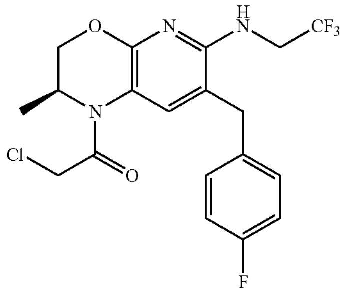 [SMILES: C[C@H]1COc2nc(NCC(F)(F)F)c(Cc3ccc(F)cc3)cc2N1C(=O)CCl]

The title compound of step 6 (66 mg, 93% yield) was prepared in a manner similar to that described in Example 1 step 9 from (S)-7-(4-fluorobenzyl)-2-methyl-N-(2,2,2-trifluoroethyl)-2,3-dihydro-1H-pyrido[2,3-b][1,4]oxazin-6-amine and 2-chloroacetyl chloride. LC-MS $(M+H)^+$=432.2.

Step 7: tert-butyl (2R,5S)-5-(((3R,5R)-3,5-dimethylmorpholino)methyl)-4-(2-((S)-7-(4-fluorobenzyl)-2-methyl-6-((2,2,2-trifluoroethyl)amino)-2,3-dihydro-1H-pyrido[2,3-b][1,4]oxazin-1-yl)-2-oxoethyl)-2-methylpiperazine-1-carboxylate

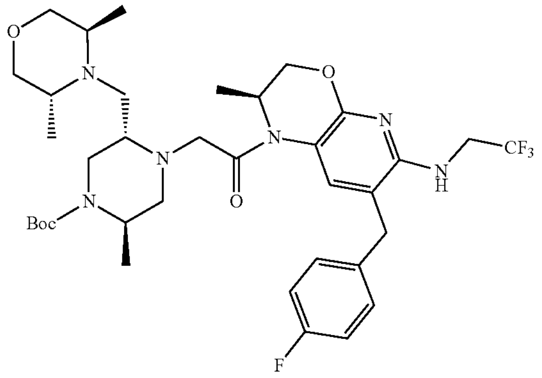 [SMILES: C[C@@H]1CN(CC(=O)N2c3cc(Cc4ccc(F)cc4)c(NCC(F)(F)F)nc3OC[C@@H]2C)[C@@H](CN2[C@H](C)COC[C@H]2C)CN1C(=O)OC(C)(C)C]

The title compound of step 7 (104 mg, 93% yield) was prepared in a manner similar to that described in Example 1 step 18 from (S)-2-chloro-1-(7-(4-fluorobenzyl)-2-methyl-6-((2,2,2-trifluoroethyl)amino)-2,3-dihydro-1H-pyrido[2,3-b][1,4]oxazin-1-yl)ethan-1-one and tert-butyl (2R,5S)-54 (3R,5R)-3,5-dimethylmorpholino)methyl)-2-methylpiperazine-1-carboxylate. LC-MS $(M+H)^+$=723.3.

Step 8: 2-((2R,5R)-2-(((3R,5R)-3,5-dimethylmorpholino)methyl)-5-methylpiperazin-1-yl)-1-((S)-7-(4-fluorobenzyl)-2-methyl-6-((2,2,2-trifluoroethyl) amino)-2,3-dihydro-1H-pyrido[2,3-b][1,4]oxazin-1-yl)ethan-1-one (Compound 112)

Compound 112 (51 mg, 57% yield) was obtained in a manner similar to that described in Example 29 step 7 from tert-butyl (2R,5S)-5-(((3R,5R)-3,5-dimethylmorpholino) methyl)-4-(2-4S)-7-(4-fluorobenzyl)-2-methyl-6-((2,2,2-trifluoroethyl)amino)-2,3-dihydro-1H-pyrido[2,3-b][1,4] oxazin-1-yl)-2-oxoethyl)-2-methylpiperazine-1-carboxylate. $^1H$ NMR (300 MHz, DMSO-$d_6$) δ 7.78 (brs, 1H), 7.26-7.15 (m, 2H), 7.20-7.03 (m, 2H), 6.56 (t, J=6.4 Hz, 1H), 4.67-4.61 (m, 1H), 4.28-3.91 (m, 4H), 3.87-3.76 (m, 1H), 3.73 (s, 2H), 3.50-3.40 (m, 2H), 3.37-3.26 (m, 1H), 3.17-3.05 (m, 2H), 2.98-2.87 (m, 1H), 2.80-2.74 (m, 1H), 2.67-2.49 (m, 3H), 2.45-2.36 (m, 1H), 2.30-2.16 (m, 1H), 2.08-2.00 (m, 2H), 2.00-1.86 (m, 1H), 1.16-1.10 (m, 3H), 0.88-0.78 (m, 9H). LC-MS $(M+H)^+$=623.5.

Example 113: 2-((2R,5R)-2-(((3R,5R)-3,5-dimethylmorpholino)methyl)-5-methylpiperazin-1-yl)-1-(((S)-7-(4-fluorobenzyl)-6-(4-fluorophenyl)-2-methyl-2,3-dihydro-1H-pyrido[2,3-b][1,4]oxazin-1-yl)ethan-1-one (Compound 113)

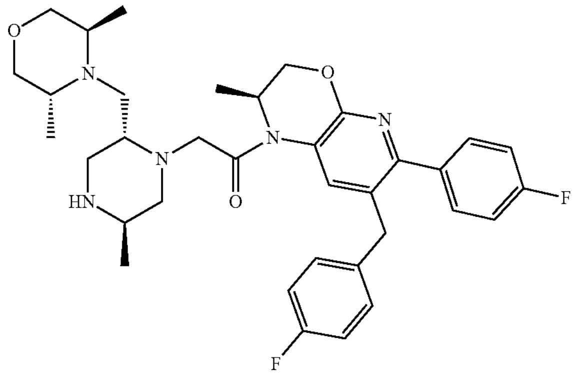 [SMILES: C[C@@H]1CN(CC(=O)N2c3cc(Cc4ccc(F)cc4)c(-c4ccc(F)cc4)nc3OC[C@@H]2C)[C@@H](CN2[C@H](C)COC[C@H]2C)CN1]

Step 1: (S)-6-chloro-7-(4-fluorobenzyl)-2-methyl-2,3-dihydro-1H-pyrido[2,3-b][1,4]oxazine

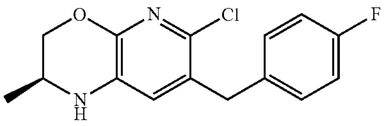 [SMILES: C[C@H]1COc2nc(Cl)c(Cc3ccc(F)cc3)cc2N1]

To a solution of (S)-1-(tert-butoxycarbonyl)-7-(4-fluorobenzyl)-2-methyl-2,3-dihydro-1H-pyrido[2,3-b][1,4] oxazine 5-oxide (1 g, 2.54 mmol) and TEA (85 mg, 0.80 mmol) in Toluene (0.8 mL) was added $POCl_3$ (5 mL) in portions at 0° C. under nitrogen atmosphere. The resulting mixture was stirred for 2 h at 65° C. under nitrogen atmosphere. When the reaction was done, the resulting mixture was concentrated under reduced pressure. The residue was dissolved in ethyl acetate (40 mL). The organic phase was washed with saturated $NaHCO_3$, brine, and dried over $Na_2SO_4$. The solvent was concentrated under reduced pressure. The residue was purified by flash chromatography eluting with MeOH in DCM (0% to 5% gradient) to yield the title compound (53 mg, 7% yield). LC-MS $(M+H)^+$=293.1.

Step 2: (S)-7-(4-fluorobenzyl)-6-(4-fluorophenyl)-2-methyl-2,3-dihydro-1H-pyrido[2,3-b][1,4]oxazine

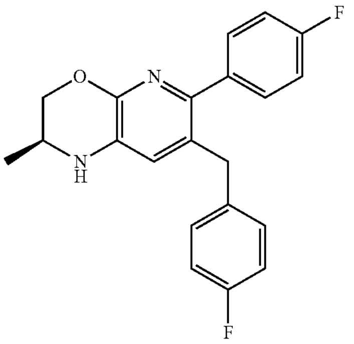 [SMILES: C[C@H]1COc2nc(-c3ccc(F)cc3)c(Cc3ccc(F)cc3)cc2N1]

To a solution of (S)-6-chloro-7-(4-fluorobenzyl)-2-methyl-2,3-dihydro-1H-pyrido[2,3-b][1,4]oxazine (53 mg, 0.18 mmol) and 4-fluorophenylboronic acid (29 mg, 0.19 mmol) in dioxane (1 mL) and $H_2O$ (0.1 mL) were added $K_2CO_3$ (47 mg, 0.32 mmol) and $Pd(PCy_3)_2Cl_2$ (63 mg, 0.081 mmol). The resulting mixture was stirred for 16 h at 100° C. under nitrogen atmosphere. When the reaction was done, the mixture was allowed to cool down to room temperature. The resulting mixture was concentrated under reduced pressure. The residue was purified by flash chromatography eluting with EtOAc in DCM (0% to 20% gradient) to yield the title compound (44 mg, 70% yield). LC-MS $(M+H)^+$=353.0.

Step 3: (S)-2-chloro-1-(7-(4-fluorobenzyl)-6-(4-fluorophenyl)-2-methyl-2,3-dihydro-1H-pyrido[2,3-b][1,4]oxazin-1-yl)ethan-1-one

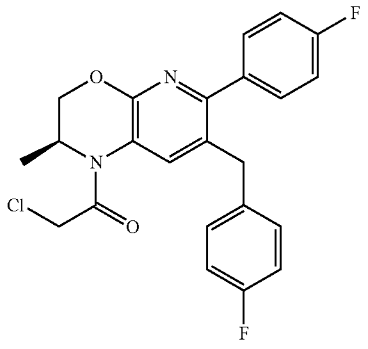 [SMILES: C[C@H]1COc2nc(-c3ccc(F)cc3)c(Cc3ccc(F)cc3)cc2N1C(=O)CCl]

The title compound of step 3 (53 mg, 98% yield) was prepared in a manner similar to that described in Example 1 step 9 from (S)-7-(4-fluorobenzyl)-6-(4-fluorophenyl)-2-methyl-2,3-dihydro-1H-pyrido[2,3-b][1,4]oxazine and 2-chloroacetyl chloride. LC-MS $(M+H)^+$=429.1.

Step 4: tert-butyl (2R,5S)-5-(((3R,5R)-3,5-dimethylmorpholino)methyl)-4-(2-((S)-7-(4-fluorobenzyl)-6-(4-fluorophenyl)-2-methyl-2,3-dihydro-1H-pyrido[2,3-b][1,4]oxazin-1-yl) oxoethyl)-2-methylpiperazine-1-carboxylate

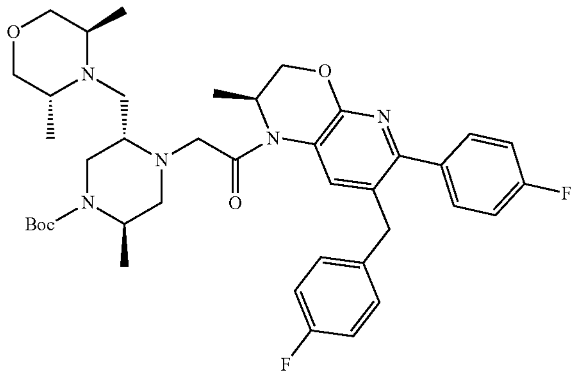 [SMILES: C[C@@H]1CN(CC(=O)N2c3cc(Cc4ccc(F)cc4)c(-c4ccc(F)cc4)nc3OC[C@@H]2C)[C@@H](CN2[C@H](C)COC[C@H]2C)CN1C(=O)OC(C)(C)C]

The title compound of step 4 (72 mg, 84% yield) was prepared in a manner similar to that described in Example 1 step 18 from (S)-2-chloro-1-(7-(4-fluorobenzyl)-6-(4-fluorophenyl)-2-methyl-2,3-dihydro-1H-pyrido[2,3-b][1,4]oxazin-1-yl)ethan-1-one and tert-butyl (2R,5S)-5-(((3R,5R)-3,5-dimethylmorpholino)methyl)-2-methylpiperazine-1-carboxylate. LC-MS $(M+H)^+$=720.4.

Step 5: 242R,5R)-24(3R,5R)-3,5-dimethylmorpholino)methyl)-5-methylpiperazin-1-yl)-1-4S)-7-(4-fluorobenzyl)-6-(4-fluorophenyl)-2-methyl-2,3-dihydro-1H-pyrido[2,3-b][1,4]oxazin-1-yl)ethan-1-one (Compound 113)

Compound 113 (6 mg, 8% yield) was prepared in a manner similar to that described in Example 29 step 7 from tert-butyl (2R,5S)-5-(((3R,5R)-3,5-dimethylmorpholino) methyl)-4-(2-((S)-7-(4-fluorobenzyl)-6-(4-fluorophenyl)-2-methyl-2,3-dihydro-1H-pyrido[2,3-b][1,4]oxazin-1-yl)-2-oxoethyl)-2-methylpiperazine-1-carboxylate. $^1H$ NMR (300 MHz, Chloroform-d) δ 8.46 (brs, 1H), 7.45-7.35 (m, 2H), 7.12-7.03 (m, 2H), 7.02-6.88 (m, 4H), 5.01-4.95 (m, 1H), 4.44-4.27 (m, 3H), 3.94 (s, 2H), 3.66-3.55 (m, 2H), 3.35-3.24 (m, 3H), 3.17-3.07 (m, 1H), 2.92-2.69 (m, 6H), 2.62-2.49 (m, 1H), 2.29-2.09 (m, 2H), 1.37 (d, J=6.7 Hz, 3H), 1.06 (d, J=6.3 Hz, 3H), 0.99-0.91 (m, 6H). LC-MS $(M+H)^+$=620.5.

Example 114: 242R,5R)-2-(((3R,5R)-3,5-dimethylmorpholino)methyl)-5-methylpiperazin-1-yl)-14S)-7-(4-fluorobenzyl)-6-((3-hydroxyazetidin-1-yl) methyl)-2-methyl-2,3-dihydro-1H-pyrido[2,3-b][1,4] oxazin-1-yl)ethan-1-one (Compound 114)

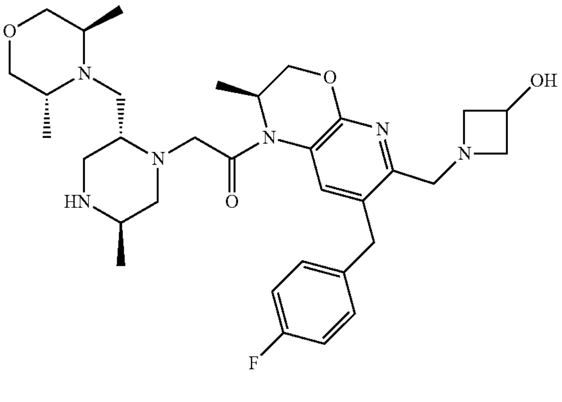 [SMILES: C[C@@H]1CN(CC(=O)N2c3cc(Cc4ccc(F)cc4)c(CN4CC(O)C4)nc3OC[C@@H]2C)[C@@H](CN2[C@H](C)COC[C@H]2C)CN1]

Step 1: tert-butyl (2R,5S)-5-(((3R,5R)-3,5-dimethylmorpholino)methyl)-4-(2-((S)-7-(4-fluorobenzyl)-6-formyl-2-methyl-2,3-dihydro-1H-pyrido[2,3-b][1,4]oxazin-1-yl)-2-oxoethyl)-2-methylpiperazine-1-carboxylate

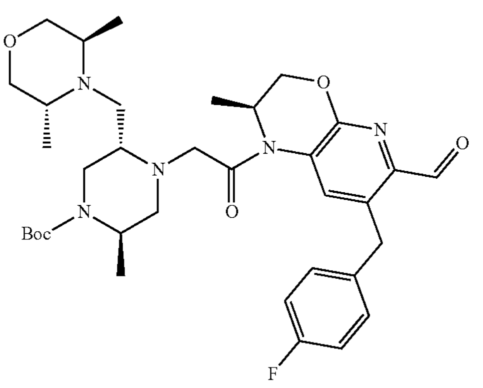 [SMILES: C[C@@H]1CN(CC(=O)N2c3cc(Cc4ccc(F)cc4)c(C=O)nc3OC[C@@H]2C)[C@@H](CN2[C@H](C)COC[C@H]2C)CN1C(=O)OC(C)(C)C]

The title compound of step 1 (100 mg, 88% yield) was prepared in a manner similar to that described in Example 76 step 8 from tert-butyl (2R,5S)-5-(((3R,5R)-3,5-dimethylmorpholino)methyl)-4-(2-4S)-7-(4-fluorobenzyl)-6-(hydroxymethyl)-2-methyl-2,3-dihydro-1H-pyrido[2,3-b][1,4]oxazin-1-yl)-2-oxoethyl)-2-methylpiperazine-1-carboxylate. LC-MS $(M+H)^+=654.2$.

Step 2: tert-butyl (2R,5S)-5-(((3R,5R)-3,5-dimethylmorpholino)methyl)-4-(2-((S)-7-(4-fluorobenzyl)-6-((3-hydroxyazetidin-1-yl)methyl)-2-methyl-2,3-dihydro-1H-pyrido[2,3-b][4]oxazin-1-yl)-2-oxoethyl)-2-methylpiperazine-1-carboxylate

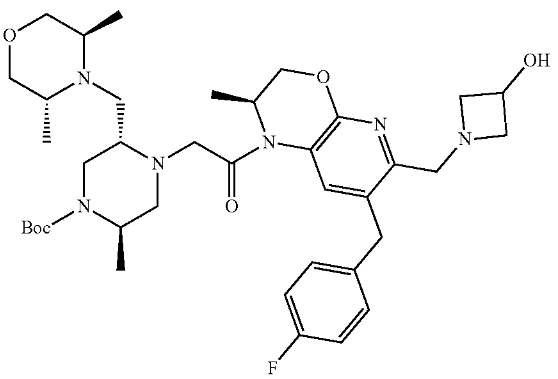 [SMILES: C[C@@H]1CN(CC(=O)N2c3cc(Cc4ccc(F)cc4)c(CN4CC(O)C4)nc3OC[C@@H]2C)[C@@H](CN2[C@H](C)COC[C@H]2C)CN1C(=O)OC(C)(C)C]

The title compound of step 2 (33 mg, 30% yield) was prepared in a manner similar to that described in Example 92 step 1 from tert-butyl (2R,5S)-5-(((3R,5R)-3,5-dimethylmorpholino)methyl)-4-(2-((S)-7-(4-fluorobenzyl)-6-formyl-2-methyl-2,3-dihydro-1H-pyrido[2,3-b][1,4]oxazin-1-yl)-2-oxoethyl)-2-methylpiperazine-1-carboxylate and azetidin-3-ol. LC-MS $(M+H)^+=711.3$.

Step 3: 2-((2R,5R)-24(3R,5R)-3,5-dimethylmorpholino)methyl)-5-methylpiperazin-1-yl)-1-((S)-7-(4-fluorobenzyl)-64(3-hydroxyazetidin-1-yl)methyl)-2-methyl-2,3-dihydro-1H-pyrido[2,3-b][1,4]oxazin-1-yl)ethan-1-one (Compound 114)

Compound 114 (9 mg, 32% yield) was prepared in a manner similar to that described in Example 29 step 7 from tert-butyl (2R,5S)-5-(((3R,5R)-3,5-dimethylmorpholino)methyl)-4-(2-((S)-7-(4-fluorobenzyl)-6-((3-hydroxyazetidin-1-yl)methyl)-2-methyl-2,3-dihydro-1H-pyrido[2,3-b][1,4]oxazin-1-yl)-2-oxoethyl)-2-methylpiperazine-1-carboxylate. $^1H$ NMR (400 MHz, DMSO-d6) δ 8.07 (brs, 1H), 7.22-7.05 (m, 4H), 5.24 (d, J=6.7 Hz, 1H), 4.75-4.70 (m, 1H), 4.35-4.28 (m, 1H), 4.24-4.08 (m, 2H), 3.97 (s, 2H), 3.94-3.86 (m, 1H), 3.59-3.52 (m, 1H), 3.51-3.40 (m, 6H), 3.15-3.06 (m, 2H), 2.97-2.89 (m, 1H), 2.86-2.76 (m, 3H), 2.71-2.62 (m, 2H), 2.62-2.49 (m, 3H), 2.30-2.21 (m, 1H), 2.16-2.06 (m, 1H), 2.00-1.91 (m, 1H), 1.17 (d, J=6.7 Hz, 3H), 0.89-0.80 (m, 9H). LC-MS $(M+H)^+=611.5$.

Example 115: 1-(((S)-6-amino-7-(4-fluorobenzyl)-2-methyl-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 115)

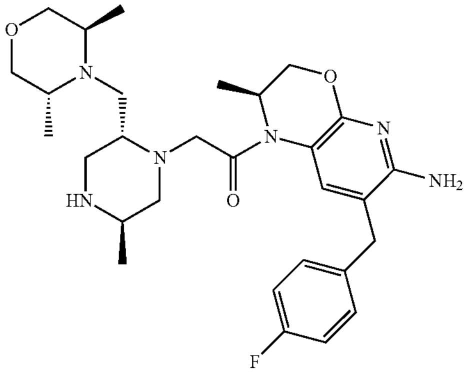 [SMILES: C[C@@H]1CN(CC(=O)N2c3cc(Cc4ccc(F)cc4)c(N)nc3OC[C@@H]2C)[C@@H](CN2[C@H](C)COC[C@H]2C)CN1]

Step 1: tert-butyl (S)-(7-(4-fluorobenzyl)-2-methyl-2,3-dihydro-1H-pyrido[2,3-b][1,4]oxazin-6-yl)carbamate

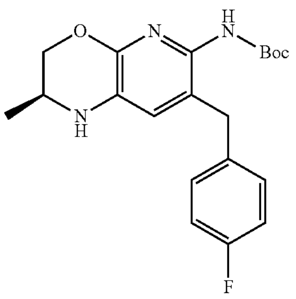 [SMILES: C[C@H]1COc2nc(NC(=O)OC(C)(C)C)c(Cc3ccc(F)cc3)cc2N1]

The title compound of step 1 (146 mg, 75% yield) was prepared in a manner similar to that described in Example 1 step 17 from benzyl (S)-6-((tert-butoxycarbonyl)amino)-7-

(4-fluorobenzyl)-2-methyl-2,3-dihydro-1H-pyrido[2,3-b][1,4]oxazine-1-carboxylate. LC-MS $(M+H)^+$=374.1.

Step 2: tert-butyl (S)-(1-(2-chloroacetyl)-7-(4-fluorobenzyl)-2-methyl-2,3-dihydro-1H-pyrido[2,3-b][1,4]oxazin-6-yl)carbamate

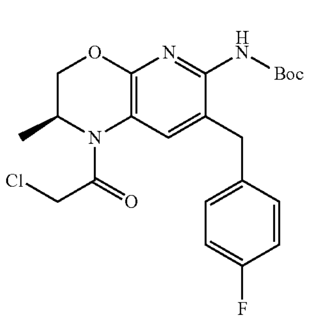 [SMILES: C[C@H]1COc2nc(NC(=O)OC(C)(C)C)c(Cc3ccc(F)cc3)cc2N1C(=O)CCl]

The title compound of step 2 (116 mg, 66% yield) was prepared in a manner similar to that described in Example 1 step 9 from tert-butyl (S)-(7-(4-fluorobenzyl)-2-methyl-2,3-dihydro-1H-pyrido[2,3-b][1,4]oxazin-6-yl)carbamate and 2-chloroacetyl chloride. LC-MS $(M+H)^+$=450.1.

Step 3: tert-butyl (2R,5S)-4-(2-((S)-6-((tert-butoxycarbonyl)amino)-7-(4-fluorobenzyl) methyl-2,3-dihydro-1H-pyrido[2,3-b][1,4]oxazin-1-yl)-2-oxoethyl)-54(3R,5R)-3, 5-dimethylmorpholino)methyl)-2-methylpiperazine-1-carboxylate

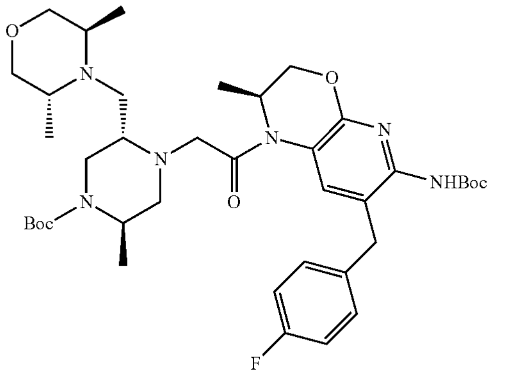 [SMILES: C[C@@H]1CN(CC(=O)N2c3cc(Cc4ccc(F)cc4)c(NC(=O)OC(C)(C)C)nc3OC[C@@H]2C)[C@@H](CN2[C@H](C)COC[C@H]2C)CN1C(=O)OC(C)(C)C]

The title compound of step 3 (116 mg, 66% yield) was prepared in a manner similar to that described in Example 1 step 18 from tert-butyl (S)-(1-(2-chloroacetyl)-7-(4-fluorobenzyl)-2-methyl-2,3-dihydro-1H-pyrido[2,3-b][1,4]oxazin-6-yl)carbamate and tert-butyl (2R,5S)-5-(((3R,5R)-3,5-dimethylmorpholino)methyl)-2-methylpiperazine-1-carboxylate. LC-MS $(M+H)^+$=741.5.

Step 4: 1-((S)-6-amino-7-(4-fluorobenzyl)-2-methyl-2,3-dihydro-1H-pyrido[2,3-b][1,4]oxazin-1-yl)-2-((2R,5R)-2-(((3R,5R)-3,5-dimethylmorpholino)methyl)-5-methylpiperazin-1-yl)ethan-1-one (Compound 115)

Compound 115 (32 mg, 24% yield) was prepared in a manner similar to that described in Example 29 step 7 from tert-butyl (2R,55)-4-(2-((S)-6-((tert-butoxycarbonyl)amino)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^1H$ NMR (400 MHz, DMSO-$d_6$) δ 7.77 (s, 1H), 7.27-7.19 (m, 2H), 7.16-7.06 (m, 2H), 5.68 (s, 2H), 4.65-4.61 (m, 1H), 4.27-4.20 (m, 1H), 4.14-4.06 (m, 1H), 3.86-3.78 (m, 1H), 3.68 (s, 2H), 3.52-3.44 (m, 2H), 3.37-3.28 (m, 1H), 3.19-3.10 (m, 2H), 3.00-2.92 (m, 1H), 2.83-2.75 (m, 1H), 2.71-2.62 (m, 2H), 2.60-2.52 (m, 2H), 2.45-2.38 (m, 1H), 2.30-2.20 (m, 1H), 2.12-1.85 (m, 2H), 1.17 (d, J=6.6 Hz, 3H), 0.90-0.82 (m, 9H). LC-MS $(M+H)^+$=541.5.

Example 116: N—((S)-1-(2-42R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazin-6-yl)acetamide (Compound 116)

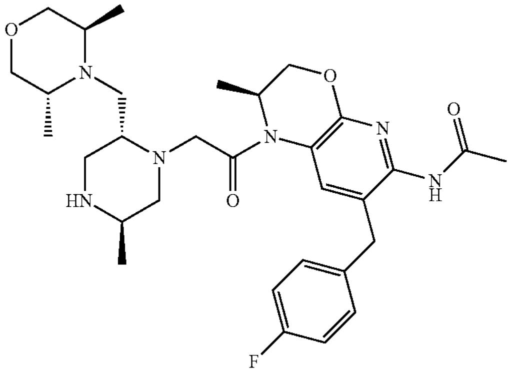 [SMILES: CC(=O)Nc1nc2c(cc1Cc1ccc(F)cc1)N(C(=O)CN1C[C@@H](C)NC[C@@H]1CN1[C@H](C)COC[C@H]1C)[C@@H](C)CO2]

Step 1: benzyl (S)-6-acetamido-7-(4-fluorobenzyl)-2-methyl-2,3-dihydro-1H-pyrido[2,3-b][1,4]oxazine-1-carboxylate

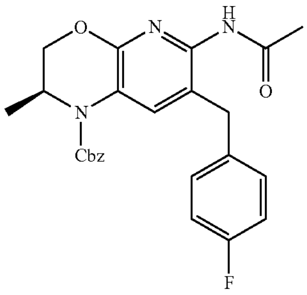 [SMILES: CC(=O)Nc1nc2c(cc1Cc1ccc(F)cc1)N(C(=O)OCc1ccccc1)[C@@H](C)CO2]

The title compound of step 1 (117 mg, 36% yield) was prepared in a manner similar to that described in Example 1 step 9 from benzyl (S)-6-amino-7-(4-fluorobenzyl)-2-methyl-2,3-dihydro-1H-pyrido[2,3-b][1,4]oxazine-1-carboxylate and acetyl chloride. LC-MS $(M+H)^+$=450.1.

Step 2: (S)—N-(7-(4-fluorobenzyl)-2-methyl-2,3-dihydro-1H-pyrido[2,3-b][1,4]oxazin-6-yl)acetamide

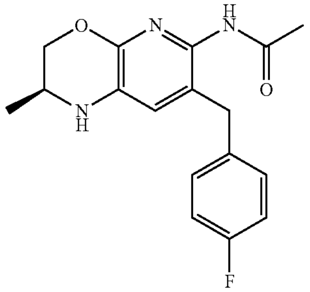 [SMILES: CC(=O)Nc1nc2c(cc1Cc1ccc(F)cc1)N[C@@H](C)CO2]

The title compound of step 2 (69 mg, 84% yield) was prepared in a manner similar to that described in Example 1 step 17 from benzyl (S)-6-acetamido-7-(4-fluorobenzyl)-2-methyl-2,3-dihydro-1H-pyrido[2,3-b][1,4]oxazine-1-carboxylate. LC-MS $(M+H)^+$=316.2.

Step 3: (S)—N-(1-(2-chloroacetyl)-7-(4-fluorobenzyl)-2-methyl-2,3-dihydro-1H-pyrido[2,3-b][1,4]oxazin-6-yl)acetamide

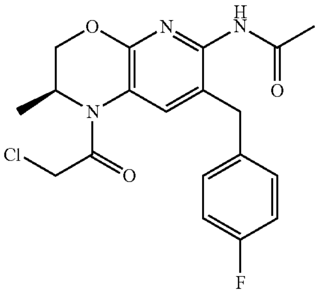 [SMILES: CC(=O)Nc1nc2c(cc1Cc1ccc(F)cc1)N(C(=O)CCl)[C@@H](C)CO2]

The title compound of step 3 (70 mg, 81% yield) was prepared in a manner similar to that described in Example 1 step 9 from (S)—N-(7-(4-fluorobenzyl)-2-methyl-2,3-dihydro-1H-pyrido[2,3-b][1,4]oxazin-6-yl)acetamide and 2-chloroacetyl chloride. LC-MS $(M+H)^+$=392.1.

Step 4: tert-butyl (2R,5S)-4-(2-((S)-6-acetamido-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl) methylpiperazine-1-carboxylate

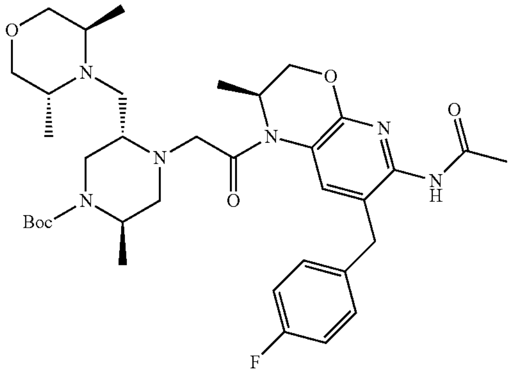 [SMILES: CC(=O)Nc1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (80 mg, 65% yield) was prepared in a manner similar to that described in Example 1 step 18 from (S)—N-(1-(2-chloroacetyl)-7-(4-fluorobenzyl)-2-methyl-2,3-dihydro-1H-pyrido[2,3-b][1,4]oxazin-6-yl)acetamide and tert-butyl (2R,5S)-5-(((3R,5R)-3,5-dimethylmorpholino)methyl)-2-methylpiperazine-1-carboxylate. LC-MS $(M+H)^+$=683.5.

Step 5: N—((S)-1-(2-42R,5R)-24(3R,5R)-3,5-dimethylmorpholino)methyl)-5-methylpiperazin-1-yl) acetyl)-7-(4-fluorobenzyl)-2-methyl-2,3-dihydro-1H-pyrido[2,3-b][1,4]oxazin-6-yl)acetamide (Compound 116)

Compound 116 (14 mg, 20% yield) was prepared in a manner similar to that described in Example 29 step 7 from tert-butyl (2R,5S)-4-(2-((S)-6-acetamido-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino) methyl)-2-methylpiperazine-1-carboxylate. $^1$H NMR (400 MHz, DMSO-d6) δ 9.82 (s, 1H), 8.13 (brs, 1H), 7.19-7.04 (m, 4H), 4.78-4.71 (m, 1H), 4.38-4.30 (m, 1H), 4.25-4.17 (m, 1H), 3.95-3.87 (m, 1H), 3.79 (s, 2H), 3.49-3.40 (m, 3H), 3.15-3.06 (m, 2H), 2.97-2.89 (m, 1H), 2.82-2.72 (m, 1H), 2.72-2.56 (m, 2H), 2.49-2.46 (m, 2H), 2.30-2.20 (m, 1H), 2.15-2.05 (m, 1H), 1.99-1.91 (m, 5H), 1.19 (d, J=6.7 Hz, 3H), 0.89-0.81 (m, 9H). LC-MS $(M+H)^+$=583.3.

Example 117: N—((S)-1-(2-42R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazin-6-yl)propionamide (Compound 117)

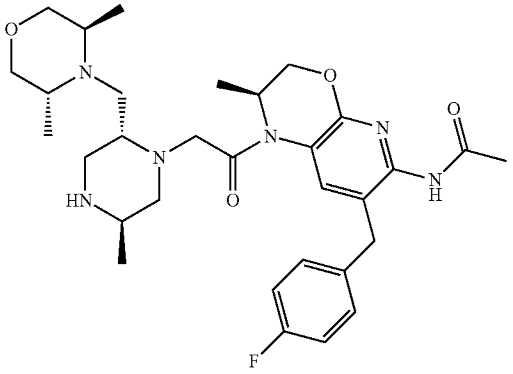 [SMILES: CC(=O)Nc1nc2c(cc1Cc1ccc(F)cc1)N(C(=O)CN1C[C@@H](C)NC[C@@H]1CN1[C@H](C)COC[C@H]1C)[C@@H](C)CO2]

Step 1: benzyl (S)-7-(4-fluorobenzyl)-2-methyl-6-propionamido-2,3-dihydro-1H-pyrido[2,3-b][1,4]oxazine-1carboxylate

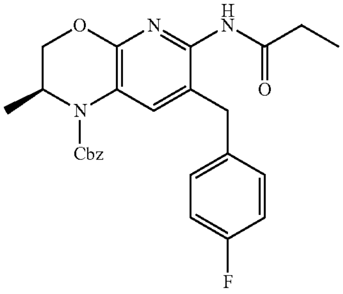 [SMILES: CCC(=O)Nc1nc2c(cc1Cc1ccc(F)cc1)N(C(=O)OCc1ccccc1)[C@@H](C)CO2]

The title compound of step 1 (320 mg, 88% yield) was prepared in a manner similar to that described in Example 1 step 9 from benzyl (S)-6-amino-7-(4-fluorobenzyl)-2-methyl-2,3-dihydro-1H-pyrido[2,3-b][1,4]oxazine-1-carboxylate and propionyl chloride. LC-MS $(M+H)^+$=464.0.

Step 2: (S)—N-(7-(4-fluorobenzyl)-2-methyl-2,3-dihydro-1H-pyrido[2,3-b][1,4]oxazin-6-yl)propionamide

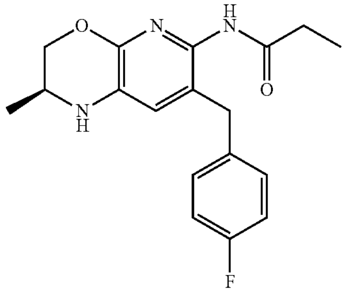 [SMILES: CCC(=O)Nc1nc2c(cc1Cc1ccc(F)cc1)N[C@@H](C)CO2]

The title compound of step 2 (200 mg, 87% yield) was prepared in a manner similar to that described in Example 1 step 17 from benzyl (S)-7-(4-fluorobenzyl)-2-methyl-6-propionamido-2,3-dihydro-1H-pyrido[2,3-b][1,4]oxazine-1-carboxylate. LC-MS $(M+H)^+$=329.9.

Step 3: (S)—N-(1-(2-chloroacetyl)-7-(4-fluorobenzyl)-2-methyl-2,3-dihydro-1H-pyrido[2,3-b][1,4]oxazin-6-yl)propionamide

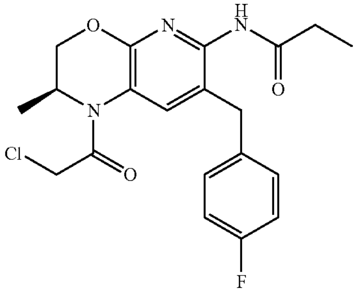 [SMILES: CCC(=O)Nc1nc2c(cc1Cc1ccc(F)cc1)N(C(=O)CCl)[C@@H](C)CO2]

The title compound of step 3 (200 mg, 81% yield) was prepared in a manner similar to that described in Example 1 step 9 from (S)—N-(7-(4-fluorobenzyl)-2-methyl-2,3-dihydro-1H-pyrido[2,3-b][1,4]oxazin-6-yl)propionamide and 2-chloroacetyl chloride. LC-MS $(M+H)^+$=405.9.

Step 4: tert-butyl (2R,5S)-5-(((3R,5R)-3,5-dimethylmorpholino)methyl)-4-(2-((S)-7-(4-fluorobenzyl)-2-methyl-6-propionamido-2,3-dihydro-1H-pyrido[2,3-b][1,4]oxazin-1-yl) oxoethyl)-2-methylpiperazine-1-carboxylate

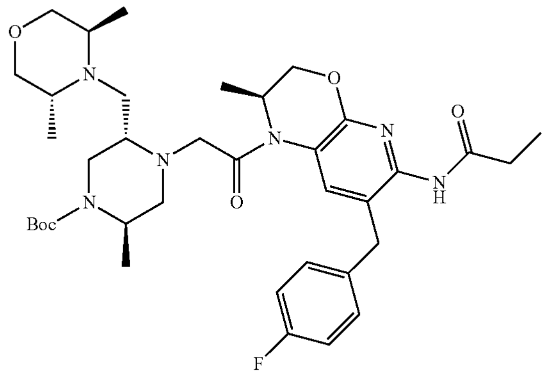 [SMILES: CCC(=O)Nc1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (247 mg, 72% yield) was prepared in a manner similar to that described in Example 1 step 18 from (S)—N-(1-(2-chloroacetyl)-7-(4-fluorobenzyl)-2-methyl-2,3-dihydro-1H-pyrido[2,3-b][1,4]oxazin-6-yl)propionamide and tert-butyl (2R,5S)-5-(((3R,5R)-3,5-dimethylmorpholino)methyl)-2-methylpiperazine-1-carboxylate. LC-MS $(M+H)^+$=697.3

Step 5: N—((S)-1-(2-((2R,5R)-24(3R,5R)-3,5-dimethylmorpholino)methyl)-5-methylpiperazin-1-yl) acetyl)-7-(4-fluorobenzyl)-2-methyl-2,3-dihydro-1H-pyrido[2,3-b][1,4]oxazin-6-yl)propionamide (Compound 117)

Compound 117 (26 mg, 18% yield) was prepared in a manner similar to that described in Example 29 step 7 from tert-butyl (2R,5S)-54(3R,5R)-3,5-dimethylmorpholino) methyl)-4-(2-4S)-7-(4-fluorobenzyl)-2-methyl-6-propionamido-2,3-dihydro-1H-pyrido[2,3-b][1,4]oxazin-1-yl)-2-oxoethyl)-2-methylpiperazine-1-carboxylate. $^1$H NMR (400 MHz, DMSO-d6) δ 9.76 (s, 1H), 8.14 (brs, 1H), 7.18-7.04 (m, 4H), 4.78-4.71 (m, 1H), 4.38-4.30 (m, 1H), 4.25-4.17 (m, 1H), 3.95-3.87 (m, 1H), 3.78 (s, 2H), 3.49-3.41 (m, 3H), 3.15-3.06 (m, 2H), 2.98-2.90 (m, 1H), 2.82-2.73 (m, 1H), 2.73-2.62 (m, 2H), 2.62-2.52 (m, 2H), 2.31-2.21 (m, 3H), 2.16-2.07 (m, 1H), 2.07-2.03 (m, 1H), 2.00-1.91 (m, 1H), 1.19 (d, J=6.6 Hz, 3H), 1.03 (t, J=7.5 Hz, 3H), 0.90-0.81 (m, 9H). LC-MS $(M+H)^+$=597.5.

Example 118: N—((S)-1-(2-((2R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazin-6-yl)isobutyramide (Compound 118)

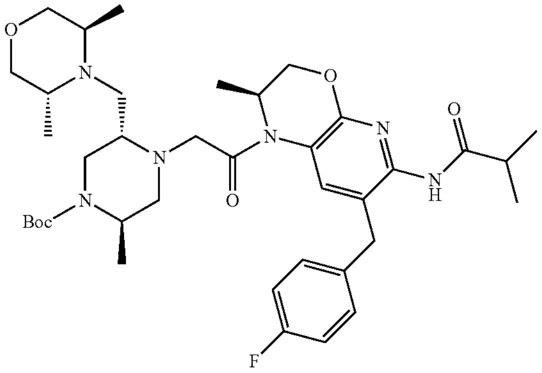 [SMILES: CC(C)C(=O)Nc1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

Step 1: benzyl (S)-7-(4-fluorobenzyl)-6-isobutyramido-2-methyl-2,3-dihydro-1H-pyrido[2,3-b][1,4]oxazine-1-carboxylate

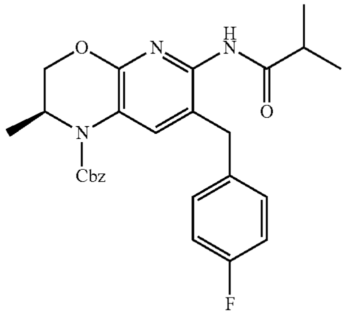 [SMILES: CC(C)C(=O)Nc1nc2c(cc1Cc1ccc(F)cc1)N(C(=O)OCc1ccccc1)[C@@H](C)CO2]

The title compound of step 1 (242 mg, 65% yield) was prepared in a manner similar to that described in Example 1 step 9 from benzyl (S)-6-amino-7-(4-fluorobenzyl)-2-methyl-2,3-dihydro-1H-pyrido[2,3-b][1,4]oxazine-1-carboxylate and isobutyryl chloride. LC-MS $(M+H)^+=478.0$.

Step 2: (S)—N-(7-(4-fluorobenzyl)-2-methyl-2,3-dihydro-1H-pyrido[2,3-b][1,4]oxazin-6-yl)isobutyramide

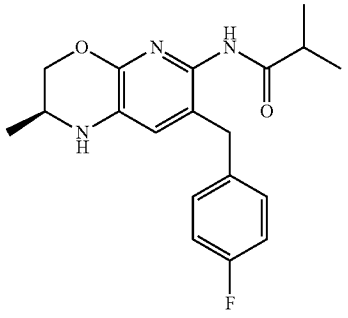 [SMILES: CC(C)C(=O)Nc1nc2c(cc1Cc1ccc(F)cc1)N[C@@H](C)CO2]

The title compound of step 2 (143 mg, 87% yield) was prepared in a manner similar to that described in Example 1 step 17 from benzyl (S)-7-(4-fluorobenzyl)-6-isobutyramido-2-methyl-2,3-dihydro-1H-pyrido[2,3-b][1,4]oxazine-1-carboxylate. LC-MS $(M+H)^+=344.1$.

Step 3: (S)—N-(1-(2-chloroacetyl)-7-(4-fluorobenzyl)-2-methyl-2,3-dihydro-1H-pyrido[2,3-b][1,4]oxazin-6-yl)isobutyramide

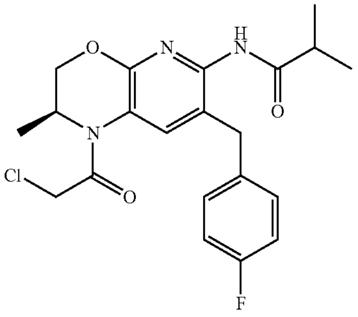 [SMILES: CC(C)C(=O)Nc1nc2c(cc1Cc1ccc(F)cc1)N(C(=O)CCl)[C@@H](C)CO2]

The title compound of step 3 (150 mg, 85% yield) was prepared in a manner similar to that described in Example 1 step 9 from (S)—N-(7-(4-fluorobenzyl)-2-methyl-2,3-dihydro-1H-pyrido[2,3-b][1,4]oxazin-6-yl)isobutyramide and 2-chloroacetyl chloride. LC-MS $(M+H)^+=420.0$.

Step 4: tert-butyl (2R,5S)-5-(((3R,5R)-3,5-dimethylmorpholino)methyl)-4-(2-((S)-7-(4-fluorobenzyl)-6-isobutyramido-2-methyl-2,3-dihydro-1H-pyrido[2,3-b][1,4]oxazin-1-yl) oxoethyl)-2-methylpiperazine-1-carboxylate

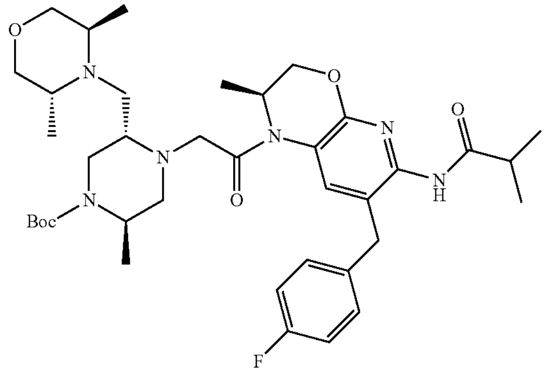 [SMILES: CC(C)C(=O)Nc1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (150 mg, 85% yield) was prepared in a manner similar to that described in Example 1 step 18 from (S)—N-(1-(2-chloroacetyl)-7-(4-fluorobenzyl)-2-methyl-2,3-dihydro-1H-pyrido[2,3-b][1,4]oxazin-6-yl)isobutyramide and tert-butyl (2R,5S)-5-(((3R,5R)-3,5-dimethylmorpholino)methyl)-2-methylpiperazine-1-carboxylate. LC-MS $(M+H)^+=711.3$.

Step 5: N—((S)-1-(2-((2R,5R)-24(3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazin-6-yl)isobutyramide (Compound 118)

Compound 118 (31 mg, 24% yield) was prepared in a manner similar to that described in Example 29 step 7 from tert-butyl (2R,5S)-5-(((3R,5R)-3,5-dimethylmorpholino)methyl)-4-(2-4S)-7-(4-fluorobenzyl)-6-isobutyramido-2-methyl-2,3-dihydro-1H-pyrido[2,3-b][1,4]oxazin-1-yl)-2-oxoethyl)-2-methylpiperazine-1-carboxylate. $^{1}$H NMR (400 MHz, DMSO-d6) δ 9.76 (s, 1H), 8.13 (s, 1H), 7.18-7.10 (m, 2H), 7.14-7.05 (m, 2H), 4.77-4.69 (m, 1H), 4.38-4.29 (m, 1H), 4.25-4.17 (m, 1H), 3.94-3.86 (m, 1H), 3.77 (s, 2H), 3.49-3.41 (m, 3H), 3.14-3.06 (m, 2H), 2.97-2.89 (m, 1H), 2.81-2.72 (m, 1H), 2.72-2.62 (m, 2H), 2.62-2.53 (m, 3H), 2.31-2.21 (m, 1H), 2.16-2.06 (m, 1H), 2.04-2.00 (m, 1H), 2.00-1.91 (m, 1H), 1.19 (d, J=6.7 Hz, 3H), 1.05 (d, J=6.9 Hz, 6H), 0.89-0.80 (m, 9H). LC-MS $(M+H)^+$=611.5.

Example 119: N—((S)-1-(2-((2R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazin-6-yl)cyclopropanecarboxamide (Compound 119)

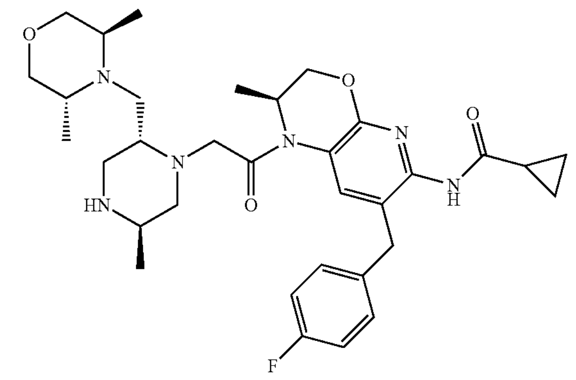 [SMILES: C[C@@H]1CN(CC(=O)N2c3cc(Cc4ccc(F)cc4)c(NC(=O)C4CC4)nc3OC[C@@H]2C)[C@@H](CN2[C@H](C)COC[C@H]2C)CN1]

Step 1: benzyl (S)-6-(cyclopropanecarboxamido)-7-(4-fluorobenzyl)-2-methyl-2,3-dihydro-1H-pyrido[2,3-b][1,4]oxazine-1carboxylate

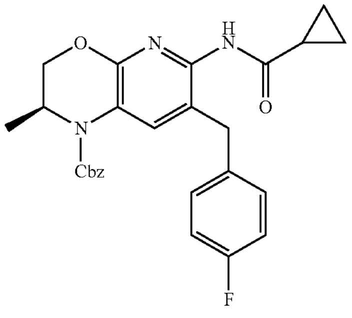 [SMILES: C[C@H]1COc2nc(NC(=O)C3CC3)c(Cc3ccc(F)cc3)cc2N1C(=O)OCc1ccccc1]

The title compound of step 1 (220 mg, 69% yield) was prepared in a manner similar to that described in Example 1 step 9 from benzyl (S)-6-amino-7-(4-fluorobenzyl)-2-methyl-2,3-dihydro-1H-pyrido[2,3-b][1,4]oxazine-1-carboxylate and cyclopropanecarbonyl chloride. LC-MS $(M+H)^+$=476.2.

Step 2: (S)—N-(7-(4-fluorobenzyl)-2-methyl-2,3-dihydro-1H-pyrido[2,3-b][1,4]oxazin-6-yl)cyclopropanecarboxamide

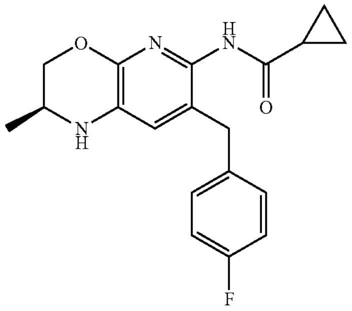 [SMILES: C[C@H]1COc2nc(NC(=O)C3CC3)c(Cc3ccc(F)cc3)cc2N1]

The title compound of step 2 (109 mg, 69% yield) was prepared in a manner similar to that described in Example 1 step 17 from benzyl (S)-6-(cyclopropanecarboxamido)-7-(4-fluorobenzyl)-2-methyl-2,3-dihydro-1H-pyrido[2,3-b][1,4]oxazine-1-carboxylate. LC-MS $(M+H)^+$=342.2.

Step 3: (S)—N-(1-(2-chloroacetyl)-7-(4-fluorobenzyl)-2-methyl-2,3-dihydro-1H-pyrido[2,3-b][1,4]oxazin-6-yl)cyclopropanecarboxamide

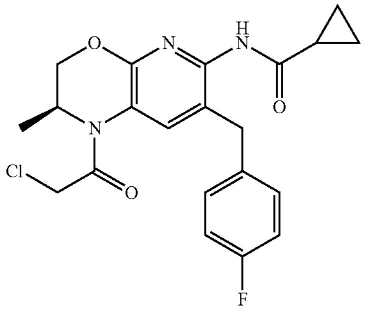 [SMILES: C[C@H]1COc2nc(NC(=O)C3CC3)c(Cc3ccc(F)cc3)cc2N1C(=O)CCl]

The title compound of step 3 (133 mg, 99% yield) was prepared in a manner similar to that described in Example 1 step 9 from (S)—N-(7-(4-fluorobenzyl)-2-methyl-2,3-dihydro-1H-pyrido[2,3-b][1,4]oxazin-6-yl)cyclopropanecarboxamide and 2-chloroacetyl chloride. LC-MS $(M+H)^+$=418.2.

Step 4: tert-butyl (2R,5S)-4-(2-((S)-6-(cyclopropanecarboxamido)-7-(4-fluorobenzyl) methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

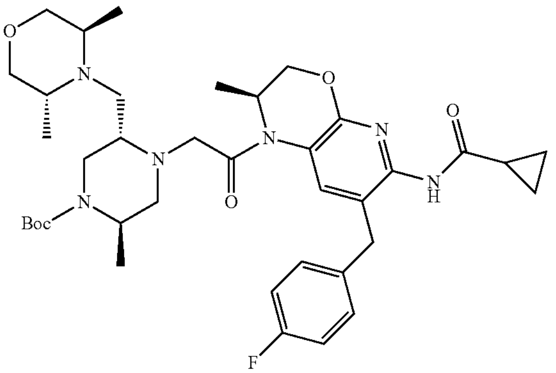 [SMILES: C[C@@H]1CN(CC(=O)N2c3cc(Cc4ccc(F)cc4)c(NC(=O)C4CC4)nc3OC[C@@H]2C)[C@@H](CN2[C@H](C)COC[C@H]2C)CN1C(=O)OC(C)(C)C]

The title compound of step 4 (178 mg, 79% yield) was prepared in a manner similar to that described in Example 1 step 18 from (S)—N-(1-(2-chloroacetyl)-7-(4-fluorobenzyl)-2-methyl-2,3-dihydro-1H-pyrido[2,3-b][1,4]oxazin-6-yl)cyclopropanecarboxamide and tert-butyl (2R,5S)-54(3R,5R)-3,5-dimethylmorpholino)methyl)-2-methylpiperazine-1-carboxylate. LC-MS $(M+H)^+$=709.3.

Step 5: N—((S)-1-(2-((2R,5R)-24(3R,5R)-3,5-dimethylmorpholino)methyl)-5-methylpiperazin-1-yl) acetyl)-7-(4-fluorobenzyl)-2-methyl-2,3-dihydro-1H-pyrido[2,3-b][1,4]oxazin-6-yl) cyclopropanecarboxamide (Compound 119)

Compound 119 (48 mg, 31% yield) was prepared in a manner similar to that described in Example 29 step 7 from tert-butyl (2R,5S)-4-(2-((S)-6-(cyclopropanecarboxamido)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^1$H NMR (400 MHz, DMSO-d6) δ 10.09 (s, 1H), 8.13 (brs, 1H), 7.19-7.05 (m, 4H), 4.77-4.71 (m, 1H), 4.38-4.31 (m, 1H), 4.25-4.18 (m, 1H), 3.95-3.86 (m, 1H), 3.77 (s, 2H), 3.50-3.41 (m, 3H), 3.15-3.06 (m, 2H), 2.98-2.90 (m, 1H), 2.82-2.73 (m, 1H), 2.72-2.63 (m, 2H), 2.62-2.52 (m, 3H), 2.31-2.21 (m, 1H), 2.17-2.07 (m, 1H), 2.00-1.91 (m, 1H), 1.83-1.72 (m, 1H), 1.19 (d, J=6.6 Hz, 3H), 0.90-0.81 (m, 9H), 0.77 (d, J=6.2 Hz, 4H). LC-MS $(M+H)^+$=609.5.

Example 120: (S)—N-(tert-butyl)-1-(242R,5R)-24(3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 120)

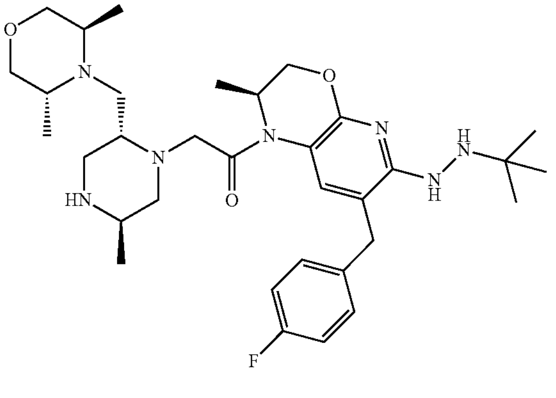 [SMILES: C[C@@H]1CN(CC(=O)N2c3cc(Cc4ccc(F)cc4)c(NNC(C)(C)C)nc3OC[C@@H]2C)[C@@H](CN2[C@H](C)COC[C@H]2C)CN1]

Step 1: tert-butyl (S)-64tert-butylcarbamoyl)-7-(4-fluorobenzyl)-2-methyl-2,3-dihydro-1H-pyrido[2,3-b][1,4]oxazine-1-carboxylate

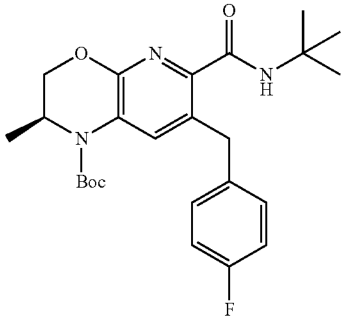 [SMILES: C[C@H]1COc2nc(C(=O)NC(C)(C)C)c(Cc3ccc(F)cc3)cc2N1C(=O)OC(C)(C)C]

The title compound of step 1 (270 mg, crude) was prepared in a manner similar to that described in Example 31 step 3 from (S)-1-(tert-butoxycarbonyl)-7-(4-fluorobenzyl)-2-methyl-2,3-dihydro-1H-pyrido[2,3-b][1,4]oxazine-6-carboxylic acid and tert-butyl amine. LC-MS $(M+H)^+$=458.5.

Step 2: (S)—N-(tert-butyl)-7-(4-fluorobenzyl)-2-methyl-2,3-dihydro-1H-pyrido[2,3-b][1,4]oxazine-6-carboxamide

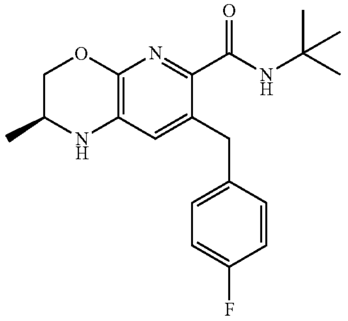 [SMILES: C[C@H]1COc2nc(C(=O)NC(C)(C)C)c(Cc3ccc(F)cc3)cc2N1]

The title compound of step 2 (210 mg, 98% yield for 2 steps) was prepared in a manner similar to that described in Example 1 step 8 from tert-butyl (S)-6-(tert-butylcarbamoyl)-7-(4-fluorobenzyl)-2-methyl-2,3-dihydro-1H-pyrido[2,3-b][1,4]oxazine-1-carboxylate. LC-MS $(M+H)^+$=358.2.

Step 3: (S)—N-(tert-butyl)-1-(2-chloroacetyl)-7-(4-fluorobenzyl)-2-methyl-2,3-dihydro-1H-pyrido[2,3-b][1,4]oxazine-6-carboxamide

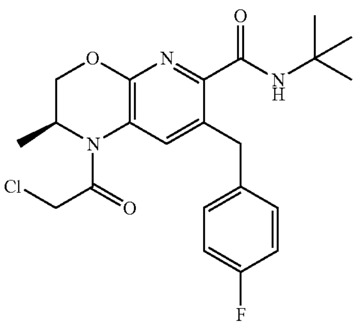 [SMILES: C[C@H]1COc2nc(C(=O)NC(C)(C)C)c(Cc3ccc(F)cc3)cc2N1C(=O)CCl]

The title compound of step 3 (220 mg, 87% yield) was prepared in a manner similar to that described in Example 1 step 9 from (S)—N-(tert-butyl)-7-(4-fluorobenzyl)-2-methyl-2,3-dihydro-1H-pyrido[2,3-b][1,4]oxazine-6-carboxamide and 2-chloroacetyl chloride. LC-MS $(M+H)^+$ =434.3.

Step 4: tert-butyl (2R,5S)-4-(2-((S)-6-(tert-butylcarbamoyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate

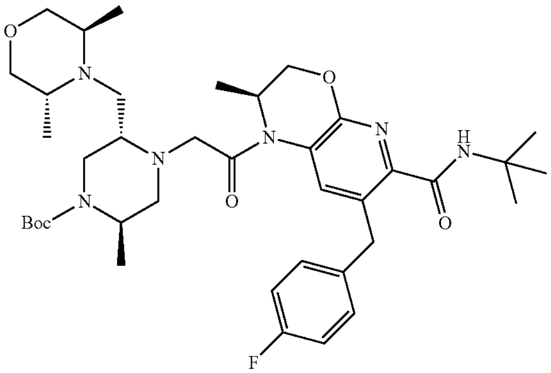 [SMILES: C[C@@H]1CN(CC(=O)N2c3cc(Cc4ccc(F)cc4)c(C(=O)NC(C)(C)C)nc3OC[C@@H]2C)[C@@H](CN2[C@H](C)COC[C@H]2C)CN1C(=O)OC(C)(C)C]

The title compound of step 4 (350 mg, 95% yield) was prepared in a manner similar to that described in Example 1 step 18 from (S)—N-(tert-butyl)-1-(2-chloroacetyl)-7-(4-fluorobenzyl)-2-methyl-2,3-dihydro-1H-pyrido[2,3-b][1,4]oxazine-6-carboxamide and tert-butyl (2R,5S)-5-(((3R,5R)-3,5-dimethylmorpholino)methyl)-2-methylpiperazine-1-carboxylate. LC-MS $(M+H)^+$=725.6.

Step 5: (S)—N-(tert-butyl)-1-(2-42R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-carboxamide (Compound 120)

Compound 120 (130 mg, 42% yield) was prepared in a manner similar to that described in Example 29 step 7 from tert-butyl (2R,5S)-4-(2-((S)-6-(tert-butylcarbamoyl)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. $^1H$ NMR (400 MHz, DMSO-d6) δ 8.25 (s, 1H), 7.78 (s, 1H), 7.22-7.10 (m, 2H), 7.07-6.96 (m, 2H), 4.67 (d, J=6.5 Hz, 1H), 4.34-4.27 (m, 1H), 4.26-4.13 (m, 3H), 3.95-3.80 (m, 1H), 3.52-3.41 (m, 1H), 3.40-3.31 (m, 2H), 3.27-3.21 (m, 1H), 3.06-2.95 (m, 2H), 2.89-2.81 (m, 1H), 2.75-2.66 (m, 1H), 2.65-2.46 (m, 5H), 2.24-2.06 (m, 2H), 1.95-1.82 (m, 1H), 1.29 (s, 9H), 1.14 (d, J=6.7 Hz, 3H), 0.80 (d, J=6.2 Hz, 3H), 0.77 (d, J=6.3 Hz, 6H). LC-MS $(M+H)^+$=625.8.

Example 121: N—((S)-1-(24(2R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazin-6-yl)-3-methoxypropanamide (Compound 121)

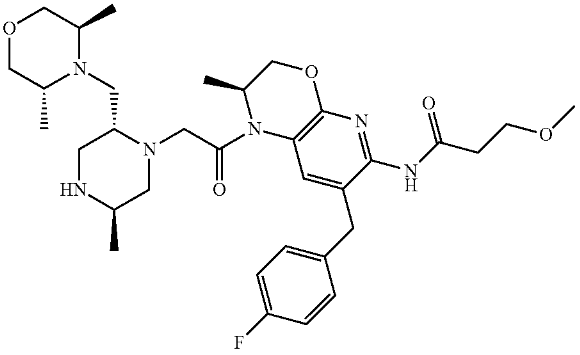 [SMILES: COCCC(=O)Nc1nc2c(cc1Cc1ccc(F)cc1)N(C(=O)CN1C[C@@H](C)NC[C@@H]1CN1[C@H](C)COC[C@H]1C)[C@@H](C)CO2]

Step 1: benzyl (S)-7-(4-fluorobenzyl)-6-(3-methoxypropanamido)-2-methyl-2,3-dihydro-1H-pyrido[2,3-b][1,4]oxazine-1-carboxylate

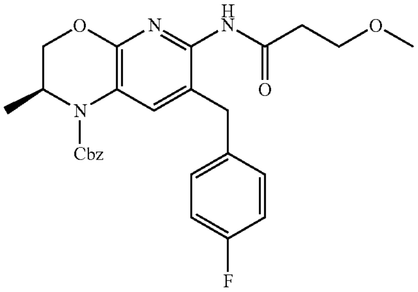

The title compound of step 1 (123 mg, 37% yield) was prepared in a manner similar to that described in Example 1 step 9 from benzyl (S)-6-amino-7-(4-fluorobenzyl)-2-methyl-2,3-dihydro-1H-pyrido[2,3-b][1,4]oxazine-1-carboxylate and 3-methoxypropanoyl chloride. LC-MS $(M+H)^+$=494.2.

Step 2: (S)—N-(7-(4-fluorobenzyl)-2-methyl-2,3-dihydro-1H-pyrido[2,3-b][1,4]oxazin-6-yl)-3-methoxypropanamide

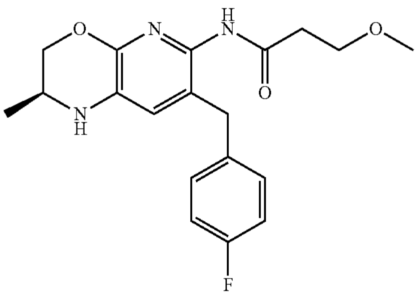

The title compound of step 2 (86 mg, 96% yield) was prepared in a manner similar to that described in Example 1 step 17 from benzyl (S)-7-(4-fluorobenzyl)-6-(3-methoxypropanamido)-2-methyl-2,3-dihydro-1H-pyrido[2,3-b][1,4]oxazine-1-carboxylate. LC-MS $(M+H)^+$=360.2.

Step 3: (S)—N-(1-(2-chloroacetyl)-7-(4-fluorobenzyl)-2-methyl-2,3-dihydro-1H-pyrido[2,3-b][1,4]oxazin-6-yl)-3-methoxypropanamide

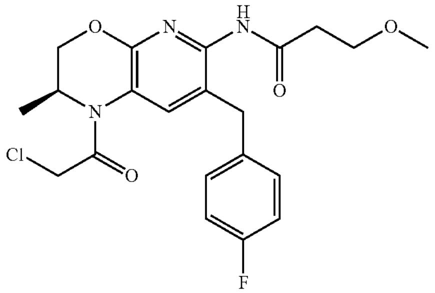

The title compound of step 3 (79 mg, 75% yield) was prepared in a manner similar to that described in Example 1 step 9 from (S)—N-(7-(4-fluorobenzyl)-2-methyl-2,3-dihydro-1H-pyrido[2,3-b][1,4]oxazin-6-yl)-3-methoxypropanamide and 2-chloroacetyl chloride. LC-MS $(M+H)^+$=436.2.

Step 4: tert-butyl (2R,5S)-5-(((3R,5R)-3,5-dimethylmorpholino)methyl)-4-(2-((S)-7-(4-fluorobenzyl)-6-(3-methoxypropanamido)-2-methyl-2,3-dihydro-1H-pyrido[2,3-b][1,4]oxazin-1-yl)-2-oxoethyl)-2-methylpiperazine-1-carboxylate

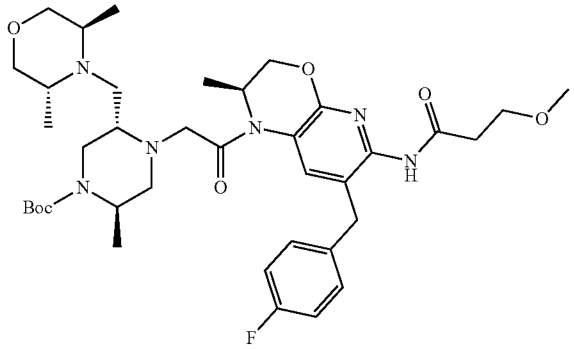 [SMILES: COCCC(=O)Nc1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (91 mg, 69% yield) was prepared in a manner similar to that described in Example 1 step 18 from (S)—N-(1-(2-chloroacetyl)-7-(4-fluorobenzyl)-2-methyl-2,3-dihydro-1H-pyrido[2,3-b][1,4]oxazin-6-yl)-3-methoxypropanamide and tert-butyl (2R,5S)-5-(((3R,5R)-3,5-dimethylmorpholino)methyl)-2-methylpiperazine-1-carboxylate. LC-MS $(M+H)^+$=727.4.

Step 5: N—((S)-1-(2-((2R,5R)-24(3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazin-6-yl)-3-methoxypropanamide (Compound 121)

Compound 121 (20 mg, 25% yield) was prepared in a manner similar to that described in Example 29 step 7 from tert-butyl (2R,5S)-5-(((3R,5R)-3,5-dimethylmorpholino)methyl)-4-(2-4S)-7-(4-fluorobenzyl)-6-(3-methoxypropanamido)-2-methyl-2,3-dihydro-1H-pyrido[2,3-b][1,4]oxazin-1-yl)-2-oxoethyl)-2-methylpiperazine-1-carboxylate. $^1H$ NMR (400 MHz, DMSO-d6) δ 9.90 (s, 1H), 8.15 (s, 1H), 7.22-7.12 (m, 2H), 7.15-7.05 (m, 2H), 4.77-4.71 (m, 1H), 4.38-4.31 (m, 1H), 4.25-4.17 (m, 1H), 3.95-3.87 (m, 1H), 3.78 (s, 2H), 3.59 (t, J=6.2 Hz, 2H), 3.53-3.41 (m, 3H), 3.33-3.24 (m, 2H), 3.22 (s, 3H), 3.14-3.05 (m, 2H), 2.98-2.89 (m, 1H), 2.82-2.73 (m, 1H), 2.71-2.63 (m, 2H), 2.62-2.52 (m, 3H), 2.31-2.21 (m, 1H), 2.17-2.07 (m, 1H), 2.00-1.91 (m, 1H), 1.19 (d, J=6.6 Hz, 3H), 0.90-0.81 (m, 9H). LC-MS $(M+H)^+$=627.4.

Example 122: N—((S)-1-(24(2R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazine-6-yl)ethanesulfonamide (Compound 122)

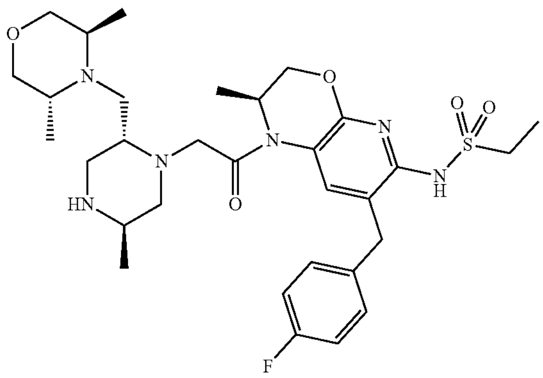 [SMILES: CCS(=O)(=O)Nc1nc2c(cc1Cc1ccc(F)cc1)N(C(=O)CN1C[C@@H](C)NC[C@@H]1CN1[C@H](C)COC[C@H]1C)[C@@H](C)CO2]

Step 1: benzyl (S)-6-(ethylsulfonamido)-7-(4-fluorobenzyl)-2-methyl-2,3-dihydro-1H-pyrido[2,3-b][1,4]oxazine-1-carboxylate

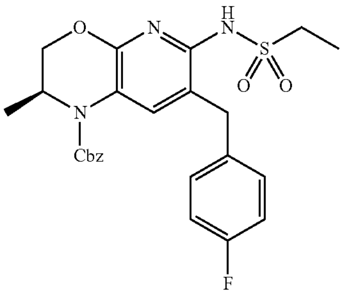 [SMILES: CCS(=O)(=O)Nc1nc2c(cc1Cc1ccc(F)cc1)N(C(=O)OCc1ccccc1)[C@@H](C)CO2]

At 0° C., to a solution of benzyl (S)-6-amino-7-(4-fluorobenzyl)-2-methyl-2,3-dihydro-1H-pyrido[2,3-b][1,4]oxazine-1-carboxylate (480 mg, 1.18 mmol) in THF (12 mL) was added LiHMDS in THF (4.6 mL, 4.6 mmol, 1M) under nitrogen atmosphere. The resulting mixture was stirred for 15 min at 0° C. under nitrogen atmosphere. To the above mixture was added ethanesulfonyl chloride (256 mg, 2.0 mmol) dropwised at 0° C. The resulting mixture was stirred for 2 h at 30° C. under nitrogen atmosphere. When the reaction was done, the reaction was then quenched by the addition of water. The resulting mixture was extracted with EtOAc (30 mL×3). The organic phases were combined, washed with brine and dried over $Na_2SO_4$. The reaction mixture was concentrated under reduced pressure. The residue was purified by flash chromatography eluting with EtOAc in PE (0% to 40% gradient) to yield the title compound (164 mg, 28% yield). LC-MS $(M+H)^+$=500.2.

Step 2: (S)—N-(7-(4-fluorobenzyl)-2-methyl-2,3-dihydro-1H-pyrido[2,3-b][1,4]oxazin-6-yl)ethanesulfonamide

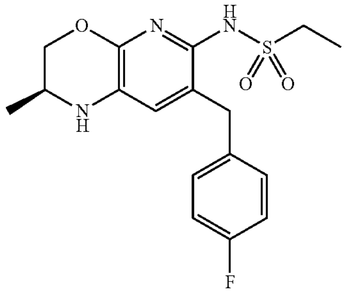 [SMILES: CCS(=O)(=O)Nc1nc2c(cc1Cc1ccc(F)cc1)N[C@@H](C)CO2]

The title compound of step 2 (89 mg, 84% yield) was prepared in a manner similar to that described in Example 1 step 17 from benzyl (S)-6-(ethylsulfonamido)-7-(4-fluorobenzyl)-2-methyl-2,3-dihydro-1H-pyrido[2,3-b][1,4]oxazine-1-carboxylate. LC-MS $(M+H)^+$=366.2. Step 3: (S)—N-(1-(2-chloroacetyl)-7-(4-fluorobenzyl)-2-methyl-2,3-dihydro-1H-pyrido[2,3-b][1,4]oxazin-6-yl)ethanesulfonamide

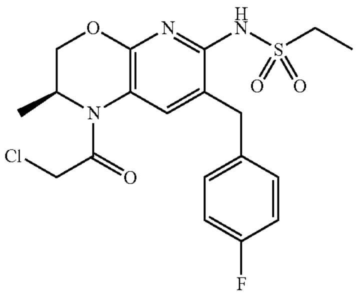 [SMILES: CCS(=O)(=O)Nc1nc2c(cc1Cc1ccc(F)cc1)N(C(=O)CCl)[C@@H](C)CO2]

The title compound of step 3 (40 mg, 36% yield) was prepared in a manner similar to that described in Example 1 step 9 from (S)—N-(7-(4-fluorobenzyl)-2-methyl-2,3-dihydro-1H-pyrido[2,3-b][1,4]oxazin-6-yl)ethanesulfonamide and 2-chloroacetyl chloride. LC-MS $(M+H)^+$=442.1.

Step 4: tert-butyl (2R,5S)-5-(((3R,5R)-3,5-dimethylmorpholino)methyl)-4-(2-((S)-6-(ethylsulfonamido)-7-(4-fluorobenzyl)-2-methyl-2,3-dihydro-1H-pyrido[2,3-b][1,4]oxazin-1-yl)-2-oxoethyl)-2-methylpiperazine-1-carboxylate

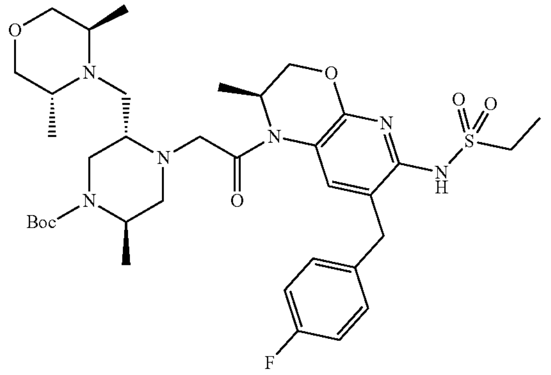 [SMILES: CCS(=O)(=O)Nc1nc2c(cc1Cc1ccc(F)cc1)N(C(=O)CN1C[C@@H](C)N(C(=O)OC(C)(C)C)C[C@@H]1CN1[C@H](C)COC[C@H]1C)[C@@H](C)CO2]

The title compound of step 4 (39 mg, 59% yield) was prepared in a manner similar to that described in Example 1 step 18 from (S)—N-(1-(2-chloroacetyl)-7-(4-fluorobenzyl)-2-methyl-2,3-dihydro-1H-pyrido[2,3-b][1,4]oxazin-6-yl)ethanesulfonamide and tert-butyl (2R,5S)-5-(((3R,5R)-3,5-dimethylmorpholino)methyl)-2-methylpiperazine-1-carboxylate. LC-MS $(M+H)^+$=733.3.

Step 5: N—((S)-1-(2-((2R,5R)-24(3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazin-6-yl)ethanesulfonamide (Compound 122)

Compound 122 (5 mg, 15% yield) was prepared in a manner similar to that described in Example 29 step 7 from tert-butyl (2R,5S)-5-(((3R,5R)-3,5-dimethylmorpholino)methyl)-4-(2-((S)-6-(ethylsulfonamido)-7-(4-fluorobenzyl)-2-methyl-2,3-dihydro-1H-pyrido[2,3-b][1,4]oxazin-1-yl)-2-oxoethyl)-2-methylpiperazine-1-carboxylate. $^1H$ NMR (400 MHz, DMSO-d6) δ 7.99 (brs, 1H), 7.27-7.19 (m, 2H), 7.15-7.06 (m, 2H), 4.69-4.64 (m, 1H), 4.32-4.25 (m, 1H), 4.22-4.14 (m, 1H), 3.93-3.84 (m, 3H), 3.51-3.40 (m, 5H), 3.14-3.06 (m, 2H), 3.06-2.99 (m, 1H), 2.82-2.53 (m, 6H), 2.39-2.23 (m, 2H), 2.02-1.93 (m, 1H), 1.23 (t, J=7.3 Hz, 3H), 1.16 (d, J=6.6 Hz, 3H), 0.92 (d, J=6.3 Hz, 3H), 0.86-0.80 (m, 6H). LC-MS $(M+H)^+$=633.4.

Example 123: N—((S)-1-(2-((2R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazin-6-yl)cyclopropanesulfonamide (Compound 123)

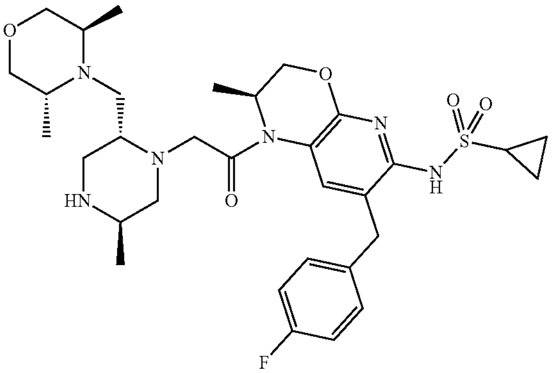 [SMILES: C[C@@H]1CN(CC(=O)N2c3cc(Cc4ccc(F)cc4)c(NS(=O)(=O)C4CC4)nc3OC[C@@H]2C)[C@@H](CN2[C@H](C)COC[C@H]2C)CN1]

Step 1: benzyl (S)-6-(cyclopropanesulfonamido)-7-(4-fluorobenzyl)-2-methyl-2,3-dihydro-1H-pyrido[2,3-b][1,4]oxazine-1-carboxylate

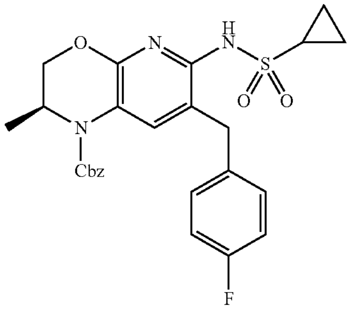 [SMILES: C[C@H]1COc2nc(NS(=O)(=O)C3CC3)c(Cc3ccc(F)cc3)cc2N1C(=O)OCc1ccccc1]

The title compound of step 1 (130 mg, 26% yield) was prepared in a manner similar to that described in Example 122 step 1 from benzyl (S)-6-amino-7-(4-fluorobenzyl)-2-methyl-2,3-dihydro-1H-pyrido[2,3-b][1,4]oxazine-1-carboxylate and cyclopropanesulfonyl chloride. LC-MS $(M+H)^+$=512.2.

Step 2: benzyl (S)-6-(N-(tert-butoxycarbonyl)cyclopropanesulfonamido)-7-(4-fluorobenzyl)-2-methyl-2,3-dihydro-1H-pyrido[2,3-b][1,4]oxazine-1-carboxylate

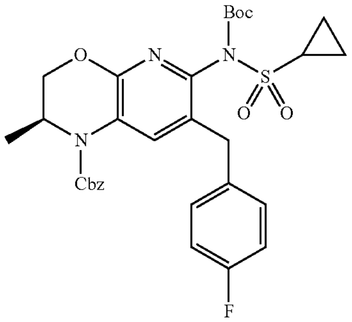 [SMILES: C[C@H]1COc2nc(N(C(=O)OC(C)(C)C)S(=O)(=O)C3CC3)c(Cc3ccc(F)cc3)cc2N1C(=O)OCc1ccccc1]

The title compound of step 2 (70 mg, 45% yield) was prepared in a manner similar to that described in Example 4 step 2 from benzyl (S)-6-(cyclopropanesulfonamido)-7-(4-fluorobenzyl)-2-methyl-2,3-dihydro-1H-pyrido[2,3-b][1,4]oxazine-1-carboxylate. LC-MS $(M+H)^+$=612.2.

Step 3: tert-butyl (S)-(cyclopropylsulfonyl)(7-(4-fluorobenzyl)-2-methyl-2,3-dihydro-1H-pyrido[2,3-b][1,4]oxazin-6-yl)carbamate

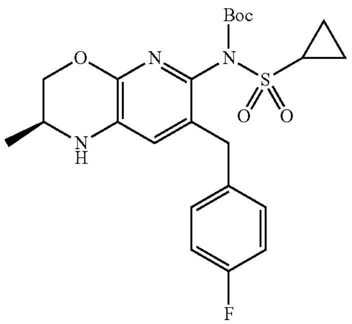 [SMILES: C[C@H]1COc2nc(N(C(=O)OC(C)(C)C)S(=O)(=O)C3CC3)c(Cc3ccc(F)cc3)cc2N1]

The title compound of step 3 (50 mg, 91% yield) was prepared in a manner similar to that described in Example 1 step 17 from benzyl (S)-6-(N-(tert-butoxycarbonyl)cyclopropanesulfonamido)-7-(4-fluorobenzyl)-2-methyl-2,3-dihydro-1H-pyrido[2,3-b][1,4]oxazine-1-carboxylate. LC-MS $(M+H)^+$=478.2.

Step 4: tert-butyl (S)-(1-(2-chloroacetyl)-7-(4-fluorobenzyl)-2-methyl-2,3-dihydro-1H-pyrido[2,3-b][1,4]oxazin-6-yl)(cyclopropylsulfonyl)carbamate

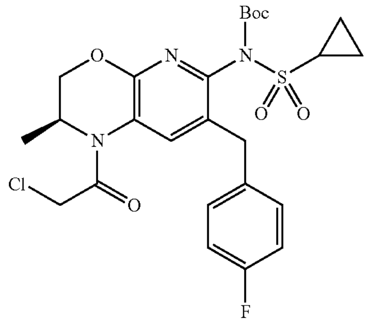 [SMILES: C[C@H]1COc2nc(N(C(=O)OC(C)(C)C)S(=O)(=O)C3CC3)c(Cc3ccc(F)cc3)cc2N1C(=O)CCl]

The title compound of step 4 (40 mg, 68% yield) was prepared in a manner similar to that described in Example 1 step 9 from tert-butyl (S)-(cyclopropylsulfonyl)(7-(4-fluorobenzyl)-2-methyl-2,3-dihydro-1H-pyrido[2,3-b][1,4]oxazin-6-yl)carbamate and 2-chloroacetyl chloride. LC-MS $(M+H)^+$=554.2.

Step 5: tert-butyl (2R,5S)-4-(2-((S)-6-(N-(tert-butoxycarbonyl)cyclopropanesulfonamido)-7-(4-fluorobenzyl)-2-methyl-2,3-dihydro-1H-pyrido[2,3-b][1,4]oxazin-1-yl)-2-oxoethyl)-5-4(3R,5R)-3,5-dimethylmorpholino)methyl)-2-methylpiperazine-1-carboxylate

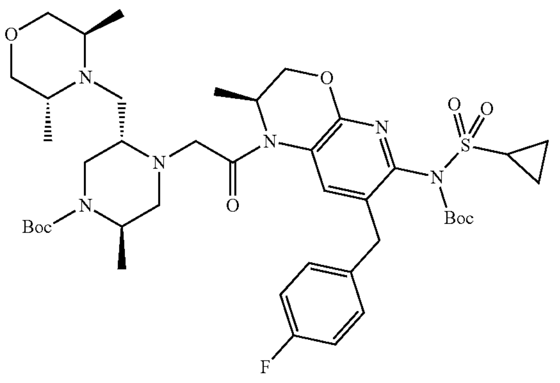 [SMILES: C[C@@H]1CN(CC(=O)N2c3cc(Cc4ccc(F)cc4)c(N(C(=O)OC(C)(C)C)S(=O)(=O)C4CC4)nc3OC[C@@H]2C)[C@@H](CN2[C@H](C)COC[C@H]2C)CN1C(=O)OC(C)(C)C]

The title compound of step 5 (50 mg, 81% yield) was prepared in a manner similar to that described in Example 1 step 18 from tert-butyl (S)-(1-(2-chloroacetyl)-7-(4-fluorobenzyl)-2-methyl-2,3-dihydro-1H-pyrido[2,3-b][1,4]oxazin-6-yl)(cyclopropylsulfonyl)carbamate and tert-butyl (2R,5S)-5-(((3R,5R)-3,5-dimethylmorpholino)methyl)-2-methylpiperazine-1-carboxylate. LC-MS $(M+H)^+$=845.4.

Step 6: N—((S)-1-(2-((2R,5R)-2-(((3R,5R)-3,5-dimethylmorpholino)methyl)-5-methylpiperazin-1-yl)acetyl)-7-(4-fluorobenzyl)-2-methyl-2,3-dihydro-1H-pyrido[2,3-b][1,4]oxazin yl)cyclopropanesulfonamide (Compound 123)

Compound 123 (6 mg, 15% yield) was prepared in a manner similar to that described in Example 29 step 7 from tert-butyl (2R,5S)-4-(2-((S)-6-(N-(tert-butoxycarbonyl)cyclopropanesulfonamido)-7-(4-fluorobenzyl)-2-methyl-2,3-dihydro-1H-pyrido[2,3-b][1,4]oxazin-1-yl)-2-oxoethyl)-5-(((3R,5R)-3,5-dimethylmorpholino)methyl)-2-methylpiperazine-1-carboxylate. LC-MS $(M+H)^+=645.3$. $^1H$ NMR (400 MHz, DMSO-d6) δ 7.98 (s, 1H), 7.27-7.18 (m, 2H), 7.15-7.05 (m, 2H), 4.68-4.64 (m, 1H), 4.32-4.10 (m, 2H), 3.92-3.83 (m, 3H), 3.51-3.37 (m, 4H), 3.25-3.15 (m, 1H), 3.18-3.06 (m, 2H), 3.06-2.99 (m, 1H), 2.82-2.56 (m, 5H), 2.38-2.20 (m, 2H), 2.02-1.93 (m, 1H), 1.17 (d, J=6.1 Hz, 3H), 1.05-0.90 (m, 7H), 0.83 (d, J=6.3 Hz, 6H). LC-MS $(M+H)^+=645.4$.

Biological Assays

I. Recombinant human c-IAP1-BIR$_3$ biochemical assay

Compounds disclosed herein were tested for blocking of recombinant human cIAP1-BIR$_3$ protein (Cat: APT-11-370, Reaction biology) with its peptide in an assay based on Homogeneous Time Resolved Fluorescence. 1.2 nM recombinant human cIAP1-BIR$_3$ protein was pre-incubated with a serial dilution of compounds disclosed herein (maximum concentration is 10 uM, 4-fold serially diluted, 10 points) at room temperature for 1 hour in an assay buffer containing 20 mM HEPES, pH 7.5, 50 mM NaCl, 0.005% Tween-20, 1 mM DTT. Then 3 nM AbuRPF-K (5-Fam)-NH2 (Cat: 709702, GL Biochem) was added to plate incubated at room temperature for 1 hour. Mab Anti-6His Tb cryptate Gold (Cat: 61HI2TLB, Cisbio Bioassays) was added to plate and further incubated at room temperature for 1 hour. The HTRF signals (ex337 nm, em520 nm/490 nm) were read on BMG PHERAstar FS instrument. The inhibition percentage of cIAP1-BIR$_3$ interaction with its peptide in presence of increasing concentrations of compounds was calculated based on the ratio of fluorescence at 520 nm to that at 490 nm. The $IC_{50}$ for each compound was derived from fitting the data to the four-parameter logistic equation by Dotmatics and summarized in table 1.

II. Recombinant Human c-IAP2-BIR3 Biochemical Assay

Compounds disclosed herein were tested for blocking of recombinant human cIAP2-BIR$_3$ protein (Cat: APT-11-372, Reaction biology) with its peptide in an assay based on Homogeneous Time Resolved Fluorescence. 3.7 nM recombinant human cIAP2-BIR$_3$ protein was pre-incubated with a serial dilution of compounds disclosed herein (maximum concentration is 10 uM, 4-fold serially diluted, 10 points) at room temperature for 1 hour in an assay buffer containing 20 mM HEPES, pH 7.5, 50 mM NaCl, 0.005% Tween-20, 1 mM DTT. Then 3.7 nM AbuRPF-K(5-Fam)-NH2 (Cat: 709702, GL Biochem) was added to plate incubated at room temperature for 1 hour. Mab Anti-6His Tb cryptate Gold (Cat: 61HI2TLB, Cisbio Bioassays) was added to plate and further incubated at room temperature for 1 hour. The HTRF signals (ex337 nm, em520 nm/490 nm) were read on BMG PHERAstar FS instrument. The inhibition percentage of cIAP2-BIR$_3$ interaction with its peptide in presence of increasing concentrations of compounds was calculated based on the ratio of fluorescence at 520 nm to that at 490 nm. The $IC_{50}$ for each compound was derived from fitting the data to the four-parameter logistic equation by Dotmatics and summarized in table 1.

III. Recombinant Human XIAP-BIR$_3$ Biochemical Assay

Compounds disclosed herein were tested for blocking of recombinant human XIAP-BIR$_3$ protein (Cat: APT-11-374, Reaction biology) with its peptide in an assay based on Homogeneous Time Resolved Fluorescence. 3.7 nM recombinant human XIAP-BIR$_3$ protein was pre-incubated with a serial dilution of compounds disclosed herein (maximum concentration is 10 uM, 4-fold serially diluted, 10 points) at room temperature for 1 hour in an assay buffer containing 20 mM HEPES, pH 7.5, 50 mM NaCl, 0.005% Tween-20, 1 mM DTT. Then 7.6 nM AbuRPF-K(5-Fam)-NH2 (Cat: 709702, GL Biochem) was added to plate incubated at room temperature for 1 hour. Mab Anti-6His Tb cryptate Gold (Cat: 61HI2TLB, Cisbio Bioassays) was added to plate and further incubated at room temperature for 1 hour. The HTRF signals (ex337 nm, em520 nm/490 nm) were read on BMG PHERAstar FS instrument. The inhibition percentage of XIAP-BIR$_3$ interaction with its peptide in presence of increasing concentrations of compounds was calculated based on the ratio of fluorescence at 520 nm to that at 490 nm. The IC50 for each compound was derived from fitting the data to the four-parameter logistic equation by Dotmatics and summarized in table 1.

TABLE 1 protein binding $IC_{50}$ (nM) for the compounds disclosed herein

| Comp No. | Protein binding $IC_{50}$ (nM) c-IAP1 | c-IAP2 | XIAP |
|---|---|---|---|
| 1 | 0.5 | 0.9 | 26 |
| 2 | 0.9 | 2.5 | 24 |
| 3 | 1.5 | 3.2 | 23 |
| 4 | 0.5 | 0.92 | 17 |
| 5 | 0.7 | 1.1 | 18 |
| 6 | 1.1 | 3 | 61 |
| 7 | 1.3 | 6.8 | 99 |
| 8 | 1 | 2.9 | 45 |
| 9 | 0.85 | 1.3 | 10 |
| 10 | 14 | 52 | 264 |
| 11 | 8 | 17 | 220 |
| 12 | 16 | 44 | 561 |
| 13 | 1.02 | 1.5 | 24 |
| 14 | 3.6 | 9.8 | 122 |
| 15 | 3.4 | 6.9 | 196 |
| 16 | 0.34 | 0.85 | 8.4 |
| 17 | 0.53 | 1.3 | 5.4 |
| 18 | >1000 | >1000 | >1000 |
| 19 | 0.82 | 1.2 | 7.7 |
| 19A | 0.13 | 0.25 | 2.7 |
| 19B | 6.4 | 27 | 33 |
| 20 | 9.9 | 25 | 140 |
| 21 | 2.6 | 5.75 | 41 |
| 22 | 0.13 | 0.21 | 3.97 |
| 23 | 0.13 | 0.18 | 6.9 |
| 24 | 0.15 | 0.24 | 4.49 |
| 25 | 0.3 | 0.5 | 6 |
| 26 | 0.48 | 1.13 | 16 |
| 27 | 0.2 | 0.5 | 14 |
| 28 | 0.26 | 0.62 | 14 |
| 29 | 0.24 | 0.32 | 22 |
| 30 | 0.35 | 0.72 | 7.3 |
| 31 | 0.33 | 0.71 | 5.6 |
| 32 | 0.25 | 0.36 | 5.8 |
| 33 | 0.74 | 1.8 | 47 |
| 34 | 0.25 | 0.32 | 23 |
| 35 | 0.33 | 0.99 | 46 |
| 36 | 0.42 | 0.80 | 50 |
| 37 | 0.29 | 0.66 | 43 |
| 38 | 0.26 | 0.83 | 49 |
| 39 | 0.15 | 0.27 | 28 |
| 40 | 0.09 | 0.14 | 8.2 |
| 41 | 0.11 | 0.24 | 12 |

TABLE 1-continued protein binding $IC_{50}$ (nM) for the compounds disclosed herein

| Comp | Protein binding $IC_{50}$ (nM) | | |
|---|---|---|---|
| No. | c-IAP1 | c-IAP2 | XIAP |
| 42 | 0.34 | 0.52 | 25 |
| 43 | 0.23 | 0.27 | 23 |
| 44 | 0.36 | 0.93 | 20 |
| 45 | 0.34 | 0.65 | 8.5 |
| 46 | 0.24 | 0.47 | 63 |
| 47 | 0.57 | 1.43 | 84 |
| 48 | 0.45 | 0.79 | 12 |
| 49 | 0.3 | 0.48 | 3.6 |
| 50 | 0.44 | 0.93 | 14 |
| 51 | 0.30 | 0.67 | 9.2 |
| 52 | 0.55 | 1.1 | 13 |
| 53 | 0.46 | 1.2 | 12 |
| 54 | 1.7 | 2.8 | 25 |
| 55 | 1.3 | 1.9 | 34 |
| 56 | 1.0 | 2.2 | 30 |
| 57 | 1.2 | 1.9 | 95 |
| 58 | 0.11 | 0.17 | 9.5 |
| 59 | 0.26 | 0.67 | 7.8 |
| 60 | 0.13 | 0.34 | 7.5 |
| 61 | 0.43 | 1.08 | 14 |
| 62 | 0.33 | 0.73 | 8.1 |
| 63 | 0.17 | 0.23 | 3.2 |
| 64 | 0.25 | 0.29 | 2.3 |
| 65 | 0.22 | 0.44 | 4.4 |
| 66 | 0.25 | 0.52 | 5.9 |
| 67 | 0.29 | 0.56 | 8.2 |
| 68 | 0.23 | 0.41 | 5.5 |
| 69 | 0.16 | 0.37 | 3.7 |
| 70 | 0.16 | 0.27 | 1.9 |
| 71 | 0.26 | 0.57 | 7.9 |
| 72 | 0.35 | 0.42 | 7.6 |
| 73 | 0.18 | 0.29 | 4.3 |
| 74 | 0.25 | 0.51 | 11 |
| 75 | 0.2 | 0.54 | 6.5 |
| 76 | 0.15 | 0.28 | 4.4 |
| 77 | 0.2 | 0.28 | 2.6 |
| 78 | 0.17 | 0.31 | 3.2 |
| 79 | 0.19 | 0.33 | 5.2 |
| 80 | 0.22 | 0.3 | 4.9 |
| 81 | 0.18 | 0.42 | 2.9 |
| 82 | 0.54 | 0.73 | 10 |
| 83 | 0.2 | 0.4 | 7.2 |
| 84A | 0.29 | 0.44 | 6.4 |
| 84B | 0.78 | 1.6 | 46 |
| 85 | 0.68 | 0.72 | 20 |
| 86 | 0.89 | 0.95 | 15 |
| 87 | 0.18 | 0.23 | 3.3 |
| 88 | 0.35 | 0.63 | 12.4 |
| 89 | 0.17 | 0.36 | 3.1 |
| 90 | 0.22 | 0.34 | 3.8 |
| 91A | 0.72 | 1.25 | 30 |
| 91B | 47 | 108 | 543 |
| 92 | 0.37 | 0.53 | 8.7 |
| 93 | 0.19 | 0.46 | 4.6 |
| 94 | 0.16 | 0.28 | 3.3 |
| 95 | 0.19 | 0.25 | 2.3 |
| 96 | 0.21 | 0.23 | 3.75 |
| 97 | 0.27 | 0.51 | 12.5 |
| 98 | 0.13 | 0.29 | 8.2 |
| 99 | 0.16 | 0.43 | 12.4 |
| 100 | 0.17 | 0.44 | 4.2 |
| 101 | 0.19 | 0.37 | 2.5 |
| 102 | 0.24 | 0.49 | 5.7 |
| 103 | 0.24 | 0.43 | 5.1 |
| 104 | 0.26 | 0.83 | 18.1 |
| 105 | 0.28 | 0.35 | 11.3 |
| 106 | 0.33 | 0.94 | 16.9 |
| 107 | 0.23 | 0.41 | 4.4 |
| 108 | 0.16 | 0.57 | 7.7 |
| 109 | 0.24 | 0.45 | 10.3 |
| 110 | 0.36 | 0.75 | 11.9 |
| 111 | 0.25 | 0.70 | 13.9 |
| 112 | 0.34 | 0.63 | 4.6 |
| 113 | 0.25 | 0.36 | 5.4 |
| 114 | 0.19 | 0.36 | 7.7 |
| 115 | 0.17 | 0.28 | 6.9 |
| 116 | 0.16 | 0.24 | 4.3 |
| 117 | 0.15 | 0.23 | 6.5 |
| 118 | 0.16 | 0.19 | 4.8 |
| 119 | 0.20 | 0.35 | 4.4 |
| 120 | 0.24 | 0.39 | 6.8 |
| 121 | 0.20 | 0.27 | 4.2 |
| 122 | 0.19 | 0.29 | 2.9 |
| 123 | 0.20 | 0.35 | 4.4 |

It is to be understood that, if any prior art publication is referred to herein; such reference does not constitute an admission that the publication forms a part of the common general knowledge in the art in any country.

The disclosures of all publications, patents, patent applications and published patent applications referred to herein by an identifying citation are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:

1. A compound selected from

24

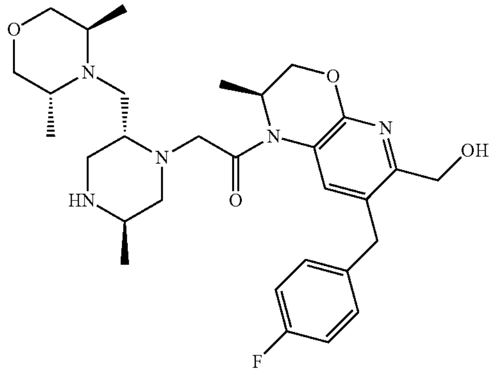

60

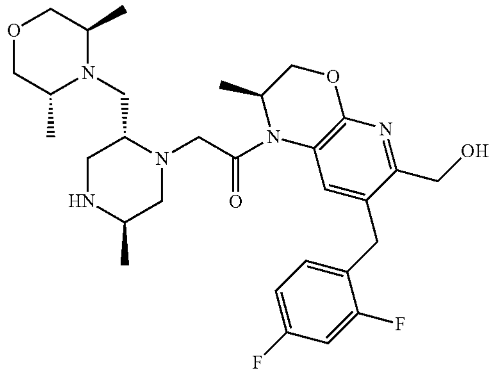

-continued
63
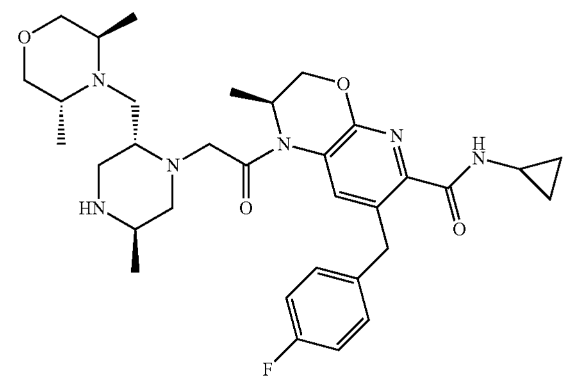
69
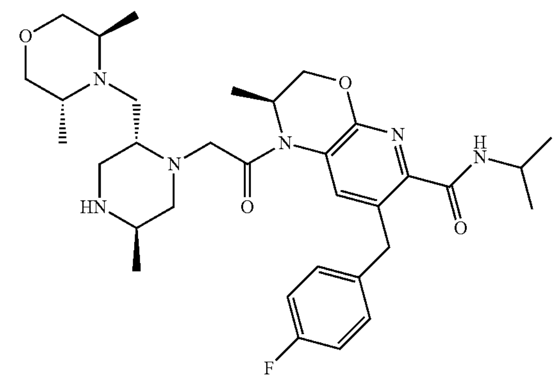
70
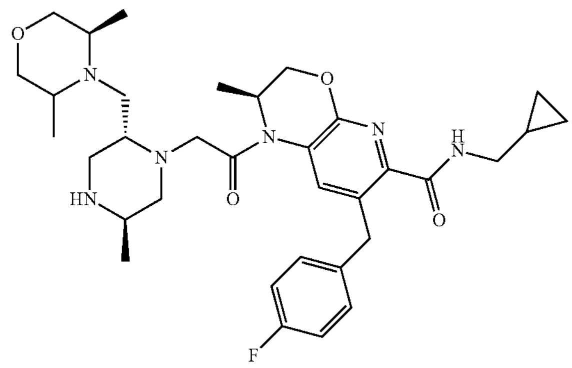
76
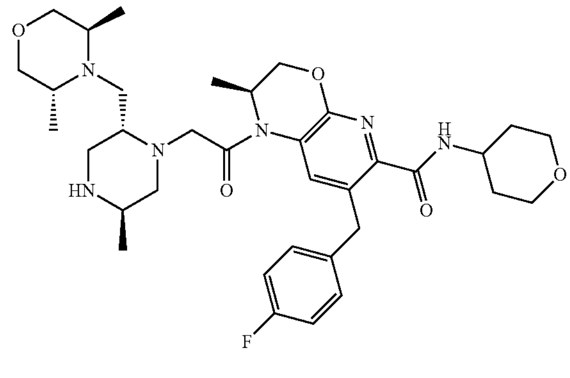
-continued
78
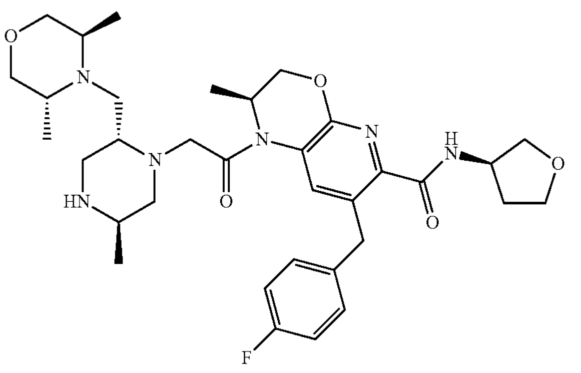
94
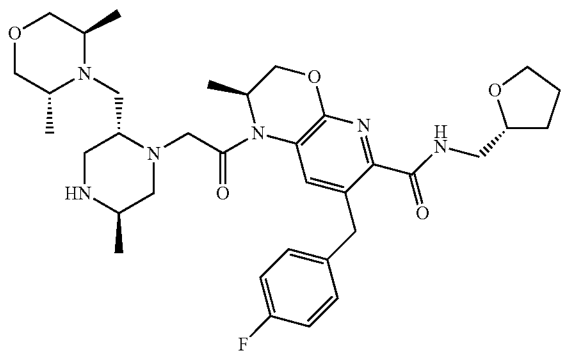
98
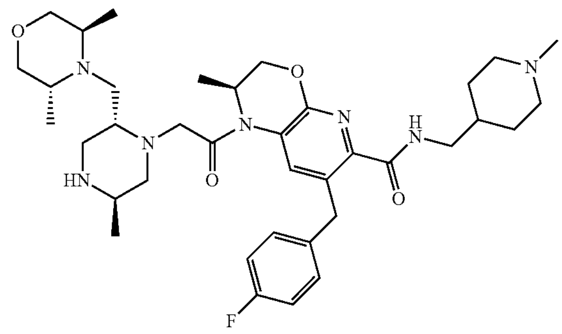
100
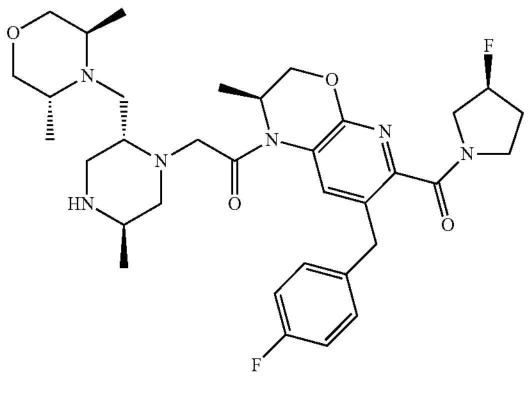

-continued

115

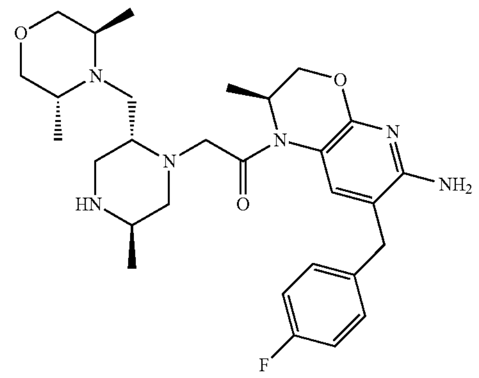

116

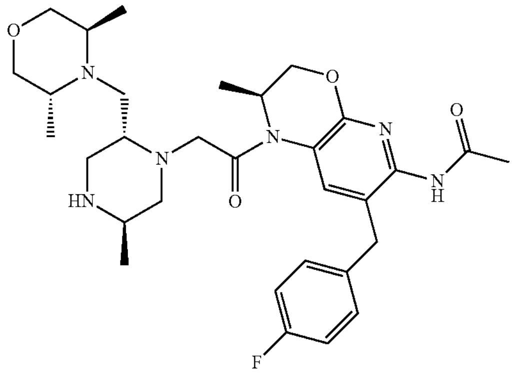

117

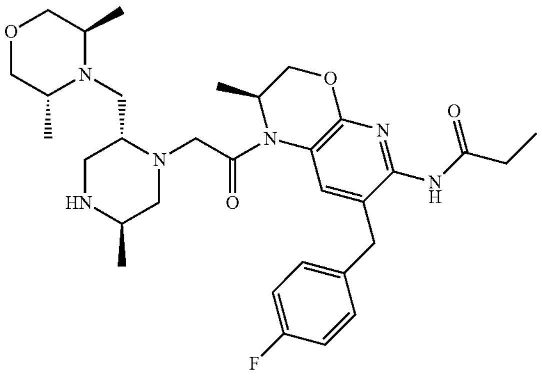

and

118

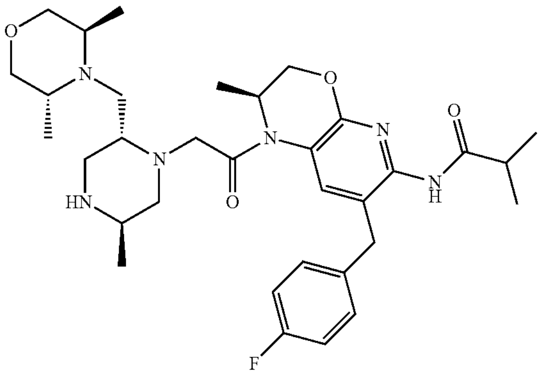

or a pharmaceutically acceptable salt or tautomer thereof.

2. A pharmaceutical composition comprising a compound of claim 1, or a pharmaceutically acceptable salt or tautomer thereof, and at least one pharmaceutically acceptable carrier or excipient.

3. A method of treating a disease responsive to inhibition of cIAPs, comprising administering to a subject in need thereof a compound of claim 1, or a pharmaceutically acceptable salt or tautomer thereof.

4. A method of treating cancer modulated by cIAPs, comprising administering to a subject in need thereof a compound of claim 1, or a pharmaceutically acceptable salt or tautomer thereof.

5. The compound of claim 1, which is:

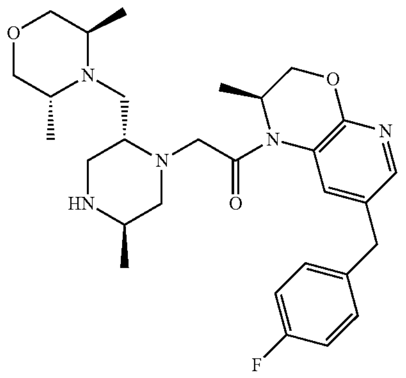 [SMILES: C[C@@H]1CN(CC(=O)N2c3cc(Cc4ccc(F)cc4)cnc3OC[C@@H]2C)[C@@H](CN2[C@H](C)COC[C@H]2C)CN1]

or a pharmaceutically acceptable salt thereof.

6. The compound of claim 1, which is:

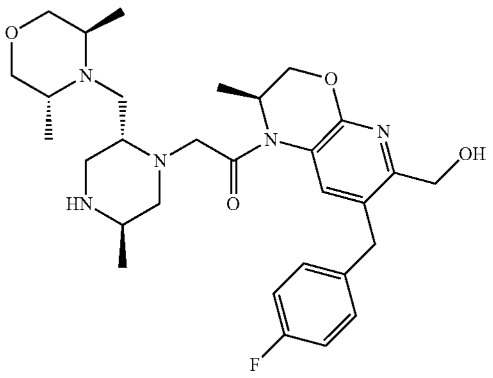 [SMILES: C[C@@H]1CN(CC(=O)N2c3cc(Cc4ccc(F)cc4)c(CO)nc3OC[C@@H]2C)[C@@H](CN2[C@H](C)COC[C@H]2C)CN1]

or a pharmaceutically acceptable salt thereof.

7. The compound of claim 1, which is:

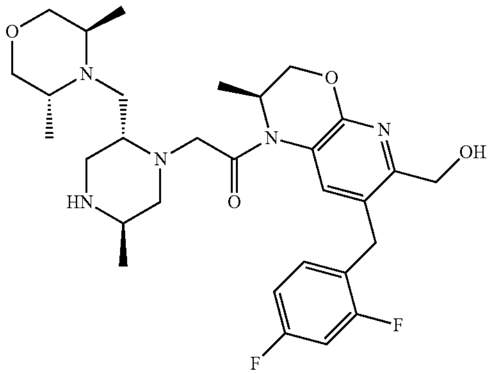 [SMILES: C[C@@H]1CN(CC(=O)N2c3cc(Cc4ccc(F)cc4F)c(CO)nc3OC[C@@H]2C)[C@@H](CN2[C@H](C)COC[C@H]2C)CN1]

or a pharmaceutically acceptable salt thereof.

8. The compound of claim 1, which is:

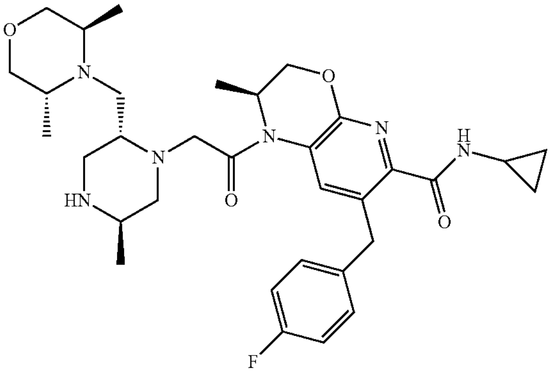 [SMILES: C[C@@H]1CN(CC(=O)N2c3cc(Cc4ccc(F)cc4)c(C(=O)NC4CC4)nc3OC[C@@H]2C)[C@@H](CN2[C@H](C)COC[C@H]2C)CN1]

or a pharmaceutically acceptable salt thereof.

9. The compound of claim 1, which is:

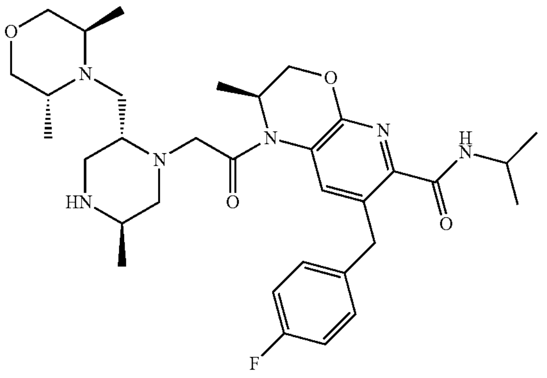 [SMILES: CC(C)NC(=O)c1nc2c(cc1Cc1ccc(F)cc1)N(C(=O)CN1C[C@@H](C)NC[C@@H]1CN1[C@H](C)COC[C@H]1C)[C@@H](C)CO2]

or a pharmaceutically acceptable salt thereof.

10. The compound of claim 1, which is:

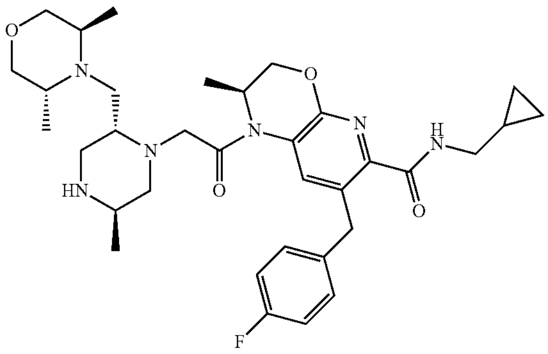 [SMILES: C[C@@H]1CN(CC(=O)N2c3cc(Cc4ccc(F)cc4)c(C(=O)NCC4CC4)nc3OC[C@@H]2C)[C@@H](CN2[C@H](C)COC[C@H]2C)CN1]

or a pharmaceutically acceptable salt thereof.

11. The compound of claim 1, which is:

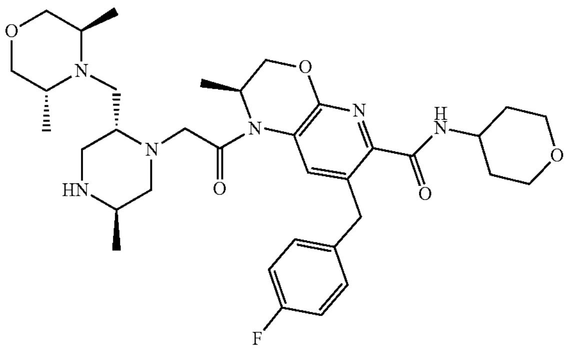 [SMILES: C[C@@H]1CN(CC(=O)N2c3cc(Cc4ccc(F)cc4)c(C(=O)NC4CCOCC4)nc3OC[C@@H]2C)[C@@H](CN2[C@H](C)COC[C@H]2C)CN1]

or a pharmaceutically acceptable salt thereof.

12. The compound of claim 1, which is:

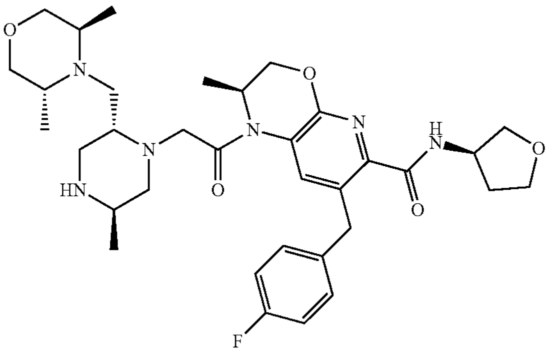 [SMILES: C[C@@H]1CN(CC(=O)N2c3cc(Cc4ccc(F)cc4)c(C(=O)N[C@@H]4CCOC4)nc3OC[C@@H]2C)[C@@H](CN2[C@H](C)COC[C@H]2C)CN1]

or a pharmaceutically acceptable salt thereof.

13. The compound of claim 1, which is:

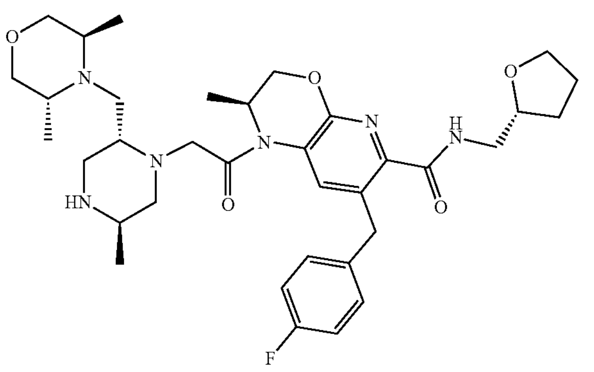 [SMILES: C[C@@H]1CN(CC(=O)N2c3cc(Cc4ccc(F)cc4)c(C(=O)NC[C@H]4CCCO4)nc3OC[C@@H]2C)[C@@H](CN2[C@H](C)COC[C@H]2C)CN1]

or a pharmaceutically acceptable salt thereof.

14. The compound of claim 1, which is:

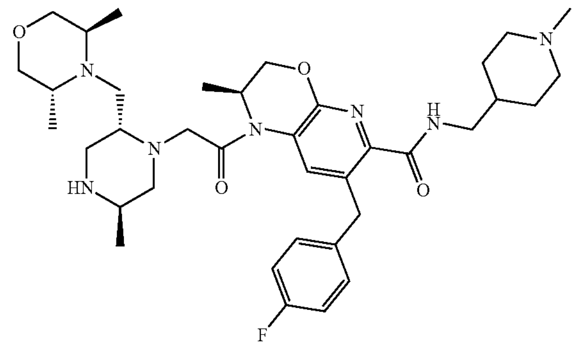 [SMILES: C[C@@H]1CN(CC(=O)N2c3cc(Cc4ccc(F)cc4)c(C(=O)NCC4CCN(C)CC4)nc3OC[C@@H]2C)[C@@H](CN2[C@H](C)COC[C@H]2C)CN1]

or a pharmaceutically acceptable salt thereof.

15. The compound of claim 1, which is:

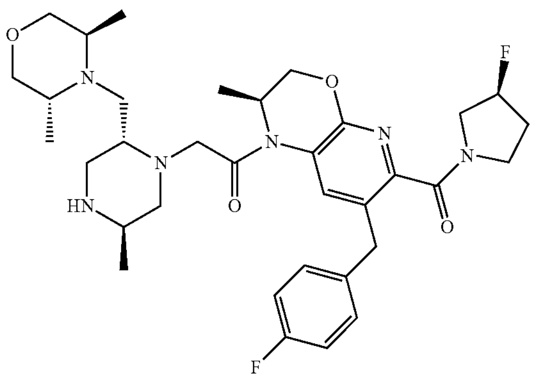 [SMILES: C[C@@H]1CN(CC(=O)N2c3cc(Cc4ccc(F)cc4)c(C(=O)N4CC[C@H](F)C4)nc3OC[C@@H]2C)[C@@H](CN2[C@H](C)COC[C@H]2C)CN1]

or a pharmaceutically acceptable salt thereof.

16. The compound of claim 1, which is:

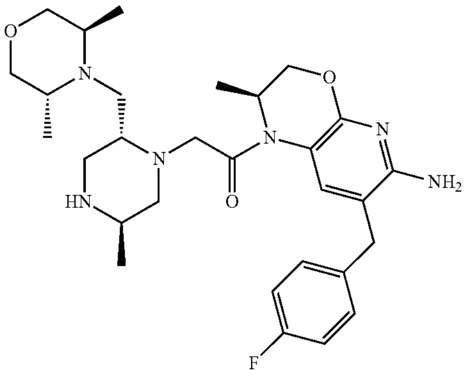 [SMILES: C[C@@H]1CN(CC(=O)N2c3cc(Cc4ccc(F)cc4)c(N)nc3OC[C@@H]2C)[C@@H](CN2[C@H](C)COC[C@H]2C)CN1]

or a pharmaceutically acceptable salt thereof.

17. The compound of claim 1, which is:

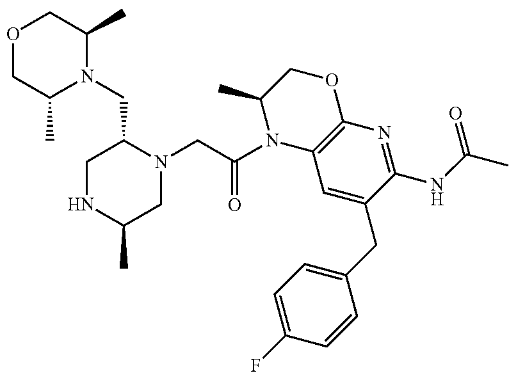 [SMILES: CC(=O)Nc1nc2c(cc1Cc1ccc(F)cc1)N(C(=O)CN1C[C@@H](C)NC[C@@H]1CN1[C@H](C)COC[C@H]1C)[C@@H](C)CO2]

or a pharmaceutically acceptable salt thereof.

18. The compound of claim 1, which is:

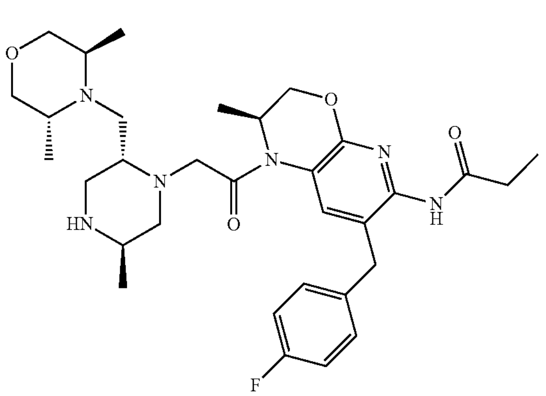 [SMILES: CCC(=O)Nc1nc2c(cc1Cc1ccc(F)cc1)N(C(=O)CN1C[C@@H](C)NC[C@@H]1CN1[C@H](C)COC[C@H]1C)[C@@H](C)CO2]

or a pharmaceutically acceptable salt thereof.

19. The compound of claim 1, which is:
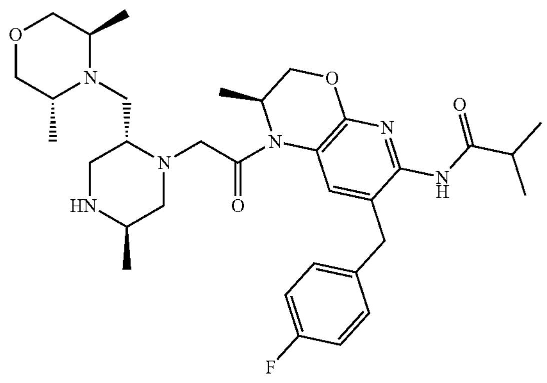 [SMILES: CC(C)C(=O)Nc1nc2c(cc1Cc1ccc(F)cc1)N(C(=O)CN1C[C@@H](C)NC[C@@H]1CN1[C@H](C)COC[C@H]1C)[C@@H](C)CO2]
or a pharmaceutically acceptable salt thereof.
* * * * *